US011673971B2

United States Patent
Loew et al.

(10) Patent No.: US 11,673,971 B2
(45) Date of Patent: Jun. 13, 2023

(54) MULTISPECIFIC ANTIBODY MOLECULES COMPRISING LAMBDA AND KAPPA LIGHT CHAINS

(71) Applicant: MARENGO THERAPEUTICS, INC., Cambridge, MA (US)

(72) Inventors: Andreas Loew, Boston, MA (US); Brian Edward Vash, Cambridge, MA (US); Stephanie J. Maiocco, Arlington, MA (US)

(73) Assignee: Marengo Therapeutics, Inc., Cambridge, MA (US)

( * ) Notice: Subject to any disclaimer, the term of this patent is extended or adjusted under 35 U.S.C. 154(b) by 385 days.

(21) Appl. No.: 16/335,822

(22) PCT Filed: Sep. 22, 2017

(86) PCT No.: PCT/US2017/053053
§ 371 (c)(1),
(2) Date: Mar. 22, 2019

(87) PCT Pub. No.: WO2018/057955
PCT Pub. Date: Mar. 29, 2018

(65) Prior Publication Data
US 2019/0218311 A1 Jul. 18, 2019

Related U.S. Application Data

(60) Provisional application No. 62/474,569, filed on Mar. 21, 2017, provisional application No. 62/399,319, filed on Sep. 23, 2016.

(51) Int. Cl.
| | | |
|---|---|---|
| C07K 16/46 | (2006.01) | |
| C07K 16/00 | (2006.01) | |
| A61P 35/00 | (2006.01) | |
| C07K 16/24 | (2006.01) | |
| C07K 16/28 | (2006.01) | |
| C07K 16/40 | (2006.01) | |
| C07K 16/44 | (2006.01) | |

(52) U.S. Cl.
CPC ............ *C07K 16/468* (2013.01); *A61P 35/00* (2018.01); *C07K 16/00* (2013.01); *C07K 16/246* (2013.01); *C07K 16/2818* (2013.01); *C07K 16/2878* (2013.01); *C07K 16/40* (2013.01); *C07K 16/44* (2013.01); *C07K 2317/31* (2013.01); *C07K 2317/515* (2013.01); *C07K 2317/567* (2013.01)

(58) Field of Classification Search
None
See application file for complete search history.

(56) References Cited

U.S. PATENT DOCUMENTS

| | | | |
|---|---|---|---|
| 4,816,567 | A | 3/1989 | Cabilly et al. |
| 5,223,409 | A | 6/1993 | Ladner et al. |
| 5,225,539 | A | 7/1993 | Winter |
| 5,585,089 | A | 12/1996 | Queen et al. |
| 5,624,821 | A | 4/1997 | Winter et al. |
| 5,648,260 | A | 7/1997 | Winter et al. |
| 5,693,762 | A | 12/1997 | Queen et al. |
| 5,731,116 | A | 3/1998 | Matsuo et al. |
| 5,811,097 | A | 9/1998 | Allison et al. |
| 5,849,500 | A | 12/1998 | Breitling et al. |
| 7,476,724 | B2 | 1/2009 | Dennis et al. |
| 7,501,121 | B2 | 3/2009 | Tchistiakova et al. |
| 7,943,873 | B2 | 5/2011 | Gopikrishnan et al. |
| 8,008,449 | B2 | 8/2011 | Korman et al. |
| 8,354,509 | B2 | 1/2013 | Carven et al. |
| 8,552,156 | B2 | 10/2013 | Takayanagi et al. |
| 8,609,089 | B2 | 12/2013 | Langermann et al. |
| 2004/0009530 | A1 | 1/2004 | Wilson et al. |
| 2010/0028330 | A1 | 2/2010 | Collins et al. |
| 2011/0150892 | A1 | 6/2011 | Thudium et al. |
| 2012/0039906 | A1 | 2/2012 | Olive |
| 2012/0114649 | A1 | 5/2012 | Langermann et al. |
| 2013/0317200 | A1 | 11/2013 | Elson et al. |
| 2014/0044728 | A1 | 2/2014 | Takayanagi et al. |
| 2019/0338048 | A1* | 11/2019 | Urosev .................. C07K 16/46 |

FOREIGN PATENT DOCUMENTS

| | | | |
|---|---|---|---|
| EP | 0125023 | A1 | 11/1984 |
| EP | 0171496 | A2 | 2/1986 |
| EP | 0173494 | A2 | 3/1986 |
| EP | 0184187 | A2 | 6/1986 |
| EP | 0388151 | A1 | 9/1990 |
| EP | 0519596 | A1 | 12/1992 |
| EP | 2581113 | A1 | 4/2013 |
| GB | 2188638 | A | 10/1987 |
| WO | WO-8605133 | A1 | 9/1986 |
| WO | WO-8702671 | A1 | 5/1987 |
| WO | WO-9002809 | A1 | 3/1990 |
| WO | WO-9100906 | A1 | 1/1991 |
| WO | WO-9110741 | A1 | 7/1991 |
| WO | WO-9117271 | A1 | 11/1991 |
| WO | WO-9201047 | A1 | 1/1992 |
| WO | WO-9203917 | A1 | 3/1992 |
| WO | WO-9203918 | A1 | 3/1992 |
| WO | WO-9209690 | A2 | 6/1992 |
| WO | WO-9215679 | A1 | 9/1992 |

(Continued)

OTHER PUBLICATIONS

Fischer et al., Nature Communications 6: 6113 (Year: 2015).*
Lloyd et al., Protein Engineering, Design & Selection 22:159-168 (Year: 2009).*

(Continued)

*Primary Examiner* — Phuong Huynh
(74) *Attorney, Agent, or Firm* — Wilson Sonsini Goodrich & Rosati

(57) ABSTRACT

Multispecific, e.g., bispecific, antibody molecules that include a kappa light chain polypeptide and one lambda light chain polypeptide, and methods of making and using the multispecific antibody molecules, are disclosed.

10 Claims, 35 Drawing Sheets

Specification includes a Sequence Listing.

(56) References Cited

FOREIGN PATENT DOCUMENTS

| | | | |
|---|---|---|---|
| WO | WO-9218619 A1 | 10/1992 | |
| WO | WO-9220791 A1 | 11/1992 | |
| WO | WO-9301288 A1 | 1/1993 | |
| WO | WO-9856915 A2 | 12/1998 | |
| WO | WO-9945110 A1 | 9/1999 | |
| WO | WO-0034784 A1 | 6/2000 | |
| WO | WO-0056772 A1 * | 9/2000 | ............. A61P 19/02 |
| WO | WO-0060070 A1 | 10/2000 | |
| WO | WO-0164942 A1 | 9/2001 | |
| WO | WO-2006105338 A2 * | 10/2006 | ............. C07K 16/00 |
| WO | WO-2006121168 A1 | 11/2006 | |
| WO | WO-2007005874 A2 | 1/2007 | |
| WO | WO-2009101611 A1 | 8/2009 | |
| WO | WO-2009114335 A2 | 9/2009 | |
| WO | WO-2010019570 A2 | 2/2010 | |
| WO | WO-2010027827 A2 | 3/2010 | |
| WO | WO-2010077634 A1 | 7/2010 | |
| WO | WO-2011066342 A2 | 6/2011 | |
| WO | WO-2011080350 A1 | 7/2011 | |
| WO | WO-2011155607 A1 | 12/2011 | |
| WO | 2012023053 A2 | 2/2012 | |
| WO | WO-2012023053 A2 * | 2/2012 | ......... C12N 15/1037 |
| WO | WO-2013079174 A1 | 6/2013 | |
| WO | WO-2013096291 A2 | 6/2013 | |
| WO | WO-2014008218 A1 | 1/2014 | |
| WO | 2015052230 A1 | 4/2015 | |
| WO | 2017059551 A1 | 4/2017 | |
| WO | WO-2018057955 A1 | 3/2018 | |

OTHER PUBLICATIONS

Edwards et al., J Mol Biol. 334(1): 103-118 (Year: 2003).*
Rudikoff et al., Proc Natl Acad Sci USA 79: 1979-1983 (Year: 1982).*
Barrios et al., J Molecular Recognition 17: 332-338 (Year: 2004).*
MacCallum et al., Mol. Biol 262: 732-745 (Year: 1996).*
Wu et al., J. Mol. Biol. 294: 151-162 (Year: 1999).*
Dhimolea et al., "World Bispecific Antibody Summit, Sep. 27-28, 2011 Boston, MA," mAbs (2012) vol. 4, Issue 1, pp. 4-13.
Fischer et al., "Exploiting light chains for the scalable generation and platform purification of native human bispecific IgG," Nature Communications (2015) vol. 6, Article 6613, 12 pages.
International Search Report and Written Opinion issued in PCT/US2017/053053, dated Feb. 27, 2018.
Jayaram et al., "Germline VH/VL pairing in antibodies," Protein Engineering, Design & Selection (2012) vol. 25, No. 10, pp. 523-529.
Malinge, presentation entitled "Maximizing Assembly and Yield of Unmodified Bispecific Antibodies," World Bispecific Summit 2015, retrieved from the internet at bispecific.com/wp-content/uploads/sites/90/2015/07/Day-1-1600-Pauline-Malinge-YES.pdf, 25 pages.
Spiess et al., "Alternative molecular formats and therapeutic applications for bispecific antibodies," Molecular Immunology (2015) vol. 67, pp. 95-106.
Toughiri et al., "Comparing domain interactions within antibody Fabs with kappa and lambda light chains," mAbs (2016) vol. 8, No. 7, pp. 1276-1285.
Agostinis, P. et al, "Photodynamic Therapy of Cancer: An Update", CA Cancer J. Clin, 2011, vol. 61, No. 4, pp. 250-281.
Al-Lazikani, B. et al, "Standard Conformations for Canonical Structures of Immunoglobulins", J. Mol. Biol., 1997, vol. 273 ,pp. 927-948.
Altschul, S. et al, "Basic Local Alignment Search Tool", J. Mol Biol., 1990, vol. 215, pp. 403-410.
Altschul, S. et al., "Gapped BLAST and PSI-BLAST: a new generation of protein database search programs", Nucleic Acids Research, 1997, vol. 25, No. 17, pp. 3389-3402.
Arnon, T.I. et al, "Recognition of viral hemagglutinins by NKp44 but not by NKp30", Eur J. Immunol., 2001, vol. 31, No. 9, pp. 2680-2689.

Barbas, C.F. et al, "Assembly of combinatorial antibody libraries on phage surfaces: The gene III site", PNAS, 1991, vol. 88, pp. 7978-7982.
Beidler,C.B. et al., "Cloning and high level expression of a chimeric antibody with specificity for human carcinoembryonic antigen", J. Immuno, 1988, vol. 141, pp. 4053-4060.
Better, M. et al., "*Escherichia coli* Secretion of an Active Chimeric Antibody Fragment", Science, 1988, vol. 240, No. 4855, pp. 1041-1043.
Bird, R. et al., "Single-Chain Antigen-Binding Proteins", Science, 1988, vol. 242, No. 4877, pp. 423-426.
Bruggemann, M. et al., Designer Mice: The Production of Human Antibody Repertoires in Transgenic Animals, Terhorst C. Malavasi F, Albertini A (eds): Generation of Antibodies by Cell and Gene Immortalization, Year Immunol, 1993, vol. 7, pp. 33-40.
Bruggemann, M. et al., "Human antibody production in transgenic mice: expression from 100kb of the human IgH locus", Eur J. Immunol, 1991, vol. 21, pp. 1323-1326.
Chothia, C. et al., "Canonical Structures for the Hypervariable Regions of Immunoglobulins", J. Mol. Biol, 1987, vol. 196, pp. 901-917.
Clackson, T. et al., Making antibody fragments using phage display libraries, Nature, 1991, vol. 352, pp. 624-628.
Colcher, D. et al., "Single-Chain Antibodies in Pancreatic Cancer", Ann Ny Acad Sci, 1999, vol. 880, pp. 263-280.
Coloma, J. et al, "Design and production of novel tetravalent bispecific antibodies", Nature Biotech, 1997, vol. 15, pp. 159-163.
Costa-Mattioli, M. et al., "RAPping production of type I interferon in pDCs through mTOR", 2008, Nature Immunol, vol. 9, No. 10, pp. 1097-1099.
Fuchs, P. et al., "Targeting Recombinant Antibodies to the surface of *Escherichia coli*: Fusion to the Peptidoglycan associated Lipoprotein", Nature Publishing Group, 1991, vol. 9, No. 12, pp. 1369-1372.
Garrard, L. et al., "FAB Assembly and Enrichment in a Monovalent Phage Display System", Nature Publishing Group, 1991, vol. 9, pp. 1373-1377.
Garrity, D. et al, "The activating NKG2D receptor assembles in the membrane with two signaling dimers into a hexameric structure", Proc Natl Acad Sci USA, 2005, vol. 102, No. 21, pp. 7641-7646.
Gram, H. et al, In vitro selection and affinity maturation of antibodies from a naïve combinatorial immunoglobulin library, PNAS, 1992, vol. 89, pp. 3576-3580.
Green, L.L. et al, "Antigen-specific human monoclonal antibodies from mice engineered with human Ig heavy and light chain YACS", Nature Genet, 1994, vol. 7, pp. 13-21.
Griffiths, A.D. et al, "Human anti-self antibodies with high specificity from phage display libraries", The EMBO Journal, 1993, vol. 12, No. 2, pp. 725-734.
Hamid, O. et al., "Safety and Tumor Responses with Lambrolizumab (Anti-PD-1) in Melanoma", The New England Journal of Medicine, 2013, vol. 369, No. 2, pp. 134-144.
Hawkins, R. et al., "Selection of phage antibodies by binding affinity. Mimicking affinity maturation", J. Mol. Biol., 1992, vol. 226, No. 3, pp. 889-896.
Hay, B. et al., "Bacteriophage cloning and *Escherichia coli* expression of a human IgM Fab" Hum Antibodies Hybridomas, 1992, vol. 3, No. 2, pp. 81-85.
Hoogenboom, H.R. et al, "Multi-subunit proteins on the surface of filamentous phage: methodologies for displaying antibody (Fab) heavy and light chains", Nuc Acid Res, 1991, vol. 19, No. 15, pp. 4133-4137.
Huse, W. et al., "Generation of a large combinatorial library of the immunoglobulin repertoire in phage lambda" Science, 1989, vol. 246, No. 4935, pp. 1275-1281.
Huston, J. et al., "Protein engineering of antibody binding sites: Recovery of specific activity in an anti-digoxin single-chain Fv analogue produces in *Escherichia coli*", Proc Natl Acad Sci, 1988, vol. 85, pp. 5879-5883.
Jones, P. T. et al., "Replacing the complementarity-determining regions in a human antibody with those from a mouse", Nature, 1986, vol. 321, No. 29, pp. 522-525.

(56) References Cited

OTHER PUBLICATIONS

Lefranc, M.P.., "IMGT, the international ImMunoGeneTics database", Nucleic Acids Research, 2001, vol. 29, No. 1, pp. 207-209.
Li, P. et al., "Design and synthesis of paclitaxel conjugated with an ErbB2-recognizing peptide, EC-1", Biopolymers, 2007, vol. 87, No. 4, pp. 225-230.
Liu, A. et al., "Production of a mouse-human chimeric monoclonal antibody to CD20 with potent Fc-dependent biologic activity", J Immunol, 1987, vol. 139, No. 10, pp. 3521-3526.
Liu, A.Y. et al., "Chimeric mouse-human IgG1 antibody that can mediate lysis of cancer cells", PNAS, 1987, vol. 84, pp. 3439-3443.
Liu, D.Z. et al, "Synthesis of 2'-paclitaxel 2-glucopyranosyl succinate for specific targeted delivery to cancer cells", Bioorganic & Medicinal Chemistry Letters, 2007, vol. 17, pp. 617-620.
Lobuglio, A. et al., "Phase I Clinical Trial of CO17-1A Monoclonal Antibody", Hybridomia, 1986, vol. 5, No. 1, pp. S117-S123.
Lonberg, N. et al., "Antigen-specific human antibodies from mice comprising four distinct genetic modifications", Nature, 1994, vol. 368, pp. 856-859.
Mandelboim, O. et al., "Recognition of hemagglutinins on virus-infected cells by NKp46 activates lysis by human NK cells", Nature, 2001, vol. 409, No. 6823, pp. 1055-1060.
Martin, A. et al., "Chapter 3: Protein Sequence and Structure Analysis of Antibody Variable Domains", In: Antibody Engineering Lab Manual (Ed: Duebel, S. and Kontermann, R., Springer-Verlag, Heidelberg), 2010, vol. 2, pp. 33-51.
Martin, F. et al., "The affinity-selection of a minibody polypeptide inhibitor of human interleukin-6", EMBO J., 1994, vol. 13, No. 22, pp. 5303-5309.
McConnell, S.J. et al., "Tendamistat as a scaffold for conformationally constrained phage peptide libraries", J Mol Biol, 1995, vol. 250, No. 4, pp. 460-470.
Meyers, E. et al., "Optimal alignments in linear space", CABIOS,1988, vol. 4, No. 1, pp. 11-17.
Morrison, Sherie L., "Transfectomas provide novel chimeric antibodies", Science, 1985, vol. 229, No. 4719, pp. 1202-1207.
Morrison, S.L. et al., "Chimeric human antibody molecules: Mouse antigen-binding domains with human constant region domains", Proc Natl Acad Sci, 1984, vol. 81, pp. 6851-6855.
Needleman, S. et al, "A General Method Applicable to the Search for Similarities in the Amino Acid Sequence of Two Proteins", J. Mol. Biol., 1970, vol. 48, pp. 444-453.
Nishimura, Y. et al., "Recombinant Human-Mouse Chimeric Monoclonal Antibody Specific for Common Acute Lymphocytic Leukemia Antigen", Canc. Res, 1987, vol. 47, pp. 999-1005.
Oi, V. et al., "Chimeric Antibodies", BioTechniques, 1986, vol. 4, No. 3, pp. 214-221.

Pardoll, D.M., "The blockade of immune checkpoints in cancer immunotherapy", Nat Rev Cancer, 2012, Vo. 12, pp. 252-264.
Park, Y.P. et al., "Complex Regulation of human NKG2D-DAP10 cell surface expression: opposing roles of the γc cytokines and TGF-β1", Blood, 2011, vol. 118, No. 11, pp. 3019-3027.
Rakoff-Nahoum, S. et al., "Toll-like receptors and cancer", Nat Revs Cancer, 2009, vol. 9, pp. 57-63.
Reiter, Y et al., "Antibody Engineering of Recombinant Fv Immunotoxins for Improved Targeting of Cancer: Disulfide-stabilized Fv Immunotoxins", Clin Cancer Res, 1996, vol. 2, pp. 245-252.
Ridgway, J. et al, Knobs-into holes engineering of antibody CH3 domains for heavy chain heterodimerization, Protein Engineering, 1996, vol. 9, No. 7. pp. 617-621.
Rosenberg, S. et al., "Use of Tumor-Infiltrating Lymphocytes and Interleukin-2 in the Immunotherapy of Patients with Metastatic Melanoma", New Eng J of Med, 1988, vol. 319, pp. 1676-1680.
Saleh, M.N. et al, "A phase II trial of murine monoclonal antibody 17-1A and interferon-γ: clinical and immunological data", Cancer Immunol Immunother, 1990, vol. 32, pp. 185-190.
Scaviner, D. et al., "Protein displays of the human immunoglobulin heavy, kappa and lambda variable and joining regions", Exp. Clin. Immunogenet., 1999, vol. 16, pp. 234-240.
Shaw, D. et al., "Mouse/human chimeric antibodies to a tumor-associated antigen: biologic activity of the four human IgG subclasses", Journal of the National Cancer Institute, 1988, vol. 80, No. 19. pp. 1553-1559.
Sun, L.K. et al., "Chimeric antibody with human constant regions and mouse variable regions directed against carcinoma-associated antigen 17-1A", PNAS, 1987, vol. 84, pp. 214-218.
Thorpe, P. E., "Vascular Targeting Agents as Cancer Therapeutics", Clinc Cancer Res, 2004, vol. 10, pp. 415-427.
Tramontano, A. et al., "The making of the minibody: An engineered β-protein for the display of conformationally constrained peptides", Journal of Molecular Recognition, 1994, vol. 7, pp. 9-24.
Tuaillon, N. et al, Human immunoglobulin heavy-chain minilocus recombination in transgenic mice: Gene-segment use in μ and γ transcripts, PNAS, 1993, vol. 90, pp. 3720-3724.
Verhoeyen, M. et al., "Reshaping Human Antibodies: Grafting an Antilysozyme Activity", Science, 1988, vol. 239, pp. 1534-1536.
Weidel, U. et al, "The Intriguing Options of Mulitspecific Antibody Formats for Treatment of Cancer", Cancer Genomics & Proteomics, 2013, vol. 1, pp. 1-18.
Wood, C. R. et al., "The synthesis and in vivo assembly of functional antibodies in yeast", Nature Publishing Group, 1985, vol. 314, No. 4, pp. 446-449.
Xu, Y. et al., "Production of bispecific antibodies in "knobs-into-holes" using a cell-free expression system", mAbs, 2015,. vol. 7. MP/1, pp. 231-242.

* cited by examiner

Gel of multispecific molecule 1

Gel of multispecific molecule 3

Gel of multispecific molecule 4

Gel of multispecific molecule 5

Gel of multispecific molecule 6

Gel of multispecific molecule 7

Gel of multispecific molecule 8

Gel of multispecific molecule 9

Gel of reduced samples of multispecific molecule 8 following kappa/lambda select analysis Intact mass spectrometry analysis of papain-cleaved multispecific molecule 5

SEQUENCE LISTING

<160> NUMBER OF SEQ ID NOS: 418

<210> SEQ ID NO 1
<211> LENGTH: 1269
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1

```
atggaaaccg acacactgct gctgtgggtg ctgttgttgt gggtgccagg atctacagga      60
caggtgcagc tggttgaatc tggtggcgga gtggtgcagc ctggcagatc tctgagactg     120
tcttgtgccg cctctggctt cgccttctct tcttacggca tgcactgggt ccgacaggcc     180
cctggaaaag gactggaatg ggtcgccgtg atttggttcg acggcaccaa gaagtactac     240
accgactccg tgaagggcag attcaccatc agccgggaca actccaagaa caccctgtac     300
ctgcagatga taccctgag agccgaggac accgccgtgt actactgtgc cagagataga     360
ggcatcggcg ctcggagagg cccttactat atggatgtgt ggggcaaggg caccaccgtg     420
acagtgtcct ctgcttctac caagggaccc agcgttttcc ctctggctcc atcctctaag     480
tccacctctg gtggaaccgc tgctctgggc tgtctggtca aggattactt ccctgagcct     540
gtgaccgtgt cctggaactc tggtgctctg acatccggcg tgcacacctt ccagctgtg     600 ctgcagtcct ctggcctgta ctctctgtcc tctgtcgtga ccgtgccttc tagctctctg     660
ggcacccaga cctacatctg caacgtgaac cacaagcctt ccaacaccaa agtggacaag     720
```

| | |
|---|---|
| agagtggaac ccaagtcctg cggatcttct ggcggcggag gaagcggagg cggaggatct | 780 |
| agcggcggag tgttcaccct ggaagatttc gtcggcgatt gggagcagac cgccgcctat | 840 |
| aatctggacc aggttctgga acaaggcggc gtgtcctctc tgctgcagaa tctggctgtg | 900 |
| tctgtgaccc ctatccagag aatcgtgcgc tctggcgaga cgccctgaa gatcgacatc | 960 |
| cacgtgatca tcccttacga gggcctgtct gccgatcaga tggctcagat cgaagaggtg | 1020 |
| ttcaaggtgg tgtaccccgt ggacgaccac cacttcaaag tgatcctgcc ttacggcacc | 1080 |
| ctggtcatcg atggcgtgac cccaaacatg ctgaactact cggcagacc ctacgaggga | 1140 |
| atcgccgtgt tcgatggcaa gaaaatcacc gtgaccggca cactgtggaa cggcaacaag | 1200 |
| atcatcgacg agcggctgat caccctgac ggctctatgc tgttcagagt gaccatcaac | 1260 |
| tcctaatga | 1269 |

<210> SEQ ID NO 2
<211> LENGTH: 789
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 2

| | |
|---|---|
| atggaaaccg acacactgct gctgtgggtg ctgttgttgt gggtgccagg ctctaccggc | 60 |
| gacatccaga tgacccagtc tccatcctct ctgtctgcct ctgtgggcga cagagtgacc | 120 |
| atcacctgta gagccagcca gtccatctcc tcctacctga actggtatca gcagaagcct | 180 |
| ggcaaggctc ccaagctgct gatctacgct gctagctctc tgcagtctgg cgtgccctct | 240 |
| agattttccg gctctggctc tggcaccgac ttcaccctga caatcagttc cctgcagcct | 300 |
| gaggacttcg ccacctacta ctgccagcag tcctacagca cccttgac ctttggcgga | 360 |
| ggcaccaagg tggaaatcaa agaaccgtg gccgctcctt ccgtgttcat cttcccacca | 420 |
| tccgacgaac agctgaagtc cggcacagct tctgtcgtgt gcctgctgaa caacttctac | 480 |
| cctcgggaag ccaaggtgca gtggaaggtg gacaatgccc tgcagtccgg caactcccaa | 540 |
| gagtctgtga ccgagcagga ctccaaggac tctacctaca gcctgtcctc cacactgacc | 600 |
| ctgtctaagg ccgactacga gaagcacaag gtgtacgcct gtgaagtgac ccaccaggga | 660 |
| ctgtctagcc ccgtgaccaa gtctttcaac agaggcgagt gcggatcttc tggtggcgga | 720 |
| ggaagcggag gcggaggatc atctggcgga gtgaccggct acagactgtt cgaagagatc | 780 |
| ctgtaatga | 789 |

<210> SEQ ID NO 3
<211> LENGTH: 708
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 3

| | |
|---|---|
| atggaaaccg acacactgct gctgtgggtg ctgttgttgt gggtgccagg ctctaccggc | 60 |
| gacatccaga tgacccagtc tccatcctct ctgtctgcct ctgtgggcga cagagtgacc | 120 |
| atcacctgta gagccagcca gtccatctcc tcctacctga actggtatca gcagaagcct | 180 |
| ggcaaggctc ccaagctgct gatctacgct gctagctctc tgcagtctgg cgtgccctct | 240 |

```
agattttccg gctctggctc tggcaccgac ttcaccctga caatcagttc cctgcagcct    300
gaggacttcg ccacctacta ctgccagcag tcctacagca cacccttgac ctttggcgga    360
ggcaccaagg tggaaatcaa gagaaccgtg ccgctcctt ccgtgttcat cttcccacca     420
tccgacgaac agctgaagtc cggcacagct tctgtcgtgt gcctgctgaa caacttctac    480
cctcgggaag ccaaggtgca gtggaaggtg acaatgccc tgcagtccgg caactcccaa    540
gagtctgtga ccgagcagga ctccaaggac tctacctaca gcctgtcctc cacactgacc    600
ctgtctaagg ccgactacga aagcacaag gtgtacgcct gtgaagtgac ccaccaggga    660
ctgtctagcc ccgtgaccaa gtctttcaac agaggcgagt gctaatga             708
```

<210> SEQ ID NO 4
<211> LENGTH: 1254
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 4

```
atggaaaccg acacactgct gctgtgggtg ctgttgttgt gggtgccagg atctacaggc     60
gaagtgcagt tggtgcagtc tggcgccgaa gtgaagaagt ccggcgagtc cctgaagatc    120
tcctgcaaag gctccggcta ctccttcacc tcttactgga tcggctgggt ccgacagatg    180
cctggcaaag gactggaatg gatgggcatc ttctaccccg gcgactcctc taccagatac    240
tcccctagct ttcagggcca agtgaccatc tccgccgaca gtctgtgaa caccgcctac    300 ctgcagtggt cctctctgaa ggcctctgac accgccatgt actactgcgc cagaagaaga    360
aactggggca cgccttcga tatctggggc cagggaacaa tggtcaccgt gtcctctgct    420
tccaccaagg gaccttccgt gtttcctctg gctccttcca gcaagtctac ctctggtgga    480
accgctgctc tgggctgcct ggtcaaggat tactttcctg agcctgtgac cgtgtcttgg    540
aactctggtg ctctgacctc cggcgtgcac acatttccag ctgtgctgca gtcctccggc    600
ctgtactctc tgtcctctgt cgtgaccgtg ccttctagct ctctgggcac ccagacctac    660
atctgcaacg tgaaccacaa gccttccaac accaaggtgg acaagagagt ggaacccaag    720
tcttgcggat cttccggtgg cggaggatct ggcggaggtg aagtagtgg cggagtgttc    780 accctggaag atttcgtcgg cgattgggag cagaccgccg cctataatct ggaccaggtt    840
ctggaacaag gcgcgtcag ctctctgctg cagaatctgg ctgtgtctgt gaccccatc     900 cagagaatcg tgcgctctgg cgagaacgct ctgaagatcg acatccacgt gatcatccct    960
tacgagggcc tgtctgccga tcagatggct cagatcgaag aggtgttcaa ggtggtgtac   1020
cccgtggacg accaccactt caaagtgatc ctgccttacg gcaccctggt catcgatggc   1080 gtgacccca acatgctgaa ctacttcggc agacccacg agggaatcgc cgtgttcgac    1140
ggcaagaaaa tcaccgtgac cggcacactg tggaacggca caagatcat cgacgagcgg   1200 ctgatcaccc ctgacggctc tatgctgttc cgcgtgacca tcaactccta atga         1254
```

<210> SEQ ID NO 5
<211> LENGTH: 792
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 5

```
atggaaaccg acacactgct gctgtgggtg ctgttgttgt gggtgccagg atctacaggc    60
gagatcgtgc tgacccagtc tcctggcaca ttgtctctga gtcctggcga gagagctacc   120
ctgtcttgca gagcttccca gtccgtgtcc tcttcctacc tggcctggta tcagcagaag   180
cctggacagg ctcccagact gctgatctac ggcgcctctt ctagagccac aggcatccct   240
gacagattct ccggctctgg ctctggcacc gacttcaccc tgaccatctc tagactggaa   300
cccgaggact tcgccgtgta ctactgccag cagtatggct cctctacctg gacctttgga   360
cagggcacca aggtggaaat caagagaacc gtggccgctc cttccgtgtt catcttccca   420
ccatctgacg agcagctgaa gtccggcaca gcttctgtcg tgtgcctgct gaacaacttc   480
taccctcggg aagccaaggt gcagtggaag gtggacaatg ccctgcagtc cggcaactcc   540
caagagtctg tgaccgagca ggactccaag gactctacct acagcctgtc ctccacactg   600
accctgtcta aggccgacta cgagaagcac aaggtgtacg cctgtgaagt gacccaccag   660
ggactgtcta gccccgtgac caagtctttc aacagaggcg agtgcggatc ttctggtggc   720
ggaggatctg gcggaggcgg atctagtggc ggagtgaccg gctacagact gttcgaagag   780
atcctgtaat ga                                                       792
```

<210> SEQ ID NO 6
<211> LENGTH: 711
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 6

```
atggaaaccg acacactgct gctgtgggtg ctgttgttgt gggtgccagg atctacaggc    60
gagatcgtgc tgacccagtc tcctggcaca ttgtctctga gtcctggcga gagagctacc   120
ctgtcttgca gagcttccca gtccgtgtcc tcttcctacc tggcctggta tcagcagaag   180
cctggacagg ctcccagact gctgatctac ggcgcctctt ctagagccac aggcatccct   240
gacagattct ccggctctgg ctctggcacc gacttcaccc tgaccatctc tagactggaa   300
cccgaggact tcgccgtgta ctactgccag cagtatggct cctctacctg gacctttgga   360
cagggcacca aggtggaaat caagagaacc gtggccgctc cttccgtgtt catcttccca   420
ccatctgacg agcagctgaa gtccggcaca gcttctgtcg tgtgcctgct gaacaacttc   480
taccctcggg aagccaaggt gcagtggaag gtggacaatg ccctgcagtc cggcaactcc   540
caagagtctg tgaccgagca ggactccaag gactctacct acagcctgtc ctccacactg   600
accctgtcta aggccgacta cgagaagcac aaggtgtacg cctgtgaagt gacccaccag   660
ggactgtcta gccccgtgac caagtctttc aacagaggcg agtgctaatg a            711
```

<210> SEQ ID NO 7
<211> LENGTH: 1257
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 7

```
atggaaaccg acacactgct gctgtgggtg ctgttgttgt gggtgccagg atctacaggc    60
gaaggccagt tggttcagtc tggcggagga cttgttcacc ctggcggatc tctgagactg   120
tcttgtgctg gctctggctt caccttctcc agctacggca tgcactgggt tcgacaggcc   180
cctggaaaag gactggaatg ggtgtccgga atcggcaccg gcggaggcac ctattctacc   240
gattctgtga agggcagatt caccatcagc cgggacaacg ccaagaactc cctgtacctg   300
cagatgaaca gcctgagagc cgaggacatg gccgtgtact actgtgccag aggcgattac   360
tacggctccg gctcttcctt cgactgttgg ggacagggca cactggtcac cgtgtcctct   420
gcttctacca agggaccctc tgtgttccct ctggctcctt ccagcaagtc tacctctggt   480
ggaaccgctg ctctgggctg cctggtcaag gattactttc ctgagcctgt gaccgtgtct   540
tggaactctg gtgctctgac ctccggcgtg cacacatttc cagctgtgct gcagtcctcc   600
ggcctgtact ctctgtcctc tgtcgtgacc gtgccttcta gctctctggg cacccagacc   660
tacatctgca acgtgaacca caagccttcc aacaccaagg tggacaagag agtggaaccc   720
aagtcttgcg atcttctgg cggcggagga agcggaggcg aggatctag tggcggagtg   780 tttaccctgg aagatttcgt cggcgattgg gagcagaccg ccgcctataa tctggaccag   840
gttctggaac aaggcggcgt cagctctctg ctgcagaatc tggctgtgtc tgtgaccct   900 atccagagaa tcgtgcgctc tggcgagaac gccctgaaga tcgacatcca cgtgatcatc   960
ccttacgagg cctgtctgc cgatcagatg gctcagatcg aagaggtgtt caaggtggtg  1020
taccccgtgg acgaccacca cttcaaagtg atcctgcctt acggcaccct ggtcatcgat  1080
ggcgtgaccc caaacatgct gaactacttc ggcagaccct acgagggaat cgccgtgttc  1140
gacggcaaga aaatcaccgt gaccggcaca ctgtggaacg caacaagat catcgacgag  1200 cggctgatca cccctgacgg ctccatgctg tttagagtga ccatcaactc ctaatga     1257
```

<210> SEQ ID NO 8
<211> LENGTH: 789
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 8

```
atggaaaccg acacactgct gctgtgggtg ctgttgttgt gggtgccagg ctctaccggc    60
gacatccaga tgacccagtc tccatcctct ctgtctgcct ctgtgggcga cagagtgacc   120
atcacctgta gagcctctca gggcatctct agctggctgg cctggtatca gcagaagcct   180
gagaaggccc ctaagagcct gatctacgct gccagttctc tgcagtctgg cgtgccctct   240
agattctctg gctctggatc tggcaccgac ttcaccctga caatctctag cctgcagcct   300
gaggacttcg ccacctacta ctgccagcag tacaacagct accctcctac ctttggccag   360
ggcaccaagc tggaaatcaa agaaccgtg gccgctcctt ccgtgttcat cttcccacca   420
tctgacgagc agctgaagtc cggcacagct tctgtcgtgt gcctgctgaa caacttctac   480
cctcgggaag ccaaggtgca gtggaaggtg gacaatgccc tgcagtccgg caactcccaa   540
gagtctgtga ccgagcagga ctccaaggac tctacctaca gcctgtcctc cacactgacc   600
ctgtctaagg ccgactacga gaagcacaag gtgtacgcct gtgaagtgac ccaccaggga   660
ctgtctagcc ccgtgaccaa gtcttcaac agaggcgagt gcggatcttc tggtggcgga   720
ggatctggcg gaggtggaag tagtggcggc gtgaccggct acagactgtt cgaagagatc   780
``` ctgtaatga                                                              789

<210> SEQ ID NO 9
<211> LENGTH: 708
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 9
atggaaaccg acacactgct gctgtgggtg ctgttgttgt gggtgccagg ctctaccggc    60
gacatccaga tgacccagtc tccatcctct ctgtctgcct ctgtgggcga cagagtgacc   120
atcacctgta gagcctctca gggcatctct agctggctgg cctggtatca gcagaagcct   180
gagaaggccc ctaagagcct gatctacgct gccagttctc tgcagtctgg cgtgccctct   240
agattctctg gctctggatc tggcaccgac ttcaccctga caatctctag cctgcagcct   300
gaggacttcg ccacctacta ctgccagcag tacaacagct accctcctac ctttggccag   360
ggcaccaagc tggaaatcaa agaaccgtg gccgctcctt ccgtgttcat cttcccacca   420
tctgacgagc agctgaagtc cggcacagct tctgtcgtgt gcctgctgaa caacttctac   480
cctcgggaag ccaaggtgca gtggaaggtg gacaatgccc tgcagtccgg caactcccaa   540
gagtctgtga ccgagcagga ctccaaggac tctacctaca gcctgtcctc cacactgacc   600
ctgtctaagg ccgactacga aagcacaag gtgtacgcct gtgaagtgac ccaccaggga   660
ctgtctagcc ccgtgaccaa gtctttcaac agaggcgagt gctaatga               708

<210> SEQ ID NO 10
<211> LENGTH: 1254
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 10
atggaaaccg acacactgct gctgtgggtg ctgttgttgt gggtgccagg atctacagga    60
caggtgcagt tggtgcagtc tggcgccgaa gtgaagaaac tggcgcttc tgtgaaggtg   120 tcctgcaagg cctctggcta ctccttcacc aactactaca tccactgggt ccgacaggcc   180
cctggacaga gattggagtg gatgggctgg atcaacgccg gcaacggcaa caccaagtac   240
tcccagaaat tccagggcag agtgaccatc accagagaca cctctgcctc caccgcctac   300
atggaactgt ccagcctgag atctgaggac accgccgtgt actactgcgt gcggagacag   360 cggttccccct actactttga ttattgggc cagggcaccc tggtcaccgt gtcctctgct   420
tctacaaagg gcccctctgt gttccctctg gctccttcct ctaaatccac ctctggcgga   480
acagctgctc tgggctgtct ggtcaaggac tactttcctg agcctgtgac cgtgtcttgg   540
aactctggtg ctctgacatc cggcgtgcac acctttccag ctgtgctgca gtcctctggc   600
ctgtactctc tgtcctctgt cgtgaccgtg ccttctagct ctctgggcac ccagacctac   660
atctgcaacg tgaaccacaa gccttctaac accaaggtgg acaagagagt ggaacccaag   720
tcttgcggat cttctggtgg cggaggatct ggcggaggcg gatctagtgg cggagtgttc   780 acctggaag atttcgtcgg cgattgggag cagaccgccg cctataatct ggaccaggtt   840

| | |
|---|---|
| ctggaacaag gcggggtgtc ctctctgctg cagaatctgg ctgtgtctgt gacccctatc | 900 |
| cagagaatcg tgcgctctgg cgagaacgcc ctgaagatcg acatccacgt gatcatccct | 960 |
| tacgagggcc tgtctgccga tcagatggct cagatcgaag aggtgttcaa ggtggtgtac | 1020 |
| cccgtggacg accaccactt caaagtgatc ctgccttacg gcaccctcgt gatcgatggc | 1080 |
| gtgaccccaa acatgctgaa ctacttcggc agaccctacg agggaatcgc cgtgttcgac | 1140 |
| ggcaagaaaa tcaccgtgac cggcacactg tggaacggaa acaagatcat cgacgagcgg | 1200 |
| ctgatcaccc tgacggctc tatgctgttt agagtgacaa tcaactccta atga | 1254 |

<210> SEQ ID NO 11
<211> LENGTH: 789
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 11

| | |
|---|---|
| atggaaaccg acacactgct gctgtgggtg ctgttgttgt gggtgccagg atctacaggc | 60 |
| gagatcgtgc tgacccagtc tcctgccaca ttgtctgtgt ctcccggcga gagagctacc | 120 |
| ctgtcttgta gagcttctca gtccgtgggc accaacgtgg cctggtatca gcagaaacct | 180 |
| ggacaggccc ctcgggtgct gatctactct acctcttcta gagccaccgg catcaccgac | 240 |
| agattctctg gctctggatc tggcaccgac ttcaccctga ccatctccag actggaacct | 300 |
| gaggacttcg ccgtgtacta ctgccagcag ttcaacaagt cccctctgac ctttggcgga | 360 |
| ggcaccaagg tggaaatcaa gagaaccgtg gccgctcctt ccgtgttcat cttcccacca | 420 |
| tctgacgagc agctgaagtc cggcacagct tctgtcgtgt gcctgctgaa caacttctac | 480 |
| cctcgggaag ccaaggtgca gtggaaggtg gacaatgccc tgcagtccgg caactcccaa | 540 |
| gagtctgtga ccgagcagga ctccaaggac tctacctaca gcctgtcctc cacactgacc | 600 |
| ctgtctaagg ccgactacga aagcacaag gtgtacgcct gtgaagtgac ccaccaggga | 660 |
| ctgtctagcc ccgtgaccaa gtctttcaac agaggcgagt gcggatcttc tggtggcgga | 720 |
| ggaagcggag gcggaggatc atctggcgga gtgaccggct acagactgtt cgaagagatc | 780 |
| ctgtaatga | 789 |

<210> SEQ ID NO 12
<211> LENGTH: 708
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 12

| | |
|---|---|
| atggaaaccg acacactgct gctgtgggtg ctgttgttgt gggtgccagg atctacaggc | 60 |
| gagatcgtgc tgacccagtc tcctgccaca ttgtctgtgt ctcccggcga gagagctacc | 120 |
| ctgtcttgta gagcttctca gtccgtgggc accaacgtgg cctggtatca gcagaaacct | 180 |
| ggacaggccc ctcgggtgct gatctactct acctcttcta gagccaccgg catcaccgac | 240 |
| agattctctg gctctggatc tggcaccgac ttcaccctga ccatctccag actggaacct | 300 |
| gaggacttcg ccgtgtacta ctgccagcag ttcaacaagt cccctctgac ctttggcgga | 360 |
| ggcaccaagg tggaaatcaa gagaaccgtg gccgctcctt ccgtgttcat cttcccacca | 420 |

```
tctgacgagc agctgaagtc cggcacagct tctgtcgtgt gcctgctgaa caacttctac    480
cctcgggaag ccaaggtgca gtggaaggtg acaatgccc tgcagtccgg caactcccaa    540
gagtctgtga ccgagcagga ctccaaggac tctacctaca gcctgtcctc cacactgacc    600
ctgtctaagg ccgactacga aagcacaag gtgtacgcct gtgaagtgac ccaccaggga    660
ctgtctagcc ccgtgaccaa gtctttcaac agaggcgagt gctaatga              708
```

<210> SEQ ID NO 13
<211> LENGTH: 1251
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 13

```
atggaaaccg acacactgct gctgtgggtg ctgctcttgt gggtgccagg atctacagga    60
caggtgcagc tggtggaatc tggtggcgga gttgtgcagc ctggcagatc cctgagactg    120
tcttgtgccg cctccggctt caccttctcc agctacacca tgcactgggt ccgacaggcc    180
cctggcaaag gattggagtg ggtcaccttc atctcttacg acggcaacaa caagtactac    240
gccgactccg tgaagggcag attcaccatc tctcgggaca actccaagaa caccctgtac    300
ctgcagatga actccctgag agccgaggac accgccatct actactgtgc tagaaccggc    360
tggctgggcc cctttgatta ttggggacag ggcacccctgg tcaccgtgtc ctctgcttct    420
accaagggac ccagcgtgtt ccctctggct ccttccagca gtctacctc tggcggaaca    480 gctgctctgg gctgcctggt caaggactac tttcctgagc ctgtgaccgt gtcttggaac    540
tctggcgctc tgacatccgg cgtgcacaca tttccagctg tgctgcagtc ctccggcctg    600
tactctctgt cctctgtcgt gaccgtgcct tccagctctc tgggaaccca gacctacatc    660
tgcaatgtga accacaagcc ttccaacacc aaggtggaca agagagtgga acccaagtcc    720
tgcggatctt ctggcggcgg aggatctggc ggaggtggta gttcaggcgg agtgttcacc    780
ctggaagatt tcgtcggcga ctgggagcag accgccgcct ataatctgga ccaggtgctg    840
gaacaaggcg gcgttagttc cctgctgcag aacctggctg tgtctgtgac ccctatccag    900
agaatcgtgc ggagcggcga gaacgccctg aagatcgata tccacgtgat catcccttac    960
gagggcctga gcgccgatca gatggctcag atcgaagagg tgttcaaggt ggtgtacccc    1020
gtggacgacc accacttcaa agtgatcctg ccttacggca ccctcgtgat cgatggcgtg    1080
accccaaaca tgctgaacta cttcggcaga ccctacgagg aatcgccgt gttcgacggc    1140 aagaaaatca ccgtgaccgg cacactgtgg aatggcaaca agatcatcga cgagcggctg    1200 atcaccccctg acggctccat gctgttcaga gtgaccatca acagctgatg a          1251
```

<210> SEQ ID NO 14
<211> LENGTH: 792
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 14

```
atggaaaccg acacactgct gctgtgggtg ctgttgttgt gggtgccagg atctacaggc    60
```

```
gagatcgtgc tgacccagtc tcctggcaca ttgtctctga gtcctggcga gagagctacc    120
ctgtcttgca gagcttccca gtccgtggga tcttcctacc tggcctggta tcagcagaag    180
cctggacagg ctcccagact gctgatctac ggcgccttt  ctagagccac aggcatccct    240
gacagattct ccggctctgg ctctggcacc gacttcaccc tgaccatctc tagactggaa    300
cccgaggact cgccgtgta  ctactgccag cagtatggct cctctccttg gacctttgga    360
cagggcacca aggtggaaat caagagaacc gtggccgctc cttccgtgtt catcttccca    420
ccatctgacg agcagctgaa gtccggcaca gcttctgtcg tgtgcctgct gaacaacttc    480
taccctcggg aagccaaggt gcagtggaag gtggacaatg ccctgcagtc cggcaactcc    540
caagagtctg tgaccgagca ggactccaag gactctacct acagcctgtc ctccacactg    600
accctgtcta aggccgacta cgagaagcac aaggtgtacg cctgtgaagt gacccaccag    660
ggactgtcta gccccgtgac caagtctttc aacagaggcg agtgcggatc ttctggtggc    720
ggaggatctg gcggaggcgg atctagtggc ggagtgaccg gctacagact gttcgaagag    780
atcctgtaat ga                                                        792

<210> SEQ ID NO 15
<211> LENGTH: 711
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 15
atggaaaccg acacactgct gctgtgggtg ctgctcttgt gggtgccagg atctacaggc     60
gagatcgtgc tgacccagtc tcctggcaca ctgtcactgt ctccaggcga gagagctacc    120
ctgtcctgta gagcctctca gtccgtgggc tcctcttacc tggcttggta tcagcagaag    180
cccggccagg ctcctagact gttgatctac ggcgccttct ccagagccac aggcatccct    240
gatagattct ccggctctgg ctctggcacc gacttcaccc tgaccatctc cagactggaa    300
cccgaggact cgccgtgta  ctactgtcag cagtacggct cctctccttg gacctttggc    360
cagggcacca aggtggaaat caagcggaca gtggccgctc cttccgtgtt catcttccca    420
ccttccgacg agcagctgaa gtccggcaca gcttctgtcg tgtgcctgct gaacaacttc    480
taccctcggg aagccaaggt gcagtggaag gtggacaatg ccctgcagtc cggcaactcc    540
caagagtctg tgaccgagca ggactccaag gacagcacct acagcctgtc ctccacactg    600
accctgtcca aggccgacta cgagaagcac aaggtgtacg cctgcgaagt gacccatcag    660
ggcctgtcta gccctgtgac caagtctttc aaccggggcg agtgctgatg a             711

<210> SEQ ID NO 16
<211> LENGTH: 1248
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 16
atggaaaccg acacactgct gctgtgggtg ctgttgttgt gggtgccagg atctacaggc     60
gaagtgcagt tggtgcagtc tggcgccgaa gtgaagaagc tggcgagtc  cctgaagatc    120 tcctgcaaag gctccggcta catcttcacc aactactgga tcgcctgggt ccgacagatg    180
```

```
cctggcaaag gcctggaatc catgggcatc atctacccg gcgactccga catcagatac      240
agcccatctt tccagggcca agtgaccatc tccgccgaca agtctatcac caccgcctac      300
ctgcagtggt cctctctgaa ggcctctgac accgccatgt actactgcgc cagacacgac      360
atcgagggct cgattattg gggcagaggc accctggtca ccgtgtcctc tgcttctaca       420
aagggcccct ctgtgttccc tctggctcct tcctctaaat ccacctctgg cggaaccgct      480
gctctgggct gtctggtcaa ggattacttc cctgagcctg tgaccgtgtc ttggaactct      540
ggtgctctga catccggcgt gcacaccttt ccagctgtgc tgcagtcctc tggcctgtac      600
tctctgtcct ctgtcgtgac cgtgccttct agctctctgg gcacccagac ctacatctgc      660
aacgtgaacc acaagccttc caacaccaag gtggacaaga gagtggaacc caagtcttgc      720
ggatcttctg tggcggagg atctggcgga ggcggatcta gtggcggagt gttcaccctg       780
gaagatttcg tcggcgattg ggagcagacc gccgcctata atctggacca ggttctggaa      840
caaggcggcg tcagctctct gctgcagaat ctggctgtgt ctgtgacccc tatccagaga      900
atcgtgcgct ctggcgagaa cgctctgaag atcgacatcc acgtgatcat cccttacgag      960
ggcctgtctg ccgatcagat ggctcagatc gaagaggtgt tcaaggtggt gtaccccgtg     1020
gacgaccacc acttcaaagt gatcctgcct tacggcaccc tcgtgatcga tggcgtgacc     1080
ccaaacatgc tgaactactt cggcagaccc tacgagggaa tcgccgtgtt cgacggcaag     1140
aaaatcaccg tgaccggcac actgtggaac ggcaacaaga tcatcgacga gcggctgatc     1200
acccctgacg gctctatgct gttccgcgtg accatcaact cctaatga                  1248

<210> SEQ ID NO 17
<211> LENGTH: 792
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 17
atggaaaccg acacactgct gctgtgggtg ctgttgttgt gggtgccagg atctacaggc       60
gagatcgtgc tgacccagtc tcctggcaca ttgtctctga gtcctggcga gagagctacc      120
ctgtcttgca gagcttccca gtccgtgtcc tctagcttct tcgcctggta tcagcagaag      180
cccggacagg ctcctagact gctgatctac ggcgcctctt ctagagccac aggcatccct      240
gatagactgt ccggctctgg ctctggcacc gactttaccc tgaccatcac cagactggaa      300
cccgaggact tcgccgtgta ctactgccag cagtacgact cctctgccat cacctttggc      360
cagggcacaa gactggaaat caagagaacc gtggccgctc cttccgtgtt catcttccca      420
ccatctgacg agcagctgaa gtccggcaca gcttctgtcg tgtgcctgct gaacaacttc      480
taccctcggg aagccaaggt gcagtggaag gtggacaatg ccctgcagtc cggcaactcc      540
caagagtctg tgaccgagca ggactccaag gactctacct acagcctgtc ctccacactg      600
accctgtcta aggccgacta cgagaagcac aaggtgtacg cctgtgaagt gacccaccag      660
ggactgtcta gccccgtgac caagtctttc aacagaggcg agtgcggatc ttctggtggc      720
ggaggatctg gcggaggcgg atctagtggc ggagtgaccg gctacagact gttcgaagag      780
atcctgtaat ga                                                          792

<210> SEQ ID NO 18
```

<211> LENGTH: 711
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 18

```
atggaaaccg acacactgct gctgtgggtg ctgttgttgt gggtgccagg atctacaggc      60
gagatcgtgc tgacccagtc tcctggcaca ttgtctctga gtcctggcga gagagctacc     120
ctgtcttgca gagcttccca gtccgtgtcc tctagcttct tcgcctggta tcagcagaag     180
cccggacagg ctcctagact gctgatctac ggcgcctctt ctagagccac aggcatccct     240
gatagactgt ccggctctgg ctctggcacc gactttaccc tgaccatcac cagactggaa     300
cccgaggact tcgccgtgta ctactgccag cagtacgact cctctgccat cacctttggc     360
cagggcacaa gactggaaat caagagaacc gtggccgctc cttccgtgtt catcttccca     420
ccatctgacg agcagctgaa gtccggcaca gcttctgtcg tgtgcctgct gaacaacttc     480
taccctcggg aagccaaggt gcagtggaag gtggacaatg ccctgcagtc cggcaactcc     540
caagagtctg tgaccgagca ggactccaag gactctacct acagcctgtc ctccacactg     600
accctgtcta aggccgacta cgagaagcac aaggtgtacg cctgtgaagt gacccaccag     660
ggactgtcta gccccgtgac caagtctttc aacagaggcg agtgctaatg a              711
```

<210> SEQ ID NO 19
<211> LENGTH: 1245
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 19

```
atggaaaccg acacactgct gctgtgggtg ctgttgttgt gggtgccagg atctacagga      60
caggtgcagt tggtgcagtc tggcgccgaa gtgaagaaac tggcgcttc tgtgaaggtg     120
tcctgcaagg cctctggcta cacctttacc agctactcca tctcctgggt ccgacaggct     180
cctggacaag gattggagtg gatgggctgg atctccgtgt acaacggcaa caccaactac     240
gcccagaaat tccagggcag agtgaccatg accaccgaca cctctacctc caccgcctac     300
ctggaactga gatccctgag atctgacgac accgccgtgt actactgcgc cagagatcct     360
atcgctgctg gctattgggg acagggcaca ctggttaccg tgtcctctgc ttctaccaag     420
ggaccctctg tgttccctct ggctccttcc agcaagtcta cctctggtgg aaccgctgct     480
ctgggctgtc tggtcaagga ttacttccct gagcctgtga ccgtgtcttg aactctggt     540
gctctgacct ccggcgtgca cacatttcca gctgtgctgc agtcctccgg cctgtactct     600
ctgtcctctg tcgtgaccgt gccttctagc tctctgggca cccagaccta catctgcaac     660
gtgaaccaca gccttccaa caccaaggtg gacaagagag tggaacccaa gtcttgcgga     720
tcttctggtg gcggaggatc tggcggaggt ggaagtagtg gcggagtgtt caccctggaa     780
gatttcgtcg gcgattggga gcagaccgcc gcctataatc tggaccaggt tctggaacaa     840
ggcggcgtca gctctctgct gcagaatctg gctgtgtctg tgacccctat ccagagaatt     900
gtgcgctctg gcgagaacgc cctgaagatc gacatccacg tgatcatccc ttacgagggc     960
ctgtctgccg atcagatggc tcagatcgaa gaggtgttca ggtggtgta cccgtggac    1020
```

```
gaccaccact tcaaagtgat cctgccttac ggcaccctgg tcatcgatgg cgtgacccca    1080
aacatgctga actacttcgg cagaccctac gagggaatcg ccgtgttcga cggcaagaaa    1140
atcaccgtga ccggcacact gtggaacgga aacaagatca tcgacgagcg gctgatcacc    1200
cctgacggct ctatgctgtt ccgcgtgacc atcaactcct aatga                    1245
```

<210> SEQ ID NO 20
<211> LENGTH: 792
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 20

```
atggaaaccg acacactgct gctgtgggtg ctgttgttgt gggtgccagg atctacaggc     60
gagatcgtgc tgacccagtc tcctggcaca ttgtctctga gtcctggcga gagagctacc    120
ctgtcttgca gagcttccca gtccgtgtcc tctacctacc tggcctggta tcagcagaag    180
cctggacagg ctcccagact gctgatctac ggcgcctctt ctagagccac aggcatccct    240
gacagattct ccggctctgg ctctggcacc gacttcaccc tgaccatctc tagactggaa    300
cccgaggact cgccgtgta ctactgccag cagtatggct cctctcctcg gacctttgga    360
cagggcacca aggtggaaat caagagaacc gtggccgctc cttccgtgtt catcttccca    420
ccatctgacg agcagctgaa gtccggcaca gcttctgtcg tgtgcctgct gaacaacttc    480
taccctcggg aagccaaggt gcagtggaag gtggacaatg ccctgcagtc cggcaactcc    540
caagagtctg tgaccgagca ggactccaag gactctacct acagcctgtc ctccacactg    600
accctgtcta aggccgacta cgagaagcac aaggtgtacg cctgtgaagt gacccaccag    660
ggactgtcta gccccgtgac caagtctttc aacagaggcg agtgcggatc ttctggtggc    720
ggaggatctg gcggaggcgg atctagtggc ggagtgaccg gctacagact gttcgaagag    780
atcctgtaat ga                                                        792
```

<210> SEQ ID NO 21
<211> LENGTH: 711
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 21

```
atggaaaccg acacactgct gctgtgggtg ctgttgttgt gggtgccagg atctacaggc     60
gagatcgtgc tgacccagtc tcctggcaca ttgtctctga gtcctggcga gagagctacc    120
ctgtcttgca gagcttccca gtccgtgtcc tctacctacc tggcctggta tcagcagaag    180
cctggacagg ctcccagact gctgatctac ggcgcctctt ctagagccac aggcatccct    240
gacagattct ccggctctgg ctctggcacc gacttcaccc tgaccatctc tagactggaa    300
cccgaggact cgccgtgta ctactgccag cagtatggct cctctcctcg gacctttgga    360
cagggcacca aggtggaaat caagagaacc gtggccgctc cttccgtgtt catcttccca    420
ccatctgacg agcagctgaa gtccggcaca gcttctgtcg tgtgcctgct gaacaacttc    480
taccctcggg aagccaaggt gcagtggaag gtggacaatg ccctgcagtc cggcaactcc    540
```

```
caagagtctg tgaccgagca ggactccaag gactctacct acagcctgtc ctccacactg    600
accctgtcta aggccgacta cgagaagcac aaggtgtacg cctgtgaagt gacccaccag    660
ggactgtcta gccccgtgac caagtctttc aacagaggcg agtgctaatg a             711
```

<210> SEQ ID NO 22
<211> LENGTH: 1254
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 22

```
atggaaaccg acacactgct gctgtgggtg ctgttgttgt gggtgccagg atctacaggc     60
caggtccagc tgcaagaatc tggccctgga ctggtcaagc cttctggcac cctgtctctg    120
acatgtgctg tgtccggcgg ctccatctcc tcctctaatt ggtggtcttg ggtccgacag    180
cctcctggca aggactgga atggatcggc gagatctacc actccggctc caccaactac    240
aaccccagcc tgaagtccag agtgaccatc tccgtggaca gtccaagaa ccagttctcc    300 ctgaagctgt cctctgtgac cgctgccgat accgccgtgt actactgtgc tagatggacc    360
ggcagaaccg acgcctttga tatctggggc cagggcacaa tggtcaccgt gtcctctgct    420
tctaccaagg gaccctctgt gttccctctg gctccttcca gcaagtctac ctctggtgga    480
accgctgctc tgggctgcct ggtcaaggat tactttcctg agcctgtgac cgtgtcttgg    540
aactctggtg ctctgaccct cggcgtgcac acatttccag ctgtgctgca gtctagcggc    600
ctgtactctc tgtctagcgt cgtgaccgtg ccttctagct ctctgggcac ccagacctac    660
atctgcaacg tgaaccacaa gccttccaac accaaggtgg acaagagagt ggaacccaag    720
tcttgcggat cttctggtgg cggaggatct ggcggaggtg aagtagtgg cggagtgttc    780 accctggaag atttcgtcgg cgattgggag cagaccgccg cctataatct ggaccaggtt    840
ctggaacaag gcggcgtcag ctctctgctg cagaatctcg ctgtgtctgt gaccccctatc    900 cagagaatcg tgcgctctgg cgagaacgcc ctgaagatcg acatccacgt gatcatccct    960
tacgagggcc tgtctgccga tcagatggct cagatcgaag aggtgttcaa ggtggtgtac   1020
cccgtggacg accaccactt caaagtgatc ctgccttacg gcaccctggt catcgatggc   1080 gtgacccaa acatgctgaa ctacttcggc agaccctacg agggaatcgc cgtgttcgac   1140
ggcaagaaaa tcaccgtgac cggcacactg tggaacggca acaagatcat cgacgagcgg   1200
ctgatcaccc ctgacggctc tatgctgttc cgcgtgacca tcaactccta atga          1254
```

<210> SEQ ID NO 23
<211> LENGTH: 804
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 23

```
atggaaaccg acacactgct gctgtgggtg ctgttgttgt gggtgccagg atctacaggc     60
gacgtcgtga tgacccagtc tcctctgtct ctgcctgtga cacctggcga gcctgcctcc    120
atctcttgca gatcttctca gtccctgctg cactccaacg gctacaacta cctggactgg    180
tatctgcaga agcccggcca gtctccacag ctgctgatct acctgggctc taacagagcc    240
```

```
tctggcgtgc ccgatagatt ctctggctct ggatctggca ccgacttcac cctgaagatc      300
tccagagtgg aagccgagga cgtgggcgtg tactactgta tgcagggcac ccactggcct      360
ctgacctttg gacagggcac caaggtggaa atcaagagaa ccgtggccgc tccttccgtg      420
ttcatcttcc caccatctga cgagcagctg aagtccggca cagcttctgt cgtgtgcctg      480
ctgaacaact ctaccctcg ggaagccaag gtgcagtgga aggtggacaa tgccctgcag       540
tccggcaact cccaagagtc tgtgaccgag caggactcca aggactctac ctacagcctg      600
tcctccacac tgaccctgtc taaggccgac tacgagaagc acaaggtgta cgcctgtgaa      660
gtgacccacc agggactgtc tagccccgtg accaagtctt tcaacagagg cgagtgcgga      720
tcttctggtg gcggaggatc tggcggaggt ggaagtagtg gcggcgtgac cggctacaga      780
ctgttcgaag agatcctgta atga                                             804
```

<210> SEQ ID NO 24
<211> LENGTH: 723
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 24

```
atggaaaccg acacactgct gctgtgggtg ctgttgttgt gggtgccagg atctacaggc       60
gacgtcgtga tgacccagtc tcctctgtct ctgcctgtga cacctggcga gcctgcctcc      120
atctcttgca gatcttctca gtccctgctg cactccaacg ctacaactac ctggactgg       180 tatctgcaga agcccggcca gtctccacag ctgctgatct acctgggctc taacagagcc      240
tctggcgtgc ccgatagatt ctctggctct ggatctggca ccgacttcac cctgaagatc      300
tccagagtgg aagccgagga cgtgggcgtg tactactgta tgcagggcac ccactggcct      360
ctgacctttg gacagggcac caaggtggaa atcaagagaa ccgtggccgc tccttccgtg      420
ttcatcttcc caccatctga cgagcagctg aagtccggca cagcttctgt cgtgtgcctg      480
ctgaacaact ctaccctcg ggaagccaag gtgcagtgga aggtggacaa tgccctgcag       540
tccggcaact cccaagagtc tgtgaccgag caggactcca aggactctac ctacagcctg      600
tcctccacac tgaccctgtc taaggccgac tacgagaagc acaaggtgta cgcctgtgaa      660
gtgacccacc agggactgtc tagccccgtg accaagtctt tcaacagagg cgagtgctaa      720
tga                                                                    723
```

<210> SEQ ID NO 25
<211> LENGTH: 1263
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 25

```
atggaaaccg acacactgct gctgtgggtg ctgttgttgt gggtgccagg atctacaggc       60
gaagtgcagt tgttgcagtc tggcggagga ttggttcagc ctggcggatc tctgagactg      120
tcttgtgccg cctccggctt catgttcagc agatacccta tgcactgggt ccgacaggcc      180
cctggaaaag gactggaatg ggtcggatct atctctggca gtggcggcgc taccccttac      240
```

```
gctgattctg tgaagggcag attcaccatc agccgggaca actccaagaa cccctgtac    300
ctgcagatga actccctgag agccgaggac accgccgtgt actactgcgc caaggacttc   360
tatcagatcc tgaccggcaa cgccttcgat tattggggcc agggcacaac cgtgaccgtg   420
tcctctgctt ctaccaaggg accctctgtg ttccctctgg ctccttccag caagtctacc   480
tctggtggaa ccgctgctct gggctgcctg gtcaaggatt actttcctga gcctgtgaca   540
gtgtcctgga actctggtgc tctgacctcc ggcgtgcaca catttccagc tgtgctgcag   600
tcctccggcc tgtactctct gtcctctgtc gtgacagtgc cttccagctc tctgggcacc   660
cagacctaca tctgcaacgt gaaccacaag ccttccaaca ccaaggtgga caagagagtg   720
gaacccaagt cttgcggatc ttctggtggc ggtggaagtg gcggaggtgg aagttcaggc   780
ggagtgttca ccctggaaga tttcgtcggc gattgggagc agaccgccgc ctataatctg   840
gaccaggttc tggaacaagg cggcgttagc tctctgctgc agaatctggc tgtgtctgtg   900
accccctatc cagagaatcg tgcgctctgg cgagaacgcc ctgaagatcga catccacgtg   960
atcatccctt acgagggcct gtctgccgat cagatggctc agatcgaaga ggtgttcaag  1020
gtggtgtacc ccgtggacga ccaccacttc aaagtgatcc tgccttacgg caccctggtc  1080
atcgatggcg tgaccccaaa catgctgaac tacttcggca gccctacga gggaatcgcc  1140
gtgttcgacg gcaagaaaat caccgtgaca ggcaccctgt ggaacggcaa caagatcatc  1200
gacgagcggc tgatcacccc tgacggctct atgctgttca gagtgaccat caactcctaa  1260
tga                                                                1263
```

```
<210> SEQ ID NO 26
<211> LENGTH: 789
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 26
atggaaaccg acacactgct gctgtgggtg ctgttgttgt gggtgccagg ctctaccggc    60
gacatccaga tgacccagtc tccaagctct ctgtctgcct ctctgggcga cagagtgacc   120
atcacctgta gagcctctca gggcatctcc tcctacctgg cctggtatca gcagaagcct   180
ggcaaggctc ccaagctgct gatctacgct aagtctaccc tgcagtccgg cgtgccctct   240
agattttctg gctctggatc tggcaccgac ttcaccctga ccatcagttc tctgcagcct   300
gaggactccg ccacctacta ctgtcagcag tactggacct ttcctctgac cttcggcgga   360
ggcaccaagg tggaaatcaa gagaaccgtg gccgctcctt ccgtgttcat cttcccacca   420
tctgacgagc agctgaagtc cggcacagct tctgtcgtgt gcctgctgaa caacttctac   480
cctcgggaag ccaaggtgca gtggaaggtg acaatgccc tgcagagcgg caactcccaa   540
gagtctgtga ccgagcagga ctccaaggac tctacctaca gcctgtcctc cacactgacc   600
ctgtctaagg ccgactacga gaagcacaag gtgtacgcct gtgaagtgac ccaccaggga  660
ctgtctagcc ccgtgaccaa gtctttcaac agaggcgagt gcggatcttc tggcggcgga  720
ggaagcggag gcggaggatc tagcggcgga gttaccggct acagactgtt cgaagagatc  780
ctgtaatga                                                          789
```

```
<210> SEQ ID NO 27
<211> LENGTH: 708
```

<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 27

```
atggaaaccg acacactgct gctgtgggtg ctgctcttgt gggtgccagg atctaccggc    60
gacatccaga tgacccagtc tccatcctct ctgtctgcca gcctgggcga cagagtgacc   120
atcacctgta gagcctctca gggcatctcc tcctacctgg cctggtatca gcagaagcct   180
ggcaaggctc ccaagctgct gatctacgcc aagagcacac tgcagtctgg cgtgccctct   240
agattctccg gctctggctc tggcaccgac tttaccctga caatctccag cctgcagcct   300
gaggactccg ccacctacta ctgtcagcag tactggacct ttccactgac cttcggcgga   360
ggcaccaagg tggaaatcaa gagaaccgtg gccgctcctt ccgtgttcat cttcccacct   420
tccgacgagc agctgaagtc cggcacagct tctgtcgtgt gcctgctgaa caacttctac   480
cctcgggaag ccaaagtgca gtggaaggtg gacaacgctc tgcagtccgg caactcccaa   540
gagtctgtga ccgagcagga ctccaaggac agcacctaca gcctgtcctc cacactgacc   600
ctgtccaagg ccgactacga aagcacaag gtgtacgcct gcgaagtgac ccatcagggc   660
ctgtctagcc ctgtgaccaa gtctttcaac cggggcgagt gctgatga               708
```

<210> SEQ ID NO 28
<211> LENGTH: 1251
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 28

```
atggaaaccg acacactgct gctgtgggtg ctgttgttgt gggtgccagg atctacaggc    60
gaagtgcagt tggttcagtc tggcggagga ctggttaagc ctggcggatc tctgagactg   120
tcttgtgccg cctctggctt caccttctct agctttgcca tgcactgggt ccgacaggcc   180
cctggaaaag gcctggaatg gatctccgtg atcgatacca gaggcgccac ctactacgcc   240
gactctgtga agggcagatt caccatctct cgggacaacg ccaagaactc cctgtacctg   300
cagatgaaca gcctgagagc cgaggacacc gccgtgtact attgtgccag actgggcaac   360
ttctactacg gcatggatgt gtggggccag ggcacaacag tgaccgtgtc ctctgcttct   420
accaagggac cctctgtgtt ccctctggct ccttccagca gtctacctc tggtggaacc   480
gctgctctgg gctgcctggt caaggattac tttcctgagc ctgtgacagt gtcctggaac   540
tctggtgctc tgacctccgg cgtgcacaca tttccagctg tgctgcagtc ctctggcctg   600
tactctctgt cctctgtcgt gaccgtgcct tctagctctc tgggcaccca gacctacatc   660
tgcaacgtga accacaagcc ttccaacacc aaggtggaca agagagtgga acccaagtct   720
tgcggatctt ctggtggcgg tggaagcgga ggcggaggat ctagtggcgg agtgttcacc   780
ctggaagatt tcgtcggcga ttgggagcag accgccgcct ataatctgga ccaggttctg   840
gaacaaggcg gcgtcagctc tctgctgcag aatctggctg tgtctgtgac ccctatccag   900
agaatcgtgc gctctggcga gaacgccctg aagatcgaca tccacgtgat catcccttac   960
gagggcctgt ctgccgatca gatggctcag atcgaagagg tgttcaaggt ggtgtacccc  1020
```

| | |
|---|---|
| gtggacgacc accacttcaa agtgatcctg ccttacggca ccctggtcat cgatggcgtg | 1080 |
| accccaaaca tgctgaacta cttcggcaga ccctacgagg gaatcgccgt gttcgacggc | 1140 |
| aagaaaatca ccgtgaccgg cacactgtgg aacggcaaca agatcatcga cgagcggctg | 1200 |
| atcacccctg acggctccat gctgtttaga gtgaccatca actcctaatg a | 1251 |

<210> SEQ ID NO 29
<211> LENGTH: 789
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 29

| | |
|---|---|
| atggaaaccg acacactgct gctgtgggtg ctgttgttgt gggtgccagg atctacaggc | 60 |
| gagatcgtgc tgacccagtc tcctggcaca ttgtctgtgt ctcccggcga gagagctacc | 120 |
| ctgtcttgta gagcttccca gtccatcggc tccagcctgc actggtatca gcagaaacct | 180 |
| ggacaggccc ctcggctgct gattaagtac gcctctcagt ccctgtctgg catccctgac | 240 |
| agattctctg gctctggctc cggcaccgac ttcaccctga caatctctag actggaaccc | 300 |
| gaggacttcg ccgtgtacta ctgccaccag tctagcagac tgcctcacac ctttggccag | 360 |
| ggcaccaagg tggaaatcaa gagaaccgtg gccgctcctt ccgtgttcat cttcccacca | 420 |
| tctgacgagc agctgaagtc tggcaccgct tctgtcgtgt gcctgctgaa caacttctac | 480 |
| cctcgggaag ccaaggtgca gtggaaggtg gacaatgccc tgcagtccgg caactcccaa | 540 |
| gagtctgtga ccgagcagga ctccaaggac tctacctaca gcctgtcctc cacactgacc | 600 |
| ctgtctaagg ccgactacga aagcacaag gtgtacgcct gtgaagtgac ccaccaggga | 660 |
| ctgtctagcc ccgtgaccaa gtctttcaac agaggcgagt gcggatcttc tggtggcgga | 720 |
| ggatctggcg gaggtggaag tagtggcggc gtgaccggct acagactgtt cgaagagatc | 780 |
| ctgtaatga | 789 |

<210> SEQ ID NO 30
<211> LENGTH: 708
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 30

| | |
|---|---|
| atggaaaccg acacactgct gctgtgggtg ctgttgttgt gggtgccagg atctacaggc | 60 |
| gagatcgtgc tgacccagtc tcctggcaca ttgtctgtgt ctcccggcga gagagctacc | 120 |
| ctgtcttgta gagcttccca gtccatcggc tccagcctgc actggtatca gcagaaacct | 180 |
| ggacaggccc ctcggctgct gattaagtac gcctctcagt ccctgtctgg catccctgac | 240 |
| agattctctg gctctggctc cggcaccgac ttcaccctga caatctctag actggaaccc | 300 |
| gaggacttcg ccgtgtacta ctgccaccag tctagcagac tgcctcacac ctttggccag | 360 |
| ggcaccaagg tggaaatcaa gagaaccgtg gccgctcctt ccgtgttcat cttcccacca | 420 |
| tctgacgagc agctgaagtc tggcaccgct tctgtcgtgt gcctgctgaa caacttctac | 480 |
| cctcgggaag ccaaggtgca gtggaaggtg gacaatgccc tgcagtccgg caactcccaa | 540 |
| gagtctgtga ccgagcagga ctccaaggac tctacctaca gcctgtcctc cacactgacc | 600 | ctgtctaagg ccgactacga gaagcacaag gtgtacgcct gtgaagtgac ccaccaggga    660 ctgtctagcc ccgtgaccaa gtctttcaac agaggcgagt gctaatga                 708

<210> SEQ ID NO 31
<211> LENGTH: 1251
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 31
atggaaaccg acacactgct gctgtgggtg ctgttgttgt gggtgccagg atctaccgga    60
caggtggaac tggttgaatc tggtggcgga gtggtgcagc tggcagatc tcagagactg    120 tcttgtgccg cctctggctt caccttctcc tcttacggca tgcactgggt ccgacaggcc    180
cctggaaaag gactggaatg ggtcgccatc atttggttcg acggctcctc tacctactac    240
gccgattctg tgcggggcag attcaccatc tctcgggaca actccaagaa caccctgtac    300
ctgcagatga actccctgag agccgaggat accgccgtgt acttctgtgc cagagagctg    360
gggagaagat acttcgatct gtggggcaga ggcaccctgg tgtctgtgtc ctctgcttct    420
accaagggac ccagcgtttt ccctctggct ccatcctcta gtccacctc tggtggaacc    480 gctgctctgg gctgtctggt caaggattac ttccctgagc ctgtgaccgt gtcctggaac    540
tctggtgctc tgacatccgg cgtgcacacc tttccagctg tgctgcagtc ctctggcctg    600
tactctctgt cctctgtcgt gaccgtgcct tcttctagcc tgggcaccca gacctacatc    660
tgcaacgtga accacaagcc ttccaacacc aaagtggaca gagagtggga acccaagtct    720
tgcggatctt ctggcggcgg aggaagcgga ggcggaggat ctagcggcgg agtgttcacc    780
ctggaagatt cgtcggcga ttgggagcag accgccgcct ataatctgga ccaggttctg    840
gaacaaggcg gcgtgtcctc tctgctgcag aatctggctg tgtctgtgac ccctatccag    900
agaatcgtgc gctctggcga gaacgccctg aagatcgaca tccacgtgat catcccttac    960
gagggcctgt ctgccgatca gatggcccag attgaagagg tgttcaaggt ggtgtacccc    1020
gtggacgacc accacttcaa agtgatcctg ccttacggca ccctcgtgat cgatggcgtg    1080
accccaaaca tgctgaacta cttcggcaga ccctacgagg aatcgccgt gttcgatggc    1140 aagaaaatca ccgtgaccgg cacactgtgg aacggcaaca agatcatcga cgagcggctg    1200
atcacccctg acggctctat gctgttcaga gtgaccatca actcctaatg a             1251

<210> SEQ ID NO 32
<211> LENGTH: 792
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 32
atggaaaccg acacactgct gctgtgggtg ctgttgttgt gggtgccagg atctacaggc    60
gagatcgtgc tgacccagtc tcctgccaca ttgtctctga gtcctggcga gagagctacc    120
ctgtcttgca gagcttccca gtccgtgtcc tcctacctgg cctggtatca gcagaaacct    180
ggacaggccc ctcggctgct gatctacgat gcttctaaga gagccacagg catccccgcc    240

| | |
|---|---|
| agattttctg gctctggatc tggcaccgac ttcaccctga ccatctctag cctggaacct | 300 |
| gaggacttcg ccgtgtacta ctgccagcag agatccaagt ggcctccttg gacctttgga | 360 |
| cagggcacca aggtggaatc taagagaacc gtggccgctc cttccgtgtt catcttccca | 420 |
| ccatctgacg agcagctgaa gtccggcaca gcttctgtcg tgtgcctgct gaacaacttc | 480 |
| taccctcggg aagccaaggt gcagtggaag gtggacaatg ccctgcagtc cggcaactcc | 540 |
| caagagtctg tgaccgagca ggactccaag gactctacct acagcctgtc ctccacactg | 600 |
| accctgtcta aggccgacta cgagaagcac aaggtgtacg cctgtgaagt gacccaccag | 660 |
| ggactgtcta gccccgtgac caagtctttc aacagaggcg agtgcggatc ttctggtggc | 720 |
| ggaggatctg gcggaggcgg atctagtggc ggagtgaccg gctacagact gttcgaagag | 780 |
| atcctgtaat ga | 792 |

<210> SEQ ID NO 33
<211> LENGTH: 711
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 33

| | |
|---|---|
| atggaaaccg acacactgct gctgtgggtg ctgttgttgt gggtgccagg atctacaggc | 60 |
| gagatcgtgc tgacccagtc tcctgccaca ttgtctctga gtcctggcga gagagctacc | 120 |
| ctgtcttgca gagcttccca gtccgtgtcc tcctacctgg cctggtatca gcagaaacct | 180 |
| ggacaggccc ctcggctgct gatctacgat gcttctaaga gagccacagg catccccgcc | 240 |
| agattttctg gctctggatc tggcaccgac ttcaccctga ccatctctag cctggaacct | 300 |
| gaggacttcg ccgtgtacta ctgccagcag agatccaagt ggcctccttg gacctttgga | 360 |
| cagggcacca aggtggaatc taagagaacc gtggccgctc cttccgtgtt catcttccca | 420 |
| ccatctgacg agcagctgaa gtccggcaca gcttctgtcg tgtgcctgct gaacaacttc | 480 |
| taccctcggg aagccaaggt gcagtggaag gtggacaatg ccctgcagtc cggcaactcc | 540 |
| caagagtctg tgaccgagca ggactccaag gactctacct acagcctgtc ctccacactg | 600 |
| accctgtcta aggccgacta cgagaagcac aaggtgtacg cctgtgaagt gacccaccag | 660 |
| ggactgtcta gccccgtgac caagtctttc aacagaggcg agtgctaatg a | 711 |

<210> SEQ ID NO 34
<211> LENGTH: 1245
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 34

| | |
|---|---|
| atggaaaccg acacactgct gctgtgggtg ctgttgttgt gggtgccagg atctacaggc | 60 |
| gaggtgcagt tggttgaatc tggcggagga ctggtgcagc ctggcagatc tctgagactg | 120 |
| tcttgcgccg cctccagatt caccttcgac gattacgcca tgcactgggt ccgacaggcc | 180 |
| cctggaaaag gattggagtg ggtgtccggc atctcctgga actctggcag aatcggctac | 240 |
| gccgactccg tgaagggcag attcacaatc tcccgggaca cgccgagaa ctccctgttc | 300 |
| ctgcagatga atgcctgag agccgaggac accgctctgt actattgcgc caagggcaga | 360 |

```
gactccttcg atatctgggg ccagggcacc atggtcaccg tgtcctctgc ttctaccaag    420
ggaccctctg tgttccctct ggctccttcc agcaagtcta cctctggtgg aaccgctgct    480
ctgggctgcc tggtcaagga ttactttcct gagcctgtga ccgtgtcttg gaactccggt    540
gctctgacat ccggcgtgca cacatttcca gctgtgctgc agtcctctgg cctgtactct    600
ctgtcctctg tcgtgaccgt gccttctagc tctctgggca cccagaccta catctgcaac    660
gtgaaccaca agccttccaa caccaaggtg acaagagag tggaacccaa gtcttgcgga     720
tcttctggtg gcggtggaag cggaggcgga ggatctagtg gcggagtgtt caccctggaa    780
gatttcgtcg gcgattggga gcagaccgcc gcctataatc tggaccaggt tctggaacaa    840
ggcggcgtca gctctctgct gcagaatctg gctgtgtctg taccccctat ccagagaatc    900
gtgcgctctg gcgagaacgc cctgaagatc gacatccacg tgatcatccc ttacgagggc    960
ctgtctgccg atcagatggc tcagatcgaa gaggtgttca aggtggtgta ccccgtggac   1020
gaccaccact tcaaagtgat cctgccttac ggcaccctgg tcatcgatgg cgtgacccca   1080
aacatgctga actacttcgg cagaccctac gagggaatcg ccgtgttcga cggcaagaaa   1140
atcaccgtga ccggcacact gtggaacggc aacaagatca tcgacgagcg gctgatcacc   1200
cctgacggct ctatgctgtt cagagtgacc atcaactcct aatga                   1245

<210> SEQ ID NO 35
<211> LENGTH: 789
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 35
atggaaaccg acacactgct gctgtggtg ctgttgttgt gggtgccagg ctctaccggc       60
gacatccaga tgacccagtc tccatcctct gtgtctgcct ctgtgggcga cagagtgacc     120
atcacctgta gagcctctca gggcatctct agctggctgg cctggtatca gcagaagcct    180
ggaaaggccc ctaagctgct gatctacggc gcctcttctc tggaatctgg cgtgccctct    240
agattctccg gctctggctc tggcaccgac tttaccctga caatcagctc cctgcagcct    300
gaggacttcg cctcttacta ctgccagcag gccaacagct cccctatac ctttggccag     360 ggcaccaagc tggaaatcaa gagaaccgtg gccgctcctt ccgtgttcat cttcccacca   420
tctgacgagc agctgaagtc cggcacagct tctgtcgtgt gcctgctgaa caacttctac   480
cctcgggaag ccaaggtgca gtggaaggtg gacaatgccc tgcagtccgg caactcccaa   540
gagtctgtga ccgagcagga ctccaaggac tctacctaca gcctgtcctc cacactgacc   600
ctgtctaagg ccgactacga aagcacaag gtgtacgcct gtgaagtgac ccaccaggga    660
ctgtctagcc ccgtgaccaa gtcttttcaac agaggcgagt gcggatcttc tggtggcgga   720
ggatctggcg gaggtggaag tagtggcggc gtgaccggct acagactgtt cgaagagatc    780
ctgtaatga                                                             789

<210> SEQ ID NO 36
<211> LENGTH: 708
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 36

| | | | | | |
|---|---|---|---|---|---|
| atggaaaccg | acacactgct | gctgtgggtg | ctgttgttgt | gggtgccagg | ctctaccggc | 60
| gacatccaga | tgacccagtc | tccatcctct | gtgtctgcct | ctgtgggcga | cagagtgacc | 120
| atcacctgta | gagcctctca | gggcatctct | agctggctgg | cctggtatca | gcagaagcct | 180
| ggaaaggccc | ctaagctgct | gatctacggc | gcctcttctc | tggaatctgg | cgtgccctct | 240
| agattctccg | gctctggctc | tggcaccgac | tttaccctga | caatcagctc | cctgcagcct | 300
| gaggacttcg | cctcttacta | ctgccagcag | gccaacagct | cccctatac | ctttggccag | 360
| ggcaccaagc | tggaaatcaa | agaaccgtg | gccgctcctt | ccgtgttcat | cttcccacca | 420
| tctgacgagc | agctgaagtc | cggcacagct | tctgtcgtgt | gcctgctgaa | caacttctac | 480
| cctcgggaag | ccaaggtgca | gtggaaggtg | gacaatgccc | tgcagtccgg | caactcccaa | 540
| gagtctgtga | ccgagcagga | ctccaaggac | tctacctaca | gcctgtcctc | cacactgacc | 600
| ctgtctaagg | ccgactacga | aagcacaag | gtgtacgcct | gtgaagtgac | ccaccaggga | 660
| ctgtctagcc | ccgtgaccaa | gtctttcaac | agaggcgagt | gctaatga | | 708

```
<210> SEQ ID NO 37
<211> LENGTH: 1251
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 37

| | | | | | |
|---|---|---|---|---|---|
| atggaaaccg | acacactgct | gctgtgggtg | ctgttgttgt | gggtgccagg | atctacaggc | 60
| gaggtgcagt | tgttggaatc | tggcggagga | ttggtgcagc | ctggcggatc | tctgagactg | 120
| tcttgtgccg | cctctggctt | caccttctcc | gcctatgaga | tgaagtgggt | ccgacaggct | 180
| cctggcaaag | gactggaatg | ggtgtccgtg | attggcccctt | ctggcggctt | tacctttac | 240
| gccgactccg | tgaagggcag | attcaccatc | tctcgggaca | actccaagaa | caccctgtac | 300
| ctgcagatga | actccctgag | agccgaggac | accgccgtgt | actattgtgc | caccgagggc | 360
| gacaacgacg | cctttgatat | ttggggccag | ggcaccaccg | tgaccgtgtc | ctctgcttct | 420
| acaaagggcc | cctctgtgtt | ccctctggct | ccttcctcta | aatccacctc | tggcggaacc | 480
| gctgctctgg | gctgtctggt | caaggattac | ttccctgagc | ctgtgacagt | gtcctggaac | 540
| tctggtgctc | tgacatccgg | cgtgcacacc | tttccagctg | tgctgcagtc | ctctggcctg | 600
| tactctctgt | cctctgtcgt | gacagtgcct | tccagctctc | tgggcaccca | gacctacatc | 660
| tgcaacgtga | accacaagcc | ttccaacacc | aaggtggaca | agagagtgga | acccaagtct | 720
| tgcggatctt | ccggcggagg | tggaagtggc | ggaggcggat | caagcggcgg | agtgttcaca | 780
| ctggaagatt | tctcggcga | ttgggagcag | accgccgcct | ataatctgga | ccaggttctg | 840
| gaacaaggcg | gcgttagctc | tctgctgcag | aatctggctg | tgtctgtgac | ccctatccag | 900
| agaatcgtgc | gctctggcga | gaacgccctg | aagatcgaca | tccacgtgat | catcccttac | 960
| gagggcctgt | ctgccgatca | gatggctcag | atcgaagagg | tgttcaaggt | ggtgtacccc | 1020
| gtggacgacc | accacttcaa | agtgatcctg | ccttacggca | ccctggtcat | cgatggcgtg | 1080
| accccaaaca | tgctgaacta | cttcggcaga | ccctacgagg | gaatcgccgt | gttcgacggc | 1140
| aagaaaatca | ccgtgacagg | caccctgtgg | aacggcaaca | agatcatcga | cgagcggctg | 1200 atcacccctg acggctctat gctgttcaga gtgaccatca actcctaatg a    1251

<210> SEQ ID NO 38
<211> LENGTH: 792
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 38
atggaaaccg acacactgct gctgtgggtg ctgttgttgt gggtgccagg atctacaggc    60
gatatccaga tgacccagtc tcctgccaca ttgtctctga gtcctggcga gagagctacc   120
ctgtcttgca gagcttccca gtccgtgtcc tcctacctgg cctggtatca gcagaaacct   180
ggacaggccc ctcggctgct gatctacgat gcctctaata gagccacagg catccccgcc   240
agattctctg gctctggatc tggcaccgac ttcaccctga ccatctctag cctggaacct   300
gaggacttcg ccgtgtacta ctgccagcag agatccaact ggcctatgta caccttcggc   360
cagggcacca agctggaaat caagagaacc gtggccgctc cttccgtgtt catcttccca   420
ccatctgacg agcagctgaa gtccggcaca gcttctgtcg tgtgcctgct gaacaacttc   480
taccctcggg aagccaaggt gcagtggaag gtggacaatg ccctgcagtc cggcaactcc   540
caagagtctg tgaccgagca ggactccaag gactctacct acagcctgtc ctccacactg   600
accctgtcta aggccgacta cgagaagcac aaggtgtacg cctgtgaagt gacccaccag   660
ggactgtcta gccccgtgac caagtctttc aacagaggcg agtgcggatc ttctggtggc   720
ggaggaagcg gaggcggagg atcatctggc ggagtgaccg gctacagact gttcgaagag   780
atcctgtaat ga                                                        792

<210> SEQ ID NO 39
<211> LENGTH: 711
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 39
atggaaaccg acacactgct gctgtgggtg ctgttgttgt gggtgccagg atctacaggc    60
gatatccaga tgacccagtc tcctgccaca ttgtctctga gtcctggcga gagagctacc   120
ctgtcttgca gagcttccca gtccgtgtcc tcctacctgg cctggtatca gcagaaacct   180
ggacaggccc ctcggctgct gatctacgat gcctctaata gagccacagg catccccgcc   240
agattctctg gctctggatc tggcaccgac ttcaccctga ccatctctag cctggaacct   300
gaggacttcg ccgtgtacta ctgccagcag agatccaact ggcctatgta caccttcggc   360
cagggcacca agctggaaat caagagaacc gtggccgctc cttccgtgtt catcttccca   420
ccatctgacg agcagctgaa gtccggcaca gcttctgtcg tgtgcctgct gaacaacttc   480
taccctcggg aagccaaggt gcagtggaag gtggacaatg ccctgcagtc cggcaactcc   540
caagagtctg tgaccgagca ggactccaag gactctacct acagcctgtc ctccacactg   600
accctgtcta aggccgacta cgagaagcac aaggtgtacg cctgtgaagt gacccaccag   660
ggactgtcta gccccgtgac caagtctttc aacagaggcg agtgctaatg a             711

```
<210> SEQ ID NO 40
<211> LENGTH: 1266
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 40
atggaaaccg acacactgct gctgtgggtg ctgttgttgt gggtgccagg atctacaggc      60
gaggtgcagt tggttgaatc tggcggagga ttggtgcagc ctggcggatc tctgagactg     120
tcttgtgccg cctccggctt caccttctcc tcttacgcta tgtcctgggt ccgacaggct     180
cctggcaaag gattggagtg ggtgtcccag atttctcccg ctggcggcta caccaactac     240
gccgattctg tgaagggcag attcaccatc tccgccgaca cctccaagaa caccgcctac     300
ctgcagatga actccctgag agctgaggac accgccgtgt actattgtgc tagaggcgag     360
ctgccctact accggatgtc aaagtgatg atgtgtggg ccagggcac actggttacc       420 gtgtcctctg cttctaccaa gggacccctct gtgttccctc tggctccttc cagcaagtct     480
acctctggtg aaccgctgc tctgggctgc tggtcaagg attactttcc tgagcctgtg       540
accgtgtctt ggaactctgg tgctctgacc tccggcgtgc acacatttcc agctgtgctg     600
cagtcctccg gcctgtactc tctgtcctct gtcgtgaccg tgccttctag ctctctgggc     660
acccagacct acatctgcaa cgtgaaccac aagccttcca acaccaaggt ggacaagaga     720
gtggaaccca gtcttgcgg atcttctggt ggcggtggaa gtggcggagg tggaagttca      780
ggcggagtgt tcaccctgga agatttcgtc ggcgattggg agcagaccgc cgcctataat     840
ctggaccagg ttctggaaca aggcggcgtc agctctctgc tgcagaatct ggctgtgtct     900
gtgaccccta tccagagaat cgtgcgctct ggcgagaacg ccctgaagat cgacatccac     960
gtgatcatcc cttacgaggg cctgtctgcc gatcagatgg ctcagatcga agaggtgttc    1020
aaggtggtgt accccgtgga cgaccaccac ttcaaagtga tcctgccttca cggcaccctg    1080 gtcatcgatg gcgtgacccc aaacatgctg aactacttcg gcagaccccta cgagggaatc    1140 gccgtgttcg acggcaagaa aatcaccgtg accggcacac tgtggaacgg caacaagatc    1200
atcgacgagc ggctgatcac ccctgacggc tctatgctgt tcagagtgac catcaactcc    1260
taatga                                                              1266

<210> SEQ ID NO 41
<211> LENGTH: 789
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 41
atggaaaccg acacactgct gctgtgggtg ctgttgttgt gggtgccagg ctctaccggc      60
gacatccaga tgacccagtc tccatcctct ctgtctgcct ctgtgggcga cagagtgacc     120
atcacctgtc gggcctctca gtacttctcc tcctacctgg cctggtatca gcagaagcct     180
ggcaaggctc ccaagctgct gatctacggc gcctcttcta gagcctctgg cgtgccatct     240
agattctccg gctctggctc tggcaccgac tttaccctga caatcagctc cctgcagcct     300
gaggacttcg ccacctacta ctgtcagcag tacctgggct ctcctccaac ctttggccag     360
```

```
ggcaccaagg tggaaatcaa gagaaccgtg gccgctcctt ccgtgttcat cttcccacca    420
tctgacgagc agctgaagtc cggcacagct tctgtcgtgt gcctgctgaa caacttctac    480
cctcgggaag ccaaggtgca gtggaaggtg gacaatgccc tgcagtccgg caactcccaa    540
gagtctgtga ccgagcagga ctccaaggac tctacctaca gcctgtcctc cacactgacc    600
ctgtctaagg ccgactacga gaagcacaag gtgtacgcct gtgaagtgac ccaccaggga    660
ctgtctagcc ccgtgaccaa gtctttcaac agaggcgagt gcggatcttc tggtggcgga    720
ggatctggcg gaggtggaag tagtggcggc gtgaccggct acagactgtt cgaagagatc    780
ctgtaatga                                                            789
```

<210> SEQ ID NO 42
<211> LENGTH: 708
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 42

```
atggaaaccg acacactgct gctgtgggtg ctgttgttgt gggtgccagg ctctaccggc     60
gacatccaga tgacccagtc tccatcctct ctgtctgcct ctgtgggcga cagagtgacc    120
atcacctgtc gggcctctca gtacttctcc tcctacctgg cctggtatca gcagaagcct    180
ggcaaggctc ccaagctgct gatctacggc gcctcttcta gagcctctgg cgtgccatct    240
agattctccg gctctggctc tggcaccgac tttaccctga caatcagctc cctgcagcct    300
gaggacttcg ccacctacta ctgtcagcag tacctgggct ctcctccaac cttt ggccag    360 ggcaccaagg tggaaatcaa gagaaccgtg gccgctcctt ccgtgttcat cttcccacca    420
tctgacgagc agctgaagtc cggcacagct tctgtcgtgt gcctgctgaa caacttctac    480
cctcgggaag ccaaggtgca gtggaaggtg gacaatgccc tgcagtccgg caactcccaa    540
gagtctgtga ccgagcagga ctccaaggac tctacctaca gcctgtcctc cacactgacc    600
ctgtctaagg ccgactacga gaagcacaag gtgtacgcct gtgaagtgac ccaccaggga    660
ctgtctagcc ccgtgaccaa gtctttcaac agaggcgagt gctaatga                 708
```

<210> SEQ ID NO 43
<211> LENGTH: 1287
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 43

```
atggaaaccg acacactgct gctgtgggtg ctgttgttgt gggtgccagg atctacaggc     60
gaagtgcagt tggtgcagtc tggcgccgaa gtgaagaaac ctggctcctc tgtgaaggtg    120
tcctgcaagg cttctggcgg caccttctcc tcttacgcca tctcttgggt ccgacaggct    180
cctggacaag gcttggagtg gatgggcggc atcatcccta tcttcggcac cgccaactac    240
gcccagaaat tccagggcag agtgaccatc accgccgaca gtctacctc caccgcctac    300 atggaactgt ccagcctgag atctgaggac accgccgtgt actactgtgc tagagcccct    360
ctgcggttcc tggaatggtc tacccaggac cactactact attactacat ggacgtgtgg    420
ggcaagggca ccaccgtgac agtttcttcc gcttccacca agggacccag cgttttccct    480
```

```
ctggctccat cctccaagtc cacctctggt ggaacagctg ctctgggctg cctggtcaag      540
gattactttc ctgagcctgt gaccgtgtcc tggaactctg gtgctctgac atccggcgtg      600
cacacctttc cagctgtgct gcagtcctct ggcctgtact ctctgtcctc tgtcgtgacc      660
gtgccttcta gctctctggg cacccagacc tacatctgca acgtgaacca caagccttcc      720
aacaccaaag tggacaagag agtggaaccc aagtcttgcg atcttccgg tggcggagga       780 tctggcggag gtgaagtag tggcggagtg ttcacctgg aagatttcgt cggcgattgg        840
gagcagaccg ccgcctataa tctggaccag gttctggaac aaggcggcgt gtcctctctg      900
ctgcagaatc tggctgtgtc tgtgacccct atccagagaa tcgtgcgctc tggcgagaac      960
gccctgaaga tcgacatcca cgtgatcatc ccttacgagg gcctgtctgc cgatcagatg     1020
gctcagatcg aagaggtgtt caaggtggt taccccgtgg acgaccacca cttcaaagtg      1080
atcctgcctt acggcaccct ggtcatcgat ggcgtgaccc caaacatgct gaactacttc     1140
ggcagaccct acgagggaat cgccgtgttc gacggcaaga aaatcaccgt gaccggcaca     1200
ctgtggaacg gcaacaagat catcgacgag cggctgatca cccctgacgg ctctatgctg     1260
tttagagtga caatcaactc ctaatga                                          1287
```

<210> SEQ ID NO 44
<211> LENGTH: 789
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 44

```
atggaaaccg acacactgct gctgtgggtg ctgttgttgt gggtgccagg ctctaccgga       60
tcctctgagt tgacacagga ccctgctgtg tctgtggctc tgggacagac agtgcggatt      120
acctgtcagg gcgactccct gagatcttac tacgccacct ggtatcagca gaagcccgga     180
caggctccca tcctggttat ctacggcgag aacaagcggc cctctggcat ccctgataga     240
ttctctggct cctcctccgg caataccgcc tctctgacaa ttactggcgc ccaggctgag     300
gacgaggccg actactattg caagtccaga gatggctctg ccagcacttt ggtgtttggc     360
ggcggaacaa aactgaccgt gctgggccag cctaaggcca tcctacagt gaccctgttt     420 cctccatcct ccgaggaact gcaggccaac aaggctaccc tcgtgtgcct gatctctgac     480
tttacccttg cgctgtgac cgtggcttgg aaggctgatg gatctcctgt gaaggccggc     540
gtggaaacca ccaagcctag caagcagtcc aacaacaaat acgccgcctc ctcctacctg     600
tctctgaccc ctgaacagtg gaagtccac cggtcctact cttgccaagt gacccatgag     660
ggctccaccg tggaaaagac agtggcccct accgagtgct ctggatcttc tggtggcgga     720
ggatctggcg gaggtggaag tagtggcggc gtgaccggct acagactgtt cgaagagatc     780
ctgtaatga                                                              789
```

<210> SEQ ID NO 45
<211> LENGTH: 708
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 45

```
atggaaaccg acacactgct gctgtgggtg ctgctcttgt gggtgccagg ctctaccgga      60
tcctctgagc tgacacagga ccctgctgtg tctgtggctc tgggccagac agtgcggatt     120
acctgtcagg gcgactccct gagatcctac tacgccacct ggtatcagca gaagcctgga     180
caggctccca tcctggtcat ctacggcgag aacaagcggc cctctggcat ccctgataga     240
ttctccggct cctccagcgg caataccgcc tctctgacaa ttaccggcgc tcaggctgag     300
gacgaggccg actactactg caagtccaga gatggctccg ccagcacct ggttttggc       360
ggaggaacaa agctgaccgt gctgggccag cctaaggcca tcctaccgt gacactgttc      420
cctccatcct ccgaggaact gcaggccaac aaggctaccc tcgtgtgcct gatctccgac     480
ttttaccctg gcgctgtgac cgtggcctgg aaggctgatg gatctcctgt gaaggctggc     540
gtggaaacca ccaagccttc caagcagtcc aacaacaaat acgccgcctc ctcctacctg     600
tctctgaccc ctgaacagtg gaagtcccac cggtcctaca gctgccaagt gacccatgag     660
ggctccaccg tggaaaagac cgtggctcct accgagtgct cctgatga                  708
```

<210> SEQ ID NO 46
<211> LENGTH: 1260
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 46

```
atggaaaccg acacactgct gctgtgggtg ctgttgttgt gggtgccagg atctacaggc      60
gaagtgcagt tggttcagtc tggcggcgga gttgaaagac ctggcggatc tctgagactg     120
tcttgtgccg cctctggctt caccttcgac gactacgcta tgtcctgggt ccgacaggct     180
cctggcaaag gattgaatgg ggtgtccggc atcaactggc aaggcggctc taccggctac     240
gccgattctg tgaagggcag agtgaccatc tctcgggaca cgccaagaa ctccctgtac      300
ctgcagatga acagcctgag agccgaggac accgccgtgt actactgtgc taagatcctc     360
ggcgctggca gaggctggta cttcgattat tggggcaagg gcaccaccgt gaccgtgtcc     420
tctgcttcta aagggccctc tgtgttcc cctctggctc cttcctctaa atccacctct       480
ggcggaaccg ctgctctggg ctgtctggtc aaggattact ccctgagcc tgtgacagtg      540
tcctggaact ctggtgctct gacatccggc gtgcacacct tccagctgt gctgcagtcc      600
tctggcctgt actctctgtc ctctgtcgtg acagtgcctt ccagctctct gggcacccag     660
acctacatct gcaacgtgaa ccacaagcct tccaacacca aggtggacaa gagagtggaa     720
cccaagtctt gtgatcttc tggcggaggt ggaagcggag gcggaggatc aagtggcgga     780
gtgttcaccc tggaagattt cgtcggcgat tgggagcaga ccgccgccta taatctggac     840
caggttctgg aacaaggcgg cgttagctct gctgctgcaga atctggctgt gtctgtgacc     900
cctatccaga aatcgtgcg ctctggcgag aacgccctga gatcgacat ccacgtgatc       960
atcccttacg agggcctgtc tgccgatcag atggctcaga tcgaagaggt gttcaaggtg    1020
gtgtaccccg tggacgacca ccacttcaaa gtgatcctgc cttacggcac cctggtcatc    1080
gatggcgtga ccccaaacat gctgaactac ttcggcagac cctacgaggg aatcgccgtg    1140
ttcgacggca gaaaaatcac cgtgacaggc acccctggaa acggcaacaa gatcatcgac    1200
gagcggctga tcaccccctga cggctccatg ctgtttcgcg tgaccatcaa ctcctaatga    1260
```

<210> SEQ ID NO 47
<211> LENGTH: 789
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 47

```
atggaaaccg acacactgct gctgtgggtg ctgttgttgt gggtgccagg ctctaccgga      60
tcctctgagt tgacacagga ccctgctgtg tctgtggctc tgggacagac agtgcggatc     120
acctgttccg gcgactccct gagatcttac tacgcctcct ggtatcagca gaagcctgga     180
caggctcccg tgctggttat ctacggcgcc aacaacagac cttctggcat ccctgacaga     240
ttctccggct ccagctctgg caataccgcc tctctgacaa ttaccggcgc tcaggctgag     300
gacgaggccg actactactg caactctgcc gactcttccg gcaatcacgt tgtgtttggc     360
ggaggcacca agctgacagt gctgggccaa cctaaggcca atcctaccgt gacactgttc     420
cctccatcct ccgaggaact gcaggctaac aaggctaccc tcgtgtgcct gatctccgat     480
ttttaccctg gcgctgtgac cgtggcttgg aaggctgatg gatctcctgt gaaggccggc     540
gtggaaacca ccaagcctag caagcagtcc aacaacaaat acgccgcctc ctcctacctg     600
tctctgaccc ctgaacagtg gaagtcccac cggtcctact cttgccaagt gacccatgag     660
ggctccaccg tggaaaagac agtggcccct accgagtgct ctggatcttc tggtggcgga     720
ggaagcggag gcggaggatc atctggcgga gtgaccggct acagactgtt cgaagagatc     780
ctgtaatga                                                            789
```

<210> SEQ ID NO 48
<211> LENGTH: 708
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 48

```
atggaaaccg acacactgct gctgtgggtg ctgttgttgt gggtgccagg ctctaccgga      60
tcctctgagt tgacacagga ccctgctgtg tctgtggctc tgggacagac agtgcggatc     120
acctgttccg gcgactccct gagatcttac tacgcctcct ggtatcagca gaagcctgga     180
caggctcccg tgctggttat ctacggcgcc aacaacagac cttctggcat ccctgacaga     240
ttctccggct ccagctctgg caataccgcc tctctgacaa ttaccggcgc tcaggctgag     300
gacgaggccg actactactg caactctgcc gactcttccg gcaatcacgt tgtgtttggc     360
ggaggcacca agctgacagt gctgggccaa cctaaggcca atcctaccgt gacactgttc     420
cctccatcct ccgaggaact gcaggctaac aaggctaccc tcgtgtgcct gatctccgat     480
ttttaccctg gcgctgtgac cgtggcttgg aaggctgatg gatctcctgt gaaggccggc     540
gtggaaacca ccaagcctag caagcagtcc aacaacaaat acgccgcctc ctcctacctg     600
tctctgaccc ctgaacagtg gaagtcccac cggtcctact cttgccaagt gacccatgag     660
ggctccaccg tggaaaagac agtggcccct accgagtgct cttaatga                 708
```

<210> SEQ ID NO 49

```
<211> LENGTH: 1248
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 49
atggaaaccg acacactgct gctgtgggtg ctgttgttgt gggtgccagg atctacaggc      60
gaagtgcagt tggtgcagtc tggcgccgaa gtgaagaagc tggcgagtc cctgaagatc     120
tcctgcaaag ctccggcta ctccttctcc aactactgga tcggctgggt ccgacagatg     180
cctggcaaag gactggaatg gatgggcatc atcgacccct ccaacagcta caccagatac     240
agccctagct tccagggcca agtgaccatc tccgccgaca gtctatctc caccgcctac     300
ctgcagtggt cctctctgaa ggcctctgac accgccatgt actactgcgc cagatggtac     360
tacaagccct tcgatgtgtg gggccagggc acactggtta ccgtgtcctc tgcttctacc     420
aagggaccct ctgtgttccc tctggctcct tccagcaagt ctacctctgg tggaaccgct     480
gctctgggct gcctggtcaa ggattacttt cctgagcctg tgaccgtgtc ttggaactct     540
ggtgctctga cctccggcgt gcacactttt ccagctgtgc tgcagtcctc cggcctgtac     600
tctctgtcct ctgtcgtgac cgtgccttct agctctctgg gcacccagac ctacatctgc     660
aacgtgaacc acaagccttc caacaccaag gtggacaaga gagtggaacc caagtcttgc     720
ggatcttctg gtggcggagg atctggcgga ggtggaagta gtggcggagt gttcacccctg    780
gaagatttcg tcggcgattg ggagcagacc gccgcctata atctggacca ggttctggaa     840
caaggcggcg tcagctctct gctgcagaat ctggctgtgt ctgtgacccc tatccagaga     900
atcgtgcgct ctggcgagaa cgctctgaag atcgacatcc acgtgatcat cccttacgag     960
ggcctgtctg ccgatcagat ggctcagatc gaagaggtgt tcaaggtggt gtaccccgtg    1020
gacgaccacc acttcaaagt gatcctgcct acggcaccc tggtcatcga tggcgtgacc    1080
ccaaacatgc tgaactactt cggcagaccc tacgagggaa tcgccgtgtt cgacggcaag    1140
aaaatcaccg tgaccggcac actgtggaac ggcaacaaga tcatcgacga gcggctgatc    1200
accctgacg gctctatgct gttccgcgtg accatcaact cctaatga                  1248

<210> SEQ ID NO 50
<211> LENGTH: 798
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 50
atggaaaccg acacactgct gctgtgggtg ctgttgttgt gggtgccagg ctctacaggc      60
cagtctgttc tgactcagcc tccttctgtt tctggcgctc ctggcagag agtgaccatc     120
tcctgtaccg gctcctcctc taacatcggc tctggctacg acgtgcactg gtatcagcag     180
ctgcctggca cagcccctaa actgctgatc tacggcaact ccaagaggcc ttctggcgtg     240
cccgatagat tctccggctc taagtctggc acctctgctt ctctggctat caccggcctg     300
cagtctgagg acgaggccga ttactactgc gcttcttgga ccgatggcct gagcctggtt     360
gtgtttggcg gcggaacaaa gctgacagtg ctgggccagc ctaaggccaa tcctaccgtg     420
acactgttcc ctccatcctc cgaggaactg caggctaaca aggctaccct cgtgtgcctg    480
```

| | |
|---|---|
| atctccgatt tttaccctgg cgctgtgacc gtggcttgga aggctgatgg atctcctgtg | 540 |
| aaggccggcg tggaaaccac caagcctagc aagcagtcca acaacaaata cgccgcctcc | 600 |
| tcctacctgt ctctgacccc tgaacagtgg aagtcccacc ggtcctactc ttgccaagtg | 660 |
| acccatgagg ctccaccgt ggaaaagaca gtggcccta ccgagtgctc tggatcttct | 720 |
| ggtggcggag atctggcgg aggtggaagt agtggcggcg tgaccggcta cagactgttc | 780 |
| gaagagatcc tgtaatga | 798 |

<210> SEQ ID NO 51
<211> LENGTH: 717
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 51

| | |
|---|---|
| atggaaaccg acacactgct gctgtgggtg ctgttgttgt gggtgccagg ctctacaggc | 60 |
| cagtctgttc tgactcagcc tccttctgtt tctggcgctc ctggccagag agtgaccatc | 120 |
| tcctgtaccg gctcctcctc taacatcggc tctggctacg acgtgcactg gtatcagcag | 180 |
| ctgcctggca gcccctaa actgctgatc tacggcaact ccaagaggcc ttctggcgtg | 240 |
| cccgatagat tctccggctc taagtctggc acctctgctt ctctggctat caccggcctg | 300 |
| cagtctgagg acgaggccga ttactactgc gcttcttgga ccgatggcct gagcctggtt | 360 |
| gtgtttggcg gcggaacaaa gctgacagtg ctgggccagc ctaaggccaa tcctaccgtg | 420 |
| acactgttcc ctccatcctc cgaggaactg caggctaaca aggctaccct cgtgtgcctg | 480 |
| atctccgatt tttaccctgg cgctgtgacc gtggcttgga aggctgatgg atctcctgtg | 540 |
| aaggccggcg tggaaaccac caagcctagc aagcagtcca acaacaaata cgccgcctcc | 600 |
| tcctacctgt ctctgacccc tgaacagtgg aagtcccacc ggtcctactc ttgccaagtg | 660 |
| acccatgagg ctccaccgt ggaaaagaca gtggcccta ccgagtgctc ttaatga | 717 |

<210> SEQ ID NO 52
<211> LENGTH: 1263
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 52

| | |
|---|---|
| atggaaaccg acacactgct gctgtgggtg ctgttgttgt gggtgccagg atctacagga | 60 |
| caggtgcagt tggttcagtc tggcggagga cttgttcagc caggcggatc tctgagactg | 120 |
| tcttgtgccg cctctggctt caccttcgac gattacgcta tgcactgggt ccgacaggcc | 180 |
| cctggaaaag gattggaatg ggtggccggc atctcctggg attctggctc taccggctac | 240 |
| gccgattccg tgaagggcag attcaccatc tctcgggaca cgccaagaa ctccctgtac | 300 |
| ctgcagatga cagcctgag agccgaggac accgctctgt actactgtgc tagagatctg | 360 |
| ggcgcctacc agtgggtgga aggctttgat tattgggcc agggcaccct ggtcaccgtg | 420 |
| tcctctgctt ctacaaaggg ccctctgtg ttccctctgg ctccttcctc taaatccacc | 480 |
| tctggcggaa ccgctgctct gggctgtctg gtcaaggatt acttccctga gcctgtgacc | 540 |

| | |
|---|---|
| gtgtcttgga actctggtgc tctgacatcc ggcgtgcaca cctttccagc tgtgctgcag | 600 |
| tcctctggcc tgtactctct gtcctctgtc gtgaccgtgc cttctagctc tctgggcacc | 660 |
| cagacctaca tctgcaacgt gaaccacaag cctagcaaca ccaaggtgga caagagagtg | 720 |
| gaacccaagt cttgcggatc ttctggcggc ggaggaagcg gaggcggagg atctagtggc | 780 |
| ggagtgttca ccctggaaga tttcgtcggc gattgggagc agaccgccgc ctataatctg | 840 |
| gaccaggttc tggaacaagg cggcgtcagc tctctgctgc agaatctggc tgtgtctgtg | 900 |
| acccctatcc agagaatcgt gcgctctggc gagaacgccc tgaagatcga catccacgtg | 960 |
| atcatccctt acgagggcct gtctgccgat cagatggctc agatcgaaga ggtgttcaag | 1020 |
| gtggtgtacc ccgtggacga ccaccacttc aaagtgatcc tgccttacgg caccctcgtg | 1080 |
| atcgatggcg tgaccccaaa catgctgaac tacttcggca gacccacga gggaatcgcc | 1140 |
| gtgttcgacg gcaagaaaat caccgtgacc ggcacactgt ggaacggcaa caagatcatc | 1200 |
| gacgagcggc tgatcacccc tgacggctcc atgctgttta gagtgaccat caactcctaa | 1260 |
| tga | 1263 |

```
<210> SEQ ID NO 53
<211> LENGTH: 792
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 53
```

| | |
|---|---|
| atggaaaccg acacactgct gctgtgggtg ctgttgttgt gggtgccagg ctctaccggc | 60 |
| tcttacgagt tgcacacagga ccctgctgtg tctgtggctc tgggacagac agtgcggatt | 120 |
| acctgtcagg gcgactccct gagatcctac tacgcctcct ggtatcagca gaagcctgga | 180 |
| caggctcccg tgctggtcat ctacggcaag aacaacagac cctctggcat ccctgaccgg | 240 |
| ttctctggct ctacctctgg caattccgcc agcctgacaa ttactggcgc tcaggctgag | 300 |
| gacgaggccg actactactg caactctaga gactcccctg gcaaccagtg ggtgttcggc | 360 |
| ggaggaacaa aagtgacagt gctcggcggc cagcctaagg ccaatcctac agtgaccctg | 420 |
| tttcctccat cctccgagga actgcaggcc aacaaggcta ccctcgtgtg cctgatctct | 480 |
| gacttttacc ctggcgctgt gaccgtggct tggaaggctg atggatctcc tgtgaaggcc | 540 |
| ggcgtggaaa ccaccaagcc tagcaagcag tccaacaaca aatacgccgc ctcctcctac | 600 |
| ctgtctctga cccctgaaca gtggaagtcc caccggtcct actcttgcca agtgacccat | 660 |
| gagggctcca ccgtggaaaa gacagtggcc cctaccgagt gctctggatc ttctggtggc | 720 |
| ggaggatctg gcggaggtgg aagtagtggc ggcgtgaccg gctacagact gttcgaagag | 780 |
| atcctgtaat ga | 792 |

```
<210> SEQ ID NO 54
<211> LENGTH: 711
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 54
```

| | |
|---|---|
| atggaaaccg acacactgct gctgtgggtg ctgctcttgt gggtgccagg ctctaccggc | 60 |

| | |
|---|---|
| tcttacgagc tgacacagga ccctgctgtg tctgtggctc tgggccagac agtgcggatt | 120 |
| acctgtcagg gcgactccct gagatcctac tacgcctcct ggtatcagca gaagcctgga | 180 |
| caggctcccg tgctggtcat ctacggcaag aacaaccggc ctagcggcat ccctgacaga | 240 |
| ttctccggct ctacctccgg caactctgcc agcctgacaa ttactggcgc ccaggctgag | 300 |
| gacgaggccg actactactg caactccaga gactcccctg caaccagtg ggttttcggc | 360 |
| ggaggcacca aagtgacagt gctcggagga cagcccaagg ccaatcctac cgtgacactg | 420 |
| ttccctccat cctccgagga actgcaggcc aacaaggcta ccctcgtgtg cctgatctcc | 480 |
| gacttttacc ctggcgctgt gaccgtggcc tggaaggctg atggatctcc tgtgaaggct | 540 |
| ggcgtggaaa ccaccaagcc ttccaagcag tccaacaaca aatacgccgc ctcctcctac | 600 |
| ctgtctctga cccctgaaca gtggaagtcc caccggtcct acagctgcca agtgacccat | 660 |
| gagggctcca ccgtggaaaa gaccgtggct cctaccgagt gctcctgatg a | 711 |

<210> SEQ ID NO 55
<211> LENGTH: 1260
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 55

| | |
|---|---|
| atggaaaccg acacactgct gctgtgggtg ctgttgttgt gggtgccagg atctacaggc | 60 |
| gaagtgcagt tggttcagtc tggcggcgga gttgaaagac ctggcggatc tctgagactg | 120 |
| tcttgtgccg cctctggctt caccttcgac gactatggca tgtcctgggt ccgacaggct | 180 |
| cctggcaaag gattgaatg ggtgtccggc atcaactgga atggcggctc taccggctac | 240 |
| gccgattctg tgaagggcag agtgaccatc tctcgggaca cgccaagaa ctccctgtac | 300 |
| ctgcagatga acagcctgag agccgaggac accgccgtgt actactgtgc taagatcctc | 360 |
| ggcgctggca gaggctggta tttcgatctg tggggcaagg gcaccaccgt gacagtgtcc | 420 |
| tctgcttcta ccaagggacc cagcgttttc cctctggctc catcctctaa gtccaccttc | 480 |
| ggtggaaccg ctgctctggg ctgtctggtc aaggattact cccctgagcc tgtgaccgtg | 540 |
| tcctggaact ctggtgctct gacatccggc gtgcacacct ttccagctgt gctgcagtcc | 600 |
| tctggcctgt actctctgtc ctctgtcgtg accgtgcctt ctagctctct gggcacccag | 660 |
| acctacatct gcaacgtgaa ccacaagcct tccaacacca agtggacaa agagtggaa | 720 |
| cccaagtcct gcggatcttc tggtggcgga ggatctggcg gaggtggaag tagtggcgga | 780 |
| gtgttcaccc tggaagattt cgtcggcgat gggagcaga ccgccgccta taatctggac | 840 |
| caggttctgg aacaaggcgg cgtgtcctct ctgctgcaga atctggctgt gtctgtgacc | 900 |
| cctatccaga gaatcgtgcg ctctggcgag aacgccctga gatcgacat ccacgtgatc | 960 |
| atcccttacg agggcctgtc tgccgatcag atggctcaga tcgaagaggt gttcaaggtg | 1020 |
| gtgtaccccg tggacgacca ccacttcaaa gtgatcctgc cttacggcac cctggtcatc | 1080 |
| gatggcgtga ccccaaacat gctgaactac ttcggcagac cctacgaggg aatcgccgtg | 1140 |
| ttcgacggca agaaaatcac cgtgaccggc acactgtgga acggcaacaa gatcatcgac | 1200 |
| gagcggctga tcacccctga cggctccatg ctgtttcgcg tgaccatcaa ctcctaatga | 1260 |

<210> SEQ ID NO 56
<211> LENGTH: 789

<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 56

| atggaaaccg acacactgct gctgtgggtg ctgttgttgt gggtgccagg ctctaccgga | 60 |
| tcctctgagt tgacacagga ccctgctgtg tctgtggctc tgggacagac agtgcggatt | 120 |
| acctgtcagg gcgactccct gagatcctac tacgcctcct ggtatcagca gaagcctgga | 180 |
| caggctcccg tgctggtcat ctacggcaag aacaacagac cctctggcat ccctgaccgg | 240 |
| ttctccggat ctagctctgg caataccgcc agcctgacaa ttactggcgc tcaggctgag | 300 |
| gacgaggccg actactactg caactccaga gactcttccg gcaatcacgt ggtgtttggc | 360 |
| ggcggaacaa agctgacagt gctgggccag cctaaggcca atcctaccgt gacactgttc | 420 |
| cctccatcct ccgaggaact gcaggctaac aaggctaccc tcgtgtgcct gatctccgat | 480 |
| ttttaccctg gcgctgtgac cgtggcttgg aaggctgatg gatctcctgt gaaggccggc | 540 |
| gtggaaacca ccaagcctag caagcagtcc aacaacaaat acgccgcctc ctcctacctg | 600 |
| tctctgaccc ctgaacagtg gaagtcccac cggtcctact cttgccaagt gacccatgag | 660 |
| ggctccaccg tggaaaagac agtggcccct accgagtgct ctggatcttc tggtggcgga | 720 |
| ggatctggcg gaggtggaag tagtggcggc gtgaccggct acagactgtt cgaagagatc | 780 |
| ctgtaatga | 789 |

<210> SEQ ID NO 57
<211> LENGTH: 708
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 57

| atggaaaccg acacactgct gctgtgggtg ctgctcttgt gggtgccagg ctctaccgga | 60 |
| tcctctgagc tgacacagga ccctgctgtg tctgtggctc tgggccagac agtgcggatt | 120 |
| acctgtcagg gcgactccct gagatcctac tacgcctcct ggtatcagca gaagcctgga | 180 |
| caggctcccg tgctggtcat ctacggcaag aacaaccggc ctagcggcat ccctgacaga | 240 |
| ttctccggat cttccagcgg caataccgcc agcctgacaa ttactggcgc ccaggctgag | 300 |
| gacgaggccg actactactg caactccaga gactcctccg gcaatcacgt ggtgtttggc | 360 |
| ggcggaacaa agctgacagt gctgggccag cctaaggcca atcctaccgt gacactgttc | 420 |
| cctccatcct ccgaggaact gcaggccaac aaggctaccc tcgtgtgcct gatctccgac | 480 |
| ttttaccctg gcgctgtgac cgtggcctgg aaggctgatg gatctcctgt gaaggctggc | 540 |
| gtggaaacca ccaagccttc caagcagtcc aacaacaaat acgccgcctc ctcctacctg | 600 |
| tctctgaccc ctgaacagtg gaagtcccac cggtcctaca gctgccaagt gacccatgag | 660 |
| ggctccaccg tggaaaagac cgtggctcct accgagtgct cctgatga | 708 |

<210> SEQ ID NO 58
<211> LENGTH: 1242
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic polynucleotide"

<400> SEQUENCE: 58

| | | | | | |
|---|---|---|---|---|---|
| atggaaaccg | acacactgct | gctgtgggtg | ctgttgttgt | gggtgccagg | atctacagga | 60 |
| caggtgcagt | tggtgcagtc | tggcgccgaa | gtgaagaaac | ctggcgcttc | tgtgaaggtg | 120 |
| tcctgcaagg | cctctggcta | cacctttacc | tccagctaca | tcaactgggt | ccgacaggct | 180 |
| cctggacagg | gacttgagtg | gatgggcacc | atcaatcctg | tgtccggctc | taccagctac | 240 |
| gcccagaaat | tcagggcag | agtgaccatg | accagagaca | cctccatctc | caccgcctac | 300 |
| atggaactgt | cccggctgag | atctgacgac | accgccgtgt | actattgtgc | cagaggcgga | 360 |
| tggttcgatt | actggggaca | gggcacactg | gtcaccgtgt | cctctgcttc | taccaaggga | 420 |
| ccctctgtgt | tccctctggc | tccttccagc | aagtctacct | ctggtggaac | cgctgctctg | 480 |
| ggctgcctgg | tcaaggatta | ctttcctgag | cctgtgaccg | tgtcttggaa | ctctggtgct | 540 |
| ctgacctccg | gcgtgcacac | atttccagct | gtgctgcagt | cctccggcct | gtactctctg | 600 |
| tcctctgtcg | tgaccgtgcc | ttctagctct | ctgggcaccc | agacctacat | ctgcaacgtg | 660 |
| aaccacaagc | cttccaacac | caaggtggac | aagagagtgg | aacccaagtc | ttgcggatct | 720 |
| tctggtggcg | gaggatctgg | cggaggtgga | agtagtggcg | gagtgttcac | cctggaagat | 780 |
| ttcgtcggca | ttgggagca | gaccgccgcc | tataatctgg | accaggttct | ggaacaaggc | 840 |
| ggcgtcagct | ctctgctgca | gaatctggct | gtgtctgtga | ccctatcca | gagaattgtg | 900 |
| cgctctggcg | agaacgccct | gaagatcgac | atccacgtga | tcatccctta | cgagggcctg | 960 |
| tctgccgatc | agatggctca | gatcgaagag | gtgttcaagg | tggtgtaccc | cgtggacgac | 1020 |
| caccacttca | aagtgatcct | gccttacggc | acccctggtca | tcgatggcgt | gaccccaaac | 1080 |
| atgctgaact | acttcggcag | accctacgag | ggaatcgccg | tgttcgacgg | caagaaaatc | 1140 |
| accgtgaccg | gcacactgtg | gaacggcaac | aagatcatcg | acgagcggct | gatcacccct | 1200 |
| gacggctcta | tgctgttccg | cgtgaccatc | aactcctaat | ga | | 1242 |

<210> SEQ ID NO 59
<211> LENGTH: 798
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 59

| | | | | | |
|---|---|---|---|---|---|
| atggaaaccg | acacactgct | gctgtgggtg | ctgttgttgt | gggtgccagg | ctctacaggc | 60 |
| cagtctgctt | tgactcagcc | tgcctctgtg | tctggctccc | ctggccagtc | tatcaccatc | 120 |
| tcttgtaccg | gcacctcctc | cgacgtgggc | tcctacaact | acgtgaactg | gtatcagcag | 180 |
| caccccggca | aggcccctaa | gctgatgatc | tacgacgtgt | ccaaacgcc | cagcggagtg | 240 |
| tctaacagat | tctccggctc | caagtctggc | aacaccgctt | ctctgacaat | cagcggactg | 300 |
| caggccgagg | acgaggctga | ttactactgt | ggcaccttcg | ctggcggctc | ctactatggt | 360 |
| gtttttggcg | gcggaacaaa | gctgaccgtg | ctgggccaac | ctaaggccaa | tcctaccgtg | 420 |
| acactgttcc | ctccatcctc | cgaggaactg | caggctaaca | aggctaccct | cgtgtgcctg | 480 |
| atctccgatt | tttaccctgg | cgctgtgacc | gtggcttgga | aggctgatgg | atctcctgtg | 540 |
| aaggccggcg | tggaaaccac | caagcctagc | aagcagtcca | acaacaaata | cgccgcctcc | 600 |

```
tcctacctgt ctctgacccc tgaacagtgg aagtcccacc ggtcctactc ttgccaagtg    660
acccatgagg gctccaccgt ggaaaagaca gtggccccta ccgagtgctc tggatcttct    720
ggtggcggag gatctggcgg aggtggaagt agtggcggcg tgaccggcta cagactgttc    780
gaagagatcc tgtaatga                                                  798
```

<210> SEQ ID NO 60
<211> LENGTH: 717
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 60

```
atggaaaccg acacactgct gctgtgggtg ctgttgttgt gggtgccagg ctctacaggc     60
cagtctgctt tgactcagcc tgcctctgtg tctggctccc ctggccagtc tatcaccatc    120
tcttgtaccg gcacctcctc cgacgtgggc tcctacaact acgtgaactg gtatcagcag    180
caccccggca aggcccctaa gctgatgatc tacggcgtgt ccaaacggcc cagcggagtg    240
tctaacagat tctccggctc caagtctggc aacaccgctt ctctgacaat cagcggactg    300
caggccgagg acgaggctga ttactactgt ggcaccttcg ctggcggctc ctactatggt    360
gtttttggcg gcggaacaaa gctgaccgtg ctgggccaac taaggccaa tcctaccgtg    420 acactgttcc ctccatcctc cgaggaactg caggctaaca aggctaccct cgtgtgcctg    480
atctccgatt tttaccctgg cgctgtgacc gtggcttgga aggctgatgg atctcctgtg    540
aaggccggcg tggaaaccac caagcctagc aagcagtcca acaacaaata cgccgcctcc    600
tcctacctgt ctctgacccc tgaacagtgg aagtcccacc ggtcctactc ttgccaagtg    660
acccatgagg gctccaccgt ggaaaagaca gtggccccta ccgagtgctc ttaatga      717
```

<210> SEQ ID NO 61
<211> LENGTH: 1245
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 61

```
atggaaaccg acacactgct gctgtgggtg ctgttgttgt gggtgccagg atctacaggc     60
gaagtgcagt tggtgcagtc tggcgccgaa gtgaagaaac ctggctcctc tgtgaaggtg    120
tcctgcaagg cttctggcgg caccttctcc tcttacgcca tctcttgggt ccgacaggct    180
cctggacaag gcttggagtg gatgggcggc atcgcccctt ttttcggcac cgccaactac    240
gcccagaaat tccagggcag agtgaccatc accgccgacg agtctacctc caccgcttac    300
atggaactgt ccagcctgag atctgaggac accgccgtgt actactgcgc cagagacacc    360
ccttacttcg attattgggg ccagggcacc ctggtcaccg tgtcctctgc ttctacaaag    420
ggcccctctg tgttccctct ggctcctagc tctaagtcta catctggcgg aaccgctgct    480
ctgggctgcc tggtcaagga ttactttcct gagcctgtga ccgtgtcttg gaactctggt    540
gctctgacct ccggcgtgca cacatttcca gctgtgctgc agtcctccgg cctgtactct    600
ctgtcctctg tcgtgaccgt gccttctagc tctctgggca cccagaccta catctgcaac    660
```

```
gtgaaccaca agccttccaa caccaaggtg gacaagagag tggaacccaa gtcttgcgga      720
tcttccggtg gcggaggaag cggaggcgga ggatctagtg gcggagtgtt caccctggaa      780
gatttcgtcg gcgattggga gcagaccgcc gcctataatc tggaccaggt tctggaacaa      840
ggcggggtgt cctctctgct gcagaatctg gctgtgtctg tgaccccat ccagagaatc       900 gtgcgctctg gcgagaacgc cctgaagatc gacatccacg tgatcatccc ttacgagggc      960
ctgtctgccg atcagatggc tcagatcgaa gaggtgttca aggtggtgta ccccgtggac     1020
gaccaccact tcaaagtgat cctgccttac ggcaccctcg tgatcgatgg cgtgaccca      1080 aacatgctga actacttcgg cagacccta cgagggaatcg ccgtgttcga cggcaagaaa     1140
atcaccgtga ccggcacact gtggaacggc aacaagatca tcgacgagcg gctgatcacc     1200
cctgacggct ctatgctgtt tagagtgaca atcaactcct aatga                    1245

<210> SEQ ID NO 62
<211> LENGTH: 789
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 62
atggaaaccg acacactgct gctgtgggtg ctgttgttgt gggtgccagg ctctaccggc       60
tcttatgagc tgacacagcc tctgtctgtg tctgtggctc tgggccagac cgccagaatc      120
acctgttctg gcgacagcat ccccaactac tacgtgtact ggtatcagca gaagcccggc      180
caggctcctg tgctggtcat ctacgacgac tccaacagac ccagcggcat ccctgagaga      240
ttctccggct ctaactctgg caacaccgcc acactgacca tctctagagc acaggctggc      300
gacgaggccg actactactg ccagtctttc gacagctctc tgaacgccga agtgttcggc      360
ggaggcacaa aactgacagt gctgggccag cctaaggcca tcctaccgt gacactgttc      420 cctccatcct ccgaggaact gcaggctaac aaggctaccc tcgtgtgcct gatctccgat      480
ttttaccctg gcgctgtgac cgtggcttgg aaggctgatg gatctcctgt gaaggccggc      540
gtggaaacca ccaagcctag caagcagtcc aacaacaaat acgccgcctc ctcctacctg      600
tctctgaccc ctgaacagtg gaagtccac cggtcctact cttgccaagt gacccatgag      660
ggctccaccg tggaaaagac agtggcccct accgagtgct tggatcttc tggtggcgga      720 ggatctggcg gaggtggaag tagtggcggc gtgaccggct acagactgtt cgaagagatc      780
ctgtaatga                                                              789

<210> SEQ ID NO 63
<211> LENGTH: 708
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 63
atggaaaccg acacactgct gctgtgggtg ctgttgttgt gggtgccagg ctctaccggc       60
tcttatgagc tgacacagcc tctgtctgtg tctgtggctc tgggccagac cgccagaatc      120
acctgttctg gcgacagcat ccccaactac tacgtgtact ggtatcagca gaagcccggc      180
caggctcctg tgctggtcat ctacgacgac tccaacagac ccagcggcat ccctgagaga      240
```

```
ttctccggct ctaactctgg caacaccgcc acactgacca tctctagagc acaggctggc    300
gacgaggccg actactactg ccagtctttc gacagctctc tgaacgccga agtgttcggc    360
ggaggcacaa aactgacagt gctgggccag cctaaggcca atcctaccgt gacactgttc    420
cctccatcct ccgaggaact gcaggctaac aaggctaccc tcgtgtgcct gatctccgat    480 tttaccctg cgctgtgac cgtggcttgg aaggctgatg gatctcctgt gaaggccggc    540
gtggaaacca ccaagcctag caagcagtcc aacaacaaat acgccgcctc ctcctacctg    600
tctctgaccc ctgaacagtg gaagtcccac cggtcctact cttgccaagt gacccatgag    660
ggctccaccg tggaaaagac agtggcccct accgagtgct cttaatga                708
```

<210> SEQ ID NO 64
<211> LENGTH: 1239
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 64

```
atggaaaccg acacactgct gctgtgggtg ctgttgttgt gggtgccagg atctacaggc     60
gaagtgcagt tggtgcagtc tggcgccgaa gtgaagaaac ctggcgcttc tgtgaaggtg    120
tcctgcaagg cctctggcta caccttttacc ggctaccaca tgcactgggt ccgacaggct    180
ccaggacaag gattggagtg gatgggctgg atcaacccca actccggcgt gaccaaatac    240
gcccagaaat tccagggcag agtgaccatg accagagaca cctccatcaa caccgcctac    300
atggaactgt cccggctgag attcgacgac accgacgtgt actattgtgc caccggcggc    360
tttggctatt ggggagaggg aacactggtc accgtgtcct ctgcttctac caagggaccc    420
tccgtgtttc ctctggctcc ttccagcaag tctacctctg gtggaaccgc tgctctgggc    480
tgcctggtca aggattactt tcctgagcct gtgaccgtgt cttggaactc tggtgctctg    540
accagcggcg tgcacacatt tccagctgtg ctgcagtcct ccggcctgta ctctctgtcc    600
tctgtcgtga ccgtgccttc tagctctctg ggcacccaga cctacatctg caacgtgaac    660
cacaagcctt ccaacaccaa ggtggacaag agagtggaac ccaagtcttg cggatcttct    720
ggtggcggag gatctggcgg aggtggaagt agtggcggag tgttcaccct ggaagatttc    780
gtcggcgatt gggagcagac cgccgcctat aatctggacc aggttctgga caaggcggc    840 gtcagctctc tgctgcagaa tctggctgtg tctgtgaccc ctatccagag aatcgtgcgc    900
tctggcgaga acgccctgaa gatcgacatc cacgtgatca tcccttacga gggcctgtct    960
gccgatcaga tggctcagat cgaagaggtg ttcaaggtgg tgtacccgcgt ggacgaccac   1020 cacttcaaag tgatcctgcc ttacggcacc ctggtcatcg atggcgtgac cccaaacatg   1080
ctgaactact cggcagacc ctacgaggga atcgccgtgt cgacggcaa gaaaatcacc     1140 gtgaccggca cactgtggaa cggcaacaag atcatcgacg agcggctgat caccctgac    1200 ggctctatgc tgttccgcgt gaccatcaac tcctaatga                         1239
```

<210> SEQ ID NO 65
<211> LENGTH: 795
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 65

```
atggaaaccg acacactgct gctgtgggtg ctgttgttgt gggtgccagg atctacaggc    60
ctgcctgttc tgacacagcc tcctagcgtg tccaagggcc tgagacagac cgctacactg   120
acctgcaccg gcaactctaa caacgtggga atcagggcg ctgcctggtt gcagcagcat   180
cagggacaac ctccaaagct gctgtcctac cggaaccaca atagaccttc cggcgtgtcc   240
gagcggttca gcccttctag atctggcgac acctctagcc tgaccatcac tggactgcag   300
cctgaggacg aggccgatta ctactgtctg gcctgggatt cttctctgcg ggcctttgtg   360
tttggcaccg gcacaaaact gaccgtgctg gccagccta aggccaatcc tacagtgacc   420
ctgtttcctc catcctccga ggaactgcag gccaacaagg ctaccctcgt gtgcctgatc   480
tctgactttt accctggcgc tgtgaccgtg gcttggaagg ctgatggatc tcctgtgaag   540
gccggcgtgg aaaccaccaa gcctagcaag cagtccaaca caaatacgc cgcctcctcc   600
tacctgtctc tgaccctga acagtggaag tcccaccggt cctactcttg ccaagtgacc   660
catgagggct ccaccgtgga aaagacagtg gcccctaccg agtgctctgg atcttctggt   720
ggcggaggat ctggcggagg tggaagtagt ggcggcgtga ccggctacag actgttcgaa   780
gagatcctgt aatga                                                   795
```

<210> SEQ ID NO 66
<211> LENGTH: 714
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 66

```
atggaaaccg acacactgct gctgtgggtg ctgctcttgt gggtgccagg atctacagga    60
ctgcccgtgt tgacccagcc tcctagcgtt tccaagggcc tgagacagac cgccacactg   120
acctgtaccg gcaactctaa caacgtgggc aatcagggcg ctgcctggtt gcagcagcat   180
cagggacagc ctccaaagct gctgtcctac cggaaccaca acagacctag cggcgtgtcc   240
gagcggttca gcccttctag atctggcgac acctccagcc tgaccatcac tggactgcag   300
cctgaggacg aggccgacta ctattgtctg gcctgggaca ctccctgcg ggcctttgtt   360
tttggcaccg gcaccaagct gaccgtgctg gacaaccta aggccaatcc taccgtgaca   420
ctgttccctc catcctccga ggaactgcag gccaacaagg ctaccctcgt gtgcctgatc   480
tccgactttt accctggcgc tgtgaccgtg gcctggaagg ctgatggatc tcctgtgaag   540
gctggcgtgg aaaccaccaa gccttccaag cagtccaaca caaatacgc cgcctcctcc   600
tacctgtctc tgaccctga acagtggaag tcccaccggt cctacagctg ccaagtgacc   660
catgagggct ccaccgtgga aaagaccgtg gctcctaccg agtgctcctg atga        714
```

<210> SEQ ID NO 67
<211> LENGTH: 1233
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 67

```
atggaaaccg acacactgct gctgtgggtg ctgttgttgt gggtgccagg atctacaggc    60
```

```
gaggtgcagt tggttgaatc tggcggagga ttggtgcagc ctggcggatc tctgagactg    120
tcttgtgtgg cctccggctt caccttctcc gactactgga tgtcctgggt ccgacaggct    180
cctggcaaag gactggaatg ggtcgccaac atcaagaaag acggctccgt gaactactac    240
gtggactccg tgaagggcag attcaccatc tctcgggaca cgccaagaa ctccctgtac     300 ctgcagatga acagcctgag agccgaggac accgccgtgt actactgcac cagattcgat    360
tattggggcc agggcaccct ggtcaccgtg tcctctgctt ctacaaaggg cccctctgtg    420
ttccctctgg ctccttcctc taaatccacc tctggcggaa ccgctgctct gggctgtctg    480
gtcaaggatt acttccctga gcctgtgacc gtgtcttgga actctggtgc tctgacatcc    540
ggcgtgcaca cctttccagc tgtgctgcag tcctctggcc tgtactctct gtcctctgtc    600
gtgaccgtgc cttctagctc tctgggcacc cagacctaca tctgcaacgt gaaccacaag    660
ccttccaaca ccaaggtgga caagagagtg aacccaagt cttgcggatc ttctggtggt     720
ggtggaagtg gcggaggcgg ttcttcaggc ggagtgttca ccctggaaga tttcgtcggc    780
gattgggagc agaccgccgc ctataatctg gaccaggttc tggaacaagg cggcgtcagc    840
tctctgctgc agaatctggc tgtgtctgtg acccctatcc agagaatcgt gcgctctggc    900
gagaacgccc tgaagatcga catccacgtg atcatccctt acgagggcct gtctgccgat    960
cagatggctc agatcgaaga ggtgttcaag gtggtgtacc ccgtggacga ccaccacttc    1020
aaagtgatcc tgccttacgg caccctcgtg atcgatggcg tgaccccaaa catgctgaac    1080
tacttcggca gaccctacga gggaatcgcc gtgttcgacg caagaaaat caccgtgacc    1140 ggcacactgt ggaacggcaa caagatcatc gacgagcggc tgatcacccc tgacggctcc    1200
atgctgttta gagtgaccat caactcctaa tga                                1233

<210> SEQ ID NO 68
<211> LENGTH: 795
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 68
atggaaaccg acacactgct gctgtgggtg ctgttgttgt gggtgccagg atctacaggc     60
caggctggat tgacacagcc tcctagcgtg tccaagggcc tgagacagac cgctacactg    120
acctgcaccg gcaactctaa caacgtggga aatcagggcg ctgcctggtt gcagcagcat    180
cagggacatc ctccaaagct gctgttctac cggaacaaca atagagcctc cggcatctcc    240
gagcggctgt ctgcttctag atctggcaat accgccagcc tgaccatcac tggactgcag    300
cctgaggacg aggccgacta ctattgcctg acctgggact cctctctgtc cgtggttgtg    360
tttggcggcg gaacaaagct gacagtgctg ggccagccta aggccaatcc taccgtgaca    420
ctgttccctc catcctccga ggaactgcag gctaacaagg ctacccctgt gtgcctgatc    480
tccgattttt accctggcgc tgtgaccgtg gcttggaagg ctgatggatc tcctgtgaag    540
gccggcgtga aaaccaccaa gcctagcaag cagtccaaca caaatacgc cgcctcctcc    600 tacctgtctc tgacccctga acagtggaag tcccaccggt cctactcttg ccaagtgacc    660
catgagggct ccaccgtgga aaagacagtg gcccctaccg agtgctctgg atcttctggt    720
ggcggaggat ctggcggagg tggaagtagt ggcggcgtga ccggctacag actgttcgaa    780
gagatcctgt aatga                                                     795
```

<210> SEQ ID NO 69
<211> LENGTH: 714
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 69

| | | | | | |
|---|---|---|---|---|---|
| atggaaaccg | acacactgct | gctgtgggtg | ctgctcttgt | gggtgccagg | atctacagga | 60 |
| caggctggct | tgacccagcc | tcctagcgtt | tccaagggcc | tgagacagac | cgccacactg | 120 |
| acctgtaccg | gcaactctaa | caacgtgggc | aatcagggcg | ctgcctggtt | gcagcagcat | 180 |
| cagggacatc | ctccaaagct | gctgttctac | cggaacaaca | acagagcctc | cggcatctcc | 240 |
| gagcggctgt | ctgcttctag | atccggcaat | accgccagcc | tgaccatcac | tggactgcag | 300 |
| cctgaggacg | aggccgacta | ctattgcctg | acctgggact | cctctctgtc | cgtggtggtt | 360 |
| tttggcggag | gcaccaagct | gacagtgctg | ggacagccta | aggccaatcc | taccgtgaca | 420 |
| ctgttccctc | catcctccga | ggaactgcag | gccaacaagg | ctaccctcgt | gtgcctgatc | 480 |
| tccgactttt | accctggcgc | tgtgaccgtg | gcctggaagg | ctgatggatc | tcctgtgaag | 540 |
| gctggcgtgg | aaaccaccaa | gccttccaag | cagtccaaca | acaaatacgc | cgcctcctcc | 600 |
| tacctgtctc | tgaccccctga | acagtggaag | tcccaccggt | cctacagctg | ccaagtgacc | 660 |
| catgagggct | ccaccgtgga | aaagaccgtg | gctcctaccg | agtgctcctg | atga | 714 |

<210> SEQ ID NO 70
<211> LENGTH: 1242
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 70

| | | | | | |
|---|---|---|---|---|---|
| atggaaaccg | acacactgct | gctgtgggtg | ctgctcttgt | gggtgccagg | atctacagga | 60 |
| caggtgcagc | tggtggaatc | tggtggcgga | gttgtgcagc | ctggcagatc | cctgagactg | 120 |
| tcttgtgccg | cctccggctt | caccttctcc | tcttacggaa | tgcactgggt | ccgacaggcc | 180 |
| cctggcaaag | gattggagtg | ggtcgccttc | atcagatacg | acggctccaa | caagtactac | 240 |
| gccgactccg | tgaagggcag | attcaccatc | tctcgggaca | actccaagaa | caccctgtac | 300 |
| ctgcagatga | actccctgag | agccgaggac | accgccgtgt | actactgcaa | gacccacggc | 360 |
| tctcacgaca | ttggggccca | gggcacaatg | gtcaccgtgt | cctctgcttc | caccaaggga | 420 |
| ccctctgtgt | tccctctggc | tccttccagc | aagtctacct | ctggcggaac | agctgctctg | 480 |
| ggctgcctgg | tcaaggacta | cttttcctgag | cctgtgaccg | tgtcttggaa | ctctggcgct | 540 |
| ctgacatccg | gcgtgcacac | ctttccagct | gtgctgcaat | cctccggcct | gtactctctg | 600 |
| tcctccgtcg | tgaccgtgcc | ttctagctct | ctgggcaccc | agacctacat | ctgcaatgtg | 660 |
| aaccacaagc | cttccaacac | caaggtggac | aagagagtgg | aacccaagtc | ctgcggatct | 720 |
| tctggcggcg | aggatctgg | cggaggtggt | agttcaggcg | gagtgttcac | cctggaagat | 780 |
| ttcgtcggcg | actgggagca | gaccgccgcc | tataatctgg | accaggtgct | ggaacaaggc | 840 |
| ggcgtcagtt | ctctgctgca | gaacctggct | gtgtctgtga | cccctatcca | gagaatcgtg | 900 |

| | |
|---|---|
| cggagcggcg agaacgccct gaagatcgat atccacgtga tcatcccttta cgagggcctg | 960 |
| agcgccgatc agatggctca gatcgaagag gtgttcaagg tggtgtaccc cgtggacgac | 1020 |
| caccacttca aagtgatcct gccttacggc accctggtca tcgatggcgt gaccccaaac | 1080 |
| atgctgaact acttcggcag accctacgag ggaatcgccg tgttcgacgg caagaaaatc | 1140 |
| accgtgaccg gcacactgtg gaacggcaac aagatcatcg acgagcggct gatcacccct | 1200 |
| gacggctcta tgctgttcag agtgaccatc aacagctgat ga | 1242 |

<210> SEQ ID NO 71
<211> LENGTH: 798
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 71

| | |
|---|---|
| atggaaaccg acacactgct gctgtgggtg ctgctcttgt gggtgccagg atctaccgga | 60 |
| cagtccgtgt tgacccagcc tccttctgtt tctggcgctc ctggccagag agtgaccatc | 120 |
| tcttgctccg gctctcggtc caacatcggc tccaataccg tgaagtggta tcagcagctg | 180 |
| cccggcacag ctcccaaact gctgatctac tacaacgacc agcggccttc tggcgtgccc | 240 |
| gatagattct ctggctccaa gtctggcacc tctgccagcc tggctattac cggactgcag | 300 |
| gctgaggacg aggccgacta ctactgccag tcttacgacc ggtacaccca tcctgctctg | 360 |
| ctgtttggca ccggcaccaa agtgacagtg ctggccagc taaggccaa tcctaccgtg | 420 |
| acactgttcc ctccatcctc cgaagaactg caggccaaca aggctaccct cgtgtgcctg | 480 |
| atctccgact tttaccctgg cgctgtgacc gtggcctgga aggctgatgg atctcctgtg | 540 |
| aaggctggcg tggaaaccac caagccttcc aagcagtcca acaacaaata cgccgcctcc | 600 |
| tcctacctgt ctctgacccc tgaacagtgg aagtcccacc ggtcctacag ctgccaagtg | 660 |
| acccatgagg gctccaccgt ggaaaagacc gtggctccta ccgagtgctc cggatcttct | 720 |
| ggtggcggag gatctggcgg aggcggttct tcaggcggag tgaccggcta cagactgttc | 780 |
| gaagagatcc tgtgatga | 798 |

<210> SEQ ID NO 72
<211> LENGTH: 717
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 72

| | |
|---|---|
| atggaaaccg acacactgct gctgtgggtg ctgctcttgt gggtgccagg atctaccgga | 60 |
| cagtccgtgt tgacccagcc tccttctgtt tctggcgctc ctggccagag agtgaccatc | 120 |
| tcttgctccg gctctcggtc caacatcggc tccaataccg tgaagtggta tcagcagctg | 180 |
| cccggcacag ctcccaaact gctgatctac tacaacgacc agcggccttc tggcgtgccc | 240 |
| gatagattct ctggctccaa gtctggcacc tctgccagcc tggctattac cggactgcag | 300 |
| gctgaggacg aggccgacta ctactgccag tcttacgacc ggtacaccca tcctgctctg | 360 |
| ctgtttggca ccggcaccaa agtgacagtg ctggccagc taaggccaa tcctaccgtg | 420 |
| acactgttcc ctccatcctc cgaagaactg caggccaaca aggctaccct cgtgtgcctg | 480 |

```
atctccgact tttaccctgg cgctgtgacc gtggcctgga aggctgatgg atctcctgtg    540
aaggctggcg tggaaaccac caagccttcc aagcagtcca acaacaaata cgccgcctcc    600
tcctacctgt ctctgacccc tgaacagtgg aagtcccacc ggtcctacag ctgccaagtg    660
acccatgagg gctccaccgt ggaaaagacc gtggctccta ccgagtgctc ctgatga       717
```

<210> SEQ ID NO 73
<211> LENGTH: 1410
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 73

```
atggaaaccg acacactgct gctgtgggtg ctgctcttgt gggtgccagg atctacagga    60
caggtgcagc tggtggaatc tggtggcgga gttgtgcagc ctggcagatc cctgagactg    120
tcttgtgccg cctccggctt caccttctcc agctacacca tgcactgggt ccgacaggcc    180
cctggcaaag gattggagtg ggtcaccttc atctcttacg acggcaacaa caagtactac    240
gccgactccg tgaagggcag attcaccatc tctcgggaca actccaagaa caccctgtac    300
ctgcagatga actccctgag agccgaggac accgccatct actactgtgc tagaaccggc    360
tggctgggcc cctttgatta ttggggacag ggcaccctgg tcaccgtgtc ctctgcttct    420
accaagggac ccagcgtgtt ccctctggct ccttccagca gtctacctc tggcggaaca     480 gctgctctgg gctgcctggt caaggactac tttcctgagc ctgtgaccgt gtcttggaac    540
tctggcgctc tgacatccgg cgtgcacaca tttccagctg tgctgcagtc ctccggcctg    600
tactctctgt cctctgtcgt gaccgtgcct tccagctctc tgggaaccca gacctacatc    660
tgcaatgtga accacaagcc ttccaacacc aaggtggaca gagagtggga acccaagtcc    720
tgcgacaaga cccacacctg tccaccatgt cctgctccag aactgctcgg cggaccttcc    780
gtgttcctgt ttcctccaaa gcctaaggac accctgatga tctctcggac ccctgaagtg    840
acctgcgtgg tggtggatgt gtctcacgag atcccgaag tgaagttcaa ttggtacgtg    900
gacggcgtgg aagtgcacaa cgccaagacc aagcctagag aggaacagta caactccacc    960
tacagagtgg tgtccgtgct gaccgtgctg caccaggatt ggctgaacgg caaagagtac    1020
aagtgcaagg tgtccaacaa ggcccctgcct gctcctatcg aaaagaccat ctccaaggcc    1080
aagggccagc ctagggaacc ccaggtttac accctgcctc aagccgggga agagatgacc    1140
aagaaccagg tgtccctgac ctgcctcgtg aagggattct acccctccga tatcgccgtg    1200
gaatgggagt ctaatggcca gcctgagaac aactacaaga caccctcc tgtgctggac    1260 tccgacggct cattcttcct gtactccaag ctgacagtgg acaagtccag atggcagcag    1320
ggcaacgtgt tctcctgctc cgtgatgcac gaggccctgc acaatcacta cacccagaag    1380
tccctgtctc tgagccccgg caagtgatga                                    1410
```

<210> SEQ ID NO 74
<211> LENGTH: 1401
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 74

```
atggaaaccg acacactgct gctgtgggtg ctgctcttgt gggtgccagg atctacagga      60
caggtgcagc tggtggaatc tggtggcgga gttgtgcagc tggcagatc cctgagactg     120
tcttgtgccg cctccggctt caccttctcc tcttacggaa tgcactgggt ccgacaggcc    180
cctggcaaag gattggagtg ggtcgccttc atcagatacg acggctccaa caagtactac    240
gccgactccg tgaagggcag attcaccatc tctcgggaca actccaagaa cacccctgtac 300
ctgcagatga actccctgag agccgaggac accgccgtgt actactgcaa gacccacggc    360
tctcacgaca ttggggcca gggcacaatg gtcaccgtgt cctctgcttc caccaaggga    420
ccctctgtgt tccctctggc tccttccagc aagtctacct ctggcggaac agctgctctg    480
ggctgcctgg tcaaggacta ctttcctgag cctgtgaccg tgtcttggaa ctctggcgct    540
ctgacatccg gcgtgcacac ctttccagct gtgctgcaat cctccggcct gtactctctg    600
tcctccgtcg tgaccgtgcc ttctagctct ctgggcaccc agacctacat ctgcaatgtg    660
aaccacaagc cttccaacac caaggtggac aagagagtgg aacccaagtc ctgcgataag    720
acccacacct gtccaccatg tcctgctcca gaactgctcg gcggaccttc cgtgttcctg    780
tttcctccaa agcctaagga cacccctgatg atctctcgga cccctgaagt gacctgcgtg   840
gtggtggatg tgtctcacga ggatcccgaa gtgaagttca attggtacgt ggacggcgtg    900
gaagtgcaca cgccaagac caagcctaga gggaacagt acaactccac ctacagagtg    960
gtgtccgtgc tgaccgtgct gcaccaggat tggctgaacg gcaaagagta caagtgcaag   1020
gtgtccaaca aggccctgcc tgctcctatc gaaaagacca tctccaaggc caagggccag   1080
cctagggaac cccaggttta caccctgcct ccaagccggg aagagatgac caagaaccag   1140
gtgtccctga cctgcctcgt gaagggattc tacccctccg atatcgccgt ggaatgggag   1200
tctaatggcc agcctgagaa caactacaag accacacctc ctgtgctgga ctccgacggc   1260
tcattcttcc tgtactccaa gctgacagtg gacaagtcca gatggcagca gggcaacgtg   1320
ttctcctgct ccgtgatgca cgaggccctg cacaatcact acacccagaa gtccctgtct   1380
ctgagccccg gcaagtgatg a                                              1401
```

<210> SEQ ID NO 75
<211> LENGTH: 1161
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 75

```
atggaaaccg acacactgct gctgtgggtg ctgctcttgt gggtgccagg atctaccgga      60
cagtccgtgt tgacccagcc tccttctgtt tctggcgctc ctggcagag agtgaccatc     120
tcttgctccg gctctcggtc caacatcggc tccaataccg tgaagtggta tcagcagctg    180
cccggcacag ctcccaaaact gctgatctac tacaacgacc agcggccttc tggcgtgccc    240
gatagattct ctggctccaa gtctggcacc tctgccagcc tggctattac cggactgcag    300
gctgaggacg aggccgacta ctactgccag tcttacgacc ggtacaccca tcctgctctg    360
ctgtttggca ccggcaccaa agtgacagtg ctgggccagc taaggccaa tcctaccgtg    420
acactgttcc ctccatcctc cgaagaactg caggccaaca aggctaccct cgtgtgcctg    480
atctccgact tttaccctgg cgctgtgacc gtggcctgga aggctgatgg atctcctgtg    540
```

```
aaggctggcg tggaaaccac caagccttcc aagcagtcca acaacaaata cgccgcctcc    600
tcctacctgt ctctgacccc tgaacagtgg aagtcccacc ggtcctacag ctgccaagtg    660
acccatgagg gctccaccgt ggaaaagacc gtggctccta cagagtgttc tggcggcgga    720
ggatctggcg gaggtggaag cggaggcggt ggatctgctc ctacctcctc cagcaccaag    780
aaaacccagc tgcagttgga gcatctgctg ctggacctgc agatgatcct gaacggcatc    840
aacaactaca gaaccccaa gctgacccgg atgctgaccg ccaagtttgc catgcctaag    900
aaggccaccg agctgaaaca tctgcagtgc ctggaagagg aactgaagcc cctggaagaa    960
gtgctgaatc tggcccagtc caagaacttc caccctgagg ctcgggacct gatcagcaac   1020
atcaacgtga tcgtgctcga gctgaagggc tccgagacaa ccttcatgtg cgagtacgcc   1080
gacgagacag ctaccatcgt ggaatttctg aaccggtgga tcaccttctg ccagtccatc   1140
atcagcaccc tgacctgatg a                                              1161

<210> SEQ ID NO 76
<211> LENGTH: 1845
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 76
atggaaaccg acacactgct gctgtgggtg ctgctcttgt gggtgccagg atctacagga     60
caggtgcagc tggtggaatc tggtggcgga gttgtgcagc tggcagatc cctgagactg    120 tcttgtgccg cctccggctt caccttctcc tcttacggaa tgcactgggt ccgacaggcc    180
cctggcaaag gattggagtg ggtcgccttc atcagatacg acggctccaa caagtactac    240
gccgactccg tgaagggcag attcaccatc tctcgggaca actccaagaa caccctgtac    300
ctgcagatga actccctgag agccgaggac accgccgtgt actactgcaa gacccacggc    360
tctcacgaca attggggcca gggcacaatg gtcaccgtgt cctctgcttc caccaaggga    420
ccctctgtgt tccctctggc tccttccagc aagtctacct ctggcggaac agctgctctg    480
ggctgcctgg tcaaggacta cttccctgag cctgtgaccg tgtcttggaa ctctggcgct    540
ctgacatccg gcgtgcacac cttttccagc tgtgctgcaat cctccggcct gtactctctg    600
tcctccgtcg tgaccgtgcc ttctagctct ctgggcaccc agacctacat ctgcaatgtg    660
aaccacaagc cttccaacac caaggtggac aagagagtgg aacccaagtc ctgcgataag    720
acccacacct gtccaccatg tcctgctcca gaactgctcg gcggaccttc cgtgttcctg    780
tttcctccaa agcctaagga caccctgatg atctctcgga cccctgaagt gacctgcgtg    840
gtggtggatg tgtctcacga ggatcccgaa gtgaagttca attggtacgt ggacggcgtg    900
gaagtgcaca cgccaagac caagcctaga gaggaacagt acaactccac ctacagagtg    960
gtgtccgtgc tgaccgtgct gcaccaggat tggctgaacg gcaaagagta caagtgcaag   1020
gtgtccaaca aggcccctgcc tgctcctatc gaaaagacca tctccaaggc caagggccag   1080
cctcgggaac ctcaagtctg taccctgcct cctagccggg aagagatgac caagaaccag   1140
gtgtccctgt cctgcgctgt gaagggcttc taccccttcg atatcgccgt ggaatgggag   1200
agcaatggcc agcctgagaa caactacaag accacacctc ctgtgctgga ctccgacggc   1260
tcattcttcc tggtgtccaa gctgacagtg gacaagtcca gatggcagca gggcaacgtg   1320
```

```
ttctcctgct ccgtgatgca cgaggccctg cacaatcact acacccagaa gtccctgtct    1380
ctgtctcccg aaaaggcgg cggaggatct ggcggaggtg gtagcggagg cggtggatct    1440
gctcctacct cctccagcac aagaaaacc cagctgcagt tggagcatct gctgctggac    1500
ctccagatga tcctgaatgg catcaacaat tacaagaacc caagctcac ccggatgctg    1560 accgccaagt ttgccatgcc taagaaggcc accgagctga acatctgca gtgcctggaa    1620 gaggaactga agcccctgga agaagtgctg aatctggccc agtccaagaa cttccacctg    1680
aggcctcggg acctgatctc caacatcaac gtgatcgtgc tcgagctgaa gggctccgag    1740
acaaccttca tgtgcgagta cgccgacgag acagctacca tcgtggaatt ctctgaaccgg    1800 tggatcacct tctgccagtc catcatcagc accctgacct gatga                    1845
```

<210> SEQ ID NO 77
<211> LENGTH: 1845
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 77

```
atggaaaccg acacactgct gctgtgggtg ctgctcttgt gggtgccagg atctacagga     60
caggtgcagc tggtggaatc tggtggcgga gttgtgcagc ctggcagatc cctgagactg    120
tcttgtgccg cctccggctt caccttctcc tcttacggaa tgcactgggt ccgacaggcc    180
cctggcaaag gattgagtg ggtcgccttc atcagatacg acggctccaa caagtactac    240
gccgactccg tgaagggcag attcaccatc tctcgggaca actccaagaa caccctgtac    300
ctgcagatga ctcccctgag agccgaggac accgccgtgt actactgcaa gacccacggc    360
tctcacgaca attggggcca gggcacaatg gtcaccgtgt cctctgcttc caccaaggga    420 cccctctgtgt tccctctggc tccttccagc aagtctacct ctggcggaac agctgctctg    480
ggctgcctgg tcaaggacta cttcctgag cctgtgaccg tgtcttggaa ctctggcgct    540
ctgacatccg gcgtgcacac ctttccagct gtgctgcaat cctccggcct gtactctctg    600
tcctccgtcg tgaccgtgcc ttctagctct ctgggcaccc agacctacat ctgcaatgtg    660
aaccacaagc cttccaacac caaggtggac aagagagtgg aacccaagtc tgccgataag    720
acccacacct gtccaccatg tcctgctcca gaactgctcg gcggaccttc cgtgttcctg    780
tttcctccaa agcctaagga caccctgatg atctctcgga cccctgaagt gacctgcgtg    840
gtggtggatg tgtctcacga ggatcccgaa gtgaagttca attggtacgt ggacggcgtg    900
gaagtgcaca acgccaagac caagcctaga gaggaacagt acaactccac ctacagagtg    960
gtgtccgtgc tgaccgtgct gcaccaggat tggctgaacg gcaaagagta caagtgcaag   1020
gtgtccaaca aggccctgcc tgctcctatc gaaaagacca tctccaaggc caagggccag   1080
cctagggaac cccaggttta caccctgcct ccaagccggg aagagatgac caagaaccag   1140
gtgtccctga cctgcctcgt gaagggattc taccctccg atatcgccgt ggaatgggag   1200
tctaatggcc agcctgagaa caactacaag accacacctc ctgtgctgga ctccgacggc   1260
tcattcttcc tgtactccaa gctgacagtg gacaagtcca gatggcagca gggcaacgtg   1320
ttctcctgct ccgtgatgca cgaggccctg cacaatcact acacccagaa gtccctgtct   1380
ctgtctcccg aaaaggcgg cggaggatct ggcggaggtg gtagcggagg cggtggatct   1440
gctcctacct cctccagcac aagaaaacc cagctgcagt tggagcatct gctgctggac   1500
```

-continued

| | |
|---|---|
| ctccagatga tcctgaatgg catcaacaat acaagaacc ccaagctcac ccggatgctg | 1560 |
| accgccaagt tgccatgcc taagaaggcc accgagctga acatctgca gtgcctggaa | 1620 |
| gaggaactga agcccctgga agaagtgctg aatctggccc agtccaagaa cttccacctg | 1680 |
| aggcctcggg acctgatctc caacatcaac gtgatcgtgc tcgagctgaa gggctccgag | 1740 |
| acaaccttca tgtgcgagta cgccgacgag acagctacca tcgtggaatt tctgaaccgg | 1800 |
| tggatcacct tctgccagtc catcatctcc acactgacct gatga | 1845 |

```
<210> SEQ ID NO 78
<211> LENGTH: 1410
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 78
```

| | |
|---|---|
| atggaaaccg acacactgct gctgtgggtg ctgctcttgt gggtgccagg atctacagga | 60 |
| caggtgcagc tggtggaatc tggtggcgga gttgtgcagc ctggcagatc cctgagactg | 120 |
| tcttgtgccg cctccggctt caccttctcc agctacacca tgcactgggt ccgacaggcc | 180 |
| cctggcaaag gattggagtg ggtcaccttc atctcttacg acggcaacaa caagtactac | 240 |
| gccgactccg tgaagggcag attcaccatc tctcgggaca ctccaagaa caccctgtac | 300 |
| ctgcagatga actccctgag agccgaggac accgccatct actactgtgc tagaaccggc | 360 |
| tggctgggcc cctttgatta ttggggacag ggcaccctgg tcaccgtgtc ctctgcttct | 420 |
| accaagggac ccagcgtgtt ccctctggct ccttccagca gtctacctc tggcggaaca | 480 |
| gctgctctgg gctgcctggt caaggactac tttcctgagc ctgtgaccgt gtcttggaac | 540 |
| tctggcgctc tgacatccgg cgtgcacaca tttccagctg tgctgcagtc ctccggcctg | 600 |
| tactctctgt cctctgtcgt gaccgtgcct tccagctctc tgggaaccca gacctacatc | 660 |
| tgcaatgtga accacaagcc ttccaacacc aaggtggaca gagagtgga acccaagtcc | 720 |
| tgcgacaaga cccacacctg tccaccatgt cctgctccag aactgctcgg cggaccttcc | 780 |
| gtgttcctgt ttcctccaaa gcctaaggac accctgatga tctctcggac ccctgaagtg | 840 |
| acctgcgtgg tggtggatgt gtctcacgag gatcccgaag tgaagttcaa ttggtacgtg | 900 |
| gacggcgtgg aagtgcacaa cgccaagacc aagcctagag aggaacagta caactccacc | 960 |
| tacagagtgg tgtccgtgct gaccgtgctg caccaggatt ggctgaacgg caaagagtac | 1020 |
| aagtgcaagg tgtccaacaa ggcccctgcct gctcctatcg aaaagaccat ctccaaggcc | 1080 |
| aagggccagc ctagggaacc ccaggtttac accctgcctc catgccggga agagatgacc | 1140 |
| aagaaccagg tgtccctgtg gtgcctggtt aagggcttct accctccga tatcgccgtg | 1200 |
| gaatgggagt ctaatggcca gcctgagaac aactacaaga caacccctcc tgtgctggac | 1260 |
| tccgacggct cattcttcct gtactccaag ctgacagtgg acaagtccag atggcagcag | 1320 |
| ggcaacgtgt tctcctgctc cgtgatgcac gaggccctgc acaatcacta cacccagaag | 1380 |
| tccctgtctc tgagccccgg caagtgatga | 1410 |

```
<210> SEQ ID NO 79
<211> LENGTH: 2241
<212> TYPE: DNA
<213> ORGANISM: Artificial Sequence
<220> FEATURE:
<221> NAME/KEY: source
```

<223> OTHER INFORMATION: /note="Description of Artificial Sequence: Synthetic polynucleotide"

<400> SEQUENCE: 79

| | | | | |
|---|---|---|---|---|
| atggaaaccg | acacactgct | gctgtgggtg | ctgctcttgt | gggtgccagg | atctacagga | 60 |
| caggtgcagc | tggtggaatc | tggtggcgga | gttgtgcagc | ctggcagatc | cctgagactg | 120 |
| tcttgtgccg | cctccggctt | caccttctcc | agctacacca | tgcactgggt | ccgacaggcc | 180 |
| cctggcaaag | gattggagtg | ggtcaccttc | atctcttacg | acggcaacaa | caagtactac | 240 |
| gccgactccg | tgaagggcag | attcaccatc | tctcgggaca | actccaagaa | caccctgtac | 300 |
| ctgcagatga | actccctgag | agccgaggac | accgccatct | actactgtgc | tagaaccggc | 360 |
| tggctgggcc | cctttgatta | ttggggacag | ggcaccctgg | tcaccgtgtc | ctctgcttct | 420 |
| accaagggac | ccagcgtgtt | ccctctggct | ccttccagca | agtctacctc | tggcggaaca | 480 |
| gctgctctgg | gctgcctggt | caaggactac | tttcctgagc | ctgtgaccgt | gtcttggaac | 540 |
| tctggcgctc | tgacatccgg | cgtgcacaca | tttccagctg | tgctgcagtc | ctccggcctg | 600 |
| tactctctgt | cctctgtcgt | gaccgtgcct | tccagctctc | tgggaaccca | gacctacatc | 660 |
| tgcaatgtga | accacaagcc | ttccaacacc | aaggtggaca | agagagtgga | acccaagtcc | 720 |
| tgcgacaaga | cccacacctg | tccaccatgt | cctgctccag | aactgctcgg | cggaccttcc | 780 |
| gtgttcctgt | tcctccaaa | gcctaaggac | accctgatga | tctctcggac | ccctgaagtg | 840 |
| acctgcgtgg | tggtggatgt | gtctcacgag | gatcccgaag | tgaagttcaa | ttggtacgtg | 900 |
| gacggcgtga | agtgcacaa | cgccaagacc | aagcctagag | aggaacagta | caactccacc | 960 |
| tacagagtgg | tgtccgtgct | gaccgtgctg | caccaggatt | ggctgaacgg | caaagagtac | 1020 |
| aagtgcaagg | tgtccaacaa | ggccctgcct | gctcctatcg | aaaagaccat | ctccaaggcc | 1080 |
| aagggccagc | ctagggaacc | ccaggtttac | accctgcctc | catgccggga | agagatgacc | 1140 |
| aagaaccagg | tgtccctgtg | gtgcctggtt | aagggcttct | acccctccga | tatcgccgtg | 1200 |
| gaatgggagt | ctaatggcca | gcctgagaac | aactacaaga | caacccctcc | tgtgctggac | 1260 |
| tccgacggct | cattcttcct | gtactccaag | ctgacagtgg | acaagtccag | atggcagcag | 1320 |
| ggcaacgtgt | tctcctgctc | cgtgatgcac | gaggccctgc | acaatcacta | cacccagaag | 1380 |
| tccctgtctc | tgtctcccgg | aaaaggcggc | ggaggatctg | gcggaggtgg | tagcggaggc | 1440 |
| ggtggatctg | aagttcagct | ggttgagagt | ggcggcggac | tggttaagcc | tggtggttct | 1500 |
| ctgagactga | gctgcgccgc | ttctggcttc | acattcagcc | cctactccgt | gttctgggtt | 1560 |
| cgacaagctc | caggcaaggg | cctcgaatgg | gtgtcctcta | tcaacaccga | cagcacctac | 1620 |
| aagtattacg | ctgacagcgt | gaaaggccgg | tttaccatca | gcagagacaa | cgccgagaac | 1680 |
| tccatcttcc | tccagatgaa | ttctctgcgc | gctgaggata | ccgctgtgta | ctactgcgcc | 1740 |
| agagacagat | cctactacgc | cttctcctcc | ggctctctgt | ctgactacta | ctacggcctg | 1800 |
| gatgtgtggg | gccagggaac | acttgtgaca | gtgtcaagtg | gcggtggcgg | tagtggcgga | 1860 |
| ggcggttctg | gtggtggtgg | ttcaggcggt | ggtggcagcg | atatcgtgat | gacccagtct | 1920 |
| ccactgagcc | tgagcgtgac | acctggcgag | cctgcctcta | tctcctgcag | atcctctcag | 1980 |
| tccctgctgc | acaccaacct | gtacaactac | ctggattggt | atgtgcagaa | gcccggccag | 2040 |
| tctcctcagc | tgctgatcta | cctggcctcc | aacagagctt | ctggcgtgcc | cgatagattc | 2100 |
| tccggttctg | gctctggcac | cgacttcacc | ctgaagattt | ccagagtgga | aacagaggac | 2160 |
| gtgggcgtgt | actattgcat | gcaggctctg | cagattcccc | ggaccttcgg | ccagggcacc | 2220 | aaactggaaa tcaagtgatg a                                              2241

<210> SEQ ID NO 80
<211> LENGTH: 1155
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 80
atggaaaccg acacactgct gctgtgggtg ctgctcttgt gggtgccagg atctacaggc      60
gagatcgtgc tgacccagtc tcctggcaca ctgtcactgt ctccaggcga gagagctacc     120
ctgtcctgta gagcctctca gtccgtgggc tcctcttacc tggcttggta tcagcagaag     180
cccggccagg ctcctagact gttgatctac ggcgccttct ccagagccac aggcatccct     240
gatagattct ccggctctgg ctctggcacc gacttcaccc tgaccatctc cagactggaa     300
cccgaggact tcgccgtgta ctactgtcag cagtacggct cctctccttg gacctttggc     360
cagggcacca aggtggaaat caagcggaca gtggccgctc cttccgtgtt catcttccca     420
ccttccgacg agcagctgaa gtccggcaca gcttctgtcg tgtgcctgct gaacaacttc     480
taccctcggg aagccaaggt gcagtggaag gtggacaatg ccctgcagtc cggcaactcc     540
caagagtctg tgaccgagca ggactccaag acagcacctc acagcctgtc ctccacactg     600
accctgtcca aggccgacta cgagaagcac aaggtgtacg cctgcgaagt gacccatcag     660
ggcctgtcta gccctgtgac caagtctttc aacagaggcg agtgtggcgg cggaggatct     720
ggcggaggtg aagcggaggc cggtggatct gctcctacct cctccagcac caagaaaacc     780
cagctgcagt tggagcatct gctgctggac ctgcagatga tcctgaacgg catcaacaac     840
tacaagaacc ccaagctgac ccggatgctg accgccaagt ttgccatgcc taagaaggcc     900
accgagctga acatctgca gtgcctggaa gaggaactga gcccctggaa gaagtgctg     960
aatctggccc agtccaagaa cttccacctg aggcctcggg acctgatctc caacatcaac    1020
gtgatcgtgc tcgagctgaa gggctccgag acaaccttca tgtgcgagta cgccgacgag    1080
actgctacca tcgtggaatt tctgaaccgg tggatcacct tctgccagtc catcatctct    1140
accctgacct gatga                                                   1155

<210> SEQ ID NO 81
<211> LENGTH: 1419
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 81
atggaaaccg acacactgct gctgtgggtg ctgctcttgt gggtgccagg atctacaggc      60
gaagtgcagc tggttcaatc tggcggcgga gtggaaagac tggcggatc tctgagactg     120
tcttgtgccg cctctggctt caccttcgac gactacggaa tgtcctgggt ccgacaggct     180
cctggcaaag gactggaatg ggtgtccggc atcaattgga cggcggctc taccggctac     240
gccgactctg tgaagggcag agtgaccatc tccagagaca acgccaagaa ctccctgtac     300
ctgcagatga acagcctgag agccgaggac accgccgtgt actactgtgc taagatcctc     360
ggcgctggca gaggctggta ctttgatctg tggggcaagg gcaccaccgt gaccgtttct     420

```
tccgcttcca ccaagggacc cagcgtgttc cctctggctc cttccagcaa gtctacctct      480
ggcggaacag ctgctctggg ctgcctggtc aaggactact ttcctgagcc tgtgaccgtg      540
tcctggaact ctggcgctct gacatctggc gtgcacacct ttccagctgt gctgcagtcc      600
tccggcctgt actctctgtc ctctgtcgtg accgtgcctt ccagctctct gggaacccag      660
acctacatct gcaatgtgaa ccacaagcct tccaacacca aggtggacaa gagagtggaa      720
cccaagtcct gcgacaagac ccacacctgt cctccatgtc ctgctccaga actgctcggc      780
ggaccttccg tgttcctgtt tcctccaaag cctaaggaca ccctgatgat ctctcggacc      840
cctgaagtga cctgcgtggt ggtggatgtg tctcacgagg atcccgaagt gaagttcaat      900
tggtacgtgg acggcgtgga agtgcacaat gccaagacca gcctagaga ggaacagtac       960 aactccacct acagagtggt gtccgtgctg accgtgctgc accaggattg gctgaacggc     1020
aaagagtaca gtgcaaggt gtccaacaag gccctgcctg ctcctatcga aagaccatc      1080 agcaaggcca agggccagcc tcgggaacct caagtctgta ccctgcctcc tagccgggaa     1140
gagatgacca gaaccaggt gtccctgtcc tgtgccgtga agggcttcta cccttccgat      1200
atcgccgtgg aatgggagag caatggccag ccagagaaca actacaagac aaccccctcct    1260 gtgctggact ccgacggctc attcttcctg gtgtccaagc tgacagtgga caagtccaga     1320
tggcagcagg gcaacgtgtt ctcctgctcc gtgatgcacg aggccctgca caatcactac     1380
acccagaagt ccctgtctct gagccccggc aagtgatga                            1419

<210> SEQ ID NO 82
<211> LENGTH: 1413
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 82
atggaaaccg atacactgct gctgtgggtg ctgctcctct gggtgccagg atctacaggc       60
caggtccagc tgcaggaaag cggccctgga ctggtcaagc ctagccagac cctgagcctg      120
acctgtaccg tgtccggcgg cagcatcaac aacaacaatt actactggac atggatccgg      180
cagcaccccg gcaagggcct ggaatggatc ggctacatct actacagcgg ctccaccttc      240
tacaacccca gcctgaagtc cagagtgacc atcagcgtgg acaccagcaa gacccagttc      300
tccctgaagc tgagcagcgt gacagccgcc gacacagccg tgtactactg cgccagagaa      360
gataccatga ccggcctgga tgtgtgggc cagggcacca cagtgacagt gtctagcgcc       420
agcaccaagg gcctagcgt gttccctctg gcccctagct ctaagagcac atctggcgga       480
acagccgccc tgggctgcct ggtcaaggat tactttcctg agcccgtgac cgtgtcctgg      540
aactctggtg ctctgaccag cggcgtgcac acctttccag ctgtgctgca gagcagcggc      600
ctgtacagcc tgtctagcgt ggtcacagtg cctagcagca gcctgggcac acagacctac      660
atctgcaacg tgaaccacaa gcccagcaac accaaggtgg acaagcgggt ggaacccaag      720
agctgcgaca gacccacac ctgtcctccc tgtcctgccc ctgaactgct gggcggacct       780
tccgtgttcc tgttccctcc aaagccccaag gacaccctga tgatcagccg gaccctgaa     840 gtgacctgcg tggtggtgga tgtgtcccac gaggatcccg aagtgaagtt caattggtac      900
gtggacggcg tggaagtgca caacgccaag accaagccca gaggaaca gtacaacagc       960
```

| | |
|---|---|
| acctaccggg tggtgtccgt gctgaccgtg ctgcaccagg actggctgaa cggcaaagag | 1020 |
| tacaagtgca aggtgtccaa caaggccctg ccagccccta tcgagaaaac catcagcaag | 1080 |
| gccaagggcc agccccgcga acctcaggtg tacacactgc ctccctgccg ggaagagatg | 1140 |
| accaagaacc aggtgtccct gtggtgtctc gtgaagggct tctaccoctc cgatatcgcc | 1200 |
| gtggaatggg agagcaacgg ccagcccgag aacaactaca agaccaccc tcccgtgctg | 1260 |
| gacagcgacg gcagcttctt cctgtactcc aaactgaccg tggacaagag ccggtggcag | 1320 |
| cagggcaatg tgttcagctg tagcgtgatg cacgaggccc tgcacaacca ctacacccag | 1380 |
| aagtccctgt ccctgagccc tggcaagtaa tga | 1413 |

<210> SEQ ID NO 83
<211> LENGTH: 705
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 83

| | |
|---|---|
| atggaaaccg atacactgct gctgtgggtg ctgctcctct gggtgccagg cagcaccggc | 60 |
| gatatccaga tgacacagag ccctagcagc ctgagcgcca gcgtgggcga tagagtgacc | 120 |
| atcacctgtc gggccagcca gagcatcaac aactacctga actggtatca gcagaagccc | 180 |
| ggcaaggccc ctaccctgct gatctatgcc gcttctagcc tgcagagcgg cgtgcccagc | 240 |
| agattttctg gcagcagatc cggcaccgac ttcaccctga caatcagcag cctgcagccc | 300 |
| gaggacttcg ccgcctactt ctgccagcag acctacagca tcccaccctt cggccagggc | 360 |
| accaaggtgg aagtgaagag aacagtggcc gctcccagcg tgttcatctt cccacccagc | 420 |
| gacgagcagc tgaagtctgg cacagccagc gtcgtgtgcc tgctgaacaa cttctacccc | 480 |
| agagaagcca aggtgcagtg gaaggtggac aacgccctgc agtccggcaa cagccaggaa | 540 |
| agcgtcaccg agcaggacag caaggactcc acctacagcc tgtccagcac cctgaccctg | 600 |
| agcaaggccg actacgagaa gcacaaagtg tacgcctgcg aagtgaccca ccagggcctg | 660 |
| agcagccccg tgaccaagag cttcaataga ggcgagtgct aatga | 705 |

<210> SEQ ID NO 84
<211> LENGTH: 1416
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 84

| | |
|---|---|
| atggaaaccg ataccctgct gctgtgggtg ctgctcctct gggtgccagg atctacaggc | 60 |
| gaggtgcagc tgctggaatc tggcggagga ctggtgcagc ctggcggctc tctgagactg | 120 |
| tcttgtgccg cctccggctt cacattctcc agctatatca tgatgtgggt ccgacaggcc | 180 |
| cctggcaagg gcctggaatg ggtgtcctct atctacccct ccggcggcat caccttttac | 240 |
| gccgacaccg tgaagggccg gttcaccatc tcccgggaca actccaagaa caccctgtac | 300 |
| ctgcagatga actccctgcg ggccgaggac accgccgtgt actactgcgc tagaatcaag | 360 |
| ctgggcaccg tgaccaccgt ggactattgg ggccagggca ccctggtcac cgtgtcctct | 420 |
| gcttctacca agggcccctc cgtgttccct ctggcccctt ccagcaagtc cacctctggc | 480 |

```
ggaaccgctg ctctgggctg cctggtcaag gactacttcc ccgagcccgt gaccgtgtct        540
tggaactctg gcgccctgac cagcggcgtg cacacatttc cagccgtgct gcagtccagc        600
ggcctgtact ctctgtcctc cgtcgtgaca gtgccctcca gctctctggg cacacagacc        660
tacatctgca acgtgaacca caagcccctcc aacaccaagg tggacaagcg ggtggaaccc       720
aagtcctgcg acaagaccca cacctgtcct ccctgtcctg cccctgaact gctgggcgga        780
cccagcgtgt tcctgttccc tccaaagcct aaggacaccc tgatgatctc ccggacccct        840
gaagtgacct gcgtggtggt ggacgtgtcc cacgaggatc ccgaagtgaa gttcaattgg        900
tacgtggacg gcgtggaagt gcacaacgcc aagaccaagc ctagagagga acagtacaac        960
tccacctacc gggtggtgtc cgtgctgaca gtgctgcatc aggactggct gaacggcaaa       1020
gagtacaagt gcaaggtgtc caacaaggcc ctgccagccc tatcgaaaa gaccatctcc        1080 aaggccaagg ccagccaag agagcctcaa gtctgcacac tgcctcccag ccgggaagag        1140
atgaccaaga accaggtgtc cctgagctgc gctgtgaagg gcttctaccc ttccgatatc       1200
gccgtggaat gggagagcaa cggccagccc gagaacaatt acaagaccac ccctcccgtg       1260
ctggactccg acggctcatt cttcctggtg tccaagctga ccgtggacaa gtcccggtgg       1320
cagcagggca acgtgttctc ctgctctgtg atgcacgagg ccctgcacaa ccactacacc       1380
cagaagtccc tgtccctgtc tcccggcaag taatga                                 1416
```

<210> SEQ ID NO 85
<211> LENGTH: 714
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 85

```
atggaaaccg ataccctgct gctgtgggtg ctgctcctct gggtgccagg ctctaccggc         60
cagtctgctc tgacccagcc tgcctctgtg tctggctccc ctggccagtc catcaccatc        120
agctgtaccg gcacctcctc cgacgtgggc ggctacaact acgtgtcctg gtatcagcag        180
catcccggca aggcccctaa gctgatgatc tacgacgtgt ccaaccggcc ctccggcgtg        240
tccaatcggt tctctggctc caagtccggc aacaccgcct ccctgacaat cagcggactg        300
caggccgagg acgaggccga ctactactgc tcctcctaca cctccagctc tacccgggtg        360
ttcggcaccg gcaccaaagt gacagtgctg ggccagccca aggccaaccc caccgtgacc        420
ctgttccctc catcctccga ggaactgcag gctaacaagg ccaccctcgt gtgcctgatc        480
tccgacttct accctggcgc cgtgaccgtg gcttggaagg ctgatggctc tcctgtgaag        540
gccggcgtgg aaaccaccaa gccctccaag cagtccaaca caaatacgc cgcctccagc        600 tacctgtccc tgacccctga gcagtggaag tccaccggt cctacagctg ccaggtcaca         660
catgagggct ccaccgtgga aaagaccgtg gcccctaccg agtgctccta atga              714
```

<210> SEQ ID NO 86
<211> LENGTH: 1425
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 86

```
atggaaaccg acacactgct gctgtgggtg ctgctcttgt gggtgccagg atctacagga      60
caggtgcagc tggttcagtc tggcggagga ttggttcagc caggcggatc cctgagactg     120
tcttgtgccg cttctggctt caccttcgac gactacgcta tgcactgggt ccgacaggcc     180
cctggcaaag gattggaatg ggtggccggc atctcttggg actctggctc taccggctac     240
gccgactctg tgaagggcag attcaccatc tctcgggaca cgccaagaa ctccctgtac      300
ctgcagatga acagcctgag agccgaggac accgctctgt actactgcgc tagagatctg     360
ggcgcctacc agtgggtgga aggctttgat tattgggggcc agggcaccct ggtcaccgtg    420
tcctctgctt ctaccaaggg acccagcgtg ttccctctgg ctccttccag caagtctacc     480
tctggcggaa cagctgctct gggctgcctg gtcaaggact actttcctga gcctgtgacc     540
gtgtcttgga actccggcgc tctgacatct ggcgtgcaca cctttccagc tgtgctgcag     600
tcctccggcc tgtactctct gtcctctgtc gtgaccgtgc cttccagctc tctgggaacc     660
cagacctaca tctgcaatgt gaaccacaag cctagcaaca ccaaggtgga caagagagtg     720
gaacccaagt cctgcaccat caagccctgt cctccatgca agtgccccgc tcctaatctg     780
ctcggaggcc cttccgtgtt catcttccca cctaagatca aggacgtgct gatgatctcc     840
ctgtctccta tcgtgacctg cgtggtggtg gacgtgtccg aggatgatcc tgacgtgcag     900
atcagttggt tcgtgaacaa cgtggaagtg cacaccgctc agacccagac acacagagag     960
gactacaaca gcaccctgag agtggtgtct gccctgccta tccagcacca ggattggatg    1020
tccggcaaag aattcaagtg caaagtcaac aacaaggacc tgcctgctcc aatcgagcgg    1080
accatctcta agcctaaggg ctctgtcagg gcccctcagg tgtacgttct gcctccttgc    1140
gaggaagaga tgaccaagaa caagtgacc ctgtggtgca tggtcaccga cttcatgccc      1200
gaggacatct acgtggaatg gaccaacaac ggcaagaccg agctgaacta caagaacacc    1260
gagcctgtgc tggactccga cggctcctac ttcatgtact ccaagctgcg cgtcgagaag    1320
aagaactggg tcgagagaaa ctcctactcc tgctccgtgg tgcacgaggg cctgcacaat    1380
caccacacca ccaagtcctt ctctcggacc cctggaaagt gatga                   1425
```

<210> SEQ ID NO 87
<211> LENGTH: 1425
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 87

```
atggaaaccg acacactgct gctgtgggtg ctgctcttgt gggtgccagg atctacaggc      60
gaagtgcagc tgttcagtc tggcggagga ttggttcagc ctggcggatc cctgagactg     120
tcttgtgccg cctctggctt catgttcagc agataccca tgcactgggt ccgacaggcc      180
cctggaaaag gactggaatg ggtcggatcc atctccggaa gtggcggcgc taccccttac     240
gccgattctg tgaagggcag attcaccatc agcgggaca actccaagaa cacccctgtac    300
ctgcagatga actccctgag agccgaggac accgccgtgt actactgcgc caaggacttc     360
taccagatcc tgaccggcaa cgccttcgac tattggggcc agggcacaac cgtgaccgtg     420
tcctctgctt ctaccaaggg acccagcgtg ttccctctgg ctccttccag caagtctacc     480
tctggcggaa cagctgctct gggctgcctg gtcaaggact actttcctga gcctgtgaca     540
```

```
gtgtcctgga actctggcgc tctgacatcc ggcgtgcaca cctttccagc tgtgctgcaa    600
tccagcggcc tgtactctct gtcctccgtc gtgacagtgc cttccagctc tctgggaacc    660
cagacctaca tctgcaatgt gaaccacaag ccttccaaca ccaaggtgga caagagagtg    720
gaacccaagt cctgcaccat caagccctgt cctccatgca gtgccccgc tcctaatctg     780 ctcggaggcc cttccgtgtt catcttccca cctaagatca aggacgtgct gatgatctcc    840
ctgtctccta tcgtgacctg cgtggtggtg gacgtgtccg aggatgatcc tgacgtgcag    900
atcagttggt tcgtgaacaa cgtggaagtg cacaccgctc agacccagac acacagagag    960
gactacaaca gcaccctgag agtggtgtct gccctgccta tccagcacca ggattggatg   1020
tccggcaaag aattcaagtg caaagtcaac aacaaggacc tgcctgctcc aatcgagcgg   1080
accatctcta agcctaaggg ctctgtgcgg gctccccaag tttgtgttct gcctccacct   1140
gaggaagaga tgaccaagaa acaagtgacc ctgtcctgcg ccgtgaccga cttcatgcct   1200
gaggacatct acgtggaatg gaccaacaac ggcaagaccg agctgaatta caagaacaca   1260
gagcctgtgc tggactccga cggctcctac ttcatggtgt ctaagctgcg cgtcgagaag   1320
aagaactggg tcgagagaaa ctcctactcc tgctccgtgg tgcacgaggg cctgcacaat   1380
caccacacca ccaagtcctt ctctcggacc cctggcaagt gatga                   1425
```

<210> SEQ ID NO 88
<211> LENGTH: 1446
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 88

```
atggaaaccg acacactgct gctgtgggtg ctgctcttgt gggtgccagg atctacaggc     60
gaagtgcagc tggttcagtc tggcgccgaa gtgaagaaac tggctcctc cgtgaaggtg    120 tcctgcaagg cttctggcgg caccttctcc tcttacgcca tctcctgggt ccgacaggct   180
cctggacaag gcttggaatg gatgggcggc atcatcccca tcttcggcac cgccaattac    240
gcccagaaat tccagggcag agtgaccatc accgccgaca gtctacctc caccgcctac    300 atggaactgt ccagcctgag atctgaggac accgccgtgt actactgcgc tagagcccct    360
ctgagattcc tggaatggtc tacccaggac cactactact attactacat ggacgtgtgg    420
ggcaagggca ccaccgtgac agtttcttcc gcctccacca agggacccag cgttttccct    480
ctggctccat cctccaagtc cacctctggt ggaacagctg ctctgggctg cctggtcaag    540
gactactttc ctgagcctgt gaccgtgtcc tggaactctg gcgctctgac atctggcgtg    600
cacacctttc cagctgtgct gcagtcctcc ggcctgtact ctctgtcctc tgtcgtgacc    660
gtgccttcca gctctctggg aacccagacc tacatctgca atgtgaacca caagccttcc    720
aacaccaagg tcgacaagag agtggaaccc aagtcctgcg acaagaccca cctgtcct    780 ccatgtcctg ctccagaact gctcggcgga ccttccgtgt tcctgtttcc tccaaagcct    840
aaggacaccc tgatgatctc tcggaccct gaagtgacct gcgtggtggt ggatgtgtct    900
cacgaggacc cagaagtgaa gttcaattgg tacgtggacg gcgtggaagt gcacaacgcc    960
aagaccaagc ctagagagga acagtacaac tccacctaca gagtggtgtc cgtgctgacc   1020
gtgctgcacc aggattggct gaacggcaaa gagtacaagt gcaaggtgtc caacaaggcc   1080
```

| | |
|---|---|
| ctgcctgctc ctatcgaaaa gaccatctcc aaggccaagg gccagcctcg ggaacctcaa | 1140 |
| gtctgtaccc tgcctcctag ccgggaagag atgaccaaga accaggtgtc cctgtcctgt | 1200 |
| gccgtgaagg gcttctaccc ttccgatatc gccgtggaat gggagagcaa tggccagcca | 1260 |
| gagaacaact acaagacaac ccctcctgtg ctggactccg acggctcatt cttcctggtg | 1320 |
| tccaagctga cagtggacaa gtccagatgg cagcagggca cgtgttctc ctgctccgtg | 1380 |
| atgcacgagg ccctgcacaa tcactacaca cagaagtccc tgtctctgag ccccggcaag | 1440 |
| tgatga | 1446 |

<210> SEQ ID NO 89
<211> LENGTH: 1395
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 89

| | |
|---|---|
| atggaaaccg acacactgct gctgtgggtg ctgctcttgt gggtgccagg atctacagga | 60 |
| caggtgcagc tggtggaatc tggtggcgga gttgtgcagc ctggcagatc tctgagactg | 120 |
| gactgcaagg cctccggcat caccttctcc aactctggca tgcactgggt ccgacaggcc | 180 |
| cctggaaaag gactggaatg ggtcgccgtg atttggtacg acggctccaa gaggtactac | 240 |
| gccgactccg tgaagggcag attcaccatc tctcgggaca actccaagaa caccctgttt | 300 |
| ctgcagatga actccctgag agccgaggac accgccgtgt actactgtgc caccaacgac | 360 |
| gattattggg gccagggcac actggtcacc gtgtcctctg cttctaccaa gggacccagc | 420 |
| gtgttccctc tggctccttc cagcaagtct acctctggcg aacagctgc tctgggctgc | 480 |
| ctggtcaagg actactttcc tgagcctgtg accgtgtctt ggaactctgg cgctctgaca | 540 |
| tccggcgtgc acacctttcc agctgtgctg caatcctccg gcctgtactc tctgtcctcc | 600 |
| gtcgtgaccg tgccttctag ctctctgggc acccagacct acatctgcaa tgtgaaccac | 660 |
| aagccttcca caccaaggt ggacaagaga gtggaaccca gtcctgcga caagacccac | 720 |
| acctgtccac catgtcctgc tccagaactg ctcggcggac cttccgtgtt cctgtttcct | 780 |
| ccaaagccta aggacaccct gatgatctct cggacccctg aagtgacctg cgtggtggtg | 840 |
| gatgtgtctc acgaggatcc cgaagtgaag ttcaattggt acgtggacgg cgtggaagtg | 900 |
| cacaacgcca agaccaagcc tagagaggaa cagtacaact ccacctacag agtggtgtcc | 960 |
| gtgctgaccg tgctgcacca ggattggctg aacggcaaag agtacaagtg caaggtgtcc | 1020 |
| aacaaggccc tgcctgctcc tatcgaaaag accatctcca aggccaaggg ccagcctagg | 1080 |
| gaaccccagg tttacaccct gcctccatgc cgggaagaga tgaccaagaa ccaggtgtcc | 1140 |
| ctgtggtgcc tggttaaggg cttctacccc tccgatatcg ccgtggaatg ggagtctaat | 1200 |
| ggccagcctg agaacaacta caagacaacc cctcctgtgc tggactccga cggctcattc | 1260 |
| ttcctgtact ccaagctgac agtggacaag tccagatggc agcagggcaa cgtgttctcc | 1320 |
| tgctccgtga tgcacgaggc cctgcacaat cactacaccc agaagtccct gtctctgtcc | 1380 |
| cctggcaagt gatga | 1395 |

<210> SEQ ID NO 90
<211> LENGTH: 708
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic polynucleotide"

<400> SEQUENCE: 90
atggaaaccg acacactgct gctgtgggtg ctgctcttgt gggtgccagg atctacaggc      60
gagatcgtgc tgacccagtc tcctgccaca ctgtcactgt ctccaggcga gagagctacc    120
ctgtcctgta gagcctctca gtccgtgtcc tcttacctgg cctggtatca gcagaagcct    180
ggacaggctc cccggctgct gatctacgat gcctctaata gagccacagg catccccgcc    240
agattctccg gatctggctc tggcacagac tttaccctga ccatctccag cctggaacct    300
gaggacttcg ccgtgtacta ctgccagcag tcctctaact ggcctcggac cttttggccag    360 ggcaccaagg tggaaatcaa gcggacagtg gccgctcctt ccgtgttcat cttcccacct    420
tccgacgagc agctgaagtc tggcaccgct tctgtcgtgt gcctgctgaa caacttctac    480
cctcgggaag ccaaggtgca gtggaaggtg gacaatgccc tgcagtccgg caactcccaa    540
gagtctgtga ccgagcagga ctccaaggac agcacctaca gcctgtcctc cacactgacc    600
ctgtccaagg ccgactacga aagcacaag gtgtacgcct gcgaagtgac ccatcagggc    660
ctgtctagcc ctgtgaccaa gtctttcaac cggggcgagt gctgatga                708

<210> SEQ ID NO 91
<211> LENGTH: 1401
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 91
atggaaaccg acacactgct gctgtgggtg ctgctcttgt gggtgccagg atctacagga      60
caggtgcagc tggtggaatc tggtggcgga gttgtgcagc ctggcagatc cctgagactg    120
tcttgtgccg cctccggctt caccttctcc tcttacggaa tgcactgggt ccgacaggcc    180
cctggcaaag gattggagtg ggtcgccttc atcagatacg acggctccaa caagtactac    240
gccgactccg tgaagggcag attcaccatc tctcgggaca actccaagaa caccctgtac    300
ctgcagatga actccctgag agccgaggac accgccgtgt actactgcaa gacccacggc    360
tctcacgaca attggggcca gggcacaatg gtcaccgtgt cctctgcttc caccaaggga    420
ccctctgtgt tccctctggc tccttccagc aagtctacct ctggcggaac agctgctctg    480
ggctgcctgg tcaaggacta ctttcctgag cctgtgaccg tgtcttggaa ctctggcgct    540
ctgacatccg gcgtgcacac ctttccagct gtgctgcaat cctccggcct gtactctctg    600
tcctccgtcg tgaccgtgcc ttctagctct ctgggcaccc agacctacat ctgcaatgtg    660
aaccacaagc cttccaacac caaggtggac aagagagtgg aacccaagtc ctgcgataag    720
acccacacct gtccaccatg tcctgctcca gaactgctcg gcggaccttc cgtgttcctg    780
tttcctccaa agcctaagga caccctgatg atctctcgga cccctgaagt gacctgcgtg    840
gtggtggatg tgtctcacga ggatcccgaa gtgaagttca attggtacgt ggacggcgtg    900
gaagtgcaca acgccaagac caagcctaga gaggaacagt acaactccac ctacagagtg    960
gtgtccgtgc tgaccgtgct gcaccaggat tggctgaacg gcaaagagta caagtgcaag   1020
gtgtccaaca aggccctgcc tgctcctatc gaaaagacca tctccaaggc caagggccag   1080
```

-continued

```
cctcgggaac ctcaagtctg taccctgcct cctagccggg aagagatgac caagaaccag    1140
gtgtccctgt cctgcgctgt gaagggcttc taccctttccg atatcgccgt ggaatgggag    1200
agcaatggcc agcctgagaa caactacaag accacacctc ctgtgctgga ctccgacggc    1260
tcattcttcc tggtgtccaa gctgacagtg gacaagtcca gatggcagca gggcaacgtg    1320
ttctcctgct ccgtgatgca cgaggccctg cacaatcact acacccagaa gtccctgtct    1380
ctgagccccg gcaagtgatg a                                              1401
```

<210> SEQ ID NO 92
<211> LENGTH: 401
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 92

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Ser Ser Tyr
            20                  25                  30

Gly Met His Trp Val Arg Gln Ala Pro Gly Lys Gly Leu Glu Trp Val
        35                  40                  45

Ala Val Ile Trp Phe Asp Gly Thr Lys Lys Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Thr Leu Arg Ala Glu Asp Thr Ala Val Tyr Tyr Cys
                85                  90                  95

Ala Arg Asp Arg Gly Ile Gly Ala Arg Arg Gly Pro Tyr Tyr Met Asp
            100                 105                 110

Val Trp Gly Lys Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Gly Ser Ser Gly Gly Gly Ser Gly Gly Gly Gly Ser
225                 230                 235                 240

Ser Gly Gly Val Phe Thr Leu Glu Asp Phe Val Gly Asp Trp Glu Gln
                245                 250                 255

Thr Ala Ala Tyr Asn Leu Asp Gln Val Leu Glu Gln Gly Gly Val Ser
            260                 265                 270

Ser Leu Leu Gln Asn Leu Ala Val Ser Val Thr Pro Ile Gln Arg Ile
        275                 280                 285
```

```
Val Arg Ser Gly Glu Asn Ala Leu Lys Ile Asp Ile His Val Ile Ile
    290                 295                 300

Pro Tyr Glu Gly Leu Ser Ala Asp Gln Met Ala Gln Ile Glu Glu Val
305                 310                 315                 320

Phe Lys Val Val Tyr Pro Val Asp Asp His His Phe Lys Val Ile Leu
                325                 330                 335

Pro Tyr Gly Thr Leu Val Ile Asp Gly Val Thr Pro Asn Met Leu Asn
                340                 345                 350

Tyr Phe Gly Arg Pro Tyr Glu Gly Ile Ala Val Phe Asp Gly Lys Lys
            355                 360                 365

Ile Thr Val Thr Gly Thr Leu Trp Asn Gly Asn Lys Ile Ile Asp Glu
370                 375                 380

Arg Leu Ile Thr Pro Asp Gly Ser Met Leu Phe Arg Val Thr Ile Asn
385                 390                 395                 400

Ser
```

```
<210> SEQ ID NO 93
<211> LENGTH: 241
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 93

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys Gly Ser Gly Gly Gly Gly Ser Gly Gly
    210                 215                 220
```

```
Gly Gly Ser Ser Gly Gly Val Thr Gly Tyr Arg Leu Phe Glu Glu Ile
225                 230                 235                 240

Leu

<210> SEQ ID NO 94
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 94

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 95
<211> LENGTH: 396
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 95

Glu Val Gln Leu Val Gln Ser Gly Ala Glu Val Lys Lys Ser Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45
```

```
Gly Ile Phe Tyr Pro Gly Asp Ser Ser Thr Arg Tyr Ser Pro Ser Phe
 50                  55                  60
Gln Gly Gln Val Thr Ile Ser Ala Asp Lys Ser Val Asn Thr Ala Tyr
 65                  70                  75                  80
Leu Gln Trp Ser Ser Leu Lys Ala Ser Asp Thr Ala Met Tyr Tyr Cys
                 85                  90                  95
Ala Arg Arg Asn Trp Gly Asn Ala Phe Asp Ile Trp Gly Gln Gly
                100                 105                 110
Thr Met Val Thr Val Ser Ser Ala Ser Thr Lys Gly Pro Ser Val Phe
             115                 120                 125
Pro Leu Ala Pro Ser Ser Lys Ser Thr Ser Gly Gly Thr Ala Ala Leu
         130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Arg Val Glu Pro Lys Ser Cys Gly Ser
210                 215                 220
Ser Gly Gly Gly Gly Ser Gly Gly Gly Gly Ser Ser Gly Gly Val Phe
225                 230                 235                 240
Thr Leu Glu Asp Phe Val Gly Asp Trp Glu Gln Thr Ala Ala Tyr Asn
                245                 250                 255
Leu Asp Gln Val Leu Glu Gln Gly Gly Val Ser Ser Leu Leu Gln Asn
            260                 265                 270
Leu Ala Val Ser Val Thr Pro Ile Gln Arg Ile Val Arg Ser Gly Glu
        275                 280                 285
Asn Ala Leu Lys Ile Asp Ile His Val Ile Ile Pro Tyr Glu Gly Leu
290                 295                 300
Ser Ala Asp Gln Met Ala Gln Ile Glu Glu Val Phe Lys Val Val Tyr
305                 310                 315                 320
Pro Val Asp Asp His His Phe Lys Val Ile Leu Pro Tyr Gly Thr Leu
                325                 330                 335
Val Ile Asp Gly Val Thr Pro Asn Met Leu Asn Tyr Phe Gly Arg Pro
            340                 345                 350
Tyr Glu Gly Ile Ala Val Phe Asp Gly Lys Lys Ile Thr Val Thr Gly
        355                 360                 365
Thr Leu Trp Asn Gly Asn Lys Ile Ile Asp Glu Arg Leu Ile Thr Pro
370                 375                 380
Asp Gly Ser Met Leu Phe Arg Val Thr Ile Asn Ser
385                 390                 395

<210> SEQ ID NO 96
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 96

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Thr
                85                  90                  95

Trp Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Ser Ser Gly Gly Gly Gly Ser Gly
    210                 215                 220

Gly Gly Ser Ser Gly Gly Val Thr Gly Tyr Arg Leu Phe Glu Glu
225                 230                 235                 240

Ile Leu

<210> SEQ ID NO 97
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 97

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Thr
                85                  90                  95

```
Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
        210                 215

<210> SEQ ID NO 98
<211> LENGTH: 397
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 98

Glu Gly Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Gly Ile Gly Thr Gly Gly Thr Tyr Ser Thr Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Gly Asp Tyr Tyr Gly Ser Gly Ser Phe Phe Asp Cys Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Gly
    210                 215                 220

Ser Ser Gly Gly Gly Gly Ser Gly Gly Gly Gly Ser Ser Gly Gly Val
```

```
                225                 230                 235                 240

Phe Thr Leu Glu Asp Phe Val Gly Asp Trp Glu Gln Thr Ala Ala Tyr
                        245                 250                 255

Asn Leu Asp Gln Val Leu Glu Gln Gly Gly Val Ser Ser Leu Leu Gln
                        260                 265                 270

Asn Leu Ala Val Ser Val Thr Pro Ile Gln Arg Ile Val Arg Ser Gly
                        275                 280                 285

Glu Asn Ala Leu Lys Ile Asp Ile His Val Ile Ile Pro Tyr Glu Gly
                        290                 295                 300

Leu Ser Ala Asp Gln Met Ala Gln Ile Glu Glu Val Phe Lys Val Val
        305                 310                 315                 320

Tyr Pro Val Asp Asp His His Phe Lys Val Ile Leu Pro Tyr Gly Thr
                        325                 330                 335

Leu Val Ile Asp Gly Val Thr Pro Asn Met Leu Asn Tyr Phe Gly Arg
                        340                 345                 350

Pro Tyr Glu Gly Ile Ala Val Phe Asp Gly Lys Lys Ile Thr Val Thr
                        355                 360                 365

Gly Thr Leu Trp Asn Gly Asn Lys Ile Ile Asp Glu Arg Leu Ile Thr
                        370                 375                 380

Pro Asp Gly Ser Met Leu Phe Arg Val Thr Ile Asn Ser
        385                 390                 395

<210> SEQ ID NO 99
<211> LENGTH: 241
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 99

Asp Ile Gln Met Thr Gln Ser Pro Ser Ser Leu Ser Ala Ser Val Gly
        1               5                   10                  15

Asp Arg Val Thr Ile Thr Cys Arg Ala Ser Gln Gly Ile Ser Ser Trp
                        20                  25                  30

Leu Ala Trp Tyr Gln Gln Lys Pro Glu Lys Ala Pro Lys Ser Leu Ile
                        35                  40                  45

Tyr Ala Ala Ser Ser Leu Gln Ser Gly Val Pro Ser Arg Phe Ser Gly
                        50                  55                  60

Ser Gly Ser Gly Thr Asp Phe Thr Leu Thr Ile Ser Ser Leu Gln Pro
        65                  70                  75                  80

Glu Asp Phe Ala Thr Tyr Tyr Cys Gln Gln Tyr Asn Ser Tyr Pro Pro
                        85                  90                  95

Thr Phe Gly Gln Gly Thr Lys Leu Glu Ile Lys Arg Thr Val Ala Ala
                        100                 105                 110

Pro Ser Val Phe Ile Phe Pro Pro Ser Asp Glu Gln Leu Lys Ser Gly
                        115                 120                 125

Thr Ala Ser Val Val Cys Leu Leu Asn Asn Phe Tyr Pro Arg Glu Ala
                        130                 135                 140

Lys Val Gln Trp Lys Val Asp Asn Ala Leu Gln Ser Gly Asn Ser Gln
        145                 150                 155                 160

Glu Ser Val Thr Glu Gln Asp Ser Lys Asp Ser Thr Tyr Ser Leu Ser
                        165                 170                 175

Ser Thr Leu Thr Leu Ser Lys Ala Asp Tyr Glu Lys His Lys Val Tyr
                        180                 185                 190
```

```
Ala Cys Glu Val Thr His Gln Gly Leu Ser Ser Pro Val Thr Lys Ser
            195                 200                 205

Phe Asn Arg Gly Glu Cys Gly Ser Ser Gly Gly Gly Ser Gly Gly
            210                 215                 220

Gly Gly Ser Ser Gly Gly Val Thr Gly Tyr Arg Leu Phe Glu Glu Ile
225                 230                 235                 240

Leu
```

```
<210> SEQ ID NO 100
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 100
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 101
<211> LENGTH: 396
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 101
```

```
Gln Val Gln Leu Val Gln Ser Gly Ala Glu Val Lys Lys Pro Gly Ala
```

```
1               5                   10                  15
Ser Val Lys Val Ser Cys Lys Ala Ser Gly Tyr Ser Phe Thr Asn Tyr
                    20                  25                  30

Tyr Ile His Trp Val Arg Gln Ala Pro Gly Gln Arg Leu Glu Trp Met
            35                  40                  45

Gly Trp Ile Asn Ala Gly Asn Gly Asn Thr Lys Tyr Ser Gln Lys Phe
        50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Val Arg Arg Gln Arg Phe Pro Tyr Tyr Phe Asp Tyr Trp Gly Gln Gly
                    100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                    180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Gly Ser
        210                 215                 220

Ser Gly Gly Gly Ser Gly Gly Gly Ser Ser Gly Gly Val Phe
225                 230                 235                 240

Thr Leu Glu Asp Phe Val Gly Asp Trp Glu Gln Thr Ala Ala Tyr Asn
                245                 250                 255

Leu Asp Gln Val Leu Glu Gln Gly Gly Val Ser Ser Leu Leu Gln Asn
                    260                 265                 270

Leu Ala Val Ser Val Thr Pro Ile Gln Arg Ile Val Arg Ser Gly Glu
            275                 280                 285

Asn Ala Leu Lys Ile Asp Ile His Val Ile Ile Pro Tyr Glu Gly Leu
        290                 295                 300

Ser Ala Asp Gln Met Ala Gln Ile Glu Glu Val Phe Lys Val Val Tyr
305                 310                 315                 320

Pro Val Asp Asp His His Phe Lys Val Ile Leu Pro Tyr Gly Thr Leu
                325                 330                 335

Val Ile Asp Gly Val Thr Pro Asn Met Leu Asn Tyr Phe Gly Arg Pro
                    340                 345                 350

Tyr Glu Gly Ile Ala Val Phe Asp Gly Lys Lys Ile Thr Val Thr Gly
            355                 360                 365

Thr Leu Trp Asn Gly Asn Lys Ile Ile Asp Glu Arg Leu Ile Thr Pro
        370                 375                 380

Asp Gly Ser Met Leu Phe Arg Val Thr Ile Asn Ser
385                 390                 395

<210> SEQ ID NO 102
<211> LENGTH: 241
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 102
```

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Gly Thr Asn
            20                  25                  30

Val Ala Trp Tyr Gln Gln Lys Pro Gly Gln Ala Pro Arg Val Leu Ile
        35                  40                  45

Tyr Ser Thr Ser Ser Arg Ala Thr Gly Ile Thr Asp Arg Phe Ser Gly
50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Phe Asn Lys Ser Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Ser Ser Gly Gly Ser Gly Gly
210                 215                 220

Gly Gly Ser Ser Gly Gly Val Thr Gly Tyr Arg Leu Phe Glu Glu Ile
225                 230                 235                 240

Leu

```
<210> SEQ ID NO 103
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 103
```

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Gly Thr Asn
            20                  25                  30

Val Ala Trp Tyr Gln Gln Lys Pro Gly Gln Ala Pro Arg Val Leu Ile
        35                  40                  45

Tyr Ser Thr Ser Ser Arg Ala Thr Gly Ile Thr Asp Arg Phe Ser Gly
50                  55                  60

Ser Gly Ser Gly Thr Asp Phe Thr Leu Thr Ile Ser Arg Leu Glu Pro

```
                65                  70                  75                  80
Glu Asp Phe Ala Val Tyr Tyr Cys Gln Gln Phe Asn Lys Ser Pro Leu
                    85                  90                  95

Thr Phe Gly Gly Gly Thr Lys Val Glu Ile Lys Arg Thr Val Ala Ala
                    100                 105                 110

Pro Ser Val Phe Ile Phe Pro Pro Ser Asp Glu Gln Leu Lys Ser Gly
                    115                 120                 125

Thr Ala Ser Val Val Cys Leu Leu Asn Asn Phe Tyr Pro Arg Glu Ala
                    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
                    180                 185                 190

Ala Cys Glu Val Thr His Gln Gly Leu Ser Ser Pro Val Thr Lys Ser
                    195                 200                 205

Phe Asn Arg Gly Glu Cys
                    210

<210> SEQ ID NO 104
<211> LENGTH: 395
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 104

Gln Val Gln Leu Val Glu Ser Gly Gly Gly Val Val Gln Pro Gly Arg
1                   5                   10                  15

Ser Leu Arg Leu Ser Cys Ala Ala Ser Gly Phe Thr Phe Ser Ser Tyr
                    20                  25                  30

Thr Met His Trp Val Arg Gln Ala Pro Gly Lys Gly Leu Glu Trp Val
                    35                  40                  45

Thr Phe Ile Ser Tyr Asp Gly Asn Asn Lys Tyr Tyr Ala Asp Ser Val
                    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                    85                  90                  95

Ala Arg Thr Gly Trp Leu Gly Pro Phe Asp Tyr Trp Gly Gln Gly Thr
                    100                 105                 110

Leu Val Thr Val Ser Ser Ala Ser Thr Lys Gly Pro Ser Val Phe Pro
                    115                 120                 125

Leu Ala Pro Ser Ser Lys Ser Thr Ser Gly Gly Thr Ala Ala Leu Gly
                    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                    165                 170                 175

Ser Ser Gly Leu Tyr Ser Leu Ser Ser Val Val Thr Val Pro Ser Ser
                    180                 185                 190

Ser Leu Gly Thr Gln Thr Tyr Ile Cys Asn Val Asn His Lys Pro Ser
                    195                 200                 205
```

-continued

```
Asn Thr Lys Val Asp Lys Arg Val Glu Pro Lys Ser Cys Gly Ser Ser
            210                 215                 220

Gly Gly Gly Gly Ser Gly Gly Gly Ser Ser Gly Gly Val Phe Thr
225                 230                 235                 240

Leu Glu Asp Phe Val Gly Asp Trp Glu Gln Thr Ala Ala Tyr Asn Leu
            245                 250                 255

Asp Gln Val Leu Glu Gln Gly Val Ser Ser Leu Leu Gln Asn Leu
            260                 265                 270

Ala Val Ser Val Thr Pro Ile Gln Arg Ile Val Arg Ser Gly Glu Asn
            275                 280                 285

Ala Leu Lys Ile Asp Ile His Val Ile Ile Pro Tyr Glu Gly Leu Ser
            290                 295                 300

Ala Asp Gln Met Ala Gln Ile Glu Glu Val Phe Lys Val Val Tyr Pro
305                 310                 315                 320

Val Asp Asp His His Phe Lys Val Ile Leu Pro Tyr Gly Thr Leu Val
                325                 330                 335

Ile Asp Gly Val Thr Pro Asn Met Leu Asn Tyr Phe Gly Arg Pro Tyr
                340                 345                 350

Glu Gly Ile Ala Val Phe Asp Gly Lys Lys Ile Thr Val Thr Gly Thr
            355                 360                 365

Leu Trp Asn Gly Asn Lys Ile Ile Asp Glu Arg Leu Ile Thr Pro Asp
370                 375                 380

Gly Ser Met Leu Phe Arg Val Thr Ile Asn Ser
385                 390                 395
```

<210> SEQ ID NO 105
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 105

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160
```

```
Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys Gly Ser Ser Gly Gly Gly Ser Gly
            210                 215                 220

Gly Gly Gly Ser Ser Gly Gly Val Thr Gly Tyr Arg Leu Phe Glu Glu
225                 230                 235                 240

Ile Leu

<210> SEQ ID NO 106
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 106

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 107
<211> LENGTH: 394
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 107

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ile Phe Thr Asn Tyr
            20                  25                  30

Trp Ile Ala Trp Val Arg Gln Met Pro Gly Lys Gly Leu Glu Ser Met
        35                  40                  45

Gly Ile Ile Tyr Pro Gly Asp Ser Asp Ile Arg Tyr Ser Pro Ser Phe
    50                  55                  60

Gln Gly Gln Val Thr Ile Ser Ala Asp Lys Ser Ile Thr Thr Ala Tyr
65                  70                  75                  80

Leu Gln Trp Ser Ser Leu Lys Ala Ser Asp Thr Ala Met Tyr Tyr Cys
                85                  90                  95

Ala Arg His Asp Ile Glu Gly Phe Asp Tyr Trp Gly Arg Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Gly Ser Ser Gly
    210                 215                 220

Gly Gly Gly Ser Gly Gly Gly Ser Gly Gly Val Phe Thr Leu
225                 230                 235                 240

Glu Asp Phe Val Gly Asp Trp Glu Gln Thr Ala Ala Tyr Asn Leu Asp
                245                 250                 255

Gln Val Leu Glu Gln Gly Gly Val Ser Ser Leu Leu Gln Asn Leu Ala
            260                 265                 270

Val Ser Val Thr Pro Ile Gln Arg Ile Val Arg Ser Gly Glu Asn Ala
        275                 280                 285

Leu Lys Ile Asp Ile His Val Ile Ile Pro Tyr Glu Gly Leu Ser Ala
    290                 295                 300

Asp Gln Met Ala Gln Ile Glu Glu Val Phe Lys Val Val Tyr Pro Val
305                 310                 315                 320

Asp Asp His His Phe Lys Val Ile Leu Pro Tyr Gly Thr Leu Val Ile
                325                 330                 335

Asp Gly Val Thr Pro Asn Met Leu Asn Tyr Phe Gly Arg Pro Tyr Glu
            340                 345                 350

Gly Ile Ala Val Phe Asp Gly Lys Lys Ile Thr Val Thr Gly Thr Leu
        355                 360                 365

Trp Asn Gly Asn Lys Ile Ile Asp Glu Arg Leu Ile Thr Pro Asp Gly
    370                 375                 380
```

Ser Met Leu Phe Arg Val Thr Ile Asn Ser
385                 390

<210> SEQ ID NO 108
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 108

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Phe Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Leu Ser
    50                  55                  60

Gly Ser Gly Ser Gly Thr Asp Phe Thr Leu Thr Ile Thr Arg Leu Glu
65                  70                  75                  80

Pro Glu Asp Phe Ala Val Tyr Tyr Cys Gln Gln Tyr Asp Ser Ser Ala
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Ser Ser Gly Gly Gly Ser Gly
    210                 215                 220

Gly Gly Gly Ser Ser Gly Gly Val Thr Gly Tyr Arg Leu Phe Glu Glu
225                 230                 235                 240

Ile Leu

<210> SEQ ID NO 109
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 109

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

```
Phe Phe Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Leu Ser
 50                  55                  60

Gly Ser Gly Ser Gly Thr Asp Phe Thr Leu Thr Ile Thr Arg Leu Glu
 65                  70                  75                  80

Pro Glu Asp Phe Ala Val Tyr Tyr Cys Gln Gln Tyr Asp Ser Ser Ala
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 110
<211> LENGTH: 393
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 110

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Ser Ile Ser Trp Val Arg Gln Ala Pro Gly Gln Gly Leu Glu Trp Met
            35                  40                  45

Gly Trp Ile Ser Val Tyr Asn Gly Asn Thr Asn Tyr Ala Gln Lys Phe
 50                  55                  60

Gln Gly Arg Val Thr Met Thr Thr Asp Thr Ser Thr Ser Thr Ala Tyr
 65                  70                  75                  80

Leu Glu Leu Arg Ser Leu Arg Ser Asp Asp Thr Ala Val Tyr Tyr Cys
                85                  90                  95

Ala Arg Asp Pro Ile Ala Ala Gly Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160
```

Ala Leu Thr Ser Gly Val His Thr Phe Pro Ala Val Leu Gln Ser Ser
               165                 170                 175

Gly Leu Tyr Ser Leu Ser Ser Val Val Thr Val Pro Ser Ser Ser Leu
           180                 185                 190

Gly Thr Gln Thr Tyr Ile Cys Asn Val Asn His Lys Pro Ser Asn Thr
           195                 200                 205

Lys Val Asp Lys Arg Val Glu Pro Lys Ser Cys Gly Ser Ser Gly Gly
       210                 215                 220

Gly Gly Ser Gly Gly Gly Ser Ser Gly Gly Val Phe Thr Leu Glu
225                 230                 235                 240

Asp Phe Val Gly Asp Trp Glu Gln Thr Ala Ala Tyr Asn Leu Asp Gln
                   245                 250                 255

Val Leu Glu Gln Gly Gly Val Ser Ser Leu Leu Gln Asn Leu Ala Val
               260                 265                 270

Ser Val Thr Pro Ile Gln Arg Ile Val Arg Ser Gly Glu Asn Ala Leu
           275                 280                 285

Lys Ile Asp Ile His Val Ile Ile Pro Tyr Glu Gly Leu Ser Ala Asp
       290                 295                 300

Gln Met Ala Gln Ile Glu Glu Val Phe Lys Val Val Tyr Pro Val Asp
305                 310                 315                 320

Asp His His Phe Lys Val Ile Leu Pro Tyr Gly Thr Leu Val Ile Asp
                   325                 330                 335

Gly Val Thr Pro Asn Met Leu Asn Tyr Phe Gly Arg Pro Tyr Glu Gly
               340                 345                 350

Ile Ala Val Phe Asp Gly Lys Lys Ile Thr Val Thr Gly Thr Leu Trp
           355                 360                 365

Asn Gly Asn Lys Ile Ile Asp Glu Arg Leu Ile Thr Pro Asp Gly Ser
       370                 375                 380

Met Leu Phe Arg Val Thr Ile Asn Ser
385                 390

<210> SEQ ID NO 111
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 111

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Arg Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser

```
                115                 120                 125
Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Ser Ser Gly Gly Gly Ser Gly
    210                 215                 220

Gly Gly Gly Ser Ser Gly Gly Val Thr Gly Tyr Arg Leu Phe Glu Glu
225                 230                 235                 240

Ile Leu

<210> SEQ ID NO 112
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 112

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Arg Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

```
<210> SEQ ID NO 113
<211> LENGTH: 396
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 113

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Trp Thr Gly Arg Thr Asp Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Gly Ser
    210                 215                 220

Ser Gly Gly Gly Gly Ser Gly Gly Gly Ser Ser Gly Gly Val Phe
225                 230                 235                 240

Thr Leu Glu Asp Phe Val Gly Asp Trp Glu Gln Thr Ala Ala Tyr Asn
                245                 250                 255

Leu Asp Gln Val Leu Glu Gln Gly Gly Val Ser Ser Leu Leu Gln Asn
            260                 265                 270

Leu Ala Val Ser Val Thr Pro Ile Gln Arg Ile Val Arg Ser Gly Glu
        275                 280                 285

Asn Ala Leu Lys Ile Asp Ile His Val Ile Ile Pro Tyr Glu Gly Leu
    290                 295                 300

Ser Ala Asp Gln Met Ala Gln Ile Glu Glu Val Phe Lys Val Val Tyr
305                 310                 315                 320

Pro Val Asp Asp His His Phe Lys Val Ile Leu Pro Tyr Gly Thr Leu
                325                 330                 335

Val Ile Asp Gly Val Thr Pro Asn Met Leu Asn Tyr Phe Gly Arg Pro
            340                 345                 350

Tyr Glu Gly Ile Ala Val Phe Asp Gly Lys Lys Ile Thr Val Thr Gly
```

```
                355                 360                 365
Thr Leu Trp Asn Gly Asn Lys Ile Ile Asp Glu Arg Leu Ile Thr Pro
    370                 375                 380

Asp Gly Ser Met Leu Phe Arg Val Thr Ile Asn Ser
385                 390                 395
```

<210> SEQ ID NO 114
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 114

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Leu Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Ser Ser Gly Gly
    210                 215                 220

Gly Gly Ser Gly Gly Gly Ser Ser Gly Gly Val Thr Gly Tyr Arg
225                 230                 235                 240

Leu Phe Glu Glu Ile Leu
                245
```

<210> SEQ ID NO 115
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 115

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Met Gln Gly
                85                  90                  95

Thr His Trp Pro Leu Thr Phe Gly Gln Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
    210                 215

<210> SEQ ID NO 116
<211> LENGTH: 399
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 116

Glu Val Gln Leu Leu Gln Ser Gly Gly Gly Leu Val Gln Pro Gly Gly
1               5                   10                  15

Ser Leu Arg Leu Ser Cys Ala Ala Ser Gly Phe Met Phe Ser Arg Tyr
            20                  25                  30

Pro Met His Trp Val Arg Gln Ala Pro Gly Lys Gly Leu Glu Trp Val
        35                  40                  45

Gly Ser Ile Ser Gly Ser Gly Gly Ala Thr Pro Tyr Ala Asp Ser Val
    50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Lys Asp Phe Tyr Gln Ile Leu Thr Gly Asn Ala Phe Asp Tyr Trp
                100                 105                 110

Gly Gln Gly Thr Thr Val Thr Val Ser Ser Ala Ser Thr Lys Gly Pro
                115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
210                 215                 220

Cys Gly Ser Ser Gly Gly Gly Ser Gly Gly Gly Ser Ser Gly
225                 230                 235                 240

Gly Val Phe Thr Leu Glu Asp Phe Val Gly Asp Trp Glu Gln Thr Ala
                245                 250                 255

Ala Tyr Asn Leu Asp Gln Val Leu Glu Gln Gly Gly Val Ser Ser Leu
            260                 265                 270

Leu Gln Asn Leu Ala Val Ser Val Thr Pro Ile Gln Arg Ile Val Arg
        275                 280                 285

Ser Gly Glu Asn Ala Leu Lys Ile Asp Ile His Val Ile Ile Pro Tyr
290                 295                 300

Glu Gly Leu Ser Ala Asp Gln Met Ala Gln Ile Glu Glu Val Phe Lys
305                 310                 315                 320

Val Val Tyr Pro Val Asp Asp His His Phe Lys Val Ile Leu Pro Tyr
                325                 330                 335

Gly Thr Leu Val Ile Asp Gly Val Thr Pro Asn Met Leu Asn Tyr Phe
            340                 345                 350

Gly Arg Pro Tyr Glu Gly Ile Ala Val Phe Asp Gly Lys Lys Ile Thr
        355                 360                 365

Val Thr Gly Thr Leu Trp Asn Gly Asn Lys Ile Ile Asp Glu Arg Leu
370                 375                 380

Ile Thr Pro Asp Gly Ser Met Leu Phe Arg Val Thr Ile Asn Ser
385                 390                 395

<210> SEQ ID NO 117
<211> LENGTH: 241
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 117

Asp Ile Gln Met Thr Gln Ser Pro Ser Ser Leu Ser Ala Ser Leu Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Lys Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Tyr Trp Thr Phe Pro Leu

```
                    85                  90                  95
Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Ser Ser Gly Gly Ser Gly Gly
            210                 215                 220

Gly Gly Ser Ser Gly Gly Val Thr Gly Tyr Arg Leu Phe Glu Glu Ile
225                 230                 235                 240

Leu
```

<210> SEQ ID NO 118
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 118

```
Asp Ile Gln Met Thr Gln Ser Pro Ser Ser Leu Ser Ala Ser Leu Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Lys Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Tyr Trp Thr Phe Pro Leu
                85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
            195                 200                 205

Phe Asn Arg Gly Glu Cys
    210

<210> SEQ ID NO 119
<211> LENGTH: 395
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 119

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Phe
            20                  25                  30

Ala Met His Trp Val Arg Gln Ala Pro Gly Lys Gly Leu Glu Trp Ile
        35                  40                  45

Ser Val Ile Asp Thr Arg Gly Ala Thr Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Leu Gly Asn Phe Tyr Tyr Gly Met Asp Val Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Gly Ser Ser
    210                 215                 220

Gly Gly Gly Gly Ser Gly Gly Gly Ser Gly Gly Val Phe Thr
225                 230                 235                 240

Leu Glu Asp Phe Val Gly Asp Trp Glu Gln Thr Ala Ala Tyr Asn Leu
                245                 250                 255

Asp Gln Val Leu Glu Gln Gly Gly Val Ser Ser Leu Leu Gln Asn Leu
            260                 265                 270

Ala Val Ser Val Thr Pro Ile Gln Arg Ile Val Arg Ser Gly Glu Asn
        275                 280                 285

Ala Leu Lys Ile Asp Ile His Val Ile Ile Pro Tyr Glu Gly Leu Ser
    290                 295                 300

Ala Asp Gln Met Ala Gln Ile Glu Glu Val Phe Lys Val Val Tyr Pro
305                 310                 315                 320

Val Asp Asp His His Phe Lys Val Ile Leu Pro Tyr Gly Thr Leu Val

```
                        325                 330                 335
Ile Asp Gly Val Thr Pro Asn Met Leu Asn Tyr Phe Gly Arg Pro Tyr
            340                 345                 350
Glu Gly Ile Ala Val Phe Asp Gly Lys Lys Ile Thr Val Thr Gly Thr
            355                 360                 365
Leu Trp Asn Gly Asn Lys Ile Ile Asp Glu Arg Leu Ile Thr Pro Asp
    370                 375                 380
Gly Ser Met Leu Phe Arg Val Thr Ile Asn Ser
385                 390                 395

<210> SEQ ID NO 120
<211> LENGTH: 241
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 120

Glu Ile Val Leu Thr Gln Ser Pro Gly Thr Leu Ser Val Ser Pro Gly
1               5                   10                  15
Glu Arg Ala Thr Leu Ser Cys Arg Ala Ser Gln Ser Ile Gly Ser Ser
            20                  25                  30
Leu His Trp Tyr Gln Gln Lys Pro Gly Gln Ala Pro Arg Leu Leu Ile
        35                  40                  45
Lys Tyr Ala Ser Gln Ser Leu Ser Gly Ile Pro Asp Arg Phe Ser Gly
    50                  55                  60
Ser Gly Ser Gly Thr Asp Phe Thr Leu Thr Ile Ser Arg Leu Glu Pro
65                  70                  75                  80
Glu Asp Phe Ala Val Tyr Tyr Cys His Gln Ser Ser Arg Leu Pro His
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys Gly Ser Ser Gly Gly Ser Gly Gly
    210                 215                 220
Gly Gly Ser Ser Gly Gly Val Thr Gly Tyr Arg Leu Phe Glu Glu Ile
225                 230                 235                 240
Leu

<210> SEQ ID NO 121
<211> LENGTH: 214
<212> TYPE: PRT
<213> ORGANISM: Artificial Sequence
<220> FEATURE:
```

-continued

```
<221> NAME/KEY: source
<223> OTHER INFORMATION: /note="Description of Artificial Sequence:
      Synthetic polypeptide"

<400> SEQUENCE: 121

Glu Ile Val Leu Thr Gln Ser Pro Gly Thr Leu Ser Val Ser Pro Gly
1               5                   10                  15

Glu Arg Ala Thr Leu Ser Cys Arg Ala Ser Gln Ser Ile Gly Ser Ser
            20                  25                  30

Leu His Trp Tyr Gln Gln Lys Pro Gly Gln Ala Pro Arg Leu Leu Ile
        35                  40                  45

Lys Tyr Ala Ser Gln Ser Leu Ser Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys His Gln Ser Ser Arg Leu Pro His
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 122
<211> LENGTH: 395
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 122

Gln Val Glu Leu Val Glu Ser Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
```

```
                100             105             110
Leu Val Ser Val Ser Ala Ser Thr Lys Gly Pro Ser Val Phe Pro
            115                 120             125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Gly Ser Ser
    210                 215                 220

Gly Gly Gly Gly Ser Gly Gly Gly Ser Ser Gly Gly Val Phe Thr
225                 230                 235                 240

Leu Glu Asp Phe Val Gly Asp Trp Glu Gln Thr Ala Ala Tyr Asn Leu
                245                 250                 255

Asp Gln Val Leu Glu Gln Gly Gly Val Ser Ser Leu Leu Gln Asn Leu
            260                 265                 270

Ala Val Ser Val Thr Pro Ile Gln Arg Ile Val Arg Ser Gly Glu Asn
            275                 280                 285

Ala Leu Lys Ile Asp Ile His Val Ile Ile Pro Tyr Glu Gly Leu Ser
    290                 295                 300

Ala Asp Gln Met Ala Gln Ile Glu Glu Val Phe Lys Val Val Tyr Pro
305                 310                 315                 320

Val Asp Asp His His Phe Lys Val Ile Leu Pro Tyr Gly Thr Leu Val
                325                 330                 335

Ile Asp Gly Val Thr Pro Asn Met Leu Asn Tyr Phe Gly Arg Pro Tyr
            340                 345                 350

Glu Gly Ile Ala Val Phe Asp Gly Lys Lys Ile Thr Val Thr Gly Thr
            355                 360                 365

Leu Trp Asn Gly Asn Lys Ile Ile Asp Glu Arg Leu Ile Thr Pro Asp
    370                 375                 380

Gly Ser Met Leu Phe Arg Val Thr Ile Asn Ser
385                 390                 395

<210> SEQ ID NO 123
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 123

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60
```

```
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Lys Trp Pro Pro
                 85                  90                  95

Trp Thr Phe Gly Gln Gly Thr Lys Val Glu Ser Lys Arg Thr Val Ala
                100                 105                 110

Ala Pro Ser Val Phe Ile Phe Pro Pro Ser Asp Glu Gln Leu Lys Ser
                115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
            195                 200                 205

Ser Phe Asn Arg Gly Glu Cys Gly Ser Gly Gly Gly Gly Ser Gly
210                 215                 220

Gly Gly Ser Ser Gly Gly Val Thr Gly Tyr Arg Leu Phe Glu Glu
225                 230                 235                 240

Ile Leu

<210> SEQ ID NO 124
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 124

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Lys Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Lys Trp Pro Pro
                 85                  90                  95

Trp Thr Phe Gly Gln Gly Thr Lys Val Glu Ser Lys Arg Thr Val Ala
                100                 105                 110

Ala Pro Ser Val Phe Ile Phe Pro Pro Ser Asp Glu Gln Leu Lys Ser
                115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
```

```
                       165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
            195                 200                 205

Ser Phe Asn Arg Gly Glu Cys
        210                 215

<210> SEQ ID NO 125
<211> LENGTH: 393
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 125

Glu Val Gln Leu Val Glu Ser Gly Gly Gly Leu Val Gln Pro Gly Arg
1               5                  10                  15

Ser Leu Arg Leu Ser Cys Ala Ala Ser Arg Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Glu Asn Ser Leu Phe
65                  70                  75                  80

Leu Gln Met Asn Gly Leu Arg Ala Glu Asp Thr Ala Leu Tyr Tyr Cys
                85                  90                  95

Ala Lys Gly Arg Asp Ser Phe Asp Ile Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Gly Ser Ser Gly Gly
    210                 215                 220

Gly Gly Ser Gly Gly Gly Gly Ser Ser Gly Gly Val Phe Thr Leu Glu
225                 230                 235                 240

Asp Phe Val Gly Asp Trp Glu Gln Thr Ala Ala Tyr Asn Leu Asp Gln
                245                 250                 255

Val Leu Glu Gln Gly Gly Val Ser Ser Leu Leu Gln Asn Leu Ala Val
            260                 265                 270

Ser Val Thr Pro Ile Gln Arg Ile Val Arg Ser Gly Glu Asn Ala Leu
        275                 280                 285

Lys Ile Asp Ile His Val Ile Ile Pro Tyr Glu Gly Leu Ser Ala Asp
    290                 295                 300
```

```
Gln Met Ala Gln Ile Glu Glu Val Phe Lys Val Val Tyr Pro Val Asp
305                 310                 315                 320

Asp His His Phe Lys Val Ile Leu Pro Tyr Gly Thr Leu Val Ile Asp
                325                 330                 335

Gly Val Thr Pro Asn Met Leu Asn Tyr Phe Gly Arg Pro Tyr Glu Gly
            340                 345                 350

Ile Ala Val Phe Asp Gly Lys Lys Ile Thr Val Thr Gly Thr Leu Trp
                355                 360                 365

Asn Gly Asn Lys Ile Ile Asp Glu Arg Leu Ile Thr Pro Asp Gly Ser
370                 375                 380

Met Leu Phe Arg Val Thr Ile Asn Ser
385                 390
```

<210> SEQ ID NO 126
<211> LENGTH: 241
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 126

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr Gly Ala Ser Ser Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Ser Tyr Tyr Cys Gln Gln Ala Asn Ser Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Ser Ser Gly Gly Ser Gly Gly
        210                 215                 220

Gly Gly Ser Ser Gly Gly Val Thr Gly Tyr Arg Leu Phe Glu Glu Ile
225                 230                 235                 240

Leu
```

<210> SEQ ID NO 127
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 127

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Ser Tyr Tyr Cys Gln Gln Ala Asn Ser Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 128
<211> LENGTH: 395
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 128

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
        35                  40                  45

Ser Val Ile Gly Pro Ser Gly Gly Phe Thr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gly Asp Asn Asp Ala Phe Asp Ile Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Gly Ser Ser
    210                 215                 220

Gly Gly Gly Gly Ser Gly Gly Gly Ser Ser Gly Gly Val Phe Thr
225                 230                 235                 240

Leu Glu Asp Phe Val Gly Asp Trp Glu Gln Thr Ala Ala Tyr Asn Leu
                245                 250                 255

Asp Gln Val Leu Glu Gln Gly Gly Val Ser Ser Leu Leu Gln Asn Leu
            260                 265                 270

Ala Val Ser Val Thr Pro Ile Gln Arg Ile Val Arg Ser Gly Glu Asn
        275                 280                 285

Ala Leu Lys Ile Asp Ile His Val Ile Ile Pro Tyr Glu Gly Leu Ser
    290                 295                 300

Ala Asp Gln Met Ala Gln Ile Glu Glu Val Phe Lys Val Val Tyr Pro
305                 310                 315                 320

Val Asp Asp His His Phe Lys Val Ile Leu Pro Tyr Gly Thr Leu Val
                325                 330                 335

Ile Asp Gly Val Thr Pro Asn Met Leu Asn Tyr Phe Gly Arg Pro Tyr
            340                 345                 350

Glu Gly Ile Ala Val Phe Asp Gly Lys Lys Ile Thr Val Thr Gly Thr
        355                 360                 365

Leu Trp Asn Gly Asn Lys Ile Ile Asp Glu Arg Leu Ile Thr Pro Asp
    370                 375                 380

Gly Ser Met Leu Phe Arg Val Thr Ile Asn Ser
385                 390                 395

<210> SEQ ID NO 129
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 129

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

```
Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Met
                 85                  90                  95

Tyr Thr Phe Gly Gln Gly Thr Lys Leu Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Ser Ser Gly Gly Gly Ser Gly
    210                 215                 220

Gly Gly Ser Ser Gly Gly Val Thr Gly Tyr Arg Leu Phe Glu Glu
225                 230                 235                 240

Ile Leu

<210> SEQ ID NO 130
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 130

Asp Ile Gln Met Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Met
                 85                  90                  95

Tyr Thr Phe Gly Gln Gly Thr Lys Leu Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
130                 135                 140
```

```
Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 131
<211> LENGTH: 400
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 131

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gln Ile Ser Pro Ala Gly Gly Tyr Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ala Arg Gly Glu Leu Pro Tyr Tyr Arg Met Ser Lys Val Met Asp Val
        100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
        180                 185                 190

Thr Val Pro Ser Ser Ser Leu Gly Thr Gln Thr Tyr Ile Cys Asn Val
    195                 200                 205

Asn His Lys Pro Ser Asn Thr Lys Val Asp Lys Arg Val Glu Pro Lys
210                 215                 220

Ser Cys Gly Ser Ser Gly Gly Gly Ser Gly Gly Gly Ser Ser
225                 230                 235                 240

Gly Gly Val Phe Thr Leu Glu Asp Phe Val Gly Asp Trp Glu Gln Thr
            245                 250                 255

Ala Ala Tyr Asn Leu Asp Gln Val Leu Glu Gln Gly Gly Val Ser Ser
            260                 265                 270
```

```
Leu Leu Gln Asn Leu Ala Val Ser Val Thr Pro Ile Gln Arg Ile Val
            275                 280                 285

Arg Ser Gly Glu Asn Ala Leu Lys Ile Asp Ile His Val Ile Ile Pro
            290                 295                 300

Tyr Glu Gly Leu Ser Ala Asp Gln Met Ala Gln Ile Glu Glu Val Phe
305                 310                 315                 320

Lys Val Val Tyr Pro Val Asp Asp His His Phe Lys Val Ile Leu Pro
                325                 330                 335

Tyr Gly Thr Leu Val Ile Asp Gly Val Thr Pro Asn Met Leu Asn Tyr
            340                 345                 350

Phe Gly Arg Pro Tyr Glu Gly Ile Ala Val Phe Asp Gly Lys Lys Ile
            355                 360                 365

Thr Val Thr Gly Thr Leu Trp Asn Gly Asn Lys Ile Ile Asp Glu Arg
            370                 375                 380

Leu Ile Thr Pro Asp Gly Ser Met Leu Phe Arg Val Thr Ile Asn Ser
385                 390                 395                 400

<210> SEQ ID NO 132
<211> LENGTH: 241
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 132

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Phe Ser Ser Tyr
            20                  25                  30

Leu Ala Trp Tyr Gln Gln Lys Pro Gly Lys Ala Pro Lys Leu Leu Ile
        35                  40                  45

Tyr Gly Ala Ser Ser Arg Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Gly Ser Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Ser Ser Gly Gly Ser Gly Gly
    210                 215                 220

Gly Gly Ser Ser Gly Gly Val Thr Gly Tyr Arg Leu Phe Glu Glu Ile
```

-continued

```
                225                 230                 235                 240

Leu

<210> SEQ ID NO 133
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 133

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Phe Ser Ser Tyr
            20                  25                  30

Leu Ala Trp Tyr Gln Gln Lys Pro Gly Lys Ala Pro Lys Leu Leu Ile
        35                  40                  45

Tyr Gly Ala Ser Ser Arg Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Gly Ser Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 134
<211> LENGTH: 407
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 134

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45
```

```
Gly Gly Ile Ile Pro Ile Phe Gly Thr Ala Asn Tyr Ala Gln Lys Phe
 50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ala Pro Leu Arg Phe Leu Glu Trp Ser Thr Gln Asp His Tyr
            100                 105                 110

Tyr Tyr Tyr Tyr Met Asp Val Trp Gly Lys Gly Thr Thr Val Thr Val
        115                 120                 125

Ser Ser Ala Ser Thr Lys Gly Pro Ser Val Phe Pro Leu Ala Pro Ser
130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Gln Thr Tyr Ile Cys Asn Val Asn His Lys Pro Ser Asn Thr Lys Val
210                 215                 220

Asp Lys Arg Val Glu Pro Lys Ser Cys Gly Ser Gly Gly Gly Gly
225                 230                 235                 240

Ser Gly Gly Gly Gly Ser Ser Gly Gly Val Phe Thr Leu Glu Asp Phe
                245                 250                 255

Val Gly Asp Trp Glu Gln Thr Ala Ala Tyr Asn Leu Asp Gln Val Leu
            260                 265                 270

Glu Gln Gly Gly Val Ser Ser Leu Leu Gln Asn Leu Ala Val Ser Val
        275                 280                 285

Thr Pro Ile Gln Arg Ile Val Arg Ser Gly Glu Asn Ala Leu Lys Ile
290                 295                 300

Asp Ile His Val Ile Ile Pro Tyr Glu Gly Leu Ser Ala Asp Gln Met
305                 310                 315                 320

Ala Gln Ile Glu Glu Val Phe Lys Val Val Tyr Pro Val Asp His
                325                 330                 335

His Phe Lys Val Ile Leu Pro Tyr Gly Thr Leu Val Ile Asp Gly Val
            340                 345                 350

Thr Pro Asn Met Leu Asn Tyr Phe Gly Arg Pro Tyr Glu Gly Ile Ala
        355                 360                 365

Val Phe Asp Gly Lys Lys Ile Thr Val Thr Gly Thr Leu Trp Asn Gly
370                 375                 380

Asn Lys Ile Ile Asp Glu Arg Leu Ile Thr Pro Asp Gly Ser Met Leu
385                 390                 395                 400

Phe Arg Val Thr Ile Asn Ser
                405

<210> SEQ ID NO 135
<211> LENGTH: 241
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 135

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Thr Trp Tyr Gln Gln Lys Pro Gly Gln Ala Pro Ile Leu Val Ile Tyr
        35                  40                  45

Gly Glu Asn Lys Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Lys Ser Arg Asp Gly Ser Gly Gln His
                85                  90                  95

Leu Val Phe Gly Gly Gly Thr Lys Leu Thr Val Leu Gly Gln Pro Lys
            100                 105                 110

Ala Asn Pro Thr Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser Gly Ser Gly Gly Gly Ser Gly Gly
    210                 215                 220

Gly Gly Ser Ser Gly Gly Val Thr Gly Tyr Arg Leu Phe Glu Glu Ile
225                 230                 235                 240

Leu
```

<210> SEQ ID NO 136
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 136

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Thr Trp Tyr Gln Gln Lys Pro Gly Gln Ala Pro Ile Leu Val Ile Tyr
        35                  40                  45

Gly Glu Asn Lys Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Lys Ser Arg Asp Gly Ser Gly Gln His
                85                  90                  95
```

```
Leu Val Phe Gly Gly Thr Lys Leu Thr Val Leu Gly Gln Pro Lys
            100             105             110

Ala Asn Pro Thr Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 137
<211> LENGTH: 398
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 137

Glu Val Gln Leu Val Gln Ser Gly Gly Gly Val Glu Arg Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Gly Ile Asn Trp Gln Gly Ser Thr Gly Tyr Ala Asp Ser Val
    50                  55                  60

Lys Gly Arg Val Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Lys Ile Leu Gly Ala Gly Arg Gly Trp Tyr Phe Asp Tyr Trp Gly
        100                 105                 110

Lys Gly Thr Thr Val Thr Val Ser Ser Ala Ser Thr Lys Gly Pro Ser
    115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Gly Ser Ser Gly Gly Gly Gly Ser Gly Gly Gly Gly Ser Ser Gly Gly
```

```
               225                 230                 235                 240

Val Phe Thr Leu Glu Asp Phe Val Gly Asp Trp Glu Gln Thr Ala Ala
                245                 250                 255

Tyr Asn Leu Asp Gln Val Leu Glu Gln Gly Gly Val Ser Ser Leu Leu
                260                 265                 270

Gln Asn Leu Ala Val Ser Val Thr Pro Ile Gln Arg Ile Val Arg Ser
                275                 280                 285

Gly Glu Asn Ala Leu Lys Ile Asp Ile His Val Ile Pro Tyr Glu
            290                 295                 300

Gly Leu Ser Ala Asp Gln Met Ala Gln Ile Glu Glu Val Phe Lys Val
305                 310                 315                 320

Val Tyr Pro Val Asp Asp His His Phe Lys Val Ile Leu Pro Tyr Gly
                325                 330                 335

Thr Leu Val Ile Asp Gly Val Thr Pro Asn Met Leu Asn Tyr Phe Gly
                340                 345                 350

Arg Pro Tyr Glu Gly Ile Ala Val Phe Asp Gly Lys Lys Ile Thr Val
                355                 360                 365

Thr Gly Thr Leu Trp Asn Gly Asn Lys Ile Ile Asp Glu Arg Leu Ile
                370                 375                 380

Thr Pro Asp Gly Ser Met Leu Phe Arg Val Thr Ile Asn Ser
385                 390                 395

<210> SEQ ID NO 138
<211> LENGTH: 241
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 138

Ser Ser Glu Leu Thr Gln Asp Pro Ala Val Ser Val Ala Leu Gly Gln
1               5                   10                  15

Thr Val Arg Ile Thr Cys Ser Gly Asp Ser Leu Arg Ser Tyr Tyr Ala
                20                  25                  30

Ser Trp Tyr Gln Gln Lys Pro Gly Gln Ala Pro Val Leu Val Ile Tyr
                35                  40                  45

Gly Ala Asn Asn Arg Pro Ser Gly Ile Pro Asp Arg Phe Ser Gly Ser
            50                  55                  60

Ser Ser Gly Asn Thr Ala Ser Leu Thr Ile Thr Gly Ala Gln Ala Glu
65              70                  75                  80

Asp Glu Ala Asp Tyr Tyr Cys Asn Ser Ala Asp Ser Ser Gly Asn His
                85                  90                  95

Val Val Phe Gly Gly Thr Lys Leu Thr Val Leu Gly Gln Pro Lys
                100                 105                 110

Ala Asn Pro Thr Val Thr Leu Phe Pro Pro Ser Ser Glu Glu Leu Gln
                115                 120                 125

Ala Asn Lys Ala Thr Leu Val Cys Leu Ile Ser Asp Phe Tyr Pro Gly
            130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
                180                 185                 190
```

```
Tyr Ser Cys Gln Val Thr His Glu Gly Ser Thr Val Glu Lys Thr Val
        195                 200                 205

Ala Pro Thr Glu Cys Ser Gly Ser Ser Gly Gly Gly Ser Gly Gly
    210                 215                 220

Gly Gly Ser Ser Gly Gly Val Thr Gly Tyr Arg Leu Phe Glu Ile
225             230                 235                 240

Leu

<210> SEQ ID NO 139
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 139

Ser Ser Glu Leu Thr Gln Asp Pro Ala Val Ser Val Ala Leu Gly Gln
1               5                   10                  15

Thr Val Arg Ile Thr Cys Ser Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Ala Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ala Asp Ser Ser Gly Asn His
                85                  90                  95

Val Val Phe Gly Gly Gly Thr Lys Leu Thr Val Leu Gly Gln Pro Lys
            100                 105                 110

Ala Asn Pro Thr Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 140
<211> LENGTH: 394
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 140

Glu Val Gln Leu Val Gln Ser Gly Ala Glu Val Lys Lys Pro Gly Glu
```

```
               1               5                  10                 15
            Ser Leu Lys Ile Ser Cys Lys Gly Ser Gly Tyr Ser Phe Ser Asn Tyr
                            20                  25                 30

Trp Ile Gly Trp Val Arg Gln Met Pro Gly Lys Gly Leu Glu Trp Met
                            35                  40                 45

Gly Ile Ile Asp Pro Ser Asn Ser Tyr Thr Arg Tyr Ser Pro Ser Phe
             50                             55                 60

Gln Gly Gln Val Thr Ile Ser Ala Asp Lys Ser Ile Ser Thr Ala Tyr
            65                  70                  75                 80

Leu Gln Trp Ser Ser Leu Lys Ala Ser Asp Thr Ala Met Tyr Tyr Cys
                                85                  90                 95

Ala Arg Trp Tyr Tyr Lys Pro Phe Asp Val Trp Gly Gln Gly Thr Leu
                            100                 105                110

Val Thr Val Ser Ser Ala Ser Thr Lys Gly Pro Ser Val Phe Pro Leu
                            115                 120                125

Ala Pro Ser Ser Lys Ser Thr Ser Gly Gly Thr Ala Ala Leu Gly Cys
                            130                 135                140

Leu Val Lys Asp Tyr Phe Pro Glu Pro Val Thr Val Ser Trp Asn Ser
            145                 150                 155                160

Gly Ala Leu Thr Ser Gly Val His Thr Phe Pro Ala Val Leu Gln Ser
                                165                 170                175

Ser Gly Leu Tyr Ser Leu Ser Ser Val Val Thr Val Pro Ser Ser Ser
                            180                 185                 190

Leu Gly Thr Gln Thr Tyr Ile Cys Asn Val Asn His Lys Pro Ser Asn
                            195                 200                 205

Thr Lys Val Asp Lys Arg Val Glu Pro Lys Ser Cys Gly Ser Ser Gly
            210                 215                 220

Gly Gly Gly Ser Gly Gly Gly Ser Gly Gly Val Phe Thr Leu
            225                 230                 235                240

Glu Asp Phe Val Gly Asp Trp Glu Gln Thr Ala Ala Tyr Asn Leu Asp
                            245                 250                 255

Gln Val Leu Glu Gln Gly Gly Val Ser Ser Leu Leu Gln Asn Leu Ala
                            260                 265                 270

Val Ser Val Thr Pro Ile Gln Arg Ile Val Arg Ser Gly Glu Asn Ala
                            275                 280                 285

Leu Lys Ile Asp Ile His Val Ile Ile Pro Tyr Glu Gly Leu Ser Ala
                            290                 295                 300

Asp Gln Met Ala Gln Ile Glu Glu Val Phe Lys Val Val Tyr Pro Val
            305                 310                 315                320

Asp Asp His His Phe Lys Val Ile Leu Pro Tyr Gly Thr Leu Val Ile
                            325                 330                335

Asp Gly Val Thr Pro Asn Met Leu Asn Tyr Phe Gly Arg Pro Tyr Glu
                            340                 345                 350

Gly Ile Ala Val Phe Asp Gly Lys Lys Ile Thr Val Thr Gly Thr Leu
                            355                 360                 365

Trp Asn Gly Asn Lys Ile Ile Asp Glu Arg Leu Ile Thr Pro Asp Gly
                            370                 375                 380

Ser Met Leu Phe Arg Val Thr Ile Asn Ser
            385                 390

<210> SEQ ID NO 141
<211> LENGTH: 244
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 141

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ser Gly
            20                  25                  30

Tyr Asp Val His Trp Tyr Gln Gln Leu Pro Gly Thr Ala Pro Lys Leu
                35                  40                  45

Leu Ile Tyr Gly Asn Ser Lys Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ser Glu Asp Glu Ala Asp Tyr Tyr Cys Ala Ser Trp Thr Asp Gly
                85                  90                  95

Leu Ser Leu Val Val Phe Gly Gly Gly Thr Lys Leu Thr Val Leu Gly
                100                 105                 110

Gln Pro Lys Ala Asn Pro Thr Val Thr Leu Phe Pro Pro Ser Ser Glu
            115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Gly Ser Pro Val
145                 150                 155                 160

Lys Ala Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser Gly Ser Gly Gly Gly Gly
    210                 215                 220

Ser Gly Gly Gly Gly Ser Ser Gly Gly Val Thr Gly Tyr Arg Leu Phe
225                 230                 235                 240

Glu Glu Ile Leu

<210> SEQ ID NO 142
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 142

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ser Gly
            20                  25                  30

Tyr Asp Val His Trp Tyr Gln Gln Leu Pro Gly Thr Ala Pro Lys Leu
                35                  40                  45

Leu Ile Tyr Gly Asn Ser Lys Arg Pro Ser Gly Val Pro Asp Arg Phe
50                  55                  60

Ser Gly Ser Lys Ser Gly Thr Ser Ala Ser Leu Ala Ile Thr Gly Leu
```

```
                65                  70                  75                  80
Gln Ser Glu Asp Glu Ala Asp Tyr Tyr Cys Ala Ser Trp Thr Asp Gly
                85                  90                  95

Leu Ser Leu Val Val Phe Gly Gly Thr Lys Leu Thr Val Leu Gly
            100                 105                 110

Gln Pro Lys Ala Asn Pro Thr Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Gly Ser Pro Val
145                 150                 155                 160

Lys Ala Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 143
<211> LENGTH: 399
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 143

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ala Gly Ile Ser Trp Asp Ser Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Leu Gly Ala Tyr Gln Trp Val Glu Gly Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205
```

```
His Lys Pro Ser Asn Thr Lys Val Asp Lys Arg Val Glu Pro Lys Ser
    210                 215                 220
Cys Gly Ser Ser Gly Gly Gly Gly Ser Gly Gly Gly Gly Ser Ser Gly
225                 230                 235                 240
Gly Val Phe Thr Leu Glu Asp Phe Val Gly Asp Trp Glu Gln Thr Ala
                245                 250                 255
Ala Tyr Asn Leu Asp Gln Val Leu Glu Gln Gly Gly Val Ser Ser Leu
            260                 265                 270
Leu Gln Asn Leu Ala Val Ser Val Thr Pro Ile Gln Arg Ile Val Arg
        275                 280                 285
Ser Gly Glu Asn Ala Leu Lys Ile Asp Ile His Val Ile Ile Pro Tyr
    290                 295                 300
Glu Gly Leu Ser Ala Asp Gln Met Ala Gln Ile Glu Glu Val Phe Lys
305                 310                 315                 320
Val Val Tyr Pro Val Asp Asp His His Phe Lys Val Ile Leu Pro Tyr
                325                 330                 335
Gly Thr Leu Val Ile Asp Gly Val Thr Pro Asn Met Leu Asn Tyr Phe
            340                 345                 350
Gly Arg Pro Tyr Glu Gly Ile Ala Val Phe Asp Gly Lys Lys Ile Thr
        355                 360                 365
Val Thr Gly Thr Leu Trp Asn Gly Asn Lys Ile Ile Asp Glu Arg Leu
    370                 375                 380
Ile Thr Pro Asp Gly Ser Met Leu Phe Arg Val Thr Ile Asn Ser
385                 390                 395

<210> SEQ ID NO 144
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 144

Ser Tyr Glu Leu Thr Gln Asp Pro Ala Val Ser Val Ala Leu Gly Gln
1               5                   10                  15
Thr Val Arg Ile Thr Cys Gln Gly Asp Ser Leu Arg Ser Tyr Tyr Ala
            20                  25                  30
Ser Trp Tyr Gln Gln Lys Pro Gly Gln Ala Pro Val Leu Val Ile Tyr
        35                  40                  45
Gly Lys Asn Asn Arg Pro Ser Gly Ile Pro Asp Arg Phe Ser Gly Ser
    50                  55                  60
Thr Ser Gly Asn Ser Ala Ser Leu Thr Ile Thr Gly Ala Gln Ala Glu
65                  70                  75                  80
Asp Glu Ala Asp Tyr Tyr Cys Asn Ser Arg Asp Ser Pro Gly Asn Gln
                85                  90                  95
Trp Val Phe Gly Gly Gly Thr Lys Val Thr Val Leu Gly Gly Gln Pro
            100                 105                 110
Lys Ala Asn Pro Thr Val Thr Leu Phe Pro Pro Ser Ser Glu Glu Leu
        115                 120                 125
Gln Ala Asn Lys Ala Thr Leu Val Cys Leu Ile Ser Asp Phe Tyr Pro
    130                 135                 140
Gly Ala Val Thr Val Ala Trp Lys Ala Asp Gly Ser Pro Val Lys Ala
145                 150                 155                 160
```

```
Gly Val Glu Thr Thr Lys Pro Ser Lys Gln Ser Asn Asn Lys Tyr Ala
            165                 170                 175

Ala Ser Ser Tyr Leu Ser Leu Thr Pro Glu Gln Trp Lys Ser His Arg
        180                 185                 190

Ser Tyr Ser Cys Gln Val Thr His Glu Gly Ser Thr Val Glu Lys Thr
            195                 200                 205

Val Ala Pro Thr Glu Cys Ser Gly Ser Ser Gly Gly Gly Ser Gly
210                 215                 220

Gly Gly Gly Ser Ser Gly Gly Val Thr Gly Tyr Arg Leu Phe Glu Glu
225                 230                 235                 240

Ile Leu

<210> SEQ ID NO 145
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 145

Ser Tyr Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Thr Ser Gly Asn Ser Ala Ser Leu Thr Ile Thr Gly Ala Gln Ala Glu
65                  70                  75                  80

Asp Glu Ala Asp Tyr Tyr Cys Asn Ser Arg Asp Ser Pro Gly Asn Gln
                85                  90                  95

Trp Val Phe Gly Gly Gly Thr Lys Val Thr Val Leu Gly Gln Pro
            100                 105                 110

Lys Ala Asn Pro Thr Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Gly Ser Pro Val Lys Ala
145                 150                 155                 160

Gly Val Glu Thr Thr Lys Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 146
<211> LENGTH: 398
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 146

```
Glu Val Gln Leu Val Gln Ser Gly Gly Gly Val Glu Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Ser Thr Gly Tyr Ala Asp Ser Val
    50                  55                  60

Lys Gly Arg Val Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Ile Leu Gly Ala Gly Arg Gly Trp Tyr Phe Asp Leu Trp Gly
            100                 105                 110

Lys Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Gly Ser Ser Gly Gly Gly Gly Ser Gly Gly Gly Ser Ser Gly Gly
225                 230                 235                 240

Val Phe Thr Leu Glu Asp Phe Val Gly Asp Trp Glu Gln Thr Ala Ala
                245                 250                 255

Tyr Asn Leu Asp Gln Val Leu Glu Gln Gly Gly Val Ser Ser Leu Leu
            260                 265                 270

Gln Asn Leu Ala Val Ser Val Thr Pro Ile Gln Arg Ile Val Arg Ser
        275                 280                 285

Gly Glu Asn Ala Leu Lys Ile Asp Ile His Val Ile Ile Pro Tyr Glu
    290                 295                 300

Gly Leu Ser Ala Asp Gln Met Ala Gln Ile Glu Glu Val Phe Lys Val
305                 310                 315                 320

Val Tyr Pro Val Asp Asp His His Phe Lys Val Ile Leu Pro Tyr Gly
                325                 330                 335

Thr Leu Val Ile Asp Gly Val Thr Pro Asn Met Leu Asn Tyr Phe Gly
            340                 345                 350

Arg Pro Tyr Glu Gly Ile Ala Val Phe Asp Gly Lys Lys Ile Thr Val
        355                 360                 365

Thr Gly Thr Leu Trp Asn Gly Asn Lys Ile Ile Asp Glu Arg Leu Ile
    370                 375                 380

Thr Pro Asp Gly Ser Met Leu Phe Arg Val Thr Ile Asn Ser
385                 390                 395
```

```
<210> SEQ ID NO 147
<211> LENGTH: 241
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 147

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu Gly Gln Pro Lys
            100                 105                 110

Ala Asn Pro Thr Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser Gly Ser Gly Gly Gly Ser Gly Gly
    210                 215                 220

Gly Gly Ser Ser Gly Gly Val Thr Gly Tyr Arg Leu Phe Glu Glu Ile
225                 230                 235                 240

Leu

<210> SEQ ID NO 148
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 148

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45
```

Gly Lys Asn Asn Arg Pro Ser Gly Ile Pro Asp Arg Phe Ser Gly Ser
            50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn His
                 85                  90                  95

Val Val Phe Gly Gly Gly Thr Lys Leu Thr Val Leu Gly Gln Pro Lys
            100                 105                 110

Ala Asn Pro Thr Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
            130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
            195                 200                 205

Ala Pro Thr Glu Cys Ser
210

<210> SEQ ID NO 149
<211> LENGTH: 392
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 149

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Tyr Ile Asn Trp Val Arg Gln Ala Pro Gly Gln Gly Leu Glu Trp Met
        35                  40                  45

Gly Thr Ile Asn Pro Val Ser Gly Ser Thr Ser Tyr Ala Gln Lys Phe
    50                  55                  60

Gln Gly Arg Val Thr Met Thr Arg Asp Thr Ser Ile Ser Thr Ala Tyr
 65                 70                  75                  80

Met Glu Leu Ser Arg Leu Arg Ser Asp Asp Thr Ala Val Tyr Tyr Cys
                85                  90                  95

Ala Arg Gly Gly Trp Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Leu Gly
                180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Gly Ser Ser Gly Gly Gly
210                 215                 220

Gly Ser Gly Gly Gly Gly Ser Gly Gly Val Phe Thr Leu Glu Asp
225                 230                 235                 240

Phe Val Gly Asp Trp Glu Gln Thr Ala Ala Tyr Asn Leu Asp Gln Val
                245                 250                 255

Leu Glu Gln Gly Gly Val Ser Ser Leu Leu Gln Asn Leu Ala Val Ser
            260                 265                 270

Val Thr Pro Ile Gln Arg Ile Val Arg Ser Gly Glu Asn Ala Leu Lys
        275                 280                 285

Ile Asp Ile His Val Ile Ile Pro Tyr Glu Gly Leu Ser Ala Asp Gln
    290                 295                 300

Met Ala Gln Ile Glu Glu Val Phe Lys Val Val Tyr Pro Val Asp Asp
305                 310                 315                 320

His His Phe Lys Val Ile Leu Pro Tyr Gly Thr Leu Val Ile Asp Gly
                325                 330                 335

Val Thr Pro Asn Met Leu Asn Tyr Phe Gly Arg Pro Tyr Glu Gly Ile
            340                 345                 350

Ala Val Phe Asp Gly Lys Lys Ile Thr Val Thr Gly Thr Leu Trp Asn
        355                 360                 365

Gly Asn Lys Ile Ile Asp Glu Arg Leu Ile Thr Pro Asp Gly Ser Met
370                 375                 380

Leu Phe Arg Val Thr Ile Asn Ser
385                 390

<210> SEQ ID NO 150
<211> LENGTH: 244
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 150

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Thr Phe Ala Gly Gly
                85                  90                  95

Ser Tyr Tyr Gly Val Phe Gly Gly Gly Thr Lys Leu Thr Val Leu Gly
            100                 105                 110

Gln Pro Lys Ala Asn Pro Thr Val Thr Leu Phe Pro Pro Ser Ser Glu
        115                 120                 125

Glu Leu Gln Ala Asn Lys Ala Thr Leu Val Cys Leu Ile Ser Asp Phe

```
              130                 135                 140
Tyr Pro Gly Ala Val Thr Val Ala Trp Lys Ala Asp Gly Ser Pro Val
145                 150                 155                 160

Lys Ala Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
                180                 185                 190

His Arg Ser Tyr Ser Cys Gln Val Thr His Glu Gly Ser Thr Val Glu
                195                 200                 205

Lys Thr Val Ala Pro Thr Glu Cys Ser Gly Ser Ser Gly Gly Gly Gly
                210                 215                 220

Ser Gly Gly Gly Gly Ser Ser Gly Gly Val Thr Gly Tyr Arg Leu Phe
225                 230                 235                 240

Glu Glu Ile Leu

<210> SEQ ID NO 151
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 151

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
                20                  25                  30

Asn Tyr Val Asn Trp Tyr Gln Gln His Pro Gly Lys Ala Pro Lys Leu
                35                  40                  45

Met Ile Tyr Gly Val Ser Lys Arg Pro Ser Gly Val Ser Asn Arg Phe
        50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Gly Thr Phe Ala Gly Gly
                85                  90                  95

Ser Tyr Tyr Gly Val Phe Gly Gly Gly Thr Lys Leu Thr Val Leu Gly
                100                 105                 110

Gln Pro Lys Ala Asn Pro Thr Val Thr Leu Phe Pro Pro Ser Ser Glu
                115                 120                 125

Glu Leu Gln Ala Asn Lys Ala Thr Leu Val Cys Leu Ile Ser Asp Phe
                130                 135                 140

Tyr Pro Gly Ala Val Thr Val Ala Trp Lys Ala Asp Gly Ser Pro Val
145                 150                 155                 160

Lys Ala Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
                180                 185                 190

His Arg Ser Tyr Ser Cys Gln Val Thr His Glu Gly Ser Thr Val Glu
                195                 200                 205

Lys Thr Val Ala Pro Thr Glu Cys Ser
                210                 215

<210> SEQ ID NO 152
<211> LENGTH: 393
```

<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 152

```
Glu Val Gln Leu Val Gln Ser Gly Ala Glu Val Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Gly Pro Phe Phe Gly Thr Ala Asn Tyr Ala Gln Lys Phe
    50                  55                  60

Gln Gly Arg Val Thr Ile Thr Ala Asp Glu Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Thr Pro Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Gly Ser Ser Gly Gly
    210                 215                 220

Gly Gly Ser Gly Gly Gly Ser Ser Gly Gly Val Phe Thr Leu Glu
225                 230                 235                 240

Asp Phe Val Gly Asp Trp Glu Gln Thr Ala Ala Tyr Asn Leu Asp Gln
                245                 250                 255

Val Leu Glu Gln Gly Gly Val Ser Ser Leu Leu Gln Asn Leu Ala Val
            260                 265                 270

Ser Val Thr Pro Ile Gln Arg Ile Val Arg Ser Gly Glu Asn Ala Leu
        275                 280                 285

Lys Ile Asp Ile His Val Ile Ile Pro Tyr Glu Gly Leu Ser Ala Asp
    290                 295                 300

Gln Met Ala Gln Ile Glu Glu Val Phe Lys Val Val Tyr Pro Val Asp
305                 310                 315                 320

Asp His His Phe Lys Val Ile Leu Pro Tyr Gly Thr Leu Val Ile Asp
                325                 330                 335

Gly Val Thr Pro Asn Met Leu Asn Tyr Phe Gly Arg Pro Tyr Glu Gly
            340                 345                 350

Ile Ala Val Phe Asp Gly Lys Lys Ile Thr Val Thr Gly Thr Leu Trp
        355                 360                 365

Asn Gly Asn Lys Ile Ile Asp Glu Arg Leu Ile Thr Pro Asp Gly Ser
```

Met Leu Phe Arg Val Thr Ile Asn Ser
385                 390

<210> SEQ ID NO 153
<211> LENGTH: 241
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 153

Ser Tyr Glu Leu Thr Gln Pro Leu Ser Val Ser Val Ala Leu Gly Gln
1               5                   10                  15

Thr Ala Arg Ile Thr Cys Ser Gly Asp Ser Ile Pro Asn Tyr Tyr Val
            20                  25                  30

Tyr Trp Tyr Gln Gln Lys Pro Gly Gln Ala Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Ser Phe Asp Ser Ser Leu Asn Ala
                85                  90                  95

Glu Val Phe Gly Gly Gly Thr Lys Leu Thr Val Leu Gly Gln Pro Lys
            100                 105                 110

Ala Asn Pro Thr Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser Gly Ser Gly Gly Gly Ser Gly Gly
    210                 215                 220

Gly Gly Ser Ser Gly Gly Val Thr Gly Tyr Arg Leu Phe Glu Glu Ile
225                 230                 235                 240

Leu

<210> SEQ ID NO 154
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 154

Ser Tyr Glu Leu Thr Gln Pro Leu Ser Val Ser Val Ala Leu Gly Gln
1               5                   10                  15

```
Thr Ala Arg Ile Thr Cys Ser Gly Asp Ser Ile Pro Asn Tyr Tyr Val
            20                  25                  30

Tyr Trp Tyr Gln Gln Lys Pro Gly Gln Ala Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Ser Phe Asp Ser Ser Leu Asn Ala
                85                  90                  95

Glu Val Phe Gly Gly Gly Thr Lys Leu Thr Val Leu Gly Gln Pro Lys
            100                 105                 110

Ala Asn Pro Thr Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 155
<211> LENGTH: 391
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 155

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

His Met His Trp Val Arg Gln Ala Pro Gly Gln Gly Leu Glu Trp Met
        35                  40                  45

Gly Trp Ile Asn Pro Asn Ser Gly Val Thr Lys Tyr Ala Gln Lys Phe
    50                  55                  60

Gln Gly Arg Val Thr Met Thr Arg Asp Thr Ser Ile Asn Thr Ala Tyr
65                  70                  75                  80

Met Glu Leu Ser Arg Leu Arg Phe Asp Asp Thr Asp Val Tyr Tyr Cys
                85                  90                  95

Ala Thr Gly Gly Phe Gly Tyr Trp Gly Glu Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
```

```
            145                 150                 155                 160
        Thr Ser Gly Val His Thr Phe Pro Ala Val Leu Gln Ser Ser Gly Leu
                        165                 170                 175
        Tyr Ser Leu Ser Ser Val Val Thr Val Pro Ser Ser Ser Leu Gly Thr
                        180                 185                 190
        Gln Thr Tyr Ile Cys Asn Val Asn His Lys Pro Ser Asn Thr Lys Val
                        195                 200                 205
        Asp Lys Arg Val Glu Pro Lys Ser Cys Gly Ser Gly Gly Gly Gly
            210                 215                 220
        Ser Gly Gly Gly Gly Ser Ser Gly Gly Val Phe Thr Leu Glu Asp Phe
        225                 230                 235                 240
        Val Gly Asp Trp Glu Gln Thr Ala Ala Tyr Asn Leu Asp Gln Val Leu
                        245                 250                 255
        Glu Gln Gly Gly Val Ser Ser Leu Leu Gln Asn Leu Ala Val Ser Val
                        260                 265                 270
        Thr Pro Ile Gln Arg Ile Val Arg Ser Gly Glu Asn Ala Leu Lys Ile
                        275                 280                 285
        Asp Ile His Val Ile Ile Pro Tyr Glu Gly Leu Ser Ala Asp Gln Met
            290                 295                 300
        Ala Gln Ile Glu Glu Val Phe Lys Val Val Tyr Pro Val Asp Asp His
        305                 310                 315                 320
        His Phe Lys Val Ile Leu Pro Tyr Gly Thr Leu Val Ile Asp Gly Val
                        325                 330                 335
        Thr Pro Asn Met Leu Asn Tyr Phe Gly Arg Pro Tyr Glu Gly Ile Ala
                        340                 345                 350
        Val Phe Asp Gly Lys Lys Ile Thr Val Thr Gly Thr Leu Trp Asn Gly
                        355                 360                 365
        Asn Lys Ile Ile Asp Glu Arg Leu Ile Thr Pro Asp Gly Ser Met Leu
                        370                 375                 380
        Phe Arg Val Thr Ile Asn Ser
        385                 390

<210> SEQ ID NO 156
<211> LENGTH: 243
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 156

Leu Pro Val Leu Thr Gln Pro Pro Ser Val Ser Lys Gly Leu Arg Gln
        1               5                   10                  15
        Thr Ala Thr Leu Thr Cys Thr Gly Asn Ser Asn Asn Val Gly Asn Gln
                        20                  25                  30
        Gly Ala Ala Trp Leu Gln Gln His Gln Gly Gln Pro Pro Lys Leu Leu
                        35                  40                  45
        Ser Tyr Arg Asn His Asn Arg Pro Ser Gly Val Ser Glu Arg Phe Ser
                50                  55                  60
        Pro Ser Arg Ser Gly Asp Thr Ser Ser Leu Thr Ile Thr Gly Leu Gln
        65                  70                  75                  80
        Pro Glu Asp Glu Ala Asp Tyr Tyr Cys Leu Ala Trp Asp Ser Ser Leu
                        85                  90                  95
        Arg Ala Phe Val Phe Gly Thr Gly Thr Lys Leu Thr Val Leu Gly Gln
                        100                 105                 110
```

```
Pro Lys Ala Asn Pro Thr Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser Gly Ser Ser Gly Gly Gly Gly Ser
210                 215                 220

Gly Gly Gly Gly Ser Ser Gly Gly Val Thr Gly Tyr Arg Leu Phe Glu
225                 230                 235                 240

Glu Ile Leu

<210> SEQ ID NO 157
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 157

Leu Pro Val Leu Thr Gln Pro Pro Ser Val Ser Lys Gly Leu Arg Gln
1               5                   10                  15

Thr Ala Thr Leu Thr Cys Thr Gly Asn Ser Asn Asn Val Gly Asn Gln
            20                  25                  30

Gly Ala Ala Trp Leu Gln Gln His Gln Gly Gln Pro Pro Lys Leu Leu
        35                  40                  45

Ser Tyr Arg Asn His Asn Arg Pro Ser Gly Val Ser Glu Arg Phe Ser
    50                  55                  60

Pro Ser Arg Ser Gly Asp Thr Ser Ser Leu Thr Ile Thr Gly Leu Gln
65                  70                  75                  80

Pro Glu Asp Glu Ala Asp Tyr Tyr Cys Leu Ala Trp Asp Ser Ser Leu
                85                  90                  95

Arg Ala Phe Val Phe Gly Thr Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
```

<210> SEQ ID NO 158
<211> LENGTH: 389
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 158

```
Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Asp Tyr
            20                  25                  30

Trp Met Ser Trp Val Arg Gln Ala Pro Gly Lys Gly Leu Glu Trp Val
        35                  40                  45

Ala Asn Ile Lys Lys Asp Gly Ser Val Asn Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg Phe Asp Tyr Trp Gly Gln Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Arg Val Glu Pro Lys Ser Cys Gly Ser Gly Gly Gly Gly Ser Gly
    210                 215                 220

Gly Gly Ser Ser Gly Gly Val Phe Thr Leu Glu Asp Phe Val Gly
225                 230                 235                 240

Asp Trp Glu Gln Thr Ala Ala Tyr Asn Leu Asp Gln Val Leu Glu Gln
                245                 250                 255

Gly Gly Val Ser Ser Leu Leu Gln Asn Leu Ala Val Ser Val Thr Pro
            260                 265                 270

Ile Gln Arg Ile Val Arg Ser Gly Glu Asn Ala Leu Lys Ile Asp Ile
        275                 280                 285

His Val Ile Ile Pro Tyr Glu Gly Leu Ser Ala Asp Gln Met Ala Gln
    290                 295                 300

Ile Glu Glu Val Phe Lys Val Val Tyr Pro Val Asp Asp His Phe
305                 310                 315                 320

Lys Val Ile Leu Pro Tyr Gly Thr Leu Val Ile Asp Gly Val Thr Pro
                325                 330                 335

Asn Met Leu Asn Tyr Phe Gly Arg Pro Tyr Glu Gly Ile Ala Val Phe
            340                 345                 350
```

```
Asp Gly Lys Lys Ile Thr Val Thr Gly Thr Leu Trp Asn Gly Asn Lys
        355                 360                 365

Ile Ile Asp Glu Arg Leu Ile Thr Pro Asp Gly Ser Met Leu Phe Arg
    370                 375                 380

Val Thr Ile Asn Ser
385

<210> SEQ ID NO 159
<211> LENGTH: 243
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 159

Gln Ala Gly Leu Thr Gln Pro Pro Ser Val Ser Lys Gly Leu Arg Gln
1               5                   10                  15

Thr Ala Thr Leu Thr Cys Thr Gly Asn Ser Asn Asn Val Gly Asn Gln
            20                  25                  30

Gly Ala Ala Trp Leu Gln Gln His Gln Gly His Pro Pro Lys Leu Leu
        35                  40                  45

Phe Tyr Arg Asn Asn Asn Arg Ala Ser Gly Ile Ser Glu Arg Leu Ser
50                  55                  60

Ala Ser Arg Ser Gly Asn Thr Ala Ser Leu Thr Ile Thr Gly Leu Gln
65                  70                  75                  80

Pro Glu Asp Glu Ala Asp Tyr Tyr Cys Leu Thr Trp Asp Ser Ser Leu
                85                  90                  95

Ser Val Val Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser Gly Ser Ser Gly Gly Gly Gly Ser
    210                 215                 220

Gly Gly Gly Gly Ser Ser Gly Gly Val Thr Gly Tyr Arg Leu Phe Glu
225                 230                 235                 240

Glu Ile Leu

<210> SEQ ID NO 160
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 160

```
Gln Ala Gly Leu Thr Gln Pro Pro Ser Val Ser Lys Gly Leu Arg Gln
1               5                   10                  15

Thr Ala Thr Leu Thr Cys Thr Gly Asn Ser Asn Asn Val Gly Asn Gln
            20                  25                  30

Gly Ala Ala Trp Leu Gln Gln His Gln Gly His Pro Pro Lys Leu Leu
        35                  40                  45

Phe Tyr Arg Asn Asn Asn Arg Ala Ser Gly Ile Ser Glu Arg Leu Ser
    50                  55                  60

Ala Ser Arg Ser Gly Asn Thr Ala Ser Leu Thr Ile Thr Gly Leu Gln
65                  70                  75                  80

Pro Glu Asp Glu Ala Asp Tyr Tyr Cys Leu Thr Trp Asp Ser Ser Leu
                85                  90                  95

Ser Val Val Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 161
<211> LENGTH: 392
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 161

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Lys Thr His Gly Ser His Asp Asn Trp Gly Gln Gly Thr Met Val Thr
            100                 105                 110

Val Ser Ser Ala Ser Thr Lys Gly Pro Ser Val Phe Pro Leu Ala Pro
        115                 120                 125
```

```
Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
                195                 200                 205

Val Asp Lys Arg Val Glu Pro Lys Ser Cys Gly Ser Gly Gly Gly
210                 215                 220

Gly Ser Gly Gly Gly Ser Ser Gly Gly Val Phe Thr Leu Glu Asp
225                 230                 235                 240

Phe Val Gly Asp Trp Glu Gln Thr Ala Ala Tyr Asn Leu Asp Gln Val
                245                 250                 255

Leu Glu Gln Gly Gly Val Ser Ser Leu Leu Gln Asn Leu Ala Val Ser
                260                 265                 270

Val Thr Pro Ile Gln Arg Ile Val Arg Ser Gly Glu Asn Ala Leu Lys
                275                 280                 285

Ile Asp Ile His Val Ile Ile Pro Tyr Glu Gly Leu Ser Ala Asp Gln
290                 295                 300

Met Ala Gln Ile Glu Glu Val Phe Lys Val Val Tyr Pro Val Asp Asp
305                 310                 315                 320

His His Phe Lys Val Ile Leu Pro Tyr Gly Thr Leu Val Ile Asp Gly
                325                 330                 335

Val Thr Pro Asn Met Leu Asn Tyr Phe Gly Arg Pro Tyr Glu Gly Ile
                340                 345                 350

Ala Val Phe Asp Gly Lys Lys Ile Thr Val Thr Gly Thr Leu Trp Asn
                355                 360                 365

Gly Asn Lys Ile Ile Asp Glu Arg Leu Ile Thr Pro Asp Gly Ser Met
370                 375                 380

Leu Phe Arg Val Thr Ile Asn Ser
385                 390
```

<210> SEQ ID NO 162
<211> LENGTH: 244
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 162

```
Gln Ser Val Leu Thr Gln Pro Pro Ser Val Ser Gly Ala Pro Gly Gln
1               5                   10                  15

Arg Val Thr Ile Ser Cys Ser Gly Arg Ser Asn Ile Gly Ser Asn
                20                  25                  30

Thr Val Lys Trp Tyr Gln Gln Leu Pro Gly Thr Ala Pro Lys Leu Leu
                35                  40                  45

Ile Tyr Tyr Asn Asp Gln Arg Pro Ser Gly Val Pro Asp Arg Phe Ser
        50                  55                  60

Gly Ser Lys Ser Gly Thr Ser Ala Ser Leu Ala Ile Thr Gly Leu Gln
65                  70                  75                  80
```

```
Ala Glu Asp Glu Ala Asp Tyr Tyr Cys Gln Ser Tyr Asp Arg Tyr Thr
                85                  90                  95

His Pro Ala Leu Leu Phe Gly Thr Gly Thr Lys Val Thr Val Leu Gly
            100                 105                 110

Gln Pro Lys Ala Asn Pro Thr Val Thr Leu Phe Pro Pro Ser Ser Glu
            115                 120                 125

Glu Leu Gln Ala Asn Lys Ala Thr Leu Val Cys Leu Ile Ser Asp Phe
            130                 135                 140

Tyr Pro Gly Ala Val Thr Val Ala Trp Lys Ala Asp Gly Ser Pro Val
145                 150                 155                 160

Lys Ala Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
            195                 200                 205

Lys Thr Val Ala Pro Thr Glu Cys Ser Gly Ser Gly Gly Gly Gly
            210                 215                 220

Ser Gly Gly Gly Gly Ser Ser Gly Gly Val Thr Gly Tyr Arg Leu Phe
225                 230                 235                 240

Glu Glu Ile Leu
```

<210> SEQ ID NO 163
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 163

```
Gln Ser Val Leu Thr Gln Pro Pro Ser Val Ser Gly Ala Pro Gly Gln
1               5                   10                  15

Arg Val Thr Ile Ser Cys Ser Gly Ser Arg Ser Asn Ile Gly Ser Asn
                20                  25                  30

Thr Val Lys Trp Tyr Gln Gln Leu Pro Gly Thr Ala Pro Lys Leu Leu
            35                  40                  45

Ile Tyr Tyr Asn Asp Gln Arg Pro Ser Gly Val Pro Asp Arg Phe Ser
        50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Tyr Asp Arg Tyr Thr
                85                  90                  95

His Pro Ala Leu Leu Phe Gly Thr Gly Thr Lys Val Thr Val Leu Gly
            100                 105                 110

Gln Pro Lys Ala Asn Pro Thr Val Thr Leu Phe Pro Pro Ser Ser Glu
            115                 120                 125

Glu Leu Gln Ala Asn Lys Ala Thr Leu Val Cys Leu Ile Ser Asp Phe
            130                 135                 140

Tyr Pro Gly Ala Val Thr Val Ala Trp Lys Ala Asp Gly Ser Pro Val
145                 150                 155                 160

Lys Ala Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190
```

-continued

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 164
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 164

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Asn Asn Asn
            20                  25                  30

Asn Tyr Tyr Trp Thr Trp Ile Arg Gln His Pro Gly Lys Gly Leu Glu
        35                  40                  45

Trp Ile Gly Tyr Ile Tyr Tyr Ser Gly Ser Thr Phe Tyr Asn Pro Ser
50                  55                  60

Leu Lys Ser Arg Val Thr Ile Ser Val Asp Thr Ser Lys Thr Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asp Thr Met Thr Gly Leu Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Cys Arg Glu Glu Met Thr Lys Asn Gln Val Ser Leu Trp
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 165
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 165

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Asn Tyr
            20                  25                  30

Leu Asn Trp Tyr Gln Gln Lys Pro Gly Lys Ala Pro Thr Leu Leu Ile
        35                  40                  45

Tyr Ala Ala Ser Ser Leu Gln Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Ala Tyr Phe Cys Gln Gln Thr Tyr Ser Asn Pro Thr
                85                  90                  95

Phe Gly Gln Gly Thr Lys Val Glu Val Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 166
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 166

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Cys
            340                 345                 350
```

Thr Leu Pro Pro Ser Arg Glu Glu Met Thr Lys Asn Gln Val Ser Leu
            355                 360                 365

Ser Cys Ala Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 167
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 167

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 168
<211> LENGTH: 448
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 168

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Cys Arg Glu Glu Met Thr Lys Asn Gln Val Ser Leu Trp Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
        435                 440                 445

<210> SEQ ID NO 169
<211> LENGTH: 725
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 169

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

-continued

```
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Cys Arg Glu Glu Met Thr Lys Asn Gln Val Ser Leu Trp Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445
Gly Gly Gly Gly Ser Gly Gly Gly Ser Gly Gly Gly Gly Ser Glu
    450                 455                 460
Val Gln Leu Val Glu Ser Gly Gly Gly Leu Val Lys Pro Gly Gly Ser
465                 470                 475                 480
Leu Arg Leu Ser Cys Ala Ala Ser Gly Phe Thr Phe Ser Pro Tyr Ser
                485                 490                 495
Val Phe Trp Val Arg Gln Ala Pro Gly Lys Gly Leu Glu Trp Val Ser
            500                 505                 510
Ser Ile Asn Thr Asp Ser Thr Tyr Lys Tyr Tyr Ala Asp Ser Val Lys
        515                 520                 525
Gly Arg Phe Thr Ile Ser Arg Asp Asn Ala Glu Asn Ser Ile Phe Leu
    530                 535                 540
Gln Met Asn Ser Leu Arg Ala Glu Asp Thr Ala Val Tyr Tyr Cys Ala
545                 550                 555                 560
Arg Asp Arg Ser Tyr Tyr Ala Phe Ser Ser Gly Ser Leu Ser Asp Tyr
                565                 570                 575
Tyr Tyr Gly Leu Asp Val Trp Gly Gln Gly Thr Leu Val Thr Val Ser
            580                 585                 590
Ser Gly Gly Gly Gly Ser Gly Gly Gly Gly Ser Gly Gly Gly Gly Ser
        595                 600                 605
Gly Gly Gly Gly Ser Asp Ile Val Met Thr Gln Ser Pro Leu Ser Leu
    610                 615                 620
Ser Val Thr Pro Gly Glu Pro Ala Ser Ile Ser Cys Arg Ser Ser Gln
625                 630                 635                 640
Ser Leu Leu His Thr Asn Leu Tyr Asn Tyr Leu Asp Trp Tyr Val Gln
                645                 650                 655
Lys Pro Gly Gln Ser Pro Gln Leu Leu Ile Tyr Leu Ala Ser Asn Arg
            660                 665                 670
Ala Ser Gly Val Pro Asp Arg Phe Ser Gly Ser Gly Ser Gly Thr Asp
        675                 680                 685
Phe Thr Leu Lys Ile Ser Arg Val Glu Thr Glu Asp Val Gly Val Tyr
    690                 695                 700
Tyr Cys Met Gln Ala Leu Gln Ile Pro Arg Thr Phe Gly Gln Gly Thr
```

```
705                 710                 715                 720
Lys Leu Glu Ile Lys
                725

<210> SEQ ID NO 170
<211> LENGTH: 445
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 170

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Lys Thr His Gly Ser His Asp Asn Trp Gly Gln Gly Thr Met Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335
```

```
Ala Lys Gly Gln Pro Arg Glu Pro Gln Val Cys Thr Leu Pro Pro Ser
            340                 345                 350

Arg Glu Glu Met Thr Lys Asn Gln Val Ser Leu Ser Cys Ala Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Val Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 171
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 171

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
            85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240
```

```
Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 172
<211> LENGTH: 445
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 172

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Lys Thr His Gly Ser His Asp Asn Trp Gly Gln Gly Thr Met Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
```

```
                145                 150                 155                 160
Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 173
<211> LENGTH: 365
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 173

Gln Ser Val Leu Thr Gln Pro Pro Ser Val Ser Gly Ala Pro Gly Gln
1               5                   10                  15

Arg Val Thr Ile Ser Cys Ser Gly Ser Arg Ser Asn Ile Gly Ser Asn
            20                  25                  30

Thr Val Lys Trp Tyr Gln Gln Leu Pro Gly Thr Ala Pro Lys Leu Leu
        35                  40                  45

Ile Tyr Tyr Asn Asp Gln Arg Pro Ser Gly Val Pro Asp Arg Phe Ser
    50                  55                  60
```

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Tyr Asp Arg Tyr Thr
                85                  90                  95

His Pro Ala Leu Leu Phe Gly Thr Gly Thr Lys Val Thr Val Leu Gly
            100                 105                 110

Gln Pro Lys Ala Asn Pro Thr Val Thr Leu Phe Pro Pro Ser Ser Glu
        115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Gly Ser Pro Val
145                 150                 155                 160

Lys Ala Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser Gly Gly Gly Ser Gly Gly
210                 215                 220

Gly Gly Ser Gly Gly Gly Ser Ala Pro Thr Ser Ser Ser Thr Lys
225                 230                 235                 240

Lys Thr Gln Leu Gln Leu Glu His Leu Leu Leu Asp Leu Gln Met Ile
                245                 250                 255

Leu Asn Gly Ile Asn Asn Tyr Lys Asn Pro Lys Leu Thr Arg Met Leu
            260                 265                 270

Thr Ala Lys Phe Ala Met Pro Lys Lys Ala Thr Glu Leu Lys His Leu
        275                 280                 285

Gln Cys Leu Glu Glu Glu Leu Lys Pro Leu Glu Glu Val Leu Asn Leu
290                 295                 300

Ala Gln Ser Lys Asn Phe His Leu Arg Pro Arg Asp Leu Ile Ser Asn
305                 310                 315                 320

Ile Asn Val Ile Val Leu Glu Leu Lys Gly Ser Glu Thr Thr Phe Met
                325                 330                 335

Cys Glu Tyr Ala Asp Glu Thr Ala Thr Ile Val Glu Phe Leu Asn Arg
            340                 345                 350

Trp Ile Thr Phe Cys Gln Ser Ile Ile Ser Thr Leu
        355                 360                 365

<210> SEQ ID NO 174
<211> LENGTH: 593
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 174

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

```
Ala Phe Ile Arg Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Lys Thr His Gly Ser His Asp Asn Trp Gly Gln Gly Thr Met Val Thr
                100                 105                 110

Val Ser Ser Ala Ser Thr Lys Gly Pro Ser Val Phe Pro Leu Ala Pro
                115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
                195                 200                 205

Val Asp Lys Arg Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
                260                 265                 270

Phe Asn Trp Tyr Val Asp Gly Val Glu Val His Asn Ala Lys Thr Lys
                275                 280                 285

Pro Arg Glu Glu Gln Tyr Asn Ser Thr Tyr Arg Val Val Ser Val Leu
                290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Cys Thr Leu Pro Pro Ser
                340                 345                 350

Arg Glu Glu Met Thr Lys Asn Gln Val Ser Leu Ser Cys Ala Val Lys
                355                 360                 365

Gly Phe Tyr Pro Ser Asp Ile Ala Val Glu Trp Glu Ser Asn Gly Gln
                370                 375                 380

Pro Glu Asn Asn Tyr Lys Thr Thr Pro Pro Val Leu Asp Ser Asp Gly
385                 390                 395                 400

Ser Phe Phe Leu Val Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys Gly Gly Gly
                435                 440                 445

Gly Ser Gly Gly Gly Gly Ser Gly Gly Gly Gly Ser Ala Pro Thr Ser
450                 455                 460

Ser Ser Thr Lys Lys Thr Gln Leu Gln Leu Glu His Leu Leu Leu Asp
```

```
                465                 470                 475                 480
Leu Gln Met Ile Leu Asn Gly Ile Asn Asn Tyr Lys Asn Pro Lys Leu
                        485                 490                 495

Thr Arg Met Leu Thr Ala Lys Phe Ala Met Pro Lys Lys Ala Thr Glu
                500                 505                 510

Leu Lys His Leu Gln Cys Leu Glu Glu Leu Lys Pro Leu Glu Glu
                515                 520                 525

Val Leu Asn Leu Ala Gln Ser Lys Asn Phe His Leu Arg Pro Arg Asp
                530                 535                 540

Leu Ile Ser Asn Ile Asn Val Ile Val Leu Glu Leu Lys Gly Ser Glu
545                 550                 555                 560

Thr Thr Phe Met Cys Glu Tyr Ala Asp Glu Thr Ala Thr Ile Val Glu
                        565                 570                 575

Phe Leu Asn Arg Trp Ile Thr Phe Cys Gln Ser Ile Ile Ser Thr Leu
                        580                 585                 590

Thr

<210> SEQ ID NO 175
<211> LENGTH: 593
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 175

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Phe Ile Arg Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Lys Thr His Gly Ser His Asp Asn Trp Gly Gln Gly Thr Met Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220
```

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
        260                 265                 270

Phe Asn Trp Tyr Val Asp Gly Val Glu Val His Asn Ala Lys Thr Lys
    275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
        340                 345                 350

Arg Glu Glu Met Thr Lys Asn Gln Val Ser Leu Thr Cys Leu Val Lys
    355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
        420                 425                 430

His Tyr Thr Gln Lys Ser Leu Ser Leu Ser Pro Gly Lys Gly Gly Gly
    435                 440                 445

Gly Ser Gly Gly Gly Ser Gly Gly Gly Ser Ala Pro Thr Ser
450                 455                 460

Ser Ser Thr Lys Lys Thr Gln Leu Gln Leu Glu His Leu Leu Leu Asp
465                 470                 475                 480

Leu Gln Met Ile Leu Asn Gly Ile Asn Asn Tyr Lys Asn Pro Lys Leu
            485                 490                 495

Thr Arg Met Leu Thr Ala Lys Phe Ala Met Pro Lys Lys Ala Thr Glu
        500                 505                 510

Leu Lys His Leu Gln Cys Leu Glu Glu Glu Leu Lys Pro Leu Glu Glu
    515                 520                 525

Val Leu Asn Leu Ala Gln Ser Lys Asn Phe His Leu Arg Pro Arg Asp
530                 535                 540

Leu Ile Ser Asn Ile Asn Val Ile Val Leu Glu Leu Lys Gly Ser Glu
545                 550                 555                 560

Thr Thr Phe Met Cys Glu Tyr Ala Asp Glu Thr Ala Thr Ile Val Glu
            565                 570                 575

Phe Leu Asn Arg Trp Ile Thr Phe Cys Gln Ser Ile Ile Ser Thr Leu
        580                 585                 590

Thr

<210> SEQ ID NO 176
<211> LENGTH: 363
<212> TYPE: PRT
<213> ORGANISM: Artificial Sequence
<220> FEATURE:
<221> NAME/KEY: source
<223> OTHER INFORMATION: /note="Description of Artificial Sequence:

```
<400> SEQUENCE: 176

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Gly Gly Ser Gly Gly Gly Gly
    210                 215                 220

Ser Gly Gly Gly Gly Ser Ala Pro Thr Ser Ser Ser Thr Lys Lys Thr
225                 230                 235                 240

Gln Leu Gln Leu Glu His Leu Leu Leu Asp Leu Gln Met Ile Leu Asn
                245                 250                 255

Gly Ile Asn Asn Tyr Lys Asn Pro Lys Leu Thr Arg Met Leu Thr Ala
            260                 265                 270

Lys Phe Ala Met Pro Lys Lys Ala Thr Glu Leu Lys His Leu Gln Cys
        275                 280                 285

Leu Glu Glu Glu Leu Lys Pro Leu Glu Glu Val Leu Asn Leu Ala Gln
    290                 295                 300

Ser Lys Asn Phe His Leu Arg Pro Arg Asp Leu Ile Ser Asn Ile Asn
305                 310                 315                 320

Val Ile Val Leu Glu Leu Lys Gly Ser Glu Thr Thr Phe Met Cys Glu
                325                 330                 335

Tyr Ala Asp Glu Thr Ala Thr Ile Val Glu Phe Leu Asn Arg Trp Ile
            340                 345                 350

Thr Phe Cys Gln Ser Ile Ile Ser Thr Leu Thr
        355                 360

<210> SEQ ID NO 177
<211> LENGTH: 451
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic polypeptide"

<400> SEQUENCE: 177
```

| | | | | | | | | | | | | | | | |
|---|---|---|---|---|---|---|---|---|---|---|---|---|---|---|---|
| Glu | Val | Gln | Leu | Val | Gln | Ser | Gly | Gly | Gly | Val | Glu | Arg | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Asp | Asp | Tyr |
| | | | 20 | | | | | 25 | | | | | 30 | | |
| Gly | Met | Ser | Trp | Val | Arg | Gln | Ala | Pro | Gly | Lys | Gly | Leu | Glu | Trp | Val |
| | | 35 | | | | | 40 | | | | | 45 | | | |
| Ser | Gly | Ile | Asn | Trp | Asn | Gly | Gly | Ser | Thr | Gly | Tyr | Ala | Asp | Ser | Val |
| | 50 | | | | | 55 | | | | | 60 | | | | |
| Lys | Gly | Arg | Val | Thr | Ile | Ser | Arg | Asp | Asn | Ala | Lys | Asn | Ser | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Lys | Ile | Leu | Gly | Ala | Gly | Arg | Gly | Trp | Tyr | Phe | Asp | Leu | Trp | Gly |
| | | | 100 | | | | | 105 | | | | | 110 | | |
| Lys | Gly | Thr | Thr | Val | Thr | Val | Ser | Ser | Ala | Ser | Thr | Lys | Gly | Pro | Ser |
| | | 115 | | | | | 120 | | | | | 125 | | | |
| Val | Phe | Pro | Leu | Ala | Pro | Ser | Ser | Lys | Ser | Thr | Ser | Gly | Gly | Thr | Ala |
| | 130 | | | | | 135 | | | | | 140 | | | | |
| Ala | Leu | Gly | Cys | Leu | Val | Lys | Asp | Tyr | Phe | Pro | Glu | Pro | Val | Thr | Val |
| 145 | | | | | 150 | | | | | 155 | | | | | 160 |
| Ser | Trp | Asn | Ser | Gly | Ala | Leu | Thr | Ser | Gly | Val | His | Thr | Phe | Pro | Ala |
| | | | | 165 | | | | | 170 | | | | | 175 | |
| Val | Leu | Gln | Ser | Ser | Gly | Leu | Tyr | Ser | Leu | Ser | Ser | Val | Val | Thr | Val |
| | | | 180 | | | | | 185 | | | | | 190 | | |
| Pro | Ser | Ser | Ser | Leu | Gly | Thr | Gln | Thr | Tyr | Ile | Cys | Asn | Val | Asn | His |
| | | 195 | | | | | 200 | | | | | 205 | | | |
| Lys | Pro | Ser | Asn | Thr | Lys | Val | Asp | Lys | Arg | Val | Glu | Pro | Lys | Ser | Cys |
| | 210 | | | | | 215 | | | | | 220 | | | | |
| Asp | Lys | Thr | His | Thr | Cys | Pro | Pro | Cys | Pro | Ala | Pro | Glu | Leu | Leu | Gly |
| 225 | | | | | 230 | | | | | 235 | | | | | 240 |
| Gly | Pro | Ser | Val | Phe | Leu | Phe | Pro | Pro | Lys | Pro | Lys | Asp | Thr | Leu | Met |
| | | | | 245 | | | | | 250 | | | | | 255 | |
| Ile | Ser | Arg | Thr | Pro | Glu | Val | Thr | Cys | Val | Val | Val | Asp | Val | Ser | His |
| | | | 260 | | | | | 265 | | | | | 270 | | |
| Glu | Asp | Pro | Glu | Val | Lys | Phe | Asn | Trp | Tyr | Val | Asp | Gly | Val | Glu | Val |
| | | 275 | | | | | 280 | | | | | 285 | | | |
| His | Asn | Ala | Lys | Thr | Lys | Pro | Arg | Glu | Glu | Gln | Tyr | Asn | Ser | Thr | Tyr |
| | 290 | | | | | 295 | | | | | 300 | | | | |
| Arg | Val | Val | Ser | Val | Leu | Thr | Val | Leu | His | Gln | Asp | Trp | Leu | Asn | Gly |
| 305 | | | | | 310 | | | | | 315 | | | | | 320 |
| Lys | Glu | Tyr | Lys | Cys | Lys | Val | Ser | Asn | Lys | Ala | Leu | Pro | Ala | Pro | Ile |
| | | | | 325 | | | | | 330 | | | | | 335 | |
| Glu | Lys | Thr | Ile | Ser | Lys | Ala | Lys | Gly | Gln | Pro | Arg | Glu | Pro | Gln | Val |
| | | | 340 | | | | | 345 | | | | | 350 | | |
| Cys | Thr | Leu | Pro | Pro | Ser | Arg | Glu | Glu | Met | Thr | Lys | Asn | Gln | Val | Ser |
| | | 355 | | | | | 360 | | | | | 365 | | | |
| Leu | Ser | Cys | Ala | Val | Lys | Gly | Phe | Tyr | Pro | Ser | Asp | Ile | Ala | Val | Glu |
| | 370 | | | | | 375 | | | | | 380 | | | | |
| Trp | Glu | Ser | Asn | Gly | Gln | Pro | Glu | Asn | Asn | Tyr | Lys | Thr | Thr | Pro | Pro |

```
                385                 390                 395                 400
Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
        450

<210> SEQ ID NO 178
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 178

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ala Gly Ile Ser Trp Asp Ser Gly Ser Thr Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Leu Gly Ala Tyr Gln Trp Val Glu Gly Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Thr Ile Lys Pro Cys Pro Pro Cys Lys Cys Pro Ala Pro Asn Leu
225                 230                 235                 240

Leu Gly Gly Pro Ser Val Phe Ile Phe Pro Pro Lys Ile Lys Asp Val
                245                 250                 255

Leu Met Ile Ser Leu Ser Pro Ile Val Thr Cys Val Val Val Asp Val
            260                 265                 270

Ser Glu Asp Asp Pro Asp Val Gln Ile Ser Trp Phe Val Asn Asn Val
        275                 280                 285
```

Glu Val His Thr Ala Gln Thr Gln Thr His Arg Glu Asp Tyr Asn Ser
            290                 295                 300

Thr Leu Arg Val Val Ser Ala Leu Pro Ile Gln His Gln Asp Trp Met
305                 310                 315                 320

Ser Gly Lys Glu Phe Lys Cys Lys Val Asn Asn Lys Asp Leu Pro Ala
                325                 330                 335

Pro Ile Glu Arg Thr Ile Ser Lys Pro Lys Gly Ser Val Arg Ala Pro
            340                 345                 350

Gln Val Tyr Val Leu Pro Pro Cys Glu Glu Glu Met Thr Lys Lys Gln
        355                 360                 365

Val Thr Leu Trp Cys Met Val Thr Asp Phe Met Pro Glu Asp Ile Tyr
370                 375                 380

Val Glu Trp Thr Asn Asn Gly Lys Thr Glu Leu Asn Tyr Lys Asn Thr
385                 390                 395                 400

Glu Pro Val Leu Asp Ser Asp Gly Ser Tyr Phe Met Tyr Ser Lys Leu
                405                 410                 415

Arg Val Glu Lys Lys Asn Trp Val Glu Arg Asn Ser Tyr Ser Cys Ser
            420                 425                 430

Val Val His Glu Gly Leu His Asn His His Thr Thr Lys Ser Phe Ser
        435                 440                 445

Arg Thr Pro Gly Lys
    450

<210> SEQ ID NO 179
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 179

Glu Val Gln Leu Leu Gln Ser Gly Gly Gly Leu Val Gln Pro Gly Gly
1               5                   10                  15

Ser Leu Arg Leu Ser Cys Ala Ala Ser Gly Phe Met Phe Ser Arg Tyr
            20                  25                  30

Pro Met His Trp Val Arg Gln Ala Pro Gly Lys Gly Leu Glu Trp Val
        35                  40                  45

Gly Ser Ile Ser Gly Ser Gly Gly Ala Thr Pro Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Phe Tyr Gln Ile Leu Thr Gly Asn Ala Phe Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

```
Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Arg Val Glu Pro Lys Ser
    210                 215                 220

Cys Thr Ile Lys Pro Cys Pro Pro Cys Lys Cys Pro Ala Pro Asn Leu
225                 230                 235                 240

Leu Gly Gly Pro Ser Val Phe Ile Phe Pro Pro Lys Ile Lys Asp Val
                245                 250                 255

Leu Met Ile Ser Leu Ser Pro Ile Val Thr Cys Val Val Asp Val
                260                 265                 270

Ser Glu Asp Asp Pro Asp Val Gln Ile Ser Trp Phe Val Asn Asn Val
            275                 280                 285

Glu Val His Thr Ala Gln Thr Gln Thr His Arg Glu Asp Tyr Asn Ser
            290                 295                 300

Thr Leu Arg Val Val Ser Ala Leu Pro Ile Gln His Gln Asp Trp Met
305                 310                 315                 320

Ser Gly Lys Glu Phe Lys Cys Lys Val Asn Asn Lys Asp Leu Pro Ala
                325                 330                 335

Pro Ile Glu Arg Thr Ile Ser Lys Pro Lys Gly Ser Val Arg Ala Pro
                340                 345                 350

Gln Val Cys Val Leu Pro Pro Glu Glu Met Thr Lys Lys Gln
                355                 360                 365

Val Thr Leu Ser Cys Ala Val Thr Asp Phe Met Pro Glu Asp Ile Tyr
370                 375                 380

Val Glu Trp Thr Asn Asn Gly Lys Thr Glu Leu Asn Tyr Lys Asn Thr
385                 390                 395                 400

Glu Pro Val Leu Asp Ser Asp Gly Ser Tyr Phe Met Val Ser Lys Leu
                405                 410                 415

Arg Val Glu Lys Lys Asn Trp Val Glu Arg Asn Ser Tyr Ser Cys Ser
                420                 425                 430

Val Val His Glu Gly Leu His Asn His His Thr Thr Lys Ser Phe Ser
            435                 440                 445

Arg Thr Pro Gly Lys
    450

<210> SEQ ID NO 180
<211> LENGTH: 460
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 180

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Lys Ser Thr Ser Thr Ala Tyr
```

```
              65                  70                  75                  80
Met Glu Leu Ser Ser Leu Arg Ser Glu Asp Thr Ala Val Tyr Tyr Cys
                    85                  90                  95

Ala Arg Ala Pro Leu Arg Phe Leu Glu Trp Ser Thr Gln Asp His Tyr
                100                 105                 110

Tyr Tyr Tyr Tyr Met Asp Val Trp Gly Lys Gly Thr Thr Val Thr Val
            115                 120                 125

Ser Ser Ala Ser Thr Lys Gly Pro Ser Val Phe Pro Leu Ala Pro Ser
130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Gln Thr Tyr Ile Cys Asn Val Asn His Lys Pro Ser Asn Thr Lys Val
    210                 215                 220

Asp Lys Arg Val Glu Pro Lys Ser Cys Asp Lys Thr His Thr Cys Pro
225                 230                 235                 240

Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Cys Thr Leu Pro Pro Ser Arg
        355                 360                 365

Glu Glu Met Thr Lys Asn Gln Val Ser Leu Ser Cys Ala Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Val Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460

<210> SEQ ID NO 181
<211> LENGTH: 443
<212> TYPE: PRT
<213> ORGANISM: Artificial Sequence
```

-continued

```
<220> FEATURE:
<221> NAME/KEY: source
<223> OTHER INFORMATION: /note="Description of Artificial Sequence:
      Synthetic polypeptide"

<400> SEQUENCE: 181

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Arg Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Cys Arg Glu
            340                 345                 350

Glu Met Thr Lys Asn Gln Val Ser Leu Trp Cys Leu Val Lys Gly Phe
        355                 360                 365

Tyr Pro Ser Asp Ile Ala Val Glu Trp Glu Ser Asn Gly Gln Pro Glu
    370                 375                 380
```

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
            405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 182
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 182

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 183
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 183

Gln Val Gln Leu Val Gln Ser Gly Ala Glu Val Lys Lys Pro Gly Ala

```
1               5                   10                  15
Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg

<210> SEQ ID NO 184
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 184

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Arg Ile Asn Pro Asn Ser Gly Gly Thr Asn Tyr Ala Gln Lys Phe
        50                  55                  60

Gln Gly Arg Val Thr Ser Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg

<210> SEQ ID NO 185
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 185

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Met His Trp Val Arg Gln Ala Pro Gly Gln Arg Leu Glu Trp Met
            35                  40                  45

Gly Trp Ile Asn Ala Gly Asn Gly Asn Thr Lys Tyr Ser Gln Lys Phe
        50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
```

```
                        85                  90                  95

Ala Arg

<210> SEQ ID NO 186
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 186

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 187
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 187

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 188
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 188
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65              70                  75                  80

Gln Met Asn Ser Leu Arg Ala Gly Asp Thr Ala Val Tyr Tyr Cys Ala
            85                  90                  95

Arg

<210> SEQ ID NO 189
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 189

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65              70                  75                  80

Leu Gln Met Asn Ser Leu Arg Ala Glu Asp Thr Ala Leu Tyr His Cys
            85                  90                  95

Ala Arg

<210> SEQ ID NO 190
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 190

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65              70                  75                  80
```

```
Leu Gln Met Asn Ser Leu Arg Ala Glu Asp Thr Ala Val Tyr Tyr Cys
                85                  90                  95

Ala Arg

<210> SEQ ID NO 191
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 191

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 192
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 192

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 193
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 193

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 194
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 194

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg

<210> SEQ ID NO 195
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 195

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

-continued

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 196
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 196

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys

<210> SEQ ID NO 197
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 197

Gln Val Gln Leu Gln Glu Ser Gly Pro Gly Leu Val Lys Pro Pro Gly
1               5                   10                  15

Thr Leu Ser Leu Thr Cys Ala Val Ser Gly Gly Ser Ile Ser Ser Ser
                20                  25                  30

Asn Trp Trp Ser Trp Val Arg Gln Pro Pro Gly Lys Gly Leu Glu Trp
            35                  40                  45

Ile Gly Glu Ile Tyr His Ser Gly Ser Thr Asn Tyr Asn Pro Ser Leu
        50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Cys Cys
                85                  90                  95

Ala Arg

<210> SEQ ID NO 198
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 198

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg

<210> SEQ ID NO 199
<211> LENGTH: 88
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 199

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys
                85

<210> SEQ ID NO 200
<211> LENGTH: 88
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 200

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys
                85

<210> SEQ ID NO 201
<211> LENGTH: 88
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 201

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys
                85

<210> SEQ ID NO 202
<211> LENGTH: 88
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 202

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys
                85

<210> SEQ ID NO 203
<211> LENGTH: 93
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 203

Asp Ile Val Met Thr Gln Ser Pro Leu Ser Leu Pro Val Thr Pro Gly

```
                1               5                   10                  15
            Glu Pro Ala Ser Ile Ser Cys Arg Ser Ser Gln Ser Leu Leu His Ser
                            20                  25                  30

Asn Gly Tyr Asn Tyr Leu Asp Trp Tyr Leu Gln Lys Pro Gly Gln Ser
                        35                  40                  45

Pro Gln Leu Leu Ile Tyr Leu Gly Ser Asn Arg Ala Ser Gly Val Pro
                    50                  55                  60

Asp Arg Phe Ser Gly Ser Gly Ser Gly Thr Asp Phe Thr Leu Lys Ile
                65                  70                  75                  80

Ser Arg Val Glu Ala Glu Asp Val Gly Val Tyr Tyr Cys
                            85                  90
```

<210> SEQ ID NO 204
<211> LENGTH: 88
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 204

```
            Glu Ile Val Leu Thr Gln Ser Pro Ala Thr Leu Ser Leu Ser Pro Gly
            1               5                   10                  15

Glu Arg Ala Thr Leu Ser Cys Arg Ala Ser Gln Ser Val Ser Ser Tyr
                            20                  25                  30

Leu Ala Trp Tyr Gln Gln Lys Pro Gly Gln Ala Pro Arg Leu Leu Ile
                        35                  40                  45

Tyr Asp Ala Ser Asn Arg Ala Thr Gly Ile Pro Ala Arg Phe Ser Gly
                    50                  55                  60

Ser Gly Ser Gly Thr Asp Phe Thr Leu Thr Ile Ser Ser Leu Glu Pro
                65                  70                  75                  80

Glu Asp Phe Ala Val Tyr Tyr Cys
                            85
```

<210> SEQ ID NO 205
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 205

```
            Glu Ile Val Leu Thr Gln Ser Pro Gly Thr Leu Ser Leu Ser Pro Gly
            1               5                   10                  15

Glu Arg Ala Thr Leu Ser Cys Arg Ala Ser Gln Ser Val Ser Ser Ser
                            20                  25                  30

Tyr Leu Ala Trp Tyr Gln Gln Lys Pro Gly Gln Ala Pro Arg Leu Leu
                        35                  40                  45

Ile Tyr Gly Ala Ser Ser Arg Ala Thr Gly Ile Pro Asp Arg Phe Ser
                    50                  55                  60

Gly Ser Gly Ser Gly Thr Asp Phe Thr Leu Thr Ile Ser Arg Leu Glu
                65                  70                  75                  80

Pro Glu Asp Phe Ala Val Tyr Tyr Cys
                            85
```

<210> SEQ ID NO 206

```
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 206

Glu Ile Val Leu Thr Gln Ser Pro Ala Thr Leu Ser Leu Ser Pro Gly
1               5                   10                  15

Glu Arg Ala Thr Leu Ser Cys Gly Ala Ser Gln Ser Val Ser Ser Ser
            20                  25                  30

Tyr Leu Ala Trp Tyr Gln Gln Lys Pro Gly Leu Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys
                85

<210> SEQ ID NO 207
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 207

Gln Ala Gly Leu Thr Gln Pro Pro Ser Val Ser Lys Gly Leu Arg Gln
1               5                   10                  15

Thr Ala Thr Leu Thr Cys Thr Gly Asn Ser Asn Asn Val Gly Asn Gln
            20                  25                  30

Gly Ala Ala Trp Leu Gln Gln His Gln Gly His Pro Pro Lys Leu Leu
        35                  40                  45

Ser Tyr Arg Asn Asn Arg Pro Ser Gly Ile Ser Glu Arg Leu Ser
    50                  55                  60

Ala Ser Arg Ser Gly Asn Thr Ala Ser Leu Thr Ile Thr Gly Leu Gln
65                  70                  75                  80

Pro Glu Asp Glu Ala Asp Tyr Tyr Cys
                85

<210> SEQ ID NO 208
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 208

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45
```

```
Leu Ile Tyr Gly Asn Ser Asn Arg Pro Ser Gly Val Pro Asp Arg Phe
            50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys
                 85                  90

<210> SEQ ID NO 209
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 209

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Asn
                20                  25                  30

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys
                85

<210> SEQ ID NO 210
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 210

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Glu Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys
                 85                  90

<210> SEQ ID NO 211
<211> LENGTH: 87
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 211

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys
                85

<210> SEQ ID NO 212
<211> LENGTH: 87
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 212

Ser Tyr Glu Leu Thr Gln Pro Leu Ser Val Ser Val Ala Leu Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Ile Tyr
        35                  40                  45

Arg Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys
                85

<210> SEQ ID NO 213
<211> LENGTH: 99
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 213

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Leu Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 214
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 214

Met Glu Thr Asp Thr Leu Leu Leu Trp Val Leu Leu Trp Val Pro
1               5                   10                  15

Gly Ser Thr Gly
            20

<210> SEQ ID NO 215
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 215

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 216
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 216

Gly Tyr Thr Phe Thr Ser Tyr Gly Ile Ser
1               5                   10

<210> SEQ ID NO 217
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 217

Trp Val Arg Gln Ala Pro Gly Gln Gly Leu Glu Trp Met Gly
1               5                   10

<210> SEQ ID NO 218
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

```
<400> SEQUENCE: 218

Trp Ile Ser Ala Tyr Asn Gly Asn Thr Asn Tyr Ala Gln Lys Leu Gln
1               5                   10                  15

Gly

<210> SEQ ID NO 219
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 219

Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys Ala Arg
            20                  25                  30

<210> SEQ ID NO 220
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 220

Gly Tyr Thr Phe Thr Gly Tyr Tyr Met His
1               5                   10

<210> SEQ ID NO 221
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 221

Arg Ile Asn Pro Asn Ser Gly Gly Thr Asn Tyr Ala Gln Lys Phe Gln
1               5                   10                  15

Gly

<210> SEQ ID NO 222
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 222

Arg Val Thr Ser Thr Arg Asp Thr Ser Ile Ser Thr Ala Tyr Met Glu
1               5                   10                  15

Leu Ser Arg Leu Arg Ser Asp Asp Thr Val Val Tyr Tyr Cys Ala Arg
            20                  25                  30

<210> SEQ ID NO 223
<211> LENGTH: 10
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 223

Gly Tyr Thr Phe Thr Ser Tyr Ala Met His
1               5                   10

<210> SEQ ID NO 224
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 224

Trp Val Arg Gln Ala Pro Gly Gln Arg Leu Glu Trp Met Gly
1               5                   10

<210> SEQ ID NO 225
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 225

Trp Ile Asn Ala Gly Asn Gly Asn Thr Lys Tyr Ser Gln Lys Phe Gln
1               5                   10                  15

Gly

<210> SEQ ID NO 226
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 226

Arg Val Thr Ile Thr Arg Asp Thr Ser Ala Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 227
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 227

Gly Tyr Thr Phe Thr Ser Tyr Tyr Met His
1               5                   10

<210> SEQ ID NO 228
<211> LENGTH: 17
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 228

Ile Ile Asn Pro Ser Gly Gly Ser Thr Ser Tyr Ala Gln Lys Phe Gln
1               5                   10                  15

Gly

<210> SEQ ID NO 229
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 229

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Ala Arg
                20                  25                  30

<210> SEQ ID NO 230
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 230

Gln Val Gln Leu Val Gln Ser Gly Ala Glu Val Lys Lys Pro Gly Ser
1               5                   10                  15

Ser Val Lys Val Ser Cys Lys Ala Ser
                20                  25

<210> SEQ ID NO 231
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 231

Gly Gly Thr Phe Ser Ser Tyr Ala Ile Ser
1               5                   10

<210> SEQ ID NO 232
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 232

Gly Ile Ile Pro Ile Phe Gly Thr Ala Asn Tyr Ala Gln Lys Phe Gln
1               5                   10                  15
```

Gly

```
<210> SEQ ID NO 233
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 233
```

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

```
<210> SEQ ID NO 234
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 234
```

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

```
<210> SEQ ID NO 235
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 235
```

Gly Phe Thr Phe Ser Ser Tyr Asp Met His
1               5                   10

```
<210> SEQ ID NO 236
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 236
```

Trp Val Arg Gln Ala Thr Gly Lys Gly Leu Glu Trp Val Ser
1               5                   10

```
<210> SEQ ID NO 237
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 237

Ala Ile Gly Thr Ala Gly Asp Thr Tyr Tyr Pro Gly Ser Val Lys Gly
1               5                   10                  15

<210> SEQ ID NO 238
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 238

Arg Phe Thr Ile Ser Arg Glu Asn Ala Lys Asn Ser Leu Tyr Leu Gln
1               5                   10                  15

Met Asn Ser Leu Arg Ala Gly Asp Thr Ala Val Tyr Tyr Cys Ala Arg
            20                  25                  30

<210> SEQ ID NO 239
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 239

Glu Val Gln Leu Val Glu Ser Gly Gly Gly Val Val Arg Pro Gly Gly
1               5                   10                  15

Ser Leu Arg Leu Ser Cys Ala Ala Ser
            20                  25

<210> SEQ ID NO 240
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 240

Gly Phe Thr Phe Asp Asp Tyr Gly Met Ser
1               5                   10

<210> SEQ ID NO 241
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 241

Trp Val Arg Gln Ala Pro Gly Lys Gly Leu Glu Trp Val Ser
1               5                   10

<210> SEQ ID NO 242
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 242

Gly Ile Asn Trp Asn Gly Gly Ser Thr Gly Tyr Ala Asp Ser Val Lys
1               5                   10                  15

Gly

<210> SEQ ID NO 243
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 243

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Leu Tyr His Cys Ala Arg
            20                  25                  30

<210> SEQ ID NO 244
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 244

Glu Val Gln Leu Val Glu Ser Gly Gly Gly Leu Val Lys Pro Gly Gly
1               5                   10                  15

Ser Leu Arg Leu Ser Cys Ala Ala Ser
            20                  25

<210> SEQ ID NO 245
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 245

Gly Phe Thr Phe Ser Ser Tyr Ser Met Asn
1               5                   10

<210> SEQ ID NO 246
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 246

Ser Ile Ser Ser Ser Ser Ser Tyr Ile Tyr Tyr Ala Asp Ser Val Lys
1               5                   10                  15

Gly

<210> SEQ ID NO 247

```
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 247

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 248
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 248

Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 249
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 249

Gly Phe Thr Phe Ser Ser Tyr Ala Met Ser
1               5                   10

<210> SEQ ID NO 250
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 250

Ala Ile Ser Gly Ser Gly Gly Ser Thr Tyr Tyr Ala Asp Ser Val Lys
1               5                   10                  15

Gly

<210> SEQ ID NO 251
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 251

Arg Phe Thr Ile Ser Arg Asp Asn Ser Lys Asn Thr Leu Tyr Leu Gln
```

```
                1               5                   10                  15
Met Asn Ser Leu Arg Ala Glu Asp Thr Ala Val Tyr Tyr Cys Ala Lys
                20                  25                  30
```

<210> SEQ ID NO 252
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 252

```
Gln Val Gln Leu Val Glu Ser Gly Gly Gly Val Val Gln Pro Gly Arg
1               5                   10                  15
Ser Leu Arg Leu Ser Cys Ala Ala Ser
                20                  25
```

<210> SEQ ID NO 253
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 253

```
Gly Phe Thr Phe Ser Ser Tyr Ala Met His
1               5                   10
```

<210> SEQ ID NO 254
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 254

```
Trp Val Arg Gln Ala Pro Gly Lys Gly Leu Glu Trp Val Ala
1               5                   10
```

<210> SEQ ID NO 255
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 255

```
Val Ile Ser Tyr Asp Gly Ser Asn Lys Tyr Tyr Ala Asp Ser Val Lys
1               5                   10                  15
Gly
```

<210> SEQ ID NO 256
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 256

Arg Phe Thr Ile Ser Arg Asp Asn Ser Lys Asn Thr Leu Tyr Leu Gln
1               5                   10                  15
Met Asn Ser Leu Arg Ala Glu Asp Thr Ala Val Tyr Tyr Cys Ala Arg
            20                  25                  30

<210> SEQ ID NO 257
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 257

Gly Phe Thr Phe Ser Ser Tyr Gly Met His
1               5                   10

<210> SEQ ID NO 258
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 258

Val Ile Trp Tyr Asp Gly Ser Asn Lys Tyr Tyr Ala Asp Ser Val Lys
1               5                   10                  15
Gly

<210> SEQ ID NO 259
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 259

Gly Phe Thr Val Ser Ser Asn Tyr Met Ser
1               5                   10

<210> SEQ ID NO 260
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 260

Val Ile Tyr Ser Gly Gly Ser Thr Tyr Tyr Ala Asp Ser Val Lys Gly
1               5                   10                  15

<210> SEQ ID NO 261
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:

```
                    Synthetic peptide"

<400> SEQUENCE: 261

Gly Phe Thr Phe Ser Ser Tyr Trp Met Ser
1               5                   10

<210> SEQ ID NO 262
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 262

Asn Ile Lys Gln Asp Gly Ser Glu Lys Tyr Tyr Val Asp Ser Val Lys
1               5                   10                  15

Gly

<210> SEQ ID NO 263
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 263

Glu Val Gln Leu Val Glu Ser Gly Gly Gly Leu Val Gln Pro Gly Arg
1               5                   10                  15

Ser Leu Arg Leu Ser Cys Ala Ala Ser
            20                  25

<210> SEQ ID NO 264
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 264

Gly Phe Thr Phe Asp Asp Tyr Ala Met His
1               5                   10

<210> SEQ ID NO 265
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 265

Gly Ile Ser Trp Asn Ser Gly Ser Ile Gly Tyr Ala Asp Ser Val Lys
1               5                   10                  15

Gly

<210> SEQ ID NO 266
<211> LENGTH: 32
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 266

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Leu Tyr Tyr Cys Ala Lys
            20                  25                  30

<210> SEQ ID NO 267
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 267

Gln Val Gln Leu Gln Glu Ser Gly Pro Gly Leu Val Lys Pro Pro Gly
1               5                   10                  15

Thr Leu Ser Leu Thr Cys Ala Val Ser
            20                  25

<210> SEQ ID NO 268
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 268

Gly Gly Ser Ile Ser Ser Ser Asn Trp Trp Ser
1               5                   10

<210> SEQ ID NO 269
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 269

Trp Val Arg Gln Pro Pro Gly Lys Gly Leu Glu Trp Ile Gly
1               5                   10

<210> SEQ ID NO 270
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 270

Glu Ile Tyr His Ser Gly Ser Thr Asn Tyr Asn Pro Ser Leu Lys Ser
1               5                   10                  15

<210> SEQ ID NO 271
<211> LENGTH: 32
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 271

Arg Val Thr Ile Ser Val Asp Lys Ser Lys Asn Gln Phe Ser Leu Lys
1               5                   10                  15

Leu Ser Ser Val Thr Ala Ala Asp Thr Ala Val Tyr Cys Cys Ala Arg
            20                  25                  30

<210> SEQ ID NO 272
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 272

Glu Val Gln Leu Val Gln Ser Gly Ala Glu Val Lys Lys Pro Gly Glu
1               5                   10                  15

Ser Leu Lys Ile Ser Cys Lys Gly Ser
            20                  25

<210> SEQ ID NO 273
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 273

Gly Tyr Ser Phe Thr Ser Tyr Trp Ile Gly
1               5                   10

<210> SEQ ID NO 274
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 274

Trp Val Arg Gln Met Pro Gly Lys Gly Leu Glu Trp Met Gly
1               5                   10

<210> SEQ ID NO 275
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 275

Ile Ile Tyr Pro Gly Asp Ser Asp Thr Arg Tyr Ser Pro Ser Phe Gln
1               5                   10                  15

Gly
```

```
<210> SEQ ID NO 276
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 276

Gln Val Thr Ile Ser Ala Asp Lys Ser Ile Ser Thr Ala Tyr Leu Gln
1               5                   10                  15

Trp Ser Ser Leu Lys Ala Ser Asp Thr Ala Met Tyr Tyr Cys Ala Arg
            20                  25                  30

<210> SEQ ID NO 277
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 277

Asp Ile Gln Met Thr Gln Ser Pro Ser Ser Val Ser Ala Ser Val Gly
1               5                   10                  15

Asp Arg Val Thr Ile Thr Cys
            20

<210> SEQ ID NO 278
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 278

Arg Ala Ser Gln Gly Ile Ser Ser Trp Leu Ala
1               5                   10

<210> SEQ ID NO 279
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 279

Trp Tyr Gln Gln Lys Pro Gly Lys Ala Pro Lys Leu Leu Ile Tyr
1               5                   10                  15

<210> SEQ ID NO 280
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 280
```

```
Ala Ala Ser Ser Leu Gln Ser
1               5
```

<210> SEQ ID NO 281
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 281

```
Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30
```

<210> SEQ ID NO 282
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 282

```
Asp Ile Gln Met Thr Gln Ser Pro Ser Ser Leu Ser Ala Ser Val Gly
1               5                   10                  15

Asp Arg Val Thr Ile Thr Cys
            20
```

<210> SEQ ID NO 283
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 283

```
Arg Ala Ser Gln Gly Ile Ser Asn Tyr Leu Ala
1               5                   10
```

<210> SEQ ID NO 284
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 284

```
Trp Tyr Gln Gln Lys Pro Gly Lys Val Pro Lys Leu Leu Ile Tyr
1               5                   10                  15
```

<210> SEQ ID NO 285
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 285

Ala Ala Ser Thr Leu Gln Ser
1               5

<210> SEQ ID NO 286
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 286

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Tyr Cys
            20                  25                  30

<210> SEQ ID NO 287
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 287

Arg Ala Ser Gln Ser Ile Ser Ser Tyr Leu Asn
1               5                   10

<210> SEQ ID NO 288
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 288

Trp Tyr Gln Gln Lys Pro Glu Lys Ala Pro Lys Ser Leu Ile Tyr
1               5                   10                  15

<210> SEQ ID NO 289
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 289

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 290
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 290

Arg Ser Ser Gln Ser Leu Leu His Ser Asn Gly Tyr Asn Tyr Leu Asp
1               5                   10                  15

<210> SEQ ID NO 291
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 291

Trp Tyr Leu Gln Lys Pro Gly Gln Ser Pro Gln Leu Leu Ile Tyr
1               5                   10                  15

<210> SEQ ID NO 292
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 292

Leu Gly Ser Asn Arg Ala Ser
1               5

<210> SEQ ID NO 293
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 293

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 294
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 294

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 295
<211> LENGTH: 11
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 295

Arg Ala Ser Gln Ser Val Ser Ser Tyr Leu Ala
1               5                   10

<210> SEQ ID NO 296
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 296

Trp Tyr Gln Gln Lys Pro Gly Gln Ala Pro Arg Leu Leu Ile Tyr
1               5                   10                  15

<210> SEQ ID NO 297
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 297

Asp Ala Ser Asn Arg Ala Thr
1               5

<210> SEQ ID NO 298
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 298

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 299
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 299

Glu Ile Val Leu Thr Gln Ser Pro Gly Thr Leu Ser Leu Ser Pro Gly
1               5                   10                  15

Glu Arg Ala Thr Leu Ser Cys
            20

<210> SEQ ID NO 300
<211> LENGTH: 12
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 300

Arg Ala Ser Gln Ser Val Ser Ser Ser Tyr Leu Ala
1               5                   10

<210> SEQ ID NO 301
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 301

Gly Ala Ser Ser Arg Ala Thr
1               5

<210> SEQ ID NO 302
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 302

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 303
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 303

Gly Ala Ser Gln Ser Val Ser Ser Ser Tyr Leu Ala
1               5                   10

<210> SEQ ID NO 304
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 304

Trp Tyr Gln Gln Lys Pro Gly Leu Ala Pro Arg Leu Leu Ile Tyr
1               5                   10                  15

<210> SEQ ID NO 305
<211> LENGTH: 7
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 305

Asp Ala Ser Ser Arg Ala Thr
1               5

<210> SEQ ID NO 306
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 306

Gln Ala Gly Leu Thr Gln Pro Pro Ser Val Ser Lys Gly Leu Arg Gln
1               5                   10                  15

Thr Ala Thr Leu Thr Cys
            20

<210> SEQ ID NO 307
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 307

Thr Gly Asn Ser Asn Asn Val Gly Asn Gln Gly Ala Ala
1               5                   10

<210> SEQ ID NO 308
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 308

Trp Leu Gln Gln His Gln Gly His Pro Pro Lys Leu Leu Ser Tyr
1               5                   10                  15

<210> SEQ ID NO 309
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 309

Arg Asn Asn Asn Arg Pro Ser
1               5

<210> SEQ ID NO 310
<211> LENGTH: 32
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic polypeptide"

<400> SEQUENCE: 310

Gly Ile Ser Glu Arg Leu Ser Ala Ser Arg Ser Gly Asn Thr Ala Ser
1               5                   10                  15

Leu Thr Ile Thr Gly Leu Gln Pro Glu Asp Glu Ala Asp Tyr Tyr Cys
            20                  25                  30

<210> SEQ ID NO 311
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 311

Gln Ser Val Leu Thr Gln Pro Pro Ser Val Ser Gly Ala Pro Gly Gln
1               5                   10                  15

Arg Val Thr Ile Ser Cys
            20

<210> SEQ ID NO 312
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 312

Thr Gly Ser Ser Ser Asn Ile Gly Ala Gly Tyr Asp Val His
1               5                   10

<210> SEQ ID NO 313
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 313

Trp Tyr Gln Gln Leu Pro Gly Thr Ala Pro Lys Leu Leu Ile Tyr
1               5                   10                  15

<210> SEQ ID NO 314
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 314

Gly Asn Ser Asn Arg Pro Ser
1               5

<210> SEQ ID NO 315
<211> LENGTH: 32
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 315

Gly Val Pro Asp Arg Phe Ser Gly Ser Lys Ser Gly Thr Ser Ala Ser
1               5                   10                  15
Leu Ala Ile Thr Gly Leu Gln Ala Glu Asp Glu Ala Asp Tyr Tyr Cys
            20                  25                  30

<210> SEQ ID NO 316
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 316

Gln Ser Val Leu Thr Gln Pro Pro Ser Ala Ser Gly Thr Pro Gly Gln
1               5                   10                  15
Arg Val Thr Ile Ser Cys
            20

<210> SEQ ID NO 317
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 317

Ser Gly Ser Ser Ser Asn Ile Gly Ser Asn Thr Val Asn
1               5                   10

<210> SEQ ID NO 318
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 318

Ser Asn Asn Gln Arg Pro Ser
1               5

<210> SEQ ID NO 319
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 319

Gly Val Pro Asp Arg Phe Ser Gly Ser Lys Ser Gly Thr Ser Ala Ser
1               5                   10                  15
Leu Ala Ile Ser Gly Leu Gln Ser Glu Asp Glu Ala Asp Tyr Tyr Cys
            20                  25                  30
```

```
<210> SEQ ID NO 320
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 320

Gln Ser Ala Leu Thr Gln Pro Ala Ser Val Ser Gly Ser Pro Gly Gln
1               5                   10                  15

Ser Ile Thr Ile Ser Cys
            20

<210> SEQ ID NO 321
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 321

Thr Gly Thr Ser Ser Asp Val Gly Gly Tyr Asn Tyr Val Ser
1               5                   10

<210> SEQ ID NO 322
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 322

Trp Tyr Gln Gln His Pro Gly Lys Ala Pro Lys Leu Met Ile Tyr
1               5                   10                  15

<210> SEQ ID NO 323
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 323

Glu Val Ser Asn Arg Pro Ser
1               5

<210> SEQ ID NO 324
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 324

Gly Val Ser Asn Arg Phe Ser Gly Ser Lys Ser Gly Asn Thr Ala Ser
1               5                   10                  15
```

```
Leu Thr Ile Ser Gly Leu Gln Ala Glu Asp Glu Ala Asp Tyr Tyr Cys
            20                  25                  30
```

<210> SEQ ID NO 325
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 325

```
Ser Ser Glu Leu Thr Gln Asp Pro Ala Val Ser Val Ala Leu Gly Gln
1               5                   10                  15

Thr Val Arg Ile Thr Cys
            20
```

<210> SEQ ID NO 326
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 326

```
Gln Gly Asp Ser Leu Arg Ser Tyr Tyr Ala Ser
1               5                   10
```

<210> SEQ ID NO 327
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 327

```
Trp Tyr Gln Gln Lys Pro Gly Gln Ala Pro Val Leu Val Ile Tyr
1               5                   10                  15
```

<210> SEQ ID NO 328
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 328

```
Gly Lys Asn Asn Arg Pro Ser
1               5
```

<210> SEQ ID NO 329
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 329

```
Gly Ile Pro Asp Arg Phe Ser Gly Ser Ser Ser Gly Asn Thr Ala Ser
```

```
1               5                   10                  15
Leu Thr Ile Thr Gly Ala Gln Ala Glu Asp Glu Ala Asp Tyr Tyr Cys
            20                  25                  30

<210> SEQ ID NO 330
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 330

Ser Tyr Glu Leu Thr Gln Pro Leu Ser Val Ser Val Ala Leu Gly Gln
1               5                   10                  15

Thr Ala Arg Ile Thr Cys
            20

<210> SEQ ID NO 331
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 331

Gly Gly Asn Asn Ile Gly Ser Lys Asn Val His
1               5                   10

<210> SEQ ID NO 332
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 332

Arg Asp Ser Asn Arg Pro Ser
1               5

<210> SEQ ID NO 333
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 333

Gly Ile Pro Glu Arg Phe Ser Gly Ser Asn Ser Gly Asn Thr Ala Thr
1               5                   10                  15

Leu Thr Ile Ser Arg Ala Gln Ala Gly Asp Glu Ala Asp Tyr Tyr Cys
            20                  25                  30

<210> SEQ ID NO 334
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 334

Gln Val Gln Leu Gln Glu Ser Gly Pro Gly Leu Val Lys Pro Ser Gln
1               5                   10                  15

Thr Leu Ser Leu Thr Cys Thr Val Ser
            20                  25

<210> SEQ ID NO 335
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 335

Gly Gly Ser Ile Ser Ser Gly Ser Tyr Tyr Trp Ser
1               5                   10

<210> SEQ ID NO 336
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 336

Trp Ile Arg Gln His Pro Gly Lys Gly Leu Glu Trp Ile Gly
1               5                   10

<210> SEQ ID NO 337
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 337

Tyr Ile Tyr Tyr Ser Gly Ser Thr Tyr Tyr Asn Pro Ser Leu Lys Ser
1               5                   10                  15

<210> SEQ ID NO 338
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 338

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr
            20                  25

<210> SEQ ID NO 339

<400> SEQUENCE: 339

000

<210> SEQ ID NO 340

<400> SEQUENCE: 340

000

<210> SEQ ID NO 341

<400> SEQUENCE: 341

000

<210> SEQ ID NO 342

<400> SEQUENCE: 342

000

<210> SEQ ID NO 343

<400> SEQUENCE: 343

000

<210> SEQ ID NO 344

<400> SEQUENCE: 344

000

<210> SEQ ID NO 345

<400> SEQUENCE: 345

000

<210> SEQ ID NO 346

<400> SEQUENCE: 346

000

<210> SEQ ID NO 347

<400> SEQUENCE: 347

000

<210> SEQ ID NO 348

<400> SEQUENCE: 348

000

<210> SEQ ID NO 349

<400> SEQUENCE: 349

000

<210> SEQ ID NO 350

<400> SEQUENCE: 350

000

<210> SEQ ID NO 351

<400> SEQUENCE: 351

000

<210> SEQ ID NO 352

<400> SEQUENCE: 352

000

<210> SEQ ID NO 353

<400> SEQUENCE: 353

000

<210> SEQ ID NO 354

<400> SEQUENCE: 354

000

<210> SEQ ID NO 355

<400> SEQUENCE: 355

000

<210> SEQ ID NO 356

<400> SEQUENCE: 356

000

<210> SEQ ID NO 357

<400> SEQUENCE: 357

000

<210> SEQ ID NO 358

<400> SEQUENCE: 358

000

<210> SEQ ID NO 359

<400> SEQUENCE: 359

000

<210> SEQ ID NO 360

<400> SEQUENCE: 360

000

<210> SEQ ID NO 361

<400> SEQUENCE: 361

000

<210> SEQ ID NO 362

<400> SEQUENCE: 362

000

<210> SEQ ID NO 363

<400> SEQUENCE: 363

000

<210> SEQ ID NO 364

<400> SEQUENCE: 364

000

<210> SEQ ID NO 365

<400> SEQUENCE: 365

000

<210> SEQ ID NO 366

<400> SEQUENCE: 366

000

<210> SEQ ID NO 367

<400> SEQUENCE: 367

000

<210> SEQ ID NO 368

<400> SEQUENCE: 368

000

<210> SEQ ID NO 369

<400> SEQUENCE: 369

000

<210> SEQ ID NO 370

<400> SEQUENCE: 370

000

<210> SEQ ID NO 371

<400> SEQUENCE: 371

000

<210> SEQ ID NO 372

<400> SEQUENCE: 372

000

<210> SEQ ID NO 373

<400> SEQUENCE: 373

000

<210> SEQ ID NO 374
<400> SEQUENCE: 374
000

<210> SEQ ID NO 375
<400> SEQUENCE: 375
000

<210> SEQ ID NO 376
<400> SEQUENCE: 376
000

<210> SEQ ID NO 377
<400> SEQUENCE: 377
000

<210> SEQ ID NO 378
<400> SEQUENCE: 378
000

<210> SEQ ID NO 379
<400> SEQUENCE: 379
000

<210> SEQ ID NO 380
<400> SEQUENCE: 380
000

<210> SEQ ID NO 381
<400> SEQUENCE: 381
000

<210> SEQ ID NO 382
<400> SEQUENCE: 382
000

<210> SEQ ID NO 383
<400> SEQUENCE: 383
000

<210> SEQ ID NO 384
<400> SEQUENCE: 384
000

<210> SEQ ID NO 385
<400> SEQUENCE: 385
000

<210> SEQ ID NO 386
<400> SEQUENCE: 386
000

<210> SEQ ID NO 387
<400> SEQUENCE: 387
000

<210> SEQ ID NO 388
<400> SEQUENCE: 388
000

<210> SEQ ID NO 389
<400> SEQUENCE: 389
000

<210> SEQ ID NO 390
<400> SEQUENCE: 390
000

<210> SEQ ID NO 391
<400> SEQUENCE: 391
000

<210> SEQ ID NO 392
<400> SEQUENCE: 392
000

<210> SEQ ID NO 393
<400> SEQUENCE: 393
000

<210> SEQ ID NO 394
<400> SEQUENCE: 394
000

<210> SEQ ID NO 395
<400> SEQUENCE: 395
000

<210> SEQ ID NO 396

```
<400> SEQUENCE: 396

000

<210> SEQ ID NO 397

<400> SEQUENCE: 397

000

<210> SEQ ID NO 398

<400> SEQUENCE: 398

000

<210> SEQ ID NO 399

<400> SEQUENCE: 399

000

<210> SEQ ID NO 400

<400> SEQUENCE: 400

000

<210> SEQ ID NO 401
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 401

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Asn Asn Asn
            20                  25                  30

Asn Tyr Tyr Trp Thr Trp Ile Arg Gln His Pro Gly Lys Gly Leu Glu
        35                  40                  45

Trp Ile Gly Tyr Ile Tyr Tyr Ser Gly Ser Thr Phe Tyr Asn Pro Ser
    50                  55                  60

Leu Lys Ser Arg Val Thr Ile Ser Val Asp Thr Ser Lys Thr Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asp Thr Met Thr Gly Leu Asp Val Trp Gly Gln Gly
            100                 105                 110

Thr Thr Val Thr Val Ser Ser
        115

<210> SEQ ID NO 402
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

-continued

<400> SEQUENCE: 402

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Asn Tyr
            20                  25                  30

Leu Asn Trp Tyr Gln Gln Lys Pro Gly Lys Ala Pro Thr Leu Leu Ile
        35                  40                  45

Tyr Ala Ala Ser Ser Leu Gln Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Ala Tyr Phe Cys Gln Gln Thr Tyr Ser Asn Pro Thr
                85                  90                  95

Phe Gly Gln Gly Thr Lys Val Glu Val Lys
            100                 105

<210> SEQ ID NO 403
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 403

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser
        115                 120

<210> SEQ ID NO 404
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 404

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

```
Met Ile Tyr Asp Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu
            100                 105                 110

<210> SEQ ID NO 405
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 405

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser
        115

<210> SEQ ID NO 406
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 406

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95
```

```
Trp Thr Phe Gly Gln Gly Thr Lys Val Glu Ile Lys
            100                 105
```

<210> SEQ ID NO 407
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 407

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Phe Ile Arg Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Lys Thr His Gly Ser His Asp Asn Trp Gly Gln Gly Thr Met Val Thr
            100                 105                 110

Val Ser Ser
        115
```

<210> SEQ ID NO 408
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 408

```
Gln Ser Val Leu Thr Gln Pro Pro Ser Val Ser Gly Ala Pro Gly Gln
1               5                   10                  15

Arg Val Thr Ile Ser Cys Ser Gly Ser Arg Ser Asn Ile Gly Ser Asn
                20                  25                  30

Thr Val Lys Trp Tyr Gln Gln Leu Pro Gly Thr Ala Pro Lys Leu Leu
            35                  40                  45

Ile Tyr Tyr Asn Asp Gln Arg Pro Ser Gly Val Pro Asp Arg Phe Ser
        50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Tyr Asp Arg Tyr Thr
                85                  90                  95

His Pro Ala Leu Leu Phe Gly Thr Gly Thr Lys Val Thr Val Leu
            100                 105                 110
```

<210> SEQ ID NO 409
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 409

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 410
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 410

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 411
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 411

Glu Val Gln Leu Val Gln Ser Gly Gly Gly Val Glu Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
            35                  40                  45

Ser Gly Ile Asn Trp Asn Gly Gly Ser Thr Gly Tyr Ala Asp Ser Val
 50                  55                  60

Lys Gly Arg Val Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Ile Leu Gly Ala Gly Arg Gly Trp Tyr Phe Asp Leu Trp Gly
            100                 105                 110

Lys Gly Thr Thr Val Thr Val Ser Ser
            115                 120

<210> SEQ ID NO 412
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 412

Ser Ser Glu Leu Thr Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
 50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn His
                 85                  90                  95

Val Val Phe Gly Gly Gly Thr Lys Leu Thr Val Leu
            100                 105

<210> SEQ ID NO 413
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 413

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asn Asp Tyr
            20                  25                  30

Ala Met His Trp Val Arg Gln Ala Pro Gly Lys Gly Leu Glu Trp Val
            35                  40                  45

Ser Thr Ile Ser Trp Asn Ser Gly Ser Ile Gly Tyr Ala Asp Ser Val
 50                  55                  60

Lys Gly Arg Phe Thr Ile Ser Arg Asp Asn Ala Lys Lys Ser Leu Tyr
 65                  70                  75                  80

Leu Gln Met Asn Ser Leu Arg Ala Glu Asp Thr Ala Leu Tyr Tyr Cys

```
                    85                  90                  95

Ala Lys Asp Ile Gln Tyr Gly Asn Tyr Tyr Tyr Gly Met Asp Val Trp
                100                 105                 110

Gly Gln Gly Thr Thr Val Thr Val Ser Ser
        115                 120

<210> SEQ ID NO 414
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 414

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
                100                 105

<210> SEQ ID NO 415
<211> LENGTH: 130
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 415

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Pro Leu Arg Phe Leu Glu Trp Ser Thr Gln Asp His Tyr
                100                 105                 110

Tyr Tyr Tyr Tyr Met Asp Val Trp Gly Lys Gly Thr Thr Val Thr Val
            115                 120                 125

Ser Ser
    130
```

<210> SEQ ID NO 416
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 416

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Thr Trp Tyr Gln Gln Lys Pro Gly Gln Ala Pro Ile Leu Val Ile Tyr
        35                  40                  45

Gly Glu Asn Lys Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Lys Ser Arg Asp Gly Ser Gly Gln His
                85                  90                  95

Leu Val Phe Gly Gly Gly Thr Lys Leu Thr Val Leu
            100                 105

<210> SEQ ID NO 417
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 417

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ser Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Lys Asn Gly Ala Phe Asp Ile Trp Gly Gln Gly
            100                 105                 110

Thr Met Val Thr Val Ser Ser
        115

<210> SEQ ID NO 418
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 418

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Gly Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
                100                 105
```

MULTISPECIFIC ANTIBODY MOLECULES COMPRISING LAMBDA AND KAPPA LIGHT CHAINS

CROSS REFERENCE TO RELATED APPLICATIONS

This application is a U.S. National Phase Application under 35 U.S.C. § 371 of International Application No. PCT/US2017/053053 filed Sep. 22, 2017, which claims priority to U.S. Ser. No. 62/399,319 filed Sep. 23, 2016, and U.S. Ser. No. 62/474,569 filed Mar. 21, 2017, the contents of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Nov. 21, 2017, is named E2070-7003WO_SL.txt and is 494,234 bytes in size.

BACKGROUND

Multispecific, e.g., bispecific, antibody molecules that include a lambda chain polypeptide and a kappa light chain polypeptide, and methods of making and using the same, are disclosed.

Mispairing of the light chains to the incorrect heavy chain, also known as light chain shuffling, is a problem frequently observed when preparing bispecific and other multispecific antibodies. This results in the formation of incorrect antibody pairings, leading to decreased production yield. Thus, the need exists to develop methods and compositions that reduce light chain shuffling.

SUMMARY OF THE INVENTION

The present application is based, at least in part, on the unexpected finding that light chain shuffle in the context of a multispecific antibody molecule, e.g., a bispecific IgG molecule, can be prevented by using one kappa light chain polypeptide and one lambda light chain polypeptide. This is based, in part, on the observation that kappa light chains do not pair with a heavy chain from a lambda antibody and vice versa. Thus, described herein are novel multispecific, e.g., bispecific, antibody molecules that include a kappa light chain polypeptide and a lambda light chain polypeptide, and methods of making and using the multispecific antibody molecules.

Accordingly, in one aspect, disclosed herein is a multispecific antibody molecule, e.g., an antibody molecule comprising two binding specificities, e.g., a bispecific antibody molecule. The multispecific antibody molecule comprises:
i) a first antigen-binding domain that binds to a first antigen, wherein the first antigen-binding domain comprises:
  a) a first heavy chain polypeptide (HCP1) comprising: a first heavy chain variable region sequence (HCVRS) sufficient that, when paired with i)b) allows the first antigen-binding domain to bind to the first antigen; and
  b) a lambda light chain polypeptide (LLCP) comprising: a lambda light chain variable region sequence (LLCVRS) sufficient that, when paired with i)a) allows the first antigen-binding domain to bind to the first antigen; and
ii) a second antigen-binding domain that binds to a second antigen, wherein the second antigen-binding domain comprises:
  a) a second heavy chain polypeptide (HCP2) comprising: a second heavy chain variable region sequence (HCVRS) sufficient that, when paired with ii)b) allows the second antigen-binding domain to bind to the second antigen; and
  b) a kappa light chain polypeptide (KLCP) comprising: a kappa light chain variable region sequence (KLCVRS) sufficient that, when paired with ii)a) allows the second antigen-binding domain to bind to the second antigen.

In one embodiment, the first HCVRS comprises one, two, or all of framework 1 sequence, framework 2 sequence, or framework 3 sequence. In one embodiment, the framework 1 sequence, framework 2 sequence, or framework 3 sequence of the first HCVRS has at least 75, 80, 85, 90, 95, 98, or 100% sequence identity with a corresponding region in a first heavy chain germline sequence selected from column 3 of Table 7, column 2 of Table 8b, or column 2 of Table 5b. In one embodiment, the framework 1 sequence, framework 2 sequence, or framework 3 sequence of the first HCVRS comprises no more than 1, 2, 3, 4, 5, 6, 7, or 8 amino acid mutations (e.g., substitutions, insertions, or deletions, e.g., conserved substitutions) relative to a corresponding region in a first heavy chain germline sequence selected from column 3 of Table 7, column 2 of Table 8b, or column 2 of Table 5b. In one embodiment, the first HCVRS comprises a framework sequence selected from Table 16.

In one embodiment, the LLCVRS comprises one, two, or all of framework 1 sequence, framework 2 sequence, or framework 3 sequence. In one embodiment, the framework 1 sequence, framework 2 sequence, or framework 3 sequence of the LLCVRS has at least 75, 80, 85, 90, 95, 98, or 100% sequence identity with a corresponding region in a lambda light chain germline sequence selected from column 4 of Table 7, column 3 of Table 8b; or column 3 of Table 5b. In one embodiment, the framework 1 sequence, framework 2 sequence, or framework 3 sequence of the LLCVRS comprises no more than 1, 2, 3, 4, 5, 6, 7, or 8 amino acid mutations (e.g., substitutions, insertions, or deletions, e.g., conserved substitutions) relative to a corresponding region in a lambda light chain germline sequence selected from column 4 of Table 7, column 3 of Table 8b; or column 3 of Table 5b. In one embodiment, the LLCVRS comprises a framework sequence selected from Table 16.

In one embodiment, the second HCVRS comprises one, two, or all of framework 1 sequence, framework 2 sequence, or framework 3 sequence. In one embodiment, the framework 1 sequence, framework 2 sequence, or framework 3 sequence of the first HCVRS has at least 75, 80, 85, 90, 95, 98, or 100% sequence identity with a corresponding region in a second heavy chain germline sequence selected from column 3 of Table 6, column 5 of Table 8b, or column 4 of Table 5b. In one embodiment, the framework 1 sequence, framework 2 sequence, or framework 3 sequence of the second HCVRS comprises no more than 1, 2, 3, 4, 5, 6, 7, or 8 amino acid mutations (e.g., substitutions, insertions, or deletions, e.g., conserved substitutions) relative to a corresponding region in a second heavy chain germline sequence selected from column 3 of Table 6, column 5 of Table 8b, or column 4 of Table 5b. In one embodiment, the second HCVRS comprises a framework sequence selected from Table 16.

In one embodiment, the KLCVRS comprises one, two, or all of framework 1 sequence, framework 2 sequence, or framework 3 sequence. In one embodiment, the framework 1 sequence, framework 2 sequence, or framework 3 sequence of the LLCVRS has at least 75, 80, 85, 90, 95, 98, or 100% sequence identity with a corresponding region in a kappa light chain germline sequence selected from column 4 of Table 6, column 6 of Table 8b, or column 5 of Table 5b. In one embodiment, the framework 1 sequence, framework 2 sequence, or framework 3 sequence of the KLCVRS comprises no more than 1, 2, 3, 4, 5, 6, 7, or 8 amino acid mutations (e.g., substitutions, insertions, or deletions, e.g., conserved substitutions) relative to a corresponding region in a kappa light chain germline sequence selected from column 4 of Table 6, column 6 of Table 8b, or column 5 of Table 5b. In one embodiment, the KLCVRS comprises a framework sequence selected from Table 16.

In one embodiment, 1) the first HCVRS has at least 75, 80, 85, 90, 95, 98, or 100% sequence identity with a first heavy chain germline sequence selected from column 3 of Table 7, column 2 of Table 8b, or column 2 of Table 5b; 2) the LLCVRS has at least 75, 80, 85, 90, 95, 98, or 100% sequence identity with a lambda light chain germline sequence selected from column 4 of Table 7, column 3 of Table 8b; or column 3 of Table 5b; 3) the second HCVRS has at least 75, 80, 85, 90, 95, 98, or 100% sequence identity with a second heavy chain germline sequence selected from column 3 of Table 6, column 5 of Table 8b, or column 4 of Table 5b; or 4) the KLCVRS has at least 75, 80, 85, 90, 95, 98, or 100% sequence identity with a kappa light chain germline sequence selected from column 4 of Table 6, column 6 of Table 8b, or column 5 of Table 5b.

In one embodiment, the first HCVRS has at least 75, 80, 85, 90, 95, 98, or 100% sequence identity with a first heavy chain germline sequence selected from column 3 of Table 7, column 2 of Table 8b, or column 2 of Table 5b. In one embodiment, the first heavy chain germline sequence and the lambda light chain germline sequence are selected from a single row of Table 7, Table 8b, or Table 5b. In one embodiment, the first heavy chain germline sequence, the lambda light chain germline sequence, and the kappa light chain germline sequence are selected from a single row of Table 7, Table 8b, or Table 5b. In one embodiment, the second heavy chain germline sequence and the kappa light chain germline sequence are selected from a single row of Table 6, Table 8b, or Table 5b. In one embodiment, the second heavy chain germline sequence, the kappa light chain germline sequence, and the lambda light chain germline sequence are selected from a single row of Table 6, Table 8b, or Table 5b. In one embodiment, at least two (e.g., two, three, or all) of the following: the first heavy chain germline sequence, the lambda light chain germline sequence, the second heavy chain germline sequence, and the kappa light chain germline sequence, are selected from a single row of Table 8b or Table 5b.

In one embodiment, the LLCVRS has at least 75, 80, 85, 90, 95, 98, or 100% sequence identity with a lambda light chain germline sequence selected from column 4 of Table 7, column 3 of Table 8b; or column 3 of Table 5b. In one embodiment, the first heavy chain germline sequence and the lambda light chain germline sequence are selected from a single row of Table 7, Table 8b, or Table 5b. In one embodiment, the first heavy chain germline sequence, the lambda light chain germline sequence, and the kappa light chain germline sequence are selected from a single row of Table 7, Table 8b, or Table 5b. In one embodiment, the second heavy chain germline sequence and the kappa light chain germline sequence are selected from a single row of Table 6, Table 8b, or Table 5b. In one embodiment, the second heavy chain germline sequence, the kappa light chain germline sequence, and the lambda light chain germline sequence are selected from a single row of Table 6, Table 8b, or Table 5b. In one embodiment, at least two (e.g., two, three, or all) of the following: the first heavy chain germline sequence, the lambda light chain germline sequence, the second heavy chain germline sequence, and the kappa light chain germline sequence, are selected from a single row of Table 8b or Table 5b.

In one embodiment, the second HCVRS has at least 75, 80, 85, 90, 95, 98, or 100% sequence identity with a second heavy chain germline sequence selected from column 3 of Table 6, column 5 of Table 8b, or column 4 of Table 5b. In one embodiment, the first heavy chain germline sequence and the lambda light chain germline sequence are selected from a single row of Table 7, Table 8b, or Table 5b. In one embodiment, the first heavy chain germline sequence, the lambda light chain germline sequence, and the kappa light chain germline sequence are selected from a single row of Table 7, Table 8b, or Table 5b. In one embodiment, the second heavy chain germline sequence and the kappa light chain germline sequence are selected from a single row of Table 6, Table 8b, or Table 5b. In one embodiment, the second heavy chain germline sequence, the kappa light chain germline sequence, and the lambda light chain germline sequence are selected from a single row of Table 6, Table 8b, or Table 5b. In one embodiment, at least two (e.g., two, three, or all) of the following: the first heavy chain germline sequence, the lambda light chain germline sequence, the second heavy chain germline sequence, and the kappa light chain germline sequence, are selected from a single row of Table 8b or Table 5b.

In one embodiment, the KLCVRS has at least 75, 80, 85, 90, 95, 98, or 100% sequence identity with a kappa light chain germline sequence selected from column 4 of Table 6, column 6 of Table 8b, or column 5 of Table 5b. In one embodiment, the first heavy chain germline sequence and the lambda light chain germline sequence are selected from a single row of Table 7, Table 8b, or Table 5b. In one embodiment, the first heavy chain germline sequence, the lambda light chain germline sequence, and the kappa light chain germline sequence are selected from a single row of Table 7, Table 8b, or Table 5b. In one embodiment, the second heavy chain germline sequence and the kappa light chain germline sequence are selected from a single row of Table 6, Table 8b, or Table 5b. In one embodiment, the second heavy chain germline sequence, the kappa light chain germline sequence, and the lambda light chain germline sequence are selected from a single row of Table 6, Table 8b, or Table 5b. In one embodiment, at least two (e.g., two, three, or all) of the following: the first heavy chain germline sequence, the lambda light chain germline sequence, the second heavy chain germline sequence, and the kappa light chain germline sequence, are selected from a single row of Table 8b or Table 5b.

In one embodiment, the first heavy chain germline sequence and the lambda light chain germline sequence are selected from a single row of Table 8b or Table 5b. In one embodiment, the first heavy chain germline sequence and the second heavy chain germline sequence are selected from a single row of Table 8b or Table 5b. In one embodiment, the first heavy chain germline sequence and the kappa light chain germline sequence are selected from a single row of Table 8b or Table 5b. In one embodiment, the lambda light chain germline sequence and the second heavy chain germline sequence are selected from a single row of Table 8b or Table 5b. In one embodiment, the lambda light chain germline sequence and the kappa light chain germline sequence are selected from a single row of Table 8b or Table 5b. In one embodiment, the second heavy chain germline sequence and the kappa light chain germline sequence are selected from a single row of Table 8b or Table 5b. In one embodiment, the first heavy chain germline sequence, the lambda light chain germline sequence, and the second heavy chain germline sequence are selected from a single row of Table 8b or Table 5b. In one embodiment, the first heavy chain germline sequence, the lambda light chain germline sequence, and the kappa light chain germline sequence are selected from a single row of Table 8b or Table 5b. In one embodiment, the first heavy chain germline sequence, the second heavy chain germline sequence, and the kappa light chain germline sequence are selected from a single row of Table 8b or Table 5b. In one embodiment, the lambda light chain germline sequence, the second heavy chain germline sequence, and the kappa light chain germline sequence are selected from a single row of Table 8b or Table 5b. In one embodiment, the first heavy chain germline sequence, the lambda light chain germline sequence, the second heavy chain germline sequence, and the kappa light chain germline sequence are selected from a single row of Table 8b or Table 5b.

In certain embodiments of the foregoing aspects, the multispecific antibody molecule further comprises an accessory moiety, wherein the accessory moiety has a property chosen from:
1) the accessory moiety has a molecular weight of at least 10, 20, 30, 40, 50, 60, 70, 80, 90, or 100 kDa;
2) the accessory moiety comprises a polypeptide having at least 30, 40, 50, 60, 70, 80, 90, or 100 amino acid residues;
3) the accessory moiety comprises a polypeptide having the ability to modulate the activity of an immune cell, e.g., a T cell, a B cell, an antigen presenting cell (APC), or an NK cell; or
4) the accessory moiety is chosen from one or more of an immune cell engager (e.g., a CD40 agonist, e.g., a CD40L polypeptide or an agonistic anti-CD40 antibody molecule, or a PD-1 binding moiety, e.g., a PD-1 binding sequence of PDL-1 or an anti-PD-1 antibody molecule), a cytokine molecule (e.g. an IL-2 molecule), a cytokine antagonist (e.g., a TGF-β antagonist), an enzyme, a toxin, or a labeling agent.

In one aspect, disclosed herein is a multispecific antibody molecule comprising:
i) a first antigen-binding domain that binds to a first antigen, wherein the first antigen-binding domain comprises:
  a) a first heavy chain polypeptide (HCP1) comprising: a first heavy chain variable region sequence (HCVRS) sufficient that, when paired with i)b) allows the first antigen-binding domain to bind to the first antigen; and
  b) a lambda light chain polypeptide (LLCP) comprising: a lambda light chain variable region sequence (LLCVRS) sufficient that, when paired with i)a) allows the first antigen-binding domain to bind to the first antigen; and
ii) a second antigen-binding domain that binds to a second antigen, wherein the second antigen-binding domain comprises:
  a) a second heavy chain polypeptide (HCP2) comprising: a second heavy chain variable region sequence (HCVRS) sufficient that, when paired with ii)b) allows the second antigen-binding domain to bind to the second antigen; and
  b) a kappa light chain polypeptide (KLCP) comprising: a kappa light chain variable region sequence (KLCVRS) sufficient that, when paired with ii)a) allows the second antigen-binding domain to bind to the second antigen, wherein:
the multispecific antibody molecule further comprises an accessory moiety, wherein the accessory moiety has a property chosen from:
1) the accessory moiety has a molecular weight of at least 10, 20, 30, 40, 50, 60, 70, 80, 90, or 100 kDa;
2) the accessory moiety comprises a polypeptide having at least 30, 40, 50, 60, 70, 80, 90, or 100 amino acid residues;
3) the accessory moiety comprises a polypeptide having the ability to modulate the activity of an immune cell, e.g., a T cell, a B cell, an antigen presenting cell (APC), or an NK cell; or
4) the accessory moiety is chosen from one or more of an immune cell engager (e.g., a CD40 agonist, e.g., a CD40L polypeptide or an agonistic anti-CD40 antibody molecule, or a PD-1 binding moiety, e.g., a PD-1 binding sequence of PDL-1 or an anti-PD-1 antibody molecule), a cytokine molecule (e.g. an IL-2 molecule), a cytokine antagonist (e.g., a TGF-β antagonist), an enzyme, a toxin, or a labeling agent.

Exemplary multispecific antibody molecules with one or more accessory moieties are shown in FIGS. 6-10 and described in Examples (e.g., multispecific molecule 8 described in Example 9, multispecific molecule 9 described in Example 10, multispecific molecule 10 described in Example 11, multispecific molecule 11 described in Example 12, multispecific molecule 12 described in Example 13).

In one embodiment, the accessory moiety has a molecular weight of at least 10, 20, 30, 40, 50, 60, 70, 80, 90, or 100 kDa. In one embodiment, the accessory moiety comprises a polypeptide having at least 30, 40, 50, 60, 70, 80, 90, or 100 amino acid residues. In one embodiment, the accessory moiety comprises a polypeptide having the ability to modulate the activity of an immune cell, e.g., a T cell, a B cell, an antigen presenting cell (APC), or an NK cell. In one embodiment, the accessory moiety is chosen from one or more of an immune cell engager (e.g., a CD40 agonist, e.g., a CD40L polypeptide or an agonistic anti-CD40 antibody molecule, or a PD-1 binding moiety, e.g., a PD-1 binding sequence of PDL-1 or an anti-PD-1 antibody molecule), a cytokine molecule (e.g. an IL-2 molecule), a cytokine antagonist (e.g., a TGF-β antagonist), an enzyme, a toxin, or a labeling agent.

In one embodiment, the accessory moiety is fused to the polypeptide of a, b, c, or d of the multispecific antibody molecule. In one embodiment, the accessory moiety is fused to any of the following: the HCP1, first HCVRS, LLCP, LLCVRS, HCP2, second HCVRS, KLCP, or KLCVRS of the multispecific antibody molecule, e.g., the C-terminus or N-terminus of HCP1, first HCVRS, LLCP, LLCVRS, HCP2, second HCVRS, KLCP, or KLCVRS of the multispecific antibody molecule. In one embodiment, the accessory moiety is fused to the HCP1. In one embodiment, the accessory moiety is fused to the first HCVRS (e.g., the C-terminus or N-terminus of the first HCVRS). In one embodiment, the accessory moiety is fused to the LLCP (e.g., the C-terminus or N-terminus of the LLCP). In one embodiment, the accessory moiety is fused to the LLCVRS (e.g., the C-terminus or N-terminus of the LLCVRS). In one embodiment, the accessory moiety is fused to the HCP2 (e.g., the C-terminus or N-terminus of the HCP2). In one embodiment, the accessory moiety is fused to the second HCVRS (e.g., the C-terminus or N-terminus of the second HCVRS). In one embodiment, the accessory moiety is fused to the KLCP (e.g., the C-terminus or N-terminus of the KLCP). In one embodiment, the accessory moiety is fused to the KLCVRS (e.g., the C-terminus or N-terminus of the KLCVRS). In one embodiment, the HCP1 comprises a first heavy chain constant region sequence (HCCRS) (e.g., CH1, CH2, and CH3 sequences), wherein the accessory moiety is fused to the first HCCRS, e.g., the C-terminus of the first HCCRS. In one embodiment, the HCP2 comprises a second heavy chain constant region sequence (HCCRS) (e.g., CH1, CH2, and CH3 sequences), wherein the accessory moiety is fused to the second HCCRS, e.g., the C-terminus of the second HCCRS. In one embodiment, the LLCP comprises a lambda light chain constant region sequence (LLCCRS), wherein the accessory moiety is fused to the LLCCRS, e.g., the C-terminus of the LLCCRS. In one embodiment, the KLCP comprises a kappa light chain constant region sequence (KLCCRS), wherein the accessory moiety is fused to the KLCCRS, e.g., the C-terminus of the KLCCRS.

In one embodiment, the multispecific antibody molecule comprises one or more (e.g., two, three, four, five, or more) accessory molecule. In one embodiment, the multispecific antibody molecule comprises a first accessory moiety and a second accessory moiety, wherein the first or second accessory moiety has a property chosen from:
1) the first or second accessory moiety has a molecular weight of at least 10, 20, 30, 40, 50, 60, 70, 80, 90, or 100 kDa;
2) the first or second accessory moiety comprises a polypeptide having at least 30, 40, 50, 60, 70, 80, 90, or 100 amino acid residues;
3) the first or second accessory moiety comprises a polypeptide having the ability to modulate the active of an immune cell, e.g., a T cell, a B cell, an antigen presenting cell (APC), or an NK cell; or
4) the first or second accessory moiety is chosen from one or more of an immune cell engager (e.g., a CD40 agonist, e.g., a CD40L polypeptide or an agonistic anti-CD40 antibody molecule, or a PD-1 binding moiety, e.g., a PD-1 binding sequence of PDL-1 or an anti-PD-1 antibody molecule), a cytokine molecule (e.g. an IL-2 molecule), a cytokine antagonist (e.g., a TGF-β antagonist), an enzyme, a toxin, or a labeling agent.

In one embodiment, the first and second accessory moieties are the same. In one embodiment, the first and second accessory moieties are different. In one embodiment, i) the first accessory moiety is fused to the HCP1 or HCP2, e.g., the C-terminus of the HCP1 or HCP2; and ii) the second accessory moiety is fused to the LLCP or KLCP, e.g., the C-terminus of the LLCP or KLCP. In one embodiment, i) the first accessory moiety is fused to the HCP1, e.g., the C-terminus of the HCP1; and ii) the second accessory moiety is fused to the LLCP, e.g., the C-terminus of the LLCP. In one embodiment, i) the first accessory moiety is fused to the HCP1, e.g., the C-terminus of the HCP1; and ii) the second accessory moiety is fused to the KLCP, e.g., the C-terminus of the KLCP. In one embodiment, i) the first accessory moiety is fused to the HCP2, e.g., the C-terminus of the HCP2; and ii) the second accessory moiety is fused to the LLCP, e.g., the C-terminus of the LLCP. In one embodiment, i) the first accessory moiety is fused to the HCP2, e.g., the C-terminus of the HCP2; and ii) the second accessory moiety is fused to the KLCP, e.g., the C-terminus of the KLCP. In one embodiment, i) the first accessory moiety is fused to the KLCP, e.g., the C-terminus of the KLCP; and ii) the second accessory moiety is fused to the LLCP, e.g., the C-terminus of the LLCP. In one embodiment, i) the first accessory moiety is fused to the LLCP, e.g., the C-terminus of the LLCP; and ii) the second accessory moiety is fused to the KLCP, e.g., the C-terminus of the KLCP. In one embodiment, i) the HCP1 comprises a first heavy chain constant region sequence (HCCRS) (e.g., CH1, CH2, and CH3 sequences), wherein the first accessory moiety is fused to the first HCCRS, e.g., the C-terminus of the first HCCRS; and ii) the LLCP comprises a lambda light chain constant region sequence (LLCCRS), wherein the second accessory moiety is fused to the LLCCRS, e.g., the C-terminus of the LLCCRS. In one embodiment, i) the HCP2 comprises a second heavy chain constant region sequence (HCCRS) (e.g., CH1, CH2, and CH3 sequences), wherein the accessory moiety is fused to the second HCCRS, e.g., the C-terminus of the second HCCRS; and ii) the KLCP comprises a kappa light chain constant region sequence (KLCCRS), wherein the accessory moiety is fused to the KLCCRS, e.g., the C-terminus of the KLCCRS. In one embodiment, i) the HCP1 comprises a first heavy chain constant region sequence (HCCRS) (e.g., CH1, CH2, and CH3 sequences), wherein the first accessory moiety is fused to the first HCCRS, e.g., the C-terminus of the first HCCRS; and ii) the KLCP comprises a kappa light chain constant region sequence (KLCCRS), wherein the accessory moiety is fused to the KLCCRS, e.g., the C-terminus of the KLCCRS. In one embodiment, i) the HCP2 comprises a second heavy chain constant region sequence (HCCRS) (e.g., CH1, CH2, and CH3 sequences), wherein the accessory moiety is fused to the second HCCRS, e.g., the C-terminus of the second HCCRS; and ii) the LLCP comprises a lambda light chain constant region sequence (LLCCRS), wherein the second accessory moiety is fused to the LLCCRS, e.g., the C-terminus of the LLCCRS.

In certain embodiments of the foregoing aspects, the multispecific antibody molecule comprises:
i)a) the HCP1 comprises a first heavy chain constant region sequence (HCCRS) (e.g., a first CH1 sequence),
i)b) the LLCP comprises a lambda light chain constant region sequence (LLCCRS),
ii)a) the HCP2 comprises a second heavy chain constant region sequence (HCCRS) (e.g., a second CH1 sequence), and
ii)b) the KLCP comprises a kappa light chain constant region sequence (KLCCRS), wherein:
1) the multispecific antibody molecule does not comprise a mutation in the first HCCRS (e.g., a mutation relative to a naturally existing heavy chain constant region sequence) that promotes the preferential pairing of the HCP1 and the LLCP, compared with pairing of the HCP1 and the LLCP without the mutation, or the multispecific antibody molecule does not comprise a mutation in the LLCCRS (e.g., a mutation relative to a naturally existing lambda light chain constant region sequence) that promotes the preferential pairing of the HCP1 and the LLCP, compared with pairing of the HCP1 and the LLCP without the mutation; and
2) the multispecific antibody molecule does not comprise a mutation in the second HCCRS (e.g., a mutation relative to a naturally existing heavy chain constant region sequence) that promotes the preferential pairing of the HCP2 and the KLCP, compared with pairing of the HCP2 and the KLCP without the mutation, or the multispecific antibody molecule does not comprise a mutation in the KLCCRS (e.g., a mutation relative to a naturally existing kappa light chain constant region sequence) that promotes the preferential pairing of the HCP2 and the KLCP, compared with pairing of the HCP2 and the KLCP without the mutation.

In one aspect, disclosed herein is a multispecific antibody comprising:
i) a first antigen-binding domain that binds to a first antigen, wherein the first antigen-binding domain comprises:
  a) a first heavy chain polypeptide (HCP1) comprising: a first heavy chain variable region sequence (HCVRS) sufficient that, when paired with i)b) allows the first antigen-binding domain to bind to the first antigen; and a first heavy chain constant region sequence (HCCRS) (e.g., a first CH1 sequence), and
  b) a lambda light chain polypeptide (LLCP) comprising: a lambda light chain variable region sequence (LLCVRS) sufficient that, when paired with i)a) allows the first antigen-binding domain to bind to the first antigen; and a lambda light chain constant region sequence (LLCCRS), and
ii) a second antigen-binding domain that binds to a second antigen, wherein the second antigen-binding domain comprises:
  a) a second heavy chain polypeptide (HCP2) comprising: a second heavy chain variable region sequence (HCVRS) sufficient that, when paired with ii)b) allows the second antigen-binding domain to bind to the second antigen; and a second heavy chain constant region sequence (HCCRS) (e.g., a second CH1 sequence) and
  b) a kappa light chain polypeptide (KLCP) comprising: a kappa light chain variable region sequence (KLCVRS) sufficient that, when paired with ii)a) allows the second antigen-binding domain to bind to the second antigen; and a kappa light chain constant region sequence (KLCCRS), wherein:
1) the multispecific antibody molecule does not comprise a mutation in the first HCCRS (e.g., a mutation relative to a naturally existing heavy chain constant region sequence) that promotes the preferential pairing of the HCP1 and the LLCP, compared with pairing of the HCP1 and the LLCP without the mutation, or the multispecific antibody molecule does not comprise a mutation in the LLCCRS (e.g., a mutation relative to a naturally existing lambda light chain constant region sequence) that promotes the preferential pairing of the HCP1 and the LLCP, compared with pairing of the HCP1 and the LLCP without the mutation; and
2) the multispecific antibody molecule does not comprise a mutation in the second HCCRS (e.g., a mutation relative to a naturally existing heavy chain constant region sequence) that promotes the preferential pairing of the HCP2 and the KLCP, compared with pairing of the HCP2 and the KLCP without the mutation, or the multispecific antibody molecule does not comprise a mutation in the KLCCRS (e.g., a mutation relative to a naturally existing kappa light chain constant region sequence) that promotes the preferential pairing of the HCP2 and the KLCP, compared with pairing of the HCP2 and the KLCP without the mutation.

In one embodiment, 1) the multispecific antibody molecule does not comprise a mutation in the first HCCRS (e.g., a mutation relative to a naturally existing heavy chain constant region sequence) that promotes the preferential pairing of the HCP1 and the LLCP, compared with pairing of the HCP1 and the LLCP without the mutation; and
2) the multispecific antibody molecule does not comprise a mutation in the second HCCRS (e.g., a mutation relative to a naturally existing heavy chain constant region sequence) that promotes the preferential pairing of the HCP2 and the KLCP, compared with pairing of the HCP2 and the KLCP without the mutation.

In one embodiment, 1) the multispecific antibody molecule does not comprise a mutation in the first HCCRS (e.g., a mutation relative to a naturally existing heavy chain constant region sequence) that promotes the preferential pairing of the HCP1 and the LLCP, compared with pairing of the HCP1 and the LLCP without the mutation; and
2) the multispecific antibody molecule does not comprise a mutation in the KLCCRS (e.g., a mutation relative to a naturally existing kappa light chain constant region sequence) that promotes the preferential pairing of the HCP2 and the KLCP, compared with pairing of the HCP2 and the KLCP without the mutation.

In one embodiment, 1) the multispecific antibody molecule does not comprise a mutation in the LLCCRS (e.g., a mutation relative to a naturally existing lambda light chain constant region sequence) that promotes the preferential pairing of the HCP1 and the LLCP, compared with pairing of the HCP1 and the LLCP without the mutation; and
2) the multispecific antibody molecule does not comprise a mutation in the second HCCRS (e.g., a mutation relative to a naturally existing heavy chain constant region sequence) that promotes the preferential pairing of the HCP2 and the KLCP, compared with pairing of the HCP2 and the KLCP without the mutation.

In one embodiment, 1) the multispecific antibody molecule does not comprise a mutation in the LLCCRS (e.g., a mutation relative to a naturally existing lambda light chain constant region sequence) that promotes the preferential pairing of the HCP1 and the LLCP, compared with pairing of the HCP1 and the LLCP without the mutation; and
2) the multispecific antibody molecule does not comprise a mutation in the KLCCRS (e.g., a mutation relative to a naturally existing kappa light chain constant region sequence) that promotes the preferential pairing of the HCP2 and the KLCP, compared with pairing of the HCP2 and the KLCP without the mutation.

In one embodiment, 1) the multispecific antibody molecule does not comprise a mutation in the first HCCRS (e.g., a mutation relative to a naturally existing heavy chain constant region sequence) that promotes the preferential pairing of the HCP1 and the LLCP, compared with pairing of the HCP1 and the LLCP without the mutation, and the multispecific antibody molecule does not comprise a mutation in the LLCCRS (e.g., a mutation relative to a naturally existing lambda light chain constant region sequence) that promotes the preferential pairing of the HCP1 and the LLCP, compared with pairing of the HCP1 and the LLCP without the mutation; and
2) the multispecific antibody molecule does not comprise a mutation in the second HCCRS (e.g., a mutation relative to a naturally existing heavy chain constant region sequence) that promotes the preferential pairing of the HCP2 and the KLCP, compared with pairing of the HCP2 and the KLCP without the mutation, or the multispecific antibody molecule does not comprise a mutation in the KLCCRS (e.g., a mutation relative to a naturally existing kappa light chain constant region sequence) that promotes the preferential pairing of the HCP2 and the KLCP, compared with pairing of the HCP2 and the KLCP without the mutation.

In one embodiment, 1) the multispecific antibody molecule does not comprise a mutation in the first HCCRS (e.g., a mutation relative to a naturally existing heavy chain constant region sequence) that promotes the preferential pairing of the HCP1 and the LLCP, compared with pairing of the HCP1 and the LLCP without the mutation, or the multispecific antibody molecule does not comprise a mutation in the LLCCRS (e.g., a mutation relative to a naturally existing lambda light chain constant region sequence) that promotes the preferential pairing of the HCP1 and the LLCP, compared with pairing of the HCP1 and the LLCP without the mutation; and 2) the multispecific antibody molecule does not comprise a mutation in the second HCCRS (e.g., a mutation relative to a naturally existing heavy chain constant region sequence) that promotes the preferential pairing of the HCP2 and the KLCP, compared with pairing of the HCP2 and the KLCP without the mutation, and the multispecific antibody molecule does not comprise a mutation in the KLCCRS (e.g., a mutation relative to a naturally existing kappa light chain constant region sequence) that promotes the preferential pairing of the HCP2 and the KLCP, compared with pairing of the HCP2 and the KLCP without the mutation.

In one embodiment, 1) the multispecific antibody molecule does not comprise a mutation in the first HCCRS (e.g., a mutation relative to a naturally existing heavy chain constant region sequence) that promotes the preferential pairing of the HCP1 and the LLCP, compared with pairing of the HCP1 and the LLCP without the mutation, and the multispecific antibody molecule does not comprise a mutation in the LLCCRS (e.g., a mutation relative to a naturally existing lambda light chain constant region sequence) that promotes the preferential pairing of the HCP1 and the LLCP, compared with pairing of the HCP1 and the LLCP without the mutation; and 2) the multispecific antibody molecule does not comprise a mutation in the second HCCRS (e.g., a mutation relative to a naturally existing heavy chain constant region sequence) that promotes the preferential pairing of the HCP2 and the KLCP, compared with pairing of the HCP2 and the KLCP without the mutation, and the multispecific antibody molecule does not comprise a mutation in the KLCCRS (e.g., a mutation relative to a naturally existing kappa light chain constant region sequence) that promotes the preferential pairing of the HCP2 and the KLCP, compared with pairing of the HCP2 and the KLCP without the mutation.

In one embodiment, the multispecific antibody molecule does not comprise a mutation in the first HCCRS (e.g., a mutation relative to a naturally existing heavy chain constant region sequence) that increases the preferential pairing of the HCP1 and the LLCP by at least 1.5, 2, 3, 4, 5, 6, 7, 8, 9, 10, 20, 30, 40, or 50 folds, compared with pairing of the HCP1 and the LLCP without the mutation. In one embodiment, the multispecific antibody molecule does not comprise a mutation in the LLCCRS (e.g., a mutation relative to a naturally existing lambda light chain constant region sequence) that increases the preferential pairing of the HCP1 and the LLCP by at least 1.5, 2, 3, 4, 5, 6, 7, 8, 9, 10, 20, 30, 40, or 50 folds, compared with pairing of the HCP1 and the LLCP without the mutation.

In one embodiment, the multispecific antibody molecule does not comprise a mutation in the second HCCRS (e.g., a mutation relative to a naturally existing heavy chain constant region sequence) that increases the preferential pairing of the HCP2 and the KLCP by at least 1.5, 2, 3, 4, 5, 6, 7, 8, 9, 10, 20, 30, 40, or 50 folds, compared with pairing of the HCP2 and the KLCP without the mutation. In one embodiment, the multispecific antibody molecule does not comprise a mutation in the KLCCRS (e.g., a mutation relative to a naturally existing kappa light chain constant region sequence) that increases the preferential pairing of the HCP2 and the KLCP by at least 1.5, 2, 3, 4, 5, 6, 7, 8, 9, 10, 20, 30, 40, or 50 folds, compared with pairing of the HCP2 and the KLCP without the mutation.

In certain embodiments of the foregoing aspects, the multispecific antibody molecule comprises:
- i)a) the HCP1 comprises a first heavy chain constant region sequence (HCCRS) (e.g., a first CH1 sequence),
- i)b) the LLCP comprises a lambda light chain constant region sequence (LLCCRS),
- ii)a) the HCP2 comprises a second heavy chain constant region sequence (HCCRS) (e.g., a second CH1 sequence), and
- ii)b) the KLCP comprises a kappa light chain constant region sequence (KLCCRS), wherein:
  1) the multispecific antibody molecule does not comprise a mutation in the first HCCRS (e.g., a mutation relative to a naturally existing heavy chain constant region sequence), or the multispecific antibody molecule does not comprise a mutation in the LLCCRS (e.g., a mutation relative to a naturally existing lambda light chain constant region sequence); and
  2) the multispecific antibody molecule does not comprise a mutation in the second HCCRS (e.g., a mutation relative to a naturally existing heavy chain constant region sequence), or the multispecific antibody molecule does not comprise a mutation in the KLCCRS (e.g., a mutation relative to a naturally existing kappa light chain constant region sequence).

In one aspect, disclosed herein is a multispecific antibody comprising:
i) a first antigen-binding domain that binds to a first antigen, wherein the first antigen-binding domain comprises:
  a) a first heavy chain polypeptide (HCP1) comprising: a first heavy chain variable region sequence (HCVRS) sufficient that, when paired with i)b) allows the first antigen-binding domain to bind to the first antigen; and a first heavy chain constant region sequence (HCCRS) (e.g., a first CH1 sequence), and
  b) a lambda light chain polypeptide (LLCP) comprising: a lambda light chain variable region sequence (LLCVRS) sufficient that, when paired with i)a) allows the first antigen-binding domain to bind to the first antigen; and a lambda light chain constant region sequence (LLCCRS), and
ii) a second antigen-binding domain that binds to a second antigen, wherein the second antigen-binding domain comprises:
  a) a second heavy chain polypeptide (HCP2) comprising: a second heavy chain variable region sequence (HCVRS) sufficient that, when paired with ii)b) allows the second antigen-binding domain to bind to the second antigen; and a second heavy chain constant region sequence (HCCRS) (e.g., a second CH1 sequence) and
  b) a kappa light chain polypeptide (KLCP) comprising: a kappa light chain variable region sequence (KLCVRS) sufficient that, when paired with ii)a) allows the second antigen-binding domain to bind to the second antigen; and a kappa light chain constant region sequence (KLCCRS), wherein:

1) the multispecific antibody molecule does not comprise a mutation in the first HCCRS (e.g., a mutation relative to a naturally existing heavy chain constant region sequence), or the multispecific antibody molecule does not comprise a mutation in the LLCCRS (e.g., a mutation relative to a naturally existing lambda light chain constant region sequence); and
2) the multispecific antibody molecule does not comprise a mutation in the second HCCRS (e.g., a mutation relative to a naturally existing heavy chain constant region sequence), or the multispecific antibody molecule does not comprise a mutation in the KLCCRS (e.g., a mutation relative to a naturally existing kappa light chain constant region sequence).

In one embodiment, the multispecific antibody molecule does not comprise a mutation in the first HCCRS (e.g., a mutation relative to a naturally existing heavy chain constant region sequence), and the multispecific antibody molecule does not comprise a mutation in the second HCCRS (e.g., a mutation relative to a naturally existing heavy chain constant region sequence).

In one embodiment, the multispecific antibody molecule does not comprise a mutation in the first HCCRS (e.g., a mutation relative to a naturally existing heavy chain constant region sequence), and the multispecific antibody molecule does not comprise a mutation in the KLCCRS (e.g., a mutation relative to a naturally existing kappa light chain constant region sequence).

In one embodiment, the multispecific antibody molecule does not comprise a mutation in the LLCCRS (e.g., a mutation relative to a naturally existing lambda light chain constant region sequence), and the multispecific antibody molecule does not comprise a mutation in the second HCCRS (e.g., a mutation relative to a naturally existing heavy chain constant region sequence).

In one embodiment, the multispecific antibody molecule does not comprise a mutation in the LLCCRS (e.g., a mutation relative to a naturally existing lambda light chain constant region sequence), and the multispecific antibody molecule does not comprise a mutation in the KLCCRS (e.g., a mutation relative to a naturally existing kappa light chain constant region sequence).

In one embodiment,
1) the multispecific antibody molecule does not comprise a mutation in the first HCCRS (e.g., a mutation relative to a naturally existing heavy chain constant region sequence), and the multispecific antibody molecule does not comprise a mutation in the LLCCRS (e.g., a mutation relative to a naturally existing lambda light chain constant region sequence); and
2) the multispecific antibody molecule does not comprise a mutation in the second HCCRS (e.g., a mutation relative to a naturally existing heavy chain constant region sequence), or the multispecific antibody molecule does not comprise a mutation in the KLCCRS (e.g., a mutation relative to a naturally existing kappa light chain constant region sequence).

In one embodiment,
1) the multispecific antibody molecule does not comprise a mutation in the first HCCRS (e.g., a mutation relative to a naturally existing heavy chain constant region sequence), or the multispecific antibody molecule does not comprise a mutation in the LLCCRS (e.g., a mutation relative to a naturally existing lambda light chain constant region sequence); and
2) the multispecific antibody molecule does not comprise a mutation in the second HCCRS (e.g., a mutation relative to a naturally existing heavy chain constant region sequence), and the multispecific antibody molecule does not comprise a mutation in the KLCCRS (e.g., a mutation relative to a naturally existing kappa light chain constant region sequence).

In one embodiment,
1) the multispecific antibody molecule does not comprise a mutation in the first HCCRS (e.g., a mutation relative to a naturally existing heavy chain constant region sequence), and the multispecific antibody molecule does not comprise a mutation in the LLCCRS (e.g., a mutation relative to a naturally existing lambda light chain constant region sequence); and
2) the multispecific antibody molecule does not comprise a mutation in the second HCCRS (e.g., a mutation relative to a naturally existing heavy chain constant region sequence), and the multispecific antibody molecule does not comprise a mutation in the KLCCRS (e.g., a mutation relative to a naturally existing kappa light chain constant region sequence).

In one embodiment, the multispecific antibody molecule does not comprise a mutation in any of the following: the first HCCRS, the LLCCRS, the second HCCRS, and the KLCCRS (e.g., a mutation relative to a naturally existing heavy chain constant region sequence, a naturally existing lambda light chain constant region sequence, or a naturally existing kappa light chain constant region sequence).

In one embodiment, the multispecific antibody molecule does not comprise a mutation disclosed in WO2017059551.

In certain embodiments of the foregoing aspects, the multispecific antibody molecule comprises:
i)a) the HCP1 comprises a first heavy chain constant region sequence (HCCRS) (e.g., a first CH1 sequence),
i)b) the LLCP comprises a lambda light chain constant region sequence (LLCCRS),
ii)a) the HCP2 comprises a second heavy chain constant region sequence (HCCRS) (e.g., a second CH1 sequence) and
ii)b) the KLCP comprises a kappa light chain constant region sequence (KLCCRS), wherein:
1) the first HCCRS comprises a naturally existing heavy chain constant region sequence, or the LLCCRS comprises a naturally existing lambda light chain constant region sequence; and
2) the second HCCRS comprises a naturally existing heavy chain constant region sequence, or the KLCCRS comprises a naturally existing kappa light chain constant region sequence.

In one aspect, disclosed herein is a multispecific antibody molecule comprising:
i) a first antigen-binding domain that binds to a first antigen, wherein the first antigen-binding domain comprises:
a) a first heavy chain polypeptide (HCP1) comprising: a first heavy chain variable region sequence (HCVRS) sufficient that, when paired with i)b) allows the first antigen-binding domain to bind to the first antigen; and a first heavy chain constant region sequence (HCCRS) (e.g., a first CH1 sequence), and
b) a lambda light chain polypeptide (LLCP) comprising: a lambda light chain variable region sequence (LLCVRS) sufficient that, when paired with i)a) allows the first antigen-binding domain to bind to the first antigen; and a lambda light chain constant region sequence (LLCCRS), and ii) a second antigen-binding domain that binds to a second antigen, wherein the second antigen-binding domain comprises:
  a) a second heavy chain polypeptide (HCP2) comprising: a second heavy chain variable region sequence (HCVRS) sufficient that, when paired with ii)b) allows the second antigen-binding domain to bind to the second antigen; and a second heavy chain constant region sequence (HCCRS) (e.g., a second CH1 sequence) and
  b) a kappa light chain polypeptide (KLCP) comprising: a kappa light chain variable region sequence (KLCVRS) sufficient that, when paired with ii)a) allows the second antigen-binding domain to bind to the second antigen; and a kappa light chain constant region sequence (KLCCRS), wherein:
1) the first HCCRS comprises a naturally existing heavy chain constant region sequence, or the LLCCRS comprises a naturally existing lambda light chain constant region sequence; and
2) the second HCCRS comprises a naturally existing heavy chain constant region sequence, or the KLCCRS comprises a naturally existing kappa light chain constant region sequence.

In one embodiment, 1) the first HCCRS comprises a naturally existing heavy chain constant region sequence; and 2) the second HCCRS comprises a naturally existing heavy chain constant region sequence. In one embodiment, 1) the first HCCRS comprises a naturally existing heavy chain constant region sequence; and 2) the KLCCRS comprises a naturally existing kappa light chain constant region sequence. In one embodiment, 1) the LLCCRS comprises a naturally existing lambda light chain constant region sequence; and 2) the second HCCRS comprises a naturally existing heavy chain constant region sequence. In one embodiment, 1) the LLCCRS comprises a naturally existing lambda light chain constant region sequence; and 2) the KLCCRS comprises a naturally existing kappa light chain constant region sequence. In one embodiment, 1) the first HCCRS comprises a naturally existing heavy chain constant region sequence, and the LLCCRS comprises a naturally existing lambda light chain constant region sequence; and 2) the second HCCRS comprises a naturally existing heavy chain constant region sequence, or the KLCCRS comprises a naturally existing kappa light chain constant region sequence. In one embodiment, 1) the first HCCRS comprises a naturally existing heavy chain constant region sequence, or the LLCCRS comprises a naturally existing lambda light chain constant region sequence; and 2) the second HCCRS comprises a naturally existing heavy chain constant region sequence, and the KLCCRS comprises a naturally existing kappa light chain constant region sequence.

In one embodiment, i) the first HCCRS comprises a naturally existing heavy chain constant region sequence, ii) the LLCCRS comprises a naturally existing lambda light chain constant region sequence, iii) the second HCCRS comprises a naturally existing heavy chain constant region sequence, and iv) the KLCCRS comprises a naturally existing kappa light chain constant region sequence.

In certain embodiments of the foregoing aspects, the HCP1 preferentially binds to the LLCP over the KLCP. In certain embodiments of the foregoing aspects, the LLCP preferentially binds to the HCP1 over the HCP2. In certain embodiments of the foregoing aspects, the HCP2 preferentially binds to the KLCP over the LLCP. In certain embodiments of the foregoing aspects, the KLCP preferentially binds to the HCP2 over the HCP1. In one embodiment, the HCP1 has a higher affinity, e.g., a substantially higher affinity, for the LLCP than for the KLCP (e.g., the KD for the binding between the HCP1 and the LLCP is no more than 50%, 40%, 30%, 20%, 10%, 1%, 0.1%, or 0.01% of the KD for the binding between the HCP1 and the KLCP). In one embodiment, the LLCP has a higher affinity, e.g., a substantially higher affinity, for the HCP1 than for the HCP2 (e.g., the KD for the binding between the LLCP and the HCP1 is no more than 50%, 40%, 30%, 20%, 10%, 1%, 0.1%, or 0.01% of the KD for the binding between the LLCP and the first HCP2). In one embodiment, the HCP2 has a higher affinity, e.g., a substantially higher affinity, for the KLCP than for the LLCP (e.g., the KD for the binding between the HCP2 and the KLCP is no more than 50%, 40%, 30%, 20%, 10%, 1%, 0.1%, or 0.01% of the KD for the binding between the HCP2 and the LLCP). In one embodiment, the KLCP has a higher affinity, e.g., a substantially higher affinity, for the HCP2 than for the HCP1 (e.g., the KD for the binding between the KLCP and the HCP2 is no more than 50%, 40%, 30%, 20%, 10%, 1%, 0.1%, or 0.01% of the KD for the binding between the KLCP and the HCP1).

In one embodiment, the percent binding between the HCP1 and the LLCP in the presence of the KLCP is at least 75, 80, 90, 95, 98, 99, or 99.5%. In one embodiment, when the HCP1, LLCP, and KLCP are present at 1:1:1, the percent binding between the HCP1 and the LLCP in the presence of the KLCP is at least 75, 80, 90, 95, 98, 99, or 99.5% (setting the binding between the HCP1 and the LLCP in the absence of any competing peptide to 100%, and the binding between the HCP1 and the LLCP in the presence of LLCP to 50%). In one embodiment, the percent binding was measured by an assay described herein, e.g., the NanoBiT assay.

In one embodiment, the percent binding between the HCP1 and the LLCP in the presence of the HCP2 is at least 75, 80, 90, 95, 98, 99, or 99.5%. In one embodiment, when HCP1, LLCP, and HCP2 are present at 1:1:1, the percent binding between the HCP1 and the LLCP in the presence of the HCP2 is at least 75, 80, 90, 95, 98, 99, or 99.5% (setting the binding between the HCP1 and the LLCP in the absence of any competing peptide to 100%, and the binding between the HCP1 and the LLCP in the presence of HCP1 to 50%). In one embodiment, the percent binding was measured by an assay described herein, e.g., the NanoBiT assay.

In one embodiment, the percent binding between the HCP2 and the KLCP in the presence of the LLCP is at least 75, 80, 90, 95, 98, 99, or 99.5%. In one embodiment, when HCP2, KLCP, and LLCP are present at 1:1:1, the percent binding between the HCP2 and the KLCP in the presence of the LLCP is at least 75, 80, 90, 95, 98, 99, or 99.5% (setting the binding between the HCP2 and the KLCP in the absence of any competing peptide to 100%, and the binding between the HCP2 and the KLCP in the presence of KLCP to 50%). In one embodiment, the percent binding was measured by an assay described herein, e.g., the NanoBiT assay.

In one embodiment, the percent binding between the HCP2 and the KLCP in the presence of the HCP1 is at least 75, 80, 90, 95, 98, 99, or 99.5%. In one embodiment, when HCP2, KLCP, and HCP1 are present at 1:1:1, the percent binding between the HCP2 and the KLCP in the presence of the HCP1 is at least 75, 80, 90, 95, 98, 99, or 99.5% (setting the binding between the HCP2 and the KLCP in the absence of any competing peptide to 100%, and the binding between the HCP2 and the KLCP in the presence of HCP2 to 50%). In one embodiment, the percent binding was measured by an assay described herein, e.g., the NanoBiT assay.

In one embodiment, when the HCP1, LLCP, HCP2, and KLCP are present under preselected conditions, e.g., in aqueous buffer, e.g., at pH 7, in saline, e.g., at pH 7, or under physiological conditions: at least 70, 75, 80, 90, 95, 98, 99, 99.5, or 99.9% of the HCP1 is complexed, or interfaced with, the LLCP. In one embodiment, when the HCP1, LLCP, HCP2, and KLCP are present under preselected conditions, e.g., in aqueous buffer, e.g., at pH 7, in saline, e.g., at pH 7, or under physiological conditions: at least 70, 75, 80, 90, 95, 98, 99, 99.5, or 99.9% of the LLCP is complexed, or interfaced with, the HCP1. In one embodiment, when the HCP1, LLCP, HCP2, and KLCP are present under preselected conditions, e.g., in aqueous buffer, e.g., at pH 7, in saline, e.g., at pH 7, or under physiological conditions: at least 70, 75, 80, 90, 95, 98, 99, 99.5, or 99.9% of the HCP2 is complexed, or interfaced with, the KLCP. In one embodiment, when the HCP1, LLCP, HCP2, and KLCP are present under preselected conditions, e.g., in aqueous buffer, e.g., at pH 7, in saline, e.g., at pH 7, or under physiological conditions: at least 70, 75, 80, 90, 95, 98, 99, 99.5, or 99.9% of the KLCP is complexed, or interfaced with, the HCP2.

In certain embodiments of the foregoing aspects, the multispecific antibody molecule comprises:
  i)a) the HCP1 comprises a first heavy chain constant region sequence (HCCRS) (e.g., a first CH1 sequence),
  i)b) the LLCP comprises a lambda light chain constant region sequence (LLCCRS),
  ii)a) the HCP2 comprises a second heavy chain constant region sequence (HCCRS) (e.g., a second CH1 sequence) and
  ii)b) the KLCP comprises a kappa light chain constant region sequence (KLCCRS), wherein:
  1) the first HCCRS is complexed, or interfaced with, LLCCRS, and
  2) the second HCCRS is complexed, or interfaced with, KLCCRS.

In certain embodiments of the foregoing aspects, the HCP1 is complexed, or interfaced with, the HCP2. In one embodiment, the HCP1 has a greater affinity, e.g., a substantially greater affinity, for HCP2, than for a second molecule of HCP1. In one embodiment, the HCP2 has a greater affinity, e.g., a substantially greater affinity, for HCP1, than for a second molecule of HCP2. In one embodiment, the HCP1 comprises a sequence element that increases the ratio of HCP1-HCP2:HCP1-HCP1 pairings, compared to the ratio that would be seen in the absence of the sequence element, e.g., where a naturally occurring sequence replaces the sequence element. In one embodiment, the HCP2 comprises a sequence element that increases the ratio of HCP1-HCP2:HCP2-HCP2 pairings, compared to the ratio that would be seen in the absence of the sequence element, e.g., where a naturally occurring sequence replaces the sequence element. In one embodiment, the sequence element is not a naturally occurring constant region sequence. In one embodiment, the sequence element is disposed in CH3. In one embodiment, one or both of HCP1 and HCP2 were selected to minimize self-dimerization (e.g., HCP1-HCP1) as opposed to heterodimerization (e.g., HCP2-HCP2). In one embodiment, HCP1 and HCP2 are members of a paired protuberance/cavity, e.g., knob and hole pair. In one embodiment, HCP1-HCP2 paring is promoted by an electrostatic interaction. In one embodiment, HCP1-HCP2 paring is promoted by strand exchange. In one embodiment, HCP1 and HCP2 are not members of a paired protuberance/cavity, e.g., knob and hole pair. In one embodiment, the HCP1 comprises a first heavy chain constant region sequence (HCCRS), wherein the first HCCRS does not comprise a mutation (e.g., a mutation relative to a naturally existing heavy chain constant region sequence). In one embodiment, the HCP2 comprises a second heavy chain constant region sequence (HCCRS), wherein the second HCCRS does not comprise a mutation (e.g., a mutation relative to a naturally existing heavy chain constant region sequence). In one embodiment, i) the HCP1 comprises a first heavy chain constant region sequence (HCCRS), wherein the first HCCRS does not comprise a mutation (e.g., a mutation relative to a naturally existing heavy chain constant region sequence); and ii) the HCP2 comprises a second heavy chain constant region sequence (HCCRS), wherein the second HCCRS does not comprise a mutation (e.g., a mutation relative to a naturally existing heavy chain constant region sequence). In one embodiment, the HCP1 comprises a first CH2 domain sequence and a first CH3 domain sequence, wherein the first CH2 domain sequence and the first CH3 domain sequence do not comprise a mutation (e.g., a mutation relative to a naturally existing CH2 domain sequence or a naturally existing CH3 domain sequence). In one embodiment, the HCP2 comprises a second CH2 domain sequence and a second CH3 domain sequence, wherein the second CH2 domain sequence and the second CH3 domain sequence do not comprise a mutation (e.g., a mutation relative to a naturally existing CH2 domain sequence or a naturally existing CH3 domain sequence). In one embodiment, i) the HCP1 comprises a first CH2 domain sequence and a first CH3 domain sequence, wherein the first CH2 domain sequence and the first CH3 domain sequence do not comprise a mutation (e.g., a mutation relative to a naturally existing CH2 domain sequence or a naturally existing CH3 domain sequence); and ii) the HCP2 comprises a second CH2 domain sequence and a second CH3 domain sequence, wherein the second CH2 domain sequence and the second CH3 domain sequence do not comprise a mutation (e.g., a mutation relative to a naturally existing CH2 domain sequence or a naturally existing CH3 domain sequence).

In certain embodiments of the foregoing aspects, the HCP1 is derived from an antibody arising, either in vivo or in vitro, as a lambda antibody. In certain embodiments of the foregoing aspects, the HCP2 is derived from an antibody arising, either in vivo or in vitro, as a kappa antibody.

In one embodiment, the HCP1 and LLCP comprise amino acid sequences selected from Table 18 (e.g., as paired in Table 18) or Table 5a (e.g., as paired in Table 5a), or functional variant or fragment thereof. In one embodiment, the HCP2 and KLCP comprise amino acid sequences selected from Table 18 (e.g., as paired in Table 18) or Table 5a (e.g., as paired in Table 5a), or functional variant or fragment thereof. In one embodiment, the HCP1, LLCP, HCP2, and KLCP comprise amino acid sequences selected from Table 18 (e.g., a single cell of Table 18) or Table 5a (e.g., a single row of Table 5a), or functional variant or fragment thereof.

In one embodiment, the first or second antigen is a tumor antigen, e.g., a pancreatic, lung, or colorectal tumor antigen. In one embodiment, the first or second antigen is chosen from: PD-L1, HER3, TROP2, mesothelin, IGF-1R, or CA19-9. In one embodiment, the first or second antigen is chosen from: PD-L1, HER3, TROP2, VEGF-A, EGFR, MUC1, DLL4, or HGF. In one embodiment, the first or second antigen is chosen from: PD-L1, HER3, TROP2, VEGF-A, EGFR, MUC1, MAGE-A3, gpA33, NY-ESO-1, ANG2, RSPO3, HER2, CEACAM5, or CEA. In one embodiment, the first or second antigen is an antigen of an immune effector cell, e.g., a T cell, an NK cell, or a myeloid cell. In one embodiment, the first or second antigen is chosen from: CD3, PD-1, LAG-3, TIM-3, CTLA-4, VISTA, TIGIT, PD-L1, B7-H3, 4-1BB, or ICOS. In one embodiment, the first antigen is a tumor antigen, e.g., mesothelin, and the second antigen is an antigen chosen from NKP30, PD-L1, CD3, NKG2D, CD47, 4-1BB, or NKP46; or the second antigen is a tumor antigen, e.g., mesothelin, and the first antigen is an antigen chosen from NKP30, PD-L1, CD3, NKG2D, CD47, 4-1BB, or NKP46. In one embodiment, the first antigen is IGF1R and the second antigen is HER3, or the second antigen is IGF1R and the first antigen is HER3. In one embodiment, the first antigen is mesothelin and the second antigen is PD-L1, or the second antigen is mesothelin and the first antigen is PD-L1. In one embodiment, the first antigen is CTLA4 and the second antigen is IL12β, or the second antigen is CTLA4 and the first antigen is IL12β. In one embodiment, the first antigen is CTLA4 and the second antigen is TRAILR2, or the second antigen is CTLA4 and the first antigen is TRAILR2. In one embodiment, the first antigen is CTLA4 and the second antigen is CD221, or the second antigen is CTLA4 and the first antigen is CD221. In one embodiment, the first antigen is PD1 and the second antigen is TRAILR2, or the second antigen is PD1 and the first antigen is TRAILR2. In one embodiment, the first antigen is PD1 and the second antigen is PDL1, or the second antigen is PD1 and the first antigen is PDL1. In one embodiment, the first antigen is PD1 and the second antigen is PDL1, or the second antigen is PD1 and the first antigen is PDL1. In one embodiment, the multispecific antibody molecule further comprises an IL-2 molecule. In one embodiment, the multispecific antibody molecule further comprises a CD40 agonist, e.g., a CD40L polypeptide or an agonistic anti-CD40 antibody molecule.

In one aspect, disclosed herein is a multispecific antibody molecule, e.g., an antibody molecule comprising two binding specificities, e.g., a bispecific antibody molecule. The multispecific antibody molecule includes:

a lambda light chain polypeptide (LLCP) specific for a first epitope;

a heavy chain polypeptide 1 (HCP1) specific for the first epitope;

a kappa light chain polypeptide (KLCP) specific for a second epitope; and a heavy chain polypeptide 2 (HCP2) specific for the second epitope.

In another aspect, disclosed herein is a multispecific, e.g., a bispecific, antibody molecule that includes:

(i) a first heavy chain polypeptide (HCP1) (e.g., a heavy chain polypeptide comprising one, two, three or all of a first heavy chain variable region (first VH), a first CH1, a first heavy chain constant region (e.g., a first CH2, a first CH3, or both)), e.g., wherein the HCP1 binds to a first epitope;

(ii) a second heavy chain polypeptide (HCP2) (e.g., a heavy chain polypeptide comprising one, two, three or all of a second heavy chain variable region (second VH), a second CH1, a second heavy chain constant region (e.g., a second CH2, a second CH3, or both)), e.g., wherein the HCP2 binds to a second epitope;

(iii) a lambda light chain polypeptide (LLCP) (e.g., a lambda light variable region (VLλ), a lambda light constant chain (VLλ), or both) that preferentially associates with the first heavy chain polypeptide (e.g., the first VH), e.g., wherein the LLCP binds to a first epitope; and (iv) a kappa light chain polypeptide (KLCP) (e.g., a lambda light variable region (VLκ), a lambda light constant chain (VLκ), or both) that preferentially associates with the second heavy chain polypeptide (e.g., the second VH), e.g., wherein the KLCP binds to a second epitope. In embodiments, the first and second heavy chain polypeptides form an Fc interface that enhances heterodimerization.

In some embodiments of the multispecific antibody molecule disclosed herein:

LLCP has a higher affinity for HCP1 than for HCP2; and/or

KLCP has a higher affinity for HCP2 than for HCP1.

In embodiments, the affinity of LLCP for HCP1 is sufficiently greater than its affinity for HCP2, such that under preselected conditions, e.g., in aqueous buffer, e.g., at pH 7, in saline, e.g., at pH 7, or under physiological conditions, at least 75%, 80, 90, 95, 98, 99, 99.5, or 99.9% of the multispecific antibody molecule molecules have a LLCP-complexed, or interfaced with, a HCP1.

In some embodiments of the multispecific antibody molecule disclosed herein:

the HCP1 has a greater affinity for HCP2, than for a second molecule of HCP1; and/or the HCP2 has a greater affinity for HCP1, than for a second molecule of HCP2.

In embodiments, the affinity of HCP1 for HCP2 is sufficiently greater than its affinity for a second molecule of HCP1, such that under preselected conditions, e.g., in aqueous buffer, e.g., at pH 7, in saline, e.g., at pH 7, or under physiological conditions, at least 75%, 80, 90, 95, 98, 99 99.5 or 99.9% of the multispecific antibody molecule molecules have a HCP1 complexed, or interfaced with, a HCP2.

In another aspect, disclosed herein is a method for making, or producing, a multispecific antibody molecule. The method includes:

(i) providing a first heavy chain polypeptide (e.g., a heavy chain polypeptide comprising one, two, three or all of a first heavy chain variable region (first VH), a first CH1, a first heavy chain constant region (e.g., a first CH2, a first CH3, or both));

(ii) providing a second heavy chain polypeptide (e.g., a heavy chain polypeptide comprising one, two, three or all of a second heavy chain variable region (second VH), a second CH1, a second heavy chain constant region (e.g., a second CH2, a second CH3, or both));

(iii) providing a lambda chain polypeptide (e.g., a lambda light variable region (VLλ), a lambda light constant chain (VLλ), or both) that preferentially associates with the first heavy chain polypeptide (e.g., the first VH); and (iv) providing a kappa chain polypeptide (e.g., a lambda light variable region (VLκ), a lambda light constant chain (VLκ), or both) that preferentially associates with the second heavy chain polypeptide (e.g., the second VH), under conditions where (i)-(iv) associate.

In embodiments, the first and second heavy chain polypeptides form an Fc interface that enhances heterodimerization.

In another aspect, disclosed herein is a method for making, or producing, a multispecific antibody molecule. The method includes:

(i) providing a first heavy chain polypeptide (e.g., a heavy chain polypeptide comprising one, two, three or all of a first heavy chain variable region (first VH), a first CH1, a first heavy chain constant region (e.g., a first CH2, a first CH3, or both));

(ii) providing a second heavy chain polypeptide (e.g., a heavy chain polypeptide comprising one, two, three or all of a second heavy chain variable region (second VH), a second CH1, a second heavy chain constant region (e.g., a second CH2, a second CH3, or both));

(iii) providing a lambda chain polypeptide (e.g., a lambda light variable region (VLλ), a lambda light constant chain (VLλ), or both) that preferentially associates with the first heavy chain polypeptide (e.g., the first VH), and further comprising an effector moiety (e.g., IL2); and (iv) providing a kappa chain polypeptide (e.g., a lambda light chain variable region (VLκ), a lambda light constant chain (VLλ), or both) that preferentially associates with the second heavy chain polypeptide (e.g., the second VH), and optionally further comprising an antigen binding moiety (e.g., a scFv), under conditions where (i)-(iv) associate. In embodiments, (i)-(iv) (e.g., nucleic acid encoding (i)-(iv)) are introduced in a single cell, e.g., a single mammalian cell, e.g., a CHO cell. In embodiments, (i)-(iv) are expressed in the cell.

In embodiments, (i)-(iv) (e.g., nucleic acid encoding (i)-(iv)) are introduced in different cells, e.g., different mammalian cells, e.g., two or more CHO cell. In embodiments, (i)-(iv) are expressed in the cells.

In one embodiments, the method further comprises purifying a cell-expressed antibody molecule, e.g., using a lambda- and/or kappa-specific purification, e.g., affinity chromatography.

In embodiments, the method further comprises evaluating the cell-expressed multispecific antibody molecule. For example, the purified cell-expressed multispecific antibody molecule can be analyzed by techniques known in the art, include mass spectrometry. In one embodiment, the purified cell-expressed antibody molecule is cleaved, e.g., digested with papain to yield the Fab moieties and evaluated using mass spectrometry.

In embodiments, the method produces correctly paired kappa/lambda multispecific, e.g., bispecific, antibody molecules in a high yield, e.g., at least 75%, 80, 90, 95, 98, 99 99.5 or 99.9%.

Nucleic acid molecules, vectors and host cells encoding the aforesaid multispecific molecules are also disclosed.

Pharmaceutical compositions comprising the aforesaid multispecific molecules and a pharmaceutical acceptable carrier are also disclosed.

In another aspect, the invention features a method of treating a subject having a disorder, e.g., cancer, using the multispecific antibody molecules disclosed herein.

Additional features and embodiments of the multispecific antibody molecules and methods disclosed herein include one or more of the following.

In some embodiments, the multispecific antibody molecule is isolated or purified.

In some embodiments, an interface of a first and second heavy chain polypeptide of the multispecific antibody molecule, e.g., the first and second heavy chain constant regions (e.g., a first and a second Fc region) is altered, e.g., mutated, to increase heterodimerization, e.g., relative to a non-engineered interface, e.g., a naturally-occurring interface. In one embodiment, heterodimerization of the first and second heavy chain polypeptides is enhanced by providing an Fc interface of a first and a second Fc region with one or more of: a paired protuberance-cavity ("knob-in-a hole"), an electrostatic interaction, or a strand-exchange, such that a greater ratio of heteromultimer to homomultimer forms, e.g., relative to a non-engineered interface. In some embodiments, the multispecific antibody molecules include a paired amino acid substitution at a position chosen from one or more of 347, 349, 350, 351, 366, 368, 370, 392, 394, 395, 397, 398, 399, 405, 407, or 409, e.g., of the Fc region of human IgG1 For example, the first immunoglobulin chain constant region (e.g., Fc region) can include a paired an amino acid substitution chosen from: T366S, L368A, or Y407V (e.g., corresponding to a cavity or hole), and the second immunoglobulin chain constant region comprises a T366W (e.g., corresponding to a protuberance or knob).

In some embodiments, an interface of a first and second heavy chain polypeptide of the multispecific antibody molecule, e.g., the first and second heavy chain constant regions (e.g., a first and a second Fc region) is not altered, e.g., not mutated, to increase heterodimerization, e.g., relative to a non-engineered interface, e.g., a naturally-occurring interface. In one embodiment, heterodimerization of the first and second heavy chain polypeptides is not enhanced by providing an Fc interface of a first and a second Fc region with one or more of: a paired protuberance-cavity ("knob-in-a hole").

In some embodiments, one or more (e.g., all) of a CH1 chain, a lambda light constant chain (VLλ), and a kappa light constant chain (VDκ) is not altered, e.g., not mutated, to increase heterodimerization, e.g., relative to a non-engineered interface, e.g., a naturally-occurring interface. In some embodiments, one or more (e.g., all) of a CH1 chain, a lambda light constant chain (VLλ), and a kappa light constant chain (VDκ) is naturally occurring.

In some embodiments, the heavy chain variable region (VH, e.g., FR1, FR2, FR3, and optionally, CDRs 1-2) is derived from a germline family described by IMGT®, the international ImMunoGeneTics (Lefranc, M.-P., "IMGT, the international ImMunoGeneTics database" *Nucl. Acids Res.*, 29, 207-209 (2001) and Scaviner, D., Barbié, V., Ruiz, M. and Lefranc, M.-P., "Protein displays of the human immunoglobulin heavy, kappa and lambda variable and joining regions", *Exp. Clin. Immunogenet.*, 16, 234-240 (1999)), or an amino acid sequence substantially identical thereto.

In some embodiments, the light chain variable region (VL kappa or lambda, e.g., FR1, FR2, FR3, and optionally, CDRs 1-2) is derived from a germline family described by IMGT, or an amino acid sequence substantially identical thereto.

In embodiments, the multispecific antibody molecules include a plurality (e.g., two, three or more) binding specificities (or functionalities).

In an embodiment, the multispecific antibody molecule is a bispecific (or bifunctional) molecule, a trispecific (or trifunctional) molecule, or a tetraspecific (or tetrafunctional) molecule.

In some embodiments, the multispecific antibody molecules include a first binding specificity to a first epitope, and a second binding specificity to a second epitope. In some embodiments, the first and second epitopes are on the same antigen, e.g., the same polypeptide. In other embodiments, the first and second epitopes are on different antigens, e.g., different polypeptide. In some embodiments, the first epitope is on a first antigen, e.g., a first polypeptide and the second epitope is on a second antigen, e.g., a second polypeptide. In some embodiments, the antigen, or polypeptide, is selected an antigen recognized by an antibody from Tables 2, 4, 5a, 17 and 18, e.g., a first and second antigen recognized by a lambda and kappa antibody disclosed in Tables 2, 4, 5a, 17 and 18. Exemplary pairings of lambda and kappa antibodies are depicted in Tables 5a and 18.

In some embodiments the multispecific antibody molecule includes a first binding specificity to a first epitope, wherein the first epitope is on a tumor antigen, e.g., a pancreatic, lung, or colorectal tumor antigen. In some embodiments, the first epitope is on an antigen chosen from: PD-L1, HER3, TROP2, mesothelin, IGF-1R, or CA19-9. In other embodiments, the first epitope is on an antigen chosen from PD-L1, HER3, TROP2, VEGF-A, EGFR, MUC1, DLL4, or HGF. In yet other embodiments, the first epitope is on an antigen chosen from PD-L1, HER3, TROP2, VEGF-A, EGFR, MUC1, MAGE-A3, gpA33, NY-ESO-1, ANG2, RSPO3, HER2, CEACAM5, or CEA.

In some embodiments, the multispecific antibody molecule includes a second binding specificity to a second epitope, wherein the second epitope is on an antigen of an immune effector cell, e.g., a T cell, an NK cell, or a myeloid cell. In some embodiments, the second epitope is chosen from CD3, PD-1, LAG-3, TIM-3, CTLA-4, VISTA, TIGIT, PD-L1, B7-H3, 4-1BB, or ICOS.

In some embodiments, the multispecific antibody molecule binds to a first epitope on a tumor antigen, e.g., mesothelin, and a second epitope on an antigen chosen from NKP30, PD-L1, CD3, NKG2D, CD47, 4-1BB, or NKP46. In some embodiments, the multispecific antibody molecule binds mesothelin and PD-L1. In some embodiments, the multispecific antibody molecule binds mesothelin and PDL1, and further comprises a cytokine (e.g., IL2). In some embodiments, the multispecific antibody molecule binds mesothelin; PDL1; and NKp30, and further comprises a cytokine (e.g., IL2).

In some embodiments, the multispecific antibody molecules include a plurality (e.g., two or more) binding specificities (or functionalities). In some embodiments, a first binding specificity selectively localizes to a cancer cell, e.g., it includes a tumor-targeting moiety; and the second (or third, or fourth) binding specificity includes one or both of: an immune cell engager (e.g., chosen from one, two, three, or all of an NK cell engager, a B cell engager, a dendritic cell engager, or a macrophage cell engager); and/or a cytokine molecule. Exemplary tumor-targeting moieties, immune cell engagers and cytokine molecules are described in the Detailed Description.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the following detailed description and claims.

DETAILED DESCRIPTION OF THE INVENTION

Disclosed herein are multispecific antibody molecules (also referred to herein as "multifunctional antibody molecules") that comprise a lambda light chain polypeptide and a kappa light chain polypeptide. In embodiments, the multispecific antibody molecules include a plurality (e.g., two or more) binding specificities (or functionalities). In some embodiments, a first binding specificity selectively localizes to a cancer cell, e.g., it includes a tumor-targeting moiety; and the second (or third, or fourth) binding specificity includes one or both of: an immune cell engager (e.g., chosen from one, two, three, or all of an NK cell engager, a B cell engager, a dendritic cell engager, or a macrophage cell engager); and/or a cytokine molecule. In an embodiment, the multispecific molecule is a bispecific (or bifunctional) molecule, a trispecific (or trifunctional) molecule, or a tetraspecific (or tetrafunctional) molecule. Accordingly, provided herein are, inter alia, multispecific molecules (e.g., multispecific antibody molecules) that include the lambda light chain polypeptide and a kappa light chain polypeptides, nucleic acids encoding the same, methods of producing the aforesaid molecules, and methods of treating a disorder, e.g., cancer, using the aforesaid molecules.

In one embodiment, the multispecific antibody molecule comprises:

(i) a first heavy chain polypeptide (e.g., a heavy chain polypeptide comprising one, two, three or all of a first heavy chain variable region (first VH having a first binding specificity), a first CH1, a first heavy chain constant region (e.g., a first CH2, a first CH3, or both));

(ii) a second heavy chain polypeptide (e.g., a heavy chain polypeptide comprising one, two, three or all of a second heavy chain variable region (second VH), a second CH1, a second heavy chain constant region (e.g., a second CH2, a second CH3, or both));

(iii) a lambda light chain polypeptide (e.g., a lambda light variable region (VLλ), a lambda light constant chain (VLλ), or both) that preferentially associates with the first heavy chain polypeptide (e.g., the first VH); and (iv) a kappa light chain polypeptide (e.g., a lambda light variable region (VLκ), a lambda light constant chain (VLκ), or both) that preferentially associates with the second heavy chain polypeptide (e.g., the second VH).

Figure 1A:
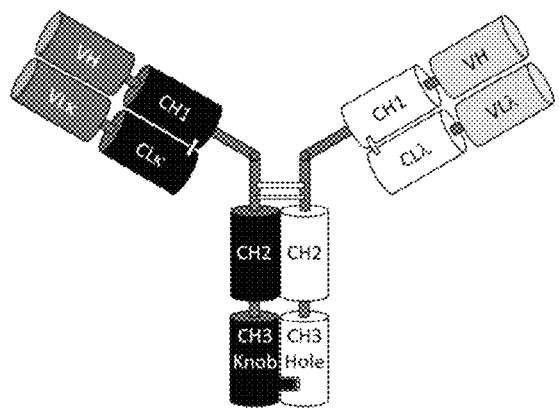
FIGS. 1A-1D depict a schematic representation of light chain shuffling.

In embodiments, the first and second heavy chain polypeptides form an Fc interface that enhances heterodimerization. An exemplary representation is depicted in FIG. 1A, which shows a multispecific antibody molecule having a first binding specificity that includes a hybrid VLλ-CLλ heterodimerized to a first heavy chain variable region connected to the Fc constant, CH2-CH3 domain (having a knob modification) and a second binding specificity that includes a hybrid VLκ-CLκ heterodimerized to a second heavy chain variable region connected to the Fc constant, CH2-CH3 domain (having a hole modification).

Figure 1B:
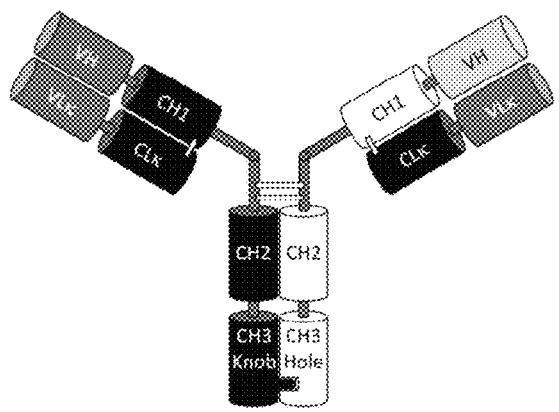
Figure 1C:
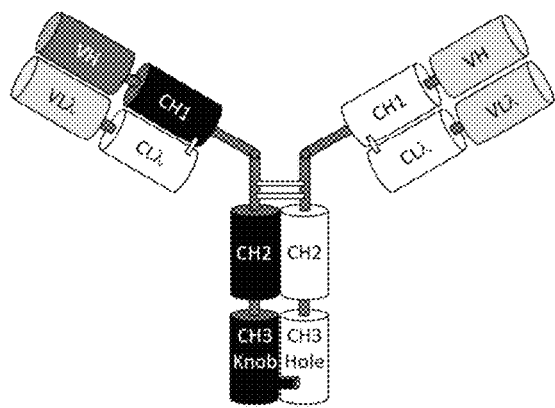
Figure 1D:
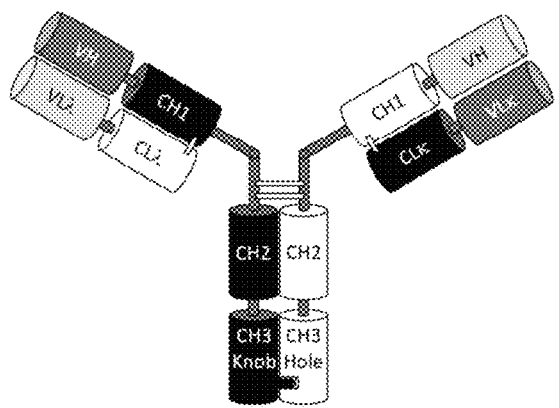

In some embodiments, disclosed herein is a novel method for generating a multispecific, e.g., a bispecific, antibody molecule. The method for generating bispecific molecules disclosed herein produces stable antibodies, while avoiding the light-chain swapping commonly described in the literature. Light chain swapping or shuffling is a common problem encountered when producing antibodies with a single kappa and a single lambda light chain. A schematic of light chain shuffling is depicted in FIGS. 1A-1D. As shown in in FIGS. 1A-1D, only 25% of the product is of the desired configuration (FIG. 1A) and the other 75% of product has the light chains mispaired (FIG. 1B-1D). The method for generating a multispecific, e.g., bispecific, antibody molecule disclosed herein uses antibodies, e.g., human antibodies, with kappa and lambda light chains to produce stable, multispecific, e.g., bispecific, antibody molecules.

Certain terms are defined below.

As used herein, the articles "a" and "an" refer to one or more than one, e.g., to at least one, of the grammatical object of the article. The use of the words "a" or "an" when used in conjunction with the term "comprising" herein may mean "one," but it is also consistent with the meaning of "one or more," "at least one," and "one or more than one."

As used herein, "about" and "approximately" generally mean an acceptable degree of error for the quantity measured given the nature or precision of the measurements. Exemplary degrees of error are within 20 percent (%), typically, within 10%, and more typically, within 5% of a given range of values.

"Antibody molecule" as used herein refers to a protein, e.g., an immunoglobulin chain or fragment thereof, comprising at least one immunoglobulin variable domain sequence. An antibody molecule encompasses antibodies (e.g., full-length antibodies) and antibody fragments. In an embodiment, an antibody molecule comprises an antigen binding or functional fragment of a full length antibody, or a full length immunoglobulin chain. For example, a full-length antibody is an immunoglobulin (Ig) molecule (e.g., an IgG antibody) that is naturally occurring or formed by normal immunoglobulin gene fragment recombinatorial processes). In embodiments, an antibody molecule refers to an immunologically active, antigen-binding portion of an immunoglobulin molecule, such as an antibody fragment. An antibody fragment, e.g., functional fragment, is a portion of an antibody, e.g., Fab, Fab', F(ab')$_2$, F(ab)$_2$, variable fragment (Fv), domain antibody (dAb), or single chain variable fragment (scFv). A functional antibody fragment binds to the same antigen as that recognized by the intact (e.g., full-length) antibody. The terms "antibody fragment" or "functional fragment" also include isolated fragments consisting of the variable regions, such as the "Fv" fragments consisting of the variable regions of the heavy and light chains or recombinant single chain polypeptide molecules in which light and heavy variable regions are connected by a peptide linker ("scFv proteins"). In some embodiments, an antibody fragment does not include portions of antibodies without antigen binding activity, such as Fc fragments or single amino acid residues. Exemplary antibody molecules include full length antibodies and antibody fragments, e.g., dAb (domain antibody), single chain, Fab, Fab', and F(ab')$_2$ fragments, and single chain variable fragments (scFvs).

As used herein, the term "molecule" as used in, e.g., antibody molecule, cytokine molecule, receptor molecule, includes full-length, naturally-occurring molecules, as well as variants, e.g., functional variants (e.g., truncations, fragments, mutated (e.g., substantially similar sequences) or derivatized form thereof), so long as at least one function and/or activity of the unmodified (e.g., naturally-occurring) molecule remains.

The term "functional variant" refers to polypeptides that have a substantially identical amino acid sequence to the naturally-occurring sequence, or are encoded by a substantially identical nucleotide sequence, and are capable of having one or more activities of the naturally-occurring sequence.

"Derived from" as used herein in reference the relationship of a first sequence, to a second sequence (e.g., in the context of nucleic acid sequence or protein sequences) imposes no process limitations and refers only to structural similarity. In embodiments a derived sequence will differ from the reference sequence by levels of homology or sequence identity described elsewhere herein.

As used herein, an "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may or may not include one, two, or more N- or C-terminal amino acids, or may include other alterations that are compatible with formation of the protein structure.

"Lambda light chain polypeptide (LLCP)", as that term is used herein, refers to a polypeptide comprising sufficient light chain (LC) sequence, such that when combined with a cognate heavy chain variable region, can mediate specific binding to its epitope and complex with an HCP1. In an embodiment it comprises all or a fragment of a CH1 region. In an embodiment, an LLCP comprises LC-CDR1, LC-CDR2, LC-CDR3, FR1, FR2, FR3, FR4, and CH1, or sufficient sequence therefrom to mediate specific binding of its epitope and complex with an HCP1. LLCP, together with its HCP1, provide specificity for a first epitope (while KLCP, together with its HCP2, provide specificity for a second epitope). As described elsewhere herein, LLCP has a higher affinity for HCP1 than for HCP2.

"Kappa light chain polypeptide (KLCP)", as that term is used herein, refers to a polypeptide comprising sufficient light chain (LC) sequence, such that when combined with a cognate heavy chain variable region, can mediate specific binding to its epitope and complex with an HCP2. In an embodiment, it comprises all or a fragment of a CH1 region. In an embodiment, a KLCP comprises LC-CDR1, LC-CDR2, LC-CDR3, FR1, FR2, FR3, FR4, and CH1, or sufficient sequence therefrom to mediate specific binding of its epitope and complex with an HCP2. KLCP, together with its HCP2, provide specificity for a second epitope (while LLCP, together with its HCP1, provide specificity for a first epitope).

"Heavy chain polypeptide 1 (HCP1)", as that term is used herein, refers to a polypeptide comprising sufficient heavy chain (HC) sequence, e.g., HC variable region sequence, such that when combined with a cognate LLCP, can mediate specific binding to its epitope and complex with an HCP1. In an embodiment, it comprises all or a fragment of a CH1 region. In an embodiment, it comprises all or a fragment of a CH2 and/or CH3 region. In an embodiment an HCP1 comprises HC-CDR1, HC-CDR2, HC-CDR3, FR1, FR2, FR3, FR4, CH1, CH2, and CH3, or sufficient sequence therefrom to: (i) mediate specific binding of its epitope and complex with an LLCP, (ii) to complex preferentially, as described herein to LLCP as opposed to KLCP; and (iii) to complex preferentially, as described herein, to an HCP2, as opposed to another molecule of HCP1. HCP1, together with its LLCP, provide specificity for a first epitope (while KLCP, together with its HCP2, provide specificity for a second epitope).

"Heavy chain polypeptide 2 (HCP2)", as that term is used herein, refers to a polypeptide comprising sufficient heavy chain (HC) sequence, e.g., HC variable region sequence, such that when combined with a cognate LLCP, can mediate specific binding to its epitope and complex with an HCP1. In an embodiment, it comprises all or a fragment of a CH1 region. In an embodiment, it comprises all or a fragment of a CH2 and/or CH3 region. In an embodiment an HCP1 comprises HC-CDR1, HC-CDR2, HC-CDR3, FR1, FR2, FR3, FR4, CH1, CH2, and CH3, or sufficient sequence therefrom to: (i) mediate specific binding of its epitope and complex with an KLCP, (ii) to complex preferentially, as described herein to KLCP as opposed to LLCP; and (iii) to complex preferentially, as described herein, to an HCP1, as opposed to another molecule of HCP2. HCP2, together with its KLCP, provide specificity for a second epitope (while LLCP, together with its HCP1, provide specificity for a first epitope).

In embodiments, an antibody molecule is monospecific, e.g., it comprises binding specificity for a single epitope. In some embodiments, an antibody molecule is multispecific, e.g., it comprises a plurality of immunoglobulin variable domain sequences, where a first immunoglobulin variable domain sequence has binding specificity for a first epitope and a second immunoglobulin variable domain sequence has binding specificity for a second epitope. In some embodiments, an antibody molecule is a bispecific antibody molecule. "Bispecific antibody molecule" as used herein refers to an antibody molecule that has specificity for more than one (e.g., two, three, four, or more) epitope and/or antigen.

"Multispecific antibody molecule" as that term is used herein, refers to an antibody molecule having specificity for two non-identical epitopes, e.g., having a first variable region specific for a first epitope and a second variable region specific for a second epitope, wherein the first and second epitopes are non-identical. Multispecific antibody molecules include bispecific antibody molecules.

"Antigen" (Ag) as used herein refers to a molecule that can provoke an immune response, e.g., involving activation of certain immune cells and/or antibody generation. Any macromolecule, including almost all proteins or peptides, can be an antigen. Antigens can also be derived from genomic recombinant or DNA. For example, any DNA comprising a nucleotide sequence or a partial nucleotide sequence that encodes a protein capable of eliciting an immune response encodes an "antigen." In embodiments, an antigen does not need to be encoded solely by a full length nucleotide sequence of a gene, nor does an antigen need to be encoded by a gene at all. In embodiments, an antigen can be synthesized or can be derived from a biological sample, e.g., a tissue sample, a tumor sample, a cell, or a fluid with other biological components. As used, herein a "tumor antigen" or interchangeably, a "cancer antigen" includes any molecule present on, or associated with, a cancer, e.g., a cancer cell or a tumor microenvironment that can provoke an immune response. As used, herein an "immune cell antigen" includes any molecule present on, or associated with, an immune cell that can provoke an immune response.

The "antigen-binding site," or "binding portion" of an antibody molecule refers to the part of an antibody molecule, e.g., an immunoglobulin (Ig) molecule, that participates in antigen binding. In embodiments, the antigen binding site is formed by amino acid residues of the variable (V) regions of the heavy (H) and light (L) chains. Three highly divergent stretches within the variable regions of the heavy and light chains, referred to as hypervariable regions, are disposed between more conserved flanking stretches called "framework regions," (FRs). FRs are amino acid sequences that are naturally found between, and adjacent to, hypervariable regions in immunoglobulins. In embodiments, in an antibody molecule, the three hypervariable regions of a light chain and the three hypervariable regions of a heavy chain are disposed relative to each other in three dimensional space to form an antigen-binding surface, which is complementary to the three-dimensional surface of a bound antigen. The three hypervariable regions of each of the heavy and light chains are referred to as "complementarity-determining regions," or "CDRs." The framework region and CDRs have been defined and described, e.g., in Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917. Each variable chain (e.g., variable heavy chain and variable light chain) is typically made up of three CDRs and four FRs, arranged from amino-terminus to carboxy-terminus in the amino acid order: FR1, CDR1, FR2, CDR2, FR3, CDR3, and FR4.

As used herein, preferential pairing of a heavy chain polypeptide and a light chain polypeptide refers to the condition, where the heavy chain polypeptide and the light chain polypeptide preferentially bind to each other, over an unrelated heavy chain polypeptide, or an unrelated light chain polypeptide. In one embodiment, the heavy chain polypeptide binds to the light chain polypeptide with a higher affinity than when the heavy chain polypeptide binds to an unrelated light chain polypeptide. In one embodiment, the light chain polypeptide binds to the heavy chain polypeptide with a higher affinity than when the light chain polypeptide binds to an unrelated heavy chain polypeptide.

As used here, a percent binding between a first heavy chain polypeptide and a first light chain polypeptide in the presence of a competing polypeptide (e.g., a second heavy chain polypeptide or a second light chain polypeptide) refers to the amount of binding between the first heavy chain polypeptide and the first light chain polypeptide in the presence of the competing polypeptide, relative to the amount of binding between the first heavy chain polypeptide and the first light chain polypeptide in the absence of any competing polypeptide (the latter was set to 100%). In one embodiment, the percent binding was measured when the first heavy chain polypeptide, the first light chain polypeptide, and the competing polypeptide are present at 1:1:1. In one embodiment, the percent binding was measured when the first heavy chain polypeptide, the first light chain polypeptide, and the competing polypeptide are present at 1:1:1, wherein the competing polypeptide is a second light chain polypeptide. In one embodiment, the percent binding was measured by an assay described herein, e.g., the NanoBiT assay.

"Cancer" as used herein can encompass all types of oncogenic processes and/or cancerous growths. In embodiments, cancer includes primary tumors as well as metastatic tissues or malignantly transformed cells, tissues, or organs. In embodiments, cancer encompasses all histopathologies and stages, e.g., stages of invasiveness/severity, of a cancer. In embodiments, cancer includes relapsed and/or resistant cancer. The terms "cancer" and "tumor" can be used interchangeably. For example, both terms encompass solid and liquid tumors. As used herein, the term "cancer" or "tumor" includes premalignant, as well as malignant cancers and tumors.

As used herein, an "immune cell" refers to any of various cells that function in the immune system, e.g., to protect against agents of infection and foreign matter. In embodiments, this term includes leukocytes, e.g., neutrophils, eosinophils, basophils, lymphocytes, and monocytes. Innate leukocytes include phagocytes (e.g., macrophages, neutrophils, and dendritic cells), mast cells, eosinophils, basophils, and natural killer cells. Innate leukocytes identify and eliminate pathogens, either by attacking larger pathogens through contact or by engulfing and then killing microorganisms, and are mediators in the activation of an adaptive immune response. The cells of the adaptive immune system are special types of leukocytes, called lymphocytes. B cells and T cells are important types of lymphocytes and are derived from hematopoietic stem cells in the bone marrow. B cells are involved in the humoral immune response, whereas T cells are involved in cell-mediated immune response. The term "immune cell" includes immune effector cells.

"Immune effector cell," as that term is used herein, refers to a cell that is involved in an immune response, e.g., in the promotion of an immune effector response. Examples of immune effector cells include, but are not limited to, T cells, e.g., alpha/beta T cells and gamma/delta T cells, B cells, natural killer (NK) cells, natural killer T (NK T) cells, and mast cells.

The term "effector function" or "effector response" refers to a specialized function of a cell. Effector function of a T cell, for example, may be cytolytic activity or helper activity including the secretion of cytokines.

In some embodiments, the multispecific antibody molecule includes a tumor-targeting moiety. A "tumor-targeting moiety," as used herein, refers to a binding agent that recognizes or associates with, e.g., binds to, a target in a cancer cell. The tumor-targeting moiety can be an antibody molecule, a receptor molecule (e.g., a full length receptor, receptor fragment, or fusion thereof (e.g., a receptor-Fc fusion)), or a ligand molecule (e.g., a full length ligand, ligand fragment, or fusion thereof (e.g., a ligand-Fc fusion)) that binds to the cancer antigen (e.g., the tumor and/or the stromal antigen). In embodiments, the tumor-targeting moiety specifically binds to the target tumor, e.g., binds preferentially to the target tumor. For example, when the tumor-targeting moiety is an antibody molecule, it binds to the cancer antigen (e.g., the tumor antigen and/or the stromal antigen) with a dissociation constant of less than about 10 nM.

In some embodiments, the multispecific antibody molecule includes an immune cell engager. "An immune cell engager" refers to one or more binding specificities that bind and/or activate an immune cell, e.g., a cell involved in an immune response. In embodiments, the immune cell is chosen from an NK cell, a B cell, a dendritic cell, and/or the macrophage cell. The immune cell engager can be an antibody molecule, a receptor molecule (e.g., a full length receptor, receptor fragment, or fusion thereof (e.g., a receptor-Fc fusion)), or a ligand molecule (e.g., a full length ligand, ligand fragment, or fusion thereof (e.g., a ligand-Fc fusion)) that binds to the immune cell antigen (e.g., the NK cell antigen, the B cell antigen, the dendritic cell antigen, and/or the macrophage cell antigen). In embodiments, the immune cell engager specifically binds to the target immune cell, e.g., binds preferentially to the target immune cell. For example, when the immune cell engager is an antibody molecule, it binds to the immune cell antigen (e.g., the NK cell antigen, the B cell antigen, the dendritic cell antigen, and/or the macrophage cell antigen) with a dissociation constant of less than about 10 nM.

In some embodiments, the multispecific antibody molecule includes a cytokine molecule. As used herein, a "cytokine molecule" refers to full length, a fragment or a variant of a cytokine; a cytokine further comprising a receptor domain, e.g., a cytokine receptor dimerizing domain; or an agonist of a cytokine receptor, e.g., an antibody molecule (e.g., an agonistic antibody) to a cytokine receptor, that elicits at least one activity of a naturally-occurring cytokine. In some embodiments the cytokine molecule is chosen from interleukin-2 (IL-2), interleukin-12 (IL-12), interleukin-15 (IL-15), interleukin-18 (IL-18), interleukin-21 (IL-21), or interferon gamma, or a fragment or variant thereof, or a combination of any of the aforesaid cytokines. The cytokine molecule can be a monomer or a dimer. In embodiments, the cytokine molecule can further include a cytokine receptor dimerizing domain. In other embodiments, the cytokine molecule is an agonist of a cytokine receptor, e.g., an antibody molecule (e.g., an agonistic antibody) to a cytokine receptor chosen from an IL-2, IL-15Ra or IL-21R.

The compositions and methods of the present invention encompass polypeptides and nucleic acids having the sequences specified, or sequences substantially identical or similar thereto, e.g., sequences at least 85%, 90%, 95% identical or higher to the sequence specified. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 85%, 90%. 91%, 92%, 93%, 94%, 95%, 96%, 97%, 98% or 99% identity to a reference sequence, e.g., a sequence provided herein.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 85%, 90%, 91%, 92%, 93%, 94%, 95%, 96%, 97%, 98% or 99% identity to a reference sequence, e.g., a sequence provided herein.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444-453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) *CABIOS,* 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to a nucleic acid (e.g., SEQ ID NO: 1) molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) *Nucleic Acids Res.* 25:3389-3402. When utilizing BLAST and Gapped BLAST programs, the default parameters of the respective programs (e.g., XBLAST and NBLAST) can be used. See http://www.ncbi.nlm.nih.gov.

It is understood that the molecules of the present invention may have additional conservative or non-essential amino acid substitutions, which do not have a substantial effect on their functions.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. As used herein the term "amino acid" includes both the D- or L-optical isomers and peptidomimetics.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The terms "polypeptide", "peptide" and "protein" (if single chain) are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures.

The terms "nucleic acid," "nucleic acid sequence," "nucleotide sequence," or "polynucleotide sequence," and "polynucleotide" are used interchangeably. They refer to a polymeric form of nucleotides of any length, either deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a non-natural arrangement.

The term "isolated," as used herein, refers to material that is removed from its original or native environment (e.g., the natural environment if it is naturally occurring). For example, a naturally-occurring polynucleotide or polypeptide present in a living animal is not isolated, but the same polynucleotide or polypeptide, separated by human intervention from some or all of the co-existing materials in the natural system, is isolated. Such polynucleotides could be part of a vector and/or such polynucleotides or polypeptides could be part of a composition, and still be isolated in that such vector or composition is not part of the environment in which it is found in nature.

Various aspects of the invention are described in further detail below. Additional definitions are set out throughout the specification.

Antibody Molecules

In one embodiment, the antibody molecule binds to an antigen, e.g., an immune effector cell, a tumor antigen or a stromal antigen. In some embodiments, the antigen is, e.g., a mammalian, e.g., a human, antigen. In other embodiments, the antibody molecule binds to an immune cell antigen, e.g., a mammalian, e.g., a human, immune cell antigen. For example, the antibody molecule binds specifically to an epitope, e.g., linear or conformational epitope, on the cancer antigen or the immune cell antigen.

In an embodiment, an antibody molecule is a monospecific antibody molecule and binds a single epitope. E.g., a monospecific antibody molecule having a plurality of immunoglobulin variable domain sequences, each of which binds the same epitope.

In an embodiment an antibody molecule is a multispecific antibody molecule, e.g., it comprises a plurality of immunoglobulin variable domains sequences, wherein a first immunoglobulin variable domain sequence of the plurality has binding specificity for a first epitope and a second immunoglobulin variable domain sequence of the plurality has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., the different proteins (or different subunits of a multimeric protein). In an embodiment a multispecific antibody molecule comprises a third, fourth or fifth immunoglobulin variable domain. In an embodiment, a multispecific antibody molecule is a bispecific antibody molecule, a trispecific antibody molecule, or a tetraspecific antibody molecule.

In an embodiment a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., the different proteins (or different subunits of a multimeric protein). In an embodiment a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In an embodiment a bispecific antibody molecule comprises a half antibody having binding specificity for a first epitope and a half antibody having binding specificity for a second epitope. In an embodiment a bispecific antibody molecule comprises a half antibody, or fragment thereof, having binding specificity for a first epitope and a half antibody, or fragment thereof, having binding specificity for a second epitope. In an embodiment a bispecific antibody molecule comprises a scFv or a Fab, or fragment thereof, have binding specificity for a first epitope and a scFv or a Fab, or fragment thereof, have binding specificity for a second epitope.

In an embodiment, an antibody molecule comprises a diabody, and a single-chain molecule, as well as an antigen-binding fragment of an antibody (e.g., Fab, F(ab')$_2$, and Fv). For example, an antibody molecule can include a heavy (H) chain variable domain sequence (abbreviated herein as VH), and a light (L) chain variable domain sequence (abbreviated herein as VL). In an embodiment an antibody molecule comprises or consists of a heavy chain and a light chain (referred to herein as a half antibody). In another example, an antibody molecule includes two heavy (H) chain variable domain sequences and two light (L) chain variable domain sequence, thereby forming two antigen binding sites, such as Fab, Fab', F(ab')$_2$, Fc, Fd, Fd', Fv, single chain antibodies (scFv for example), single variable domain antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments retain the ability to selectively bind with their respective antigen or receptor. Antibodies and antibody fragments can be from any class of antibodies including, but not limited to, IgG, IgA, IgM, IgD, and IgE, and from any subclass (e.g., IgG1, IgG2, IgG3, and IgG4) of antibodies. The a preparation of antibody molecules can be monoclonal or polyclonal. An antibody molecule can also be a human, humanized, CDR-grafted, or in vitro generated antibody. The antibody can have a heavy chain constant region chosen from, e.g., IgG1, IgG2, IgG3, or IgG4. The antibody can also have a light chain chosen from, e.g., kappa or lambda. The term "immunoglobulin" (Ig) is used interchangeably with the term "antibody" herein.

Examples of antigen-binding fragments of an antibody molecule include: (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) Science 242:423-426; and Huston et al. (1988) Proc. Natl. Acad. Sci. USA 85:5879-5883); (viii) a single domain antibody. These antibody fragments are obtained using conventional techniques known to those with skill in the art, and the fragments are screened for utility in the same manner as are intact antibodies.

Antibody molecules include intact molecules as well as functional fragments thereof. Constant regions of the antibody molecules can be altered, e.g., mutated, to modify the properties of the antibody (e.g., to increase or decrease one or more of: Fc receptor binding, antibody glycosylation, the number of cysteine residues, effector cell function, or complement function).

Antibody molecules can also be single domain antibodies. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, fish, shark, goat, rabbit, and bovine. According to another aspect of the invention, a single domain antibody is a naturally occurring single domain antibody known as heavy chain antibody devoid of light chains. Such single domain antibodies are disclosed in WO 9404678, for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in Camelidae species, for example in camel, llama, dromedary, alpaca and guanaco. Other species besides Camelidae may produce heavy chain antibodies naturally devoid of light chain; such VHHs are within the scope of the invention.

The VH and VL regions can be subdivided into regions of hypervariability, termed "complementarity determining regions" (CDR), interspersed with regions that are more conserved, termed "framework regions" (FR or FW).

The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242; Chothia, C. et al. (1987) J. Mol. Biol. 196:901-917; and the AbM definition used by Oxford Molecular's AbM antibody modeling software. See, generally, e.g., Protein Sequence and Structure Analysis of Antibody Variable Domains. In: Antibody Engineering Lab Manual (Ed.: Duebel, S. and Kontermann, R., Springer-Verlag, Heidelberg).

The terms "complementarity determining region," and "CDR," as used herein refer to the sequences of amino acids within antibody variable regions which confer antigen specificity and binding affinity. In general, there are three CDRs in each heavy chain variable region (HCDR1, HCDR2, HCDR3) and three CDRs in each light chain variable region (LCDR1, LCDR2, LCDR3).

The precise amino acid sequence boundaries of a given CDR can be determined using any of a number of known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273, 927-948 ("Chothia" numbering scheme). As used herein, the CDRs defined according the "Chothia" number scheme are also sometimes referred to as "hypervariable loops."

For example, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia, the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3).

Each VH and VL typically includes three CDRs and four FRs, arranged from amino-terminus to carboxy-terminus in the following order: FR1, CDR1, FR2, CDR2, FR3, CDR3, FR4.

The antibody molecule can be a polyclonal or a monoclonal antibody.

The terms "monoclonal antibody" or "monoclonal antibody composition" as used herein refer to a preparation of antibody molecules of single molecular composition. A monoclonal antibody composition displays a single binding specificity and affinity for a particular epitope. A monoclonal antibody can be made by hybridoma technology or by methods that do not use hybridoma technology (e.g., recombinant methods).

The antibody can be recombinantly produced, e.g., produced by phage display or by combinatorial methods.

Phage display and combinatorial methods for generating antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, the contents of all of which are incorporated by reference herein).

In one embodiment, the antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Methods of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856-859; Green, L. L. et al. 1994 *Nature Genet.* 7:13-21; Morrison, S. L. et al. 1994 *Proc. Natl. Acad. Sci. USA* 81:6851-6855; Bruggeman et al. 1993 *Year Immunol* 7:33-40; Tuaillon et al. 1993 *PNAS* 90:3720-3724; Bruggeman et al. 1991 *Eur J Immunol* 21:1323-1326).

An antibody molecule can be one in which the variable region, or a portion thereof, e.g., the CDRs, are generated in a non-human organism, e.g., a rat or mouse. Chimeric, CDR-grafted, and humanized antibodies are within the invention. Antibody molecules generated in a non-human organism, e.g., a rat or mouse, and then modified, e.g., in the variable framework or constant region, to decrease antigenicity in a human are within the invention.

An "effectively human" protein is a protein that does substantially not evoke a neutralizing antibody response, e.g., the human anti-murine antibody (HAMA) response. HAMA can be problematic in a number of circumstances, e.g., if the antibody molecule is administered repeatedly, e.g., in treatment of a chronic or recurrent disease condition. A HAMA response can make repeated antibody administration potentially ineffective because of an increased antibody clearance from the serum (see, e.g., Saleh et al., *Cancer Immunol. Immunother.*, 32:180-190 (1990)) and also because of potential allergic reactions (see, e.g., LoBuglio et al., *Hybridoma*, 5:5117-5123 (1986)).

Chimeric antibodies can be produced by recombinant DNA techniques known in the art (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 *Science* 240:1041-1043); Liu et al. (1987) *PNAS* 84:3439-3443; Liu et al., 1987, *J. Immunol.* 139:3521-3526; Sun et al. (1987) *PNAS* 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559).

A humanized or CDR-grafted antibody will have at least one or two but generally all three recipient CDRs (of heavy and or light immuoglobulin chains) replaced with a donor CDR. The antibody may be replaced with at least a portion of a non-human CDR or only some of the CDRs may be replaced with non-human CDRs. It is only necessary to replace the number of CDRs required for binding to the antigen. Preferably, the donor will be a rodent antibody, e.g., a rat or mouse antibody, and the recipient will be a human framework or a human consensus framework. Typically, the immunoglobulin providing the CDRs is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody molecule can be humanized by methods known in the art (see e.g., Morrison, S. L., 1985, *Science* 229:1202-1207, by Oi et al., 1986, *BioTechniques* 4:214, and by Queen et al. U.S. Pat. Nos. 5,585,089, 5,693,761 and 5,693,762, the contents of all of which are hereby incorporated by reference).

Humanized or CDR-grafted antibody molecules can be produced by CDR-grafting or CDR substitution, wherein one, two, or all CDRs of an immunoglobulin chain can be replaced. See e.g., U.S. Pat. No. 5,225,539; Jones et al. 1986 *Nature* 321:552-525; Verhoeyan et al. 1988 *Science* 239:1534; Beidler et al. 1988 *J. Immunol.* 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibody molecules in which specific amino acids have been substituted, deleted or added. Criteria for selecting amino acids from the donor are described in U.S. Pat. No. 5,585,089, e.g., columns 12-16 of U.S. Pat. No. 5,585,089, e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

The antibody molecule can be a single chain antibody. A single-chain antibody (scFV) may be engineered (see, for example, Colcher, D. et al. (1999) *Ann N Y Acad Sci* 880:263-80; and Reiter, Y. (1996) *Clin Cancer Res* 2:245-52). The single chain antibody can be dimerized or multimerized to generate multivalent antibodies having specificities for different epitopes of the same target protein.

In yet other embodiments, the antibody molecule has a heavy chain constant region chosen from, e.g., the heavy chain constant regions of IgG1, IgG2, IgG3, IgG4, IgM, IgA1, IgA2, IgD, and IgE; particularly, chosen from, e.g., the (e.g., human) heavy chain constant regions of IgG1, IgG2, IgG3, and IgG4. In another embodiment, the antibody molecule has a light chain constant region chosen from, e.g., the (e.g., human) light chain constant regions of kappa or lambda. The constant region can be altered, e.g., mutated, to modify the properties of the antibody (e.g., to increase or decrease one or more of: Fc receptor binding, antibody glycosylation, the number of cysteine residues, effector cell function, and/or complement function). In one embodiment the antibody has: effector function; and can fix complement. In other embodiments the antibody does not; recruit effector cells; or fix complement. In another embodiment, the antibody has reduced or no ability to bind an Fc receptor. For example, it is a isotype or subtype, fragment or other mutant, which does not support binding to an Fc receptor, e.g., it has a mutagenized or deleted Fc receptor binding region.

Methods for altering an antibody constant region are known in the art. Antibodies with altered function, e.g. altered affinity for an effector ligand, such as FcR on a cell, or the C1 component of complement can be produced by replacing at least one amino acid residue in the constant portion of the antibody with a different residue (see e.g., EP 388,151 A1, U.S. Pat. Nos. 5,624,821 and 5,648,260, the contents of all of which are hereby incorporated by reference). Similar type of alterations could be described which if applied to the murine, or other species immunoglobulin would reduce or eliminate these functions.

An antibody molecule can be derivatized or linked to another functional molecule (e.g., another peptide or protein). As used herein, a "derivatized" antibody molecule is one that has been modified. Methods of derivatization include but are not limited to the addition of a fluorescent moiety, a radionucleotide, a toxin, an enzyme or an affinity ligand such as biotin. Accordingly, the antibody molecules of the invention are intended to include derivatized and otherwise modified forms of the antibodies described herein, including immunoadhesion molecules. For example, an antibody molecule can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate association of the antibody or antibody portion with another molecule (such as a streptavidin core region or a polyhistidine tag).

One type of derivatized antibody molecule is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Multispecific Antibody Molecules

In embodiments, multispecific antibody molecules can comprise more than one antigen-binding site, where different sites are specific for different antigens. In embodiments, multispecific antibody molecules can bind more than one (e.g., two or more) epitopes on the same antigen. In embodiments, multispecific antibody molecules comprise an antigen-binding site specific for a target cell (e.g., cancer cell) and a different antigen-binding site specific for an immune effector cell. In one embodiment, the multispecific antibody molecule is a bispecific antibody molecule. Bispecific antibody molecules can be classified into five different structural groups: (i) bispecific immunoglobulin G (BsIgG); (ii) IgG appended with an additional antigen-binding moiety; (iii) bispecific antibody fragments; (iv) bispecific fusion proteins; and (v) bispecific antibody conjugates.

BsIgG is a format that is monovalent for each antigen. Exemplary BsIgG formats include but are not limited to crossMab, DAF (two-in-one), DAF (four-in-one), DutaMab, DT-IgG, knobs-in-holes common LC, knobs-in-holes assembly, charge pair, Fab-arm exchange, SEEDbody, triomab, LUZ-Y, Fcab, κλ-body, orthogonal Fab. See Spiess et al. Mol. Immunol. 67(2015):95-106. Exemplary BsIgGs include catumaxomab (Fresenius Biotech, Trion Pharma, Neopharm), which contains an anti-CD3 arm and an anti-EpCAM arm; and ertumaxomab (Neovii Biotech, Fresenius Biotech), which targets CD3 and HER2. In some embodiments, BsIgG comprises heavy chains that are engineered for heterodimerization. For example, heavy chains can be engineered for heterodimerization using a "knobs-into-holes" strategy, a SEED platform, a common heavy chain (e.g., in κλ-bodies), and use of heterodimeric Fc regions. See Spiess et al. Mol. Immunol. 67(2015):95-106. Strategies that have been used to avoid heavy chain pairing of homodimers in BsIgG include knobs-in-holes, duobody, azymetric, charge pair, HA-TF, SEEDbody, and differential protein A affinity. See Id.

BsIgG can be produced by separate expression of the component antibodies in different host cells and subsequent purification/assembly into a BsIgG. BsIgG can also be produced by expression of the component antibodies in a single host cell. BsIgG can be purified using affinity chromatography, e.g., using protein A and sequential pH elution.

IgG appended with an additional antigen-binding moiety is another format of bispecific antibody molecules. For example, monospecific IgG can be engineered to have bispecificity by appending an additional antigen-binding unit onto the monospecific IgG, e.g., at the N- or C-terminus of either the heavy or light chain. Exemplary additional antigen-binding units include single domain antibodies (e.g., variable heavy chain or variable light chain), engineered protein scaffolds, and paired antibody variable domains (e.g., single chain variable fragments or variable fragments). See Id. Examples of appended IgG formats include dual variable domain IgG (DVD-Ig), IgG(H)-scFv, scFv-(H)IgG, IgG(L)-scFv, scFv-(L)IgG, IgG(L,H)-Fv, IgG(H)-V, V(H)-IgG, IgG(L)-V, V(L)-IgG, KIH IgG-scFab, 2scFv-IgG, IgG-2scFv, scFv4-Ig, zybody, and DVI-IgG (four-in-one). See Spiess et al. Mol. Immunol. 67(2015):95-106. An example of an IgG-scFv is MM-141 (Merrimack Pharmaceuticals), which binds IGF-1R and HER3. Examples of DVD-Ig include ABT-981 (AbbVie), which binds IL-1α and IL-1β; and ABT-122 (AbbVie), which binds TNF and IL-17A.

Bispecific antibody fragments (BsAb) are a format of bispecific antibody molecules that lack some or all of the antibody constant domains. For example, some BsAb lack an Fc region. In embodiments, bispecific antibody fragments include heavy and light chain regions that are connected by a peptide linker that permits efficient expression of the BsAb in a single host cell. Exemplary bispecific antibody fragments include but are not limited to nanobody, nanobody-HAS, BiTE, Diabody, DART, TandAb, scDiabody, scDiabody-CH3, Diabody-CH3, triple body, miniantibody, minibody, TriBi minibody, scFv-CH3 KIH, Fab-scFv, scFv-CH-CL-scFv, F(ab')2, F(ab')2-scFv2, scFv-KIH, Fab-scFv- Fc, tetravalent HCAb, scDiabody-Fc, Diabody-Fc, tandem scFv-Fc, and intrabody. See Id. For example, the BiTE format comprises tandem scFvs, where the component scFvs bind to CD3 on T cells and a surface antigen on cancer cells Bispecific fusion proteins include antibody fragments linked to other proteins, e.g., to add additional specificity and/or functionality. An example of a bispecific fusion protein is an immTAC, which comprises an anti-CD3 scFv linked to an affinity-matured T-cell receptor that recognizes HLA-presented peptides. In embodiments, the dock-and-lock (DNL) method can be used to generate bispecific antibody molecules with higher valency. Also, fusions to albumin binding proteins or human serum albumin can be extend the serum half-life of antibody fragments. See Id.

CDR-Grafted Scaffolds

In embodiments, the antibody molecule is a CDR-grafted scaffold domain. In embodiments, the scaffold domain is based on a fibronectin domain, e.g., fibronectin type III domain. The overall fold of the fibronectin type III (Fn3) domain is closely related to that of the smallest functional antibody fragment, the variable domain of the antibody heavy chain. There are three loops at the end of Fn3; the positions of BC, DE and FG loops approximately correspond to those of CDR1, 2 and 3 of the VH domain of an antibody. Fn3 does not have disulfide bonds; and therefore Fn3 is stable under reducing conditions, unlike antibodies and their fragments (see, e.g., WO 98/56915; WO 01/64942; WO 00/34784). An Fn3 domain can be modified (e.g., using CDRs or hypervariable loops described herein) or varied, e.g., to select domains that bind to an antigen/marker/cell described herein.

In embodiments, a scaffold domain, e.g., a folded domain, is based on an antibody, e.g., a "minibody" scaffold created by deleting three beta strands from a heavy chain variable domain of a monoclonal antibody (see, e.g., Tramontano et al., 1994, J Mol. Recognit. 7:9; and Martin et al., 1994, EMBO J. 13:5303-5309). The "minibody" can be used to present two hypervariable loops. In embodiments, the scaffold domain is a V-like domain (see, e.g., Coia et al. WO 99/45110) or a domain derived from tendamistatin, which is a 74 residue, six-strand beta sheet sandwich held together by two disulfide bonds (see, e.g., McConnell and Hoess, 1995, J Mol. Biol. 250:460). For example, the loops of tendamistatin can be modified (e.g., using CDRs or hypervariable loops) or varied, e.g., to select domains that bind to a marker/antigen/cell described herein. Another exemplary scaffold domain is a beta-sandwich structure derived from the extracellular domain of CTLA-4 (see, e.g., WO 00/60070).

Other exemplary scaffold domains include but are not limited to T-cell receptors; MHC proteins; extracellular domains (e.g., fibronectin Type III repeats, EGF repeats); protease inhibitors (e.g., Kunitz domains, ecotin, BPTI, and so forth); TPR repeats; trifoil structures; zinc finger domains; DNA-binding proteins; particularly monomeric DNA binding proteins; RNA binding proteins; enzymes, e.g., proteases (particularly inactivated proteases), RNase; chaperones, e.g., thioredoxin, and heat shock proteins; and intracellular signaling domains (such as SH2 and SH3 domains). See, e.g., US 20040009530 and U.S. Pat. No. 7,501,121, incorporated herein by reference.

In embodiments, a scaffold domain is evaluated and chosen, e.g., by one or more of the following criteria: (1) amino acid sequence, (2) sequences of several homologous domains, (3) 3-dimensional structure, and/or (4) stability data over a range of pH, temperature, salinity, organic solvent, oxidant concentration. In embodiments, the scaffold domain is a small, stable protein domain, e.g., a protein of less than 100, 70, 50, 40 or 30 amino acids. The domain may include one or more disulfide bonds or may chelate a metal, e.g., zinc.

Exemplary structures of the multifunctional molecules defined herein are described below. Exemplary structures are further described in: Weidle U et al. (2013) The Intriguing Options of Multispecific Antibody Formats for Treatment of Cancer. *Cancer Genomics & Proteomics* 10: 1-18 (2013); and Spiess C et al. (2015) Alternative molecular formats and therapeutic applications for bispecific antibodies. *Molecular Immunology* 67: 95-106; the full contents of each of which is incorporated by reference herein).

Heterodimerized Antibody Molecules

Heterodimerized bispecific antibodies are based on the natural IgG structure, wherein the two binding arms recognize different antigens. IgG derived formats that enable defined monovalent (and simultaneous) antigen binding are generated by forced heavy chain heterodimerization, combined with technologies that minimize light chain mispairing (e.g., common light chain). Forced heavy chain heterodimerization can be obtained using, e.g., knob-in-hole OR strand exchange engineered domains (SEED).

Knob-in-Hole

Knob-in-Hole as described in U.S. Pat. Nos. 5,731,116, 7,476,724 and Ridgway, J. et al. (1996) *Prot. Engineering* 9(7): 617-621, broadly involves: (1) mutating the CH3 domain of one or both antibodies to promote heterodimerization; and (2) combining the mutated antibodies under conditions that promote heterodimerization. "Knobs" or "protuberances" are typically created by replacing a small amino acid in a parental antibody with a larger amino acid (e.g., T366Y or T366W); "Holes" or "cavities" are created by replacing a larger residue in a parental antibody with a smaller amino acid (e.g., Y407T, T366S, L368A and/or Y407V). In one embodiment, a heavy chain polypeptide containing a knob comprises T366W and S354C substitutions, numbered according to the Eu numbering system. In one embodiment, a heavy chain polypeptide containing a hole comprises T366S, L368A, Y407V and Y349C substitutions, numbered according to the Eu numbering system. In one embodiment, the multispecific antibody molecule disclosed herein comprises a first heavy chain polypeptide and a second heavy chain polypeptide, wherein the first heavy chain polypeptide comprises T366W and S354C substitutions, numbered according to the Eu numbering system, and the second heavy chain polypeptide comprises T366S, L368A, Y407V and Y349C substitutions, numbered according to the Eu numbering system.

Strand Exchange Engineered Domains (SEED)

SEED is based on sequence exchanges between IgG1 and IgA to create non-identical chains which heterodimerize preferentially. Alternating sequences from human IgA and IgG in the SEED CH3 domains generate two asymmetric but complementary domains, designated AG and GA. The SEED design allows efficient generation of AG/GA heterodimers, while disfavoring homodimerization of AG and GA SEED CH3 domains.

Common Light Chain & CrossMab

Light chain mispairing must be avoided to generate homogenous preparations of bispecific IgGs. One way to achieve this is through the use of the common light chain principle, i.e. combining two binders that share one light chain but still have separate specificities. Another option is the CrossMab technology which avoids non-specific L chain mispairing by exchanging CH1 and CL domains in the Fab of one half of the bispecific antibody. Such crossover variants retain binding specificity and affinity, but make the two arms so different that L chain mispairing is prevented.

Antibody-Based Fusions

A variety of formats can be generated which contain additional binding entities attached to the N or C terminus of antibodies. These fusions with single chain or disulfide stabilized Fvs or Fabs result in the generation of tetravalent molecules with bivalent binding specificity for each antigen. Combinations of scFvs and scFabs with IgGs enable the production of molecules which can recognize three or more different antigens.

Antibody-Fab Fusion

Antibody-Fab fusions are bispecific antibodies comprising a traditional antibody to a first target and a Fab to a second target fused to the C terminus of the antibody heavy chain. Commonly the antibody and the Fab will have a common light chain. Antibody fusions can be produced by (1) engineering the DNA sequence of the target fusion, and (2) transfecting the target DNA into a suitable host cell to express the fusion protein. It seems like the antibody-scFv fusion may be linked by a (Gly)-Ser linker between the C-terminus of the CH3 domain and the N-terminus of the scFv, as described by Coloma, J. et al. (1997) *Nature Biotech* 15:159.

Antibody-scFv Fusion

Antibody-scFv Fusions are bispecific antibodies comprising a traditional antibody and a scFv of unique specificity fused to the C terminus of the antibody heavy chain. The scFv can be fused to the C terminus through the Heavy Chain of the scFv either directly or through a linker peptide. Antibody fusions can be produced by (1) engineering the DNA sequence of the target fusion, and (2) transfecting the target DNA into a suitable host cell to express the fusion protein. It seems like the antibody-scFv fusion may be linked by a (Gly)-Ser linker between the C-terminus of the CH3 domain and the N-terminus of the scFv, as described by Coloma, J. et al. (1997) *Nature Biotech* 15:159.

Variable Domain Immunoglobulin DVD

A related format is the dual variable domain immunoglobulin (DVD), which are composed of VH and VL domains of a second specificity place upon the N termini of the V domains by shorter linker sequences.

Fc-Containing Entities (Mini-Antibodies)

Fc-containing entities, also known as mini-antibodies, can be generated by fusing scFv to the C-termini of constant heavy region domain 3 (CH3-scFv) and/or to the hinge region (scFv-hinge-Fc) of an antibody with a different specificity. Trivalent entities can also be made which have disulfide stabilized variable domains (without peptide linker) fused to the C-terminus of CH3 domains of IgGs.

Fc-Containing Multispecific Molecules

In some embodiments, the multispecific molecules disclosed herein includes an immunoglobulin constant region (e.g., an Fc region). Exemplary Fc regions can be chosen from the heavy chain constant regions of IgG1, IgG2, IgG3 or IgG4; more particularly, the heavy chain constant region of human IgG1, IgG2, IgG3, or IgG4.

In some embodiments, the immunoglobulin chain constant region (e.g., the Fc region) is altered, e.g., mutated, to increase or decrease one or more of: Fc receptor binding, antibody glycosylation, the number of cysteine residues, effector cell function, or complement function.

In other embodiments, an interface of a first and second immunoglobulin chain constant regions (e.g., a first and a second Fc region) is altered, e.g., mutated, to increase or decrease dimerization, e.g., relative to a non-engineered interface, e.g., a naturally-occurring interface. For example, dimerization of the immunoglobulin chain constant region (e.g., the Fc region) can be enhanced by providing an Fc interface of a first and a second Fc region with one or more of: a paired protuberance-cavity ("knob-in-a hole"), an electrostatic interaction, or a strand-exchange, such that a greater ratio of heteromultimer to homomultimer forms, e.g., relative to a non-engineered interface.

In some embodiments, the multispecific molecules include a paired amino acid substitution at a position chosen from one or more of 347, 349, 350, 351, 366, 368, 370, 392, 394, 395, 397, 398, 399, 405, 407, or 409, e.g., of the Fc region of human IgG1 For example, the immunoglobulin chain constant region (e.g., Fc region) can include a paired an amino acid substitution chosen from: T366S, L368A, or Y407V (e.g., corresponding to a cavity or hole), and T366W (e.g., corresponding to a protuberance or knob).

In some embodiments, the immunoglobulin chain constant region (e.g., the Fc region) is not altered, e.g., not mutated, to increase or decrease one or more of: Fc receptor binding, antibody glycosylation, the number of cysteine residues, effector cell function, or complement function. In some embodiments, the multispecific molecules does not include a paired amino acid substitution at a position chosen from one or more of 347, 349, 350, 351, 366, 368, 370, 392, 394, 395, 397, 398, 399, 405, 407, or 409, e.g., of the Fc region of human IgG1 For example, the immunoglobulin chain constant region (e.g., Fc region) does not include a paired amino acid substitution chosen from: T366S, L368A, or Y407V (e.g., corresponding to a cavity or hole), and T366W (e.g., corresponding to a protuberance or knob).

In other embodiments, the multispecific molecule includes a half-life extender, e.g., a human serum albumin or an antibody molecule to human serum albumin.

Multispecific Molecules Comprising Non-Contiguous Polypeptides

In one embodiment, the multispecific molecule is not a single polypeptide chain.

In one embodiment, the antibody molecule includes two, complete heavy chains and two, complete light chains. In one embodiment, the multispecific molecules having at least two or at least three non-contiguous polypeptide chains include a first and second immunoglobulin chain constant regions (e.g., a first and second Fc region) in at least two non-contiguous polypeptide chains, e.g., as described herein.

In embodiments, the multispecific molecule is a bispecific or bifunctional molecule, wherein the first and second polypeptides (i) and (ii) are non-contiguous, e.g., are two separate polypeptide chains. In some embodiments, the first and second polypeptides (i) and (ii) include a paired amino acid substitution at a position chosen from one or more of 347, 349, 350, 351, 366, 368, 370, 392, 394, 395, 397, 398, 399, 405, 407, or 409, e.g., of the Fc region of human IgG1. For example, the first immunoglobulin chain constant region (e.g., the first Fc region) can include an amino acid substitution chosen from: T366S, L368A, or Y407V (e.g., corresponding to a cavity or hole), and the second immunoglobulin chain constant region (e.g., the second Fc region) includes a T366W (e.g., corresponding to a protuberance or knob). In some embodiments, the first and second polypeptides are a first and second member of a heterodimeric first and second Fc region.

In embodiments, the multispecific molecule is a bispecific or bifunctional molecule, wherein the first and second polypeptides (i) and (ii) are non-contiguous, e.g., are two separate polypeptide chains. In some embodiments, the first and second polypeptides (i) and (ii) do not include a paired amino acid substitution at a position chosen from one or more of 347, 349, 350, 351, 366, 368, 370, 392, 394, 395, 397, 398, 399, 405, 407, or 409, e.g., of the Fc region of human IgG1.

In some embodiments, the first polypeptide has the following configuration from N-to-C:

(a) a first portion of a first antigen domain, e.g., a first VH-CH1 of a Fab molecule, that binds to a first antigen, e.g., a cancer antigen, e.g., a solid tumor, stromal or hematological antigen, connected, optionally via a linker to, the first immunoglobulin constant region (e.g., the CH2 connected to the CH3 region) (e.g., a first Fc region);

(b) a first portion of a second antigen domain, e.g., a first VH-CH1 of a Fab molecule, that binds to a second antigen, e.g., a cancer antigen, e.g., a solid tumor, stromal or hematological antigen, connected, optionally via a linker to, the first immunoglobulin constant region (e.g., the CH2 connected to the CH3 region) (e.g., a first Fc region);

(c) the third polypeptide has the following configuration from N-to-C: a second portion of the first antigen domain, e.g., a first VL-CL of the Fab, where the VL is of kappa subtype and binds to a first antigen, e.g., a cancer antigen, e.g., a solid tumor, stromal or hematological antigen (e.g., the same cancer antigen bound by the first VH-CH1);

(d) the fourth polypeptide has the following configuration from N-to-C: a second portion of the second antigen domain, e.g. a second VL-CL of the Fab, where the VL is of lambda subtype and binds to a second antigen, e.g., a cancer antigen, e.g., a solid tumor, stromal, or hematological antigen (e.g., the same cancer antigen bound by the second VH-CH1) (e.g. an example of this configuration is depicted in FIG. 1A).

In embodiments, the first immunoglobulin constant region (e.g., the first CH2-CH3 region) includes a protuberance or knob, e.g., as described herein. In embodiments, the first immunoglobulin constant region (e.g., the first CH2-CH3 region) does not include a protuberance or knob, e.g., as described herein.

In embodiments, the second immunoglobulin constant region (e.g., the second CH2-CH3 region) includes a cavity or hole. In embodiments, the first and second immunoglobulin constant region promote heterodimerization of the bispecific molecule. In embodiments, the second immunoglobulin constant region (e.g., the second CH2-CH3 region) does not include a cavity or hole. In embodiments, the first and second immunoglobulin constant region does not promote heterodimerization of the bispecific molecule.

Tumor Specific Targeting Moieties

In certain embodiments, the multispecific antibody molecules disclosed herein include a tumor-targeting moiety. The tumor targeting moiety can be chosen from an antibody molecule (e.g., an antigen binding domain as described herein), a receptor or a receptor fragment, or a ligand or a ligand fragment, or a combination thereof. In some embodiments, the tumor targeting moiety associates with, e.g., binds to, a tumor cell (e.g., a molecule, e.g., antigen, present on the surface of the tumor cell). In certain embodiments, the tumor targeting moiety targets, e.g., directs the multispecific molecules disclosed herein to a cancer (e.g., a cancer or tumor cells). In some embodiments, the cancer is chosen from a hematological cancer, a solid cancer, a metastatic cancer, or a combination thereof.

In some embodiments, the multispecific molecule, e.g., the tumor-targeting moiety, binds to a solid tumor antigen or a stromal antigen. The solid tumor antigen or stromal antigen can be present on a solid tumor, or a metastatic lesion thereof. In some embodiments, the solid tumor is chosen from one or more of pancreatic (e.g., pancreatic adenocarcinoma), breast, colorectal, lung (e.g., small or non-small cell lung cancer), skin, ovarian, or liver cancer. In one embodiment, the solid tumor is a fibrotic or desmoplastic solid tumor. For example, the solid tumor antigen or stromal antigen can be present on a tumor, e.g., a tumor of a class typified by having one or more of: limited tumor perfusion, compressed blood vessels, or fibrotic tumor interstitium.

In certain embodiments, the solid tumor antigen is chosen from one or more of: mesothelin, gangioside 2 (GD2), prostate stem cell antigen (PSCA), prostate specific membrane antigen (PMSA), prostate-specific antigen (PSA), carcinoembryonic antigen (CEA), Ron Kinase, c-Met, Immature laminin receptor, TAG-72, BING-4, Calcium-activated chloride channel 2, Cyclin-B1, 9D7, Ep-CAM, EphA3, Her2/neu, Telomerase, SAP-1, Survivin, NY-ESO-1/LAGE-1, PRAME, SSX-2, Melan-A/MART-1, Gp100/pmel17, Tyrosinase, TRP-1/-2, MC1R, β-catenin, BRCA1/2, CDK4, CML66, Fibronectin, p53, Ras, TGF-B receptor, AFP, ETA, MAGE, MUC-1, CA-125, BAGE, GAGE, NY-ESO-1, β-catenin, CDK4, CDC27, α actinin-4, TRP1/gp75, TRP2, gp100, Melan-A/MART1, gangliosides, WT1, EphA3, Epidermal growth factor receptor (EGFR), CD20, MART-2, MART-1, MUC1, MUC2, MUM1, MUM2, MUM3, NA88-1, NPM, OA1, OGT, RCC, RUI1, RUI2, SAGE, TRG, TRP1, or TSTA. In some embodiments, the solid tumor antigen is chosen from: Mesothelin, GD2, PMSA, PSCA, CEA, Ron Kinase, or c-Met. In some embodiments, the solid tumor antigen is Mesothelin.

Cytokine Molecules

In certain embodiments, the multispecific antibody molecules disclosed herein can further include a cytokine molecule.

Cytokines are proteinaceous signaling compounds that are mediators of the immune response. They control many different cellular functions including proliferation, differentiation and cell survival/apoptosis; cytokines are also involved in several pathophysiological processes including viral infections and autoimmune diseases. Cytokines are synthesized under various stimuli by a variety of cells of both the innate (monocytes, macrophages, dendritic cells) and adaptive (T- and B-cells) immune systems. Cytokines can be classified into two groups: pro- and anti-inflammatory. Pro-inflammatory cytokines, including IFNgamma, IL-1, IL-6 and TNF-alpha, are predominantly derived from the innate immune cells and Th1 cells. Anti-inflammatory cytokines, including IL-10, IL-4, IL-13 and IL-5, are synthesized from Th2 immune cells.

The present disclosure provides, inter alia, multi-specific (e.g., bi-, tri-, quad-specific) proteins, that include, e.g., are engineered to contain, one or more cytokine molecules, e.g., immunomodulatory (e.g., proinflammatory) cytokines and variants, e.g., functional variants, thereof. Accordingly, in some embodiments, the cytokine molecule is an interleukin or a variant, e.g., a functional variant thereof. In some embodiments the interleukin is a proinflammatory interleukin. In some embodiments the interleukin is chosen from interleukin-2 (IL-2), interleukin-12 (IL-12), interleukin-15 (IL-15), interleukin-18 (IL-18), interleukin-21 (IL-21), or interferon gamma. In some embodiments the interleukin is interleukin-2 (IL-2). In some embodiments, the cytokine molecule is a proinflammatory cytokine.

In some embodiments, the multispecific molecules disclosed herein include a cytokine molecule. In embodiments, the cytokine molecule includes a full length, a fragment or a variant of a cytokine; a cytokine receptor domain, e.g., a cytokine receptor dimerizing domain; or an agonist of a cytokine receptor, e.g., an antibody molecule (e.g., an agonistic antibody) to a cytokine receptor.

In some embodiments the cytokine molecule is chosen from IL-2, IL-12, IL-15, IL-18, IL-21, or interferon gamma, or a fragment or variant thereof, or a combination of any of the aforesaid cytokines. The cytokine molecule can be a monomer or a dimer. In embodiments, the cytokine molecule can further include a cytokine receptor dimerizing domain.

In other embodiments, the cytokine molecule is an agonist of a cytokine receptor, e.g., an antibody molecule (e.g., an agonistic antibody) to a cytokine receptor chosen from an IL-15Ra or IL-21R.

Immune Cell Engagers

In certain embodiments, the multispecific antibody molecules disclosed herein can include an immune cell engager.

The immune cell engagers of the multispecific molecules disclosed herein can mediate binding to, and/or activation of, an immune cell, e.g., an immune effector cell. In some embodiments, the immune cell is chosen from an NK cell, a B cell, a dendritic cell, or a macrophage cell engager, or a combination thereof. In some embodiments, the immune cell engager is chosen from one, two, three, or all of an NK cell engager, a B cell engager, a dendritic cell engager, or a macrophage cell engager, or a combination thereof. The immune cell engager can be an agonist of the immune system. In some embodiments, the immune cell engager can be an antibody molecule, a ligand molecule (e.g., a ligand that further comprises an immunoglobulin constant region, e.g., an Fc region), a small molecule, a nucleotide molecule.

Natural Killer Cell Engagers

Natural Killer (NK) cells recognize and destroy tumors and virus-infected cells in an antibody-independent manner. The regulation of NK cells is mediated by activating and inhibiting receptors on the NK cell surface. One family of activating receptors is the natural cytotoxicity receptors (NCRs) which include NKp30, NKp44 and NKp46. The NCRs initiate tumor targeting by recognition of heparan sulfate on cancer cells. NKG2D is a receptor that provides both stimulatory and costimulatory innate immune responses on activated killer (NK) cells, leading to cytotoxic activity. DNAM1 is a receptor involved in intercellular adhesion, lymphocyte signaling, cytotoxicity and lymphokine secretion mediated by cytotoxic T-lymphocyte (CTL) and NK cell. DAP10 (also known as HCST) is a transmembrane adapter protein which associates with KLRK1 to form an activation receptor KLRK1-HCST in lymphoid and myeloid cells; this receptor plays a major role in triggering cytotoxicity against target cells expressing cell surface ligands such as MHC class I chain-related MICA and MICB, and U (optionally L1)6-binding proteins (ULBPs); it KLRK1-HCST receptor plays a role in immune surveillance against tumors and is required for cytolysis of tumors cells; indeed, melanoma cells that do not express KLRK1 ligands escape from immune surveillance mediated by NK cells. CD16 is a receptor for the Fc region of IgG, which binds complexed or aggregated IgG and also monomeric IgG and thereby mediates antibody-dependent cellular cytotoxicity (ADCC) and other antibody-dependent responses, such as phagocytosis.

In some embodiments, the NK cell engager is a viral hemagglutinin (HA), HA is a glycoprotein found on the surface of influenza viruses. It is responsible for binding the virus to cells with sialic acid on the membranes, such as cells in the upper respiratory tract or erythrocytes. HA has at least 18 different antigens. These subtypes are named H1 through H18. NCRs can recognize viral proteins. NKp46 has been shown to be able to interact with the HA of influenza and the HA-NA of Paramyxovirus, including Sendai virus and Newcastle disease virus. Besides NKp46, NKp44 can also functionally interact with HA of different influenza subtypes.

The present disclosure provides, inter alia, multi-specific (e.g., bi-, tri-, quad-specific) proteins, that are engineered to contain one or more NK cell engager that mediate binding to and/or activation of an NK cell. Accordingly, in some embodiments, the NK cell engager is selected from an antigen binding domain or ligand that binds to (e.g., activates): NKp30, NKp40, NKp44, NKp46, NKG2D, DNAM1, DAP10, CD16 (e.g., CD16a, CD16b, or both), CRTAM, CD27, PSGL1, CD96, CD100 (SEMA4D), NKp80 or CD244 (also known as SLAMF4 or 2B4). in some embodiments, the NK cell engager is selected from an antigen binding domain or ligand that binds to (e.g., activates): NKp30 or NKp46.

In other embodiments, the NK cell engager is a ligand of NKp44 or NKp46, which is a viral HA. Viral hemagglutinins (HA) are glyco proteins which are on the surface of viruses. HA proteins allow viruses to bind to the membrane of cells via sialic acid sugar moieties which contributes to the fusion of viral membranes with the cell membranes (see e.g., Eur J Immunol. 2001 September; 31(9):2680-9 "Recognition of viral hemagglutinins by NKp44 but not by NKp30"; and Nature. 2001 Feb. 22; 409(6823):1055-60 "Recognition of haemagglutinins on virus-infected cells by NKp46 activates lysis by human NK cells" the contents of each of which are incorporated by reference herein).

In other embodiments, the NK cell engager is a ligand of NKG2D chosen from MICA, MICB, or ULBP1.

In other embodiments, the NK cell engager is a ligand of DNAM1 chosen from NECTIN2 or NECL5.

In yet other embodiments, the NK cell engager is a ligand of DAP10, which is an adapter for NKG2D (see e.g., Proc Natl Acad Sci USA. 2005 May 24; 102(21): 7641-7646; and Blood, 15 Sep. 2011 Volume 118, Number 11, the full contents of each of which is incorporated by reference herein).

In other embodiments, the NK cell engager is a ligand of CD16, which is a CD16a/b ligand, e.g., a CD16a/b ligand further comprising an antibody Fc region (see e.g., Front Immunol. 2013; 4: 76 discusses how antibodies use the Fc to trigger NK cells through CD16, the full contents of which are incorporated herein).

B Cell, Macrophage & Dendritic Cell Engagers

Broadly, B cells, also known as B lymphocytes, are a type of white blood cell of the lymphocyte subtype. They function in the humoral immunity component of the adaptive immune system by secreting antibodies. Additionally, B cells present antigen (they are also classified as professional antigen-presenting cells (APCs)) and secrete cytokines. Macrophages are a type of white blood cell that engulfs and digests cellular debris, foreign substances, microbes, cancer cells via phagocytosis. Besides phagocytosis, they play important roles in nonspecific defense (innate immunity) and also help initiate specific defense mechanisms (adaptive immunity) by recruiting other immune cells such as lymphocytes. For example, they are important as antigen presenters to T cells. Beyond increasing inflammation and stimulating the immune system, macrophages also play an important anti-inflammatory role and can decrease immune reactions through the release of cytokines. Dendritic cells (DCs) are antigen-presenting cells that function in processing antigen material and present it on the cell surface to the T cells of the immune system.

The present disclosure provides, inter alia, multi-specific (e.g., bi-, tri-, quad-specific) proteins, that include, e.g., are engineered to contain, one or more B cell, macrophage, and/or dendritic cell engager that mediate binding to and/or activation of a B cell, macrophage, and/or dendritic cell.

Accordingly, in some embodiments, the immune cell engager comprises a B cell, macrophage, and/or dendritic cell engager chosen from one or more of CD40 ligand (CD40L) or a CD70 ligand; an antibody molecule that binds to CD40 or CD70; an antibody molecule to OX40; an OX40 ligand (OX40L); an agonist of a Toll-like receptor (e.g., as described herein, e.g., a TLR4, e.g., a constitutively active TLR4 (caTLR4), or a TLR9 agonists); a 41BB; a CD2; a CD47; or a STING agonist, or a combination thereof.

In some embodiments, the B cell engager is a CD40L, an OX40L, or a CD70 ligand, or an antibody molecule that binds to OX40, CD40 or CD70.

In some embodiments, the macrophage engager is a CD2 agonist. In some embodiments, the macrophage engager is an antigen binding domain that binds to: CD40L or antigen binding domain or ligand that binds CD40, a Toll like receptor (TLR) agonist (e.g., as described herein), e.g., a TLR9 or TLR4 (e.g., caTLR4 (constitutively active TLR4)), CD47, or a STING agonist. In some embodiments, the STING agonist is a cyclic dinucleotide, e.g., cyclic di-GMP (cdGMP) or cyclic di-AMP (cdAMP). In some embodiments, the STING agonist is biotinylated.

In some embodiments, the dendritic cell engager is a CD2 agonist. In some embodiments, the dendritic cell engager is a ligand, a receptor agonist, or an antibody molecule that binds to one or more of: OX40L, 41BB, a TLR agonist (e.g., as described herein) (e.g., TLR9 agonist, TLR4 (e.g., caTLR4 (constitutively active TLR4)), CD47, or and a STING agonist. In some embodiments, the STING agonist is a cyclic dinucleotide, e.g., cyclic di-GMP (cdGMP) or cyclic di-AMP (cdAMP). In some embodiments, the STING agonist is biotinylated.

In other embodiments, the immune cell engager mediates binding to, or activation of, one or more of a B cell, a macrophage, and/or a dendritic cell. Exemplary B cell, macrophage, and/or dendritic cell engagers can be chosen from one or more of CD40 ligand (CD40L) or a CD70 ligand; an antibody molecule that binds to CD40 or CD70; an antibody molecule to OX40; an OX40 ligand (OX40L); a Toll-like receptor agonist (e.g., a TLR4, e.g., a constitutively active TLR4 (caTLR4) or a TLR9 agonist); a 41BB agonist; a CD2; a CD47; or a STING agonist, or a combination thereof.

In some embodiments, the B cell engager is chosen from one or more of a CD40L, an OX40L, or a CD70 ligand, or an antibody molecule that binds to OX40, CD40 or CD70.

In other embodiments, the macrophage cell engager is chosen from one or more of a CD2 agonist; a CD40L; an OX40L; an antibody molecule that binds to OX40, CD40 or CD70; a Toll-like receptor agonist or a fragment thereof (e.g., a TLR4, e.g., a constitutively active TLR4 (caTLR4)); a CD47 agonist; or a STING agonist.

In other embodiments, the dendritic cell engager is chosen from one or more of a CD2 agonist, an OX40 antibody, an OX40L, 41BB agonist, a Toll-like receptor agonist or a fragment thereof (e.g., a TLR4, e.g., a constitutively active TLR4 (caTLR4)), CD47 agonist, or a STING agonist.

In yet other embodiments, the STING agonist comprises a cyclic dinucleotide, e.g., a cyclic di-GMP (cdGMP), a cyclic di-AMP (cdAMP), or a combination thereof, optionally with 2',5' or 3',5' phosphate linkages.

Toll-Like Receptors

Toll-Like Receptors (TLRs) are evolutionarily conserved receptors are homologues of the *Drosophila* Toll protein, and recognize highly conserved structural motifs known as pathogen-associated microbial patterns (PAMPs), which are exclusively expressed by microbial pathogens, or danger-associated molecular patterns (DAMPs) that are endogenous molecules released from necrotic or dying cells. PAMPs include various bacterial cell wall components such as lipopolysaccharide (LPS), peptidoglycan (PGN) and lipopeptides, as well as flagellin, bacterial DNA and viral double-stranded RNA. DAMPs include intracellular proteins such as heat shock proteins as well as protein fragments from the extracellular matrix. Stimulation of TLRs by the corresponding PAMPs or DAMPs initiates signaling cascades leading to the activation of transcription factors, such as AP-1, NF-κB and interferon regulatory factors (IRFs). Signaling by TLRs results in a variety of cellular responses, including the production of interferons (IFNs), pro-inflammatory cytokines and effector cytokines that direct the adaptive immune response. TLRs are implicated in a number of inflammatory and immune disorders and play a role in cancer (Rakoff-Nahoum S. & Medzhitov R., 2009. Toll-like receptors and cancer. Nat Revs Cancer 9:57-63.)

TLRs are type I transmembrane proteins characterized by an extracellular domain containing leucine-rich repeats (LRRs) and a cytoplasmic tail that contains a conserved region called the Toll/IL-1 receptor (TIR) domain. Ten human and twelve murine TLRs have been characterized, TLR1 to TLR10 in humans, and TLR1 to TLR9, TLR11, TLR12 and TLR13 in mice, the homolog of TLR10 being a pseudogene. TLR2 is essential for the recognition of a variety of PAMPs from Gram-positive bacteria, including bacterial lipoproteins, lipomannans and lipoteichoic acids. TLR3 is implicated in virus-derived double-stranded RNA. TLR4 is predominantly activated by lipopolysaccharide. TLR5 detects bacterial flagellin and TLR9 is required for response to unmethylated CpG DNA. Finally, TLR7 and TLR8 recognize small synthetic antiviral molecules, and single-stranded RNA was reported to be their natural ligand. TLR11 has been reported to recognize uropathogenic *E. coli* and a profilin-like protein from *Toxoplasma gondii*. The repertoire of specificities of the TLRs is apparently extended by the ability of TLRs to heterodimerize with one another. For example, dimers of TLR2 and TLR6 are required for responses to diacylated lipoproteins while TLR2 and TLR1 interact to recognize triacylated lipoproteins. Specificities of the TLRs are also influenced by various adapter and accessory molecules, such as MD-2 and CD14 that form a complex with TLR4 in response to LPS.

TLR signaling consists of at least two distinct pathways: a MyD88-dependent pathway that leads to the production of inflammatory cytokines, and a MyD88-independent pathway associated with the stimulation of IFN-β and the maturation of dendritic cells. The MyD88-dependent pathway is common to all TLRs, except TLR3 (Adachi O. et al., 1998. Targeted disruption of the MyD88 gene results in loss of IL-1- and IL-18-mediated function. Immunity. 9(1):143-50). Upon activation by PAMPs or DAMPs, TLRs hetero- or homodimerize inducing the recruitment of adaptor proteins via the cytoplasmic TIR domain. Individual TLRs induce different signaling responses by usage of the different adaptor molecules. TLR4 and TLR2 signaling requires the adaptor TIRAP/Mal, which is involved in the MyD88-dependent pathway. TLR3 triggers the production of IFN-β in response to double-stranded RNA, in a MyD88-independent manner, through the adaptor TRIF/TICAM-1. TRAM/TICAM-2 is another adaptor molecule involved in the MyD88-independent pathway which function is restricted to the TLR4 pathway.

TLR3, TLR7, TLR8 and TLR9 recognize viral nucleic acids and induce type I IFNs. The signaling mechanisms leading to the induction of type I IFNs differ depending on the TLR activated. They involve the interferon regulatory factors, IRFs, a family of transcription factors known to play a critical role in antiviral defense, cell growth and immune regulation. Three IRFs (IRF3, IRF5 and IRF7) function as direct transducers of virus-mediated TLR signaling. TLR3 and TLR4 activate IRF3 and IRF7, while TLR7 and TLR8 activate IRF5 and IRF7 (Doyle S. et al., 2002. IRF3 mediates a TLR3/TLR4-specific antiviral gene program. Immunity. 17(3):251-63). Furthermore, type I IFN production stimulated by TLR9 ligand CpG-A has been shown to be mediated by PI(3)K and mTOR (Costa-Mattioli M. & Sonenberg N. 2008. RAPping production of type I interferon in pDCs through mTOR. Nature Immunol. 9: 1097-1099).

TLR-9

TLR9 recognizes unmethylated CpG sequences in DNA molecules. CpG sites are relatively rare (~1%) on vertebrate genomes in comparison to bacterial genomes or viral DNA. TLR9 is expressed by numerous cells of the immune system such as B lymphocytes, monocytes, natural killer (NK) cells, and plasmacytoid dendritic cells. TLR9 is expressed intracellularly, within the endosomal compartments and functions to alert the immune system of viral and bacterial infections by binding to DNA rich in CpG motifs. TLR9 signals leads to activation of the cells initiating pro-inflammatory reactions that result in the production of cytokines such as type-I interferon and IL-12.

TLR Agonists

A TLR agonist can agonize one or more TLR, e.g., one or more of human TLR-1, 2, 3, 4, 5, 6, 7, 8, 9, or 10. In some embodiments, an adjunctive agent described herein is a TLR agonist. In some embodiments, the TLR agonist specifically agonizes human TLR-9. In some embodiments, the TLR-9 agonist is a CpG moiety. As used herein, a CpG moiety, is a linear dinucleotide having the sequence: 5'-C-phosphate-G-3', that is, cytosine and guanine separated by only one phosphate.

In some embodiments, the CpG moiety comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more CpG dinucleotides. In some embodiments, the CpG moiety consists of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 CpG dinucleotides. In some embodiments, the CpG moiety has 1-5, 1-10, 1-20, 1-30, 1-40, 1-50, 5-10, 5-20, 5-30, 10-20, 10-30, 10-40, or 10-50 CpG dinucleotides.

In some embodiments, the TLR-9 agonist is a synthetic ODN (oligodeoxynucleotides). CpG ODNs are short synthetic single-stranded DNA molecules containing unmethylated CpG dinucleotides in particular sequence contexts (CpG motifs). CpG ODNs possess a partially or completely phosphorothioated (PS) backbone, as opposed to the natural phosphodiester (PO) backbone found in genomic bacterial DNA. There are three major classes of CpG ODNs: classes A, B and C, which differ in their immunostimulatory activities. CpG-A ODNs are characterized by a PO central CpG-containing palindromic motif and a PS-modified 3' poly-G string. They induce high IFN-α production from pDCs but are weak stimulators of TLR9-dependent NF-κB signaling and pro-inflammatory cytokine (e.g. IL-6) production. CpG-B ODNs contain a full PS backbone with one or more CpG dinucleotides. They strongly activate B cells and TLR9-dependent NF-κB signaling but weakly stimulate IFN-α secretion. CpG-C ODNs combine features of both classes A and B. They contain a complete PS backbone and a CpG-containing palindromic motif. C-Class CpG ODNs induce strong IFN-α production from pDC as well as B cell stimulation.

Exemplary Multispecific Antibody Molecules

Exemplary kappa and lambda multispecific antibody molecules are provided in Tables 17 and 18.

TABLE 17

Exemplary amino acid sequences of antibodies

| Target Sequence | Antibody Sequence | Heavy Chain Variable Domain | Light Chain Variable Domain |
| --- | --- | --- | --- |
| Rabphilin 3A | Ab237 | SEQ ID NO: 401<br>QVQLQESGPGLVKPSQTLSLTCTV<br>SGGSINNNNYYWTWIRQHPGKGLE<br>WIGYIYYSGSTFYNPSLKSRVTIS<br>VDTSKTQFSLKLSSVTAADTAVYY<br>CAREDTMTGLDVWGQGTTVTVSS | SEQ ID NO 402:<br>DIQMTQSPSSLSASVGDRVTIT<br>CRASQSINNYLNWYQQKPGKAP<br>TLLIYAASSLQSGVPSRFSGSR<br>SGTDFTLTISSLQPEDFAAYFC<br>QQTYSNPTFGQGTKVEVK |
| PD-L1 | Avelumab | SEQ ID NO 403:<br>EVQLLESGGGLVQPGGSLRLSCAA<br>SGFTFSSYIMMWVRQAPGKGLEWV<br>SSIYPSGGITFYADTVKGRFTISR<br>DNSKNTLYLQMNSLRAEDTAVYYC<br>ARIKLGTVTTVDYWGQGTLVTVSS | SEQ ID NO 404:<br>QSALTQPASVSGSPGQSITISC<br>TGTSSDVGGYNYVSWYQQHPGK<br>APKLMIYDVSNRPSGVSNRFSG<br>SKSGNTASLTISGLQAEDEADY<br>YCSSYTSSSTRVFGTGTKVTVL |
| CTLA-4 | Ipilumumab | SEQ ID NO 405:<br>QVQLVESGGGVVQPGRSLRLSCAA<br>SGFTFSSYTMHWVRQAPGKGLEWV<br>TFISYDGNNKYYADSVKGRFTISR<br>DNSKNTLYLQMNSLRAEDTAIYYC<br>ARTGWLGPFDYWGQGTLVTVSS | SEQ ID NO 406:<br>EIVLTQSPGTLSLSPGERATLS<br>CRASQSVGSSYLAWYQQKPGQA<br>PRLLIYGAFSRATGIPDRFSGS<br>GSGTDFTLTISRLEPEDFAVYY<br>CQQYGSSPWTFGQGTKVEIK |
| IL-12/23 | Briakinumab | SEQ ID NO 407:<br>QVQLVESGGGVVQPGRSLRLSCAA<br>SGFTFSSYGMHWVRQAPGKGLEWV<br>AFIRYDGSNKYYADSVKGRFTISR<br>DNSKNTLYLQMNSLRAEDTAVYYC<br>KTHGSHDNWGQGTMVTVSS | SEQ ID NO 408:<br>QSVLTQPPSVSGAPGQRVTISC<br>SGSRSNIGSNTVKWYQQLPGTA<br>PKLLIYYNDQRPSGVPDRFSGS<br>KSGTSASLAITGLQAEDEADYY<br>CQSYDRYTHPALLFGTGTKVTV<br>L |

TABLE 17-continued

Exemplary amino acid sequences of antibodies

| Target Sequence | Antibody Sequence | Heavy Chain Variable Domain | Light Chain Variable Domain |
|---|---|---|---|
| PD-1 | Nivolumab | SEQ ID NO 409:<br>QVQLVESGGGVVQPGRSLRLDCKA<br>SGITFSNSGMHWVRQAPGKGLEWV<br>AVIWYDGSKRYYADSVKGRFTISR<br>DNSKNTLFLQMNSLRAEDTAVYYC<br>ATNDDYWGQGTLVTVSS | SEQ ID NO 410:<br>EIVLTQSPATLSLSPGERATLS<br>CRASQSVSSYLAWYQQKPGQAP<br>RLLIYDASNRATGIPARFSGSG<br>SGTDFTLTISSLEPEDFAVYYC<br>QQSSNWPRTFGQGTKVEIK |
| TRAIL-R2 | Lexatumumab | SEQ ID NO 411:<br>EVQLVQSGGGVERPGGSLRLSCAA<br>SGFTFDDYGMSWVRQAPGKGLEWV<br>SGINWNGGSTGYADSVKGRVTISR<br>DNAKNSLYLQMNSLRAEDTAVYYC<br>AKILGAGRGWYFDLWGKGTTVTVS<br>S | SEQ ID NO 412:<br>SSELTQDPAVSVALGQTVRITC<br>QGDSLRSYYASWYQQKPGQAPV<br>LVIYGKNNRPSGIPDRFSGSSS<br>GNTASLTITGAQAEDEADYYCN<br>SRDSSGNHVVFGGGTKLTVL |
| CD20 | Ofatumumab | SEQ ID NO 413:<br>EVQLVESGGGLVQPGRSLRLSCAA<br>SGFTFNDYAMHWVRQAPGKGLEWV<br>STISWNSGSIGYADSVKGRFTISR<br>DNAKKSLYLQMNSLRAEDTALYYC<br>AKDIQYGNYYYGMDVWGQGTTVTV<br>SS | SEQ ID NO 414:<br>EIVLTQSPATLSLSPGERATLS<br>CRASQSVSSYLAWYQQKPGQAP<br>RLLIYDASNRATGIPARFSGSG<br>SGTDFTLTISSLEPEDFAVYYC<br>QQRSNWPITFGQGTRLEIK |
| IGF-1R | Cixutumumab | SEQ ID NO 415:<br>EVQLVQSGAEVKKPGSSVKVSCKA<br>SGGTFSSYAISWVRQAPGQGLEWM<br>GGIIPIFGTANYAQKFQGRVTITA<br>DKSTSTAYMELSSLRSEDTAVYYC<br>ARAPLRFLEWSTQDHYYYYMDVW<br>GKGTTVTVSS | SEQ ID NO 416:<br>SSELTQDPAVSVALGQTVRITC<br>QGDSLRSYYATWYQQKPGQAPI<br>LVIYGENKRPSGIPDRFSGSSS<br>GNTASLTITGAQAEDEADYYCK<br>SRDGSGQHLVFGGGTKLTVL |
| Mesothelin | m912 | SEQ ID NO: 417<br>QVQLQESGPGLVKPSETLSLTCTV<br>SGGSVSSGSYYWSWIRQPPGKGLE<br>WIGYIYYSGSTNYNPSLKSRVTIS<br>VDTSKNQFSLKLSSVTAADTAVYY<br>CAREGKNGAFDIWGQGTMVTVSS | SEQ ID NO: 418<br>DIQMTQSPSSLSASVGDRVTIT<br>CRASQSISSYLNWYQQKPGKAP<br>KLLIYAASSLQSGVPSGFSGSG<br>SGTDFTLTISSLQPEDFATYYC<br>QQSYSTPLTFGGGTKVEIK |

TABLE 18

Exemplary pairings of kappa and lambda antibodies

| Kappa Antibodies | Lambda Antibodies | | | |
|---|---|---|---|---|
| | Avelumab | Briakinumab | Lexatumumab | Cixutumumab |
| Ab237 | SEQ ID NO: 401,<br>SEQ ID NO: 402,<br>SEQ ID NO: 403,<br>SEQ ID NO: 404 | SEQ ID NO: 401,<br>SEQ ID NO: 402,<br>SEQ ID NO: 407,<br>SEQ ID NO: 408 | SEQ ID NO: 401,<br>SEQ ID NO: 402,<br>SEQ ID NO: 411,<br>SEQ ID NO: 412 | SEQ ID NO: 401,<br>SEQ ID NO: 402,<br>SEQ ID NO: 415,<br>SEQ ID NO: 416 |
| Ipilumumab | SEQ ID NO: 405,<br>SEQ ID NO: 406,<br>SEQ ID NO: 403,<br>SEQ ID NO: 404 | SEQ ID NO: 405,<br>SEQ ID NO: 406,<br>SEQ ID NO: 407,<br>SEQ ID NO: 408 | SEQ ID NO: 405,<br>SEQ ID NO: 406,<br>SEQ ID NO: 411,<br>SEQ ID NO: 412 | SEQ ID NO: 405,<br>SEQ ID NO: 406,<br>SEQ ID NO: 415,<br>SEQ ID NO: 416 |
| Nivolumab | SEQ ID NO: 409,<br>SEQ ID NO: 410,<br>SEQ ID NO: 403,<br>SEQ ID NO: 404 | SEQ ID NO: 409,<br>SEQ ID NO: 410,<br>SEQ ID NO: 407,<br>SEQ ID NO: 408 | SEQ ID NO: 409,<br>SEQ ID NO: 410,<br>SEQ ID NO: 411,<br>SEQ ID NO: 412 | SEQ ID NO: 409,<br>SEQ ID NO: 410,<br>SEQ ID NO: 415,<br>SEQ ID NO: 416 |
| Ofatumumab | SEQ ID NO: 413,<br>SEQ ID NO: 414,<br>SEQ ID NO: 403,<br>SEQ ID NO: 404 | SEQ ID NO: 413,<br>SEQ ID NO: 414,<br>SEQ ID NO: 407,<br>SEQ ID NO: 408 | SEQ ID NO: 413,<br>SEQ ID NO: 414,<br>SEQ ID NO: 411,<br>SEQ ID NO: 412 | SEQ ID NO: 413,<br>SEQ ID NO: 414,<br>SEQ ID NO: 415,<br>SEQ ID NO: 416 |
| m912 | SEQ ID NO: 417,<br>SEQ ID NO: 418,<br>SEQ ID NO: 403,<br>SEQ ID NO: 404 | SEQ ID NO: 417,<br>SEQ ID NO: 418,<br>SEQ ID NO: 407,<br>SEQ ID NO: 408 | SEQ ID NO: 417,<br>SEQ ID NO: 418,<br>SEQ ID NO: 411,<br>SEQ ID NO: 412 | SEQ ID NO: 417,<br>SEQ ID NO: 418,<br>SEQ ID NO: 415,<br>SEQ ID NO: 416 |

Nucleic Acids

The invention also features nucleic acids comprising nucleotide sequences that encode heavy and light chain variable regions and CDRs or hypervariable loops of the antibody molecules, as described herein. For example, the invention features a first and second nucleic acid encoding heavy and light chain variable regions, respectively, of an antibody molecule chosen from one or more of the antibody molecules disclosed herein. The nucleic acid can comprise a nucleotide sequence as set forth in the tables herein, or a sequence substantially identical thereto (e.g., a sequence at least about 85%, 90%, 95%, 99% or more identical thereto, or which differs by no more than 3, 6, 15, 30, or 45 nucleotides from the sequences shown in the tables herein.

In certain embodiments, the nucleic acid can comprise a nucleotide sequence encoding at least one, two, or three CDRs or hypervariable loops from a heavy chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In other embodiments, the nucleic acid can comprise a nucleotide sequence encoding at least one, two, or three CDRs or hypervariable loops from a light chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In yet another embodiment, the nucleic acid can comprise a nucleotide sequence encoding at least one, two, three, four, five, or six CDRs or hypervariable loops from heavy and light chain variable regions having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions).

In certain embodiments, the nucleic acid can comprise a nucleotide sequence encoding at least one, two, or three CDRs or hypervariable loops from a heavy chain variable region having the nucleotide sequence as set forth in the tables herein, a sequence substantially homologous thereto (e.g., a sequence at least about 85%, 90%, 95%, 99% or more identical thereto, and/or capable of hybridizing under the stringency conditions described herein). In another embodiment, the nucleic acid can comprise a nucleotide sequence encoding at least one, two, or three CDRs or hypervariable loops from a light chain variable region having the nucleotide sequence as set forth in the tables herein, or a sequence substantially homologous thereto (e.g., a sequence at least about 85%, 90%, 95%, 99% or more identical thereto, and/or capable of hybridizing under the stringency conditions described herein). In yet another embodiment, the nucleic acid can comprise a nucleotide sequence encoding at least one, two, three, four, five, or six CDRs or hypervariable loops from heavy and light chain variable regions having the nucleotide sequence as set forth in the tables herein, or a sequence substantially homologous thereto (e.g., a sequence at least about 85%, 90%, 95%, 99% or more identical thereto, and/or capable of hybridizing under the stringency conditions described herein).

In another aspect, the application features host cells and vectors containing the nucleic acids described herein. The nucleic acids may be present in a single vector or separate vectors present in the same host cell or separate host cell, as described in more detail hereinbelow.

Vectors

Further provided herein are vectors comprising the nucleotide sequences encoding an antibody molecule described herein. In one embodiment, the vectors comprise nucleotides encoding an antibody molecule described herein. In one embodiment, the vectors comprise the nucleotide sequences described herein. The vectors include, but are not limited to, a virus, plasmid, cosmid, lambda phage or a yeast artificial chromosome (YAC).

Numerous vector systems can be employed. For example, one class of vectors utilizes DNA elements which are derived from animal viruses such as, for example, bovine papilloma virus, polyoma virus, adenovirus, vaccinia virus, baculovirus, retroviruses (Rous Sarcoma Virus, MMTV or MOMLV) or SV40 virus. Another class of vectors utilizes RNA elements derived from RNA viruses such as Semliki Forest virus, Eastern Equine Encephalitis virus and Flaviviruses.

Additionally, cells which have stably integrated the DNA into their chromosomes may be selected by introducing one or more markers which allow for the selection of transfected host cells. The marker may provide, for example, prototropy to an auxotrophic host, biocide resistance (e.g., antibiotics), or resistance to heavy metals such as copper, or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals.

Once the expression vector or DNA sequence containing the constructs has been prepared for expression, the expression vectors may be transfected or introduced into an appropriate host cell. Various techniques may be employed to achieve this, such as, for example, protoplast fusion, calcium phosphate precipitation, electroporation, retroviral transduction, viral transfection, gene gun, lipid based transfection or other conventional techniques. In the case of protoplast fusion, the cells are grown in media and screened for the appropriate activity.

Methods and conditions for culturing the resulting transfected cells and for recovering the antibody molecule produced are known to those skilled in the art, and may be varied or optimized depending upon the specific expression vector and mammalian host cell employed, based upon the present description.

Cells

In another aspect, the application features host cells and vectors containing the nucleic acids described herein. The nucleic acids may be present in a single vector or separate vectors present in the same host cell or separate host cell. The host cell can be a eukaryotic cell, e.g., a mammalian cell, an insect cell, a yeast cell, or a prokaryotic cell, e.g., *E. coli*. For example, the mammalian cell can be a cultured cell or a cell line. Exemplary mammalian cells include lymphocytic cell lines (e.g., NSO), Chinese hamster ovary cells (CHO), COS cells, oocyte cells, and cells from a transgenic animal, e.g., mammary epithelial cell.

The invention also provides host cells comprising a nucleic acid encoding an antibody molecule as described herein.

In one embodiment, the host cells are genetically engineered to comprise nucleic acids encoding the antibody molecule.

In one embodiment, the host cells are genetically engineered by using an expression cassette. The phrase "expression cassette," refers to nucleotide sequences, which are capable of affecting expression of a gene in hosts compatible with such sequences. Such cassettes may include a promoter, an open reading frame with or without introns, and a termination signal. Additional factors necessary or helpful in effecting expression may also be used, such as, for example, an inducible promoter.

The invention also provides host cells comprising the vectors described herein.

The cell can be, but is not limited to, a eukaryotic cell, a bacterial cell, an insect cell, or a human cell. Suitable eukaryotic cells include, but are not limited to, Vero cells, HeLa cells, COS cells, CHO cells, HEK293 cells, BHK cells and MDCKII cells. Suitable insect cells include, but are not limited to, Sf9 cells.

Methods of Making the Multispecific Molecules

The multispecific antibody molecules can be produced by recombinant expression, e.g., of at least one or more component, in a host system. Exemplary host systems include eukaryotic cells (e.g., mammalian cells, e.g., CHO cells, or insect cells, e.g., SF9 or S2 cells) and prokaryotic cells (e.g., E. coli). In one embodiment, the host cell is a mammalian cell, a stable mammalian cell, e.g., a CHO cell. Bispecific antibody molecules can be produced by separate expression of the components in different host cells and subsequent purification/assembly. Alternatively, the antibody molecules can be produced by expression of the components in a single host cell. Purification of bispecific antibody molecules can be performed by various methods such as affinity chromatography, e.g., using protein A and sequential pH elution. In other embodiments, affinity tags can be used for purification, e.g., histidine-containing tag, myc tag, or streptavidin tag.

In some embodiments, a method for generating bispecific antibodies disclosed herein comprises: generating a human antibody with a light chain of a lambda subtype; generating a human antibody with a light chain of kappa subtype; transfecting cells with DNA of both antibody arms; purifying the antibody with Protein A resin; confirming the presence of both lambda and kappa light chains with KappaSelect and LambdaFabSelect resin; analyzing the correct lambda and kappa heavy and light chain pairing by cleaving Fab arms with papain and running mass spectrometry. Experimental conditions for making and testing the multispecific molecules are provided in the Examples below.

Uses and Combination Therapies

Methods described herein include treating a cancer in a subject by using a multispecific molecule described herein, e.g., using a pharmaceutical composition described herein. Also provided are methods for reducing or ameliorating a symptom of a cancer in a subject, as well as methods for inhibiting the growth of a cancer and/or killing one or more cancer cells. In embodiments, the methods described herein decrease the size of a tumor and/or decrease the number of cancer cells in a subject administered with a described herein or a pharmaceutical composition described herein.

In embodiments, the cancer is a hematological cancer. In embodiments, the hematological cancer is a leukemia or a lymphoma. As used herein, a "hematologic cancer" refers to a tumor of the hematopoietic or lymphoid tissues, e.g., a tumor that affects blood, bone marrow, or lymph nodes. Exemplary hematologic malignancies include, but are not limited to, leukemia (e.g., acute lymphoblastic leukemia (ALL), acute myeloid leukemia (AML), chronic lymphocytic leukemia (CLL), chronic myelogenous leukemia (CML), hairy cell leukemia, acute monocytic leukemia (AMoL), chronic myelomonocytic leukemia (CMML), juvenile myelomonocytic leukemia (JMML), or large granular lymphocytic leukemia), lymphoma (e.g., AIDS-related lymphoma, cutaneous T-cell lymphoma, Hodgkin lymphoma (e.g., classical Hodgkin lymphoma or nodular lymphocyte-predominant Hodgkin lymphoma), mycosis fungoides, non-Hodgkin lymphoma (e.g., B-cell non-Hodgkin lymphoma (e.g., Burkitt lymphoma, small lymphocytic lymphoma (CLL/SLL), diffuse large B-cell lymphoma, follicular lymphoma, immunoblastic large cell lymphoma, precursor B-lymphoblastic lymphoma, or mantle cell lymphoma) or T-cell non-Hodgkin lymphoma (mycosis fungoides, anaplastic large cell lymphoma, or precursor T-lymphoblastic lymphoma)), primary central nervous system lymphoma, Sézary syndrome, Waldenström macroglobulinemia), chronic myeloproliferative neoplasm, Langerhans cell histiocytosis, multiple myeloma/plasma cell neoplasm, myelodysplastic syndrome, or myelodysplastic/myeloproliferative neoplasm.

In embodiments, the cancer is a solid cancer. Exemplary solid cancers include, but are not limited to, ovarian cancer, rectal cancer, stomach cancer, testicular cancer, cancer of the anal region, uterine cancer, colon cancer, rectal cancer, renal-cell carcinoma, liver cancer, non-small cell carcinoma of the lung, cancer of the small intestine, cancer of the esophagus, melanoma, Kaposi's sarcoma, cancer of the endocrine system, cancer of the thyroid gland, cancer of the parathyroid gland, cancer of the adrenal gland, bone cancer, pancreatic cancer, skin cancer, cancer of the head or neck, cutaneous or intraocular malignant melanoma, uterine cancer, brain stem glioma, pituitary adenoma, epidermoid cancer, carcinoma of the cervix squamous cell cancer, carcinoma of the fallopian tubes, carcinoma of the endometrium, carcinoma of the vagina, sarcoma of soft tissue, cancer of the urethra, carcinoma of the vulva, cancer of the penis, cancer of the bladder, cancer of the kidney or ureter, carcinoma of the renal pelvis, spinal axis tumor, neoplasm of the central nervous system (CNS), primary CNS lymphoma, tumor angiogenesis, metastatic lesions of said cancers, or combinations thereof.

In embodiments, the multispecific molecules (or pharmaceutical composition) are administered in a manner appropriate to the disease to be treated or prevented. The quantity and frequency of administration will be determined by such factors as the condition of the patient, and the type and severity of the patient's disease. Appropriate dosages may be determined by clinical trials. For example, when "an effective amount" or "a therapeutic amount" is indicated, the precise amount of the pharmaceutical composition (or multispecific molecules) to be administered can be determined by a physician with consideration of individual differences in tumor size, extent of infection or metastasis, age, weight, and condition of the subject. In embodiments, the pharmaceutical composition described herein can be administered at a dosage of $10^4$ to $10^9$ cells/kg body weight, e.g., $10^5$ to $10^6$ cells/kg body weight, including all integer values within those ranges. In embodiments, the pharmaceutical composition described herein can be administered multiple times at these dosages. In embodiments, the pharmaceutical composition described herein can be administered using infusion techniques described in immunotherapy (see, e.g., Rosenberg et al., New Eng. J. of Med. 319:1676, 1988).

In embodiments, the multispecific molecules or pharmaceutical composition is administered to the subject parenterally. In embodiments, the cells are administered to the subject intravenously, subcutaneously, intratumorally, intranodally, intramuscularly, intradermally, or intraperitoneally. In embodiments, the cells are administered, e.g., injected, directly into a tumor or lymph node. In embodiments, the cells are administered as an infusion (e.g., as described in Rosenberg et al., New Eng. J. of Med. 319: 1676, 1988) or an intravenous push. In embodiments, the cells are administered as an injectable depot formulation. In embodiments, the subject is a mammal. In embodiments, the subject is a human, monkey, pig, dog, cat, cow, sheep, goat, rabbit, rat, or mouse. In embodiments, the subject is a human. In embodiments, the subject is a pediatric subject, e.g., less than 18 years of age, e.g., less than 17, 16, 15, 14, 13, 12, 11, 10, 9, 8, 7, 6, 5, 4, 3, 2, 1 or less years of age. In embodiments, the subject is an adult, e.g., at least 18 years of age, e.g., at least 19, 20, 21, 22, 23, 24, 25, 25-30, 30-35, 35-40, 40-50, 50-60, 60-70, 70-80, or 80-90 years of age.

Combination Therapies

The multispecific molecules disclosed herein can be used in combination with a second therapeutic agent or procedure.

In embodiments, the multispecific molecule and the second therapeutic agent or procedure are administered/performed after a subject has been diagnosed with a cancer, e.g., before the cancer has been eliminated from the subject. In embodiments, the multispecific molecule and the second therapeutic agent or procedure are administered/performed simultaneously or concurrently. For example, the delivery of one treatment is still occurring when the delivery of the second commences, e.g., there is an overlap in administration of the treatments. In other embodiments, the multispecific molecule and the second therapeutic agent or procedure are administered/performed sequentially. For example, the delivery of one treatment ceases before the delivery of the other treatment begins.

In embodiments, combination therapy can lead to more effective treatment than monotherapy with either agent alone. In embodiments, the combination of the first and second treatment is more effective (e.g., leads to a greater reduction in symptoms and/or cancer cells) than the first or second treatment alone. In embodiments, the combination therapy permits use of a lower dose of the first or the second treatment compared to the dose of the first or second treatment normally required to achieve similar effects when administered as a monotherapy. In embodiments, the combination therapy has a partially additive effect, wholly additive effect, or greater than additive effect.

In one embodiment, the multispecific molecule is administered in combination with a therapy, e.g., a cancer therapy (e.g., one or more of anti-cancer agents, immunotherapy, photodynamic therapy (PDT), surgery and/or radiation). The terms "chemotherapeutic," "chemotherapeutic agent," and "anti-cancer agent" are used interchangeably herein. The administration of the multispecific molecule and the therapy, e.g., the cancer therapy, can be sequential (with or without overlap) or simultaneous. Administration of the multispecific molecule can be continuous or intermittent during the course of therapy (e.g., cancer therapy). Certain therapies described herein can be used to treat cancers and non-cancerous diseases. For example, PDT efficacy can be enhanced in cancerous and non-cancerous conditions (e.g., tuberculosis) using the methods and compositions described herein (reviewed in, e.g., Agostinis, P. et al. (2011) *CA Cancer J. Clin.* 61:250-281).

Anti-Cancer Therapies

In other embodiments, the multispecific molecule is administered in combination with a low or small molecular weight chemotherapeutic agent. Exemplary low or small molecular weight chemotherapeutic agents include, but not limited to, 13-cis-retinoic acid (isotretinoin, ACCUTANE®), 2-CdA (2-chlorodeoxyadenosine, cladribine, LEUSTATIN™), 5-azacitidine (azacitidine, VIDAZA®), 5-fluorouracil (5-FU, fluorouracil, ADRUCIL®), 6-mercaptopurine (6-MP, mercaptopurine, PURINETHOL®), 6-TG (6-thioguanine, thioguanine, THIOGUANINE TABLOID®), abraxane (paclitaxel protein-bound), actinomycin-D (dactinomycin, COSMEGEN®), alitretinoin (PANRETIN®), all-transretinoic acid (ATRA, tretinoin, VESANOID®), altretamine (hexamethylmelamine, HMM, HEXALEN®), amethopterin (methotrexate, methotrexate sodium, MTX, TREXALL™, RHEUMATREX®), amifostine (ETHYOL®), arabinosylcytosine (Ara-C, cytarabine, CYTOSAR-U®), arsenic trioxide (TRISENOX®), asparaginase (Erwinia L-asparaginase, L-asparaginase, ELSPAR®, KIDROLASE®), BCNU (carmustine, BiCNU®), bendamustine (TREANDA®), bexarotene (TARGRETIN®), bleomycin (BLENOXANE®), busulfan (BUSULFEX®, MYLERAN®), calcium leucovorin (Citrovorum Factor, folinic acid, leucovorin), camptothecin-11 (CPT-11, irinotecan, CAMPTOSAR®), capecitabine (XELODA®), carboplatin (PARAPLATIN®), carmustine wafer (prolifeprospan 20 with carmustine implant, GLIADEL® wafer), CCI-779 (temsirolimus, TORISEL®), CCNU (lomustine, CeeNU), CDDP (cisplatin, PLATINOL®, PLATINOL-AQ®), chlorambucil (leukeran), cyclophosphamide (CYTOXAN®, NEOSAR®), dacarbazine (DIC, DTIC, imidazole carboxamide, DTIC-DOME®), daunomycin (daunorubicin, daunorubicin hydrochloride, rubidomycin hydrochloride, CERUBIDINE®), decitabine (DACOGEN®), dexrazoxane (ZINECARD®), DHAD (mitoxantrone, NOVANTRONE®), docetaxel (TAXOTERE®), doxorubicin (ADRIAMYCIN®, RUBEX®), epirubicin (ELLENCE™), estramustine (EMCYT®), etoposide (VP-16, etoposide phosphate, TOPOSAR®, VEPESID®, ETOPOPHOS®), floxuridine (FUDR®), fludarabine (FLUDARA®), fluorouracil (cream) (CARAC™, EFUDEX®, FLUOROPLEX®), gemcitabine (GEMZAR®), hydroxyurea (HYDREA®, DROXIA™, MYLOCEL™), idarubicin (IDAMYCIN®), ifosfamide (IFEX®), ixabepilone (IXEMPRA™), LCR (leurocristine, vincristine, VCR, ONCOVIN®, VINCASAR PFS®), L-PAM (L-sarcolysin, melphalan, phenylalanine mustard, ALKERAN®), mechlorethamine (mechlorethamine hydrochloride, mustine, nitrogen mustard, MUSTARGEN®), mesna (MESNEX™), mitomycin (mitomycin-C, MTC, MUTAMYCIN®), nelarabine (ARRANON®), oxaliplatin (ELOXATIN™), paclitaxel (TAXOL®, ONXAL™), pegaspargase (PEG-L-asparaginase, ONCOSPAR®), PEMETREXED (ALIMTA®), pentostatin (NIPENT®), procarbazine (MATULANE®), streptozocin (ZANOSAR®), temozolomide (TEMODAR®), teniposide (VM-26, VUMON®), TESPA (thiophosphoamide, thiotepa, TSPA, THIOPLEX®), topotecan (HYCAMTIN®), vinblastine (vinblastine sulfate, vincaleukoblastine, VLB, ALKABAN-AQ®, VELBAN®), vinorelbine (vinorelbine tartrate, NAVELBINE®), and vorinostat (ZOLINZA®).

In another embodiment, the multispecific molecule is administered in conjunction with a biologic. Biologics useful in the treatment of cancers are known in the art and a binding molecule of the invention may be administered, for example, in conjunction with such known biologics. For example, the FDA has approved the following biologics for the treatment of breast cancer: HERCEPTIN® (trastuzumab, Genentech Inc., South San Francisco, Calif.; a humanized monoclonal antibody that has anti-tumor activity in HER2-positive breast cancer); FASLODEX® (fulvestrant, AstraZeneca Pharmaceuticals, LP, Wilmington, Del.; an estrogen-receptor antagonist used to treat breast cancer); ARIMIDEX® (anastrozole, AstraZeneca Pharmaceuticals, LP; a nonsteroidal aromatase inhibitor which blocks aromatase, an enzyme needed to make estrogen); Aromasin® (exemestane, Pfizer Inc., New York, N.Y.; an irreversible, steroidal aromatase inactivator used in the treatment of breast cancer); FEMARA® (letrozole, Novartis Pharmaceuticals, East Hanover, N.J.; a nonsteroidal aromatase inhibitor approved by the FDA to treat breast cancer); and NOLVADEX® (tamoxifen, AstraZeneca Pharmaceuticals, LP; a nonsteroidal antiestrogen approved by the FDA to treat breast cancer). Other biologics with which the binding molecules of the invention may be combined include: AVASTIN® (bevacizumab, Genentech Inc.; the first FDA-approved therapy designed to inhibit angiogenesis); and ZEVALIN® (ibritumomab tiuxetan, Biogen Idec, Cambridge, Mass.; a radiolabeled monoclonal antibody currently approved for the treatment of B-cell lymphomas).

In addition, the FDA has approved the following biologics for the treatment of colorectal cancer: AVASTIN®; ERBITUX® (cetuximab, ImClone Systems Inc., New York, N.Y., and Bristol-Myers Squibb, New York, N.Y.; is a monoclonal antibody directed against the epidermal growth factor receptor (EGFR)); GLEEVEC® (imatinib mesylate; a protein kinase inhibitor); and ERGAMISOL® (levamisole hydrochloride, Janssen Pharmaceutica Products, LP, Titusville, N.J.; an immunomodulator approved by the FDA in 1990 as an adjuvant treatment in combination with 5-fluorouracil after surgical resection in patients with Dukes' Stage C colon cancer).

For the treatment of lung cancer, exemplary biologics include TARCEVA® (erlotinib HCL, OSI Pharmaceuticals Inc., Melville, N.Y.; a small molecule designed to target the human epidermal growth factor receptor 1 (HER1) pathway).

For the treatment of multiple myeloma, exemplary biologics include VELCADE® Velcade (bortezomib, Millennium Pharmaceuticals, Cambridge Mass.; a proteasome inhibitor). Additional biologics include THALIDOMID® (thalidomide, Clegene Corporation, Warren, N.J.; an immunomodulatory agent and appears to have multiple actions, including the ability to inhibit the growth and survival of myeloma cells and anti-angiogenesis).

Additional exemplary cancer therapeutic antibodies include, but are not limited to, 3F8, abagovomab, adecatumumab, afutuzumab, alacizumab pegol, alemtuzumab (CAMPATH®, MABCAMPATH®), altumomab pentetate (HYBRI-CEAKER®), anatumomab mafenatox, anrukinzumab (IMA-638), apolizumab, arcitumomab (CEA-SCAN®), bavituximab, bectumomab (LYMPHOSCAN®), belimumab (BENLYSTA®, LYMPHOSTAT-B®), besilesomab (SCINTIMUN®), bevacizumab (AVASTIN®), bivatuzumab mertansine, blinatumomab, brentuximab vedotin, cantuzumab mertansine, capromab pendetide (PROSTASCINT®), catumaxomab (REMOVAB®), CC49, cetuximab (C225, ERBITUX®), citatuzumab bogatox, cixutumumab, clivatuzumab tetraxetan, conatumumab, dacetuzumab, denosumab (PROLIA®), detumomab, ecromeximab, edrecolomab (PANOREX®), elotuzumab, epitumomab cituxetan, epratuzumab, ertumaxomab (REXOMUN®), etaracizumab, farletuzumab, figitumumab, fresolimumab, galiximab, gemtuzumab ozogamicin (MYLOTARG®), girentuximab, glembatumumab vedotin, ibritumomab (ibritumomab tiuxetan, ZEVALIN®), igovomab (INDIMACIS-125®), intetumumab, inotuzumab ozogamicin, ipilimumab, iratumumab, labetuzumab (CEA-CIDE®), lexatumumab, lintuzumab, lucatumumab, lumiliximab, mapatumumab, matuzumab, milatuzumab, minretumomab, mitumomab, nacolomab tafenatox, naptumomab estafenatox, necitumumab, nimotuzumab (THERACIM®, THERALOC®), nofetumomab merpentan (VERLUMA®), ofatumumab (ARZERRA®), olaratumab, oportuzumab monatox, oregovomab (OVAREX®), panitumumab (VECTIBIX®), pemtumomab (THERAGYN®), pertuzumab (OMNITARG®), pintumomab, pritumumab, ramucirumab, ranibizumab (LUCENTIS®), rilotumumab, rituximab (MABTHERA®, RITUXAN®), robatumumab, satumomab pendetide, sibrotuzumab, siltuximab, sontuzumab, tacatuzumab tetraxetan (AFP-CIDE®), taplitumomab paptox, tenatumomab, TGN1412, ticilimumab (tremelimumab), tigatuzumab, TNX-650, tositumomab (BEXXAR®), trastuzumab (HERCEPTIN®), tremelimumab, tucotuzumab celmoleukin, veltuzumab, volociximab, votumumab (HUMASPECT®), zalutumumab (HUMAX-EGFR®), and zanolimumab (HUMAX-CD4®).

In other embodiments, the multispecific molecule is administered in combination with a viral cancer therapeutic agent. Exemplary viral cancer therapeutic agents include, but not limited to, vaccinia virus (vvDD-CDSR), carcinoembryonic antigen-expressing measles virus, recombinant vaccinia virus (TK-deletion plus GM-CSF), Seneca Valley virus-001, Newcastle virus, coxsackie virus A21, GL-ONC1, EBNA1 C-terminal/LMP2 chimeric protein-expressing recombinant modified vaccinia Ankara vaccine, carcinoembryonic antigen-expressing measles virus, G207 oncolytic virus, modified vaccinia virus Ankara vaccine expressing p53, OncoVEX GM-CSF modified herpes-simplex 1 virus, fowlpox virus vaccine vector, recombinant vaccinia prostate-specific antigen vaccine, human papillomavirus 16/18 L1 virus-like particle/AS04 vaccine, MVA-EBNA1/LMP2 Inj. vaccine, quadrivalent HPV vaccine, quadrivalent human papillomavirus (types 6, 11, 16, 18) recombinant vaccine (GARDASIL®), recombinant fowlpox-CEA(6D)/TRICOM vaccine; recombinant vaccinia-CEA(6D)-TRICOM vaccine, recombinant modified vaccinia Ankara-5T4 vaccine, recombinant fowlpox-TRICOM vaccine, oncolytic herpes virus NV1020, HPV L1 VLP vaccine V504, human papillomavirus bivalent (types 16 and 18) vaccine (CERVARIX®), herpes simplex virus HF10, Ad5CMV-p53 gene, recombinant vaccinia DF3/MUC1 vaccine, recombinant vaccinia-MUC-1 vaccine, recombinant vaccinia-TRICOM vaccine, ALVAC MART-1 vaccine, replication-defective herpes simplex virus type I (HSV-1) vector expressing human Preproenkephalin (NP2), wild-type reovirus, reovirus type 3 Dearing (REOLYSIN®), oncolytic virus HSV1716, recombinant modified vaccinia Ankara (MVA)-based vaccine encoding Epstein-Barr virus target antigens, recombinant fowlpox-prostate specific antigen vaccine, recombinant vaccinia prostate-specific antigen vaccine, recombinant vaccinia-B7.1 vaccine, rAd-p53 gene, Ad5-delta24RGD, HPV vaccine 580299, JX-594 (thymidine kinase-deleted vaccinia virus plus GM-CSF), HPV-16/18 L1/AS04, fowlpox virus vaccine vector, vaccinia-tyrosinase vaccine, MEDI-517 HPV-16/18 VLP AS04 vaccine, adenoviral vector containing the thymidine kinase of herpes simplex virus TK99UN, HspE7, FP253/Fludarabine, ALVAC(2) melanoma multi-antigen therapeutic vaccine, ALVAC-hB7.1, canarypox-hIL-12 melanoma vaccine, Ad-REIC/Dkk-3, rAd-IFN SCH 721015, TIL-Ad-INFg, Ad-ISF35, and coxsackievirus A21 (CVA21, CAVATAK®).

In other embodiments, the multispecific molecule is administered in combination with a nanopharmaceutical. Exemplary cancer nanopharmaceuticals include, but not limited to, ABRAXANE® (paclitaxel bound albumin nanoparticles), CRLX101 (CPT conjugated to a linear cyclodextrin-based polymer), CRLX288 (conjugating docetaxel to the biodegradable polymer poly (lactic-co-glycolic acid)), cytarabine liposomal (liposomal Ara-C, DEPOCYT™), daunorubicin liposomal (DAUNOXOME®), doxorubicin liposomal (DOXIL®, CAELYX®), encapsulated-daunorubicin citrate liposome (DAUNOXOME®), and PEG anti-VEGF aptamer (MACUGEN®).

In some embodiments, the multispecific molecule is administered in combination with paclitaxel or a paclitaxel formulation, e.g., TAXOL®, protein-bound paclitaxel (e.g., ABRAXANE®). Exemplary paclitaxel formulations include, but are not limited to, nanoparticle albumin-bound paclitaxel (ABRAXANE®, marketed by Abraxis Bioscience), docosahexaenoic acid bound-paclitaxel (DHA-paclitaxel, Taxoprexin, marketed by Protarga), polyglutamate bound-paclitaxel (PG-paclitaxel, paclitaxel poliglumex, CT-2103, XYOTAX, marketed by Cell Therapeutic), the tumor-activated prodrug (TAP), ANG105 (Angiopep-2 bound to three molecules of paclitaxel, marketed by ImmunoGen), paclitaxel-EC-1 (paclitaxel bound to the erbB2-recognizing peptide EC-1; see Li et al., *Biopolymers* (2007) 87:225-230), and glucose-conjugated paclitaxel (e.g., 2'-paclitaxel methyl 2-glucopyranosyl succinate, see Liu et al., *Bioorganic & Medicinal Chemistry Letters* (2007) 17:617-620).

Exemplary RNAi and antisense RNA agents for treating cancer include, but not limited to, CALAA-01, siG12D LODER (Local Drug EluteR), and ALN-VSP02.

Other cancer therapeutic agents include, but not limited to, cytokines (e.g., aldesleukin (IL-2, Interleukin-2, PROLEUKIN®), alpha Interferon (IFN-alpha, Interferon alfa, INTRON® A (Interferon alfa-2b), ROFERON-A® (Interferon alfa-2a)), Epoetin alfa (PROCRIT®), filgrastim (G-CSF, Granulocyte—Colony Stimulating Factor, NEUPOGEN®), GM-CSF (Granulocyte Macrophage Colony Stimulating Factor, sargramostim, LEUKINE™), IL-11 (Interleukin-11, oprelvekin, NEUMEGA®), Interferon alfa-2b (PEG conjugate) (PEG interferon, PEG-INTRON™), and pegfilgrastim (NEULASTA™)), hormone therapy agents (e.g., aminoglutethimide (CYTADREN®), anastrozole (ARIMIDEX®), bicalutamide (CASODEX®), exemestane (AROMASIN®), fluoxymesterone (HALOTESTIN®), flutamide (EULEXIN®), fulvestrant (FASLODEX®), goserelin (ZOLADEX®), letrozole (FEMARA®), leuprolide (ELIGARD™, LUPRON®, LUPRON DEPOT®, VIADUR™), megestrol (megestrol acetate, MEGACE®), nilutamide (ANANDRON®, NILANDRON®), octreotide (octreotide acetate, SANDOSTATIN®, SANDOSTATIN LAR®), raloxifene (EVISTA®), romiplostim (NPLATE®), tamoxifen (NOVALDEX®), and toremifene (FARESTON®)), phospholipase A2 inhibitors (e.g., anagrelide (AGRYLIN®)), biologic response modifiers (e.g., BCG (THERACYS®, TICE®), and Darbepoetin alfa (ARANESP®)), target therapy agents (e.g., bortezomib (VELCADE®), dasatinib (SPRYCEL™), denileukin diftitox (ONTAK®), erlotinib (TARCEVA®), everolimus (AFINITOR®), gefitinib (IRESSA®), imatinib mesylate (STI-571, GLEEVEC™), lapatinib (TYKERB®), sorafenib (NEXAVAR®), and SU11248 (sunitinib, SUTENT®)), immunomodulatory and antiangiogenic agents (e.g., CC-5013 (lenalidomide, REVLIMID®), and thalidomide (THALOMID®)), glucocorticosteroids (e.g., cortisone (hydrocortisone, hydrocortisone sodium phosphate, hydrocortisone sodium succinate, ALA-CORT®, HYDROCORT ACETATE®, hydrocortone phosphate LANACORT®, SOLU-CORTEF®), decadron (dexamethasone, dexamethasone acetate, dexamethasone sodium phosphate, DEXASONE®, DIODEX®, HEXADROL®, MAXIDEX®), methylprednisolone (6-methylprednisolone, methylprednisolone acetate, methylprednisolone sodium succinate, DURALONE®, MEDRALONE®, MEDROL®, M-PREDNISOL®, SOLU-MEDROL®), prednisolone (DELTA-CORTEF®, ORAPRED®, PEDIAPRED®, PRELONE®), and prednisone (DELTASONE®, LIQUID PRED®, METI-CORTEN®, ORASONE®)), and bisphosphonates (e.g., pamidronate (AREDIA®), and zoledronic acid (ZOMETA®))

In some embodiments, the multispecific molecule is used in combination with a tyrosine kinase inhibitor (e.g., a receptor tyrosine kinase (RTK) inhibitor). Exemplary tyrosine kinase inhibitor include, but are not limited to, an epidermal growth factor (EGF) pathway inhibitor (e.g., an epidermal growth factor receptor (EGFR) inhibitor), a vascular endothelial growth factor (VEGF) pathway inhibitor (e.g., an antibody against VEGF, a VEGF trap, a vascular endothelial growth factor receptor (VEGFR) inhibitor (e.g., a VEGFR-1 inhibitor, a VEGFR-2 inhibitor, a VEGFR-3 inhibitor)), a platelet derived growth factor (PDGF) pathway inhibitor (e.g., a platelet derived growth factor receptor (PDGFR) inhibitor (e.g., a PDGFR-ß inhibitor)), a RAF-1 inhibitor, a KIT inhibitor and a RET inhibitor. In some embodiments, the anti-cancer agent used in combination with the AHCM agent is selected from the group consisting of: axitinib (AG013736), bosutinib (SKI-606), cediranib (RECENTIN™, AZD2171), dasatinib (SPRYCEL®, BMS-354825), erlotinib (TARCEVA®), gefitinib (IRESSA®)), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®)), panitumumab (VECTIBIX®), ranibizumab (Lucentis®), nilotinib (TASIGNA®), sorafenib (NEXAVAR®), alemtuzumab (CAMPATH®), gemtuzumab ozogamicin (MYLOTARG®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, XL228, AEE788, AG-490, AST-6, BMS-599626, CUDC-101, PD153035, pelitinib (EKB-569), vandetanib (zactima), WZ3146, WZ4002, WZ8040, ABT-869 (linifanib), AEE788, AP24534 (ponatinib), AV-951 (tivozanib), axitinib, BAY 73-4506 (regorafenib), brivanib alaninate (BMS-582664), brivanib (BMS-540215), cediranib (AZD2171), CHIR-258 (dovitinib), CP 673451, CYC116, E7080, Ki8751, masitinib (AB1010), MGCD-265, motesanib diphosphate (AMG-706), MP-470, OSI-930, Pazopanib Hydrochloride, PD173074, nSorafenib Tosylate (Bay 43-9006), SU 5402, TSU-68 (SU6668), vatalanib, XL880 (GSK1363089, EXEL-2880). Selected tyrosine kinase inhibitors are chosen from sunitinib, erlotinib, gefitinib, or sorafenib. In one embodiment, the tyrosine kinase inhibitor is sunitinib.

In one embodiment, the multispecific molecule is administered in combination with one of more of: an anti-angiogenic agent, or a vascular targeting agent or a vascular disrupting agent. Exemplary anti-angiogenic agents include, but are not limited to, VEGF inhibitors (e.g., anti-VEGF antibodies (e.g., bevacizumab); VEGF receptor inhibitors (e.g., itraconazole); inhibitors of cell proliferatin and/or migration of endothelial cells (e.g., carboxyamidotriazole, TNP-470); inhibitors of angiogenesis stimulators (e.g., suramin), among others. A vascular-targeting agent (VTA) or vascular disrupting agent (VDA) is designed to damage the vasculature (blood vessels) of cancer tumors causing central necrosis (reviewed in, e.g., Thorpe, P. E. (2004) *Clin.*

*Cancer Res.* Vol. 10:415-427). VTAs can be small-molecule. Exemplary small-molecule VTAs include, but are not limited to, microtubule destabilizing drugs (e.g., combretastatin A-4 disodium phosphate (CA4P), ZD6126, AVE8062, Oxi 4503); and vadimezan (ASA404).

Immune Checkpoint Inhibitors

In other embodiments, methods described herein comprise use of an immune checkpoint inhibitor in combination with the multispecific molecule. The methods can be used in a therapeutic protocol in vivo.

In embodiments, an immune checkpoint inhibitor inhibits a checkpoint molecule. Exemplary checkpoint molecules include but are not limited to CTLA4, PD1, PD-L1, PD-L2, TIM3, LAG3, CD160, 2B4, CD80, CD86, B7-H3 (CD276), B7-H4 (VTCN1), HVEM (TNFRSF14 or CD270), BTLA, KIR, MHC class I, MHC class II, GALS, VISTA, BTLA, TIGIT, LAIR1, and A2aR. See, e.g., Pardoll. Nat. Rev. Cancer 12.4(2012):252-64, incorporated herein by reference.

In embodiments, the immune checkpoint inhibitor is a PD-1 inhibitor, e.g., an anti-PD-1 antibody such as Nivolumab, Pembrolizumab or Pidilizumab. Nivolumab (also called MDX-1106, MDX-1106-04, ONO-4538, or BMS-936558) is a fully human IgG4 monoclonal antibody that specifically inhibits PD1. See, e.g., U.S. Pat. No. 8,008,449 and WO2006/121168. Pembrolizumab (also called Lambrolizumab, MK-3475, MK03475, SCH-900475 or KEYTRUDA®; Merck) is a humanized IgG4 monoclonal antibody that binds to PD-1. See, e.g., Hamid, O. et al. (2013) *New England Journal of Medicine* 369 (2): 134-44, U.S. Pat. No. 8,354,509 and WO2009/114335. Pidilizumab (also called CT-011 or Cure Tech) is a humanized IgG1k monoclonal antibody that binds to PD1. See, e.g., WO2009/101611. In one embodiment, the inhibitor of PD-1 is an antibody molecule having a sequence substantially identical or similar thereto, e.g., a sequence at least 85%, 90%, 95% identical or higher to the sequence of Nivolumab, Pembrolizumab or Pidilizumab. Additional anti-PD1 antibodies, e.g., AMP 514 (Amplimmune), are described, e.g., in U.S. Pat. No. 8,609,089, US 2010028330, and/or US 20120114649.

In some embodiments, the PD-1 inhibitor is an immunoadhesin, e.g., an immunoadhesin comprising an extracellular/PD-1 binding portion of a PD-1 ligand (e.g., PD-L1 or PD-L2) that is fused to a constant region (e.g., an Fc region of an immunoglobulin). In embodiments, the PD-1 inhibitor is AMP-224 (B7-DCIg, e.g., described in WO2011/066342 and WO2010/027827), a PD-L2 Fc fusion soluble receptor that blocks the interaction between B7-H1 and PD-1. In embodiments, the immune checkpoint inhibitor is a PD-L1 inhibitor, e.g., an antibody molecule. In some embodiments, the PD-L1 inhibitor is YW243.55.570, MPDL3280A, MEDI-4736, MSB-0010718C, or MDX-1105. In some embodiments, the anti-PD-L1 antibody is MSB0010718C (also called A09-246-2; Merck Serono), which is a monoclonal antibody that binds to PD-L1. Exemplary humanized anti-PD-L1 antibodies are described, e.g., in WO2013/079174. In one embodiment, the PD-L1 inhibitor is an anti-PD-L1 antibody, e.g., YW243.55.S70. The YW243.55.S70 antibody is described, e.g., in WO 2010/077634. In one embodiment, the PD-L1 inhibitor is MDX-1105 (also called BMS-936559), which is described, e.g., in WO2007/005874. In one embodiment, the PD-L1 inhibitor is MDPL3280A (Genentech/Roche), which is a human Fc-optimized IgG1 monoclonal antibody against PD-L1. See, e.g., U.S. Pat. No. 7,943,743 and U.S. Publication No.: 20120039906. In one embodiment, the inhibitor of PD-L1 is an antibody molecule having a sequence substantially identical or similar thereto, e.g., a sequence at least 85%, 90%, 95% identical or higher to the sequence of YW243.55.570, MPDL3280A, MEDI-4736, MSB-0010718C, or MDX-1105.

In embodiments, the immune checkpoint inhibitor is a PD-L2 inhibitor, e.g., AMP-224 (which is a PD-L2 Fc fusion soluble receptor that blocks the interaction between PD1 and B7-H1. See, e.g., WO2010/027827 and WO2011/066342.

In one embodiment, the immune checkpoint inhibitor is a LAG-3 inhibitor, e.g., an anti LAG-3 antibody molecule. In embodiments, the anti-LAG-3 antibody is BMS-986016 (also called BMS986016; Bristol-Myers Squibb). BMS-986016 and other humanized anti-LAG-3 antibodies are described, e.g., in US 2011/0150892, WO2010/019570, and WO2014/008218.

In embodiments, the immune checkpoint inhibitor is a TIM-3 inhibitor, e.g., anti-TIM3 antibody molecule, e.g., described in U.S. Pat. No. 8,552,156, WO 2011/155607, EP 2581113 and U.S. Publication No.: 2014/044728.

In embodiments, the immune checkpoint inhibitor is a CTLA-4 inhibitor, e.g., anti-CTLA-4 antibody molecule. Exemplary anti-CTLA4 antibodies include Tremelimumab (IgG2 monoclonal antibody from Pfizer, formerly known as ticilimumab, CP-675,206); and Ipilimumab (also called MDX-010, CAS No. 477202-00-9). Other exemplary anti-CTLA-4 antibodies are described, e.g., in U.S. Pat. No. 5,811,097.

EXAMPLES

The following examples are intended to be illustrative, and are not meant in any way to be limiting.

Methods

1. Construction of the Plasmids of NanoBiT Constructs.

The DNA encoding the protein sequences was optimized for expression in *Cricetulus griseus*, synthesized, and cloned into the pcDNA3.4-TOPO (Life Technologies A14697) using Gateway cloning. The nucleic acid sequences used are shown in Table 1.

TABLE 1

Nucleic acid sequences of ORFs.

| SEQ ID NO | Description | Nucleic Acid Sequence |
|---|---|---|
| SEQ ID NO: 1 | α-amyloid β heavy-LgBiT | ATGGAAACCGACACACTGCTGCTGTGGGTGCTGTTGTTGTGGGTGCCAGGAT CTACAGGACAGGTGCAGCTGGTTGAATCTGGTGGCGGAGTGGTGCAGCCTGG CAGATCTCTGAGACTGTCTTGTGCCGCCTCTGGCTTCGCCTTCTCTTCTTAC GGCATGCACTGGGTCCGACAGGCCCCTGGAAAAGGACTGGAATGGGTCGCCG TGATTTGGTTCGACGGCACCAAGAAGTACTACACCGACTCCGTGAAGGGCAG ATTCACCATCAGCCGGGACAACTCCAAGAACACCCTGTACCTGCAGATGAAT ACCCTGAGAGCCGAGGACACCGCCGTGTACTACTGTGCCAGAGATAGAGGCA TCGGCGCTCGGAGAGGCCCTTACTATATGGATGTGTGGGGCAAGGGCACCAC |

TABLE 1-continued

Nucleic acid sequences of ORFs.

| SEQ ID NO | Description | Nucleic Acid Sequence |
|---|---|---|
| | | CGTGACAGTGTCCTCTGCTTCTACCAAGGGACCCAGCGTTTTCCCTCTGGCT
CCATCCTCTAAGTCCACCTCTGGTGGAACCGCTGCTCTGGGCTGTCTGGTCA
AGGATTACTTCCCTGAGCCTGTGACCGTGTCCTGGAACTCTGGTGCTCTGAC
ATCCGGCGTGCACACCTTTCCAGCTGTGCTGCAGTCCTCTGGCCTGTACTCT
CTGTCCTCTGTCGTGACCGTGCCTTCTAGCTCTCTGGGCACCCAGACCTACA
TCTGCAACGTGAACCACAAGCCTTCCAACACCAAAGTGGACAAGAGAGTGGA
ACCCAAGTCCTGCGGATCTTCTGGCGGCGGAGGAAGCGGAGGCGGAGGATCT
AGCGGCGGAGTGTTCACCCTGGAAGATTTCGTCGGCGATTGGGAGCAGACCG
CCGCCTATAATCTGGACCAGGTTCTGGAACAAGGCGGCGTGTCCTCTCTGCT
GCAGAATCTGGCTGTGTCTGTGACCCCTATCCAGAGAATCGTGCGCTCTGGC
GAGAACGCCCTGAAGATCGACATCCACGTGATCATCCCTTACGAGGGCCTGT
CTGCCGATCAGATGGCTCAGATCGAAGAGGTGTTCAAGGTGGTGTACCCCGT
GGACGACCACCACTTCAAAGTGATCCTGCCTTACGGCACCCTGGTCATCGAT
GGCGTGACCCCAAACATGCTGAACTACTTCGGCAGACCCTACGAGGGAATCG
CCGTGTTCGATGGCAAGAAAATCACCGTGACCGGCACACTGTGGAACGGCAA
CAAGATCATCGACGAGCGGCTGATCACCCCTGACGGCTCTATGCTGTTCAGA
GTGACCATCAACTCCTAATGA |
| SEQ ID NO: 2 | α-amyloid β light-SmBiT | ATGGAAACCGACACACTGCTGCTGTGGGTGCTGTTGTTGTGGGTGCCAGGCT
CTACCGGCGACATCCAGATGACCCAGTCTCCATCCTCTCTGTCTGCCTCTGT
GGGCGACAGAGTGACCATCACCTGTAGAGCCAGCCAGTCCATCTCCTCCTAC
CTGAACTGGTATCAGCAGAAGCCTGGCAAGGCTCCCAAGCTGCTGATCTACG
CTGCTAGCTCTCTGCAGTCTGGCGTGCCCTCTAGATTTTCCGGCTCTGGCTC
TGGCACCGACTTCACCCTGACAATCAGTTCCCTGCAGCCTGAGGACTTCGCC
ACCTACTACTGCCAGCAGTCCTACAGCACACCCTTGACCTTTGGCGGAGGCA
CCAAGGTGGAAATCAAGAGAACCGTGGCCGCTCCTTCCGTGTTCATCTTCCC
ACCATCCGACGAACAGCTGAAGTCCGGCACAGCTTCTGTCGTGTGCCTGCTG
AACAACTTCTACCCTCGGGAAGCCAAGGTGCAGTGGAAGGTGGACAATGCCC
TGCAGTCCGGCAACTCCCAAGAGTCTGTGACCGAGCAGGACTCCAAGGACTC
TACCTACAGCCTGTCCTCCACACTGACCCTGTCTAAGGCCGACTACGAGAAG
CACAAGGTGTACGCCTGTGAAGTGACCCACCAGGGACTGTCTAGCCCCGTGA
CCAAGTCTTTCAACAGAGGCGAGTGCGGATCTTCTGGTGGCGGAGGAAGCGG
AGGCGGAGGATCATCTGGCGGAGTGACCGGCTACAGACTGTTCGAAGAGATC
CTGTAATGA |
| SEQ ID NO: 3 | α-amyloid β light | ATGGAAACCGACACACTGCTGCTGTGGGTGCTGTTGTTGTGGGTGCCAGGCT
CTACCGGCGACATCCAGATGACCCAGTCTCCATCCTCTCTGTCTGCCTCTGT
GGGCGACAGAGTGACCATCACCTGTAGAGCCAGCCAGTCCATCTCCTCCTAC
CTGAACTGGTATCAGCAGAAGCCTGGCAAGGCTCCCAAGCTGCTGATCTACG
CTGCTAGCTCTCTGCAGTCTGGCGTGCCCTCTAGATTTTCCGGCTCTGGCTC
TGGCACCGACTTCACCCTGACAATCAGTTCCCTGCAGCCTGAGGACTTCGCC
ACCTACTACTGCCAGCAGTCCTACAGCACACCCTTGACCTTTGGCGGAGGCA
CCAAGGTGGAAATCAAGAGAACCGTGGCCGCTCCTTCCGTGTTCATCTTCCC
ACCATCCGACGAACAGCTGAAGTCCGGCACAGCTTCTGTCGTGTGCCTGCTG
AACAACTTCTACCCTCGGGAAGCCAAGGTGCAGTGGAAGGTGGACAATGCCC
TGCAGTCCGGCAACTCCCAAGAGTCTGTGACCGAGCAGGACTCCAAGGACTC
TACCTACAGCCTGTCCTCCACACTGACCCTGTCTAAGGCCGACTACGAGAAG
CACAAGGTGTACGCCTGTGAAGTGACCCACCAGGGACTGTCTAGCCCCGTGA
CCAAGTCTTTCAACAGAGGCGAGTGCTAATGA |
| SEQ ID NO: 4 | α-Clostridium difficile toxin B heavy - LgBiT | ATGGAAACCGACACACTGCTGCTGTGGGTGCTGTTGTTGTGGGTGCCAGGAT
CTACAGGCGAAGTGCAGTTGGTGCAGTCTGGCGCCGAAGTGAAGAAGTCCGG
CGAGTCCCTGAAGATCTCCTGCAAAGGCTCCGGCTACTCCTTCACCTCTTAC
TGGATCGGCTGGGTCCGACAGATGCCTGGCAAAGGACTGGAATGGATGGGCA
TCTTCTACCCCGGCGACTCCTCTACCAGATACTCCCCTAGCTTTCAGGGCCA
AGTGACCATCTCCGCCGACAAGTCTGTGAACACCGCCTACTGCAGTGGTCC
TCTCTGAAGGCCTCTGACACCGCCATGTACTACTGCGCCAGAAGAAGAAACT
GGGGCAACGCCTTCGATATCTGGGGCCAGGGAACAATGGTCACCGTGTCCTC
TGCTTCCACCAAGGGACCTTCCGTGTTTCCTCTGGCTCCTTCCAGCAAGTCT
ACCTCTGGTGGAACCGCTGCTCTGGGCTGCCTGGTCAAGGATTACTTTCCTG
AGCCTGTGACCGTGTCTTGGAACTCTGGTGCTCTGACCTCCGGCGTGCACAC
ATTTCCAGCTGTGCTGCAGTCCTCCGGCCTGTACTCTCTGTCCTCTGTCGTG
ACCGTGCCTTCTAGCTCTCTGGGCACCCAGACCTACATCTGCAACGTGAACC
ACAAGCCTTCCAACACCAAGGTGGACAAGAGAGTGGAACCCAAGTCTTGCGG
ATCTTCCGGTGGCGGAGGATCTGGCGGAGGTGGAAGTAGTGGCGGAGTGTTC
ACCCTGGAAGATTTCGTCGGCGATTGGGAGCAGACCGCCGCCTATAATCTGG
ACCAGGTTCTGGAACAAGGCGGCGTCAGCTCTCTGCTGCAGAATCTGGCTGT
GTCTGTGACCCCTATCCAGAGAATCGTGCGCTCTGGCGAGAACGCTCTGAAG
ATCGACATCCACGTGATCATCCCTTACGAGGGCCTGTCTGCCGATCAGATGG
CTCAGATCGAAGAGGTGTTCAAGGTGGTGTACCCCGTGGACGACCACCACTT
CAAAGTGATCCTGCCTTACGGCACCCTGGTCATCGATGGCGTGACCCCAAAC
ATGCTGAACTACTTCGGCAGACCCTACGAGGGAATCGCCGTGTTCGACGGCA
AGAAAATCACCGTGACCGGCACACTGTGGAACGGCAACAAGATCATCGACGA
GCGGCTGATCACCCCTGACGGCTCTATGCTGTTCCGCGTGACCATCAACTCC
TAATGA |

TABLE 1-continued

Nucleic acid sequences of ORFs.

| SEQ ID NO | Description | Nucleic Acid Sequence |
|---|---|---|
| SEQ ID NO: 5 | α-Clostridium difficile toxin B light - SmBiT | ATGGAAACCGACACACTGCTGCTGTGGGTGCTGTTGTTGTGGGTGCCAGGAT<br>CTACAGGCGAGATCGTGCTGACCCAGTCTCCTGGCACATTGTCTCTGAGTCC<br>TGGCGAGAGAGCTACCCTGTCTTGCAGAGCTTCCCAGTCCGTGTCCTCTTCC<br>TACCTGGCCTGGTATCAGCAGAAGCCTGGACAGGCTCCCAGACTGCTGATCT<br>ACGGCGCCTCTTCTAGAGCCACAGGCATCCCTGACAGATTCTCCGGCTCTGG<br>CTCTGGCACCGACTTCACCCTGACCATCTCTAGACTGGAACCCGAGGACTTC<br>GCCGTGTACTACTGCCAGCAGTATGGCTCCTCTACCTGGACCTTTGGACAGG<br>GCACCAAGGTGGAAATCAAGAGAACCGTGGCCGCTCCTTCCGTGTTCATCTT<br>CCCACCATCTGACGAGCAGCTGAAGTCCGGCACAGCTTCTGTCGTGTGCCTG<br>CTGAACAACTTCTACCCTCGGGAAGCCAAGGTGCAGTGGAAGGTGGACAATG<br>CCCTGCAGTCCGGCAACTCCCAAGAGTCTGTGACCGAGCAGGACTCCAAGGA<br>CTCTACCTACAGCCTGTCCTCCACACTGACCCTGTCTAAGGCCGACTACGAG<br>AAGCACAAGGTGTACGCCTGTGAAGTGACCCACCAGGGACTGTCTAGCCCCG<br>TGACCAAGTCTTTCAACAGAGGCGAGTGCGGATCTTCTGGTGGCGGAGGATC<br>TGGCGGAGGCGGATCTAGTGGCGGAGTGACCGGCTACAGACTGTTCGAAGAG<br>ATCCTGTAATGA |
| SEQ ID NO: 6 | α-Clostridium difficile toxin B light | ATGGAAACCGACACACTGCTGCTGTGGGTGCTGTTGTTGTGGGTGCCAGGAT<br>CTACAGGCGAGATCGTGCTGACC TABLE 1-continued Nucleic acid sequences of ORFs.

| SEQ ID NO | Description | Nucleic Acid Sequence |
|---|---|---|
| SEQ ID NO: 9 | α-connective tissue growth factor light | ATGGAAACCGACACACTGCTGCTGTGGGTGCTGTTGTTGTGGGTGCCAGGCT<br>CTACCGGCGACATCCAGATGACCCAGTCTCCATCCTCTCTGTCTGCCTCTGT<br>GGGCGACAGAGTGACCATCACCTGTAGAGCCTCTCAGGGCATCTCTAGCTGG<br>CTGGCCTGGTATCAGCAGAAGCCTGAGAAGGCCCCTAAGAGCCTGATCTACG<br>CTGCCAGTTCTCTGCAGTCTGGCGTGCCCTCTAGATTCTCTGGCTCTGGATC<br>TGGCACCGACTTCACCCTGACAATCTCTAGCCTGCAGCCTGAGGACTTCGCC<br>ACCTACTACTGCCAGCAGTACAACAGCTACCCTCCTACCTTTGGCCAGGGCA<br>CCAAGCTGGAAATCAAGAGAACCGTGGCCGCTCCTTCCGTGTTCATCTTCCC<br>ACCATCTGACGAGCAGCTGAAGTCCGGCACAGCTTCTGTCGTGTGCCTGCTG<br>AACAACTTCTACCCTCGGGAAGCCAAGGTGCAGTGGAAGGTGGACAATGCCC<br>TGCAGTCCGGCAACTCCCAAGAGTCTGTGACCGAGCAGGACTCCAAGGACTC<br>TACCTACAGCCTGTCCTCCACACTGACCCTGTCTAAGGCCGACTACGAGAAG<br>CACAAGGTGTACGCCTGTGAAGTGACCCACCAGGGACTGTCTAGCCCCGTGA<br>CCAAGTCTTTCAACAGAGGCGAGTGCTAATGA |
| SEQ ID NO: 10 | α-CSF2 heavy - LgBiT | ATGGAAACCGACACACTGCTGCTGTGGGTGCTGTTGTTGTGGGTGCCAGGAT<br>CTACAGGACAGGTGCAGTTGGTGCAGTCTGGCGCCGAAGTGAAGAAACCTGG<br>CGCTTCTGTGAAGGTGTCCTGCAAGGCCTCTGGCTACTCCTTCACCAACTAC<br>TACATCCACTGGGTCCGACAGGCCCCTGGACAGAGATTGGAGTGGATGGGCT<br>GGATCAACGCCGGCAACGGCAACACCAAGTACTCCCAGAAATTCCAGGGCAG<br>AGTGACCATCACCAGAGACACCTCTGCCTCCACCGCCTACATGGAACTGTCC<br>AGCCTGAGATCTGAGGACACCGCCGTGTACTACTGCGTGCGGAGACAGCGGT<br>TCCCCTACTACTTTGATTATTGGGGCCAGGGCACCCTGGTCACCGTGTCCTC<br>TGCTTCTACAAAGGGCCCCTCTGTGTTCCCTCTGGCTCCTTCCTCTAAATCC<br>ACCTCTGGCGGAACAGCTGCTCTGGGCTGTCTGGTCAAGGACTACTTTCCTG<br>AGCCTGTGACCGTGTCTTGGAACTCTGGTGCTCTGACATCCGGCGTGCACAC<br>CTTTCCAGCTGTGCTGCAGTCCTCTGGCCTGTACTCTCTGTCCTCTGTCGTG<br>ACCGTGCCTTCTAGCTCTCTGGGCACCCAGACCTACATCTGCAACGTGAACC<br>ACAAGCCTTCTAACACCAAGGTGGACAAGAGAGTGGAACCCAAGTCTTGCGG<br>ATCTTCTGGTGGCGGAGGATCTGGCGGAGGCGGATCTAGTGGCGGAGTGTTC<br>ACCCTGGAAGATTTCGTCGGCGATTGGGAGCAGACCGCCGCCTATAATCTGG<br>ACCAGGTTCTGGAACAAGGCGGGGTGTCCTCTCTGCTGCAGAATCTGGCTGT<br>GTCTGTGACCCCTATCCAGAGAATCGTGCGCTCTGGCGAGAACGCCCTGAAG<br>ATCGACATCCACGTGATCATCCCTTACGAGGGCCTGTCTGCCGATCAGATGG<br>CTCAGATCGAAGAGGTGTTCAAGGTGGTGTACCCCGTGGACGACGCCACCAC<br>TTCAAAGTGATCCTGCCTTACGGCACCCTCGTGATCGATGGCGTGACCCCAAAC<br>ATGCTGAACTACTTCGGCAGACCCTACGAGGGAATCGCCGTGTTCGACGGCA<br>AGAAAATCACCGTGACCGGCACACTGTGGAACGGAAACAAGATCATCGACGA<br>GCGGCTGATCACCCCTGACGGCTCTATGCTGTTTAGAGTGACAATCAACTCC<br>TAATGA |
| SEQ ID NO: 11 | α-CSF2 light - SmBiT | ATGGAAACCGACACACTGCTGCTGTGGGTGCTGTTGTTGTGGGTGCCAGGAT<br>CTACAGGCGAGATCGTGCTGACCCAGTCTCCTGCCACATTGTCTGTGTCTCC<br>CGGCGAGAGAGCTACCCTGTCTTGTAGAGCTTCTCAGTCCGTGGGCACCAAC<br>GTGGCCTGGTATCAGCAGAAACCTGGACAGGCCCCTCGGGTGCTGATCTACT<br>CTACCTCTTCTAGAGCCACCGGCATCACCGACAGATTCTCTGGCTCTGGATC<br>TGGCACCGACTTCACCCTGACCATCTCCAGACTGGAACCTGAGGACTTCGCC<br>GTGTACTACTGCCAGCAGTTCAACAAGTCCCCTCTGACCTTTGGCGGAGGCA<br>CCAAGGTGGAAATCAAGAGAACCGTGGCCGCTCCTTCCGTGTTCATCTTCCC<br>ACCATCTGACGAGCAGCTGAAGTCCGGCACAGCTTCTGTCGTGTGCCTGCTG<br>AACAACTTCTACCCTCGGGAAGCCAAGGTGCAGTGGAAGGTGGACAATGCCC<br>TGCAGTCCGGCAACTCCCAAGAGTCTGTGACCGAGCAGGACTCCAAGGACTC<br>TACCTACAGCCTGTCCTCCACACTGACCCTGTCTAAGGCCGACTACGAGAAG<br>CACAAGGTGTACGCCTGTGAAGTGACCCACCAGGGACTGTCTAGCCCCGTGA<br>CCAAGTCTTTCAACAGAGGCGAGTGCGGATCTTCTGGTGGCGGAGGAAGCGG<br>AGGCGGAGGATCATCTGGCGGAGTGACCGGCTACAGACTGTTCGAAGAGATC<br>CTGTAATGA |
| SEQ ID NO: 12 | α-CSF2 light | ATGGAAACCGACACACTGCTGCTGTGGGTGCTGTTGTTGTGGGTGCCAGGAT<br>CTACAGGCGAGATCGTGCTGACCCAGTCTCCTGCCACATTGTCTGTGTCTCC<br>CGGCGAGAGAGCTACCCTGTCTTGTAGAGCTTCTCAGTCCGTGGGCACCAAC<br>GTGGCCTGGTATCAGCAGAAACCTGGACAGGCCCCTCGGGTGCTGATCTACT<br>CTACCTCTTCTAGAGCCACCGGCATCACCGACAGATTCTCTGGCTCTGGATC<br>TGGCACCGACTTCACCCTGACCATCTCCAGACTGGAACCTGAGGACTTCGCC<br>GTGTACTACTGCCAGCAGTTCAACAAGTCCCCTCTGACCTTTGGCGGAGGCA<br>CCAAGGTGGAAATCAAGAGAACCGTGGCCGCTCCTTCCGTGTTCATCTTCCC<br>ACCATCTGACGAGCAGCTGAAGTCCGGCACAGCTTCTGTCGTGTGCCTGCTG<br>AACAACTTCTACCCTCGGGAAGCCAAGGTGCAGTGGAAGGTGGACAATGCCC<br>TGCAGTCCGGCAACTCCCAAGAGTCTGTGACCGAGCAGGACTCCAAGGACTC<br>TACCTACAGCCTGTCCTCCACACTGACCCTGTCTAAGGCCGACTACGAGAAG<br>CACAAGGTGTACGCCTGTGAAGTGACCCACCAGGGACTGTCTAGCCCCGTGA<br>CCAAGTCTTTCAACAGAGGCGAGTGCTAATGA |

TABLE 1-continued

Nucleic acid sequences of ORFs.

| SEQ ID NO | Description | Nucleic Acid Sequence |
|---|---|---|
| SEQ ID NO: 13 | α-CTLA4 heavy - LgBiT | ATGGAAACCGACACACTGCTGCTGTGGGTGCTGCTCTTGTGGGTGCCAGGAT<br>CTACAGGACAGGTGCAGCTGGTGGAATCTGGTGGCGGAGTTGTGCAGCCTGG<br>CAGATCCCTGAGACTGTCTTGTGCCGCCTCCGGCTTCACCTTCTCCAGCTAC<br>ACCATGCACTGGGTCCGACAGGCCCCTGGCAAAGGATTGGAGTGGGTCACCT<br>TCATCTCTTACGACGGCAACAACAAGTACTACGCCGACTCCGTGAAGGGCAG<br>ATTCACCATCTCTCGGGACAACTCCAAGAACACCCTGTACCTGCAGATGAAC<br>TCCCTGAGAGCCGAGGACACCGCCATCTACTACTGTGCTAGAACCGGCTGGC<br>TGGGCCCCTTTGATTATTGGGACAGGGCACCCTGGTCACCGTGTCCTCTGC<br>TTCTACCAAGGGACCCAGCGTGTTCCCTCTGGCTCCTTCCAGCAAGTCTACC<br>TCTGGCGGAACAGCTGCTCTGGGCTGCCTGGTCAAGGACTACTTTCCTGAGC<br>CTGTGACCGTGTCTTGGAACTCTGGCGCTCTGACATCCGGCGTGCACACATT<br>TCCAGCTGTGCTGCAGTCCTCCGGCCTGTACTCTCTGTCCTCTGTCGTGACC<br>GTGCCTTCCAGCTCTCTGGGAACCCAGACCTACATCTGCAATGTGAACCACA<br>AGCCTTCCAACACCAAGGTGGACAAGAGAGTGGAACCCAAGTCCTGCGGATC<br>TTCTGGCGGCGGAGGATCTGGCGGAGGTGGTAGTTCAGGCGGAGTGTTCACC<br>CTGGAAGATTTCGTCGGCGACTGGGAGCAGACCGCCGCCTATAATCTGGACC<br>AGGTGCTGGAACAAGGCGGCGTTAGTTCCCTGCTGCAGAACCTGGCTGTGTC<br>TGTGACCCCTATCCAGAGAATCGTGCGGAGCGGCGAGAACGCCCTGAAGATC<br>GATATCCACGTGATCATCCCTTACGAGGGCCTGAGCGCCGATCAGATGGCTC<br>AGATCGAAGAGGTGTTCAAGGTGGTGTACCCCGTGGACGACCACCACTTCAA<br>AGTGATCCTGCCTTACGGCACCCTCGTGATCGATGGCGTGACCCCAAACATG<br>CTGAACTACTTCGGCAGACCCTACGAGGGAATCGCCGTGTTCGACGGCAAGA<br>AAATCACCGTGACCGGCACACTGTGGAATGGCAACAAGATCATCGACGAGCG<br>GCTGATCACCCCTGACGGCTCCATGCTGTTCAGAGTGACCATCAACAGCTGA<br>TGA |
| SEQ ID NO: 14 | α-CTLA4 light - SmBiT | ATGGAAACCGACACACTGCTGCTGTGGGTGCTGTTGTTGTGGGTGCCAGGAT<br>CTACAGGCGAGATCGTCTGCTGACCCAGTCTCCTGGCACACTGTCTCTGAGTCC<br>TGGCGAGAGAGCTACCCTGTCTTGCAGAGCTTCCCAGTCCGTGGGATCTTCC<br>TACCTGGCCTGGTATCAGCAGAAGCCTGGACAGGCTCCCAGACTGCTGATCT<br>ACGGCGCCTTTTCTAGAGCCACAGGCATCCCTGACAGATTCTCCGGCTCTGG<br>CTCTGGCACCGACTTCACCCTGACCATCTCTAGACTGGAACCCGAGGACTTC<br>GCCGTGTACTACTGCCAGCAGTATGGCTCCTCTCCTTGGACCTTTGGACAGG<br>GCACCAAGGTGGAAATCAAGAGAACCGTGGCCGCTCCTTCCGTGTTCATCTT<br>CCCACCATCTGACGAGCAGCTGAAGTCCGGCACAGCTTCTGTCGTGTGCCTG<br>CTGAACAACTTCTACCCTCGGGAAGCCAAGGTGCAGTGGAAGGTGGACAATG<br>CCCTGCAGTCCGGCAACTCCCAAGAGTCTGTGACCGAGCAGGACTCCAAGGA<br>CTCTACCTACAGCCTGTCCTCCACACTGACCCTGTCTAAGGCCGACTACGAG<br>AAGCACAAGGTGTACGCCTGTGAAGTGACCCACCAGGGACTGTCTAGCCCCG<br>TGACCAAGTCTTTCAACAGAGGCGAGTGCGGATCTTCTGGTGGCGGAGGATC<br>TGGCGGAGGCGGATCTAGTGGCGGAGTGACCGGCTACAGACTGTTCGAAGAG<br>ATCCTGTAATGA |
| SEQ ID NO: 15 | α-CTLA4 light | ATGGAAACCGACACACTGCTGCTGTGGGTGCTGCTCTTGTGGGTGCCAGGAT<br>CTACAGGCGAGATCGTCTGCTGACCCAGTCTCCTGGCACACTGTCTCACTGTCC<br>AGGCGAGAGAGCTACCCTGTCCTGTAGAGCCTCTCAGTCCGTGGGCTCCTCT<br>TACCTGGCTTGGTATCAGCAGAAGCCCGGCCAGGCTCCTAGACTGTTGATCT<br>ACGGCGCCTTCTCCAGAGCCACAGGCATCCCTGATAGATTCTCCGGCTCTGG<br>CTCTGGCACCGACTTCACCCTGACCATCTCCAGACTGGAACCCGAGGACTTC<br>GCCGTGTACTACTGTCAGCAGTACGGCTCCTCTCCTTGGACCTTTGGCCAGG<br>GCACCAAGGTGGAAATCAAGCGGACAGTGGCCGCTCCTTCCGTGTTCATCTT<br>CCCACCTTCCGACGAGCAGCTGAAGTCCGGCACAGCTTCTGTCGTGTGCCTG<br>CTGAACAACTTCTACCCTCGGGAAGCCAAGGTGCAGTGGAAGGTGGACAATG<br>CCCTGCAGTCCGGCAACTCCCAAGAGTCTGTGACCGAGCAGGACTCCAAGGA<br>CAGCACCTACAGCCTGTCCTCCACACTGACCCTGTCCAAGGCCGACTACGAG<br>AAGCACAAGGTGTACGCCTGCGAAGTGACCCATCAGGGCCTGTCTAGCCCTG<br>TGACCAAGTCTTTCAACCGGGGCGAGTGCTGATGA |
| SEQ ID NO: 16 | α-IFN heavy - LgBiT | ATGGAAACCGACACACTGCTGCTGTGGGTGCTGTTGTTGTGGGTGCCAGGAT<br>CTACAGGCGAAGTGCAGTTGGTGCAGTCTGGCGCCGAAGTGAAGAAGCCTGG<br>CGAGTCCCTGAAGATCTCCTGCAAAGGCTCCGGCTACATCTTCACCAACTAC<br>TGGATCGCCTGGGTCCGACAGATGCCTGGCAAAGGCCTGGAATGCATGGCA<br>TCATCTACCCCGGCGACTCCGACATCAGATACAGCCCATCTTTCCAGGGCCA<br>AGTGACCATCTCCGCCGACAAGTCTATCACCACCGCCTACCTGCAGTGGTCC<br>TCTCTGAAGGCCTCTGACACCGCCATGTACTACTGCGCCAGACACGACATCG<br>AGGGCTTCGATTATTGGGGCAGAGGCACCCTGGTCACCGTGTCCTCTGCTTC<br>TACAAAGGGCCCCTCTGTGTTCCCTCTGGCTCCTTCCTCTAAATCCACCTCT<br>GGCGGAACCGCTGCTCTGGGCTGTCTGGTCAAGGATTACTTCCCTGAGCCTG<br>TGACCGTGTCTTGGAACTCTGGTGCTCTGACATCCGGCGTGCACACCTTTCC<br>AGCTGTGCTGCAGTCCTCTGGCCTGTACTCTCTGTCCTCTGTCGTGACCGTG<br>CCTTCCAGCTCTCTGGGCACCCAGACCTACATCTGCAACGTGAACCACAAGC<br>CTTCCAACACCAAGGTGGACAAGAGAGTGGAACCCAAGTCTTGCGGATCTTC<br>TGGTGGCGGAGGATCTGGCGGAGGCGGATCTAGTGGCGGAGTGTTCACCCTG<br>GAAGATTTCGTCGGCGATTGGGAGCAGACCGCCGCCTATAATCTGGACCAGG<br>TTCTGGAACAAGGCGGCGTCAGCTCTCTGCTGCAGAATCTGGCTGTGTCTGT |

TABLE 1-continued

Nucleic acid sequences of ORFs.

| SEQ ID NO | Description | Nucleic Acid Sequence |
|---|---|---|
| | | GACCCCTATCCAGAGAATCGTGCGCTCTGGCGAGAACGCTCTGAAGATCGAC<br>ATCCACGTGATCATCCCTTACGAGGGCCTGTCTGCCGATCAGATGGCTCAGA<br>TCGAAGAGGTGTTCAAGGTGGTGTACCCCGTGGACGACCACCACTTCAAAGT<br>GATCCTGCCTTACGGCACCCTCGTGATCGATGGCGTGACCCCAAACATGCTG<br>AACTACTTCGGCAGACCCTACGAGGGAATCGCCGTGTTCGACGGCAAGAAAA<br>TCACCGTGACCGGCACACTGTGGAACGGCAACAAGATCATCGACGAGCGGCT<br>GATCACCCCTGACGGCTCTATGCTGTTCCGCGTGACCATCAACTCCTAATGA |
| SEQ ID NO: 17 | α-IFN light - SmBiT | ATGGAAACCGACACACTGCTGCTGTGGGTGCTGTTGTTGTGGGTGCCAGGAT<br>CTACAGGCGAGATCGTGCTGACCCAGTCTCCTGGCACATTGTCTCTGAGTCC<br>TGGCGAGAGAGCTACCCTGTCTTGCAGAGCTTCCCAGTCCGTGTCCTCTAGC<br>TTCTTCGCCTGGTATCAGCAGAAGCCCGGACAGGCTCCTAGACTGCTGATCT<br>CGGCGCCTCTTCTAGAGCCACAGGCATCCCTGATAGACTGTCCGGCTCTGG<br>CTCTGGCACCGACTTTACCCTGACCATCACCAGACTGGAACCCGAGGACTTC<br>GCCGTGTACTACTGCCAGCAGTACGACTCCTCTGCCATCACCTTTGGCCAGG<br>GCACAAGACTGGAAATCAAGAGAACCGTGGCCGCTCCTTCCGTGTTCATCTT<br>CCCACCATCTGACGAGCAGCTGAAGTCCGGCACAGCTTCTGTCGTGTGCCTG<br>CTGAACAACTTCTACCCTCGGGAAGCCAAGGTGCAGTGGAAGGTGGACAATG<br>CCCTGCAGTCCGGCAACTCCCAAGAGTCTGTGACCGAGCAGGACTCCAAGGA<br>CTCTACCTACAGCCTGTCCTCCACACTGACCCTGTCTAAGGCCGACTACGAG<br>AAGCACAAGGTGTACGCCTGTGAAGTGACCCACCAGGGACTGTCTAGCCCCG<br>TGACCAAGTCTTTCAACAGAGGCGAGTGCGGATCTTCTGGTGGCGGAGGATC<br>TGGCGGAGGCGGATCTAGTGGCGGAGTGACCGGCTACAGACTGTTCGAAGAG<br>ATCCTGTAATGA |
| SEQ ID NO: 18 | α-IFN light | ATGGAAACCGACACACTGCTGCTGTGGGTGCTGTTGTTGTGGGTGCCAGGAT<br>CTACAGGCGAGATCGTGCTGACCCAGTCTCCTGGCACATTGTCTCTGAGTCC<br>TGGCGAGAGAGCTACCCTGTCTTGCAGAGCTTCCCAGTCCGTGTCCTCTAGC<br>TTCTTCGCCTGGTATCAGCAGAAGCCCGGACAGGCTCCTAGACTGCTGATCT<br>ACGGCGCCTCTTCTAGAGCCACAGGCATCCCTGATAGACTGTCCGGCTCTGG<br>CTCTGGCACCGACTTTACCCTGACCATCACCAGACTGGAACCCGAGGACTTC<br>GCCGTGTACTACTGCCAGCAGTACGACTCCTCTGCCATCACCTTTGGCCAGG<br>GCACAAGACTGGAAATCAAGAGAACCGTGGCCGCTCCTTCCGTGTTCATCTT<br>CCCACCATCTGACGAGCAGCTGAAGTCCGGCACAGCTTCTGTCGTGTGCCTG<br>CTGAACAACTTCTACCCTCGGGAAGCCAAGGTGCAGTGGAAGGTGGACAATG<br>CCCTGCAGTCCGGCAACTCCCAAGAGTCTGTGACCGAGCAGGACTCCAAGGA<br>CTCTACCTACAGCCTGTCCTCCACACTGACCCTGTCTAAGGCCGACTACGAG<br>AAGCACAAGGTGTACGCCTGTGAAGTGACCCACCAGGGACTGTCTAGCCCCG<br>TGACCAAGTCTTTCAACAGAGGCGAGTGCTAATGA |
| SEQ ID NO: 19 | α-IFNα heavy - LgBiT | ATGGAAACCGACACACTGCTGCTGTGGGTGCTGTTGTTGTGGGTGCCAGGAT<br>CTACAGGACAGGTGCAGTTGGTGCAGTCTGGCGCCGAAGTGAAGAAACCTGG<br>CGCTTCTGTGAAGGTGTCCTGCAAGGCCTCTGGCTACACCTTTACCAGCTAC<br>TCCATCTCCTGGGTCCGACAGGCTCCTGGACAAGGATTGGAGTGGATGGGCT<br>GGATCTCCGTGTACAACGGCAACACCAACTACGCCCAGAAATTCCAGGGCAG<br>AGTGACCATGACCACCGACACCTCTACCTCCACCGCCTACCTGGAACTGAGA<br>TCCCTGAGATCTGACGACACCGCCGTGTACTACTGCGCCAGAGATCCTATCG<br>CTGCTGGCTATTGGGGACAGGGCACACTGGTTACCGTGTCCTCTGCTTCTAC<br>CAAGGGACCCTCTGTGTTCCCTCTGGCTCCTTCCAGCAAGTCTACCTCTGGT<br>GGAACCGCTGCTCTGGGCTGTCTGGTCAAGGATTACTTCCCTGAGCCTGTGA<br>CCGTGTCTTGGAACTCTGGTGCTCTGACCTCCGGCGTGCACACATTTCCAGC<br>TGTGCTGCAGTCCTCCGGCCTGTACTCTCTGTCCTCTGTCGTGACCGTGCCT<br>TCTAGCTCTCTGGGCACCCAGACCTACATCTGCAACGTGAACCACAAGCCTT<br>CCAACACCAAGGTGGACAAGAGAGTGGAACCCAAGTCTTGCGGGATCTTCTGG<br>TGGCGGAGGATCTGGCGGAGGTGGAAGTAGTGGCGGAGTGTTCACCCTGGAA<br>GATTTCGTCGGCGATTGGGAGCAGACCGCCGCCTATAATCTGGACCAGGTTC<br>TGGAACAAGGCGGCGTCAGCTCTCTGCTGCAGAATCTGGCTGTGTCTGTGAC<br>CCCTATCCAGAGAATTGTGCGCTCTGGCGAGAACGCCCTGAAGATCGACATC<br>CACGTGATCATCCCTTACGAGGGCCTGTCTGCCGATCAGATGGCTCAGATCG<br>AAGAGGTGTTCAAGGTGGTGTACCCCGTGGACGACCACCACTTCAAAGTGAT<br>CCTGCCTTACGGCACCCTGGTCATCGATGGCGTGACCCCAAACATGCTGAAC<br>TACTTCGGCAGACCCTACGAGGGAATCGCCGTGTTCGACGGCAAGAAAATCA<br>CCGTGACCGGCACACTGTGGAACGGAAACAAGATCATCGACGAGCGGCTGAT<br>CACCCCTGACGGCTCTATGCTGTTCCGCGTGACCATCAACTCCTAATGA |
| SEQ ID NO: 20 | α-IFNα light - SmBiT | ATGGAAACCGACACACTGCTGCTGTGGGTGCTGTTGTTGTGGGTGCCAGGAT<br>CTACAGGCGAGATCGTGCTGACCCAGTCTCCTGGCACATTGTCTCTGAGTCC<br>TGGCGAGAGAGCTACCCTGTCTTGCAGAGCTTCCCAGTCCGTGTCCTCTACC<br>TACTGGCCTGGTATCAGCAGAAGCCTGGACAGGCTCCCAGACTGCTGATCT<br>ACGGCGCCTCTTCTAGAGCCACAGGCATCCCTGACAGATTCTCCGGCTCTGG<br>CTCTGGCACCGACTTCACCCTGACCATCTCTAGACTGGAACCCGAGGACTTC<br>GCCGTGTACTACTGCCAGCAGTATGGCTCCTCTCCTCGGACCTTTGGACAGG<br>GCACCAAGGTGGAAATCAAGAGAACCGTGGCCGCTCCTTCCGTGTTCATCTT<br>CCCACCATCTGACGAGCAGCTGAAGTCCGGCACAGCTTCTGTCGTGTGCCTG<br>CTGAACAACTTCTACCCTCGGGAAGCCAAGGTGCAGTGGAAGGTGGACAATG |

TABLE 1-continued

Nucleic acid sequences of ORFs.

| SEQ ID NO | Description | Nucleic Acid Sequence |
|---|---|---|
| | | CCCTGCAGTCCGGCAACTCCCAAGAGTCTGTGACCGAGCAGGACTCCAAGGA<br>CTCTACCTACAGCCTGTCCTCCACACTGACCCTGTCTAAGGCCGACTACGAG<br>AAGCACAAGGTGTACGCCTGTGAAGTGACCCACCAGGGACTGTCTAGCCCG<br>TGACCAAGTCTTTCAACAGAGGCGAGTGCGGATCTTCTGGTGGCGGAGGATC<br>TGGCGGAGGCGGATCTAGTGGCGGAGTGACCGGCTACAGACTGTTCGAAGAG<br>ATCCTGTAATGA |
| SEQ ID NO: 21 | α-IFNα light | ATGGAAACCGACACACTGCTGCTGTGGGTGCTGTTGTTGTGGGTGCCAGGAT<br>CTACAGGCGAGATCGTGCTGACCCAGTCTCCTGGCACATTGTCTCTGAGTCC<br>TGGCGAGAGAGCTACCCTGTCTTGCAGAGCTTCCCAGTCCGTGTCCTCTACC<br>TACCTGGCCTGGTATCAGCAGAAGCCTGGACAGGCTCCCAGACTGCTGATCT<br>ACGGCGCCTCTTCTAGAGCCACAGGCATCCCTGACAGATTCTCCGGCTCTGG<br>CTCTGGCACCGACTTCACCCTGACCATCTCTAGACTGGAACCCGAGGACTTC<br>GCCGTGTACTACTGCCAGCAGTATGGCTCCTCTCCTCGGACCTTTGGACAGG<br>GCACCAAGGTGGAAATCAAGAGAACCGTGGCCGCTCCTTCCGTGTTCATCTT<br>CCCACCATCTGACGAGCAGCTGAAGTCCGGCACAGCTTCTGTCGTGTGCCTG<br>CTGAACAACTTCTACCCTCGGGAAGCCAAGGTGCAGTGGAAGGTGGACAATG<br>CCCTGCAGTCCGGCAACTCCCAAGAGTCTGTGACCGAGCAGGACTCCAAGGA<br>CTCTACCTACAGCCTGTCCTCCACACTGACCCTGTCTAAGGCCGACTACGAG<br>AAGCACAAGGTGTACGCCTGTGAAGTGACCCACCAGGGACTGTCTAGCCCCG<br>TGACCAAGTCTTTCAACAGAGGCGAGTGCTAATGA |
| SEQ ID NO: 22 | α-IGF1R heavy - LgBiT | ATGGAAACCGACACACTGCTGCTGTGGGTGCTGTTGTTGTGGGTGCCAGGAT<br>CTACAGGCCAGGTCCAGCTGCAAGAATCTGGCCCTGGACTGGTCAAGCCTTC<br>TGGCACCCTGTCTCTGACATGTGCTGTGTCCGGCGGCTCCATCTCCTCCTCT<br>AATTGGTGGTCTTGGGTCCGACAGCCTCCTGGCAAAGGACTGGAATGGATCG<br>GCGAGATCTACCACTCCGGCTCCACCAACTACAACCCCAGCCTGAAGTCCAG<br>AGTGACCATCTCCGTGGACAAGTCCAAGAACCAGTTCTCCCTGAAGCTGTCC<br>TCTGTGACCGCTGCCGATACCGCCGTGTACTACTGTGCTAGATGGACCGGCA<br>GAACCGACGCCTTTGATATCTGGGGCCAGGGCACAATGGTCACCGTGTCCTC<br>TGCTTCTACCAAGGGACCCTCTGTGTTCCCTCTGGCTCCTTCCAGCAAGTCT<br>ACCTCTGGTGGAACCGCTGCTCTGGGCTGCCTGGTCAAGGATTACTTTCCTG<br>AGCCTGTGACCGTGTCTTGGAACTCTGGTGCTCTGACCTCCGGCGTGCACAC<br>ATTTCCAGCTGTGCTGCAGTCTAGCGGCCTGTACTCTCTGTCTAGCGTCGTG<br>ACCGTGCCTTCTAGCTCTCTGGGCACCCAGACCTACATCTGCAACGTGAACC<br>ACAAGCCTTCCAACACCAAGGTGGACAAGAGAGTGGAACCCAAGTCTTGCGG<br>ATCTTCTGGTGGCGGAGGATCTGGCGGAGGTGGAAGTAGTGGCGGAGTGTTC<br>ACCCTGGAAGATTTCGTCGGCGATTGGGAGCAGACCGCCGCCTATAATCTGG<br>ACCAGGTTCTGGAACAAGGCGGCGTCAGCTCTCTGCTGCAGAATCTCGCTGT<br>GTCTGTGACCCCTATCCAGAGAATCGTGCGCTCTGGCGAGAACGCCCTGAAG<br>ATCGACATCCACGTGATCATCCCTTACGAGGGCCTGTCTGCCGATCAGATGG<br>CTCAGATCGAAGAGGTGTTCAAGGTGGTGTACCCCGTGGACGACCACCACTT<br>CAAAGTGATCCTGCCTTACGGCACCCTGGTCATCGATGGCGTGACCCCAAAC<br>ATGCTGAACTACTTCGGCAGACCCTACGAGGGAATCGCCGTGTTCGACGGCA<br>AGAAAATCACCGTGACCGGCACACTGTGGAACGGCAACAAGATCATCGACGA<br>GCGGCTGATCACCCCTGACGGCTCTATGCTGTTCCGCGTGACCATCAACTCC<br>TAATGA |
| SEQ ID NO: 23 | α-IGF1R light - SmBiT | ATGGAAACCGACACACTGCTGCTGTGGGTGCTGTTGTTGTGGGTGCCAGGAT<br>CTACAGGCGACGTCGTGATGACCCAGTCTCCTCGTCTCTGCCTGTGACACC<br>TGGCGAGCCTGCCTCCATCTCTTGCAGATCTTCTCAGTCCCTGCTGCACTCC<br>AACGGCTACAACTACCTGGACTGGTATCTGCAGAAGCCCGGCCAGTCTCCAC<br>AGCTGCTGATCTACCTGGGCTCTAACAGAGCCTCTGGCGTGCCCGATAGATT<br>CTCTGGCTCTGGATCTGGCACCGACTTCACCCTGAAGATCTCCAGAGTGGAA<br>GCCGAGGACGTGGGCGTGTACTACTGTATGCAGGGCACCCACTGGCCTCTGA<br>CCTTTGGACAGGGCACCAAGGTGGAAATCAAGAGAACCGTGGCCGCTCCTTC<br>CGTGTTCATCTTCCCACCATCTGACGAGCAGCTGAAGTCCGGCACAGCTTCT<br>GTCGTGTGCCTGCTGAACAACTTCTACCCTCGGGAAGCCAAGGTGCAGTGGA<br>AGGTGGACAATGCCCTGCAGTCCGGCAACTCCCAAGAGTCTGTGACCGAGCA<br>GGACTCCAAGGACTCTACCTACAGCCTGTCCTCCACACTGACCCTGTCTAAG<br>GCCGACTACGAGAAGCACAAGGTGTACGCCTGTGAAGTGACCCACCAGGGAC<br>TGTCTAGCCCCGTGACCAAGTCTTTCAACAGAGGCGAGTGCGGATCTTCTGG<br>TGGCGGAGGATCTGGCGGAGGTGGAAGTAGTGGCGGCGTGACCGGCTACAGA<br>CTGTTCGAAGAGATCCTGTAATGA |
| SEQ ID NO: 24 | α-IGF1R light | ATGGAAACCGACACACTGCTGCTGTGGGTGCTGTTGTTGTGGGTGCCAGGAT<br>CTACAGGCGACGTCGTGATGACCCAGTCTCCTCGTCTCTGCCTGTGACACC<br>TGGCGAGCCTGCCTCCATCTCTTGCAGATCTTCTCAGTCCCTGCTGCACTCC<br>AACGGCTACAACTACCTGGACTGGTATCTGCAGAAGCCCGGCCAGTCTCCAC<br>AGCTGCTGATCTACCTGGGCTCTAACAGAGCCTCTGGCGTGCCCGATAGATT<br>CTCTGGCTCTGGATCTGGCACCGACTTCACCCTGAAGATCTCCCAGAGTGGAA<br>GCCGAGGACGTGGGCGTGTACTACTGTATGCAGGGCACCCACTGGCCTCTGA<br>CCTTTGGACAGGGCACCAAGGTGGAAATCAAGAGAACCGTGGCCGCTCCTTC<br>CGTGTTCATCTTCCCACCATCTGACGAGCAGCTGAAGTCCGGCACAGCTTCT<br>GTCGTGTGCCTGCTGAACAACTTCTACCCTCGGGAAGCCAAGGTGCAGTGGA |

TABLE 1-continued

Nucleic acid sequences of ORFs.

| SEQ ID NO | Description | Nucleic Acid Sequence |
|---|---|---|
| | | AGGTGGACAATGCCCTGCAGTCCGGCAACTCCCAAGAGTCTGTGACCGAGCA<br>GGACTCCAAGGACTCTACCTACAGCCTGTCCTCCACACTGACCCTGTCTAAG<br>GCCGACTACGAGAAGCACAAGGTGTACGCCTGTGAAGTGACCCACCAGGGAC<br>TGTCTAGCCCCGTGACCAAGTCTTTCAACAGAGGCGAGTGCTAATGA |
| SEQ ID NO: 25 | α-IGF1R heavy - LgBiT | ATGGAAACCGACACACTGCTGCTGTGGGTGCTGTTGTTGTGGGTGCCAGGAT<br>CTACAGGCGAAGTGCAGTTGTTGCAGTCTGGCGGAGGATTGGTTCAGCCTGG<br>CGGATCTCTGAGACTGTCTTGTGCCGCCTCCGGCTTCATGTTCAGCAGATAC<br>CCTATGCACTGGGTCCGACAGGCCCCTGGAAAAGGACTGGAATGGGTCGGAT<br>CTATCTCTGGCAGTGGCGGCGCTACCCCTTACGCTGATTCTGTGAAGGGCAG<br>ATTCACCATCAGCCGGGACAACTCCAAGAACACCCTGTACCTGCAGATGAAC<br>TCCCTGAGAGCCGAGGACACCGCCGTGTACTACTGCGCCAAGGACTTCTATC<br>AGATCCTGACCGGCAACGCCTTCGATTATTGGGGCCAGGGCACAACCGTGAC<br>CGTGTCCTCTGCTTCTACCAAGGGACCCTCTGTGTTCCCTCTGGCTCCTTCC<br>AGCAAGTCTACCTCTGGTGGAACCGCTGCTCTGGGCTGCCTGGTCAAGGATT<br>ACTTTCCTGAGCCTGTGACAGTGTCCTGGAACTCTGGTGCTCTGACCTCCGG<br>CGTGCACACATTTCCAGCTGTGCTGCAGTCCTCCGGCCTGTACTCTCTGTCC<br>TCTGTCGTGACAGTGCCTTCCAGCTCTCTGGGCACCCAGACCTACATCTGCA<br>ACGTGAACCACAAGCCTTCCAACACCAAGGTGGACAAGAGAGTGGAACCCAA<br>GTCTTGCGGATCTTCTGGTGGCGGTGGAAGTGGCGGAGGTGGAAGTTCAGGC<br>GGAGTGTTCACCCTGGAAGATTTCGTCGGCGATTGGGAGCAGACCGCCGCCT<br>ATAATCTGGACCAGGTTCTGGAACAAGGCGGCGTTAGCTCTCTGCTGCAGAA<br>TCTGGCTGTGTCTGTGACCCCTATCCAGAGAATCGTGCGCTCTGGCGAGAAC<br>GCCCTGAAGATCGACATCCACGTGATCATCCCTTACGAGGGCCTGTCTGCCG<br>ATCAGATGGCTCAGATCGAAGAGGTGTTCAAGGTGGTGTACCCCGTGGACGA<br>CCACCACTTCAAAGTGATCCTGCCTTACGGCACCCTGGTCATCGATGGCGTG<br>ACCCCAAACATGCTGAACTACTTCGGCAGACCCTACGAGGGAATCGCCGTGT<br>TCGACGGCAAGAAAATCACCGTGACAGGCACCCTGTGGAACGGCAACAAGAT<br>CATCGACGAGCGGCTGATCACCCCTGACGGCTCTATGCTGTTCAGAGTGACC<br>ATCAACTCCTAATGA |
| SEQ ID NO: 26 | α-IGF1R light - SmBiT | ATGGAAACCGACACACTGCTGCTGTGGGTGCTGTTGTTGTGGGTGCCAGGCT<br>CTACCGGCGACATCCAGATGACCCAGTCTCCAAGCTCTCTGTCTGCCTCTCT<br>GGGCGACAGAGTGACCATCACCTGTAGAGCCTCTCAGGGCATCTCCTCCTAC<br>CTGGCCTGGTATCAGCAGAAGCCTGGCAAGGCTCCCAAGCTGCTGATCTACG<br>CTAAGTCTACCCTGCAGTCCGGCGTGCCCTCTAGATTTTCTGGCTCTGGATC<br>TGGCACCGACTTCACCCTGACCATCAGTTCTCTGCAGCCTGAGGACTCCGCC<br>ACCTACTACTGTCAGCAGTACTGGACCTTTCCTCTGACCTTCGGCGGAGGCA<br>CCAAGGTGGAAATCAAGCGAACCGTGGCCGCTCCTTCCGTGTTCATCTTCCC<br>ACCATCTGACGAGCAGCTGAAGTCCGGCACAGCTTCTGTCGTGTGCCTGCTG<br>AACAACTTCTACCCTCGGGAAGCCAAGGTGCAGTGGAAGGTGGACAATGCTC<br>TGCAGAGCGGCAACTCCCAAGAGTCTGTGACCGAGCAGGACTCCAAGGACTC<br>TACCTACAGCCTGTCCTCCACACTGACCCTGTCTAAGGCCGACTACGAGAAG<br>CACAAGGTGTACGCCTGTGAAGTGACCCACCAGGGACTGTCTAGCCCCGTGA<br>CCAAGTCTTTCAACAGAGGCGAGTGCGGATCTTCTGGCGGCGGAGGAAGCGG<br>AGGCGGAGGATCTAGCGGCGGAGTTACCGGCTACAGACTGTTCGAAGAGATC<br>CTGTAATGA |
| SEQ ID NO: 27 | α-IGF1R light | ATGGAAACCGACACACTGCTGCTGTGGGTGCTGCTCTTGTGGGTGCCAGGAT<br>CTACCGGCGACATCCAGATGACCCAGTCTCCATCCTCTCTGTCTGCCAGCCT<br>GGGCGACAGAGTGACCATCACCTGTAGAGCCTCTCAGGGCATCTCCTCCTAC<br>CTGGCCTGGTATCAGCAGAAGCCTGGCAAGGCTCCCAAGCTGCTGATCTACG<br>CCAAGAGCACACTGCAGTCTGGCGTGCCCTCTAGATTCTCCGGCTCTGGCTC<br>TGGCACCGACTTTACCCTGACAATCTCCAGCCTGCAGCCTGAGGACTCCGCC<br>ACCTACTACTGTCAGCAGTACTGGACCTTTCCACTGACCTTCGGCGGAGGCA<br>CCAAGGTGGAAATCAAGCGAACCGTGGCCGCTCCTTCCGTGTTCATCTTCCC<br>ACCTTCCGACGAGCAGCTGAAGTCCGGCACAGCTTCTGTCGTGTGCCTGCTG<br>AACAACTTCTACCCTCGGGAAGCCAAAGTGCAGTGGAAGGTGGACAACGCTC<br>TGCAGTCCGGCAACTCCCAAGAGTCTGTGACCGAGCAGGACTCCAAGGACAG<br>CACCTACAGCCTGTCCTCCACACTGACCCTGTCAAGGCCGACTACGAGAAG<br>CACAAGGTGTACGCCTGCGAAGTGACCCATCAGGGCCTGTCTAGCCCCTGTGA<br>CCAAGTCTTTCAACCGGGGCGAGTGCTGATGA |
| SEQ ID NO: 28 | α-IGF1R heavy - LgBiT | ATGGAAACCGACACACTGCTGCTGTGGGTGCTGTTGTTGTGGGTGCCAGGAT<br>CTACAGGCGAAGTGCAGTTGGTTCAGTCTGGCGGAGGACTGGTTAAGCCTGG<br>CGGATCTCTGAGACTGTCTTGTGCCGCCTCTGGCTTCACCTTCTCTAGCTTT<br>GCCATGCACTGGGTCCGACAGGCCCCTGGAAAAGGCCTGGAATGGATCTCCG<br>TGATCGATACCAGAGGCGCCACCTACTACGCCGACTCTGTGAAGGGCAGATT<br>CACCATCTCTCGGGACAACGCCAAGAACTCCCTGTACCTGCAGATGAACAGC<br>CTGAGAGCCGAGGACACCGCCGTGTACTATTGTGCCAGACTGGGCAACTTCT<br>ACTACGGCATGGATGTGTGGGGCCAGGGCACAACAGTGACCGTGTCCTCTGC<br>TTCTACCAAGGGACCCTCTGTGTTCCCTCTGGCTCCTTCCAGCAAGTCTACC<br>TCTGGTGGAACCGCTGCTCTGGGCTGCCTGGTCAAGGATTACTTTCCTGAGC<br>CTGTGACAGTGTCCTGGAACTCTGGTGCTCTGACCTCCGGCGTGCACACATT<br>TCCAGCTGTGCTGCAGTCCTCTGGCCTGTACTCTCTGTCCTCTGTCGTGACC |

TABLE 1-continued

Nucleic acid sequences of ORFs.

| SEQ ID NO | Description | Nucleic Acid Sequence |
|---|---|---|
| | | GTGCCTTCTAGCTCTCTGGGCACCCAGACCTACATCTGCAACGTGAACCACA<br>AGCCTTCCAACACCAAGGTGGACAAGAGAGTGGAACCCAAGTCTTGCGGATC<br>TTCTGGTGGCGGTGGAAGCGGAGGCGGAGGATCTAGTGGCGGAGTGTTCACC<br>CTGGAAGATTTCGTCGGCGATTGGGAGCAGACCGCCGCCTATAATCTGGACC<br>AGGTTCTGAACAAGGCGGCGTCAGCTCTCTGCTGCAGAATCTGGCTGTGTC<br>TGTGACCCCTATCCAGAGAATCGTGCGCTCTGGCGAGAACGCCCTGAAGATC<br>GACATCCACGTGATCATCCCTTACGAGGGCCTGTCTGCCGATCAGATGGCTC<br>AGATCGAAGAGGTGTTCAAGGTGGTGTACCCCGTGGACGACCACCACTTCAA<br>AGTGATCCTGCCTTACGGCACCCTGGTCATCGATGGCGTGACCCCAAACATG<br>CTGAACTACTTCGGCAGACCCTACGAGGGAATCGCCGTGTTCGACGGCAAGA<br>AAATCACCGTGACCGGCACACTGTGGAACGGCAACAAGATCATCGACGAGCG<br>GCTGATCACCCCTGACGGCTCCATGCTGTTTAGAGTGACCATCAACTCCTAA<br>TGA |
| SEQ ID NO: 29 | α-IGF1R light - SmBiT | ATGGAAACCGACACACTGCTGCTGTGGGTGCTGTTGTTGTGGGTGCCAGGAT<br>CTACAGGCGAGATCGTGCTGACCCAGTCTCCTGGCACATTGTCTGTGTCTCC<br>CGGCGAGAGAGCTACCCTGTCTTGTAGAGCTTCCCAGTCCATCGGCTCCAGC<br>CTGCACTGGTATCAGCAGAAACCTGGACAGGCCCCTCGGCTGCTGATTAAGT<br>ACGCCTCTCAGTCCCTGTCTGGCATCCCTGACAGATTCTCTGGCTCTGGCTC<br>CGGCACCGACTTCACCCTGACAATCTCTAGACTGGAACCCGAGGACTTCGCC<br>GTGTACTACTGCCACCAGTCTAGCAGACTGCCTCACACCTTTGGCCAGGGCA<br>CCAAGGTGGAAATCAAGAGAACCGTGGCCGCTCCTTCCGTGTTCATCTTCCC<br>ACCATCTGACGAGCAGCTGAAGTCTGGCACCGCTTCTGTCGTGTGCCTGCTG<br>AACAACTTCTACCCTCGGGAAGCCAAGGTGCAGTGGAAGGTGGACAATGCCC<br>TGCAGTCCGGCAACTCCCAAGAGTCTGTGACCGAGCAGGACTCCAAGGACTC<br>TACCTACAGCCTGTCCTCCACACTGACCCTGTCTAAGGCCGACTACGAGAAG<br>CACAAGGTGTACGCCTGTGAAGTGACCCACCAGGGACTGTCTAGCCCCGTGA<br>CCAAGTCTTTCAACAGAGGCGAGTGCGGATCTTCTGGTGGCGGAGGATCTGG<br>CGGAGGTGGAAGTAGTGGCGGCGTGACCGGCTACAGACTGTTCGAAGAGATC<br>CTGTAATGA |
| SEQ ID NO: 30 | α-IGF1R light | ATGGAAACCGACACACTGCTGCTGTGGGTGCTGTTGTTGTGGGTGCCAGGAT<br>CTACAGGCGAGATCGTGCTGACCCAGTCTCCTGGCACATTGTCTGTGTCTCC<br>CGGCGAGAGAGCTACCCTGTCTTGTAGAGCTTCCCAGTCCATCGGCTCCAGC<br>CTGCACTGGTATCAGCAGAAACCTGGACAGGCCCCTCGGCTGCTGATTAAGT<br>ACGCCTCTCAGTCCCTGTCTGGCATCCCTGACAGATTCTCTGGCTCTGGCTC<br>CGGCACCGACTTCACCCTGACAATCTCTAGACTGGAACCCGAGGACTTCGCC<br>GTGTACTACTGCCACCAGTCTAGCAGACTGCCTCACACCTTTGGCCAGGGCA<br>CCAAGGTGGAAATCAAGAGAACCGTGGCCGCTCCTTCCGTGTTCATCTTCCC<br>ACCATCTGACGAGCAGCTGAAGTCTGGCACCGCTTCTGTCGTGTGCCTGCTG<br>AACAACTTCTACCCTCGGGAAGCCAAGGTGCAGTGGAAGGTGGACAATGCCC<br>TGCAGTCCGGCAACTCCCAAGAGTCTGTGACCGAGCAGGACTCCAAGGACTC<br>TACCTACAGCCTGTCCTCCACACTGACCCTGTCTAAGGCCGACTACGAGAAG<br>CACAAGGTGTACGCCTGTGAAGTGACCCACCAGGGACTGTCTAGCCCCGTGA<br>CCAAGTCTTTCAACAGAGGCGAGTGCTAATGA |
| SEQ ID NO: 31 | α-IGF1R heavy - LgBiT | ATGGAAACCGACACACTGCTGCTGTGGGTGCTGTTGTTGTGGGTGCCAGGAT<br>CTACCGGACAGGTGGAACTGGTTGAATCTGGTGGCGGAGTGGTGCAGCCTGG<br>CAGATCTCAGAGACTGTCTTGTGCCGCCTCTGGCTTCACCTTCTCCTCTTAC<br>GGCATGCACTGGGTCCGACAGGCCCCTGGAAAAGGACTGGAATGGGTCGCCA<br>TCATTTGGTTCGACGGCTCCTCTACCTACTACGCCGATTCTGTGCGGGGCAG<br>ATTCACCATCTCTCGGGACAACTCCAAGAACACCCTGTACCTGCAGATGAAC<br>TCCCTGAGAGCCGAGGATACCGCCGTGTACTTCTGTGCCAGAGAGCTGGGGA<br>GAAGATACTTCGATCTGTGGGGCAGAGGCACCCTGGTGTCTGTGTCCTCTGC<br>TTCTACCAAGGGACCCAGCGTTTTCCCTCTGGCTCCATCCTCTAAGTCCACC<br>TCTGGTGGAACCGCTGCTCTGGGCTGTCTGGTCAAGGATTACTTCCCTGAGC<br>CTGTGACCGTGTCCTGGAACTCTGGTGCTCTGACATCCGGCGTGCACACCTT<br>TCCAGCTGTGCTGCAGTCCTCTGGCCTGTACTCTCTGTCCTCTGTCGTGACC<br>GTGCCTTCTTCTAGCTCTGGGCACCCAGACCTACATCTGCAACGTGAACCACA<br>AGCCTTCCAACACCAAAGTGGACAAGAGAGTGGAACCCAAGTCTTGCGGATC<br>TTCTGGCGGCGGAGGAAGCGGAGGCGGAGGATCTAGCGGCGGAGTGTTCACC<br>CTGGAAGATTTCGTCGGCGATTGGGAGCAGACCGCCGCCTATAATCTGGACC<br>AGGTTCTGAACAAGGCGGCGTGTCCTCTCTGCTGCAGAATCTGGCTGTGTC<br>TGTGACCCCTATCCAGAGAATCGTGCGCTCTGGCGAGAACGCCCTGAAGATC<br>GACATCCACGTGATCATCCCTTACGAGGGCCTGTCTGCCGATCAGATGGCCC<br>AGATTGAAGAGGTGTTCAAGGTGGTGTACCCCGTGGACGACCACCACTTCAA<br>AGTGATCCTGCCTTACGGCACCCTCGTGATCGATGGCGTGACCCCAAACATG<br>CTGAACTACTTCGGCAGACCCTACGAGGGAATCGCCGTGTTCGATGGCAAGA<br>AAATCACCGTGACCGGCACACTGTGGAACGGCAACAAGATCATCGACGAGCG<br>GCTGATCACCCCTGACGGCTCCTATGCTGTTCAGAGTGACCATCAACTCCTAA<br>TGA |

TABLE 1-continued

Nucleic acid sequences of ORFs.

| SEQ ID NO | Description | Nucleic Acid Sequence |
|---|---|---|
| SEQ ID NO: 32 | α-IGF1R light - SmBiT | ATGGAAACCGACACACTGCTGCTGTGGGTGCTGTTGTTGTGGGTGCCAGGAT<br>CTACAGGCGAGATCGTGCTGACCCAGTCTCCTGCCACATTGTCTCTGAGTCC<br>TGGCGAGAGAGCTACCCTGTCTTGCAGAGCTTCCCAGTCCGTGTCCTCCTAC<br>CTGGCCTGGTATCAGCAGAAACCTGGACAGGCCCCTCGGCTGCTGATCTACG<br>ATGCTTCTAAGAGAGCCACAGGCATCCCCGCCAGATTTTCTGGCTCTGGATC<br>TGGCACCGACTTCACCCTGACCATCTCTAGCCTGGAACCTGAGGACTTCGCC<br>GTGTACTACTGCCAGCAGAGATCCAAGTGGCCTCCTTGGACCTTTGGACAGG<br>GCACCAAGGTGGAATCTAAGAGAACCGTGGCCGCTCCTTCCGTGTTCATCTT<br>CCCACCATCTGACGAGCAGCTGAAGTCCGGCACAGCTTCTGTCGTGTGCCTG<br>CTGAACAACTTCTACCCTCGGGAAGCCAAGGTGCAGTGGAAGGTGGACAATG<br>CCCTGCAGTCCGGCAACTCCCAAGAGTCTGTGACCGAGCAGGACTCCAAGGA<br>CTCTACCTACAGCCTGTCCTCCACACTGACCCTGTCTAAGGCCGACTACGAG<br>AAGCACAAGGTGTACGCCTGTGAAGTGACCCACCAGGGACTGTCTAGCCCCG<br>TGACCAAGTCTTTCAACAGAGGCGAGTGCGGATCTTCTGGTGGCGGAGGATC<br>TGGCGGAGGCGGATCTAGTGGCGGAGTGACCGGCTACAGACTGTTCGAAGAG<br>ATCCTGTAATGA |
| SEQ ID NO: 33 | α-IGF1R light | ATGGAAACCGACACACTGCTGCTGTGGGTGCTGTTGTTGTGGGTGCCAGGAT<br>CTACAGGCGAGATCGTGCTGACCCAGTCTCCTGCCACATTGTCTCTGAGTCC<br>TGGCGAGAGAGCTACCCTGTCTTGCAGAGCTTCCCAGTCCGTGTCCTCCTAC<br>CTGGCCTGGTATCAGCAGAAACCTGGACAGGCCCCTCGGCTGCTGATCTACG<br>ATGCTTCTAAGAGAGCCACAGGCATCCCCGCCAGATTTTCTGGCTCTGGATC<br>TGGCACCGACTTCACCCTGACCATCTCTAGCCTGGAACCTGAGGACTTCGCC<br>GTGTACTACTGCCAGCAGAGATCCAAGTGGCCTCCTTGGACCTTTGGACAGG<br>GCACCAAGGTGGAATCTAAGAGAACCGTGGCCGCTCCTTCCGTGTTCATCTT<br>CCCACCATCTGACGAGCAGCTGAAGTCCGGCACAGCTTCTGTCGTGTGCCTG<br>CTGAACAACTTCTACCCTCGGGAAGCCAAGGTGCAGTGGAAGGTGGACAATG<br>CCCTGCAGTCCGGCAACTCCCAAGAGTCTGTGACCGAGCAGGACTCCAAGGA<br>CTCTACCTACAGCCTGTCCTCCACACTGACCCTGTCTAAGGCCGACTACGAG<br>AAGCACAAGGTGTACGCCTGTGAAGTGACCCACCAGGGACTGTCTAGCCCCG<br>TGACCAAGTCTTTCAACAGAGGCGAGTGCTAATGA |
| SEQ ID NO: 34 | α-IL6R heavy - LgBiT | ATGGAAACCGACACACTGCTGCTGTGGGTGCTGTTGTTGTGGGTGCCAGGAT<br>CTACAGGCGAGGTGCAGTTGGTTGAATCTGGCGGAGGACTGGTGCAGCCTGG<br>CAGATCTCTGAGACTGTCTTGCGCCGCCTCCAGATTCACCTTCGACGATTAC<br>GCCATGCACTGGGTCCGACAGGCCCCTGGAAAAGGATTGGAGTGGGTGTCCG<br>GCATCTCCTGGAACTCTGGCAGAATCGGCTACGCCGACTCCGTGAAGGGCAG<br>ATTCACAATCTCCCGGGACAACGCCGAGAACTCCCTGTTCCTGCAGATGAAT<br>GGCCTGAGAGCCGAGGACACCGCTCTGTACTATTGCGCCAAGGGCAGAGACT<br>CCTTCGATATCTGGGGCCAGGGCACCATGGTCACCGTGTCCTCTGCTTCTAC<br>CAAGGGACCCTCTGTGTTCCCTCTGGCTCCTTCCAGCAAGTCTACCTCTGGT<br>GGAACCGCTGCTCTGGGCTGCCTGGTCAAGGATTACTTTCCTGAGCCTGTGA<br>CCGTGTCTTGGAACTCCGGTGCTCTGACATCCGGCGTGCACACATTTCCAGC<br>TGTGCTGCAGTCCTCTGGCCTGTACTCTCTGTCCTCTGTCGTGACCGTGCCT<br>TCTAGCTCTCTGGGCACCCAGACCTACATCTGCAACGTGAACCACAAGCCTT<br>CCAACACCAAGGTGGACAAGAGAGTGGAACCCAAGTCTTGCGGATCTTCTGG<br>TGGCGGTGGAAGCGGAGGCGGAGGATCTAGTGGCGGAGTGTTCACCCTGGAA<br>GATTTCGTCGGCGATTGGGAGCAGACCGCCGCCTATAATCTGGACCAGGTTC<br>TGGAACAAGGCGGCGTCAGCTCTCTGCTGCAGAATCTGGCTGTGTCTGTGAC<br>CCCTATCCAGAGAATCGTGCGCTCTGGCGAGAACGCCCTGAAGATCGACATC<br>CACGTGATCATCCCTTACGAGGGCCTGTCTGCCGATCAGATGGCTCAGATCG<br>AAGAGGTGTTCAAGGTGGTGTACCCCGTGGACGACCACCACTTCAAAGTGAT<br>CCTGCCTTACGGCACCCTGGTCATCGATGGCGTGACCCCAAACATGCTGAAC<br>TACTTCGGCAGACCCTACGAGGGAATCGCCGTGTTCGACGGCAAGAAAATCA<br>CCGTGACCGGCACACTGTGGAACGGCAACAAGATCATCGACGAGCGGCTGAT<br>CACCCCTGACGGCTCTATGCTGTTCAGAGTGACCATCAACTCCTAATGA |
| SEQ ID NO: 35 | α-IL6R light - SmBiT | ATGGAAACCGACACACTGCTGCTGTGGGTGCTGTTGTTGTGGGTGCCAGGCT<br>CTACCGGCGACATCCAGATGACCCAGTCTCCATCCTCTGTGTCTGCCTCTGT<br>GGGCGACAGAGTGACCATCACCTGTAGAGCCTCTCAGGGCATCTCTAGCTGG<br>CTGGCCTGGTATCAGCAGAAGCCTGGAAAGGCCCCTAAGCTGCTGATCTACG<br>GCGCCTCTTCTCTGGAATCTGGCGTGCCCTCTAGATTCTCCGGCTCTGGCTC<br>TGGCACCGACTTTACCCTGACAATCAGCTCCCTGCAGCCTGAGGACTTCGCC<br>TCTTACTACTGCCAGCAGGCCAACAGCTTCCCCTATACCTTTGGCCAGGGCA<br>CCAAGCTGGAAATCAAGAGAACCGTGGCCGCTCCTTCCGTGTTCATCTTCCC<br>ACCATCTGACGAGCAGCTGAAGTCCGGCACAGCTTCTGTCGTGTGCCTGCTG<br>AACAACTTCTACCCTCGGGAAGCCAAGGTGCAGTGGAAGGTGGACAATGCCC<br>TGCAGTCCGGCAACTCCCAAGAGTCTGTGACCGAGCAGGACTCCAAGGACTC<br>TACCTACAGCCTGTCCTCCACACTGACCCTGTCTAAGGCCGACTACGAGAAG<br>CACAAGGTGTACGCCTGTGAAGTGACCCACCAGGGACTGTCTAGCCCCGTGA<br>CCAAGTCTTTCAACAGAGGCGAGTGCGGATCTTCTGGTGGCGGAGGATCTGG<br>CGGAGGTGGAAGTAGTGGCGGCGTGACCGGCTACAGACTGTTCGAAGAGATC<br>CTGTAATGA |

TABLE 1-continued

Nucleic acid sequences of ORFs.

| SEQ ID NO | Description | Nucleic Acid Sequence |
|---|---|---|
| SEQ ID NO: 36 | α-IL6R light | ATGGAAACCGACACACTGCTGCTGTGGGTGCTGTTGTTGTGGGTGCCAGGCT<br>CTACCGGCGACATCCAGATGACCCAGTCTCCATCCTCTGTGTCTGCCTCTGT<br>GGGCGACAGAGTGACCATCACCTGTAGAGCCTCTCAGGGCATCTCTAGCTGG<br>CTGGCCTGGTATCAGCAGAAGCCTGGAAAGGCCCCTAAGCTGCTGATCTACG<br>GCGCCTCTTCTCTGGAATCTGGCGTGCCCTCTAGATTCTCCGGCTCTGGCTC<br>TGGCACCGACTTTACCCTGACAATCAGCTCCCTGCAGCCTGAGGACTTCGCC<br>TCTTACTACTGCCAGCAGGCCAACAGCTTCCCCTATACCTTTGGCCAGGGCA<br>CCAAGCTGGAAATCAAGAGAACCGTGGCCGCTCCTTCCGTGTTCATCTTCCC<br>ACCATCTGACGAGCAGCTGAAGTCCGGCACAGCTTCTGTCGTGTGCCTGCTG<br>AACAACTTCTACCCTCGGGAAGCCAAGGTGCAGTGGAAGGTGGACAATGCCC<br>TGCAGTCCGGCAACTCCCAAGAGTCTGTGACCGAGCAGGACTCCAAGGACTC<br>TACCTACAGCCTGTCCTCCACACTGACCCTGTCTAAGGCCGACTACGAGAAG<br>CACAAGGTGTACGCCTGTGAAGTGACCCACCAGGGACTGTCTAGCCCCGTGA<br>CCAAGTCTTTCAACAGAGGCGAGTGCTAATGA |
| SEQ ID NO: 37 | α-LINGO-1 heavy - LgBiT | ATGGAAACCGACACACTGCTGCTGTGGGTGCTGTTGTTGTGGGTGCCAGGAT<br>CTACAGGCGAGGTGCAGTTGTTGGAATCTGGCGAGGATTGGTGCAGCCTGG<br>CGGATCTCTGAGACTGTCTTGTGCCGCCTCTGGCTTCACCTTCTCCGCCTAT<br>GAGATGAAGTGGGTCCGACAGGCTCCTGGCAAAGGACTGGAATGGGTGTCCG<br>TGATTGGCCTTCTGGCGGCTTTACCTTTTACGCCGACTCCGTGAAGGGCAG<br>ATTCACCATCTCTCGGGACAACTCCAAGAACACCCTGTACCTGCAGATGAAC<br>TCCCTGAGAGCCGAGGACACCGCCGTGTACTATTGTGCCACCGAGGGCGACA<br>ACGACGCCTTTGATATTTGGGGCCAGGGCACCACCGTGACCGTGTCCTCTGC<br>TTCTACAAAGGGCCCCTCTGTGTTCCCTCTGGCTCCTTCCTCTAAATCCACC<br>TCTGGCGGAACCGCTGCTCTGGGCTGTCTGGTCAAGGATTACTTCCCTGAGC<br>CTGTGACAGTGTCCTGGAACTCTGGTGCTCTGACATCCGGCGTGCACACCTT<br>TCCAGCTGTGCTGCAGTCCTCTGGCCTGTACTCTCTGTCCTCTGTCGTGACA<br>GTGCCTTCCAGCTCTCTGGGCACCCAGACCTACATCTGCAACGTGAACCACA<br>AGCCTTCCAACACCAAGGTGGACAAGAGAGTGGAACCCAAGTCTTGCGGATC<br>TTCCGGCGGAGGTGGAAGTGGCGGAGGCGGATCAAGCGGCGGAGTGTTCACA<br>CTGGAAGATTTCGTCGGCGATTGGGAGCAGACCGCCGCCTATAATCTGGACC<br>AGGTTCTGGAACAAGGCGGCGTTAGCTCTCTGCTGCAGAATCTGGCTGTGTC<br>TGTGACCCCTATCCAGAGAATCGTGCGCTCTGGCGAGAACGCCCTGAAGATC<br>GACATCCACGTGATCATCCCTTACGAGGGCCTGTCTGCCGATCAGATGGCTC<br>AGATCGAAGAGGTGTTCAAGGTGGTGTACCCCGTGGACGACCACCACTTCAA<br>AGTGATCCTGCCTTACGGCACCCCTGGTCATCGATGGCGTGACCCCAAACATG<br>CTGAACTACTTCGGCAGACCCTACGAGGGAATCGCCGTGTTCGACGGCAAGA<br>AAATCACCGTGACAGGCACCCTGTGGAACGGCAACAAGATCATCGACGAGCG<br>GCTGATCACCCCTGACGGCTCTATGCTGTTCAGAGTGACCATCAACTCCTAA<br>TGA |
| SEQ ID NO: 38 | α-LINGO-1 light - SmBiT | ATGGAAACCGACACACTGCTGCTGTGGGTGCTGTTGTTGTGGGTGCCAGGAT<br>CTACAGGCGATATCCAGATGACCCAGTCTCCTGCCACATTGTCTCTGAGTCC<br>TGGCGAGAGAGCTACCCTGTCTTGCAGAGCTTCCCAGTCCGTGTCCTCCTAC<br>CTGGCCTGGTATCAGCAGAAACCTGGACAGGCCCCTCGGCTGCTGATCTACG<br>ATGCCTCTAATAGAGCCACAGGCATCCCCGCCAGATTCTCTGGCTCTGGATC<br>TGGCACCGACTTCACCCTGACCATCTCTAGCCTGGAACCTGAGGACTTCGCC<br>GTGTACTACTGCCAGCAGAGATCCAACTGGCCTATGTACACCTTCGGCCAGG<br>GCACCAAGCTGGAAATCAAGAGAACCGTGGCCGCTCCTTCCGTGTTCATCTT<br>CCCACCATCTGACGAGCAGCTGAAGTCCGGCACAGCTTCTGTCGTGTGCCTG<br>CTGAACAACTTCTACCCTCGGGAAGCCAAGGTGCAGTGGAAGGTGGACAATG<br>CCCTGCAGTCCGGCAACTCCCAAGAGTCTGTGACCGAGCAGGACTCCAAGGA<br>CTCTACCTACAGCCTGTCCTCCACACTGACCCTGTCTAAGGCCGACTACGAG<br>AAGCACAAGGTGTACGCCTGTGAAGTGACCCACCAGGGACTGTCTAGCCCCG<br>TGACCAAGTCTTTCAACAGAGGCGAGTGCGGATCTTCTGGTGGCGGAGGAAG<br>CGGAGGCGGAGGATCATCTGGCGGAGTGACCGGCTACAGACTGTTCGAAGAG<br>ATCCTGTAATGA |
| SEQ ID NO: 39 | α-LINGO-1 light | ATGGAAACCGACACACTGCTGCTGTGGGTGCTGTTGTTGTGGGTGCCAGGAT<br>CTACAGGCGATATCCAGATGACCCAGTCTCCTGCCACATTGTCTCTGAGTCC<br>TGGCGAGAGAGCTACCCTGTCTTGCAGAGCTTCCCAGTCCGTGTCCTCCTAC<br>CTGGCCTGGTATCAGCAGAAACCTGGACAGGCCCCTCGGCTGCTGATCTACG<br>ATGCCTCTAATAGAGCCACAGGCATCCCCGCCAGATTCTCTGGCTCTGGATC<br>TGGCACCGACTTCACCCTGACCATCTCTAGCCTGGAACCTGAGGACTTCGCC<br>GTGTACTACTGCCAGCAGAGATCCAACTGGCCTATGTACACCTTCGGCCAGG<br>GCACCAAGCTGGAAATCAAGAGAACCGTGGCCGCTCCTTCCGTGTTCATCTT<br>CCCACCATCTGACGAGCAGCTGAAGTCCGGCACAGCTTCTGTCGTGTGCCTG<br>CTGAACAACTTCTACCCTCGGGAAGCCAAGGTGCAGTGGAAGGTGGACAATG<br>CCCTGCAGTCCGGCAACTCCCAAGAGTCTGTGACCGAGCAGGACTCCAAGGA<br>CTCTACCTACAGCCTGTCCTCCACACTGACCCTGTCTAAGGCCGACTACGAG<br>AAGCACAAGGTGTACGCCTGTGAAGTGACCCACCAGGGACTGTCTAGCCCCG<br>TGACCAAGTCTTTCAACAGAGGCGAGTGCTAATGA |

TABLE 1-continued

Nucleic acid sequences of ORFs.

| SEQ ID NO | Description | Nucleic Acid Sequence |
|---|---|---|
| SEQ ID NO: 40 | α-neuropilin 1 heavy - LgBiT | ATGGAAACCGACACACTGCTGCTGTGGGTGCTGTTGTTGTGGGTGCCAGGAT<br>CTACAGGCGAGGTGCAGTTGGTTGAATCTGGCGGAGGATTGGTGCAGCCTGG<br>CGGATCTCTGAGACTGTCTTGTGCCGCCTCCGGCTTCACCTTCTCCTCTTAC<br>GCTATGTCCTGGGTCCGACAGGCTCCTGGCAAAGGATTGGAGTGGGTGTCCC<br>AGATTTCTCCCGCTGGCGGCTACACCAACTACGCCGATTCTGTGAAGGGCAG<br>ATTCACCATCTCCGCCGACACCTCCAAGAACACCGCCTACTGCAGATGAAC<br>TCCCTGAGAGCTGAGGACACCGCCGTGTACTATTGTGCTAGAGGCGAGCTGC<br>CCTACTACCGGATGTCCAAAGTGATGGATGTGTGGGGCCAGGGCACACTGGT<br>TACCGTGTCCTCTGCTTCTACCAAGGGACCCTCTGTGTTCCCTCTGGCTCCT<br>TCCAGCAAGTCTACCTCTGGTGGAACCGCTGCTCTGGGCTGCCTGGTCAAGG<br>ATTACTTTCCTGAGCCTGTGACCGTGTCTTGGAACTCTGGTGCTCTGACCTC<br>CGGCGTGCACACATTTCCAGCTGTGCTGCAGTCCTCCGGCCTGTACTCTCTG<br>TCCTCTGTCGTGACCGTGCCTTCTAGCTCTCTGGGCACCCAGACCTACATCT<br>GCAACGTGAACCACAAGCCTTCCAACACCAAGGTGGACAAGAGAGTGGAACC<br>CAAGTCTTGCGGATCTTCTGGTGGCGGTGGAAGTGGCGGAGGTGGAAGTTCA<br>GGCGGAGTGTTCACCCTGGAAGATTTCGTCGGCGATTGGGAGCAGACCGCCG<br>CCTATAATCTGGACCAGGTTCTGGAACAAGGCGGCGTCAGCTCTCTGCTGCA<br>GAATCTGGCTGTGTCTGTGACCCCTATCCAGAGAATCGTGCGCTCTGGCGAG<br>AACGCCCTGAAGATCGACATCCACGTGATCATCCCTTACGAGGGCCTGTCTG<br>CCGATCAGATGGCTCAGATCGAAGAGGTGTTCAAGGTGGTGTACCCCGTGGA<br>CGACCACCACTTCAAAGTGATCCTGCCTTACGGCACCCTGGTCATCGATGGC<br>GTGACCCCAAACATGCTGAACTACTTCGGCAGACCCTACGAGGGAATCGCCG<br>TGTTCGACGGCAAGAAAATCACCGTGACCGGCACACTGTGGAACGGCAACAA<br>GATCATCGACGAGCGGCTGATCACCCCTGACGGCTCTATGCTGTTCAGAGTG<br>ACCATCAACTCCTAATGA |
| SEQ ID NO: 41 | α-neuropilin 1 light - SmBiT | ATGGAAACCGACACACTGCTGCTGTGGGTGCTGTTGTTGTGGGTGCCAGGCT<br>CTACCGGCGACATCCAGATGACCCAGTCTCCATCCTCTCTGTCTGCCTCTGT<br>GGGCGACAGAGTGACCATCACCTGTCGGGCCTCTCAGTACTTCTCCTCCTAC<br>CTGGCCTGGTATCAGCAGAAGCCTGGCAAGGCTCCCAAGCTGCTGATCTACG<br>GCGCCTCTTCTAGAGCCTCTGGCGTGCCATCTAGATTCTCCGGCTCTGGCTC<br>TGGCACCGACTTTACCCTGACAATCAGCTCCCTGCAGCCTGAGGACTTCGCC<br>ACCTACTACTGTCAGCAGTACCTGGGCTCTCCTCCAACCTTTGGCCAGGGCA<br>CCAAGGTGGAAATCAAGAGAACCGTGGCCGCTCCTTCCGTGTTCATCTTCCC<br>ACCATCTGACGAGCAGCTGAAGTCCGGCACAGCTTCTGTCGTGTGCCTGCTG<br>AACAACTTCTACCCTCGGGAAGCCAAGGTGCAGTGGAAGGTGGACAATGCCC<br>TGCAGTCCGGCAACTCCCAAGAGTCTGTGACCGAGCAGGACTCCAAGGACTC<br>TACCTACAGCCTGTCCTCCACACTGACCCTGTCTAAGGCCGACTACGAGAAG<br>CACAAGGTGTACGCCTGTGAAGTGACCCACCAGGGACTGTCTAGCCCCGTGA<br>CCAAGTCTTTCAACAGAGGCGAGTGCGGATCTTCTGGTGGCGGAGGATCTGG<br>CGGAGGTGGAAGTAGTGGCGGCGTGACCGGCTACAGACTGTTCGAAGAGATC<br>CTGTAATGA |
| SEQ ID NO: 42 | α-neuropilin 1 light | ATGGAAACCGACACACTGCTGCTGTGGGTGCTGTTGTTGTGGGTGCCAGGCT<br>CTACCGGCGACATCCAGATGACCCAGTCTCCATCCTCTCTGTCTGCCTCTGT<br>GGGCGACAGAGTGACCATCACCTGTCGGGCCTCTCAGTACTTCTCCTCCTAC<br>CTGGCCTGGTATCAGCAGAAGCCTGGCAAGGCTCCCAAGCTGCTGATCTACG<br>GCGCCTCTTCTAGAGCCTCTGGCGTGCCATCTAGATTCTCCGGCTCTGGCTC<br>TGGCACCGACTTTACCCTGACAATCAGCTCCCTGCAGCCTGAGGACTTCGCC<br>ACCTACTACTGTCAGCAGTACCTGGGCTCTCCTCCAACCTTTGGCCAGGGCA<br>CCAAGGTGGAAATCAAGAGAACCGTGGCCGCTCCTTCCGTGTTCATCTTCCC<br>ACCATCTGACGAGCAGCTGAAGTCCGGCACAGCTTCTGTCGTGTGCCTGCTG<br>AACAACTTCTACCCTCGGGAAGCCAAGGTGCAGTGGAAGGTGGACAATGCCC<br>TGCAGTCCGGCAACTCCCAAGAGTCTGTGACCGAGCAGGACTCCAAGGACTC<br>TACCTACAGCCTGTCCTCCACACTGACCCTGTCTAAGGCCGACTACGAGAAG<br>CACAAGGTGTACGCCTGTGAAGTGACCCACCAGGGACTGTCTAGCCCCGTGA<br>CCAAGTCTTTCAACAGAGGCGAGTGCTAATGA |
| SEQ ID NO: 43 | α-CD221 heavy - LgBiT | ATGGAAACCGACACACTGCTGCTGTGGGTGCTGTTGTTGTGGGTGCCAGGAT<br>CTACAGGCGAAGTGCAGTTGGTGCAGTCTGGCGCCGAAGTGAAGAAACCTGG<br>CTCCTCTGTGAAGGTGTCCTGCAAGGCTTCTGGCGGCACCTTCTCCTCTTAC<br>GCCATCTCTTGGGTCCGACAGGCTCCTGGACAAGGCTTGGAGTGGATGGGCG<br>GCATCATCCCTATCTTCGGCACCGCCAACTACGCCCAGAAATTCCAGGGCAG<br>AGTGACCATCACCGCCGACAAGTCTACCTCCACCGCCTACATGGAACTGTCC<br>AGCCTGAGATCTGAGGACACCGCCGTGTACTACTGTGCTAGAGCCCCTCTGC<br>GGTTCCTGGAATGGTCTACCCAGGACACTACTACTATTACTACATGGACGT<br>GTGGGGCAAGGGCACCACCGTGACAGTTTCTTCCGCTTCCACCAAGGGACCC<br>AGCGTTTTCCCTCTGGCTCCATCCTCCAAGTCCACCTCTGGTGGAACAGCTG<br>CTCTGGGCTGCCTGGTCAAGGATTACTTTCCTGAGCCTGTGACCGTGTCCTG<br>GAACTCTGGTGCTCTGACATCCGGCGTGCACACCTTTCCAGCTGTGCTGCAG<br>TCCTCTGGCCTGTACTCTCTGTCCTCTGTCGTGACCGTGCCTTCTAGCTCTC<br>TGGGCACCCAGACCTACATCTGCAACGTGAACCACAAGCCTTCCAACACCAA<br>AGTGGACAAGAGAGTGGAACCCAAGTCTTGCGGATCTTCCGGTGGCGGAGGA<br>TCTGGCGGAGGTGGAAGTAGTGGCGGAGTGTTCACCCTGGAAGATTTCGTCG<br>GCGATTGGGAGCAGACCGCCGCCTATAATCTGGACCAGGTTCTGGAACAAGG |

TABLE 1-continued

Nucleic acid sequences of ORFs.

| SEQ ID NO | Description | Nucleic Acid Sequence |
|---|---|---|
| | | CGGCGTGTCCTCTCTGCTGCAGAATCTGGCTGTGTCTGTGACCCCTATCCAG<br>AGAATCGTGCGCTCTGGCGAGAACGCCCTGAAGATCGACATCCACGTGATCA<br>TCCCTTACGAGGGCCTGTCTGCCGATCAGATGGCTCAGATCGAAGAGGTGTT<br>CAAGGTGGTGTACCCCGTGGACGACCACCACTTCAAAGTGATCCTGCCTTAC<br>GGCACCCTGGTCATCGATGGCGTGACCCCAAACATGCTGAACTACTTCGGCA<br>GACCCTACGAGGGAATCGCCGTGTTCGACGGCAAGAAAATCACCGTGACCGG<br>CACACTGTGGAACGGCAACAAGATCATCGACGAGCGGCTGATCACCCCTGAC<br>GGCTCTATGCTGTTTAGAGTGACAATCAACTCCTAATGA |
| SEQ ID NO: 44 | α-CD221 light - SmBiT | ATGGAAACCGACACACTGCTGCTGTGGGTGCTGTTGTTGTGGGTGCCAGGCT<br>CTACCGGATCCTCTGAGTTGACACAGGACCCTGCTGTGTCTGTGGCTCTGGG<br>ACAGACAGTGCGGATTACCTGTCAGGGCGACTCCCTGAGATCTTACTACGCC<br>ACCTGGTATCAGCAGAAGCCCGGACAGGCTCCCATCCTGGTTATCTACGGCG<br>AGAACAAGCGGCCCTCTGGCATCCCTGATAGATTCTCTGGCTCCTCCTCCGG<br>CAATACCGCCTCTCTGACAATTACTGGCGCCCAGGCTGAGGACGAGGCCGAC<br>TACTATTGCAAGTCCAGAGATGGCTCTGGCCAGCACTTGGTGTTTGGCGGCG<br>GAACAAAACTGACCGTGCTGGGCCAGCCTAAGGCCAATCCTACAGTGACCCT<br>GTTTCCTCCATCCTCCGAGGAACTGCAGGCCAACAAGGCTACCCTCGTGTGC<br>CTGATCTCTGACTTTTACCCTGGCGCTGTGACCGTGGCTTGGAAGGCTGATG<br>GATCTCCTGTGAAGGCCGGCGTGGAAACCACCAAGCCTAGCAAGCAGTCCAA<br>CAACAAATACGCCGCCTCCTCCTACCTGTCTCTGACCCCTGAACAGTGGAAG<br>TCCCACCGGTCCTACTCTTGCCAAGTGACCCATGAGGGCTCCACCGTGGAAA<br>AGACAGTGGCCCCTACCGAGTGCTCTGGATCTTCTGGTGGCGGAGGATCTGG<br>CGGAGGTGGAAGTAGTGGCGGCGTGACCGGCTACAGACTGTTCGAAGAGATC<br>CTGTAATGA |
| SEQ ID NO: 45 | α-CD221 light | ATGGAAACCGACACACTGCTGCTGTGGGTGCTGCTCTTGTGGGTGCCAGGCT<br>CTACCGGATCCTCTGAGCTGACACAGGACCCTGCTGTGTCTGTGGCTCTGGG<br>CCAGACAGTGCGGATTACCTGTCAGGGCGACTCCCTGAGATCCTACTACGCC<br>ACCTGGTATCAGCAGAAGCCTGGACAGGCTCCCATCCTGGTCATCTACGGCG<br>AGAACAAGCGGCCCTCTGGCATCCCTGATAGATTCTCCGGCTCCTCCAGCGG<br>CAATACCGCCTCTCTGACAATTACCGGCGCTCAGGCTGAGGACGAGGCCGAC<br>TACTACTGCAAGTCCAGAGATGGCTCCGGCCAGCACTTGGTTTTTGGCGGAG<br>GAACAAAGCTGACCGTGCTGGGCCAGCCTAAGGCCAATCCTACCGTGACACT<br>GTTCCCTCCATCCTCCGAGGAACTGCAGGCCAACAAGGCTACCCTCGTGTGC<br>CTGATCTCCGACTTTTACCCTGGCGCTGTGACCGTGGCCTGGAAGGCTGATG<br>GATCTCCTGTGAAGGCTGGCGTGGAAACCACCAAGCCTTCCAAGCAGTCCAA<br>CAACAAATACGCCGCCTCCTCCTACCTGTCTCTGACCCCTGAACAGTGGAAG<br>TCCCACCGGTCCTACAGCTGCCAAGTGACCCATGAGGGCTCCACCGTGGAAA<br>AGACCGTGGCTCCTACCGAGTGCTCCTGATGA |
| SEQ ID NO: 46 | α-death receptor 5 heavy - LgBiT | ATGGAAACCGACACACTGCTGCTGTGGGTGCTGTTGTTGTGGGTGCCAGGAT<br>CTACAGGCGAAGTGCAGTTGGTTCAGTCTGGCGGCGGAGTTGAAAGACCTGG<br>CGGATCTCTGAGACTGTCTTGTGCCGCCTCTGGCTTCACCTTCGACGACTAC<br>GCTATGTCCTGGGTCCGACAGGCTCCTGGCAAAGGATTGGAATGGGTGTCCG<br>GCATCAACTGGCAAGGCGGCTCTACCGGCTACGCCGATTCTGTGAAGGGCAG<br>AGTGACCATCTCTCGGGACAACGCCAAGAACTCCCTGTACCTGCAGATGAAC<br>AGCCTGAGAGCCGAGGACACCGCCGTGTACTACTGTGCTAAGATCCTCGGCG<br>CTGGCAGAGGCTGGTACTTCGATTATTGGGGCAAGGGCACCACCGTGACCGT<br>GTCCTCTGCTTCTACAAAGGGCCCCTCTGTGTTCCCTCTGGCTCCTTCCTCT<br>AAATCCACCTCTGGCGGAACCGCTGCTCTGGGCTGTCTGGTCAAGGATTACT<br>TCCCTGAGCCTGTGACAGTGTCCTGGAACTCTGGTGCTCTGACATCCGGCGT<br>GCACACCTTTCCAGCTGTGCTGCAGTCCTCTGGCCTGTACTCTCTGTCCTCT<br>GTCGTGACAGTGCCTTCCAGCTCTCTGGGCACCCAGACCTACATCTGCAACG<br>TGAACCACAAGCCTTCCAACACCAAGGTGGACAAGAGAGTGGAACCCAAGTC<br>TTGTGGATCTTCTGGCGGAGGTGGAAGCGGAGGCGGAGGATCAAGTGGCGGA<br>GTGTTCACCCTGGAAGATTTCGTCGGCGATTGGGAGCAGACCGCCGCCTATA<br>ATCTGGACCAGGTTCTGGAACAAGGCGGCGTTAGCTCTCTGCTGCAGAATCT<br>GGCTGTGTCTGTGACCCCTATCCAGAGAATCGTGCGCTCTGGCGAGAACGCC<br>CTGAAGATCGACATCCACGTGATCATCCCTTACGAGGGCCTGTCTGCCGATC<br>AGATGGCTCAGATCGAAGAGGTGTTCAAGGTGGTGTACCCCGTGGACGACCA<br>CCACTTCAAAGTGATCCTGCCTTACGGCACCCTGGTCATCGATGGCGTGACC<br>CCAAACATGCTGAACTACTTCGGCAGACCCTACGAGGGAATCGCCGTGTTCG<br>ACGGCAAGAAAATCACCGTGACAGGCACCCTGTGGAACGGCAACAAGATCAT<br>CGACGAGCGGCTGATCACCCCTGACGGCTCCATGCTGTTTCGCGTGACCATC<br>AACTCCTAATGA |
| SEQ ID NO: 47 | α-death receptor 5 light - SmBiT | ATGGAAACCGACACACTGCTGCTGTGGGTGCTGTTGTTGTGGGTGCCAGGCT<br>CTACCGGATCCTCTGAGTTGACACAGGACCCTGCTGTGTCTGTGGCTCTGGG<br>ACAGACAGTGCGGATCACCTGTTCCGGCGACTCCCTGAGATCTTACTACGCC<br>TCCTGGTATCAGCAGAAGCCTGGACAGGCTCCCGTGCTGGTTATCTACGCG<br>CCAACAACAGACCTTCTGGCATCCCTGACAGATTCTCCGGCTCCAGCTCTGG<br>CAATACCGCCTCTCTGACAATTACCGGCGCTCAGGCTGAGGACGAGGCCGAC<br>TACTACTGCAACTCTGCCGACTCTTCCGGCAATCACGTTGTGTTTGGCGGAG<br>GCACCAAGCTGACAGTGCTGGGCCAACCTAAGGCCAATCCTACCGTGACACT |

TABLE 1-continued

Nucleic acid sequences of ORFs.

| SEQ ID NO | Description | Nucleic Acid Sequence |
|---|---|---|
| | | GTTCCCTCCATCCTCCGAGGAACTGCAGGCTAACAAGGCTACCCTCGTGTGC<br>CTGATCTCCGATTTTTACCCTGGCGCTGTGACCGTGGCTTGGAAGGCTGATG<br>GATCTCCTGTGAAGGCCGGCGTGGAAACCACCAAGCCTAGCAAGCAGTCCAA<br>CAACAAATACGCCGCCTCCTCCTACCTGTCTCTGACCCCTGAACAGTGGAAG<br>TCCCACCGGTCCTACTCTTGCCAAGTGACCCATGAGGGCTCCACCGTGGAAA<br>AGACAGTGGCCCCTACCGAGTGCTCTGGATCTTCTGGTGGCGGAGGAAGCGG<br>AGGCGGAGGATCATCTGGCGGAGTGACCGGCTACAGACTGTTCGAAGAGATC<br>CTGTAATGA |
| SEQ ID NO: 48 | α-death receptor 5 light | ATGGAAACCGACACACTGCTGCTGTGGGTGCTGTTGTTGTGGGTGCCAGGCT<br>CTACCGGATCCTCTGAGTTGACACAGGACCCTGCTGTGTCTGTGGCTCTGGG<br>ACAGACAGTGCGGATCACCTGTTCCGGCGACTCCCTGAGATCTTACTACGCC<br>TCCTGGTATCAGCAGAAGCCTGGACAGGCTCCCGTGCTGGTTATCTACGGCG<br>CCAACAACAGACCTTCTGGCATCCCTGACAGATTCTCCGGCTCCAGCTCTGG<br>CAATACCGCCTCTCTGACAATTACCGGCGCTCAGGCTGAGGACGAGGCCGAC<br>TACTACTGCAACTCTGCCGACTCTTCCGGCAATCACGTTGTGTTTGGCGGAG<br>GCACCAAGCTGACAGTGCTGGGCCAACCTAAGGCCAATCCTACCGTGACACT<br>GTTCCCTCCATCCTCCGAGGAACTGCAGGCTAACAAGGCTACCCTCGTGTGC<br>CTGATCTCCGATTTTTACCCTGGCGCTGTGACCGTGGCTTGGAAGGCTGATG<br>GATCTCCTGTGAAGGCCGGCGTGGAAACCACCAAGCCTAGCAAGCAGTCCAA<br>CAACAAATACGCCGCCTCCTCCTACCTGTCTCTGACCCCTGAACAGTGGAAG<br>TCCCACCGGTCCTACTCTTGCCAAGTGACCCATGAGGGCTCCACCGTGGAAA<br>AGACAGTGGCCCCTACCGAGTGCTCTTAATGA |
| SEQ ID NO: 49 | α-IL23 heavy - LgBiT | ATGGAAACCGACACACTGCTGCTGTGGGTGCTGTTGTTGTGGGTGCCAGGAT<br>CTACAGGCGAAGTGCAGTTGGTGCAGTCTGGCGCCGAAGTGAAGAAGCCTGG<br>CGAGTCCCTGAAGATCTCCTGCAAAGGCTCCGGCTACTCCTTCTCCAACTAC<br>TGGATCGGCTGGGTCCGACAGATGCCTGGCAAAGGACTGGAATGGATGGGCA<br>TCATCGACCCCTCCAACAGCTACACCAGATACAGCCCTAGCTTCCAGGGCCA<br>AGTGACCATCTCCGCCGACAAGTCTATCTCCACCGCCTACCTGCAGTGGTCC<br>TCTCTGAAGGCCTCTGACACCGCCATGTACTACTGCGCCAGATGGTACTACA<br>AGCCCTTCGATGTGTGGGGCCAGGGCACACTGGTTACCGTGTCCTCTGCTTC<br>TACCAAGGGACCCTCTGTGTTCCCTCTGGCTCCTTCCAGCAAGTCTACCTCT<br>GGTGGAACCGCTGCTCTGGGCTGCCTGGTCAAGGATTACTTTCCTGAGCCTG<br>TGACCGTGTCTTGGAACTCTGGTGCTCTGACCTCCGGCGTGCACACATTTCC<br>AGCTGTGCTGCAGTCCTCCGGCCTGTACTCTCTGTCCTCTGTCGTGACCGTG<br>CCTTCTAGCTCTCTGGGCACCCAGACCTACATCTGCAACGTGAACCACAAGC<br>CTTCCAACACCAAGGTGGACAAGAGAGTGGAACCCAAGTCTTGCGGATCTTC<br>TGGTGGCGGAGGATCTGGCGGAGGTGGAAGTAGTGGCGGAGTGTTCACCCTG<br>GAAGATTTCGTCGGCGATTGGGAGCAGACCGCCGCCTATAATCTGGACCAGG<br>TTCTGGAACAAGGCGGCGTCAGCTCTCTGCTGCAGAATCTGGCTGTGTCTGT<br>GACCCCTATCCAGAGAATCGTGCGCTCTGGCGAGAACGCTCTGAAGATCGAC<br>ATCCACGTGATCATCCCTTACGAGGGCCTGTCTGCCGATCAGATGGCTCAGA<br>TCGAAGAGGTGTTCAAGGTGGTGTACCCCGTGGACGACCACCACTTCAAAGT<br>GATCCTGCCTTACGGCACCCTGGTCATCGATGGCGTGACCCCAAACATGCTG<br>AACTACTTCGGCAGACCCTACGAGGGAATCGCCGTGTTCGACGGCAAGAAAA<br>TCACCGTGACCGGCACACTGTGGAACGGCAACAAGATCATCGACGAGCGGCT<br>GATCACCCCTGACGGCTCTATGCTGTTCCGCGTGACCATCAACTCCTAATGA |
| SEQ ID NO: 50 | α-IL23 light - SmBiT | ATGGAAACCGACACACTGCTGCTGTGGGTGCTGTTGTTGTGGGTGCCAGGCT<br>CTACAGGCCAGTCTGTTCTGACTCAGCCTCCTTCTGTTTCTGGCGCTCCTGG<br>CCAGAGAGTGACCATCTCCTGTACCGGCTCCTCCTCTAACATCGGCTCTGGC<br>TACGACGTGCACTGGTATCAGCAGCTGCCTGGCACAGCCCCTAAACTGCTGA<br>TCTACGGCAACTCCAAGAGGCCTTCTGGCGTGCCCGATAGATTCTCCGGCTC<br>TAAGTCTGGCACCTCTGCTTCTCTGGCTATCACCGGCCTGCAGTCTGAGGAC<br>GAGGCCGATTACTACTGCGCTTCTTGGACCGATGGCCTGAGCCTGGTTGTGT<br>TTGGCGGCGGAACAAAGCTGACAGTGCTGGGCCAGCCTAAGGCCAATCCTAC<br>CGTGACACTGTTCCCTCCATCCTCCGAGGAACTGCAGGCTAACAAGGCTACC<br>CTCGTGTGCCTGATCTCCGATTTTTACCCTGGCGCTGTGACCGTGGCTTGGA<br>AGGCTGATGGATCTCCTGTGAAGGCCGGCGTGGAAACCACCAAGCCTAGCAA<br>GCAGTCCAACAACAAATACGCCGCCTCCTCCTACCTGTCTCTGACCCCTGAA<br>CAGTGGAAGTCCCACCGGTCCTACTCTTGCCAAGTGACCCATGAGGGCTCCA<br>CCGTGGAAAAGACAGTGGCCCCTACCGAGTGCTCTGGATCTTCTGGTGGCGG<br>AGGATCTGGCGGAGGTGGAAGTAGTGGCGGCGTGACCGGCTACAGACTGTTC<br>GAAGAGATCCTGTAATGA |
| SEQ ID NO: 51 | α-IL23 light | ATGGAAACCGACACACTGCTGCTGTGGGTGCTGTTGTTGTGGGTGCCAGGCT<br>CTACAGGCCAGTCTGTTCTGACTCAGCCTCCTTCTGTTTCTGGCGCTCCTGG<br>CCAGAGAGTGACCATCTCCTGTACCGGCTCCTCCTCTAACATCGGCTCTGGC<br>TACGACGTGCACTGGTATCAGCAGCTGCCTGGCACAGCCCCTAAACTGCTGA<br>TCTACGGCAACTCCAAGAGGCCTTCTGGCGTGCCCGATAGATTCTCCGGCTC<br>TAAGTCTGGCACCTCTGCTTCTCTGGCTATCACCGGCCTGCAGTCTGAGGAC<br>GAGGCCGATTACTACTGCGCTTCTTGGACCGATGGCCTGAGCCTGGTTGTGT<br>TTGGCGGCGGAACAAAGCTGACAGTGCTGGGCCAGCCTAAGGCCAATCCTAC<br>CGTGACACTGTTCCCTCCATCCTCCGAGGAACTGCAGGCTAACAAGGCTACC |

TABLE 1-continued

Nucleic acid sequences of ORFs.

| SEQ ID NO | Description | Nucleic Acid Sequence |
|---|---|---|
| | | CTCGTGTGCCTGATCTCCGATTTTTACCCTGGCGCTGTGACCGTGGCTTGGA AGGCTGATGGATCTCCTGTGAAGGCCGGCGTGGAAACCACCAAGCCTAGCAA GCAGTCCAACAACAAATACGCCGCCTCCTCCTACCTGTCTCTGACCCCTGAA CAGTGGAAGTCCCACCGGTCCTACTCTTGCCAAGTGACCCATGAGGGCTCCA CCGTGGAAAAGACAGTGGCCCCTACCGAGTGCTCTTAATGA |
| SEQ ID NO: 52 | α-HER3 heavy - LgBiT | ATGGAAACCGACACACTGCTGCTGTGGGTGCTGTTGTTGTGGGTGCCAGGAT CTACAGGACAGGTGCAGTTGGTTCAGTCTGGCGGAGGACTTGTTCAGCCAGG CGGATCTCTGAGACTGTCTTGTGCCGCCTCTGGCTTCACCTTCGACGATTAC GCTATGCACTGGGTCCGACAGGCCCCTGGAAAAGGATTGGAATGGGTGGCCG GCATCTCCTGGGATTCTGGCTCTACCGGCTACGCCGATTCCGTGAAGGGCAG ATTCACCATCTCTCGGGACAACGCCAAGAACTCCCTGTACCTGCAGATGAAC AGCCTGAGAGCCGAGGACACCGCTCTGTACTACTGTGCTAGAGATCTGGGCG CCTACCAGTGGGTGGAAGGCTTTGATTATTGGGGCCAGGGCACCCTGGTCAC CGTGTCCTCTGCTTCTACAAAGGGCCCCTCTGTGTTCCCTCTGGCTCCTTCC TCTAAATCCACCTCTGGCGGAACCGCTGCTCTGGGCTGTCTGGTCAAGGATT ACTTCCCTGAGCCTGTGACCGTGTCTTGGAACTCTGGTGCTCTGACATCCGG CGTGCACACCTTTCCAGCTGTGCTGCAGTCCTCTGGCCTGTACTCTCTGTCC TCTGTCGTGACCGTGCCTTCTAGCTCTCTGGGCACCCAGACCTACATCTGCA ACGTGAACCACAAGCCTAGCAACACCAAGGTGGACAAGAGAGTGGAACCCAA GTCTTGCGGATCTTCTGGCGGCGGAGGAAGCGGAGGCGGAGGATCTAGTGGC GGAGTGTTCACCCTGGAAGATTTCGTCGGCGATTGGGAGCAGACCGCCGCCT ATAATCTGGACCAGGTTCTGGAACAAGGCGGCGTCAGCTCTCTGCTGCAGAA TCTGGCTGTGTCTGTGACCCCTATCCAGAGAATCGTGCGCTCTGGCGAGAAC GCCCTGAAGATCGACATCCACGTGATCATCCCTTACGAGGGCCTGTCTGCCG ATCAGATGGCTCAGATCGAAGAGGTGTTCAAGGTGGTGTACCCCGTGGACGA CCACCACTTCAAAGTGATCCTGCCTTACGGCACCCTCGTGATCGATGGCGTG ACCCCAAACATGCTGAACTACTTCGGCAGACCCTACGAGGGAATCGCCGTGT TCGACGGCAAGAAAATCACCGTGACCGGCACACTGTGGAACGGCAACAAGAT CATCGACGAGCGGCTGATCACCCCTGACGGCTCCATGCTGTTTAGAGTGACC ATCAACTCCTAATGA |
| SEQ ID NO: 53 | α-HER3 light - SmBiT | ATGGAAACCGACACACTGCTGCTGTGGGTGCTGTTGTTGTGGGTGCCAGGCT CTACCGGCTCTTACGAGTTGACACAGGACCCTGCTGTGTCTGTGGCTCTGGG ACAGACAGTGCGGATTACCTGTCAGGGCGACTCCCTGAGATCCTACTACGCC TCCTGGTATCAGCAGAAGCCTGGACAGGCTCCCGTGCTGGTCATCTACGGCA AGAACAACAGACCCTCTGGCATCCCTGACCGGTTCTCTGGCTCTACCTCTGG CAATTCCGCCAGCCTGACAATTACTGGCGCTCAGGCTGAGGACGAGGCCGAC TACTACTGCAACTCTAGAGACTCCCCTGGCAACCAGTGGGTGTTCGGCGGAG GAACAAAAGTGACAGTGCTCGGCGGCCAGCCTAAGGCCAATCCTACAGTGAC CCTGTTTCCTCCATCCTCCGAGGAACTGCAGGCCAACAAGGCTACCCTCGTG TGCCTGATCTCTGACTTTTACCCTGGCGCTGTGACCGTGGCTTGGAAGGCTG ATGGATCTCCTGTGAAGGCCGGCGTGGAAACCACCAAGCCTAGCAAGCAGTC CAACAACAAATACGCCGCCTCCTCCTACCTGTCTCTGACCCCTGAACAGTGG AAGTCCCACCGGTCCTACTCTTGCCAAGTGACCCATGAGGGCTCCACCGTGG AAAAGACAGTGGCCCCTACCGAGTGCTCTGGATCTTCTGGTGGCGGAGGATC TGGCGGAGGTGGAAGTAGTGGCGGCGTGACCGGCTACAGACTGTTCGAAGAG ATCCTGTAATGA |
| SEQ ID NO: 54 | α-HER3 light | ATGGAAACCGACACACTGCTGCTGTGGGTGCTGCTCTTGTGGGTGCCAGGCT CTACCGGCTCTTACGAGCTGACACAGGACCCTGCTGTGTCTGTGGCTCTGGG CCAGACAGTGCGGATTACCTGTCAGGGCGACTCCCTGAGATCCTACTACGCC TCCTGGTATCAGCAGAAGCCTGGACAGGCTCCCGTGCTGGTCATCTACGGCA AGAACAACCGGCCTAGCGGCATCCCTGACAGATTCTCCGGCTCTACCTCCGG CAACTCTGCCAGCCTGACAATTACTGGCGCCCAGGCTGAGGACGAGGCCGAC TACTACTGCAACTCCAGAGACTCCCCTGGCAACCAGTGGGTTTTCGGCGGAG GCACCAAAGTGACAGTGCTCGGAGGACAGCCCAAGGCCAATCCTACCGTGAC ACTGTTCCCTCCATCCTCCGAGGAACTGCAGGCCAACAAGGCTACCCTCGTG TGCCTGATCTCCGACTTTTACCCTGGCGCTGTGACCGTGGCCTGGAAGGCTG ATGGATCTCCTGTGAAGGCTGGCGTGGAAACCACCAAGCCTTCCAAGCAGTC CAACAACAAATACGCCGCCTCCTCCTACCTGTCTCTGACCCCTGAACAGTGG AAGTCCCACCGGTCCTACAGCTGCCAAGTGACCCATGAGGGCTCCACCGTGG AAAAGACCGTGGCTCCTACCGAGTGCTCCTGATGA |
| SEQ ID NO: 55 | α-TRAILR2 heavy - LgBiT | ATGGAAACCGACACACTGCTGCTGTGGGTGCTGTTGTTGTGGGTGCCAGGAT CTACAGGCGAAGTGCAGTTGGTTCAGTCTGGCGGCGGAGTTGAAAGACCTGG CGGATCTCTGAGACTGTCTTGTGCCGCCTCTGGCTTCACCTTCGACGACTAT GGCATGTCCTGGGTCCGACAGGCTCCTGGCAAAGGATTGGAATGGGTGTCCG GCATCAACTGGAATGGCGGCTCTACCGGCTACGCCGATTCTGTGAAGGGCAG AGTGACCATCTCTCGGGACAACGCCAAGAACTCCCTGTACCTGCAGATGAAC AGCCTGAGAGCCGAGGACACCGCCGTGTACTACTGTGCTAAGATCCTCGGCG CTGGCAGAGGCTGGTATTTCGATCTGTGGGGCAAGGGCACCACCGTGACAGT GTCCTCTGCTTCTACCAAGGGACCCAGCGTTTTCCCTCTGGCTCCATCCTCT AAGTCCACCTCTGGTGGAACCGCTGCTCTGGGCTGTCTGGTCAAGGATTACT TCCCTGAGCCTGTGACCGTGTCCTGGAACTCTGGTGCTCTGACATCCGGCGT |

TABLE 1-continued

Nucleic acid sequences of ORFs.

| SEQ ID NO | Description | Nucleic Acid Sequence |
|---|---|---|
| | | GCACACCTTTCCAGCTGTGCTGCAGTCCTCTGGCCTGTACTCTCTGTCCTCT<br>GTCGTGACCGTGCCTTCTAGCTCTCTGGGCACCCAGACCTACATCTGCAACG<br>TGAACCACAAGCCTTCCAACACCAAAGTGGACAAGAGAGTGGAACCCAAGTC<br>CTGCGGATCTTCTGGTGGCGGAGGATCTGGCGGAGGTGGAAGTAGTGGCGGA<br>GTGTTCACCCTGGAAGATTTCGTCGGCGATTGGGAGCAGACCGCCGCCTATA<br>ATCTGGACCAGGTTCTGGAACAAGGCGGCGTGTCCTCTCTGCTGCAGAATCT<br>GGCTGTGTCTGTGACCCCTATCCAGAGAATCGTGCGCTCTGGCGAGAACGCC<br>CTGAAGATCGACATCCACGTGATCATCCCTTACGAGGGCCTGTCTGCCGATC<br>AGATGGCTCAGATCGAAGAGGTGTTCAAGGTGGTGTACCCCGTGGACGACCA<br>CCACTTCAAAGTGATCCTGCCTTACGGCACCCTGGTCATCGATGGCGTGACC<br>CCAAACATGCTGAACTACTTCGGCAGACCCTACGAGGGAATCGCCGTGTTCG<br>ACGGCAAGAAAATCACCGTGACCGGCACACTGTGGAACGGCAACAAGATCAT<br>CGACGAGCGGCTGATCACCCCTGACGGCTCCATGCTGTTTCGCGTGACCATC<br>AACTCCTAATGA |
| SEQ ID NO: 56 | α-TRAILR2 light - SmBiT | ATGGAAACCGACACACTGCTGCTGTGGGTGCTGTTGTTGTGGGTGCCAGGCT<br>CTACCGGATCCTCTGAGTTGACACAGGACCCTGCTGTGTCTGTGGCTCTGGG<br>ACAGACAGTGCGGATTACCTGTCAGGGCGACTCCCTGAGATCCTACTACGCC<br>TCCTGGTATCAGCAGAAGCCTGGACAGGCTCCCGTGCTGGTCATCTACGGCA<br>AGAACAACAGACCCTCTGGCATCCCTGACCGGTTCTCCGGATCTAGCTCTGG<br>CAATACCGCCAGCCTGACAATTACTGGCGCTCAGGCTGAGGACGAGGCCGAC<br>TACTACTGCAACTCCAGAGACTCTTCCGGCAATCACGTGGTGTTTGGCGGCG<br>GAACAAAGCTGACAGTGCTGGGCCAGCCTAAGGCCAATCCTACCGTGACACT<br>GTTCCCTCCATCCTCCGAGGAACTGCAGGCTAACAAGGCTACCCTCGTGTGC<br>CTGATCTCCGATTTTTACCCTGGCGCTGTGACCGTGGCTTGGAAGGCTGATG<br>GATCTCCTGTGAAGGCCGGCGTGGAAACCACCAAGCCTAGCAAGCAGTCCAA<br>CAACAAATACGCCGCCTCCTCCTACCTGTCTCTGACCCCTGAACAGTGGAAG<br>TCCCACCGGTCCTACTCTTGCCAAGTGACCCATGAGGGCTCCACCGTGGAAA<br>AGACAGTGGCCCCTACCGAGTGCTCTGGATCTTCTGGTGGCGGAGGATCTGG<br>CGGAGGTGGAAGTAGTGGCGGCGTGACCGGCTACAGACTGTTCGAAGAGATC<br>CTGTAATGA |
| SEQ ID NO: 57 | α-TRAILR2 light | ATGGAAACCGACACACTGCTGCTGTGGGTGCTGCTCTTGTGGGTGCCAGGCT<br>CTACCGGATCCTCTGAGCTGACACAGGACCCTGCTGTGTCTGTGGCTCTGGG<br>CCAGACAGTGCGGATTACCTGTCAGGGCGACTCCCTGAGATCCTACTACGCC<br>TCCTGGTATCAGCAGAAGCCTGGACAGGCTCCCGTGCTGGTCATCTACGGCA<br>AGAACAACCGGCCTAGCGGCATCCCTGACAGATTCTCCGGATCTTCCAGCGG<br>CAATACCGCCAGCCTGACAATTACTGGCGCCCAGGCTGAGGACGAGGCCGAC<br>TACTACTGCAACTCCAGAGACTCCTCCGGCAATCACGTGGTGTTTGGCGGCG<br>GAACAAAGCTGACAGTGCTGGGCCAGCCTAAGGCCAATCCTACCGTGACACT<br>GTTCCCTCCATCCTCCGAGGAACTGCAGGCCAACAAGGCTACCCTCGTGTGC<br>CTGATCTCCGACTTTTACCCTGGCGCTGTGACCGTGGCTGGAAGGCTGATG<br>GATCTCCTGTGAAGGCTGGCGTGGAAACCACCAAGCCTTCCAAGCAGTCCAA<br>CAACAAATACGCCGCCTCCTCCTACCTGTCTCTGACCCCTGAACAGTGGAAG<br>TCCCACCGGTCCTACAGCTGCCAAGTGACCCATGAGGGCTCCACCGTGGAAA<br>AGACCGTGGCTCCTACCGAGTGCTCCTGATGA |
| SEQ ID NO: 58 | α-activin receptors heavy - LgBiT | ATGGAAACCGACACACTGCTGCTGTGGGTGCTGTTGTTGTGGGTGCCAGGAT<br>CTACAGGACAGGTGCAGTTGGTGCAGTCTGGCGCCGAAGTGAAGAAACCTGG<br>CGCTTCTGTGAAGGTGTCCTGCAAGGCCTCTGGCTACACCTTTACCTCCAGC<br>TACATCAACTGGGTCCGACAGGCTCCTGGACAGGGACTTGAGTGGATGGGCA<br>CCATCAATCCTGTGTCCGGCTCTACCAGCTACGCCCAGAAATTCCAGGGCAG<br>AGTGACCATGACCAGAGACACCTCCATCTCCACCGCCTACATGGAACTGTCC<br>CGGCTGAGATCTGACGACACCGCCGTGTACTATTGTGCCAGAGGCGGATGGT<br>TCGATTACTGGGGACAGGGCACACTGGTCACCGTGTCCTCTGCTTCTACCAA<br>GGGACCCTCTGTGTTCCCTCTGGCTCCTTCCAGCAAGTCTACCTCTGGTGGA<br>ACCGCTGCTCTGGGCTGCCTGGTCAAGGATTACTTTCCTGAGCCTGTGACCG<br>TGTCTTGGAACTCTGGTGCTCTGACCTCCGGCGTGCACACATTTCCAGCTGT<br>GCTGCAGTCCTCCGGCCTGTACTCTCTGTCCTCTGTCGTGACCGTGCCTTCT<br>AGCTCTCTGGGCACCCAGACCTACATCTGCAACGTGAACCACAAGCCTTCCA<br>ACACCAAGGTGGACAAGAGAGTGGAACCCAAGTCTTGCGGATCTTCTGGTGG<br>CGGAGGATCTGGCGGAGGTGGAAGTAGTGGCGGAGTGTTCACCCTGGAAGAT<br>TTCGTCGGCGATTGGGAGCAGACCGCCGCCTATAATCTGGACCAGGTTCTGG<br>AACAAGGCGGCGTCAGCTCTCTGCTGCAGAATCTGGCTGTGTCTGTGACCCC<br>TATCCAGAGAATTGTGCGCTCTGGCGAGAACGCCCTGAAGATCGACATCCAC<br>GTGATCATCCCTTACGAGGGCCTGTCTGCCGATCAGATGGCTCAGATCGAAG<br>AGGTGTTCAAGGTGGTGTACCCCGTGGACGACCACCACTTCAAAGTGATCCT<br>GCCTTACGGCACCCTGGTCATCGATGGCGTGACCCCAAACATGCTGAACTAC<br>TTCGGCAGACCCTACGAGGGAATCGCCGTGTTCGACGGCAAGAAAATCACCG<br>TGACCGGCACACTGTGGAACGGCAACAAGATCATCGACGAGCGGCTGATCAC<br>CCCTGACGGCTCTATGCTGTTCCGCGTGACCATCAACTCCTAATGA |

TABLE 1-continued

Nucleic acid sequences of ORFs.

| SEQ ID NO | Description | Nucleic Acid Sequence |
|---|---|---|
| SEQ ID NO: 59 | α-activin receptors light - SmBiT | ATGGAAACCGACACACTGCTGCTGTGGGTGCTGTTGTTGTGGGTGCCAGGCT<br>CTACAGGCCAGTCTGCTTTGACTCAGCCTGCCTCTGTGTCTGGCTCCCCTGG<br>CCAGTCTATCACCATCTCTTGTACCGGCACCTCCTCCGACGTGGGCTCCTAC<br>AACTACGTGAACTGGTATCAGCAGCACCCCGGCAAGGCCCCTAAGCTGATGA<br>TCTACGGCGTGTCCAAACGGCCCAGCGGAGTGTCTAACAGATTCTCCGGCTC<br>CAAGTCTGGCAACACCGCTTCTCTGACAATCAGCGGACTGCAGGCCGAGGAC<br>GAGGCTGATTACTACTGTGGCACCTTCGCTGGCGGCTCCTACTATGGTGTTT<br>TTGGCGGCGGAACAAAGCTGACCGTGCTGGGCCAACCTAAGGCCAATCCTAC<br>CGTGACACTGTTCCCTCCATCCTCCGAGGAACTGCAGGCTAACAAGGCTACC<br>CTCGTGTGCCTGATCTCCGATTTTTACCCTGGCGCTGTGACCGTGGCTTGGA<br>AGGCTGATGGATCTCCTGTGAAGGCCGGCGTGGAAACCACCAAGCCTAGCAA<br>GCAGTCCAACAACAAATACGCCGCCTCCTCCTACCTGTCTCTGACCCCTGAA<br>CAGTGGAAGTCCCACCGGTCCTACTCTTGCCAAGTGACCCATGAGGGCTCCA<br>CCGTGGAAAAGACAGTGGCCCCTACCGAGTGCTCTGGATCTTCTGGTGGCGG<br>AGGATCTGGCGGAGGTGGAAGTAGTGGCGGCGTGACCGGCTACAGACTGTTC<br>GAAGAGATCCTGTAATGA |
| SEQ ID NO: 60 | α-activin receptors light | ATGGAAACCGACACACTGCTGCTGTGGGTGCTGTTGTTGTGGGTGCCAGGCT<br>CTACAGGCCAGTCTGCTTTGACTCAGCCTGCCTCTGTGTCTGGCTCCCCTGG<br>CCAGTCTATCACCATCTCTTGTACCGGCACCTCCTCCGACGTGGGCTCCTAC<br>AACTACGTGAACTGGTATCAGCAGCACCCCGGCAAGGCCCCTAAGCTGATGA<br>TCTACGGCGTGTCCAAACGGCCCAGCGGAGTGTCTAACAGATTCTCCGGCTC<br>CAAGTCTGGCAACACCGCTTCTCTGACAATCAGCGGACTGCAGGCCGAGGAC<br>GAGGCTGATTACTACTGTGGCACCTTCGCTGGCGGCTCCTACTATGGTGTTT<br>TTGGCGGCGGAACAAAGCTGACCGTGCTGGGCCAACCTAAGGCCAATCCTAC<br>CGTGACACTGTTCCCTCCATCCTCCGAGGAACTGCAGGCTAACAAGGCTACC<br>CTCGTGTGCCTGATCTCCGATTTTTACCCTGGCGCTGTGACCGTGGCTTGGA<br>AGGCTGATGGATCTCCTGTGAAGGCCGGCGTGGAAACCACCAAGCCTAGCAA<br>GCAGTCCAACAACAAATACGCCGCCTCCTCCTACCTGTCTCTGACCCCTGAA<br>CAGTGGAAGTCCCACCGGTCCTACTCTTGCCAAGTGACCCATGAGGGCTCCA<br>CCGTGGAAAAGACAGTGGCCCCTACCGAGTGCTCTTAATGA |
| SEQ ID NO: 61 | α-complement C5 heavy - LgBiT | ATGGAAACCGACACACTGCTGCTGTGGGTGCTGTTGTTGTGGGTGCCAGGAT<br>CTACAGGCGAAGTGCAGTTGGTGCAGTCTGGCGCCGAAGTGAAGAAACCTGG<br>CTCCTCTGTGAAGGTGTCCTGCAAGGCTTCTGGCGGCACCTTCTCCTCTTAC<br>GCCATCTCTTGGGTCCGACAGGCTCCTGGACAAGGCTTGGAGTGGATGGGCG<br>GCATCGGCCCTTTTTTCGGCACCGCCAACTACGCCCAGAAATTCCAGGGCAG<br>AGTGACCATCACCGCCGACGAGTCTACCTCCACCGCTTACATGGAACTGTCC<br>AGCCTGAGATCTGAGGACACCGCCGTGTACTACTGCGCCAGAGACACCCCTT<br>ACTTCGATTATTGGGGCCAGGGCACCCTGGTCACCGTGTCCTCTGCTTCTAC<br>AAAGGGCCCCTCTGTGTTCCCTCTGGCTCCTAGCTCTAAGTCTACATCTGGC<br>GGAACCGCTGCTCTGGGCTGCCTGGTCAAGGATTACTTTCCTGAGCCTGTGA<br>CCGTGTCTTGGAACTCTGGTGCTCTGACCTCCGGCGTGCACACATTTCCAGC<br>TGTGCTGCAGTCCTCCGGCCTGTACTCTCTGTCCTCTGTCGTGACCGTGCCT<br>TCTAGCTCTCTGGGCACCCAGACCTACATCTGCAACGTGAACCACAAGCCTT<br>CCAACACCAAGGTGGACAAGAGAGTGGAACCCAAGTCTTGCGGATCTTCCGG<br>TGGCGGAGGAAGCGGAGGCGGAGGATCTAGTGGCGGAGTGTTCACCCTGGAA<br>GATTTCGTCGGCGATTGGGAGCAGACCGCCGCCTATAATCTGGACCAGGTTC<br>TGGAACAAGGCGGGGTGTCCTCTCTGCTGCAGAATCTGGCTGTGTCTGTGAC<br>CCCTATCCAGAGAATCGTGCGCTCTGGCGAGAACGCCCTGAAGATCGACATC<br>CACGTGATCATCCCTTACGAGGGCCTGTCTGCCGATCAGATGGCTCAGATCG<br>AAGAGGTGTTCAAGGTGGTGTACCCCGTGGACGACCACCACTTCAAAGTGAT<br>CCTGCCTTACGGCACCCTCGTGATCGATGGCGTGACCCCAAACATGCTGAAC<br>TACTTCGGCAGACCCTACGAGGGAATCGCCGTGTTCGACGGCAAGAAAATCA<br>CCGTGACCGGCACACTGTGGAACGGCAACAAGATCATCGACGAGCGGCTGAT<br>CACCCCTGACGGCTCTATGCTGTTTAGAGTGACAATCAACTCCTAATGA |
| SEQ ID NO: 62 | α-complement C5 light - SmBiT | ATGGAAACCGACACACTGCTGCTGTGGGTGCTGTTGTTGTGGGTGCCAGGCT<br>CTACCGGCTCTTATGAGCTGACACAGCCTCTGTCTGTGTCTGTGGCTCTGGG<br>CCAGACCGCCAGAATCACCTGTTCTGGCGACAGCATCCCCAACTACTACGTG<br>TACTGGTATCAGCAGAAGCCCGGCCAGGTCCTGTGCTGGTCATCTACGACG<br>ACTCCAACAGACCCAGCGGCATCCCTGAGAGATTCTCCGGCTCTAACTCTGG<br>CAACACCGCCACACTGACCATCTCTAGAGCACAGGCTGGCGACGAGGCCGAC<br>TACTACTGCCAGTCTTTCGACAGCTCTCTGAACGCCGAAGTGTTCGGCGGAG<br>GCACAAAACTGACAGTGCTGGGCAGCCTAAGGCCAATCCTACCGTGACACT<br>GTTCCCTCCATCCTCCGAGGAACTGCAGGCTAACAAGGCTACCCTCGTGTGC<br>CTGATCTCCGATTTTTACCCTGGCGCTGTGACCGTGGCTTGGAAGGCTGATG<br>GATCTCCTGTGAAGGCCGGCGTGGAAACCACCAAGCCTAGCAAGCAGTCCAA<br>CAACAAATACGCCGCCTCCTCCTACCTGTCTCTGACCCCTGAACAGTGGAAG<br>TCCCACCGGTCCTACTCTTGCCAAGTGACCCATGAGGGCTCCACCGTGGAAA<br>AGACAGTGGCCCCTACCGAGTGCTCTGGATCTTCTGGTGGCGGAGGATCTGG<br>CGGAGGTGGAAGTAGTGGCGGCGTGACCGGCTACAGACTGTTCGAAGAGATC<br>CTGTAATGA |

TABLE 1-continued

Nucleic acid sequences of ORFs.

| SEQ ID NO | Description | Nucleic Acid Sequence |
|---|---|---|
| SEQ ID NO: 63 | α-complement C5 light | ATGGAAACCGACACACTGCTGCTGTGGGTGCTGTTGTTGTGGGTGCCAGGCT<br>CTACCGGCTCTTATGAGCTGACACAGCCTCTGTCTGTGTCTGTGGCTCTGGG<br>CCAGACCGCCAGAATCACCTGTTCTGGCGACAGCATCCCCAACTACTACGTG<br>TACTGGTATCAGCAGAAGCCCGGCCAGGCTCCTGTGCTGGTCATCTACGACG<br>ACTCCAACAGACCCAGCGGCATCCCTGAGAGATTCTCCGGCTCTAACTCTGG<br>CAACACCGCCACACTGACCATCTCTAGAGCACAGGCTGGCGACGAGGCCGAC<br>TACTACTGCCAGTCTTTCGACAGCTCTCTGAACGCCGAAGTGTTCGGCGGAG<br>GCACAAAACTGACAGTGCTGGGCCAGCCTAAGGCCAATCCTACCGTGACACT<br>GTTCCCTCCATCCTCCGAGGAACTGCAGGCTAACAAGGCTACCCTCGTGTGC<br>CTGATCTCCGATTTTTACCCTGGCGCTGTGACCGTGGCTTGGAAGGCTGATG<br>GATCTCCTGTGAAGGCCGGCGTGGAAACCACCAAGCCTAGCAAGCAGTCCAA<br>CAACAAATACGCCGCCTCCTCCTACCTGTCTCTGACCCCTGAACAGTGGAAG<br>TCCCACCGGTCCTACTCTTGCCAAGTGACCCATGAGGGCTCCACCGTGGAAA<br>AGACAGTGGCCCCTACCGAGTGCTCTTAATGA |
| SEQ ID NO: 64 | α-CCR2 heavy - LgBiT | ATGGAAACCGACACACTGCTGCTGTGGGTGCTGTTGTTGTGGGTGCCAGGAT<br>CTACAGGCGAAGTGCAGTTGGTGCAGTCTGGCGCCGAAGTGAAGAAACCTGG<br>CGCTTCTGTGAAGGTGTCCTGCAAGGCCTCTGGCTACACCTTTACCGGCTAC<br>CACATGCACTGGGTCCGACAGGCTCCAGGACAAGGATTGGAGTGGATGGGCT<br>GGATCAACCCCAACTCCGGCGTGACCAAATACGCCCAGAAATTCCAGGGCAG<br>AGTGACCATGACCAGAGACACCTCCATCAACACCGCCTACATGGAACTGTCC<br>CGGCTGAGATTCGACGACACCGACGTGTACTATTGTGCCACCGGCGGCTTTG<br>GCTATTGGGGAGAGGGAACACTGGTCACCGTGTCCTCTGCTTCTACCAAGGG<br>ACCCTCCGTGTTTCCTCTGGCTCCTTCCAGCAAGTCTACCTCTGGTGGAACC<br>GCTGCTCTGGGCTGCCTGGTCAAGGATTACTTTCCTGAGCCTGTGACCGTGT<br>CTTGGAACTCTGGTGCTCTGACCAGCGGCGTGCACACATTTCCAGCTGTGCT<br>GCAGTCCTCCGGCCTGTACTCTCTGTCCTCTGTCGTGACCGTGCCTTCTAGC<br>TCTCTGGGCACCCAGACCTACATCTGCAACGTGAACCACAAGCCTTCCAACA<br>CCAAGGTGGACAAGAGAGTGGAACCCAAGTCTTGCGGATCTTCTGGTGGCCG<br>AGGATCTGGCGGAGGTGGAAGTAGTGGCGGAGTGTTCACCCTGGAAGATTTC<br>GTCGGCGATTGGGAGCAGACCGCCGCCTATAATCTGGACCAGGTTCTGGAAC<br>AAGGCGGCGTCAGCTCTCTGCTGCAGAATCTGGCTGTGTCTGTGACCCCTAT<br>CCAGAGAATCGTGCGCTCTGGCGAGAACGCCCTGAAGATCGACATCCACGTG<br>ATCATCCCTTACGAGGGCCTGTCTGCCGATCAGATGGCTCAGATCGAAGAGG<br>TGTTCAAGGTGGTGTACCCCGTGGACGACCACCACTTCAAAGTGATCCTGCC<br>TTACGGCACCCTGGTCATCGATGGCGTGACCCCAAACATGCTGAACTACTTC<br>GGCAGACCCTACGAGGGAATCGCCGTGTTCGACGGCAAGAAAATCACCGTGA<br>CCGGCACACTGTGGAACGGCAACAAGATCATCGACGAGCGGCTGATCACCCC<br>TGACGGCTCTATGCTGTTCCGCGTGACCATCAACTCCTAATGA |
| SEQ ID NO: 65 | α-CCR2 light - SmBiT | ATGGAAACCGACACACTGCTGCTGTGGGTGCTGTTGTTGTGGGTGCCAGGAT<br>CTACAGGCCTGCCTGTTCTGACACAGCCTCCTAGCGTGTCCAAGGGCCTGAG<br>ACAGACCGCTACACTGACCTGCACCGGCAACTCTAACAACGTGGGAAATCAG<br>GGCGCTGCCTGGTTGCAGCAGCATCAGGGACAACCTCCAAAGCTGCTGTCCT<br>ACCGGAACCACAATAGACCTTCCGGCGTGTCCGAGCGGTTCAGCCCTTCTAG<br>ATCTGGCGACACCTCTAGCCTGACCATCACTGGACTGCAGCCTGAGGACGAG<br>GCCGATTACTACTGTCTGGCCTGGGATTCTTCTCTGCGGGCCTTTGTGTTTG<br>GCACCGGCACAAAACTGACCGTGCTGGGCCAGCCTAAGGCCAATCCTACAGT<br>GACCCTGTTTCCTCCATCCTCCGAGGAACTGCAGGCCAACAAGGCTACCCTC<br>GTGTGCCTGATCTCTGACTTTTACCCTGGCGCTGTGACCGTGGCTTGGAAGG<br>CTGATGGATCTCCTGTGAAGGCCGGCGTGGAAACCACCAAGCCTAGCAAGCA<br>GTCCAACAACAAATACGCCGCCTCCTCCTACCTGTCTCTGACCCCTGAACAG<br>TGGAAGTCCCACCGGTCCTACTCTTGCCAAGTGACCCATGAGGGCTCCACCG<br>TGGAAAAGACAGTGGCCCCTACCGAGTGCTCTGGATCTTCTGGTGGCGGAGG<br>ATCTGGCGGAGGTGGAAGTAGTGGCGGCGTGACCGGCTACAGACTGTTCGAA<br>GAGATCCTGTAATGA |
| SEQ ID NO: 66 | α-CCR2 light | ATGGAAACCGACACACTGCTGCTGTGGGTGCTGCTCTTGTGGGTGCCAGGAT<br>CTACAGGACTGCCCGTGTTGACCCAGCCTCCTAGCGTTTCCAAGGGCCTGAG<br>ACAGACCGCCACACTGACCTGTACCGGCAACTCTAACAACGTGGGCAATCAG<br>GGCGCTGCCTGGTTGCAGCAGCATCAGGGACAGCCTCCAAAGCTGCTGTCCT<br>ACCGGAACCACAACAGACCTAGCGGCGTGTCCGAGCGGTTCAGCCCTTCTAG<br>ATCTGGCGACACCTCCAGCCTGACCATCACTGGACTGCAGCCTGAGGACGAG<br>GCCGACTACTATTGTCTGGCCTGGGACAGCTCCCTGCGGGCCTTTGTTTTTG<br>GCACCGGCACCAAGCTGACCGTGCTGGGACAACCTAAGGCCAATCCTACCGT<br>GACACTGTTCCCTCCATCCTCCGAGGAACTGCAGGCCAACAAGGCTACCCTC<br>GTGTGCCTGATCTCCGACTTTTACCCTGGCGCTGTGACCGTGGCCTGGAAGG<br>CTGATGGATCTCCTGTGAAGGCTGGCGTGGAAACCACCAAGCCTTCCAAGCA<br>GTCCAACAACAAATACGCCGCCTCCTCCTACCTGTCTCTGACCCCTGAACAG<br>TGGAAGTCCCACCGGTCCTACAGCTGCCAAGTGACCCATGAGGGCTCCACCG<br>TGGAAAAGACCGTGGCTCCTACCGAGTGCTCCTGATGA |

TABLE 1-continued

Nucleic acid sequences of ORFs.

| SEQ ID NO | Description | Nucleic Acid Sequence |
|---|---|---|
| SEQ ID NO: 67 | α-CCR2 heavy - LgBiT | ATGGAAACCGACACACTGCTGCTGTGGGTGCTGTTGTTGTGGGTGCCAGGAT<br>CTACAGGCGAGGTGCAGTTGGTTGAATCTGGCGGAGGATTGGTGCAGCCTGG<br>CGGATCTCTGAGACTGTCTTGTGTGGCCTCCGGCTTCACCTTCTCCGACTAC<br>TGGATGTCCTGGGTCCGACAGGCTCCTGGCAAAGGACTGGAATGGGTCGCCA<br>ACATCAAGAAAGACGGCTCCGTGAACTACTACGTGGACTCCGTGAAGGGCAG<br>ATTCACCATCTCTCGGGACAACGCCAAGAACTCCCTGTACCTGCAGATGAAC<br>AGCCTGAGAGCCGAGGACACCGCCGTGTACTACTGCACCAGATTCGATTATT<br>GGGGCCAGGGCACCCTGGTCACCGTGTCCTCTGCTTCTACAAAGGGCCCCTC<br>TGTGTTCCCTCTGGCTCCTTCCTCTAAATCCACCTCTGGCGGAACCGCTGCT<br>CTGGGCTGTCTGGTCAAGGATTACTTCCCTGAGCCTGTGACCGTGTCTTGGA<br>ACTCTGGTGCTCTGACATCCGGCGTGCACACCTTTCCAGCTGTGCTGCAGTC<br>CTCTGGCCTGTACTCTCTGTCCTCTGTCGTGACCGTGCCTTCTAGCTCTCTG<br>GGCACCCAGACCTACATCTGCAACGTGAACCACAAGCCTTCCAACACCAAGG<br>TGGACAAGAGAGTGGAACCCAAGTCTTGCGGATCTTCTGGTGGTGGTGGAAG<br>TGGCGGAGGCGGTTCTTCAGGCGGAGTGTTCACCCTGGAAGATTTCGTCGGC<br>GATTGGGAGCAGACCGCCGCCTATAATCTGGACCAGGTTCTGGAACAAGGCG<br>GCGTCAGCTCTCTGCTGCAGAATCTGGCTGTGTCTGTGACCCCTATCCAGAG<br>AATCGTGCGCTCTGGCGAGAACGCCCTGAAGATCGACATCCACGTGATCATC<br>CCTTACGAGGGCCTGTCTGCCGATCAGATGGCTCAGATCGAAGAGGTGTTCA<br>AGGTGGTGTACCCCGTGGACGACCACCACTTCAAAGTGATCCTGCCTTACGG<br>CACCCTCGTGATCGATGGCGTGACCCCAAACATGCTGAACTACTTCGGCAGA<br>CCCTACGAGGGAATCGCCGTGTTCGACGGCAAGAAAATCACCGTGACCGGCA<br>CACTGTGGAACGGCAACAAGATCATCGACGAGCGGCTGATCACCCCTGACGG<br>CTCCATGCTGTTTAGAGTGACCATCAACTCCTAATGA |
| SEQ ID NO: 68 | α-CCR2 light - SmBiT | ATGGAAACCGACACACTGCTGCTGTGGGTGCTGTTGTTGTGGGTGCCAGGAT<br>CTACAGGCCAGGCTGGATTGACACAGCCTCCTAGCGTGTCCAAGGGCCTGAG<br>ACAGACCGCTACACTGACCTGCACCGGCAACTCTAACAACGTGGGCAATCAG<br>GGCGCTGCCTGGTTGCAGCAGCATCAGGGACATCCTCCAAAGCTGCTGTTCT<br>ACCGGAACAACAATAGAGCCTCCGGCATCTCCGAGCGGCTGTCTGCTTCTAG<br>ATCTGGCAATACCGCCAGCCTGACCATCACTGGACTGCAGCCTGAGGACGAG<br>GCCGACTACTATTGCCTGACCTGGGACTCCTCTCTGTCCGTGGTTGTGTTTG<br>GCGGCGGAACAAAGCTGACAGTGCTGGGCCAGCCTAAGGCCAATCCTACCGT<br>GACACTGTTCCCTCCATCCTCCGAGGAACTGCAGGCTAACAAGGCTACCCTC<br>GTGTGCCTGATCTCCGATTTTTACCCTGGCGCTGTGACCGTGGCTTGGAAGG<br>CTGATGGATCTCCTGTGAAGGCCGGCGTGGAAACCACCAAGCCTAGCAAGCA<br>GTCCAACAACAAATACGCCGCCTCCTCCTACCTGTCTCTGACCCCTGAACAG<br>TGGAAGTCCCACCGGTCCTACTCTTGCCAAGTGACCCATGAGGGCTCCACCG<br>TGGAAAAGACAGTGGCCCCTACCGAGTGCTCTGGATCTTCTGGTGGCGGAGG<br>ATCTGGCGGAGGTGGAAGTAGTGGCGGCGTGACCGGCTACAGACTGTTCGAA<br>GAGATCCTGTAATGA |
| SEQ ID NO: 69 | α-CCR2 light | ATGGAAACCGACACACTGCTGCTGTGGGTGCTGCTCTTGTGGGTGCCAGGAT<br>CTACAGGACAGGCTGGCTTGACCCAGCCTCCTAGCGTTTCCAAGGGCCTGAG<br>ACAGACCGCCACACTGACCTGTACCGGCAACTCTAACAACGTGGGCAATCAG<br>GGCGCTGCCTGGTTGCAGCAGCATCAGGGACATCCTCCAAAGCTGCTGTTCT<br>ACCGGAACAACAACAGAGCCTCCGGCATCTCCGAGCGGCTGTCTGCTTCTAG<br>ATCCGGCAATACCGCCAGCCTGACCATCACTGGACTGCAGCCTGAGGACGAG<br>GCCGACTACTATTGCCTGACCTGGGACTCCTCTCTGTCCGTGGTGGTTTTTG<br>GCGGAGGCACCAAGCTGACAGTGCTGGGACAGCCTAAGGCCAATCCTACCGT<br>GACACTGTTCCCTCCATCCTCCGAGGAACTGCAGGCCAACAAGGCTACCCTC<br>GTGTGCCTGATCTCCGACTTTTACCCTGGCGCTGTGACCGTGGCCTGGAAGG<br>CTGATGGATCTCCTGTGAAGGCTGGCGTGGAAACCACCAAGCCTTCCAAGCA<br>GTCCAACAACAAATACGCCGCCTCCTCCTACCTGTCTCTGACCCCTGAACAG<br>TGGAAGTCCCACCGGTCCTACAGCTGCCAAGTGACCCATGAGGGCTCCACCG<br>TGGAAAAGACCGTGGCTCCTACCGAGTGCTCCTGATGA |
| SEQ ID NO: 70 | α-IL12β heavy - LgBiT | ATGGAAACCGACACACTGCTGCTGTGGGTGCTGCTCTTGTGGGTGCCAGGAT<br>CTACAGGACAGGTGCAGCTGGTGGAATCTGGTGGCGGAGTTGTGCAGCCTGG<br>CAGATCCCTGAGACTGTCTTGTGCCGCCTCCGGCTTCACCTTCTCCTCTTAC<br>GGAATGCACTGGGTCCGACAGGCCCCTGGCAAAGGATTGGAGTGGGTCGCCT<br>TCATCAGATACGACGGCTCCAACAAGTACTACGCCGACTCCGTGAAGGGCAG<br>ATTCACCATCTCTCGGGACAACTCCAAGAACACCCTGTACCTGCAGATGAAC<br>TCCCTGAGAGCCGAGGACACCGCCGTGTACTACTGCAAGACCCACGGCTCTC<br>ACGACAATTGGGGCCAGGGCACAATGGTCACCGTGTCCTCTGCTTCCACCAA<br>GGGACCCTCTGTGTTCCCTCTGGCTCCTTCCAGCAAGTCTACCTCTGGCGGA<br>ACAGCTGCTCTGGGCTGCCTGGTCAAGGACTACTTTCCTGAGCCTGTGACCG<br>TGTCTTGGAACTCTGGCGCTCTGACATCCGGCGTGCACACCTTCCAGCTGT<br>GCTGCAATCCTCCGGCCTGTACTCTCTGTCCTCCGTCGTGACCGTGCCTTCT<br>AGCTCTCTGGGCACCCAGACCTACATCTGCAATGTGAACCACAAGCCTTCCA<br>ACACCAAGGTGGACAAGAGAGTGGAACCCAAGTCCTGCGGATCTTCTGGCGG<br>CGGAGGATCTGGCGGAGGTGGTAGTTCAGGCGGAGTGTTCACCCTGGAAGAT<br>TTCGTCGGCGACTGGGAGCAGACCGCCGCCTATAATCTGGACCAGGTGCTGG<br>AACAAGGCGGCGTCAGTTCTCTGCTGCAGAACCTGGCTGTGTCTGTGACCCC<br>TATCCAGAGAATCGTGCGGAGCGGCGAGAACGCCCTGAAGATCGATATCCAC |

TABLE 1-continued

Nucleic acid sequences of ORFs.

| SEQ ID NO | Description | Nucleic Acid Sequence |
|---|---|---|
| | | GTGATCATCCCTTACGAGGGCCTGAGCGCCGATCAGATGGCTCAGATCGAAG
AGGTGTTCAAGGTGGTGTACCCCGTGGACGACCACCACTTCAAAGTGATCCT
GCCCTTACGGCACCCTGGTCATCGATGGCGTGACCCCAAACATGCTGAACTAC
TTCGGCAGACCCTACGAGGGAATCGCCGTGTTCGACGGCAAGAAAATCACCG
TGACCGGCACACTGTGGAACGGCAACAAGATCATCGACGAGGCGCTGATCAC
CCCTGACGGCTCTATGCTGTTCAGAGTGACCATCAACAGCTGATGA |
| SEQ ID NO: 71 | α-IL12β light - SmBiT | ATGGAAACCGACACACTGCTGCTGTGGGTGCTGCTCTTGTGGGTGCCAGGAT
CTACCGGACAGTCCGTGTTGACCCAGCCTCCTTCTGTTTCTGGCGCTCCTGG
CCAGAGAGTGACCATCTCTTGCTCCGGCTCTCGGTCCAACATCGGCTCCAAT
ACCGTGAAGTGGTATCAGCAGCTGCCCGGCACAGCTCCCAAACTGCTGATCT
ACTACAACGACCAGCGGCCTTCTGGCGTGCCCGATAGATTCTCTGGCTCCAA
GTCTGGCACCTCTGCCAGCCTGGCTATTACCGGACTGCAGGCTGAGGACGAG
GCCGACTACTACTGCCAGTCTTACGACCGGTACACCCATCCTGCTCTGCTGT
TTGGCACCGGCACCAAAGTGACAGTGCTGGGCCAGCCTAAGGCCAATCCTAC
CGTGACACTGTTCCCTCCATCCTCCGAAGAACTGCAGGCCAACAAGGCTACC
CTCGTGTGCCTGATCTCCGACTTTTACCCTGGCGCTGTGACCGTGGCCTGGA
AGGCTGATGGATCTCCTGTGAAGGCTGGCGTGGAAACCACCAAGCCTTCCAA
GCAGTCCAACAACAAATACGCCGCCTCCTCCTACCTGTCTCTGACCCCTGAA
CAGTGGAAGTCCCACCGGTCCTACAGCTGCCAAGTGACCCATGAGGGCTCCA
CCGTGGAAAAGACCGTGGCTCCTACCGAGTGCTCCGGATCTTCTGGTGGCGG
AGGATCTGGCGGAGGCGGTTCTTCAGGCGGAGTGACCGGCTACAGACTGTTC
GAAGAGATCCTGTGATGA |
| SEQ ID NO: 72 | α-IL12β light | ATGGAAACCGACACACTGCTGCTGTGGGTGCTGCTCTTGTGGGTGCCAGGAT
CTACCGGACAGTCCGTGTTGACCCAGCCTCCTTCTGTTTCTGGCGCTCCTGG
CCAGAGAGTGACCATCTCTTGCTCCGGCTCTCGGTCCAACATCGGCTCCAAT
ACCGTGAAGTGGTATCAGCAGCTGCCCGGCACAGCTCCCAAACTGCTGATCT
ACTACAACGACCAGCGGCCTTCTGGCGTGCCCGATAGATTCTCTGGCTCCAA
GTCTGGCACCTCTGCCAGCCTGGCTATTACCGGACTGCAGGCTGAGGACGAG
GCCGACTACTACTGCCAGTCTTACGACCGGTACACCCATCCTGCTCTGCTGT
TTGGCACCGGCACCAAAGTGACAGTGCTGGGCCAGCCTAAGGCCAATCCTAC
CGTGACACTGTTCCCTCCATCCTCCGAAGAACTGCAGGCCAACAAGGCTACC
CTCGTGTGCCTGATCTCCGACTTTTACCCTGGCGCTGTGACCGTGGCCTGGA
AGGCTGATGGATCTCCTGTGAAGGCTGGCGTGGAAACCACCAAGCCTTCCAA
GCAGTCCAACAACAAATACGCCGCCTCCTCCTACCTGTCTCTGACCCCTGAA
CAGTGGAAGTCCCACCGGTCCTACAGCTGCCAAGTGACCCATGAGGGCTCCA
CCGTGGAAAAGACCGTGGCTCCTACCGAGTGCTCCTGATGA |
| SEQ ID NO: 73 | α-CTLA4 heavy - hCHIg | ATGGAAACCGACACACTGCTGCTGTGGGTGCTGCTCTTGTGGGTGCCAGGAT
CTACAGGACAGGTGCAGCTGGTGGAATCTGGTGGCGGAGTTGTGCAGCCTGG
CAGATCCCTGAGACTGTCTTGTGCCGCCTCCGGCTTCACCTTCTCCAGCTAC
ACCATGCACTGGGTCCGACAGGCCCCTGGCAAAGGATTGGAGTGGGTCACCT
TCATCTCTTACGACGGCAACAACAAGTACTACGCCGACTCCGTGAAGGGCAG
ATTCACCATCTCTCGGGACAACTCCAAGAACACCCTGTACCTGCAGATGAAC
TCCCTGAGAGCCGAGGACACCGCCATCTACTACTGTGCTAGAACCGGCTGGC
TGGGCCCCTTTGATTATTGGGGACAGGGCACCCTGGTCACCGTGTCCTCTGC
TTCTACCAAGGGACCCAGCGTGTTCCCTCTGGCTCCTTCCAGCAAGTCTACC
TCTGGCGGAACAGCTGCTCTGGGCTGCCTGGTCAAGGACTACTTTCCTGAGC
CTGTGACCGTGTCTTGGAACTCTGGCGCTCTGACATCCGGCGTGCACACATT
TCCAGCTGTGCTGCAGTCCTCCGGCCTGTACTCTCTGTCCTCTGTCGTGACC
GTGCCTTCCAGCTCTCTGGGAACCCAGACCTACATCTGCAATGTGAACCACA
AGCCTTCCAACACCAAGGTGGACAAGAGAGTGGAACCCAAGTCCTGCGACAA
GACCCACACCTGTCCACCATGTCCTGCTCCAGAACTGCTCGGCGGACCTTCC
GTGTTCCTGTTTCCTCCAAAGCCTAAGGACACCCTGATGATCTCTCGGACCC
CTGAAGTGACCTGCGTGGTGGTGGATGTGTCTCACGAGGATCCCGAAGTGAA
GTTCAATTGGTACGTGGACGGCGTGGAAGTGCACAACGCCAAGACCAAGCCT
AGAGAGGAACAGTACAACTCCACCTACAGAGTGGTGTCCGTGCTGACCGTGC
TGCACCAGGATTGGCTGAACGGCAAAGAGTACAAGTGCAAGGTGTCCAACAA
GGCCCTGCCTGCTCCTATCGAAAAGACCATCTCCAAGGCCAAGGGCCAGCCT
AGGGAACCCCAGGTTTACACCCTGCCTCCAAGCCGGGAAGAGATGACCAAGA
ACCAGGTGTCCCTGACCTGCCTCGTGAAGGGATTCTACCCCTCCGATATCGC
CGTGGAATGGGAGTCTAATGGCCAGCCTGAGAACAACTACAAGACAACCCCT
CCTGTGCTGGACTCCGACGGCTCATTCTTCCTGTACTCCAAGCTGACAGTGG
ACAAGTCCAGATGGCAGCAGGGCAACGTGTTCTCCTGCTCCGTGATGCACGA
GGCCCTGCACAATCACTACACCCAGAAGTCCCTGTCTCTGAGCCCCGGCAAG
TGATGA |
| SEQ ID NO: 74 | α-IL12β heavy - hCHIg | ATGGAAACCGACACACTGCTGCTGTGGGTGCTGCTCTTGTGGGTGCCAGGAT
CTACAGGACAGGTGCAGCTGGTGGAATCTGGTGGCGGAGTTGTGCAGCCTGG
CAGATCCCTGAGACTGTCTTGTGCCGCCTCCGGCTTCACCTTCTCCTCTTAC
GGAATGCACTGGGTCCGACAGGCCCCTGGCAAAGGATTGGAGTGGGTCGCCT
TCATCAGATACGACGGCTCCAACAAGTACTACGCCGACTCCGTGAAGGGCAG
ATTCACCATCTCTCGGGACAACTCCAAGAACACCCTGTACCTGCAGATGAAC
TCCCTGAGAGCCGAGGACACCGCCGTGTACTACTGCAAGACCCACGGCTCTC |

TABLE 1-continued

Nucleic acid sequences of ORFs.

| SEQ ID NO | Description | Nucleic Acid Sequence |
|---|---|---|
| | | ACGACAATTGGGGCCAGGGCACAATGGTCACCGTGTCCTCTGCTTCCACCAA<br>GGGACCCTCTGTGTTCCCTCTGGCTCCTTCCAGCAAGTCTACCTCTGGCGGA<br>ACAGCTGCTCTGGGCTGCCTGGTCAAGGACTACTTTCCTGAGCCTGTGACCG<br>TGTCTTGGAACTCTGGCGCTCTGACATCCGGCGTGCACACCTTTCCAGCTGT<br>GCTGCAATCCTCCGGCCTGTACTCTCTGTCCTCCGTCGTGACCGTGCCTTCT<br>AGCTCTCTGGGCACCCAGACCTACATCTGCAATGTGAACCACAAGCCTTCCA<br>ACACCAAGGTGGACAAGAGAGTGGAACCCAAGTCCTGCGATAAGACCCACAC<br>CTGTCCACCATGTCCTGCTCCAGAACTGCTCGGCGGACCTTCCGTGTTCCTG<br>TTTCCTCCAAAGCCTAAGGACACCCTGATGATCTCTCGGACCCCTGAAGTGA<br>CCTGCGTGGTGGTGGATGTGTCTCACGAGGATCCCGAAGTGAAGTTCAATTG<br>GTACGTGGACGGCGTGGAAGTGCACAACGCCAAGACCAAGCCTAGAGAGGAA<br>CAGTACAACTCCACCTACAGAGTGGTGTCCGTGCTGACCGTGCTGCACCAGG<br>ATTGGCTGAACGGCAAAGAGTACAAGTGCAAGGTGTCCAACAAGGCCCTGCC<br>TGCTCCTATCGAAAAGACCATCTCCAAGGCCAAGGGCCAGCCTAGGGAACCC<br>CAGGTTTACACCCTGCCTCCAAGCCGGGAAGAGATGACCAAGAACCAGGTGT<br>CCCTGACCTGCCTCGTGAAGGGATTCTACCCCTCCGATATCGCCGTGGAATG<br>GGAGTCTAATGGCCAGCCTGAGAACAACTACAAGACCACACCTCCTGTGCTG<br>GACTCCGACGGCTCATTCTTCCTGTACTCCAAGCTGACAGTGGACAAGTCCA<br>GATGGCAGCAGGGCAACGTGTTCTCCTGCTCCGTGATGCACGAGGCCCTGCA<br>CAATCACTACACCCAGAAGTCCCTGTCTCTGAGCCCCGGCAAGTGATGA |
| SEQ ID NO: 75 | α-IL12β light-hCLIg_v1 - IL2 | ATGGAAACCGACACACTGCTGCTGTGGGTGCTGCTCTTGTGGGTGCCAGGAT<br>CTACCGGACAGTCCGTGTTGACCCAGCCTCCTTCTGTTTCTGGCGCTCCTGG<br>CCAGAGAGTGACCATCTCTTGCTCCGGCTCTCGGTCCAACATCGGCTCCAAT<br>ACCGTGAAGTGGTATCAGCAGCTGCCCGGCACAGCTCCCAAACTGCTGATCT<br>ACTACAACGACCAGCGGCCTTCTGGCGTGCCCGATAGATTCTCTGGCTCCAA<br>GTCTGGCACCTCTGCCAGCCTGGCTATTACCGGACTGCAGGCTGAGGACGAG<br>GCCGACTACTACTGCCAGTCTTACGACGGTACACCCATCCTGCTCTGCTGT<br>TTGGCACCGGCACCAAAGTGACAGTGCTGGGCCAGCCTAAGGCCAATCCTAC<br>CGTGACACTGTTCCCTCCATCCTCCGAAGAACTGCAGGCCAACAAGGCTACC<br>CTCGTGTGCCTGATCTCCGACTTTTACCCTGGCGCTGTGACCGTGGCCTGGA<br>AGGCTGATGGATCTCCTGTGAAGGCTGGCGTGGAAACCACCAAGCCTTCCAA<br>GCAGTCCAACAACAAATACGCCGCCTCCTCCTACCTGTCTCTGACCCCTGAA<br>CAGTGGAAGTCCCACCGGTCCTACAGCTGCCAAGTGACCCATGAGGGCTCCA<br>CCGTGGAAAAGACCGTGGCTCCTACAGAGTGTTCTGGCGGCGGAGGATCTGG<br>CGGAGGTGGAAGCGGAGGCGGTGGATCTGCTCCTACCTCCTCCAGCACCAAG<br>AAAACCCAGCTGCAGTTGGAGCATCTGCTGCTGGACCTGCAGATGATCCTGA<br>ACGGCATCAACAACTACAAGAACCCCAAGCTGACCCGGATGCTGACCGCCAA<br>GTTTGCCATGCCTAAGAAGGCCACCGAGCTGAAACATCTGCAGTGCCTGGAA<br>GAGGAACTGAAGCCCCTGGAAGAAGTGCTGAATCTGGCCCAGTCCAAGAACT<br>TCCACCTGAGGCCTCGGGACCTGATCAGCAACATCAACGTGATCGTGCTCGA<br>GCTGAAGGGCTCCGAGACAACCTTCATGTGCGAGTACGCCGACGAGACAGCT<br>ACCATCGTGGAATTTCTGAACCGGTGGATCACCTTCTGCCAGTCCATCATCA<br>GCACCCTGACCTGATGA |
| SEQ ID NO: 76 | α-IL12β heavy - hCHIg_Hole_Cys | ATGGAAACCGACACACTGCTGCTGTGGGTGCTGCTCTTGTGGGTGCCAGGAT<br>CTACAGGACAGGTGCAGCTGGTGGAATCTGGTGGCGGAGTTGTGCAGCCTGG<br>CAGATCCCTGAGACTGTCTTGTGCCGCCTCCGGCTTCACCTTCTCCTCTTAC<br>GGAATGCACTGGGTCCGACAGGCCCCTGGCAAAGGATTGGAGTGGGTGGCCT<br>TCATCAGATACGACGGCTCCAACAAGTACTACGCCGACTCCGTGAAGGGCAG<br>ATTCACCATCTCTCGGGACAACTCCAAGAACACCCTGTACCTGCAGATGAAC<br>TCCCTGAGAGCCGAGGACACCGCCGTGTACTACTGCAAGACCCACGGCTCTC<br>ACGACAATTGGGGCCAGGGCACAATGGTCACCGTGTCCTCTGCTTCCACCAA<br>GGGACCCTCTGTGTTCCCTCTGGCTCCTTCCAGCAAGTCTACCTCTGGCGGA<br>ACAGCTGCTCTGGGCTGCCTGGTCAAGGACTACTTTCCTGAGCCTGTGACCG<br>TGTCTTGGAACTCTGGCGCTCTGACATCCGGCGTGCACACCTTTCCAGCTGT<br>GCTGCAATCCTCCGGCCTGTACTCTCTGTCCTCCGTCGTGACCGTGCCTTCT<br>AGCTCTCTGGGCACCCAGACCTACATCTGCAATGTGAACCACAAGCCTTCCA<br>ACACCAAGGTGGACAAGAGAGTGGAACCCAAGTCCTGCGATAAGACCCACAC<br>CTGTCCACCATGTCCTGCTCCAGAACTGCTCGGCGGACCTTCCGTGTTCCTG<br>TTTCCTCCAAAGCCTAAGGACACCCTGATGATCTCTCGGACCCCTGAAGTGA<br>CCTGCGTGGTGGTGGATGTGTCTCACGAGGATCCCGAAGTGAAGTTCAATTG<br>GTACGTGGACGGCGTGGAAGTGCACAACGCCAAGACCAAGCCTAGAGAGGAA<br>CAGTACAACTCCACCTACAGAGTGGTGTCCGTGCTGACCGTGCTGCACCAGG<br>ATTGGCTGAACGGCAAAGAGTACAAGTGCAAGGTGTCCAACAAGGCCCTGCC<br>TGCTCCTATCGAAAAGACCATCTCCAAGGCCAAGGGCCAGCCTCGGGAACCC<br>CAAGTCTGTACCCTGCCTCCTAGCCGGGAAGAGATGACCAAGAACCAGGTGT<br>CCCTGTCCTGCGCTGTGAAGGGCTTCTACCCTTCCGATATCGCCGTGGAATG<br>GGAGAGCAATGGCCAGCCTGAGAACAACTACAAGACCACACCTCCTGTGCTG<br>GACTCCGACGGCTCATTCTTCCTGGTGTCCAAGCTGACAGTGGACAAGTCCA<br>GATGGCAGCAGGGCAACGTGTTCTCCTGCTCCGTGATGCACGAGGCCCTGCA<br>CAATCACTACACCCAGAAGTCCCTGTCTCTGTCCCGAAAAGGCGGCGGA<br>GGATCTGGCGGAGGTGGTAGCGGAGGCGGTGGATCTGCTCCTACCTCCTCCA<br>GCACCAAGAAAACCCAGCTGCAGTTGGAGCATCTGCTGCTGGACCTCCAGAT<br>GATCCTGAATGGCATCAACAATTACAAGAACCCCAAGCTCACCCGGATGCTG |

TABLE 1-continued

Nucleic acid sequences of ORFs.

| SEQ ID NO | Description | Nucleic Acid Sequence |
|---|---|---|
|  |  | ACCGCCAAGTTTGCCATGCCTAAGAAGGCCACCGAGCTGAAACATCTGCAGT<br>GCCTGGAAGAGGAACTGAAGCCCCTGGAAGAAGTGCTGAATCTGGCCCAGTC<br>CAAGAACTTCCACCTGAGGCCTCGGGACCTGATCTCCAACATCAACGTGATC<br>GTGCTCGAGCTGAAGGGCTCCGAGACAACCTTCATGTGCGAGTACGCCGACG<br>AGACAGCTACCATCGTGGAATTTCTGAACCGGTGGATCACCTTCTGCCAGTC<br>CATCATCAGCACCCTGACCTGATGA |
| SEQ ID NO: 77 | α-IL12β heavy - hCHIg | ATGGAAACCGACACACTGCTGCTGTGGGTGCTGCTCTTGTGGGTGCCAGGAT<br>CTACAGGACAGGTGCAGCTGGTGGAATCTGGTGGCGGAGTTGTGCAGCCTGG<br>CAGATCCCTGAGACTGTCTTGTGCCGCCTCCGGCTTCACCTTCTCCTCTTAC<br>GGAATGCACTGGGTCCGACAGGCCCCTGGCAAAGGATTGGAGTGGGTCGCCT<br>TCATCAGATACGACGGCTCCAACAAGTACTACGCCGACTCCGTGAAGGGCAG<br>ATTCACCATCTCTCGGGACAACTCCAAGAACACCCTGTACCTGCAGATGAAC<br>TCCCTGAGAGCCGAGGACACCGCCGTGTACTACTGCAAGACCCACGGCTCTC<br>ACGACAATTGGGGCCAGGGCACAATGGTCACCGTGTCCTCTGCTTCCACCAA<br>GGGACCCTCTGTGTTCCCTCTGGCTCCTTCCAGCAAGTCTACCTCTGGCGGA<br>ACAGCTGCTCTGGGCTGCCTGGTCAAGGACTACTTTCCTGAGCCTGTGACCG<br>TGTCTTGGAACTCTGGCGCTCTGACATCCGGCGTGCACACCTTTCCAGCTGT<br>GCTGCAATCCTCCGGCCTGTACTCTCTGTCCTCCGTCGTGACCGTGCCTTCT<br>AGCTCTCTGGGCACCCAGACCTACATCTGCAATGTGAACCACAAGCCTTCCA<br>ACACCAAGGTGGACAAGAGAGTGGAACCCAAGTCCTGCGATAAGACCCACAC<br>CTGTCCACCATGTCCTGCTCCAGAACTGCTCGGCGGACCTTCCGTGTTCCTG<br>TTTCCTCCAAAGCCTAAGGACACCCTGATGATCTCTCGGACCCCTGAAGTGA<br>CCTGCGTGGTGGTGGATGTGTCTCACGAGGATCCCGAAGTGAAGTTCAATTG<br>GTACGTGGACGGCGTGGAAGTGCACAACGCCAAGACCAAGCCTAGAGAGGAA<br>CAGTACAACTCCACCTACAGAGTGGTGTCCGTGCTGACCGTGCTGCACCAGG<br>ATTGGCTGAACGGCAAAGAGTACAAGTGCAAGGTGTCCAACAAGGCCCTGCC<br>TGCTCCTATCGAAAAGACCATCTCCAAGGCCAAGGGCCAGCCTAGGGAACCC<br>CAGGTTTACACCCTGCCTCCAAGCCGGGAAGAGATGACCAAGAACCAGGTGT<br>CCCTGACCTGCCTCGTGAAGGGATTCTACCCCTCCGATATCGCCGTGGAATG<br>GGAGTCTAATGGCCAGCCTGAGAACAACTACAAGACCACACCTCCTGTGCTG<br>GACTCCGACGGCTCATTCTTCCTGTACTCCAAGCTGACAGTGGACAAGTCCA<br>GATGGCAGCAGGGCAACGTGTTCTCCTGCTCCGTGATGCACGAGGCCCTGCA<br>CAATCACTACACCCAGAAGTCCCTGTCTCTGTCTCCCGGAAAAGGCGGCGGA<br>GGATCTGGCGGAGGTGGTAGCGGAGGCGGTGGATCTGCTCCTACCTCCTCCA<br>GCACCAAGAAAACCCAGCTGCAGTTGGAGCATCTGCTGCTGGACCTCCAGAT<br>GATCCTGAATGGCATCAACAATTACAAGAACCCCAAGCTCACCCGGATGCTG<br>ACCGCCAAGTTTGCCATGCCTAAGAAGGCCACCGAGCTGAAACATCTGCAGT<br>GCCTGGAAGAGGAACTGAAGCCCCTGGAAGAAGTGCTGAATCTGGCCCAGTC<br>CAAGAACTTCCACCTGAGGCCTCGGGACCTGATCTCCAACATCAACGTGATC<br>GTGCTCGAGCTGAAGGGCTCCGAGACAACCTTCATGTGCGAGTACGCCGACG<br>AGACAGCTACCATCGTGGAATTTCTGAACCGGTGGATCACCTTCTGCCAGTC<br>CATCATCTCCACACTGACCTGATGA |
| SEQ ID NO: 78 | α-CTLA4 heavy - hCHIg_Knob_Cys | ATGGAAACCGACACACTGCTGCTGTGGGTGCTGCTCTTGTGGGTGCCAGGAT<br>CTACAGGACAGGTGCAGCTGGTGGAATCTGGTGGCGGAGTTGTGCAGCCTGG<br>CAGATCCCTGAGACTGTCTTGTGCCGCCTCCGGCTTCACCTTCTCCCAGCTAC<br>ACCATGCACTGGGTCCGACAGGCCCCTGGCAAAGGATTGGAGTGGGTCACCT<br>TCATCTCTTACGACGGCAACAACAAGTACTACGCCGACTCCGTGAAGGGCAG<br>ATTCACCATCTCTCGGGACAACTCCAAGAACACCCTGTACCTGCAGATGAAC<br>TCCCTGAGAGCCGAGGACACCGCCATCTACTACTGTGCTAGAACCGGCTGGC<br>TGGGCCCCTTTGATTATTGGGGACAGGGCACCCTGGTCACCGTGTCCTCTGC<br>TTCTACCAAGGGACCCAGCGTGTTCCCTCTGGCTCCTTCCAGCAAGTCTACC<br>TCTGGCGGAACAGCTGCTCTGGGCTGCCTGGTCAAGGACTACTTTCCTGAGC<br>CTGTGACCGTGTCTTGGAACTCTGGCGCTCTGACATCCGGCGTGCACACATT<br>TCCAGCTGTGCTGCAGTCCTCCGGCCTGTACTCTCTGTCCTCTGTCGTGACC<br>GTGCCTTCCAGCTCTCTGGGAACCCAGACCTACATCTGCAATGTGAACCACA<br>AGCCTTCCAACACCAAGGTGGACAAGAGAGTGGAACCCAAGTCCTGCGACAA<br>GACCCACACCTGTCCACCATGTCCTGCTCCAGAACTGCTCGGCGGACCTTCC<br>GTGTTCCTGTTTCCTCCAAAGCCTAAGGACACCCTGATGATCTCTCGGACCC<br>CTGAAGTGACCTGCGTGGTGGTGGATGTGTCTCACGAGGATCCCGAAGTGAA<br>GTTCAATTGGTACGTGGACGGCGTGGAAGTGCACAACGCCAAGACCAAGCCT<br>AGAGAGGAACAGTACAACTCCACCTACAGAGTGGTGTCCGTGCTGACCGTGC<br>TGCACCAGGATTGGCTGAACGGCAAAGAGTACAAGTGCAAGGTGTCCAACAA<br>GGCCCTGCCTGCTCCTATCGAAAAGACCATCTCCAAGGCCAAGGGCCAGCCT<br>AGGGAACCCCAGGTTTACACCCTGCCTCCATGCCGGGAAGAGATGACCAAGA<br>ACCAGGTGTCCCTGTGGTGCCTGGTTAAGGGCTTCTACCCCTCCGATATCGC<br>CGTGGAATGGGAGTCTAATGGCCAGCCTGAGAACAACTACAAGACAACCCCT<br>CCTGTGCTGGACTCCGACGGCTCATTCTTCCTGTACTCCAAGCTGACAGTGG<br>ACAAGTCCAGATGGCAGCAGGGCAACGTGTTCTCCTGCTCCGTGATGCACGA<br>GGCCCTGCACAATCACTACACCCAGAAGTCCCTGTCTCTGAGCCCCGGCAAG<br>TGATGA |

TABLE 1-continued

Nucleic acid sequences of ORFs.

| SEQ ID NO | Description | Nucleic Acid Sequence |
|---|---|---|
| SEQ ID NO: 79 | α-CTLA4 heavy - hCHIg_Knob_ Cys - GH_scFv | ATGGAAACCGACACACTGCTGCTGTGGGTGCTGCTCTTGTGGGTGCCAGGAT
CTACAGGACAGGTGCAGCTGGTGGAATCTGGTGGCGGAGTTGTGCAGCCTGG
CAGATCCCTGAGACTGTCTTGTGCCGCCTCCGGCTTCACCTTCTCCAGCTAC
ACCATGCACTGGGTCCGACAGGCCCCTGGCAAAGGATTGGAGTGGGTCACCT
TCATCTCTTACGACGGCAACAACAAGTACTACGCCGACTCCGTGAAGGGCAG
ATTCACCATCTCTCGGGACAACTCCAAGAACACCCTGTACCTGCAGATGAAC
TCCCTGAGAGCCGAGGACACCGCCATCTACTACTGTGCTAGAACCGGCTGGC
TGGGCCCCTTTGATTATTGGGGACAGGGCACCCTGGTCACCGTGTCCTCTGC
TTCTACCAAGGGACCCAGCGTGTTCCCTCTGGCTCCTTCCAGCAAGTCTACC
TCTGGCGGAACAGCTGCTCTGGGCTGCCTGGTCAAGGACTACTTTCCTGAGC
CTGTGACCGTGTCTTGGAACTCTGGCGCTCTGACATCCGGCGTGCACACATT
TCCAGCTGTGCTGCAGTCCTCCGGCCTGTACTCTCTGTCCTCTGTCGTGACC
GTGCCTTCCAGCTCTCTGGGAACCCAGACCTACATCTGCAATGTGAACCACA
AGCCTTCCAACACCAAGGTGGACAAGAGAGTGGAACCCAAGTCCTGCGACAA
GACCCACACCTGTCCACCATGTCCTGCTCCAGAACTGCTCGGCGGACCTTCC
GTGTTCCTGTTTCCTCCAAAGCCTAAGGACACCCTGATGATCTCTCGGACCC
CTGAAGTGACCTGCGTGGTGGTGGATGTGTCTCACGAGGATCCCGAAGTGAA
GTTCAATTGGTACGTGGACGGCGTGGAAGTGCACAACGCCAAGACCAAGCCT
AGAGAGGAACAGTACAACTCCACCTACAGAGTGGTGTCCGTGCTGACCGTGC
TGCACCAGGATTGGCTGAACGGCAAAGAGTACAAGTGCAAGGTGTCCAACAA
GGCCCTGCCTGCTCCTATCGAAAAGACCATCTCCAAGGCCAAGGGCCAGCCT
AGGGAACCCCAGGTTTACACCCTGCCTCCATGCGGGAAGAGATGACCAAGA
ACCAGGTGTCCCTGTGGTGCCTGGTTAAGGGCTTCTACCCCTCCGATATCGC
CGTGGAATGGGAGTCTAATGGCCAGCCTGAGAACAACTACAAGACAACCCCT
CCTGTGCTGGACTCCGACGGCTCATTCTTCCTGTACTCCAAGCTGACAGTGG
ACAAGTCCAGATGGCAGCAGGGCAACGTGTTCTCCTGCTCCGTGATGCACGA
GGCCCTGCACAATCACTACACCCAGAAGTCCCTGTCTCTGTCTCCCGGAAAA
GGCGGCGGAGGATCTGGCGGAGGTGGTAGCGGAGGCGGTGGATCTGAAGTTC
AGCTGGTTGAGAGTGGCGGCGGACTGGTTAAGCCTGGTGGTTCTCTGAGACT
GAGCTGCGCCGCTTCTGGCTTCACATTCAGCCCCTACTCCGTGTTCTGGGTT
CGACAAGCTCCAGGCAAGGGCCTCGAATGGGTGTCCTCTATCAACACCGACA
GCACCTACAAGTATTACGCTGACAGCGTGAAAGGCCGGTTTACCATCAGCAG
AGACAACGCCGAGAACTCCATCTTCCTCCAGATGAATTCTCTGCGCGCTGAG
GATACCGCTGTGTACTACTGCGCCAGAGACAGATCCTACTACGCCTTCTCCT
CCGGCTCTCTGTCTGACTACTACTACGGCCTGGATGTGTGGGGCCAGGGAAC
ACTTGTGACAGTGTCAAGTGGCGGTGGCGGTAGTGGCGGAGGCGGTTCTGGT
GGTGGTGGTTCAGGCGGTGGTGGCAGCGATATCGTGATGACCCAGTCTCCAC
TGAGCCTGAGCGTGACACCTGGCGAGCCTGCCTCTATCTCCTGCAGATCCTC
TCAGTCCCTGCTGCACACCAACCTGTACAACTACCTGGATTGGTATGTGCAG
AAGCCCGGCCAGTCTCCTCAGCTGCTGATCTACCTGGCCTCCAACAGAGCTT
CTGGCGTGCCCGATAGATTCTCCGGTTCTGGCTCTGGCACCGACTTCACCCT
GAAGATTTCCAGAGTGGAAACAGAGGACGTGGGCGTGTACTATTGCATGCAG
GCTCTGCAGATTCCCCGGACCTTCGGCCAGGGCACCAAACTGGAAATCAAGT
GATGA |
| SEQ ID NO: 80 | α-CTLA4 light - hCLIg_vk - IL2 | ATGGAAACCGACACACTGCTGCTGTGGGTGCTGCTCTTGTGGGTGCCAGGAT
CTACAGGCGAGATCGTGCTGACCCAGTCTCCTGGCACACTGTCACTGTCTCC
AGGCGAGAGAGCTACCCTGTCCTGTAGAGCCTCTCAGTCCGTGGGCTCCTCT
TACCTGGCTTGGTATCAGCAGAAGCCCGGCCAGGCTCCTAGACTGTTGATCT
ACGGCGCCTTCTCCAGAGCCACAGGCATCCCTGATAGATTCTCCGGCTCTGG
CTCTGGCACCGACTTCACCCTGACCATCTCCAGACTGGAACCCGAGGACTTC
GCCGTGTACTACTGTCAGCAGTACGGCTCCTCTCCTTGGACCTTTGGCCAGG
GCACCAAGGTGGAAATCAAGCGGACAGTGGCCGCTCCTTCCGTGTTCATCTT
CCCACCTTCCGACGAGCAGCTGAAGTCCGGCACAGCTTCTGTCGTGTGCCTG
CTGAACAACTTCTACCCTCGGGAAGCCAAGGTGCAGTGGAAGGTGGACAATG
CCCTGCAGTCCGGCAACTCCCAAGAGTCTGTGACCGAGCAGGACTCCAAGGA
CAGCACCTACAGCCTGTCCTCCACACTGACCCTGTCCAAGGCCGACTACGAG
AAGCACAAGGTGTACGCCTGCGAAGTGACCCATCAGGGCCTGTCTAGCCCTG
TGACCAAGTCTTTCAACAGAGGCGAGTGTGGCGGCGGAGGATCTGGCGGAGG
TGGAAGCGGAGGCGGTGGATCTGCTCCTACCTCCAGCACCAAGAAAACC
CAGCTGCAGTTGGAGCATCTGCTGCTGGACCTGCAGATGATCCTGAACGGCA
TCAACAACTACAAGAACCCCAAGCTGACCCGGATGCTGACCGCCAAGTTTGC
CATGCCTAAGAAGGCCACCGAGCTGAAACATCTGCAGTGCCTGGAAGAGGAA
CTGAAGCCCCTGGAAGAAGTGCTGAATCTGGCCCAGTCCAAGAACTTCCACC
TGAGGCCTCGGGACCTGATCTCCAACATCAACGTGATCGTGCTCGAGCTGAA
GGGCTCCGAGACAACCTTCATGTGCGAGTACGCCGACGAGACTGCTACCATC
GTGGAATTTCTGAACCGGTGGATCACCTTCTGCCAGTCCATCATCTCTACCC
TGACCTGATGA |
| SEQ ID NO: 81 | α-TRAILR2 heavy - hCHIg_Hole_ Cys | ATGGAAACCGACACACTGCTGCTGTGGGTGCTGCTCTTGTGGGTGCCAGGAT
CTACAGGCGAAGTGCAGCTGGTTCAATCTGGCGGCGGAGTGGAAGACCTGG
CGGATCTCTGAGACTGTCTTGTGCCGCCTCTGGCTTCACCTTCGACGACTAC
GGAATGTCCTGGGTCCGACAGGCTCCTGGCAAAGGACTGGAATGGGTGTCCG
GCATCAATTGGAACGGCGGCTCTACCGGCTACGCCGACTCTGTGAAGGGCAG
AGTGACCATCTCCAGAGACAACGCCAAGAACTCCCTGTACCTGCAGATGAAC |

TABLE 1-continued

Nucleic acid sequences of ORFs.

| SEQ ID NO | Description | Nucleic Acid Sequence |
|---|---|---|
|  |  | AGCCTGAGAGCCGAGGACACCGCCGTGTACTACTGTGCTAAGATCCTCGGCG<br>CTGGCAGAGGCTGGTACTTTGATCTGTGGGGCAAGGGCACCACCGTGACCGT<br>TTCTTCCGCTTCCACCAAGGGACCCAGCGTGTTCCCTCTGGCTCCTTCCAGC<br>AAGTCTACCTCTGGCGGAACAGCTGCTCTGGGCTGCCTGGTCAAGGACTACT<br>TTCCTGAGCCTGTGACCGTGTCCTGGAACTCTGGCGCTCTGACATCTGGCGT<br>GCACACCTTTCCAGCTGTGCTGCAGTCCTCCGGCCTGTACTCTCTGTCCTCT<br>GTCGTGACCGTGCCTTCCAGCTCTCTGGGAACCCAGACCTACATCTGCAATG<br>TGAACCACAAGCCTTCCAACACCAAGGTGGACAAGAGAGTGGAACCCAAGTC<br>CTGCGACAAGACCCACACCTGTCCTCCATGTCCTGCTCCAGAACTGCTCGGC<br>GGACCTTCCGTGTTCCTGTTTCCTCCAAAGCCTAAGGACACCCTGATGATCT<br>CTCGGACCCCTGAAGTGACCTGCGTGGTGGTGGATGTGTCTCACGAGGATCC<br>CGAAGTGAAGTTCAATTGGTACGTGGACGGCGTGGAAGTGCACAATGCCAAG<br>ACCAAGCCTAGAGAGGAACAGTACAACTCCACCTACAGAGTGGTGTCCGTGC<br>TGACCGTGCTGCACCAGGATTGGCTGAACGGCAAAGAGTACAAGTGCAAGGT<br>GTCCAACAAGGCCCTGCCTGCTCCTATCGAAAAGACCATCAGCAAGGCCAAG<br>GGCCAGCCTCGGGAACCTCAAGTCTGTACCCTGCCTCCTAGCCGGGAAGAGA<br>TGACCAAGAACCAGGTGTCCCTGTCCTGTGCCGTGAAGGGCTTCTACCCCTTC<br>CGATATCGCCGTGGAATGGGAGAGCAATGGCCAGCCAGAGAACAACTACAAG<br>ACAACCCCTCCTGTGCTGGACTCCGACGGCTCATTCTTCCTGGTGTCCAAGC<br>TGACAGTGGACAAGTCCAGATGGCAGCAGGGCAACGTGTTCTCCTGCTCCGT<br>GATGCACGAGGCCCTGCACAATCACTACACCCAGAAGTCCCTGTCTCTGAGC<br>CCCGGCAAGTGATGA |
| SEQ ID NO: 82 | α-meso AB237 heavy - hCHIg_Knob_Cys | ATGGAAACCGATACACTGCTGCTGTGGGTGCTGCTCCTCTGGGTGCCAGGAT<br>CTACAGGCCAGGTCCAGCTGCAGGAAAGCGGCCCTGGACTGGTCAAGCCTAG<br>CCAGACCCTGAGCCTGACCTGTACCGTGTCCGGCGGCAGCATCAACAACAAC<br>AATTACTACTGGACATGGATCCGGCAGCACCCCGGCAAGGGCCTGGAATGGA<br>TCGGCTACATCTACTACAGCGGCTCCACCTTCTACAACCCCAGCCTGAAGTC<br>CAGAGTGACCATCAGCGTGGACACCAGCAAGAACCCAGTTCTCCCTGAAGCTG<br>AGCAGCGTGACAGCCGCCGACACAGCCGTGTACTACTGCGCCAGAGAAGATA<br>CCATGACCGGCCTGGATGTGTGGGGCCAGGGCACCACAGTGACAGTGTCTAG<br>CGCCAGCACCAAGGGCCCTAGCGTCTTCCCTCTGGCCCCTAGCTCTAAGAGC<br>ACATCTGGCGGAACAGCCGCCCTGGGCTGCCTGGTCAAGGATTACTTTCCTG<br>AGCCCGTGACCGTGTCCTGGAACTCTGGTGCTCTGACCAGCGGCGTGCACAC<br>CTTTCCAGCTGTGCTGCAGAGCAGCGGCCTGTACAGCCTGTCTAGCGTGGTC<br>ACAGTGCCTAGCAGCAGCCTGGGCACACAGACCTACATCTGCAACGTGAACC<br>ACAAGCCCAGCAACACCAAGGTGGACAAGCGGGTGGAACCCAAGAGCTGCGA<br>CAAGACCCACACCTGTCCTCCTGTCCTGCCCCTGAACTGCTGGGCGGACCT<br>TCCGTGTTCCTGTTCCCTCCAAAGCCCAAGGACACCCTGATGATCAGCCGGA<br>CCCCTGAAGTGACCTGCGTGGTGGTGGATGTGTCCCACGAGGATCCCGAAGT<br>GAAGTTCAATTGGTACGTGGACGGCGTGGAAGTGCACAACGCCAAGACCAAG<br>CCCAGAGAGGAACAGTACAACAGCACCTACCGGGTGGTGTCCGTGCTGACCG<br>TGCTGCACCAGGACTGGCTGAACGGCAAAGAGTACAAGTGCAAGGTGTCCAA<br>CAAGGCCCTGCCAGCCCCTATCGAGAAAACCATCAGCAAGGCCAAGGGCCAG<br>CCCCGCGAACCTCAGGTGTACACACTGCCTCCCTGCCGGGAAGAGATGACCA<br>AGAACCAGGTGTCCCTGTGGTGTCTCGTGAAGGGCTTCTACCCCTCCGATAT<br>CGCCGTGGAATGGGAGAGCAACGGCCAGCCCGAGAACAACTACAAGACCACC<br>CCTCCCGTGCTGGACAGCGACGGCAGCTTCTTCCTGTACTCCAAACTGACCG<br>TGGACAAGAGCCGGTGGCAGCAGGGCAATGTGTTCAGCTGTAGCGTGATGCA<br>CGAGGCCCTGCACAACCACTACACCCAGAAGTCCCTGTCCCTGAGCCCTGGC<br>AAGTAATGA |
| SEQ ID NO: 83 | α-meso AB237 light - hCLIg_vk | ATGGAAACCGATACACTGCTGCTGTGGGTGCTGCTCCTCTGGGTGCCAGGCA<br>GCACCGGCGATATCCAGATGACACAGAGCCCTAGCAGCCTGAGCGCCAGCGT<br>GGGCGATAGAGTGACCATCACCTGTCGGGCCAGCCAGAGCATCAACAACTAC<br>CTGAACTGGTATCAGCAGAAGCCCGGCAAGGCCCCTACCCTGCTGATCTATG<br>CCGCTTCTAGCCTGCAGAGCGGCGTGCCCAGCAGATTTTCTGGCAGCAGATC<br>CGGCACCGACTTCACCCTGACAATCAGCAGCCTGCAGCCCGAGGACTTCGCC<br>GCCTACTTCTGCCAGCAGACCTACAGCAATCCCACCTTCGGCCAGGGCACCA<br>AGGTGGAAGTGAAGAGAACAGTGGCCGCTCCCAGCGTGTTCATCTTCCCACC<br>CAGCGACGAGCAGCTGAAGTCTGGACAGCCAGCGTCGTGTGCCTGCTGAAC<br>AACTTCTACCCCAGAGAAGCCAAGGTGCAGTGGAAGGTGGACAACGCCCTGC<br>AGTCCGGCAACAGCCAGGAAAGCGTCACCGAGCAGGACAGCAAGGACTCCAC<br>CTACAGCCTGTCCAGCACCCTGACCCTGAGCAAGGCCGACTACGAGAAGCAC<br>AAAGTGTACGCCTGCGAAGTGACCCACCAGGGCCTGAGCAGCCCCGTGACCA<br>AGAGCTTCAATAGAGGCGAGTGCTAATGA |
| SEQ ID NO: 84 | α-PDL1 heavy - hCHIg_Hole_Cys | ATGGAAACCGATACCCTGCTGCTGTGGGTGCTGCTCCTCTGGGTGCCAGGAT<br>CTACAGGCGAGGTGCAGCTGCTGGAATCTGGCGGAGGACTGGTGCAGCCTGG<br>CGGCTCTCTGAGACTGTCTTGTGCCGCCTCCGGCTTCACCTTCTCCAGCTAT<br>ATCATGATGTGGGTCCGACAGGCCCCTGGCAAGGGCCTGGAATGGGTGTCCT<br>CTATCTACCCCTCCGGCGGCATCACCTTTTACGCCGACACCGTGAAGGGCCG<br>GTTCACCATCTCCCGGGACAACTCCAAGAACACCCTGTACCTGCAGATGAAC<br>TCCCTGCGGGCCGAGGACACCGCCGTGTACTACTGCGCTAGAATCAAGCTGG<br>GCACCGTGACCACCGTGGACTATTGGGGCCAGGGCACCCTGGTCACCGTGTC |

TABLE 1-continued

Nucleic acid sequences of ORFs.

| SEQ ID NO | Description | Nucleic Acid Sequence |
|---|---|---|
| | | CTCTGCTTCTACCAAGGGCCCCTCCGTGTTCCCTCTGGCCCCTTCCAGCAAG<br>TCCACCTCTGGCGGAACCGCTGCTCTGGGCTGCCTGGTCAAGGACTACTTCC<br>CCGAGCCCGTGACCGTGTCTTGGAACTCTGGCGCCCTGACCAGCGGCGTGCA<br>CACATTTCCAGCCGTGCTGCAGTCCAGCGGCCTGTACTCTCTGTCCTCCGTC<br>GTGACAGTGCCCTCCAGCTCTCTGGGCACACAGACCTACATCTGCAACGTGA<br>ACCACAAGCCCTCCAACACCAAGGTGGACAAGCGGGTGGAACCCAAGTCCTG<br>CGACAAGACCCACACCTGTCCTCCCTGTCCTGCCCCTGAACTGCTGGGCGGA<br>CCCAGCGTGTTCCTGTTCCCTCCAAAGCCTAAGGACACCCTGATGATCTCCC<br>GGACCCCTGAAGTGACCTGCGTGGTGGTGGACGTGTCCCACGAGGATCCCGA<br>AGTGAAGTTCAATTGGTACGTGGACGGCGTGGAAGTGCACAACGCCAAGACC<br>AAGCCTAGAGAGGAACAGTACAACTCCACCTACCGGGTGGTGTCCGTGCTGA<br>CAGTGCTGCATCAGGACTGGCTGAACGGCAAAGAGTACAAGTGCAAGGTGTC<br>CAACAAGGCCCTGCCAGCCCCTATCGAAAAGACCATCTCCAAGGCCAAGGGC<br>CAGCCAAGAGAGCCTCAAGTCTGCACACTGCCTCCCAGCCGGGAAGAGATGA<br>CCAAGAACCAGGTGTCCCTGAGCTGCGCTGTGAAGGGCTTCTACCCTTCCGA<br>TATCGCCGTGGAATGGGAGAGCAACGGCCAGCCCGAGAACAATTACAAGACC<br>ACCCCTCCCGTGCTGGACTCCGACGGCTCATTCTTCCTGGTGTCCAAGCTGA<br>CCGTGGACAAGTCCCGGTGGCAGCAGGGCAACGTGTTCTCCTGCTCTGTGAT<br>GCACGAGGCCCTGCACAACCACTACACCCAGAAGTCCCTGTCCCTGTCTCCC<br>GGCAAGTAATGA |
| SEQ ID NO: 85 | α-PDL1 light - hCLIg_v1 | ATGGAAACCGATACCCTGCTGCTGTGGGTGCTGCTCCTCTGGGTGCCAGGCT<br>CTACCGGCCAGTCTGCTCTGACCCAGCCTGCCTCTGTGTCTGGCTCCCCTGG<br>CCAGTCCATCACCATCAGCTGTACCGGCACCTCCTCCGACGTGGGCGGCTAC<br>AACTACGTGTCCTGGTATCAGCAGCATCCCGGCAAGGCCCCTAAGCTGATGA<br>TCTACGACGTGTCCAACCGGCCCTCCGGCGTGTCCAATCGGTTCTCTGGCTC<br>CAAGTCCGGCAACACCGCCTCCCTGACAATCAGCGGACTGCAGGCCGAGGAC<br>GAGGCCGACTACTACTGCTCCTCCTACACCTCCAGCTCTACCCGGGTGTTCG<br>GCACCGGCACCAAAGTGACAGTGCTGGGCCAGCCCAAGGCCAACCCCACCGT<br>GACCCTGTTCCTCCATCCTCCGAGGAACTGCAGGCTAACAAGGCCACCCTC<br>GTGTGCCTGATCTCCGACTTCTACCCTGGCGCCGTGACCGTGGCTTGGAAGG<br>CTGATGGCTCTCCTGTGAAGGCCGGCGTGGAAACCACCAAGCCCTCCAAGCA<br>GTCCAACAACAAATACGCCGCCTCCAGCTACCTGTCCCTGACCCCTGAGCAG<br>TGGAAGTCCCACCGGTCCTACAGCTGCCAGGTCACACATGAGGGCTCCACCG<br>TGGAAAAGACCGTGGCCCCTACCGAGTGCTCCTAATGA |
| SEQ ID NO: 86 | α-HER3 heavy - mFc_Knob_Cys | ATGGAAACCGACACACTGCTGCTGTGGGTGCTGCTCTTGTGGGTGCCAGGAT<br>CTACAGGACAGGTGCAGCTGGTTCAGTCTGGCGGAGGATTGGTTCAGCCAGG<br>CGGGATCCCTGAGACTGTCTTGTGCCGCTTCTGGCTTCACCTTCGACGACTAC<br>GCTATGCACTGGGTCCGACAGGCCCCTGGCAAAGGATTGGAATGGGTGGCCG<br>GCATCTCTTGGGACTCTGGCTACTACCGGCTACGCCGACTCTGTGAAGGGCAG<br>ATTCACCATCTCTCGGGACAACGCCAAGAACTCCCTGTACCTGCAGATGAAC<br>AGCCTGAGAGCCGAGGACACCGCTCTGTACTACTGCGCTAGAGATCTGGGCG<br>CCTACCAGTGGGTGGAAGGCTTTGATTATTGGGGCCAGGGCACCCTGGTCAC<br>CGTGTCCTCTGCTTCTACCAAGGGACCCAGCGTGTTCCCTCTGGCTCCTTCC<br>AGCAAGTCTACCTCTGGCGGAACAGCTGCTCTGGGCTGCCTGGTCAAGGACT<br>ACTTTCCTGAGCCTGTGACCGTGTCTTGGAACTCCGGCGCTCTGACATCTGG<br>CGTGCACACCTTTCCAGCTGTGCTGCAGTCCTCCGGCCTGTACTCTCTGTCC<br>TCTGTCGTGACCGTGCCTTCCAGCTCTCTGGGAACCCAGACCTACATCTGCA<br>ATGTGAACCACAAGCCTAGCAACACCAAGGTGGACAAGAGAGTGGAACCCAA<br>GTCCTGCACCATCAAGCCCTGTCCTCCATGCAAGTGCCCCGCTCCTAATCTG<br>CTCGGAGGCCCTTCCGTGTTCATCTTCCCACCTAAGATCAAGGACGTGCTGA<br>TGATCTCCCTGTCTCCTATCGTGACCTGCGTGGTGGTGGACGTGTCCGAGGA<br>TGATCCTGACGTGCAGATCAGTTGGTTCGTGAACAACGTGGAAGTGCACACC<br>GCTCAGACCCAGACACACAGAGAGGACTACAACAGCACCCTGAGAGTGGTGT<br>CTGCCCTGCCTATCCAGCACCAGGATTGGATGTCCGGCAAAGAATTCAAGTG<br>CAAAGTCAACAACAAGGACCTGCCTGCTCCAATCGAGCGGACCATCTCTAAG<br>CCTAAGGGCTCTGTCAGGGCCCCTCAGGTGTACGTTCTGCCTCCTTGCGAGG<br>AAGAGATGACCAAGAAACAAGTGACCCTGTGGTGCATGGTCACCGACTTCAT<br>GCCCGAGGACATCTACGTGGAATGGACCAACAACGGCAAGACCGAGCTGAAC<br>TACAAGAACACCGAGCCTGTGCTGGACTCCGACGGCTCCTACTTCATGTACT<br>CCAAGCTGCGCGTCGAGAAGAAGAACTGGGTCGAGAAATCCTACTCCTG<br>CTCCGTGGTGCACGAGGGCCTGCACAATCACCACACCAAGTCCTTCTCT<br>CGGACCCCTGGAAAGTGATGA |
| SEQ ID NO: 87 | α-IGF1R heavy - mFc_Hole_Cys | ATGGAAACCGACACACTGCTGCTGTGGGTGCTGCTCTTGTGGGTGCCAGGAT<br>CTACAGGCGAAGTGCAGCTGTTCAGTCTGGCGGAGGATTGGTTCAGCCTGG<br>CGGATCCCTGAGACTGTCTTGTGCCGCCTCTGGCTTCATGTTCAGCAGATAC<br>CCCATGCACTGGGTCCGACAGGCCCCTGGAAAAGGACTGGAATGGGTCGGAT<br>CCATCTCCGGAAGTGGCGGCGTACCCCTTACGCCGATTCTGTGAAGGGCAG<br>ATTCACCATCAGCCGGGACAACTCCAAGAACACCCTGTACCTGCAGATGAAC<br>TCCCTGAGAGCCGAGGACACCGCCGTGTACTACTGCGCCAAGGACTTCTACC<br>AGATCCTGACCGGCAACGCCTTCGACTATTGGGGCCAGGGCACAACCGTGAC<br>CGTGTCCTCTGCTTCTACCAAGGGACCCAGCGTGTTCCCTCTGGCTCCTTCC<br>AGCAAGTCTACCTCTGGCGGAACAGCTGCTCTGGGCTGCCTGGTCAAGGACT |

TABLE 1-continued

Nucleic acid sequences of ORFs.

| SEQ ID NO | Description | Nucleic Acid Sequence |
|---|---|---|
| | | ACTTTCCTGAGCCTGTGACAGTGTCCTGGAACTCTGGCGCTCTGACATCCGG<br>CGTGCACACCTTTCCAGCTGTGCTGCAATCCAGCGGCCTGTACTCTCTGTCC<br>TCCGTCGTGACAGTGCCTTCCAGCTCTCTGGGAACCCAGACCTACATCTGCA<br>ATGTGAACCACAAGCCTTCCAACACCAAGGTGGACAAGAGAGTGGAACCCAA<br>GTCCTGCACCATCAAGCCCTGTCCTCCATGCAAGTGCCCCGCTCCTAATCTG<br>CTCGGAGGCCCTTCCGTGTTCATCTTCCCACCTAAGATCAAGGACGTGCTGA<br>TGATCTCCCTGTCTCCTATCGTGACCTGCGTGGTGGTGGACGTGTCCGAGGA<br>TGATCCTGACGTGCAGATCAGTTGGTTCGTGAACAACGTGGAAGTGCACACC<br>GCTCAGACCCAGACACACAGAGAGGACTACAACAGCACCCTGAGAGTGGTGT<br>CTGCCCTGCCTATCCAGCACCAGGATTGGATGTCCGGCAAGAATTCAAGTG<br>CAAAGTCAACAACAAGGACCTGCCTGCTCCAATCGAGCGGACCATCTCTAAG<br>CCTAAGGGCTCTGTGCGGGCTCCCCAAGTTTGTGTTCTGCCTCCACCTGAGG<br>AAGAGATGACCAAGAAACAAGTGACCCTGTCCTGCGCCGTGACCGACTTCAT<br>GCCTGAGGACATCTACGTGGAATGGACCAACAACGGCAAGACCGAGCTGAAT<br>TACAAGAACACAGAGCCTGTGCTGGACTCCGACGGCTCCTACTTCATGGTGT<br>CTAAGCTGCGCGTCGAGAAGAAGAACTGGGTCGAGAGAAATCCTACTCCTG<br>CTCCGTGGTGCACGAGGGCCTGCACAATCACCACACCACCAAGTCCTTCTCT<br>CGGACCCCTGGCAAGTGATGA |
| SEQ ID NO: 88 | α-CD221 heavy - hCHIg_Hole_Cys | ATGGAAACCGACACACTGCTGCTGTGGGTGCTGCTCTTGTGGGTGCCAGGAT<br>CTACAGGCGAAGTGCAGCTGGTTCAGTCTGGCGCCGAAGTGAAGAAACCTGG<br>CTCCTCCGTGAAGGTGTCCTGCAAGGCTTCTGGCGGACACCTTCTCCTCTTAC<br>GCCATCTCCTGGGTCCGACAGGCTCCTGGACAAGGCTTGGAATGGATGGGCG<br>GCATCATCCCCATCTTCGGCACCGCCAATTACGCCCAGAAATTCCAGGGCAG<br>AGTGACCATCACCGCCGACAAGTCTACCTCCACCGCCTACATGGAACTGTCC<br>AGCCTGAGATCTGAGGACACCGCCGTGTACTACTGCGCTAGAGCCCCTCTGA<br>GATTCCTGGAATGGTCTACCCAGGACCACTACTACTATTACTACATGGACGT<br>GTGGGGCAAGGGCACCACCGTGACAGTTTCTTCCGCCTCCACCAAGGGACCC<br>AGCGTTTTCCCTCTGGCTCCATCCTCCAAGTCCACCTCTGGTGGAACAGCTG<br>CTCTGGGCTGCCTGGTCAAGGACTACTTTCCTGAGCCTGTGACCGTGTCCTG<br>GAACTCTGGCGCTCTGACATCTGGCGTGCACACCTTTCCAGCTGTGCTGCAG<br>TCCTCCGGCCTGTACTCTCTGTCCTCTGTCGTGACCGTGCCTTCCAGCTCTC<br>TGGGAACCCAGACCTACATCTGCAATGTGAACCACAAGCCTTCCAACACCAA<br>GGTCGACAAGAGAGTGGAACCCAAGTCCTGCGACAAGACCCACACCTGTCCT<br>CCATGTCCTGCTCCAGAACTGCTCGGCGGACCTTCCGTGTTCCTGTTTCCTC<br>CAAAGCCTAAGGACACCCTGATGATCTCTCGGACCCCTGAAGTGACCTGCGT<br>GGTGGTGGATGTGTCTCACGAGGACCCAGAAGTGAAGTTCAATTGGTACGTG<br>GACGGCGTGGAAGTGCACAACGCCAAGACCAAGCCTAGAGAGGAACAGTACA<br>ACTCCACCTACAGAGTGGTGTCCGTGCTGACCGTGCTGCACCAGGATTGGCT<br>GAACGGCAAAGAGTACAAGTGCAAGGTGTCCAACAAGGCCCTGCCTGCTCCT<br>ATCGAAAAGACCATCTCCAAGGCCAAGGGCCAGCCTCGGGAACCTCAAGTCT<br>GTACCCTGCCTCCTAGCCGGGAAGAGATGACCAAGAACCAGGTGTCCCTGTC<br>CTGTGCCGTGAAGGGCTTCTACCCTTCCGATATCGCCGTGGAATGGGAGAGC<br>AATGGCCAGCCAGAGAACAACTACAAGACAACCCCTCCTGTGCTGGACTCCG<br>ACGGCTCATTCTTCCTGGTGTCCAAGCTGACAGTGGACAAGTCCAGATGGCA<br>GCAGGGCAACGTGTTCTCCTGCTCCGTGATGCACGAGGCCCTGCACAATCAC<br>TACACACAGAAGTCCCTGTCTCTGAGCCCCGGCAAGTGATGA |
| SEQ ID NO: 89 | α-PD1 heavy - hCHIg_Knob_Cys | ATGGAAACCGACACACTGCTGCTGTGGGTGCTGCTCTTGTGGGTGCCAGGAT<br>CTACAGGACAGGTGCAGCTGGTGGAATCTGGTGGCGGAGTTGTGCAGCCTGG<br>CAGATCTCTGAGACTGGACTGCAAGGCCTCCGGCATCACCTTCTCCAACTCT<br>GGCATGCACTGGGTCCGACAGGCCCCTGGAAAAGGACTGGAATGGGTCGCCG<br>TGATTTGGTACGACGGCTCCAAGAGGTACTACGCCGACTCCGTGAAGGGCAG<br>ATTCACCATCTCTCGGGACAACTCCAAGAACACCCTGTTTCTGCAGATGAAC<br>TCCCTGAGAGCCGAGGACACCGCCGTGTACTACTGTGCCACCAACGACGATT<br>ATTGGGGCCAGGGCACACTGGTCACCGTGTCCTCTGCTTCTACCAAGGGACC<br>CAGCGTGTTCCCTCTGGCTCCTTCCAGCAAGTCTACCTCTGGCGGAACAGCT<br>GCTCTGGGCTGCCTGGTCAAGGACTACTTTCCTGAGCCTGTGACCGTGTCTT<br>GGAACTCTGGCGCTCTGACATCCGGCGTGCACACCTTTCCAGCTGTGCTGCA<br>ATCCTCCGGCCTGTACTCTCTGTCCTCCGTCGTGACCGTGCCTTCTAGCTCT<br>CTGGGCACCCAGACCTACATCTGCAATGTGAACCACAAGCCTTCCAACACCA<br>AGGTGGACAAGAGAGTGGAACCCAAGTCCTGCGACAAGACCCACACCTGTCC<br>ACCATGTCCTGCTCCAGAACTGCTCGGCGGACCTTCCGTGTTCCTGTTTCCT<br>CCAAAGCCTAAGGACACCCTGATGATCTCTCGGACCCCTGAAGTGACCTGCG<br>TGGTGGTGGATGTGTCTCACGAGGATCCCGAAGTGAAGTTCAATTGGTACGT<br>GGACGGCGTGGAAGTGCACAACGCCAAGACCAAGCCTAGAGAGGAACAGTAC<br>AACTCCACCTACAGAGTGGTGTCCGTGCTGACCGTGCTGCACCAGGATTGGC<br>TGAACGGCAAAGAGTACAAGTGCAAGGTGTCCAACAAGGCCCTGCCTGCTCC<br>TATCGAAAAGACCATCTCCAAGGCCAAGGGCCAGCCTAGGGAACCCCAGGTT<br>TACACCCTGCCTCCATGCCGGGAAGAGATGACCAAGAACCAGGTGTCCCTGT<br>GGTGCCTGGTTAAGGGCTTCTACCCCTCCGATATCGCCGTGGAATGGGAGTC<br>TAATGGCCAGCCTGAGAACAACTACAAGACAACCCCTCCTGTGCTGGACTCC<br>GACGGCTCATTCTTCCTGTACTCCAAGCTGACAGTGGACAAGTCCAGATGGC<br>AGCAGGGCAACGTGTTCTCCTGCTCCGTGATGCACGAGGCCCTGCACAATCA<br>CTACACCCAGAAGTCCCTGTCTCTGTCCCCTGGCAAGTGATGA |

TABLE 1-continued

Nucleic acid sequences of ORFs.

| SEQ ID NO | Description | Nucleic Acid Sequence |
|---|---|---|
| SEQ ID NO: 90 | α-PD1 light - hCLIg_vk | ATGGAAACCGACACACTGCTGCTGTGGGTGCTGCTCTTGTGGGTGCCAGGAT<br>CTACAGGCGAGATCGTGCTGACCCAGTCTCCTGCCACACTGTCACTGTCTCC<br>AGGCGAGAGAGCTACCCTGTCCTGTAGAGCCTCTCAGTCCGTGTCCTCTTAC<br>CTGGCCTGGTATCAGCAGAAGCCTGGACAGGCTCCCCGGCTGCTGATCTACG<br>ATGCCTCTAATAGAGCCACAGGCATCCCCGCCAGATTCTCCGGATCTGGCTC<br>TGGCACAGACTTTACCCTGACCATCTCCAGCCTGGAACCTGAGGACTTCGCC<br>GTGTACTACTGCCAGCAGTCCTCTAACTGGCCTCGGACCTTTGGCCAGGGCA<br>CCAAGGTGGAAATCAAGCGGACAGTGGCCGCTCCTTCCGTGTTCATCTTCCC<br>ACCTTCCGACGAGCAGCTGAAGTCTGGCACCGCTTCTGTCGTGTGCCTGCTG<br>AACAACTTCTACCCTCGGGAAGCCAAGGTGCAGTGGAAGGTGGACAATGCCC<br>TGCAGTCCGGCAACTCCCAAGAGTCTGTGACCGAGCAGGACTCCAAGGACAG<br>CACCTACAGCCTGTCCTCCACACTGACCCTGTCCAAGGCCGACTACGAGAAG<br>CACAAGGTGTACGCCTGCGAAGTGACCCATCAGGGCCTGTCTAGCCCTGTGA<br>CCAAGTCTTTCAACCGGGGCGAGTGCTGATGA |
| SEQ ID NO: 91 | α-IL12β heavy - hCHIg_Hole_Cys | ATGGAAACCGACACACTGCTGCTGTGGGTGCTGCTCTTGTGGGTGCCAGGAT<br>CTACAGGACAGGTGCAGCTGGTGGAATCTGGTGGCGGAGTTGTGCAGCCTGG<br>CAGATCCCTGAGACTGTCTTGTGCCGCCTCCGGCTTCACCTTCTCCTCTTAC<br>GGAATGCACTGGGTCCGACAGGCCCCTGGCAAAGGATTGGAGTGGGTCGCCT<br>TCATCAGATACGACGGCTCCAACAAGTACTACGCCGACTCCGTGAAGGGCAG<br>ATTCACCATCTCTCGGGACAACTCCAAGAACACCCTGTACCTGCAGATGAAC<br>TCCCTGAGAGCCGAGGACACCGCCGTGTACTACTGCAAGACCCACGGCTCTC<br>ACGACAATTGGGGCCAGGGCACAATGGTCACCGTGTCCTCTGCTTCCACCAA<br>GGGACCCTCTGTGTTCCCTCTGGCTCCTTCCAGCAAGTCTACCTCTGGCGGA<br>ACAGCTGCTCTGGGCTGCCTGGTCAAGGACTACTTTCCTGAGCCTGTGACCG<br>TGTCTTGGAACTCTGGCGCTCTGACATCCGGCGTGCACACCTTTCCAGCTGT<br>GCTGCAATCCTCCGGCCTGTACTCTCTGTCCTCCGTCGTGACCGTGCCTTCT<br>AGCTCTCTGGGCACCCAGACCTACATCTGCAATGTGAACCACAAGCCTTCCA<br>ACACCAAGGTGGACAAGAGAGTGGAACCCAAGTCCTGCGATAAGACCCACAC<br>CTGTCCACCATGTCCTGCTCCAGAACTGCTCGGCGGACCTTCCGTGTTCCTG<br>TTTCCTCCAAAGCCTAAGGACACCCTGATGATCTCTCGGACCCCTGAAGTGA<br>CCTGCGTGGTGGTGGATGTGTCTCACGAGGATCCCGAAGTGAAGTTCAATTG<br>GTACGTGGACGGCGTGGAAGTGCACAACGCCAAGACCAAGCCTAGAGAGGAA<br>CAGTACAACTCCACCTACAGAGTGGTGTCCGTGCTGACCGTGCTGCACCAGG<br>ATTGGCTGAACGGCAAAGAGTACAAGTGCAAGGTGTCCAACAAGGCCCTGCC<br>TGCTCCTATCGAAAAGACCATCTCCAAGGCCAAGGGCCAGCCTCGGGAACCT<br>CAAGTCTGTACCCTGCCTCCTAGCCGGGAAGAGATGACCAAGAACCAGGTGT<br>CCCTGTCCTGCGCTGTGAAGGGCTTCTACCCTTCCGATATCGCCGTGGAATG<br>GGAGAGCAATGGCCAGCCTGAGAACAACTACAAGACCACACCTCCTGTGCTG<br>GACTCCGACGGCTCATTCTTCCTGGTGTCCAAGCTGACAGTGGACAAGTCCA<br>GATGGCAGCAGGGCAACGTGTTCTCCTGCTCCGTGATGCACGAGGCCCTGCA<br>CAATCACTACACCCAGAAGTCCCTGTCTCTGAGCCCCGGCAAGTGATGA |

2. Expression and Purification of NanoBiT Constructs.

The plasmids were co-transfected into ExpiCHO cells (Life Technologies A29127). Transfections were performed using 1 mg of total DNA per liter for a multispecific construct with a 1:1:1 heavy chain to light chain to competing light chain ratio. The ExpiCHO transfection was performed according to the manufacturer's instructions. ExpiCHO cells were grown for 7 days at 32° C. with 5% $CO_2$ after transfection. The cells were pelleted by centrifugation at 3000×g. CaptureSelect CH1-XL affinity resin (GE 2943452010) was added to the supernatant and incubated for 1-3 hours at room temperature. The resin was packed into a fritted filter plate (Nunc fritted deepwell filter plates 278011), washed with 3×1 mL of Dulbecco's phosphate-buffered saline (DPBS, Life Technologies 14190-144). The bound protein was eluted from the column with 20 mM citrate, 100 mM NaCl, pH 2.9. The elution fractions were neutralized using 1 M Tris-HCl, pH 8.0. Table 2 shows the amino acid sequences for all the NanoBiT constructs.

TABLE 2

Amino Acid sequences for NanoBiT constructs. All constructs contained an Ig Kappa leader sequence (SEQ ID NO 214: METDTLLLWVLLLWVPGSTG).

| SEQ ID NO | Amino Acid Sequence | Description | Germline | Corresponding DNA SEQ ID NO |
|---|---|---|---|---|
| SEQ ID NO: 92 | QVQLVESGGGVVQPGRSLRLSCAASGFAFSSYGM<br>HWVRQAPGKGLEWVAVIWFDGTKKYYTDSVKGRF<br>TISRDNSKNTLYLQMNTLRAEDTAVYYCARDRGI<br>GARRGPYYMDVWGKGTTVTVSSASTKGPSVFPLA<br>PSSKSTSGGTAALGCLVKDYFPEPVTVSWNSGAL<br>TSGVHTFPAVLQSSGLYSLSSVVTVPSSSLGTQT<br>YICNVNHKPSNTKVDKRVEPKSCGSSGGGGSGGG<br>GSSGGVFTLEDFVGDWEQTAAYNLDQVLEQGGVS | α-amyloid β heavy - LgBiT | VH3-33*01 (SEQ ID NO: 193) | SEQ ID NO: 1 |

TABLE 2-continued

Amino Acid sequences for NanoBiT constructs. All constructs contained an Ig Kappa leader sequence (SEQ ID NO 214: METDTLLLWVLLLWVPGSTG).

| SEQ ID NO | Amino Acid Sequence | Description | Germline | Corresponding DNA SEQ ID NO |
|---|---|---|---|---|
| | SLLQNLAVSVTPIQRIVRSGENALKIDIHVIIPY EGLSADQMAQIEEVFKVVYPVDDHHFKVILPYGT LVIDGVTPNMLNYFGRPYEGIAVFDGKKITVTGT LWNGNKIIDERLITPDGSMLFRVTINS | | | |
| SEQ ID NO: 93 | DIQMTQSPSSLSASVGDRVTITCRASQSISSYLN WYQQKPGKAPKLLIYAASSLQSGVPSRFSGSGSG TDFTLTISSLQPEDFATYYCQQSYSTPLTFGGGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGECGSSGGGGSGGGGSSGGVTGYRLFE EIL | α-amyloid β light - SmBiT | Vk1-39*01 (SEQ ID NO: 201) | SEQ ID NO: 2 |
| SEQ ID NO: 94 | DIQMTQSPSSLSASVGDRVTITCRASQSISSYLN WYQQKPGKAPKLLIYAASSLQSGVPSRFSGSGSG TDFTLTISSLQPEDFATYYCQQSYSTPLTFGGGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC | α-amyloid β light | Vk1-39*01 (SEQ ID NO: 201) | SEQ ID NO: 3 |
| SEQ ID NO: 95 | EVQLVQSGAEVKKSGESLKISCKGSGYSFTSYWI GWVRQMPGKGLEWMGIFYPGDSSTRYSPSFQGQV TISADKSVNTAYLQWSSLKASDTAMYYCARRRNW GNAFDIWGQGTMVTVSSASTKGPSVFPLAPSSKS TSGGTAALGCLVKDYFPEPVTVSWNSGALTSGVH TFPAVLQSSGLYSLSSVVTVPSSSLGTQTYICNV NHKPSNTKVDKRVEPKSCGSSGGGGSGGGGSSGG VFTLEDFVGDWEQTAAYNLDQVLEQGGVSSLLQN LAVSVTPIQRIVRSGENALKIDIHVIIPYEGLSA DQMAQIEEVFKVVYPVDDHHFKVILPYGTLVIDG VTPNMLNYFGRPYEGIAVFDGKKITVTGTLWNGN KIIDERLITPDGSMLFRVTINS | α-*Clostridium difficile* toxin B heavy - LgBiT | VH5-51*01 (SEQ ID NO: 198) | SEQ ID NO: 4 |
| SEQ ID NO: 96 | EIVLTQSPGTLSLSPGERATLSCRASQSVSSSYL AWYQQKPGQAPRLLIYGASSRATGIPDRFSGSGS GTDFTLTISRLEPEDFAVYYCQQYGSSTWTFGQG TKVEIKRTVAAPSVFIFPPSDEQLKSGTASVVCL LNNFYPREAKVQWKVDNALQSGNSQESVTEQDSK DSTYSLSSTLTLSKADYEKHKVYACEVTHQGLSS PVTKSFNRGECGSSGGGGSGGGGSSGGVTGYRLF EEIL | α-*Clostridium difficile* toxin B light - SmBiT | Vk3-20*01 (SEQ ID NO: 205) | SEQ ID NO: 5 |
| SEQ ID NO: 97 | EIVLTQSPGTLSLSPGERATLSCRASQSVSSSYL AWYQQKPGQAPRLLIYGASSRATGIPDRFSGSGS GTDFTLTISRLEPEDFAVYYCQQYGSSTWTFGQG TKVEIKRTVAAPSVFIFPPSDEQLKSGTASVVCL LNNFYPREAKVQWKVDNALQSGNSQESVTEQDSK DSTYSLSSTLTLSKADYEKHKVYACEVTHQGLSS PVTKSFNRGEC | α-*Clostridium difficile* toxin B light | Vk3-20*01 (SEQ ID NO: 205) | SEQ ID NO: 6 |
| SEQ ID NO: 98 | EGQLVQSGGGLVHPGGSLRLSCAGSGFTFSSYGM HWVRQAPGKGLEWVSGIGTGGGTYSTDSVKGRFT ISRDNAKNSLYLQMNSLRAEDMAVYYCARGDYYG SGSFFDCWGQGTLVTVSSASTKGPSVFPLAPSSK STSGGTAALGCLVKDYFPEPVTVSWNSGALTSGV HTFPAVLQSSGLYSLSSVVTVPSSSLGTQTYICN VNHKPSNTKVDKRVEPKSCGSSGGGGSGGGGSSG GVFTLEDFVGDWEQTAAYNLDQVLEQGGVSSLLQ NLAVSVTPIQRIVRSGENALKIDIHVIIPYEGLS ADQMAQIEEVFKVVYPVDDHHFKVILPYGTLVID GVTPNMLNYFGRPYEGIAVFDGKKITVTGTLWNG NKIIDERLITPDGSMLFRVTINS | α-connective growth tissue factor heavy - LgBiT | VH3-13*01 (SEQ ID NO: 188) | SEQ ID NO: 7 |
| SEQ ID NO: 99 | DIQMTQSPSSLSASVGDRVTITCRASQGISSWLA WYQQKPEKAPKSLIYAASSLQSGVPSRFSGSGSG TDFTLTISSLQPEDFATYYCQQYNSYPPTFGQGT KLEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGECGSSGGGGSGGGGSSGGVTGYRLFE EIL | α-connective tissue growth factor light - SmBiT | Vk1D-16*01 (SEQ ID NO: 202) | SEQ ID NO: 8 |

TABLE 2-continued

Amino Acid sequences for NanoBiT constructs. All constructs contained an Ig Kappa leader sequence (SEQ ID NO 214: METDTLLLWVLLLWVPGSTG).

| SEQ ID NO | Amino Acid Sequence | Description | Germline | Corresponding DNA SEQ ID NO |
|---|---|---|---|---|
| SEQ ID NO: 100 | DIQMTQSPSSLSASVGDRVTITCRASQGISSWLAWYQQKPEKAPKSLIYAASSLQSGVPSRFSGSGSGTDFTLTISSLQPEDFATYYCQQYNSYPPTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | α-connective tissue growth factor light | Vk1D-16*01 (SEQ ID NO: 202) | SEQ ID NO: 9 |
| SEQ ID NO: 101 | QVQLVQSGAEVKKPGASVKVSCKASGYSFTNYYIHWVRQAPGQRLEWMGWINAGNGNTKSQKFQGRVTITRDTSASTAYMELSSLRSEDTAVYYCVRRQRFPYYFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCGSSGGGGSGGGGSSGGVFTLEDFVGDWEQTAAYNLDQVLEQGGVSSLLQNLAVSVTPIQRIVRSGENALKIDIHVIIPYEGLSADQMAQIEEVFKVVYPVDDHHFKVILPYGTLVIDGVTPNMLNYFGRPYEGIAVFDGKKITVTGTLWNGNKIIDERLITPDGSMLFRVTINS | α-CSF2 heavy - LgBiT | VH1-3*01 (SEQ ID NO: 185) | SEQ ID NO: 10 |
| SEQ ID NO: 102 | EIVLTQSPATLSVSPGERATLSCRASQSVGTNVAWYQQKPGQAPRVLIYSTSSRATGITDRFSGSGSGTDFTLTISRLEPEDFAVYYCQQFNKSPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECGSSGGGGSGGGGSSGGVTGYRLFEEIL | α-CSF2 light - SmBiT | Vk3D-20*01 (SEQ ID NO: 206) | SEQ ID NO: 11 |
| SEQ ID NO: 103 | EIVLTQSPATLSVSPGERATLSCRASQSVGTNVAWYQQKPGQAPRVLIYSTSSRATGITDRFSGSGSGTDFTLTISRLEPEDFAVYYCQQFNKSPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | α-CSF2 light | Vk3D-20*01 (SEQ ID NO: 206) | SEQ ID NO: 12 |
| SEQ ID NO: 104 | QVQLVESGGGVVQPGRSLRLSCAASGFTFSSYTMHWVRQAPGKGLEWVTFISYDGNNKYYADSVKGRFTISRDNSKNTLYLQMNSLRAEDTAIYYCARTGWLGPFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCGSSGGGGSGGGGSSGGVFTLEDFVGDWEQTAAYNLDQVLEQGGVSSLLQNLAVSVTPIQRIVRSGENALKIDIHVIIPYEGLSADQMAQIEEVFKVVYPVDDHHFKVILPYGTLVIDGVTPNMLNYFGRPYEGIAVFDGKKITVTGTLWNGNKIIDERLITPDGSMLFRVTINS | α-CTLA4 heavy - LgBiT | VH3-30*01 (SEQ ID NO: 192) | SEQ ID NO: 13 |
| SEQ ID NO: 105 | EIVLTQSPGTLSLSPGERATLSCRASQSVGSSYLAWYQQKPGQAPRLLIYGAFSRATGIPDRFSGSGSGTDFTLTIRLEPEDFAVYYCQQYGSSPWTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECGSSGGGGSGGGGSSGGVTGYRLFEEIL | α-CTLA4 light SmBiT | Vk3-20*01 (SEQ ID NO: 205) | SEQ ID NO: 14 |
| SEQ ID NO: 106 | EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | α-CTLA4 light | Vk3-20*01 (SEQ ID NO: 205) | SEQ ID NO: 15 |
| SEQ ID NO: 107 | EVQLVQSGAEVKKPGESLKISCKGSGYIFTNYWIAWVRQMPGKGLESMGIIYPGDSDIRYSPSFQGQVTISADKSITTAYLQWSSLKASDTAMYYCARHDIEGFDYWGRGTLVTVSSASTKGPSVFPLAPSSKSTSGGTAALGCLVKDYFPEPVTVSWNSGALTSGVHTF | α-IFN heavy - LgBiT | VH5-51*01 (SEQ ID NO: 198) | SEQ ID NO: 16 |

TABLE 2-continued

Amino Acid sequences for NanoBiT constructs. All constructs contained an Ig Kappa leader sequence (SEQ ID NO 214: METDTLLLWVLLLWVPGSTG).

| SEQ ID NO | Amino Acid Sequence | Description | Germline | Corresponding DNA SEQ ID NO |
|---|---|---|---|---|
| | PAVLQSSGLYSLSSVVTVPSSSLGTQTYICNVNH KPSNTKVDKRVEPKSCGSSGGGGSGGGGSSGGVF TLEDFVGDWEQTAAYNLDQVLEQGGVSSLLQNLA VSVTPIQRIVRSGENALKIDIHVIIPYEGLSADQ MAQIEEVFKVVYPVDDHHFKVILPYGTLVIDGVT PNMLNYFGRPYEGIAVFDGKKITVTGTLWNGNKI IDERLITPDGSMLFRVTINS | | | |
| SEQ ID NO: 108 | EIVLTQSPGTLSLSPGERATLSCRASQSVSSSFF AWYQQKPGQAPRLLIYGASSRATGIPDRLSGSGS GTDFTLTITRLEPEDFAVYYCQQYDSSAITFGQG TRLEIKRTVAAPSVFIFPPSDEQLKSGTASVVCL LNNFYPREAKVQWKVDNALQSGNSQESVTEQDSK DSTYSLSSTLTLSKADYEKHKVYACEVTHQGLSS PVTKSFNRGECGSSGGGGSGGGGSSGGVTGYRLF EEIL | α-IFN light - SmBiT | Vk3-20*01 (SEQ ID NO: 205) | SEQ ID NO: 17 |
| SEQ ID NO: 109 | EIVLTQSPGTLSLSPGERATLSCRASQSVSSSFF AWYQQKPGQAPRLLIYGASSRATGIPDRLSGSGS GTDFTLTITRLEPEDFAVYYCQQYDSSAITFGQG TRLEIKRTVAAPSVFIFPPSDEQLKSGTASVVCL LNNFYPREAKVQWKVDNALQSGNSQESVTEQDSK DSTYSLSSTLTLSKADYEKHKVYACEVTHQGLSS PVTKSFNRGEC | α-IFN light | Vk3-20*01 (SEQ ID NO: 205) | SEQ ID NO: 18 |
| SEQ ID NO: 110 | QVQLVQSGAEVKKPGASVKVSCKASGYTFTSYSI SWVRQAPGQGLEWMGWISVYNGNTNYAQKFQGRV TMTTDDTSTAYLELRSLRSDDTAVYYCARDPIA AGYWGQGTLVTVSSASTKGPSVFPLAPSSKSTSG GTAALGCLVKDYFPEPVTVSWNSGALTSGVHTFP AVLQSSGLYSLSSVVTVPSSSLGTQTYICNVNHK PSNTKVDKRVEPKSCGSSGGGGSGGGGSSGGVFT LEDFVGDWEQTAAYNLDQVLEQGGVSSLLQNLAV SVTPIQRIVRSGENALKIDIHVIIPYEGLSADQM AQIEEVFKVVYPVDDHHFKVILPYGTLVIDGVTP NMLNYFGRPYEGIAVFDGKKITVTGTLWNGNKII DERLITPDGSMLFRVTINS | α-IFNα heavy - LgBiT | VH1-18*01 (SEQ ID NO: 183) | SEQ ID NO: 19 |
| SEQ ID NO: 111 | EIVLTQSPGTLSLSPGERATLSCRASQSVSSTYL AWYQQKPGQAPRLLIYGASSRATGIPDRFSGSGS GTDFTLTISRLEPEDFAVYYCQQYGSSPRTFGQG TKVEIKRTVAAPSVFIFPPSDEQLKSGTASVVCL LNNFYPREAKVQWKVDNALQSGNSQESVTEQDSK DSTYSLSSTLTLSKADYEKHKVYACEVTHQGLSS PVTKSFNRGECGSSGGGGSGGGGSSGGVTGYRLF EEIL | α-IFNα light - SmBiT | Vk3-20*01 (SEQ ID NO: 205) | SEQ ID NO: 20 |
| SEQ ID NO: 112 | EIVLTQSPGTLSLSPGERATLSCRASQSVSSTYL AWYQQKPGQAPRLLIYGASSRATGIPDRFSGSGS GTDFTLTISRLEPEDFAVYYCQQYGSSPRTFGQG TKVEIKRTVAAPSVFIFPPSDEQLKSGTASVVCL LNNFYPREAKVQWKVDNALQSGNSQESVTEQDSK DSTYSLSSTLTLSKADYEKHKVYACEVTHQGLSS PVTKSFNRGEC | α-IFNα light | Vk3-20*01 (SEQ ID NO: 205) | SEQ ID NO: 21 |
| SEQ ID NO: 113 | QVQLQESGPGLVKPSGTLSLTCAVSGGSISSSNW WSWVRQPPGKGLEWIGEIYHSGSTNYNPSLKSRV TISVDKSKNQFSLKLSSVTAADTAVYYCARWTGR TDAFDIWGQGTMVTVSSASTKGPSVFPLAPSSKS TSGGTAALGCLVKDYFPEPVTVSWNSGALTSGVH TFPAVLQSSGLYSLSSVVTVPSSSLGTQTYICNV NHKPSNTKVDKRVEPKSCGSSGGGGSGGGGSSGG VFTLEDFVGDWEQTAAYNLDQVLEQGGVSSLLQN LAVSVTPIQRIVRSGENALKIDIHVIIPYEGLSA DQMAQIEEVFKVVYPVDDHHFKVILPYGTLVIDG VTPNMLNYFGRPYEGIAVFDGKKITVTGTLWNGN KIIDERLITPDGSMLFRVTINS | α-IGF1R heavy - LgBiT | VH4-4*01 (SEQ ID NO: 197) | SEQ ID NO: 22 |
| SEQ ID NO: 114 | DVVMTQSPLSLPVTPGEPASISCRSSQSLLHSNG YNYLDWYLQKPGQSPQLLIYLGSNRASGVPDRFS GSGSGTDFTLKISRVEAEDVGVYYCMQGTHWPLT FGQGTKVEIKRTVAAPSVFIFPPSDEQLKSGTAS VVCLLNNFYPREAKVQWKVDNALQSGNSQESVTE | α-IGF1R light - SmBiT | Vk2-28*01 (SEQ ID NO: 203) | SEQ ID NO: 23 |

TABLE 2-continued

Amino Acid sequences for NanoBiT constructs. All constructs contained an Ig Kappa leader sequence (SEQ ID NO 214: METDTLLLWVLLLWVPGSTG).

| SEQ ID NO | Amino Acid Sequence | Description | Germline | Corresponding DNA SEQ ID NO |
|---|---|---|---|---|
| | QDSKDSTYSLSSTLTLSKADYEKHKVYACEVTHQ GLSSPVTKSFNRGECGSSGGGGSGGGGSSGGVTG YRLFEEIL | | | |
| SEQ ID NO: 115 | DVVMTQSPLSLPVTPGEPASISCRSSQSLLHSNG YNYLDWYLQKPGQSPQLLIYLGSNRASGVPDRFS GSGSGTDFTLKISRVEAEDVGVYYCMQGTHWPLT FGQGTKVEIKRTVAAPSVFIFPPSDEQLKSGTAS VVCLLNNFYPREAKVQWKVDNALQSGNSQESVTE QDSKDSTYSLSSTLTLSKADYEKHKVYACEVTHQ GLSSPVTKSFNRGEC | α-IGF1R light | Vk2-28*01 (SEQ ID NO: 203) | SEQ ID NO: 24 |
| SEQ ID NO: 116 | EVQLLQSGGGLVQPGGSLRLSCAASGFMFSRYPM HWVRQAPGKGLEWVGSISGSGGATPYADSVKGRF TISRDNSKNTLYLQMNSLRAEDTAVYYCAKDFYQ ILTGNAFDYWGQGTTVTVSSASTKGPSVFPLAPS SKSTSGGTAALGCLVKDYFPEPVTVSWNSGALTS GVHTFPAVLQSSGLYSLSSVVTVPSSSLGTQTYI CNVNHKPSNTKVDKRVEPKSCGSSGGGGSGGGGS SGGVFTLEDFVGDWEQTAAYNLDQVLEQGGVSSL LQNLAVSVTPIQRIVRSGENALKIDIHVIIPYEG LSADQMAQIEEVFKVVYPVDDHHFKVILPYGTLV IDGVTPNMLNYFGRPYEGIAVFDGKKITVTGTLW NGNKIIDERLITPDGSMLFRVTINS | α-IGF1R heavy - LgBiT | VH3-23*01 (SEQ ID NO: 191) | SEQ ID NO: 25 |
| SEQ ID NO: 117 | DIQMTQSPSSLSASLGDRVTITCRASQGISSYLA WYQQKPGKAPKLLIYAKSTLQSGVPSRFSGSGSG TDFTLTISSLQPEDSATYYCQQYWTFPLTFGGGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGECGSSGGGGSGGGGSSGGVTGYRLFE EIL | α-IGF1R light-SmBiT | Vk1-27*01 (SEQ ID NO: 200) | SEQ ID NO: 26 |
| SEQ ID NO: 118 | DIQMTQSPSSLSASLGDRVTITCRASQGISSYLA WYQQKPGKAPKLLIYAKSTLQSGVPSRFSGSGSG TDFTLTISSLQPEDSATYYCQQYWTFPLTFGGGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC | α-IGF1R light | Vk1-27*01 (SEQ ID NO: 200) | SEQ ID NO: 27 |
| SEQ ID NO: 119 | EVQLVQSGGGLVKPGGSLRLSCAASGFTFSSFAM HWVRQAPGKGLEWISVIDTRGATYYADSVKGRFT ISRDNAKNSLYLQMNSLRAEDTAVYYCARLGNFY YGMDVWGQGTTVTVSSASTKGPSVFPLAPSSKST SGGTAALGCLVKDYFPEPVTVSWNSGALTSGVHT FPAVLQSSGLYSLSSVVTVPSSSLGTQTYICNVN HKPSNTKVDKRVEPKSCGSSGGGGSGGGGSSGGV FTLEDFVGDWEQTAAYNLDQVLEQGGVSSLLQNL AVSVTPIQRIVRSGENALKIDIHVIIPYEGLSAD QMAQIEEVFKVVYPVDDHHFKVILPYGTLVIDGV TPNMLNYFGRPYEGIAVFDGKKITVTGTLWNGNK IIDERLITPDGSMLFRVTINS | α-IGF1R heavy - LgBiT | VH3-21*01 (SEQ ID NO: 190) | SEQ ID NO: 28 |
| SEQ ID NO: 120 | EIVLTQSPGTLSVSPGERATLSCRASQSIGSSLH WYQQKPGQAPRLLIKYASQSLSGIPDRFSGSGSG TDFTLTISRLEPEDFAVYYCHQSSRLPHTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGECGSSGGGGSGGGGSSGGVTGYRLFE EIL | α-IGF1R light - SmBiT | Vk3-20*01 (SEQ ID NO: 205) | SEQ ID NO: 29 |
| SEQ ID NO: 121 | EIVLTQSPGTLSVSPGERATLSCRASQSIGSSLH WYQQKPGQAPRLLIKYASQSLSGIPDRFSGSGSG TDFTLTISRLEPEDFAVYYCHQSSRLPHTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC | α-IGF1R light | Vk3-20*01 (SEQ ID NO: 205) | SEQ ID NO: 30 |

TABLE 2-continued

Amino Acid sequences for NanoBiT constructs. All constructs contained an Ig Kappa leader sequence (SEQ ID NO 214: METDTLLLWVLLLWVPGSTG).

| SEQ ID NO | Amino Acid Sequence | Description | Germline | Corresponding DNA SEQ ID NO |
|---|---|---|---|---|
| SEQ ID NO: 122 | QVELVESGGGVVQPGRSQRLSCAASGFTFSSYGM HWVRQAPGKGLEWVAIIWFDGSSTYYADSVRGRF TISRDNSKNTLYLQMNSLRAEDTAVYFCARELGR RYFDLWGRGTLVSVSSASTKGPSVFPLAPSSKST SGGTAALGCLVKDYFPEPVTVSWNSGALTSGVHT FPAVLQSSGLYSLSSVVTVPSSSLGTQTYICNVN HKPSNTKVDKRVEPKSCGSSGGGGSGGGGSSGGV FTLEDFVGDWEQTAAYNLDQVLEQGGVSSLLQNL AVSVTPIQRIVRSGENALKIDIHVIIPYEGLSAD QMAQIEEVFKVVYPVDDHHFKVILPYGTLVIDGV TPNMLNYFGRPYEGIAVFDGKKITVTGTLWNGNK IIDERLITPDGSMLFRVTINS | α-IGF1R heavy - LgBiT | VH3-33*01 (SEQ ID NO: 193) | SEQ ID NO: 31 |
| SEQ ID NO: 123 | EIVLTQSPATLSLSPGERATLSCRASQSVSSYLA WYQQKPGQAPRLLIYDASKRATGIPARFSGSGSG TDFTLTISSLEPEDFAVYYCQQRSKWPPWTFGQG TKVESKRTVAAPSVFIFPPSDEQLKSGTASVVCL LNNFYPREAKVQWKVDNALQSGNSQESVTEQDSK DSTYSLSSTLTLSKADYEKHKVYACEVTHQGLSS PVTKSFNRGECGSSGGGGSGGGGSSGGVTGYRLF EEIL | α-IGF1R light - SmBiT | Vk3-11*01 (SEQ ID NO: 204) | SEQ ID NO: 32 |
| SEQ ID NO: 124 | EIVLTQSPATLSLSPGERATLSCRASQSVSSYLA WYQQKPGQAPRLLIYDASKRATGIPARFSGSGSG TDFTLTISSLEPEDFAVYYCQQRSKWPPWTFGQG TKVESKRTVAAPSVFIFPPSDEQLKSGTASVVCL LNNFYPREAKVQWKVDNALQSGNSQESVTEQDSK DSTYSLSSTLTLSKADYEKHKVYACEVTHQGLSS PVTKSFNRGEC | α-IGF1R light | Vk3-11*01 (SEQ ID NO: 204) | SEQ ID NO: 33 |
| SEQ ID NO: 125 | EVQLVESGGGLVQPGRSLRLSCAASRFTFDDYAM HWVRQAPGKGLEWVSGISWNSGRIGYADSVKGRF TISRDNAENSLFLQMNGLRAEDTALYYCAKGRDS FDIWGQGTMVTVSSASTKGPSVFPLAPSSKSTSG GTAALGCLVKDYFPEPVTVSWNSGALTSGVHTFP AVLQSSGLYSLSSVVTVPSSSLGTQTYICNVNHK PSNTKVDKRVEPKSCGSSGGGGSGGGGSSGGVFT LEDFVGDWEQTAAYNLDQVLEQGGVSSLLQNLAV SVTPIQRIVRSGENALKIDIHVIIPYEGLSADQM AQIEEVFKVVYPVDDHHFKVILPYGTLVIDGVTP NMLNYFGRPYEGIAVFDGKKITVTGTLWNGNKII DERLITPDGSMLFRVTINS | α-IL6R heavy - LgBiT | VH3-9*01 (SEQ ID NO: 196) | SEQ ID NO: 34 |
| SEQ ID NO: 126 | DIQMTQSPSSVSASVGDRVTITCRASQGISSWLA WYQQKPGKAPKLLIYGASSLESGVPSRFSGSGSG TDFTLTISSLQPEDFASYYCQQANSFPYTFGQGT KLEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGECGSSGGGGSGGGGSSGGVTGYRLFE EIL | α-IL6R light - SmBiT | Vk1-12*01 (SEQ ID NO: 199) | SEQ ID NO: 35 |
| SEQ ID NO: 127 | DIQMTQSPSSVSASVGDRVTITCRASQGISSWLA WYQQKPGKAPKLLIYGASSLESGVPSRFSGSGSG TDFTLTISSLQPEDFASYYCQQANSFPYTFGQGT KLEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC | α-IL6R light | Vk1-12*01 (SEQ ID NO: 199) | SEQ ID NO: 36 |
| SEQ ID NO: 128 | EVQLLESGGGLVQPGGSLRLSCAASGFTFSAYEM KWVRQAPGKGLEWVSVIGPSGGFTFYADSVKGRF TISRDNSKNTLYLQMNSLRAEDTAVYYCATEGDN DAFDIWGQGTTVTVSSASTKGPSVFPLAPSSKST SGGTAALGCLVKDYFPEPVTVSWNSGALTSGVHT FPAVLQSSGLYSLSSVVTVPSSSLGTQTYICNVN HKPSNTKVDKRVEPKSCGSSGGGGSGGGGSSGGV FTLEDFVGDWEQTAAYNLDQVLEQGGVSSLLQNL AVSVTPIQRIVRSGENALKIDIHVIIPYEGLSAD QMAQIEEVFKVVYPVDDHHFKVILPYGTLVIDGV TPNMLNYFGRPYEGIAVFDGKKITVTGTLWNGNK IIDERLITPDGSMLFRVTINS | α-LINGO-1 heavy - LgBiT | VH3-23*01 (SEQ ID NO: 191) | SEQ ID NO: 37 |

TABLE 2-continued

Amino Acid sequences for NanoBiT constructs. All constructs contained an Ig Kappa leader sequence (SEQ ID NO 214: METDTLLLWVLLLWVPGSTG).

| SEQ ID NO | Amino Acid Sequence | Description | Germline | Corresponding DNA SEQ ID NO |
|---|---|---|---|---|
| SEQ ID NO: 129 | DIQMTQSPATLSLSPGERATLSCRASQSVSSYLAWYQQKPGQAPRLLIYDASNRATGIPARFSGSGSGTDFTLTISSLEPEDFAVYYCQQRSNWPMYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECGSSGGGGSGGGGSSGGVTGYRLFEEIL | α-LINGO-1 light - SmBiT | Vk3-11*01 (SEQ ID NO: 204) | SEQ ID NO: 38 |
| SEQ ID NO: 130 | DIQMTQSPATLSLSPGERATLSCRASQSVSSYLAWYQQKPGQAPRLLIYDASNRATGIPARFSGSGSGTDFTLTISSLEPEDFAVYYCQQRSNWPMYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | α-LINGO-1 light | Vk3-11*01 (SEQ ID NO: 204) | SEQ ID NO: 39 |
| SEQ ID NO: 131 | EVQLVESGGGLVQPGGSLRLSCAASGFTFSSYAMSWVRQAPGKGLEWVSQISPAGGYTNYADSVKGRFTISADTSKNTAYLQMNSLRAEDTAVYYCARGELPYYRMSKVMDVWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCGSSGGGGSGGGGSSGGVFTLEDFVGDWEQTAAYNLDQVLEQGGVSSLLQNLAVSVTPIQRIVRSGENALKIDIHVIIPYEGLSADQMAQIEEVFKVVYPVDDHHFKVILPYGTLVIDGVTPNMLNYFGRPYEGIAVFDGKKITVTGTLWNGNKIIDERLITPDGSMLFRVTINS | α-neuropilin 1 heavy - LgBiT | VH3-66*01 (SEQ ID NO: 194) | SEQ ID NO: 40 |
| SEQ ID NO: 132 | DIQMTQSPSSLSASVGDRVTITCRASQYFSSYLAWYQQKPGKAPKLLIYGASSRASGVPSRFSGSGSGTDFTLTISSLQPEDFATYYCQQYLGSPPTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECGSSGGGGSGGGGSSGGVTGYRLFEEIL | α-neuropilin 1 light - SmBiT | Vk1-39*01 (SEQ ID NO: 201) | SEQ ID NO: 41 |
| SEQ ID NO: 133 | DIQMTQSPSSLSASVGDRVTITCRASQYFSSYLAWYQQKPGKAPKLLIYGASSRASGVPSRFSGSGSGTDFTLTISSLQPEDFATYYCQQYLGSPPTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | α-neuropilin 1 light | Vk1-39*01 (SEQ ID NO: 201) | SEQ ID NO: 42 |
| SEQ ID NO: 134 | EVQLVQSGAEVKKPGSSVKVSCKASGGTFSSYAISWVRQAPGQGLEWMGGIIPIFGTANYAQKFQGRVTITADKSTSTAYMELSSLRSEDTAVYYCARAPLRFLEWSTQDHYYYYMDVWGKGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCGSSGGGGSGGGGSSGGVFTLEDFVGDWEQTAAYNLDQVLEQGGVSSLLQNLAVSVTPIQRIVRSGENALKIDIHVIIPYEGLSADQMAQIEEVFKVVYPVDDHHFKVILPYGTLVIDGVTPNMLNYFGRPYEGIAVFDGKKITVTGTLWNGNKIIDERLITPDGSMLFRVTINS | α-CD221 heavy - LgBiT | VH1-69*01 (SEQ ID NO: 187) | SEQ ID NO: 43 |
| SEQ ID NO: 135 | SSELTQDPAVSVALGQTVRITCQGDSLRSYYATWYQQKPGQAPILVIYGENKRPSGIPDRFSGSSSGNTASLTITGAQAEDEADYYCKSRDGSGQHLVFGGGTKLTVLGQPKANPTVTLFPPSSEELQANKATLVCLISDFYPGAVTVAWKADGSPVKAGVETTKPSKQSNNKYAASSYLSLTPEQWKSHRSYSCQVTHEGSTVEKTVAPTECGSSGGGGSGGGGSSGGVTGYRLFEEIL | α-CD221 light - SmBiT | Vl3-19*01 (SEQ ID NO: 211) | SEQ ID NO: 44 |
| SEQ ID NO: 136 | SSELTQDPAVSVALGQTVRITCQGDSLRSYYATWYQQKPGQAPILVIYGENKRPSGIPDRFSGSSSGNTASLTITGAQAEDEADYYCKSRDGSGQHLVFGGGTKLTVLGQPKANPTVTLFPPSSEELQANKATLVC | α-CD221 light | Vl3-19*01 (SEQ ID NO: 211) | SEQ ID NO: 45 |

TABLE 2-continued

Amino Acid sequences for NanoBiT constructs. All constructs contained an Ig Kappa leader sequence (SEQ ID NO 214: METDTLLLWVLLLWVPGSTG).

| SEQ ID NO | Amino Acid Sequence | Description | Germline | Corresponding DNA SEQ ID NO |
|---|---|---|---|---|
| | LISDFYPGAVTVAWKADGSPVKAGVETTKPSKQS NNKYAASSYLSLTPEQWKSHRSYSCQVTHEGSTV EKTVAPTECS | | | |
| SEQ ID NO: 137 | EVQLVQSGGGVERPGGSLRLSCAASGFTFDDYAM SWVRQAPGKGLEWVSGINWQGGSTGYADSVKGRV TISRDNAKNSLYLQMNSLRAEDTAVYYCAKILGA GRGWYFDYWGKGTTVTVSSASTKGPSVFPLAPSS KSTSGGTAALGCLVKDYFPEPVTVSWNSGALTSG VHTFPAVLQSSGLYSLSSVVTVPSSSLGTQTYIC NVNHKPSNTKVDKRVEPKSCGSSGGGGSGGGGSS GGVFTLEDFVGDWEQTAAYNLDQVLEQGGVSSLL QNLAVSVTPIQRIVRSGENALKIDIHVIIPYEGL SADQMAQIEEVFKVVYPVDDHHFKVILPYGTLVI DGVTPNMLNYFGRPYEGIAVFDGKKITVTGTLWN GNKIIDERLITPDGSMLFRVTINS | α-death receptor 5 heavy - LgBiT | VH3-20*01 (SEQ ID NO: 189) | SEQ ID NO: 46 |
| SEQ ID NO: 138 | SSELTQDPAVSVALGQTVRITCSGDSLRSYYASW YQQKPGQAPVLVIYGANNRPSGIPDRFSGSSSGN TASLTITGAQAEDEADYYCNSADSSGNHVVFGGG TKLTVLGQPKANPTVTLFPPSSEELQANKATLVC LISDFYPGAVTVAWKADGSPVKAGVETTKPSKQS NNKYAASSYLSLTPEQWKSHRSYSCQVTHEGSTV EKTVAPTECSGSSGGGGSGGGGSSGGVTGYRLFE EIL | α-death receptor 5 light - SmBiT | Vl3-19*01 (SEQ ID NO: 211) | SEQ ID NO: 47 |
| SEQ ID NO: 139 | SSELTQDPAVSVALGQTVRITCSGDSLRSYYASW YQQKPGQAPVLVIYGANNRPSGIPDRFSGSSSGN TASLTITGAQAEDEADYYCNSADSSGNHVVFGGG TKLTVLGQPKANPTVTLFPPSSEELQANKATLVC LISDFYPGAVTVAWKADGSPVKAGVETTKPSKQS NNKYAASSYLSLTPEQWKSHRSYSCQVTHEGSTV EKTVAPTECS | α-death receptor 5 light | Vl3-19*01 (SEQ ID NO: 211) | SEQ ID NO: 48 |
| SEQ ID NO: 140 | EVQLVQSGAEVKKPGESLKISCKGSGYSFSNYWI GWVRQMPGKGLEWMGIIDPSNSYTRYSPSFQGQV TISADKSISTAYLQWSSLKASDTAMYYCARWYYK PFDVWGQGTLVTVSSASTKGPSVFPLAPSSKSTS GGTAALGCLVKDYFPEPVTVSWNSGALTSGVHTF PAVLQSSGLYSLSSVVTVPSSSLGTQTYICNVNH KPSNTKVDKRVEPKSCGSSGGGGSGGGGSSGGVF TLEDFVGDWEQTAAYNLDQVLEQGGVSSLLQNLA VSVTPIQRIVRSGENALKIDIHVIIPYEGLSADQ MAQIEEVFKVVYPVDDHHFKVILPYGTLVIDGVT PNMLNYFGRPYEGIAVFDGKKITVTGTLWNGNKI IDERLITPDGSMLFRVTINS | α-IL23 heavy - LgBiT | VH5-51*01 (SEQ ID NO: 198) | SEQ ID NO: 49 |
| SEQ ID NO: 141 | QSVLTQPPSVSGAPGQRVTISCTGSSSNIGSGYD VHWYQQLPGTAPKLLIYGNSKRPSGVPDRFSGSK SGTSASLAITGLQSEDEADYYCASWTDGLSLVVF GGGTKLTVLGQPKANPTVTLFPPSSEELQANKAT LVCLISDFYPGAVTVAWKADGSPVKAGVETTKPS KQSNNKYAASSYLSLTPEQWKSHRSYSCQVTHEG STVEKTVAPTECSGSSGGGGSGGGGSSGGVTGYR LFEEIL | α-IL23 light - SmBiT | Vl1-40*01 (SEQ ID NO: 208) | SEQ ID NO: 50 |
| SEQ ID NO: 142 | QSVLTQPPSVSGAPGQRVTISCTGSSSNIGSGYD VHWYQQLPGTAPKLLIYGNSKRPSGVPDRFSGSK SGTSASLAITGLQSEDEADYYCASWTDGLSLVVF GGGTKLTVLGQPKANPTVTLFPPSSEELQANKAT LVCLISDFYPGAVTVAWKADGSPVKAGVETTKPS KQSNNKYAASSYLSLTPEQWKSHRSYSCQVTHEG STVEKTVAPTECS | α-IL23 light | Vl1-40*01 (SEQ ID NO: 208) | SEQ ID NO: 51 |
| SEQ ID NO: 143 | QVQLVQSGGGLVQPGGSLRLSCAASGFTFDDYAM HWVRQAPGKGLEWVAGISWDSGSTGYADSVKGRF TISRDNAKNSLYLQMNSLRAEDTALYYCARDLGA YQWVEGFDYWGQGTLVTVSSASTKGPSVFPLAPS SKSTSGGTAALGCLVKDYFPEPVTVSWNSGALTS GVHTFPAVLQSSGLYSLSSVVTVPSSSLGTQTYI CNVNHKPSNTKVDKRVEPKSCGSSGGGGSGGGGS SGGVFTLEDFVGDWEQTAAYNLDQVLEQGGVSSL LQNLAVSVTPIQRIVRSGENALKIDIHVIIPYEG | α-HER3 heavy - LgBiT | VH3-9*01 (SEQ ID NO: 196) | SEQ ID NO: 52 |

TABLE 2-continued

Amino Acid sequences for NanoBiT constructs. All constructs contained an Ig Kappa leader sequence (SEQ ID NO 214: METDTLLLWVLLLWVPGSTG).

| SEQ ID NO | Amino Acid Sequence | Description | Germline | Corresponding DNA SEQ ID NO |
|---|---|---|---|---|
| | LSADQMAQIEEVFKVVYPVDDHHFKVILPYGTLV IDGVTPNMLNYFGRPYEGIAVFDGKKITVTGTLW NGNKIIDERLITPDGSMLFRVTINS | | | |
| SEQ ID NO: 144 | SYELTQDPAVSVALGQTVRITCQGDSLRSYYASW YQQKPGQAPVLVIYGKNNRPSGIPDRFSGSTSGN SASLTITGAQAEDEADYYCNSRDSPGNQWVFGGG TKVTVLGGQPKANPTVTLFPPSSEELQANKATLV CLISDFYPGAVTVAWKADGSPVKAGVETTKPSKQ SNNKYAASSYLSLTPEQWKSHRSYSCQVTHEGST VEKTVAPTECSGSSGGGGSGGGGSSGGVTGYRLF EEIL | α-HER3 light - SmBiT | Vl3-19*01 (SEQ ID NO: 211) | SEQ ID NO: 53 |
| SEQ ID NO: 145 | SYELTQDPAVSVALGQTVRITCQGDSLRSYYASW YQQKPGQAPVLVIYGKNNRPSGIPDRFSGSTSGN SASLTITGAQAEDEADYYCNSRDSPGNQWVFGGG TKVTVLGGQPKANPTVTLFPPSSEELQANKATLV CLISDFYPGAVTVAWKADGSPVKAGVETTKPSKQ SNNKYAASSYLSLTPEQWKSHRSYSCQVTHEGST VEKTVAPTECS | α-HER3 light | Vl3-19*01 (SEQ ID NO: 211) | SEQ ID NO: 54 |
| SEQ ID NO: 146 | EVQLVQSGGGVERPGGSLRLSCAASGFTFDDYGM SWVRQAPGKGLEWVSGINWNGGSTGYADSVKGRV TISRDNAKNSLYLQMNSLRAEDTAVYYCAKILGA GRGWYFDLWGKGTTVTVSSASTKGPSVFPLAPSS KSTSGGTAALGCLVKDYFPEPVTVSWNSGALTSG VHTFPAVLQSSGLYSLSSVVTVPSSSLGTQTYIC NVNHKPSNTKVDKRVEPKSCGSSGGGGSGGGGSS GGVFTLEDFVGDWEQTAAYNLDQVLEQGGVSSLL QNLAVSVTPIQRIVRSGENALKIDIHVIIPYEGL SADQMAQIEEVFKVVYPVDDHHFKVILPYGTLVI DGVTPNMLNYFGRPYEGIAVFDGKKITVTGTLWN GNKIIDERLITPDGSMLFRVTINS | α-TRAILR2 heavy - LgBiT | VH3-20*01 (SEQ ID NO: 189) | SEQ ID NO: 55 |
| SEQ ID NO: 147 | SSELTQDPAVSVALGQTVRITCQGDSLRSYYASW YQQKPGQAPVLVIYGKNNRPSGIPDRFSGSSSGN TASLTITGAQAEDEADYYCNSRDSSGNHVVFGGG TKLTVLGQPKANPTVTLFPPSSEELQANKATLVC LISDFYPGAVTVAWKADGSPVKAGVETTKPSKQS NNKYAASSYLSLTPEQWKSHRSYSCQVTHEGSTV EKTVAPTECSGSSGGGGSGGGGSSGGVTGYRLFE EIL | α-TRAILR2 light - SmBiT | Vl3-19*01 (SEQ ID NO: 211) | SEQ ID NO: 56 |
| SEQ ID NO: 148 | SSELTQDPAVSVALGQTVRITCQGDSLRSYYASW YQQKPGQAPVLVIYGKNNRPSGIPDRFSGSSSGN TASLTITGAQAEDEADYYCNSRDSSGNHVVFGGG TKLTVLGQPKANPTVTLFPPSSEELQANKATLVC LISDFYPGAVTVAWKADGSPVKAGVETTKPSKQS NNKYAASSYLSLTPEQWKSHRSYSCQVTHEGSTV EKTVAPTECS | α-TRAILR2 light | Vl3-19*01 (SEQ ID NO: 211) | SEQ ID NO: 57 |
| SEQ ID NO: 149 | QVQLVQSGAEVKKPGASVKVSCKASGYTFTSSYI NWVRQAPGQGLEWMGTINPVSGSTSYAQKFQGRV TMTRDTSISTAYMELSRLRSDDTAVYYCARGGWF DYWGQGTLVTVSSASTKGPSVFPLAPSSKSTSGG TAALGCLVKDYFPEPVTVSWNSGALTSGVHTFPA VLQSSGLYSLSSVVTVPSSSLGTQTYICNVNHKP SNTKVDKRVEPKSCGSSGGGGSGGGGSSGGVFTL EDFVGDWEQTAAYNLDQVLEQGGVSSLLQNLAVS VTPIQRIVRSGENALKIDIHVIIPYEGLSADQMA QIEEVFKVVYPVDDHHFKVILPYGTLVIDGVTPN MLNYFGRPYEGIAVFDGKKITVTGTLWNGNKIID ERLITPDGSMLFRVTINS | α-activin receptors heavy - LgBiT | VH1-46*01 (SEQ ID NO: 186) | SEQ ID NO: 58 |
| SEQ ID NO: 150 | QSALTQPASVSGSPGQSITISCTGTSSDVGSYNY VNWYQQHPGKAPKLMIYGVSKRPSGVSNRFSGSK SGNTASLTISGLQAEDEADYYCGTFAGGSYYGVF GGGTKLTVLGQPKANPTVTLFPPSSEELQANKAT LVCLISDFYPGAVTVAWKADGSPVKAGVETTKPS KQSNNKYAASSYLSLTPEQWKSHRSYSCQVTHEG STVEKTVAPTECSGSSGGGGSGGGGSSGGVTGYR LFEEIL | α-activin receptors light - SmBiT | Vl2-14*01 (SEQ ID NO: 210) | SEQ ID NO: 59 |

TABLE 2-continued

Amino Acid sequences for NanoBiT constructs. All constructs contained an Ig Kappa leader sequence (SEQ ID NO 214: METDTLLLWVLLLWVPGSTG).

| SEQ ID NO | Amino Acid Sequence | Description | Germline | Corresponding DNA SEQ ID NO |
|---|---|---|---|---|
| SEQ ID NO: 151 | QSALTQPASVSGSPGQSITISCTGTSSDVGSYNY VNWYQQHPGKAPKLMIYGVSKRPSGVSNRFSGSK SGNTASLTISGLQAEDEADYYCGTFAGGSYYGVF GGGTKLTVLGQPKANPTVTLFPPSSEELQANKAT LVCLISDFYPGAVTVAWKADGSPVKAGVETTKPS KQSNNKYAASSYLSLTPEQWKSHRSYSCQVTHEG STVEKTVAPTECS | α-activin receptors light | Vl2-14*01 (SEQ ID NO: 210) | SEQ ID NO: 60 |
| SEQ ID NO: 152 | EVQLVQSGAEVKKPGSSVKVSCKASGGTFSSYAI SWVRQAPGQGLEWMGGIGPFFGTANYAQKFQGRV TITADESTSTAYMELSSLRSEDTAVYYCARDTPY FDYWGQGTLVTVSSASTKGPSVFPLAPSSKSTSG GTAALGCLVKDYFPEPVTVSWNSGALTSGVHTFP AVLQSSGLYSLSSVVTVPSSSLGTQTYICNVNHK PSNTKVDKRVEPKSCGSSGGGGSGGGGSSGGVFT LEDFVGDWEQTAAYNLDQVLEQGGVSSLLQNLAV SVTPIQRIVRSGENALKIDIHVIIPYEGLSADQM AQIEEVFKVVYPVDDHHFKVILPYGTLVIDGVTP NMLNYFGRPYEGIAVFDGKKITVTGTLWNGNKII DERLITPDGSMLFRVTINS | α-complement C5 heavy - LgBiT | VH1-69*01 (SEQ ID NO: 187) | SEQ ID NO: 61 |
| SEQ ID NO: 153 | SYELTQPLSVSVALGQTARITCSGDSIPNYYVYW YQQKPGQAPVLVIYDDSNRPSGIPERFSGSNSGN TATLTISRAQAGDEADYYCQSFDSSLNAEVFGGG TKLTVLGQPKANPTVTLFPPSSEELQANKATLVC LISDFYPGAVTVAWKADGSPVKAGVETTKPSKQS NNKYAASSYLSLTPEQWKSHRSYSCQVTHEGSTV EKTVAPTECSGSSGGGGSGGGGSSGGVTGYRLFE EIL | α-complement C5 light - SmBiT | Vl3-9*01 (SEQ ID NO: 212) | SEQ ID NO: 62 |
| SEQ ID NO: 154 | SYELTQPLSVSVALGQTARITCSGDSIPNYYVYW YQQKPGQAPVLVIYDDSNRPSGIPERFSGSNSGN TATLTISRAQAGDEADYYCQSFDSSLNAEVFGGG TKLTVLGQPKANPTVTLFPPSSEELQANKATLVC LISDFYPGAVTVAWKADGSPVKAGVETTKPSKQS NNKYAASSYLSLTPEQWKSHRSYSCQVTHEGSTV EKTVAPTECS | α-complement C5 light | Vl3-9*01 (SEQ ID NO: 212) | SEQ ID NO: 63 |
| SEQ ID NO: 155 | EVQLVQSGAEVKKPGASVKVSCKASGYTFTGYHM HWVRQAPGQGLEWMGWINPNSGVTKYAQKFQGRV TMTRDTSINTAYMELSRLRFDDTDVYYCATGGFG YWGEGTLVTVSSASTKGPSVFPLAPSSKSTSGGT AALGCLVKDYFPEPVTVSWNSGALTSGVHTFPAV LQSSGLYSLSSVVTVPSSSLGTQTYICNVNHKPS NTKVDKRVEPKSCGSSGGGGSGGGGSSGGVFTLE DFVGDWEQTAAYNLDQVLEQGGVSSLLQNLAVSV TPIQRIVRSGENALKIDIHVIIPYEGLSADQMAQ IEEVFKVVYPVDDHHFKVILPYGTLVIDGVTPNM LNYFGRPYEGIAVFDGKKITVTGTLWNGNKIIDE RLITPDGSMLFRVTINS | α-CCR2 heavy - LgBiT | VH1-2*01 (SEQ ID NO: 184) | SEQ ID NO: 64 |
| SEQ ID NO: 156 | LPVLTQPPSVSKGLRQTATLTCTGNSNNVGNQGA AWLQQHQGQPPKLLSYRNHNRPSGVSERFSPSRS GDTSSLTITGLQPEDEADYYCLAWDSSLRAFVFG TGTKLTVLGQPKANPTVTLFPPSSEELQANKATL VCLISDFYPGAVTVAWKADGSPVKAGVETTKPSK QSNNKYAASSYLSLTPEQWKSHRSYSCQVTHEGS TVEKTVAPTECSGSSGGGGSGGGGSSGGVTGYRL FEEIL | α-CCR2 light - SmBiT | Vl10-54*01 (SEQ ID NO: 207) | SEQ ID NO: 65 |
| SEQ ID NO: 157 | LPVLTQPPSVSKGLRQTATLTCTGNSNNVGNQGA AWLQQHQGQPPKLLSYRNHNRPSGVSERFSPSRS GDTSSLTITGLQPEDEADYYCLAWDSSLRAFVFG TGTKLTVLGQPKANPTVTLFPPSSEELQANKATL VCLISDFYPGAVTVAWKADGSPVKAGVETTKPSK QSNNKYAASSYLSLTPEQWKSHRSYSCQVTHEGS TVEKTVAPTECS | α-CCR2 light | Vl10-54*01 (SEQ ID NO: 207) | SEQ ID NO: 66 |
| SEQ ID NO: 158 | EVQLVESGGGLVQPGGSLRLSCVASGFTFSDYWM SWVRQAPGKGLEWVANIKKDGSVNYYVDSVKGRF TISRDNAKNSLYLQMNSLRAEDTAVYYCTRFDYW GQGTLVTVSSASTKGPSVFPLAPSSKSTSGGTAA LGCLVKDYFPEPVTVSWNSGALTSGVHTFPAVLQ | α-CCR2 heavy - LgBiT | VH3-7*01 (SEQ ID NO: 195) | SEQ ID NO: 67 |

TABLE 2-continued

Amino Acid sequences for NanoBiT constructs. All constructs contained an Ig Kappa leader sequence (SEQ ID NO 214: METDTLLLWVLLLWVPGSTG).

| SEQ ID NO | Amino Acid Sequence | Description | Germline | Corresponding DNA SEQ ID NO |
|---|---|---|---|---|
| | SSGLYSLSSVVTVPSSSLGTQTYICNVNHKPSNT KVDKRVEPKSCGSSGGGGSGGGGSSGGVFTLEDF VGDWEQTAAYNLDQVLEQGGVSSLLQNLAVSVTP IQRIVRSGENALKIDIHVIIPYEGLSADQMAQIE EVFKVVYPVDDHHFKVILPYGTLVIDGVTPNMLN YFGRPYEGIAVFDGKKITVTGTLWNGNKIIDERL ITPDGSMLFRVTINS | | | |
| SEQ ID NO: 159 | QAGLTQPPSVSKGLRQTATLTCTGNSNNVGNQGA AWLQQHQGHPPKLLFYRNNNRASGISERLSASRS GNTASLTITGLQPEDEADYYCLTWDSSLSVVVFG GGTKLTVLGQPKANPTVTLFPPSSEELQANKATL VCLISDFYPGAVTVAWKADGSPVKAGVETTKPSK QSNNKYAASSYLSLTPEQWKSHRSYSCQVTHEGS TVEKTVAPTECSGSSGGGGSGGGGSSGGVTGYRL FEEIL | α-CCR2 light - SmBiT | V110-54*01 (SEQ ID NO: 207) | SEQ ID NO: 68 |
| SEQ ID NO: 160 | QAGLTQPPSVSKGLRQTATLTCTGNSNNVGNQGA AWLQQHQGHPPKLLFYRNNNRASGISERLSASRS GNTASLTITGLQPEDEADYYCLTWDSSLSVVVFG GGTKLTVLGQPKANPTVTLFPPSSEELQANKATL VCLISDFYPGAVTVAWKADGSPVKAGVETTKPSK QSNNKYAASSYLSLTPEQWKSHRSYSCQVTHEGS TVEKTVAPTECS | α-CCR2 light (SEQ ID NO: 207) | V110-54*01 | SEQ ID NO: 69 |
| SEQ ID NO: 161 | QVQLVESGGGVVQPGRSLRLSCAASGFTFSSYGM HWVRQAPGKGLEWVAFIRYDGSNKYYADSVKGRF TISRDNSKNTLYLQMNSLRAEDTAVYYCKTHGSH DNWGQGTMVTVSSASTKGPSVFPLAPSSKSTSGG TAALGCLVKDYFPEPVTVSWNSGALTSGVHTFPA VLQSSGLYSLSSVVTVPSSSLGTQTYICNVNHKP SNTKVDKRVEPKSCGSSGGGGSGGGGSSGGVFTL EDFVGDWEQTAAYNLDQVLEQGGVSSLLQNLAVS VTPIQRIVRSGENALKIDIHVIIPYEGLSADQMA QIEEVFKVVYPVDDHHFKVILPYGTLVIDGVTPN MLNYFGRPYEGIAVFDGKKITVTGTLWNGNKIID ERLITPDGSMLFRVTINS | α-IL12β heavy - LgBiT | VH3-33*01 (SEQ ID NO: 193) | SEQ ID NO: 70 |
| SEQ ID NO: 162 | QSVLTQPPSVSGAPGQRVTISCSGSRSNIGSNTV KWYQQLPGTAPKLLIYYNDQRPSGVPDRFSGSKS GTSASLAITGLQAEDEADYYCQSYDRYTHPALLF GTGTKVTVLGQPKANPTVTLFPPSSEELQANKAT LVCLISDFYPGAVTVAWKADGSPVKAGVETTKPS KQSNNKYAASSYLSLTPEQWKSHRSYSCQVTHEG STVEKTVAPTECSGSSGGGGSGGGGSSGGVTGYR LFEEIL | α-IL12β light - SmBiT | VH1-44*01 (SEQ ID NO: 209) | SEQ ID NO: 71 |
| SEQ ID NO: 163 | QSVLTQPPSVSGAPGQRVTISCSGSRSNIGSNTV KWYQQLPGTAPKLLIYYNDQRPSGVPDRFSGSKS GTSASLAITGLQAEDEADYYCQSYDRYTHPALLF GTGTKVTVLGQPKANPTVTLFPPSSEELQANKAT LVCLISDFYPGAVTVAWKADGSPVKAGVETTKPS KQSNNKYAASSYLSLTPEQWKSHRSYSCQVTHEG STVEKTVAPTECS | α-IL12β light | V11-44*01 (SEQ ID NO: 209) | SEQ ID NO: 72 |

3. NanoBiT Competition Assay.

Figure 3A:
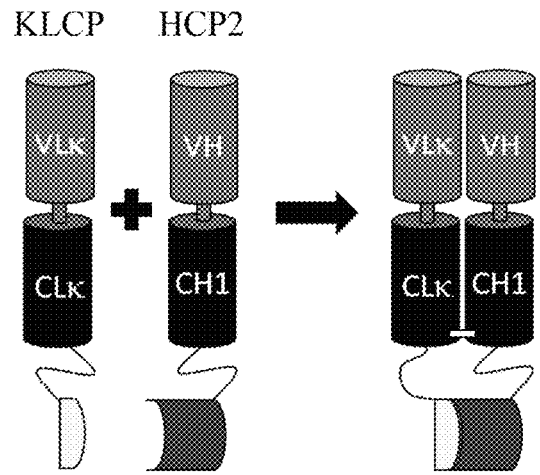
FIGS. 3A-3C depict the competition of a lambda light chain polypeptide (LLCP) and a kappa light chain polypeptide (KLCP) for a heavy chain polypeptide (HCP2) when mixed at a 1:1:1 molar ratio utilizing the NanoBiT® Protein: Protein Interaction System (ACS Chem Biol. 2016 Feb. 19; 11(2):400-8.). HCP2 has the LgBiT as a C-terminal fusion, KLCP has the SmBiT as a C-terminal fusion, and LLCP is a native light chain. When HCP2 and KLCP form a Fab region, the LgBiT and SmBiT create a fully functional NanoLuc domain (FIG. 3A). When HCP2 and LLCP form a Fab region, the NanoLuc is not complete and is inactive (FIG. 3B). A 1:1:1 competition of LLCP and KLCP for HCP2 purified by CH1 affinity results in the HCP2/KLCP functional NanoLuc and the HCP2/LLCP nonfunctional NanoLuc Fab regions (FIG. 3C).
Figure 3B:
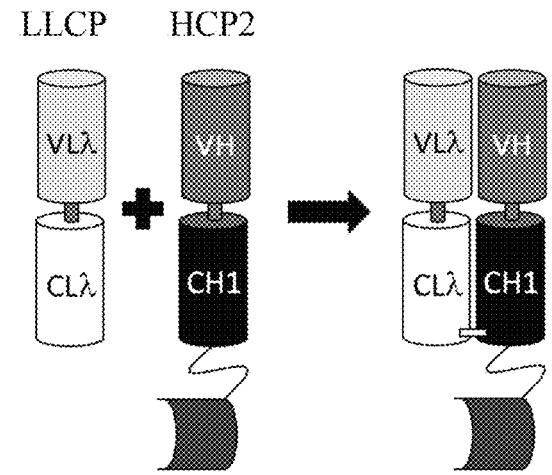
Figure 3C:
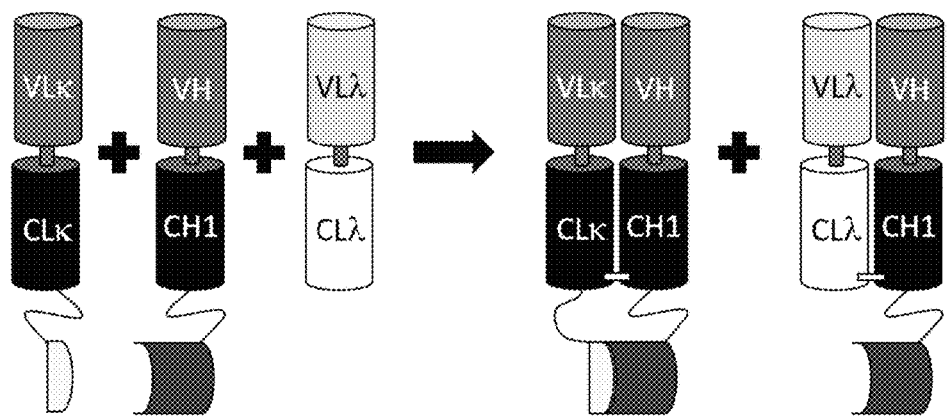

First, a NanoBiT assay was conducted to test the binding between a heavy chain polypeptide (HCP2) and its cognate kappa light chain polypeptide (KLCP) in the presence of a competing lambda light chain polypeptide (LLCP). As shown in FIGS. 3A-3C, a LgBiT was fused to the C-terminus of the HCP2 and a SmBiT was fused to the C-terminus of the KLCP. The competing LLCP was expressed as an un-modified chain. When HCP2 and KLCP form a Fab, the LgBiT and SmBiT generate a fully functional NanoLuc domain, which has luciferase activity (FIG. 3A). When HCP2 and LLCP form a Fab, the NanoLuc is not complete and is inactive (FIG. 3B). A 1:1:1 competition of LLCP and KLCP for HCP2 results in the HCP2/KLCP Fab with a functional NanoLuc and the HCP2/LLCP Fab with a non-functional NanoLuc (FIG. 3C). Each testing included a positive control where the competing light chain was absent, as well as a negative control where the competing light chain was the same KLCP without the SmBiT fusion. The positive control represented 100% pairing; whereas, the negative control represented 50% pairing. The luminescence readings for the positive and negative controls (100% and 50%, respectively) and the luminescence readings for each test pair in the presence of a competing light chain, were compared to quantify the percent pairing for each test pair.

Figure 4A:
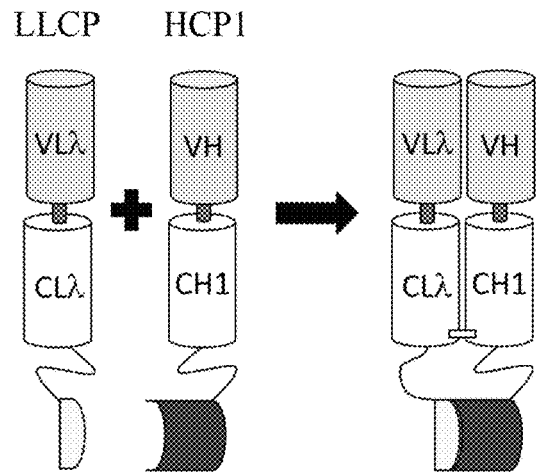
FIGS. 4A-4C depict the competition of a lambda light chain polypeptide (LLCP) and a kappa light chain polypeptide (KLCP) for a heavy chain polypeptide (HCP1) when mixed at a 1:1:1 molar ratio utilizing the NanoBiT® Protein: Protein Interaction System. HCP1 has the LgBiT as a C-terminal fusion, LLCP has the SmBiT as a C-terminal fusion, and KLCP is a native light chain. When HCP1 and LLCP form a Fab region, the LgBiT and SmBiT create a fully functional NanoLuc domain (FIG. 4A). When HCP1 and KLCP form a Fab region, the NanoLuc is not complete and is inactive (FIG. 4B). A 1:1:1 competition of LLCP and KLCP for HCP1 purified by CH1 affinity results in the HCP1/LLCP functional NanoLuc and the HCP1/KLCP non-functional NanoLuc Fab regions (FIG. 4C).
Figure 4B:
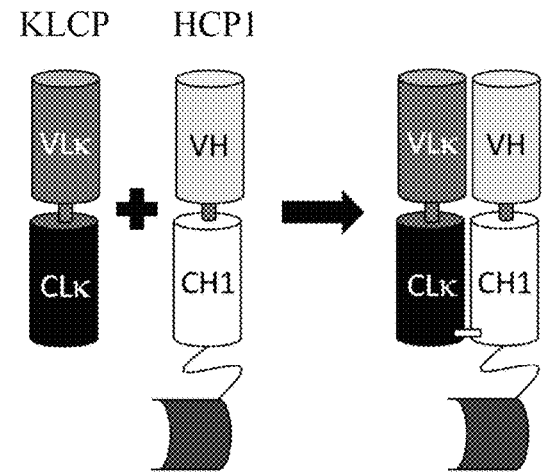
Figure 4C:
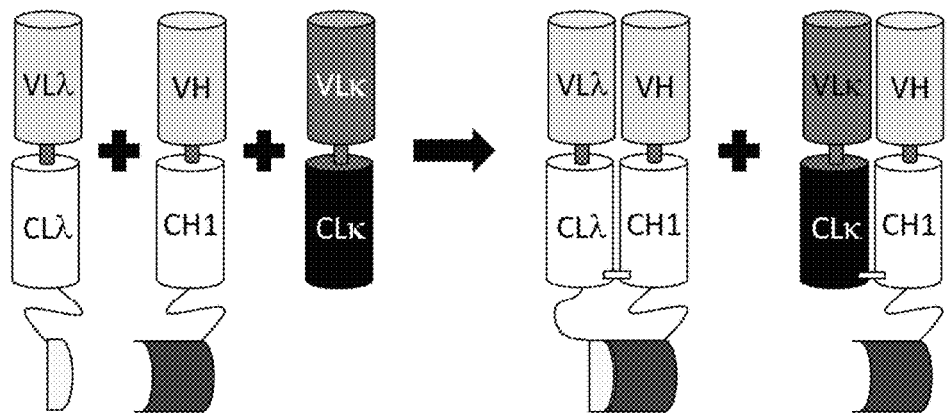

A similar NanoBiT assay was used to test the binding between a heavy chain polypeptide (HCP1) and a lambda light chain polypeptide (LLCP) in the presence of a competing kappa chain polypeptide (KLCP) (FIGS. 4A-4C). In this assay, a LgBiT was fused to the C-terminus of the HCP1 and a SmBiT was fused to the C-terminus of the LLCP. The competing KLCP was expressed as an un-modified light chain. Expression of the HCP1, LLCP, and KLCP at 1:1:1 leads to formation of the HCP1/LLCP Fab with a functional NanoLuc, and the HCP1/KLCP Fab with a nonfunctional NanoLuc (FIG. 4C). Similarly, luminescence readings for each test pair in the presence of a competing light chain were compared with those for positive controls (the competing light chain was absent; 100% pairing) and negative controls (the competing light chain was the same LLCP without the SmBiT fusion; 50% pairing) to determine the percent pairing for each test pair.

The NanoBiT competition assays were performed with 100 μL of protein at 1 μg/mL in 96 well plates. A 5× stock solution was made of the Promega Nano-Glo (N1110) assay system following the manufacturer's instructions. Each well received 20 μL of 5× NanoLuc stock solution and the luminescence of the plate was immediately read using a SpectraMax i3× plate reader.

4. Expression and Purification of Multispecific Molecules.

The plasmids were co-transfected into either Expi293 cells (Life Technologies A14527) or ExpiCHO cells (Life Technologies A29127). Transfections were performed using 1 mg of total DNA for a multispecific construct with a 1:1 knob to hole heavy chain ratio and 3:2 light chain to heavy chain ratio. To investigate possible misbalance in expression of the chains, the transfections were performed using varying ratios of heavy chain ranging from 3:1 to 1:3 of knob to hole heavy chain DNA, with the same 3:2 light chain to heavy chain ratio. Transfection in Expi293 cells was done using linear 25,000 Da polyethylenimine (PEI, Polysciences Inc 23966) in a 3:1 ratio with the total DNA. The DNA and PEI were each added to 50 mL of OptiMem (Life Technologies 31985088) medium and sterile filtered. The DNA and PEI were combined for 10 minutes and added to the Expi293 cells with a cell density of 1.8-2.8×10$^6$ cells/mL and a viability of at least 95%. The ExpiCHO transfection was performed according to the manufacturer's instructions. Expi293 cells were grown in a humidified incubator at 37° C. with 8% $CO_2$ for 5-7 days after transfection and ExpiCHO cells were grown for 14 days at 32° C. with 5% $CO_2$. The cells were pelleted by centrifugation at 18,000×g and the supernatant was filtered through a 0.2 μm membrane. Protein A resin (GE 17-1279-03) was added to the filtered supernatant and incubated for 1-3 hours at room temperature. The resin was packed into a column, washed with 3×10 column volumes of Dulbecco's phosphate-buffered saline (DPBS, Life Technologies 14190-144). The bound protein was eluted from the column with 20 mM citrate, 100 mM NaCl, pH 2.9. When necessary, the proteins were further purified using size exclusion chromatography on a Superdex 200 column with a running buffer of DPBS.

Table 4 contains the sequences unique to the multispecific constructs. Some of the light chain sequences shown in Table 2 were also used to express the multispecific constructs. A total of 12 multispecific molecules were expressed as described above. The amino acid sequences of these molecules are provided in Table 5a. Table 5b provides the corresponding germline sequences for the multispecific molecules.

TABLE 4

Amino acid sequences used to construct multispecific constructs.

| SEQ ID NO | Amino Acid Sequence | Description | Germline | Corresponding DNA SEQ ID NO |
|---|---|---|---|---|
| SEQ ID NO: 164 | QVQLQESGPGLVKPSQTLSLTCTVSGGSINNNNYYWTWIRQHPGKGLEWIGYIYYSGSTFYNPSLKSRVTISVDTSKTQFSLKLSSVTAADTAVYYCAREDTMTGLDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPCREEMTKNQVSLWCLVKGFYPSDIAVEWESNGQPENNYKTTPPVLDSDGSFFLYSKLTVDKSRWQQGNVFSCSVMHEALHNHYTQKSLSLSPGK | α-mesothelin AB237 heavy - hCHIg_Knob_Cys | VH4-31*01 (SEQ ID NO: 213) | SEQ ID NO: 82 |
| SEQ ID NO: 165 | DIQMTQSPSSLSASVGDRVTITCRASQSINNYLNWYQQKPGKAPTLLIYAASSLQSGVPSRFSGSRSGTDFTLTISSLQPEDFAAYFCQQTYSNPTFGQGTKVEVKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | α-mesothelin AB237 light - hCLIg_vk | Vk1-39*01 (SEQ ID NO: 201) | SEQ ID NO: 83 |
| SEQ ID NO: 166 | EVQLLESGGGLVQPGGSLRLSCAASGFTFSSYIMMWVRQAPGKGLEWVSSIYPSGGITFYADTVKGRFTISRDNSKNTLYLQMNSLRAEDTAVYYCARIKLGTVTTVDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVCTLPPSREEMTKNQVSLSCAVKGFYPSDIAVEWESNGQPENNYKTTPPVLDSDGSFFLVSKLTVDKSRWQQGNVFSCSVMHEALHNHYTQKSLSLSPGK | α-PDL1 heavy - hCHIg_Hole_Cys | VH3-66*01 (SEQ ID NO: 194) | SEQ ID NO: 84 |

TABLE 4-continued

Amino acid sequences used to construct multispecific constructs.

| SEQ ID NO | Amino Acid Sequence | Description | Germline | Corresponding DNA SEQ ID NO |
|---|---|---|---|---|
| SEQ ID NO: 167 | QSALTQPASVSGSPGQSITISCTGTSSDVGGYNYV SWYQQHPGKAPKLMIYDVSNRPSGVSNRFSGSKSG NTASLTISGLQAEDEADYYCSSYTSSSTRVFGTGT KVTVLGQPKANPTVTLFPPSSEELQANKATLVCLI SDFYPGAVTVAWKADGSPVKAGVETTKPSKQSNNK YAASSYLSLTPEQWKSHRSYSCQVTHEGSTVEKTV APTECS | α-PDL1 light - hCLIg_v1 | V12-14*01 (SEQ ID NO: 210) | SEQ ID NO: 85 |
| SEQ ID NO: 168 | QVQLVESGGGVVQPGRSLRLSCAASGFTFSSYTMH WVRQAPGKGLEWVTFISYDGNNKYYADSVKGRFTI SRDNSKNTLYLQMNSLRAEDTAIYYCARTGWLGPF DYWGQGTLVTVSSASTKGPSVFPLAPSSKSTSGGT AALGCLVKDYFPEPVTVSWNSGALTSGVHTFPAVL QSSGLYSLSSVVTVPSSSLGTQTYICNVNHKPSNT KVDKRVEPKSCDKTHTCPPCPAPELLGGPSVFLFP PKPKDTLMISRTPEVTCVVVDVSHEDPEVKFNWYV DGVEVHNAKTKPREEQYNSTYRVVSVLTVLHQDWL NGKEYKCKVSNKALPAPIEKTISKAKGQPREPQVY TLPPCREEMTKNQVSLWCLVKGFYPSDIAVEWESN GQPENNYKTTPPVLDSDGSFFLYSKLTVDKSRWQQ GNVFSCSVMHEALHNHYTQKSLSLSPGK | α-CTLA4 heavy - hCHIg_Knob_ Cys | VH3-30*01 (SEQ ID NO: 192) | SEQ ID NO: 78 |
| SEQ ID NO: 169 | QVQLVESGGGVVQPGRSLRLSCAASGFTFSSYTMH WVRQAPGKGLEWVTFISYDGNNKYYADSVKGRFTI SRDNSKNTLYLQMNSLRAEDTAIYYCARTGWLGPF DYWGQGTLVTVSSASTKGPSVFPLAPSSKSTSGGT AALGCLVKDYFPEPVTVSWNSGALTSGVHTFPAVL QSSGLYSLSSVVTVPSSSLGTQTYICNVNHKPSNT KVDKRVEPKSCDKTHTCPPCPAPELLGGPSVFLFP PKPKDTLMISRTPEVTCVVVDVSHEDPEVKFNWYV DGVEVHNAKTKPREEQYNSTYRVVSVLTVLHQDWL NGKEYKCKVSNKALPAPIEKTISKAKGQPREPQVY TLPPCREEMTKNQVSLWCLVKGFYPSDIAVEWESN GQPENNYKTTPPVLDSDGSFFLYSKLTVDKSRWQQ GNVFSCSVMHEALHNHYTQKSLSLSPGKGGGGSGG GGSGGGGSEVQLVESGGGLVKPGGSLRLSCAASGF TFSPYSVFWVRQAPGKGLEWVSSINTDSTYKYYAD SVKGRFTISRDNAENSIFLQMNSLRAEDTAVYYCA RDRSYYAFSSGSLSDYYYGLDVWGQGTLVTVSSGG GGSGGGGSGGGGSGGGGSDIVMTQSPLSLSVTPGE PASISCRSSQSLLHTNLYNYLDWYVQKPGQSPQLL IYLASNRASGVPDRFSGSGSGTDFTLKISRVETED VGVYYCMQALQIPRTFGQGTKLEIK | α-CTLA4 heavy - hCHIg_Knob_ Cys - GH_scFv | VH3-30*01 (SEQ ID NO: 192) | SEQ ID NO: 79 |
| SEQ ID NO: 170 | QVQLVESGGGVVQPGRSLRLSCAASGFTFSSYGMH WVRQAPGKGLEWVAFIRYDGSNKYYADSVKGRFTI SRDNSKNTLYLQMNSLRAEDTAVYYCKTHGSHDNW GQGTMVTVSSASTKGPSVFPLAPSSKSTSGGTAAL GCLVKDYFPEPVTVSWNSGALTSGVHTFPAVLQSS GLYSLSSVVTVPSSSLGTQTYICNVNHKPSNTKVD KRVEPKSCDKTHTCPPCPAPELLGGPSVFLFPPKP KDTLMISRTPEVTCVVVDVSHEDPEVKFNWYVDGV EVHNAKTKPREEQYNSTYRVVSVLTVLHQDWLNGK EYKCKVSNKALPAPIEKTISKAKGQPREPQVCTLP PSREEMTKNQVSLSCAVKGFYPSDIAVEWESNGQP ENNYKTTPPVLDSDGSFFLVSKLTVDKSRWQQGNV FSCSVMHEALHNHYTQKSLSLSPGK | α-IL12β heavy - hCHIg_Hole_ Cys | VH3-33*01 (SEQ ID NO: 193) | SEQ ID NO: 91 |
| SEQ ID NO: 171 | QVQLVESGGGVVQPGRSLRLSCAASGFTFSSYTMH WVRQAPGKGLEWVTFISYDGNNKYYADSVKGRFTI SRDNSKNTLYLQMNSLRAEDTAIYYCARTGWLGPF DYWGQGTLVTVSSASTKGPSVFPLAPSSKSTSGGT AALGCLVKDYFPEPVTVSWNSGALTSGVHTFPAVL QSSGLYSLSSVVTVPSSSLGTQTYICNVNHKPSNT KVDKRVEPKSCDKTHTCPPCPAPELLGGPSVFLFP PKPKDTLMISRTPEVTCVVVDVSHEDPEVKFNWYV DGVEVHNAKTKPREEQYNSTYRVVSVLTVLHQDWL NGKEYKCKVSNKALPAPIEKTISKAKGQPREPQVY TLPPSREEMTKNQVSLTCLVKGFYPSDIAVEWESN GQPENNYKTTPPVLDSDGSFFLYSKLTVDKSRWQQ GNVFSCSVMHEALHNHYTQKSLSLSPGK | α-CTLA4 heavy - hCHIg | VH3-30*01 (SEQ ID NO: 192) | SEQ ID NO: 73 |

TABLE 4-continued

Amino acid sequences used to construct multispecific constructs.

| SEQ ID NO | Amino Acid Sequence | Description | Germline | Corresponding DNA SEQ ID NO |
|---|---|---|---|---|
| SEQ ID NO: 172 | QVQLVESGGGVVQPGRSLRLSCAASGFTFSSYGMH WVRQAPGKGLEWVAFIRYDGSNKYYADSVKGRFTI SRDNSKNTLYLQMNSLRAEDTAVYYCKTHGSHDNW GQGTMVTVSSASTKGPSVFPLAPSSKSTSGGTAAL GCLVKDYFPEPVTVSWNSGALTSGVHTFPAVLQSS GLYSLSSVVTVPSSSLGTQTYICNVNHKPSNTKVD KRVEPKSCDKTHTCPPCPAPELLGGPSVFLFPPKP KDTLMISRTPEVTCVVVDVSHEDPEVKFNWYVDGV EVHNAKTKPREEQYNSTYRVVSVLTVLHQDWLNGK EYKCKVSNKALPAPIEKTISKAKGQPREPQVYTLP PSREEMTKNQVSLTCLVKGFYPSDIAVEWESNGQP ENNYKTTPPVLDSDGSFFLYSKLTVDKSRWQQGNV FSCSVMHEALHNHYTQKSLSLSPGK | α-IL12β heavy - hCHIg | VH3-33*01 (SEQ ID NO: 193) | SEQ ID NO: 74 |
| SEQ ID NO: 173 | QSVLTQPPSVSGAPGQRVTISCSGSRSNIGSNTVK WYQQLPGTAPKLLIYYNDQRPSGVPDRFSGSKSGT SASLAITGLQAEDEADYYCQSYDRYTHPALLFGTG TKVTVLGQPKANPTVTLFPPSSEELQANKATLVCL ISDFYPGAVTVAWKADGSPVKAGVETTKPSKQSNN KYAASSYLSLTPEQWKSHRSYSCQVTHEGSTVEKT VAPTECSGGGGSGGGGSGGGGSAPTSSSTKKTQLQ LEHLLLDLQMILNGINNYKNPKLTRMLTAKFAMPK KATELKHLQCLEEELKPLEEVLNLAQSKNFHLRPR DLISNINVIVLELKGSETTFMCEYADETATIVEFL NRWITFCQSIISTLT | α-IL12β light - hCLIg_vl - IL2 | Vl1-44*01 (SEQ ID NO: 209) | SEQ ID NO: 75 |
| SEQ ID NO: 174 | QVQLVESGGGVVQPGRSLRLSCAASGFTFSSYGMH WVRQAPGKGLEWVAFIRYDGSNKYYADSVKGRFTI SRDNSKNTLYLQMNSLRAEDTAVYYCKTHGSHDNW GQGTMVTVSSASTKGPSVFPLAPSSKSTSGGTAAL GCLVKDYFPEPVTVSWNSGALTSGVHTFPAVLQSS GLYSLSSVVTVPSSSLGTQTYICNVNHKPSNTKVD KRVEPKSCDKTHTCPPCPAPELLGGPSVFLFPPKP KDTLMISRTPEVTCVVVDVSHEDPEVKFNWYVDGV EVHNAKTKPREEQYNSTYRVVSVLTVLHQDWLNGK EYKCKVSNKALPAPIEKTISKAKGQPREPQVCTLP PSREEMTKNQVSLSCAVKGFYPSDIAVEWESNGQP ENNYKTTPPVLDSDGSFFLVSKLTVDKSRWQQGNV FSCSVMHEALHNHYTQKSLSLSPGKGGGGSGGGGS GGGGSAPTSSSTKKTQLQLEHLLLDLQMILNGINN YKNPKLTRMLTAKFAMPKKATELKHLQCLEEELKP LEEVLNLAQSKNFHLRPRDLISNINVIVLELKGSE TTFMCEYADETATIVEFLNRWITFCQSIISTLT | α-IL12β heavy - hCHIg_Hole_ Cys | VH3-33*01 (SEQ ID NO: 193) | SEQ ID NO: 76 |
| SEQ ID NO: 175 | QVQLVESGGGVVQPGRSLRLSCAASGFTFSSYGMH WVRQAPGKGLEWVAFIRYDGSNKYYADSVKGRFTI SRDNSKNTLYLQMNSLRAEDTAVYYCKTHGSHDNW GQGTMVTVSSASTKGPSVFPLAPSSKSTSGGTAAL GCLVKDYFPEPVTVSWNSGALTSGVHTFPAVLQSS GLYSLSSVVTVPSSSLGTQTYICNVNHKPSNTKVD KRVEPKSCDKTHTCPPCPAPELLGGPSVFLFPPKP KDTLMISRTPEVTCVVVDVSHEDPEVKFNWYVDGV EVHNAKTKPREEQYNSTYRVVSVLTVLHQDWLNGK EYKCKVSNKALPAPIEKTISKAKGQPREPQVYTLP PSREEMTKNQVSLTCLVKGFYPSDIAVEWESNGQP ENNYKTTPPVLDSDGSFFLYSKLTVDKSRWQQGNV FSCSVMHEALHNHYTQKSLSLSPGKGGGGSGGGGS GGGGSAPTSSSTKKTQLQLEHLLLDLQMILNGINN YKNPKLTRMLTAKFAMPKKATELKHLQCLEEELKP LEEVLNLAQSKNFHLRPRDLISNINVIVLELKGSE TTFMCEYADETATIVEFLNRWITFCQSIISTLT | α-IL12β heavy - hCHIg | VH3-33*01 (SEQ ID NO: 193) | SEQ ID NO: 77 |
| SEQ ID NO: 176 | EIVLTQSPGTLSLSPGERATLSCRASQSVGSSYLA WYQQKPGQAPRLLIYGAFSRATGIPDRFSGSGSGT DFTLTISRLEPEDFAVYYCQQYGSSPWTFGQGTKV EIKRTVAAPSVFIFPPSDEQLKSGTASVVCLLNNF YPREAKVQWKVDNALQSGNSQESVTEQDSKDSTYS LSSTLTLSKADYEKHKVYACEVTHQGLSSPVTKSF NRGECGGGGSGGGGSGGGGSAPTSSSTKKTQLQLE HLLLDLQMILNGINNYKNPKLTRMLTAKFAMPKKA TELKHLQCLEEELKPLEEVLNLAQSKNFHLRPRDL ISNINVIVLELKGSETTFMCEYADETATIVEFLNR WITFCQSIISTLT | α-CTLA4 light - hCLIg_vk - IL2 | Vk3-20*01 (SEQ ID NO: 205) | SEQ ID NO: 80 |

TABLE 4-continued

Amino acid sequences used to construct multispecific constructs.

| SEQ ID NO | Amino Acid Sequence | Description | Germline | Corresponding DNA SEQ ID NO |
|---|---|---|---|---|
| SEQ ID NO: 177 | EVQLVQSGGGVERPGGSLRLSCAASGFTFDDYGMS WVRQAPGKGLEWVSGINWNGGSTGYADSVKGRVTI SRDNAKNSLYLQMNSLRAEDTAVYYCAKILGAGRG WYFDLWGKGTTVTVSSASTKGPSVFPLAPSSKSTS GGTAALGCLVKDYFPEPVTVSWNSGALTSGVHTFP AVLQSSGLYSLSSVVTVPSSSLGTQTYICNVNHKP SNTKVDKRVEPKSCDKTHTCPPCPAPELLGGPSVF LFPPKPKDTLMISRTPEVTCVVVDVSHEDPEVKFN WYVDGVEVHNAKTKPREEQYNSTYRVVSVLTVLHQ DWLNGKEYKCKVSNKALPAPIEKTISKAKGQPREP QVCTLPPSREEMTKNQVSLSCAVKGFYPSDIAVEW ESNGQPENNYKTTPPVLDSDGSFFLVSKLTVDKSR WQQGNVFSCSVMHEALHNHYTQKSLSLSPGK | α-INFR10β heavy - hCHIg_Hole_Cys | Vk3-20*01 (SEQ ID NO: 205) | SEQ ID NO: 81 |
| SEQ ID NO: 178 | QVQLVQSGGGLVQPGGSLRLSCAASGFTFDDYAMH WVRQAPGKGLEWVAGISWDSGSTGYADSVKGRFTI SRDNAKNSLYLQMNSLRAEDTALYYCARDLGAYQW VEGFDYWGQGTLVTVSSASTKGPSVFPLAPSSKST SGGTAALGCLVKDYFPEPVTVSWNSGALTSGVHTF PAVLQSSGLYSLSSVVTVPSSSLGTQTYICNVNHK PSNTKVDKRVEPKSCTIKPCPPCKCPAPNLLGGPS VFIFPPKIKDVLMISLSPIVTCVVVDVSEDDPDVQ ISWFVNNVEVHTAQTQTHREDYNSTLRVVSALPIQ HQDWMSGKEFKCKVNNKDLPAPIERTISKPKGSVR APQVYVLPPCEEEMTKKQVTLWCMVTDFMPEDIYV EWTNNGKTELNYKNTEPVLDSDGSYFMYSKLRVEK KNWVERNSYSCSVVHEGLHNHHTTKSFSRTPGK | α-HER3 heavy - mFc_Knob_Cys | VH3-9*01 (SEQ ID NO: 196) | SEQ ID NO: 86 |
| SEQ ID NO: 179 | EVQLLQSGGGLVQPGGSLRLSCAASGFMFSRYPMH WVRQAPGKGLEWVGSISGSGGATPYADSVKGRFTI SRDNSKNTLYLQMNSLRAEDTAVYYCAKDFYQILT GNAFDYWGQGTTVTVSSASTKGPSVFPLAPSSKST SGGTAALGCLVKDYFPEPVTVSWNSGALTSGVHTF PAVLQSSGLYSLSSVVTVPSSSLGTQTYICNVNHK PSNTKVDKRVEPKSCTIKPCPPCKCPAPNLLGGPS VFIFPPKIKDVLMISLSPIVTCVVVDVSEDDPDVQ ISWFVNNVEVHTAQTQTHREDYNSTLRVVSALPIQ HQDWMSGKEFKCKVNNKDLPAPIERTISKPKGSVR APQVCVLPPPEEEMTKKQVTLSCAVTDFMPEDIYV EWTNNGKTELNYKNTEPVLDSDGSYFMVSKLRVEK KNWVERNSYSCSVVHEGLHNHHTTKSFSRTPGK | α-IGF1R heavy - mFc_Hole_Cys | VH3-23*01 (SEQ ID NO: 191) | SEQ ID NO: 87 |
| SEQ ID NO: 180 | EVQLVQSGAEVKKPGSSVKVSCKASGGTFSSYAIS WVRQAPGQGLEWMGGIIPIFGTANYAQKFQGRVTI TADKSTSTAYMELSSLRSEDTAVYYCARAPLRFLE WSTQDHYYYYYMDVWGKGTTVTVSSASTKGPSVFP LAPSSKSTSGGTAALGCLVKDYFPEPVTVSWNSGA LTSGVHTFPAVLQSSGLYSLSSVVTVPSSSLGTQT YICNVNHKPSNTKVDKRVEPKSCDKTHTCPPCPAP ELLGGPSVFLFPPKPKDTLMISRTPEVTCVVVDVS HEDPEVKFNWYVDGVEVHNAKTKPREEQYNSTYRV VSVLTVLHQDWLNGKEYKCKVSNKALPAPIEKTIS KAKGQPREPQVCTLPPSREEMTKNQVSLSCAVKGF YPSDIAVEWESNGQPENNYKTTPPVLDSDGSFFLV SKLTVDKSRWQQGNVFSCSVMHEALHNHYTQKSLS LSPGK | α-CD221 heavy - hCHIg_Hole_Cys | VH1-69*01 (SEQ ID NO: 187) | SEQ ID NO: 88 |
| SEQ ID NO: 181 | QVQLVESGGGVVQPGRSLRLDCKASGITFSNSGMH WVRQAPGKGLEWVAVIWYDGSKRYYADSVKGRFTI SRDNSKNTLFLQMNSLRAEDTAVYYCATNDDYWGQ GTLVTVSSASTKGPSVFPLAPSSKSTSGGTAALGC LVKDYFPEPVTVSWNSGALTSGVHTFPAVLQSSGL YSLSSVVTVPSSSLGTQTYICNVNHKPSNTKVDKR VEPKSCDKTHTCPPCPAPELLGGPSVFLFPPKPKD TLMISRTPEVTCVVVDVSHEDPEVKFNWYVDGVEV HNAKTKPREEQYNSTYRVVSVLTVLHQDWLNGKEY KCKVSNKALPAPIEKTISKAKGQPREPQVYTLPPC REEMTKNQVSLWCLVKGFYPSDIAVEWESNGQPEN NYKTTPPVLDSDGSFFLYSKLTVDKSRWQQGNVFS CSVMHEALHNHYTQKSLSLSPGK | α-PD1 heavy - hCHIg_Knob_Cys | VH3-33*01 (SEQ ID NO: 193) | SEQ ID NO: 89 |

TABLE 4-continued

Amino acid sequences used to construct multispecific constructs.

| SEQ ID NO | Amino Acid Sequence | Description | Germline | Corresponding DNA SEQ ID NO |
|---|---|---|---|---|
| SEQ ID NO: 182 | EIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | α-PD1 light - hCLIg_vk | Vk3-11*01 (SEQ ID NO: 204) | SEQ ID NO: 90 |

TABLE 15

Germline sequences shown in Tables 2 and 4 (full-length sequences).

| SEQ ID NO | Description | Amino acid sequences |
|---|---|---|
| 183 | VH1-18*01 | QVQLVQSGAEVKKPGASVKVSCKASGYTFTSYGISWVRQAPGQGLEWMGWISAYNGNTNYAQKLQGRVTMTTDTSTSTAYMELRSLRSDDTAVYYCAR |
| 184 | VH1-2*01 | QVQLVQSGAEVKKPGASVKVSCKASGYTFTGYYMHWVRQAPGQGLEWMGRINPNSGGTNYAQKFQGRVTSTRDTSISTAYMELSRLRSDDTVVYYCAR |
| 185 | VH1-3*01 | QVQLVQSGAEVKKPGASVKVSCKASGYTFTSYAMHWVRQAPGQRLEWMGWINAGNGNTKYSQKFQGRVTITRDTSASTAYMELSSLRSEDTAVYYCAR |
| 186 | VH1-46*01 | QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCAR |
| 187 | VH1-69*01 | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCAR |
| 188 | VH3-13*01 | EVQLVESGGGLVQPGGSLRLSCAASGFTFSSYDMHWVRQATGKGLEWVSAIGTAGDTYYPGSVKGRFTISRENAKNSLYLQMNSLRAGDTAVYYCAR |
| 189 | VH3-20*01 | EVQLVESGGGVVRPGGSLRLSCAASGFTFDDYGMSWVRQAPGKGLEWVSGINWNGGSTGYADSVKGRFTISRDNAKNSLYLQMNSLRAEDTALYHCAR |
| 190 | VH3-21*01 | EVQLVESGGGLVKPGGSLRLSCAASGFTFSSYSMNWVRQAPGKGLEWVSSISSSSSYIYYADSVKGRFTISRDNAKNSLYLQMNSLRAEDTAVYYCAR |
| 191 | VH3-23*01 | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAK |
| 192 | VH3-30*01 | QVQLVESGGGVVQPGRSLRLSCAASGFTFSSYAMHWVRQAPGKGLEWVAVISYDGSNKYYADSVKGRFTISRDNSKNTLYLQMNSLRAEDTAVYYCAR |
| 193 | VH3-33*01 | QVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCAR |
| 194 | VH3-66*01 | EVQLVESGGGLVQPGGSLRLSCAASGFTVSSNYMSWVRQAPGKGLEWVSVIYSGGSTYYADSVKGRFTISRDNSKNTLYLQMNSLRAEDTAVYYCAR |
| 195 | VH3-7*01 | EVQLVESGGGLVQPGGSLRLSCAASGFTFSSYWMSWVRQAPGKGLEWVANIKQDGSEKYYVDSVKGRFTISRDNAKNSLYLQMNSLRAEDTAVYYCAR |
| 196 | VH3-9*01 | EVQLVESGGGLVQPGRSLRLSCAASGFTFDDYAMHWVRQAPGKGLEWVSGISWNSGSIGYADSVKGRFTISRDNAKNSLYLQMNSLRAEDTALYYCAK |
| 197 | VH4-4*01 | QVQLQESGPGLVKPPGTLSLTCAVSGGSISSSNWWSWVRQPPGKGLEWIGEIYHSGSTNYNPSLKSRVTISVDKSKNQFSLKLSSVTAADTAVYYCCAR |
| 198 | VH5-51*01 | EVQLVQSGAEVKKPGESLKISCKGSGYSFTSYWIGWVRQMPGKGLEWMGIIYPGDSDTRYSPSFQGQVTISADKSISTAYLQWSSLKASDTAMYYCAR |
| 199 | Vk1-12*01 | DIQMTQSPSSVSASVGDRVTITCRASQGISSWLAWYQQKPGKAPKLLIYAASSLQSGVPSRFSGSGSGTDFTLTISSLQPEDFATYYC |
| 200 | Vk1-27*01 | DIQMTQSPSSLSASVGDRVTITCRASQGISNYLAWYQQKPGKVPKLLIYAASTLQSGVPSRFSGSGSGTDFTLTISSLQPEDVATYYC |

TABLE 15-continued

Germline sequences shown in Tables 2 and 4 (full-length sequences).

| SEQ ID NO | Description | Amino acid sequences |
|---|---|---|
| 201 | Vk1-39*01 | DIQMTQSPSSLSASVGDRVTITCRASQSISSYLNWYQQKPGKAPKLLIYAASSLQSGVPSRFSGSGSGTDFTLTISSLQPEDFATYYC |
| 202 | Vk1D-16*01 | DIQMTQSPSSLSASVGDRVTITCRASQGISSWLAWYQQKPEKAPKSLIYAASSLQSGVPSRFSGSGSGTDFTLTISSLQPEDFATYYC |
| 203 | Vk2-28*01 | DIVMTQSPLSLPVTPGEPASISCRSSQSLLHSNGYNYLDWYLQKPGQSPQLLIYLGSNRASGVPDRFSGSGSGTDFTLKISRVEAEDVGVYYC |
| 204 | Vk3-11*01 | EIVLTQSPATLSLSPGERATLSCRASQSVSSYLAWYQQKPGQAPRLLIYDASNRATGIPARFSGSGSGTDFTLTISSLEPEDFAVYYC |
| 205 | Vk3-20*01 | EIVLTQSPGTLSLSPGERATLSCRASQSVSSSYLAWYQQKPGQAPRLLIYGASSRATGIPDRFSGSGSGTDFTLTISRLEPEDFAVYYC |
| 206 | Vk3D-20*01 | EIVLTQSPATLSLSPGERATLSCGASQSVSSSYLAWYQQKPGLAPRLLIYDASSRATGIPDRFSGSGSGTDFTLTISRLEPEDFAVYYC |
| 207 | Vl10-54*01 | QAGLTQPPSVSKGLRQTATLTCTGNSNNVGNQGAAWLQQHQGHPPKLLSYRNNNRPSGISERLSASRSGNTASLTITGLQPEDEADYYC |
| 208 | Vl1-40*01 | QSVLTQPPSVSGAPGQRVTISCTGSSSNIGAGYDVHWYQQLPGTAPKLLIYGNSNRPSGVPDRFSGSKSGTSASLAITGLQAEDEADYYC |
| 209 | Vl1-44*01 | QSVLTQPPSASGTPGQRVTISCSGSSSNIGSNTVNWYQQLPGTAPKLLIYSNNQRPSGVPDRFSGSKSGTSASLAISGLQSEDEADYYC |
| 210 | Vl2-14*01 | QSALTQPASVSGSPGQSITISCTGTSSDVGGYNYVSWYQQHPGKAPKLMIYEVSNRPSGVSNRFSGSKSGNTASLTISGLQAEDEADYYC |
| 211 | Vl3-19*01 | SSELTQDPAVSVALGQTVRITCQGDSLRSYYASWYQQKPGQAPVLVIYGKNNRPSGIPDRFSGSSSGNTASLTITGAQAEDEADYYC |
| 212 | Vl3-9*01 | SYELTQPLSVSVALGQTARITCGGNNIGSKNVHWYQQKPGQAPVLVIYRDSNRPSGIPERFSGSNSGNTATLTISRAQAGDEADYYC |
| 213 | VH4-31*01 | QVQLQESGPGLVKPSQTLSLTCTVSGGSISSGGYYWSWIRQHPGKGLEWIGYIYYSGSTYYNPSLKSLVTISVDTSKNQFSLKLSSVTAADTAVYYCAR |

TABLE 16

Germline sequences shown in Tables 2 and 4 (framework 1, CDR1, framework 2, CDR2, and framework 3 sequences).

| Germline | Framework 1 | Kabat CDR 1 | Framework 2 | Kabat CDR 2 | Framework 3 |
|---|---|---|---|---|---|
| VH1-18*01 (SEQ ID NO: 183) | QVQLVQSGAEVKKPGASVKVSCKAS (SEQ ID NO: 215) | GYTFTSYGIS (SEQ ID NO: 216) | WVRQAPGQGLEWMG (SEQ ID NO: 217) | WISAYNGNTNYAQKLQG (SEQ ID NO: 218) | RVTMTTDTSTSTAYMELRSLRSDDTAVYYCAR (SEQ ID NO: 219) |
| VH1-2*01 (SEQ ID NO: 184) | QVQLVQSGAEVKKPGASVKVSCKAS (SEQ ID NO: 215) | GYTFTGYYMH (SEQ ID NO: 220) | WVRQAPGQGLEWMG (SEQ ID NO: 217) | RINPNSGGTNYAQKFQG (SEQ ID NO: 221) | RVTSTRDTSISTAYMELSRLRSDDTVVYYCAR (SEQ ID NO: 222) |
| VH1-3*01 (SEQ ID NO: 185) | QVQLVQSGAEVKKPGASVKVSCKAS (SEQ ID NO: 215) | GYTFTSYAMH (SEQ ID NO: 223) | WVRQAPGQRLEWMG (SEQ ID NO: 224) | WINAGNGNTKYSQKFQG (SEQ ID NO: 225) | RVTITRDTSASTAYMELSSLRSEDTAVYYCAR (SEQ ID NO: 226) |
| VH1-46*01 (SEQ ID NO: 186) | QVQLVQSGAEVKKPGASVKVSCKAS (SEQ ID NO: 215) | GYTFTSYYMH (SEQ ID NO: 227) | WVRQAPGQGLEWMG (SEQ ID NO: 217) | IINPSGGSTSYAQKFQG (SEQ ID NO: 228) | RVTMTRDTSTSTVYMELSSLRSEDTAVYYCAR (SEQ ID NO: 229) |

TABLE 16-continued

Germline sequences shown in Tables 2 and 4 (framework 1, CDR1, framework 2, CDR2, and framework 3 sequences).

| Germline | Framework 1 | Kabat CDR 1 | Framework 2 | Kabat CDR 2 | Framework 3 |
|---|---|---|---|---|---|
| VH140*01 (SEQ ID NO: 187) | QVQLVQSGAEV KKPGSSVKVSC KAS (SEQ ID NO: 230) | GGTFSSYAIS (SEQ ID NO: 231) | WVRQAPGQGLE WMG (SEQ ID NO: 217) | GIIPIFGTANY AQKFQG (SEQ ID NO: 232) | RVTITADESTS TAYMELSSLRS EDTAVYYCAR (SEQ ID NO: 233) |
| VH3-13*01 (SEQ ID NO: 188) | EVQLVESGGGL VQPGGSLRLSC AAS (SEQ ID NO: 234) | GFTFSSYDMH (SEQ ID NO: 235) | WVRQATGKGLE WVS (SEQ ID NO: 236) | AIGTAGDTYYP GSVKG (SEQ ID NO: 237) | RFTISRENAKN SLYLQMNSLRA GDTAVYYCAR (SEQ ID NO: 238) |
| VH3-20*01 (SEQ ID NO: 189) | EVQLVESGGGV VRPGGSLRLSC AAS (SEQ ID NO: 239) | GFTFDDYGMS (SEQ ID NO: 240) | WVRQAPGKGLE WVS (SEQ ID NO: 241) | GINWNGGSTGY ADSVKG (SEQ ID NO: 242) | RFTISRDNAKN SLYLQMNSLRA EDTALYHCAR (SEQ ID NO: 243) |
| VH3-21*01 SEQ ID NO: 190 | EVQLVESGGGL VKPGGSLRLSC AAS (SEQ ID NO: 244) | GFTFSSYSMN (SEQ ID NO: 245) | WVRQAPGKGLE WVS (SEQ ID NO: 241) | SISSSSSYIYY ADSVKG (SEQ ID NO: 246) | RFTISRDNAKN SLYLQMNSLRA EDTAVYYCAR (SEQ ID NO: 247) |
| VH3-23*01 SEQ ID NO: 191 | EVQLLESGGGL VQPGGSLRLSC AAS (SEQ ID NO: 248) | GFTFSSYAMS (SEQ ID NO: 249) | WVRQAPGKGLE WVS (SEQ ID NO: 241) | AISGSGGSTYY ADSVKG (SEQ ID NO: 250) | RFTISRDNSKN TLYLQMNSLRA EDTAVYYCAK (SEQ ID NO: 251) |
| VH3-30*01 SEQ ID NO: 192 | QVQLVESGGGV VQPGRSLRLSC AAS (SEQ ID NO: 252) | GFTFSSYAMH (SEQ ID NO: 253) | WVRQAPGKGLE WVA (SEQ ID NO: 254) | VISYDGSNKYY ADSVKG (SEQ ID NO: 255) | RFTISRDNSKN TLYLQMNSLRA EDTAVYYCAR (SEQ ID NO: 256) |
| VH3-33*01 SEQ ID NO: 193 | QVQLVESGGGV VQPGRSLRLSC AAS (SEQ ID NO: 252) | GFTFSSYGMH (SEQ ID NO: 257) | WVRQAPGKGLE WVA (SEQ ID NO: 254) | VIWYDGSNKYY ADSVKG (SEQ ID NO: 258) | RFTISRDNSKN TLYLQMNSLRA EDTAVYYCAR (SEQ ID NO: 256) |
| VH3-66*01 SEQ ID NO: 194 | EVQLVESGGGL VQPGGSLRLSC AAS (SEQ ID NO: 234) | GFTVSSNYMS (SEQ ID NO: 259) | WVRQAPGKGLE WVS (SEQ ID NO: 241) | VIYSGGSTYYA DSVKG (SEQ ID NO: 260) | RFTISRDNSKN TLYLQMNSLRA EDTAVYYCAR (SEQ ID NO: 256) |
| VH3-7*01 SEQ ID NO: 195 | EVQLVESGGGL VQPGGSLRLSC AAS (SEQ ID NO: 234) | GFTFSSYWMS (SEQ ID NO: 261) | WVRQAPGKGLE WVA (SEQ ID NO: 254) | NIKQDGSEKYY VDSVKG (SEQ ID NO: 262) | RFTISRDNAKN SLYLQMNSLRA EDTAVYYCAR (SEQ ID NO: 247) |
| VH3-9*01 (SEQ ID NO: 196) | EVQLVESGGGL VQPGRSLRLSC AAS (SEQ ID NO: 263) | GFTFDDYAMH (SEQ ID NO: 264) | WVRQAPGKGLE WVS (SEQ ID NO: 241) | GISWNSGSIGY ADSVKG (SEQ ID NO: 265) | RFTISRDNAKN SLYLQMNSLRA EDTALYYCAK (SEQ ID NO: 266) |
| VH4-4*01 (SEQ ID NO: 197) | QVQLQESGPGL VKPPGTLSLTC AVS (SEQ ID NO: 267) | GGSISSSNWWS (SEQ ID NO: 268) | WVRQPPGKGLE WIG (SEQ ID NO: 269) | EIYHSGSTNYN PSLKS (SEQ ID NO: 270) | RVTISVDKSKN QFSLKLSSVTA ADTAVYCCAR (SEQ ID NO: 271) |
| VH5-51*01 (SEQ ID NO: 198) | EVQLVQSGAEV KKPGESLKISC KGS (SEQ ID NO: 272) | GYSFTSYWIG (SEQ ID NO: 273) | WVRQMPGKGLE WMG (SEQ ID NO: 274) | IIYPGDSDTRY SPSFQG (SEQ ID NO: 275) | QVTISADKSIS TAYLQWSSLKA SDTAMYYCAR (SEQ ID NO: 276) |

TABLE 16-continued

Germline sequences shown in Tables 2 and 4 (framework 1, CDR1, framework 2, CDR2, and framework 3 sequences).

| Germline | Framework 1 | Kabat CDR 1 | Framework 2 | Kabat CDR 2 | Framework 3 |
|---|---|---|---|---|---|
| Vk1-12*01 (SEQ ID NO: 199) | DIQMTQSPSSV SASVGDRVTIT C (SEQ ID NO: 277) | RASQGISSWLA (SEQ ID NO: 278) | WYQQKPGKAPK LLIY (SEQ ID NO: 279) | AASSLQS (SEQ ID NO: 280) | GVPSRFSGSGS GTDFTLTISSL QPEDFATYYC (SEQ ID NO: 281) |
| Vk1-27*01 (SEQ ID NO: 200) | DIQMTQSPSSL SASVGDRVTIT C (SEQ ID NO: 282) | RASQGISNYLA (SEQ ID NO: 283) | WYQQKPGKVPK LLIY (SEQ ID NO: 284) | AASTLQS (SEQ ID NO: 285) | GVPSRFSGSGS GTDFTLTISSL QPEDVATYYC (SEQ ID NO: 286) |
| Vk1-39*01 (SEQ ID NO:201) | DIQMTQSPSSL SASVGDRVTIT C (SEQ ID NO: 282 | RASQSISSYLN (SEQ ID NO: 287) | WYQQKPGKAPK LLIY (SEQ ID NO: 279) | AASSLQS (SEQ ID NO: 280) | GVPSRFSGSGS GTDFTLTISSL QPEDFATYYC (SEQ ID NO: 281) |
| Vk1D-16*01 (SEQ ID NO: 202) | DIQMTQSPSSL SASVGDRVTIT C (SEQ ID NO: 282 | RASQGISSWLA (SEQ ID NO: 278) | WYQQKPEKAPK SLIY (SEQ ID NO: 288) | AASSLQS (SEQ ID NO: 280) | GVPSRFSGSGS GTDFTLTISSL QPEDFATYYC (SEQ ID NO: 281) |
| Vk2-28*01 (SEQ ID NO: 203) | DIVMTQSPLSL PVTPGEPASIS C (SEQ ID NO: 289) | RSSQSLLHSNG YNYLD (SEQ ID NO: 290) | WYLQKPGQSPQ LLIY (SEQ ID NO: 291) | LGSNRAS (SEQ ID NO: 292) | GVPDRFSGSGS GTDFTLKISRV EAEDVGVYYC (SEQ ID NO: 293) |
| Vk3-11*01 (SEQ ID NO: 204) | EIVLTQSPATL SLSPGERATLS C (SEQ ID NO: 294) | RASQSVSSYLA (SEQ ID NO: 295) | WYQQKPGQAPR LLIY (SEQ ID NO: 296) | DASNRAT (SEQ ID NO: 297) | GIPARFSGSGS GTDFTLTISSL EPEDFAVYYC (SEQ ID NO: 298) |
| Vk3-20*01 (SEQ ID NO: 205) | EIVLTQSPGTL SLSPGERATLS C (SEQ ID NO: 299) | RASQSVSSSYL A (SEQ ID NO: 300) | WYQQKPGQAPR LLIY (SEQ ID NO: 296) | GASSRAT (SEQ ID NO: 301) | GIPDRFSGSGS GTDFTLTISRL EPEDFAVYYC (SEQ ID NO: 302) |
| Vk3D-20*01 (SEQ ID NO: 206) | EIVLTQSPATL SLSPGERATLS C (SEQ ID NO: 294) | GASQSVSSSYL A (SEQ ID NO: 303) | WYQQKPGLAPR LLIY (SEQ ID NO: 304) | DASSRAT (SEQ ID NO: 305) | GIPDRFSGSGS GTDFTLTISRL EPEDFAVYYC (SEQ ID NO: 302) |
| Vl10-54*01 (SEQ ID NO: 207) | QAGLTQPPSVS KGLRQTATLTC (SEQ ID NO: 306) | TGNSNNVGNQG AA (SEQ ID NO: 307) | WLQQHQGHPPK LLSY (SEQ ID NO: 308) | RNNNRPS (SEQ ID NO: 309) | GISERLSASRS GNTASLTITGL QPEDEADYYC (SEQ ID NO: 310) |
| Vl140*01 (SEQ ID NO: 208) | QSVLTQPPSVS GAPGQRVTISC (SEQ ID NO: 311) | TGSSSNIGAGY DVH (SEQ ID NO: 312) | WYQQLPGTAPK LLIY (SEQ ID NO: 313) | GNSNRPS (SEQ ID NO: 314) | GVPDRFSGSKS GTSASLAITGL QAEDEADYYC (SEQ ID NO: 315) |
| Vl1-44*01 (SEQ ID NO: 209) | QSVLTQPPSAS GTPGQRVTISC (SEQ ID NO: 316) | SGSSSNIGSNT VN (SEQ ID NO: 317) | WYQQLPGTAPK LLIY (SEQ ID NO: 313) | SNNQRPS (SEQ ID NO: 318) | GVPDRFSGSKS GTSASLAISGL QSEDEADYYC (SEQ ID NO: 319) |
| Vl2-14*01 (SEQ ID NO: 210) | QSALTQPASVS GSPGQSITISC (SEQ ID NO: 320) | TGTSSDVGGYN YVS (SEQ ID NO: 321) | WYQQHPGKAPK LMIY (SEQ ID NO: 322) | EVSNRPS (SEQ ID NO: 323) | GVSNRFSGSKS GNTASLTISGL QAEDEADYYC (SEQ ID NO: 324) |

TABLE 16-continued

Germline sequences shown in Tables 2 and 4 (framework 1, CDR1, framework 2, CDR2, and framework 3 sequences).

| Germline | Framework 1 | Kabat CDR 1 | Framework 2 | Kabat CDR 2 | Framework 3 |
|---|---|---|---|---|---|
| Vl3-19*01 (SEQ ID NO: 211) | SSELTQDPAVS VALGQTVRITC (SEQ ID NO: 325) | QGDSLRSYYAS (SEQ ID NO: 326) | WYQQKPGQAPV LVIY (SEQ ID NO: 327) | GKNNRPS (SEQ ID NO: 328) | GIPDRFSGSSS GNTASLTITGA QAEDEADYYC (SEQ ID NO: 329) |
| Vl3-9*01 (SEQ ID NO: 212) | SYELTQPLSVS VALGQTARITC (SEQ ID NO: 330) | GGNNIGSKNVH (SEQ ID NO: 331) | WYQQKPGQAPV LVIY (SEQ ID NO: 327) | RDSNRPS (SEQ ID NO: 332) | GIPERFSGSNS GNTATLTISRA QAGDEADYYC (SEQ ID NO: 333) |
| Vl14-31*01 (SEQ ID NO: 213) | QVQLQESGPGL VKPSQTLSLTC TVS (SEQ ID NO: 334) | GGSISSGSYYW S (SEQ ID NO: 335) | WIRQHPGKGLE WIG (SEQ ID NO: 336) | YIYYSGSTYYN PSLKS (SEQ ID NO: 337) | RVTISVDTSKN QFSLKLSSVTA ADTAVYY (SEQ ID NO: 338) |

TABLE 5a

Sequences used to construct multispecific molecules.

| Column 1: Construct | Column 2: heavy chain polypeptide 1 (HCP1) | Column 3: lambda light chain polypeptide (LLCP) | Column 4: heavy chain polypeptide 2 (HCP2) | Column 5: kappa light chain polypeptide (KLCP) |
|---|---|---|---|---|
| Multispecific molecule 1 | SEQ ID NO: 178 | SEQ ID NO: 145 | SEQ ID NO: 179 | SEQ ID NO: 118 |
| Multispecific molecule 2 | SEQ ID NO: 166 | SEQ ID NO: 167 | SEQ ID NO: 164 | SEQ ID NO: 165 |
| Multispecific molecule 3 | SEQ ID NO: 170 | SEQ ID NO: 163 | SEQ ID NO: 168 | SEQ ID NO: 106 |
| Multispecific molecule 4 | SEQ ID NO: 177 | SEQ ID NO: 148 | SEQ ID NO: 168 | SEQ ID NO: 106 |
| Multispecific molecule 5 | SEQ ID NO: 180 | SEQ ID NO: 136 | SEQ ID NO: 168 | SEQ ID NO: 106 |
| Multispecific molecule 6 | SEQ ID NO: 177 | SEQ ID NO: 148 | SEQ ID NO: 181 | SEQ ID NO: 182 |
| Multispecific molecule 7 | SEQ ID NO: 166 | SEQ ID NO: 167 | SEQ ID NO: 181 | SEQ ID NO: 182 |
| Multispecific molecule 8 | SEQ ID NO: 172 | SEQ ID NO: 173 | SEQ ID NO: 171 | SEQ ID NO: 106 |
| Multispecific molecule 9 | SEQ ID NO: 170 | SEQ ID NO: 173 | SEQ ID NO: 168 | SEQ ID NO: 106 |
| Multispecific molecule 10 | SEQ ID NO: 175 | SEQ ID NO: 173 | SEQ ID NO: 171 | SEQ ID NO: 106 |
| Multispecific molecule 11 | SEQ ID NO: 174 | SEQ ID NO: 173 | SEQ ID NO: 168 | SEQ ID NO: 106 |
| Multispecific molecule 12 | SEQ ID NO: 177 | SEQ ID NO: 148 | SEQ ID NO: 169 | SEQ ID NO: 176 |

TABLE 5b

Corresponding germline sequences of multispecific molecules.

| Column 1: Construct | Column 2: heavy chain polypeptide 1 (HCP1) corresponding germline sequence | Column 3: lambda light chain polypeptide (LLCP) corresponding germline sequence | Column 4: heavy chain polypeptide 2 (HCP2) corresponding germline sequence | Column 5: kappa light chain polypeptide (KLCP) corresponding germline sequence |
|---|---|---|---|---|
| Multispecific molecule 1 | VH3-9*01 (SEQ ID NO: 196) | Vl3-19*01 (SEQ ID NO: 211) | VH3-23*01 (SEQ ID NO: 191) | Vk1-27*01 (SEQ ID NO: 200) |
| Multispecific molecule 2 | VH3-66*01 (SEQ ID NO: 194) | Vl2-14*01 (SEQ ID NO: 210) | VH4-31*01 (SEQ ID NO: 213) | Vk1-39*01 (SEQ ID NO: 201) |
| Multispecific molecule 3 | VH3-33*01 (SEQ ID NO: 193) | Vl1-44*01 (SEQ ID NO: 209) | VH3-30*01 (SEQ ID NO: 192) | Vk3-20*01 (SEQ ID NO: 205) |

TABLE 5b-continued

Corresponding germline sequences of multispecific molecules.

| Column 1: Construct | Column 2: heavy chain polypeptide 1 (HCP1) corresponding germline sequence | Column 3: lambda light chain polypeptide (LLCP) corresponding germline sequence | Column 4: heavy chain polypeptide 2 (HCP2) corresponding germline sequence | Column 5: kappa light chain polypeptide (KLCP) corresponding germline sequence |
|---|---|---|---|---|
| Multispecific molecule 4 | Vk3-20*01 (SEQ ID NO: 205) | Vl3-19*01 (SEQ ID NO: 211) | VH3-30*01 (SEQ ID NO: 192) | Vk3-20*01 (SEQ ID NO: 205) |
| Multispecific molecule 5 | VH1-69*01 (SEQ ID NO: 187) | Vl3-19*01 (SEQ ID NO: 211) | VH3-30*01 (SEQ ID NO: 192) | Vk3-20*01 (SEQ ID NO: 205) |
| Multispecific molecule 6 | Vk3-20*01 (SEQ ID NO: 205) | Vl3-19*01 (SEQ ID NO: 211) | VH3-33*01 (SEQ ID NO: 193) | Vk3-11*01 (SEQ ID NO: 204) |
| Multispecific molecule 7 | VH3-66*01 (SEQ ID NO: 194) | Vl2-14*01 (SEQ ID NO: 210) | VH3-33*01 (SEQ ID NO: 193) | Vk3-11*01 (SEQ ID NO: 204) |
| Multispecific molecule 8 | VH3-33*01 (SEQ ID NO: 193) | Vl1-44*01 (SEQ ID NO: 209) | VH3-30*01 (SEQ ID NO: 192) | Vk3-20*01 (SEQ ID NO: 205) |
| Multispecific molecule 9 | VH3-33*01 (SEQ ID NO: 193) | Vl1-44*01 (SEQ ID NO: 209) | VH3-30*01 (SEQ ID NO: 192) | Vk3-20*01 (SEQ ID NO: 205) |
| Multispecific molecule 10 | VH3-33*01 (SEQ ID NO: 193) | Vl1-44*01 (SEQ ID NO: 209) | VH3-30*01 (SEQ ID NO: 192) | Vk3-20*01 (SEQ ID NO: 205) |
| Multispecific molecule 11 | VH3-33*01 (SEQ ID NO: 193) | Vl1-44*01 (SEQ ID NO: 209) | VH3-30*01 (SEQ ID NO: 192) | Vk3-20*01 (SEQ ID NO: 205) |
| Multispecific molecule 12 | Vk3-20*01 (SEQ ID NO: 205) | Vl3-19*01 (SEQ ID NO: 211) | VH3-30*01 (SEQ ID NO: 192) | Vk3-20*01 (SEQ ID NO: 205) |

5. Kappa/Lambda Select Resin Analysis of Chain Pairing.

The kappa and lambda light chain pairing of bispecific constructs was analyzed by incubating 1 mg of protein with 100 μL of either KappaSelect (GE 17-5458-01) or Lambda-FabSelect (GE 17-5482-01) resin. After incubating for 1-3 hours, the resin was packed into a column, washed with 3×10 column volumes of Dulbecco's phosphate-buffered saline (DPBS, Life Technologies 14190-144). The bound protein was eluted from the column with 100 mM citrate, pH 2.46. The content of the load, flow-through, and elution fractions was analyzed using gels of samples reduced with 200 mM Bond-Breaker TCEP (Thermo Scientific 77720), allowing for the identification of the various chains. For quantitative assessment of the chain pairing, the amount of protein in the load and flow-through fractions was assessed using the absorbance at 280 nm with a NanoDrop.

The KappaSelect resin is an affinity resin that binds to the constant light chain of kappa antibodies. The elution from the KappaSelect will contain molecules with both a lambda and kappa light chain, where there are three possibilities (FIGS. 1A, 1B, and 1D). The LambdaFabSelect resin is an affinity resin that binds to the constant light chain of lambda antibodies. The elution from the LambdaFabSelect will contain molecules with both lambda and kappa light chain, where there are three possibilities (FIGS. 1A, 1C, and 1D).

6. Mass Spectrometry for Analysis of Chain Pairing.

Figure 2:
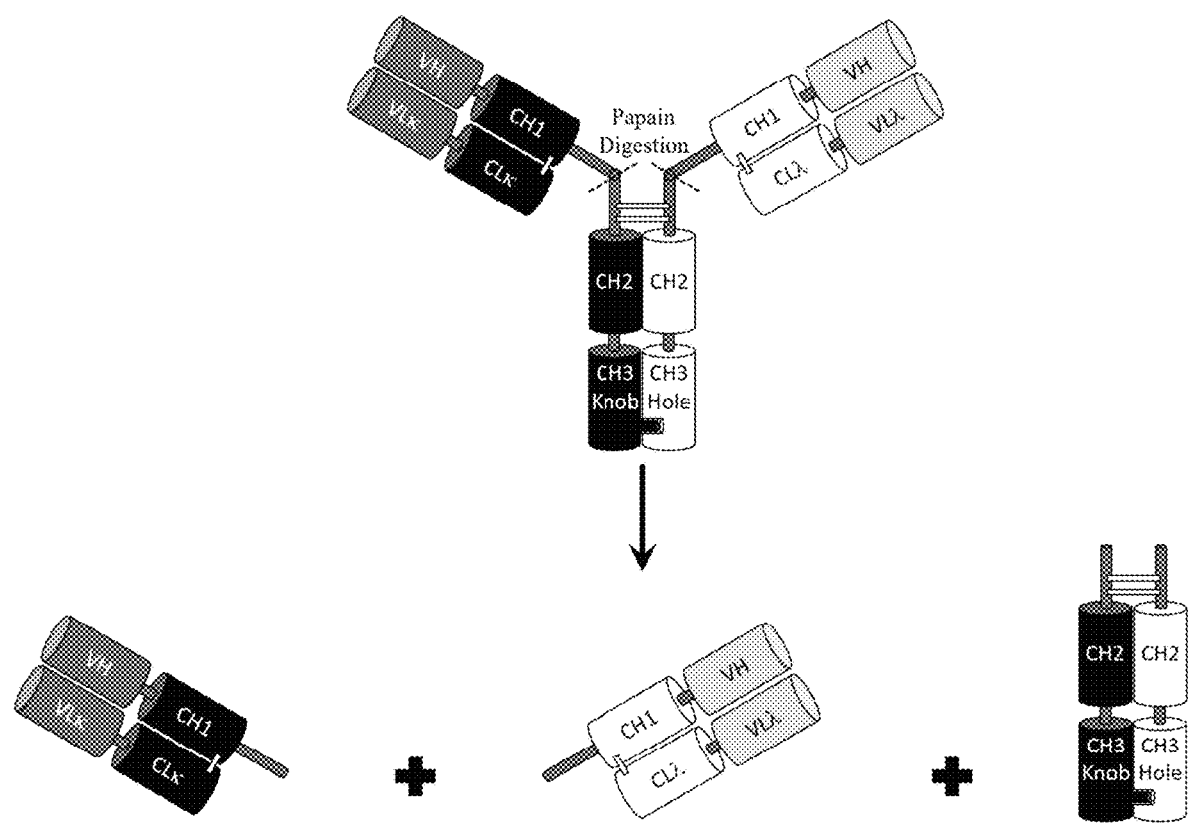
FIG. 2 depicts a schematic representation of a papain-cleaved bispecific antibody showing the location of cleavage in the hinge region by a dotted line. In embodiments, the multispecific antibody molecule having a first binding specificity that includes a hybrid VLλ-CLλ heterodimerized to a first heavy chain variable region-CH1 connected to the Fc constant, CH2-CH3 domain (having a hole modification) and a second binding specificity that includes a hybrid VLκ-CLκ heterodimerized to a second heavy chain variable region-CH1 connected to the Fc constant, CH2-CH3 domain (having a knob modification). Two Fab fragments are released after papain treatment.

To characterize the chain pairing in multispecific molecules, the purified samples were digested with immobilized papain (Thermo Scientific 20341) according to the manufacturer's instructions. Papain cleaves after the hinge region (FIG. 2), yielding two Fab arms. The digested molecules were run on a mass spectrometer, allowing identification of the two Fab arms based on the intact masses measured. The MS analysis allows for the discrimination of the different configurations (FIG. 1A vs. FIG. 1D), and the characterization of the extent of light-chain swapping.

Results

Example 1

NanoBiT based constructs were expressed by co-transfecting cells with DNA in a 1:1:1 heavy chain to light chain to competing light chain ratio. Table 3 shows individual combinations of a heavy chain (column 2), a light chain (column 3), and a competing light chain (column 4). Column 1 in Table 3 provides identifiers for each sequence combination. The molecules were purified and the luminescence assay was performed using the Nano-Glo reagent. The positive controls and negative controls are indicated. Positive controls represented 100% perfect pairing and the negative controls represented 50% perfect pairing. These values were used to quantify the pairing of the test constructs.

Table 6 shows the percent pairing for heavy chains and kappa light chains in the presence of competing lambda light chains (only the sequence combinations with a percent pairing of 75% or greater were included). Table 7 shows the percent pairing for heavy chains and lambda light chains in the presence of competing kappa light chains (only the sequence combinations with a percent pairing of 75% or greater were included). The identifiers shown in column 1 of Tables 6 and 7 correspond to the identifiers in column 1 of Table 3. In addition, Tables 6 and 7 also provide the corresponding germline sequences for the heavy chains (column 3), the light chains (column 4), and the competing light chains (column 5) used in each sequence combination.

Table 8a is a compilation of Tables 6 and 7 with samples that were successful in both directions. Each row of Table 8a shows a heavy chain/kappa light chain pair and a heavy chain/lambda light chain pair (indicated by the ID number), where the swapping of light chains between these two pairs is low based on the NanoBiT assay. Table 8b provides the corresponding germline sequences for the heavy chain/light chain pairs included in Table 8a. The identifiers shown in Tables 8a and 8b correspond to the identifiers in column 1 of Table 3.

TABLE 3

Sequences used to generate competition constructs.

| Identifier for sequence combinations | Heavy chain | Light chain | Competing light chain |
|---|---|---|---|
| ID183 (positive control) | SEQ ID NO: 92 | SEQ ID NO: 93 | |
| ID184 (negative control) | SEQ ID NO: 92 | SEQ ID NO: 93 | SEQ ID NO: 94 |
| ID185 | SEQ ID NO: 92 | SEQ ID NO: 93 | SEQ ID NO: 136 |
| ID186 | SEQ ID NO: 92 | SEQ ID NO: 93 | SEQ ID NO: 139 |
| ID187 | SEQ ID NO: 92 | SEQ ID NO: 93 | SEQ ID NO: 142 |
| ID188 | SEQ ID NO: 92 | SEQ ID NO: 93 | SEQ ID NO: 145 |
| ID189 | SEQ ID NO: 92 | SEQ ID NO: 93 | SEQ ID NO: 148 |
| ID190 | SEQ ID NO: 92 | SEQ ID NO: 93 | SEQ ID NO: 151 |
| ID191 | SEQ ID NO: 92 | SEQ ID NO: 93 | SEQ ID NO: 154 |
| ID192 | SEQ ID NO: 92 | SEQ ID NO: 93 | SEQ ID NO: 157 |
| ID193 | SEQ ID NO: 92 | SEQ ID NO: 93 | SEQ ID NO: 160 |
| ID194 | SEQ ID NO: 92 | SEQ ID NO: 93 | SEQ ID NO: 163 |
| ID195 (positive control) | SEQ ID NO: 95 | SEQ ID NO: 96 | |
| ID196 (negative control) | SEQ ID NO: 95 | SEQ ID NO: 96 | SEQ ID NO: 97 |
| ID197 | SEQ ID NO: 95 | SEQ ID NO: 96 | SEQ ID NO: 136 |
| ID198 | SEQ ID NO: 95 | SEQ ID NO: 96 | SEQ ID NO: 139 |
| ID199 | SEQ ID NO: 95 | SEQ ID NO: 96 | SEQ ID NO: 142 |
| ID200 | SEQ ID NO: 95 | SEQ ID NO: 96 | SEQ ID NO: 145 |
| ID201 | SEQ ID NO: 95 | SEQ ID NO: 96 | SEQ ID NO: 148 |
| ID202 | SEQ ID NO: 95 | SEQ ID NO: 96 | SEQ ID NO: 151 |
| ID203 | SEQ ID NO: 95 | SEQ ID NO: 96 | SEQ ID NO: 154 |
| ID204 | SEQ ID NO: 95 | SEQ ID NO: 96 | SEQ ID NO: 157 |
| ID205 | SEQ ID NO: 95 | SEQ ID NO: 96 | SEQ ID NO: 160 |
| ID206 | SEQ ID NO: 95 | SEQ ID NO: 96 | SEQ ID NO: 163 |
| ID207 (positive control) | SEQ ID NO: 99 | SEQ ID NO: 98 | |
| ID208 (negative control) | SEQ ID NO: 98 | SEQ ID NO: 99 | SEQ ID NO: 100 |
| ID209 | SEQ ID NO: 98 | SEQ ID NO: 99 | SEQ ID NO: 136 |
| ID210 | SEQ ID NO: 98 | SEQ ID NO: 99 | SEQ ID NO: 139 |
| ID211 | SEQ ID NO: 98 | SEQ ID NO: 99 | SEQ ID NO: 142 |
| ID212 | SEQ ID NO: 98 | SEQ ID NO: 99 | SEQ ID NO: 145 |
| ID213 | SEQ ID NO: 98 | SEQ ID NO: 99 | SEQ ID NO: 148 |
| ID214 | SEQ ID NO: 98 | SEQ ID NO: 99 | SEQ ID NO: 151 |
| ID215 | SEQ ID NO: 98 | SEQ ID NO: 99 | SEQ ID NO: 154 |
| ID216 | SEQ ID NO: 98 | SEQ ID NO: 99 | SEQ ID NO: 157 |
| ID217 | SEQ ID NO: 98 | SEQ ID NO: 99 | SEQ ID NO: 160 |
| ID218 | SEQ ID NO: 98 | SEQ ID NO: 99 | SEQ ID NO: 163 |
| ID219 (positive control) | SEQ ID NO: 101 | SEQ ID NO: 102 | |
| ID220 (negative control) | SEQ ID NO: 101 | SEQ ID NO: 102 | SEQ ID NO: 103 |
| ID221 | SEQ ID NO: 101 | SEQ ID NO: 102 | SEQ ID NO: 136 |
| ID222 | SEQ ID NO: 101 | SEQ ID NO: 102 | SEQ ID NO: 139 |
| ID223 | SEQ ID NO: 101 | SEQ ID NO: 102 | SEQ ID NO: 142 |
| ID224 | SEQ ID NO: 101 | SEQ ID NO: 102 | SEQ ID NO: 145 |
| ID225 | SEQ ID NO: 101 | SEQ ID NO: 102 | SEQ ID NO: 148 |
| ID226 | SEQ ID NO: 101 | SEQ ID NO: 102 | SEQ ID NO: 151 |
| ID227 | SEQ ID NO: 101 | SEQ ID NO: 102 | SEQ ID NO: 154 |
| ID228 | SEQ ID NO: 101 | SEQ ID NO: 102 | SEQ ID NO: 157 |
| ID229 | SEQ ID NO: 101 | SEQ ID NO: 102 | SEQ ID NO: 160 |
| ID230 | SEQ ID NO: 101 | SEQ ID NO: 102 | SEQ ID NO: 163 |
| ID231 (positive control) | SEQ ID NO: 104 | SEQ ID NO: 105 | |
| ID232 (negative control) | SEQ ID NO: 104 | SEQ ID NO: 105 | SEQ ID NO: 106 |
| ID233 | SEQ ID NO: 104 | SEQ ID NO: 105 | SEQ ID NO: 136 |
| ID234 | SEQ ID NO: 104 | SEQ ID NO: 105 | SEQ ID NO: 139 |
| ID235 | SEQ ID NO: 104 | SEQ ID NO: 105 | SEQ ID NO: 142 |
| ID236 | SEQ ID NO: 104 | SEQ ID NO: 105 | SEQ ID NO: 145 |
| ID237 | SEQ ID NO: 104 | SEQ ID NO: 105 | SEQ ID NO: 148 |
| ID238 | SEQ ID NO: 104 | SEQ ID NO: 105 | SEQ ID NO: 151 |
| ID239 | SEQ ID NO: 104 | SEQ ID NO: 105 | SEQ ID NO: 154 |
| ID240 | SEQ ID NO: 104 | SEQ ID NO: 105 | SEQ ID NO: 157 |
| ID241 | SEQ ID NO: 104 | SEQ ID NO: 105 | SEQ ID NO: 160 |
| ID242 | SEQ ID NO: 104 | SEQ ID NO: 105 | SEQ ID NO: 163 |
| ID243 (positive control) | SEQ ID NO: 107 | SEQ ID NO: 108 | |
| ID244 (negative control) | SEQ ID NO: 107 | SEQ ID NO: 108 | SEQ ID NO: 109 |
| ID245 | SEQ ID NO: 107 | SEQ ID NO: 108 | SEQ ID NO: 136 |
| ID246 | SEQ ID NO: 107 | SEQ ID NO: 108 | SEQ ID NO: 139 |
| ID247 | SEQ ID NO: 107 | SEQ ID NO: 108 | SEQ ID NO: 142 |
| ID248 | SEQ ID NO: 107 | SEQ ID NO: 108 | SEQ ID NO: 145 |
| ID249 | SEQ ID NO: 107 | SEQ ID NO: 108 | SEQ ID NO: 148 |
| ID250 | SEQ ID NO: 107 | SEQ ID NO: 108 | SEQ ID NO: 151 |
| ID251 | SEQ ID NO: 107 | SEQ ID NO: 108 | SEQ ID NO: 154 |
| ID252 | SEQ ID NO: 107 | SEQ ID NO: 108 | SEQ ID NO: 157 |
| ID253 | SEQ ID NO: 107 | SEQ ID NO: 108 | SEQ ID NO: 160 |
| ID254 | SEQ ID NO: 107 | SEQ ID NO: 108 | SEQ ID NO: 163 |
| ID255 (positive control) | SEQ ID NO: 110 | SEQ ID NO: 111 | |
| ID256 (negative control) | SEQ ID NO: 110 | SEQ ID NO: 111 | SEQ ID NO: 112 |
| ID257 | SEQ ID NO: 110 | SEQ ID NO: 111 | SEQ ID NO: 136 |
| ID258 | SEQ ID NO: 110 | SEQ ID NO: 111 | SEQ ID NO: 139 |
| ID259 | SEQ ID NO: 110 | SEQ ID NO: 111 | SEQ ID NO: 142 |
| ID260 | SEQ ID NO: 110 | SEQ ID NO: 111 | SEQ ID NO: 145 |
| ID261 | SEQ ID NO: 110 | SEQ ID NO: 111 | SEQ ID NO: 148 |
| ID262 | SEQ ID NO: 110 | SEQ ID NO: 111 | SEQ ID NO: 151 |
| ID263 | SEQ ID NO: 110 | SEQ ID NO: 111 | SEQ ID NO: 154 |
| ID264 | SEQ ID NO: 110 | SEQ ID NO: 111 | SEQ ID NO: 157 |
| ID265 | SEQ ID NO: 110 | SEQ ID NO: 111 | SEQ ID NO: 160 |
| ID266 | SEQ ID NO: 110 | SEQ ID NO: 111 | SEQ ID NO: 163 |
| ID267 (positive control) | SEQ ID NO: 113 | SEQ ID NO: 114 | |
| ID268 (negative control) | SEQ ID NO: 113 | SEQ ID NO: 114 | SEQ ID NO: 115 |
| ID269 | SEQ ID NO: 113 | SEQ ID NO: 114 | SEQ ID NO: 136 |
| ID270 | SEQ ID NO: 113 | SEQ ID NO: 114 | SEQ ID NO: 139 |
| ID271 | SEQ ID NO: 113 | SEQ ID NO: 114 | SEQ ID NO: 142 |
| ID272 | SEQ ID NO: 113 | SEQ ID NO: 114 | SEQ ID NO: 145 |
| ID273 | SEQ ID NO: 113 | SEQ ID NO: 114 | SEQ ID NO: 148 |
| ID274 | SEQ ID NO: 113 | SEQ ID NO: 114 | SEQ ID NO: 151 |
| ID275 | SEQ ID NO: 113 | SEQ ID NO: 114 | SEQ ID NO: 154 |
| ID276 | SEQ ID NO: 113 | SEQ ID NO: 114 | SEQ ID NO: 157 |
| ID277 | SEQ ID NO: 113 | SEQ ID NO: 114 | SEQ ID NO: 160 |
| ID278 | SEQ ID NO: 113 | SEQ ID NO: 114 | SEQ ID NO: 163 |
| ID279 (positive control) | SEQ ID NO: 116 | SEQ ID NO: 117 | |
| ID280 (negative control) | SEQ ID NO: 116 | SEQ ID NO: 117 | SEQ ID NO: 118 |
| ID281 | SEQ ID NO: 116 | SEQ ID NO: 117 | SEQ ID NO: 136 |
| ID282 | SEQ ID NO: 116 | SEQ ID NO: 117 | SEQ ID NO: 139 |
| ID283 | SEQ ID NO: 116 | SEQ ID NO: 117 | SEQ ID NO: 142 |
| ID284 | SEQ ID NO: 116 | SEQ ID NO: 117 | SEQ ID NO: 145 |
| ID285 | SEQ ID NO: 116 | SEQ ID NO: 117 | SEQ ID NO: 148 |
| ID286 | SEQ ID NO: 116 | SEQ ID NO: 117 | SEQ ID NO: 151 |
| ID287 | SEQ ID NO: 116 | SEQ ID NO: 117 | SEQ ID NO: 154 |
| ID288 | SEQ ID NO: 116 | SEQ ID NO: 117 | SEQ ID NO: 157 |
| ID289 | SEQ ID NO: 116 | SEQ ID NO: 117 | SEQ ID NO: 160 |
| ID290 | SEQ ID NO: 116 | SEQ ID NO: 117 | SEQ ID NO: 163 |

TABLE 3-continued

Sequences used to generate competition constructs.

| Identifier for sequence combinations | Heavy chain | Light chain | Competing light chain |
|---|---|---|---|
| ID291 (positive control) | SEQ ID NO: 119 | SEQ ID NO: 120 | |
| ID292 (negative control) | SEQ ID NO: 119 | SEQ ID NO: 120 | SEQ ID NO: 121 |
| ID293 | SEQ ID NO: 119 | SEQ ID NO: 120 | SEQ ID NO: 136 |
| ID294 | SEQ ID NO: 119 | SEQ ID NO: 120 | SEQ ID NO: 139 |
| ID295 | SEQ ID NO: 119 | SEQ ID NO: 120 | SEQ ID NO: 142 |
| ID296 | SEQ ID NO: 119 | SEQ ID NO: 120 | SEQ ID NO: 145 |
| ID297 | SEQ ID NO: 119 | SEQ ID NO: 120 | SEQ ID NO: 148 |
| ID298 | SEQ ID NO: 119 | SEQ ID NO: 120 | SEQ ID NO: 151 |
| ID299 | SEQ ID NO: 119 | SEQ ID NO: 120 | SEQ ID NO: 154 |
| ID300 | SEQ ID NO: 119 | SEQ ID NO: 120 | SEQ ID NO: 157 |
| ID301 | SEQ ID NO: 119 | SEQ ID NO: 120 | SEQ ID NO: 160 |
| ID302 | SEQ ID NO: 119 | SEQ ID NO: 120 | SEQ ID NO: 163 |
| ID303 (positive control) | SEQ ID NO: 122 | SEQ ID NO: 123 | |
| ID304 (negative control) | SEQ ID NO: 122 | SEQ ID NO: 123 | SEQ ID NO: 124 |
| ID305 | SEQ ID NO: 122 | SEQ ID NO: 123 | SEQ ID NO: 136 |
| ID306 | SEQ ID NO: 122 | SEQ ID NO: 123 | SEQ ID NO: 139 |
| ID307 | SEQ ID NO: 122 | SEQ ID NO: 123 | SEQ ID NO: 142 |
| ID308 | SEQ ID NO: 122 | SEQ ID NO: 123 | SEQ ID NO: 145 |
| ID309 | SEQ ID NO: 122 | SEQ ID NO: 123 | SEQ ID NO: 148 |
| ID310 | SEQ ID NO: 122 | SEQ ID NO: 123 | SEQ ID NO: 151 |
| ID311 | SEQ ID NO: 122 | SEQ ID NO: 123 | SEQ ID NO: 154 |
| ID312 | SEQ ID NO: 122 | SEQ ID NO: 123 | SEQ ID NO: 157 |
| ID313 | SEQ ID NO: 122 | SEQ ID NO: 123 | SEQ ID NO: 160 |
| ID314 | SEQ ID NO: 122 | SEQ ID NO: 123 | SEQ ID NO: 163 |
| ID315 (positive control) | SEQ ID NO: 125 | SEQ ID NO: 126 | |
| ID316 (negative control) | SEQ ID NO: 125 | SEQ ID NO: 126 | SEQ ID NO: 127 |
| ID317 | SEQ ID NO: 125 | SEQ ID NO: 126 | SEQ ID NO: 136 |
| ID318 | SEQ ID NO: 125 | SEQ ID NO: 126 | SEQ ID NO: 139 |
| ID319 | SEQ ID NO: 125 | SEQ ID NO: 126 | SEQ ID NO: 142 |
| ID320 | SEQ ID NO: 125 | SEQ ID NO: 126 | SEQ ID NO: 145 |
| ID321 | SEQ ID NO: 125 | SEQ ID NO: 126 | SEQ ID NO: 148 |
| ID322 | SEQ ID NO: 125 | SEQ ID NO: 126 | SEQ ID NO: 151 |
| ID323 | SEQ ID NO: 125 | SEQ ID NO: 126 | SEQ ID NO: 154 |
| ID324 | SEQ ID NO: 125 | SEQ ID NO: 126 | SEQ ID NO: 157 |
| ID325 | SEQ ID NO: 125 | SEQ ID NO: 126 | SEQ ID NO: 160 |
| ID326 | SEQ ID NO: 125 | SEQ ID NO: 126 | SEQ ID NO: 163 |
| ID327 (positive control) | SEQ ID NO: 128 | SEQ ID NO: 129 | |
| ID328 (negative control) | SEQ ID NO: 128 | SEQ ID NO: 129 | SEQ ID NO: 130 |
| ID329 | SEQ ID NO: 128 | SEQ ID NO: 129 | SEQ ID NO: 136 |
| ID330 | SEQ ID NO: 128 | SEQ ID NO: 129 | SEQ ID NO: 139 |
| ID331 | SEQ ID NO: 128 | SEQ ID NO: 129 | SEQ ID NO: 142 |
| ID332 | SEQ ID NO: 128 | SEQ ID NO: 129 | SEQ ID NO: 145 |
| ID333 | SEQ ID NO: 128 | SEQ ID NO: 129 | SEQ ID NO: 148 |
| ID334 | SEQ ID NO: 128 | SEQ ID NO: 129 | SEQ ID NO: 151 |
| ID335 | SEQ ID NO: 128 | SEQ ID NO: 129 | SEQ ID NO: 154 |
| ID336 | SEQ ID NO: 128 | SEQ ID NO: 129 | SEQ ID NO: 157 |
| ID337 | SEQ ID NO: 128 | SEQ ID NO: 129 | SEQ ID NO: 160 |
| ID338 | SEQ ID NO: 128 | SEQ ID NO: 129 | SEQ ID NO: 163 |
| ID339 (positive control) | SEQ ID NO: 131 | SEQ ID NO: 132 | |
| ID340 (negative control) | SEQ ID NO: 131 | SEQ ID NO: 132 | SEQ ID NO: 133 |
| ID341 | SEQ ID NO: 131 | SEQ ID NO: 132 | SEQ ID NO: 136 |
| ID342 | SEQ ID NO: 131 | SEQ ID NO: 132 | SEQ ID NO: 139 |
| ID343 | SEQ ID NO: 131 | SEQ ID NO: 132 | SEQ ID NO: 142 |
| ID344 | SEQ ID NO: 131 | SEQ ID NO: 132 | SEQ ID NO: 145 |
| ID345 | SEQ ID NO: 131 | SEQ ID NO: 132 | SEQ ID NO: 148 |
| ID346 | SEQ ID NO: 131 | SEQ ID NO: 132 | SEQ ID NO: 151 |
| ID347 | SEQ ID NO: 131 | SEQ ID NO: 132 | SEQ ID NO: 154 |
| ID348 | SEQ ID NO: 131 | SEQ ID NO: 132 | SEQ ID NO: 157 |
| ID349 | SEQ ID NO: 131 | SEQ ID NO: 132 | SEQ ID NO: 160 |
| ID350 | SEQ ID NO: 131 | SEQ ID NO: 132 | SEQ ID NO: 163 |
| ID351 (positive control) | SEQ ID NO: 134 | SEQ ID NO: 135 | |
| ID352 (negative control) | SEQ ID NO: 134 | SEQ ID NO: 135 | SEQ ID NO: 136 |
| ID353 | SEQ ID NO: 134 | SEQ ID NO: 135 | SEQ ID NO: 94 |
| ID354 | SEQ ID NO: 134 | SEQ ID NO: 135 | SEQ ID NO: 97 |
| ID355 | SEQ ID NO: 134 | SEQ ID NO: 135 | SEQ ID NO: 100 |
| ID356 | SEQ ID NO: 134 | SEQ ID NO: 135 | SEQ ID NO: 103 |
| ID357 | SEQ ID NO: 134 | SEQ ID NO: 135 | SEQ ID NO: 106 |
| ID358 | SEQ ID NO: 134 | SEQ ID NO: 135 | SEQ ID NO: 109 |
| ID359 | SEQ ID NO: 134 | SEQ ID NO: 135 | SEQ ID NO: 112 |
| ID360 | SEQ ID NO: 134 | SEQ ID NO: 135 | SEQ ID NO: 115 |
| ID361 | SEQ ID NO: 134 | SEQ ID NO: 135 | SEQ ID NO: 118 |
| ID362 | SEQ ID NO: 134 | SEQ ID NO: 135 | SEQ ID NO: 121 |
| ID363 | SEQ ID NO: 134 | SEQ ID NO: 135 | SEQ ID NO: 124 |
| ID364 | SEQ ID NO: 134 | SEQ ID NO: 135 | SEQ ID NO: 127 |
| ID365 | SEQ ID NO: 134 | SEQ ID NO: 135 | SEQ ID NO: 130 |
| ID366 | SEQ ID NO: 134 | SEQ ID NO: 135 | SEQ ID NO: 133 |
| ID367 (positive control) | SEQ ID NO: 137 | SEQ ID NO: 138 | |
| ID368 (negative control) | SEQ ID NO: 137 | SEQ ID NO: 138 | SEQ ID NO: 139 |
| ID369 | SEQ ID NO: 137 | SEQ ID NO: 138 | SEQ ID NO: 94 |
| ID370 | SEQ ID NO: 137 | SEQ ID NO: 138 | SEQ ID NO: 97 |
| ID371 | SEQ ID NO: 137 | SEQ ID NO: 138 | SEQ ID NO: 100 |
| ID372 | SEQ ID NO: 137 | SEQ ID NO: 138 | SEQ ID NO: 103 |
| ID373 | SEQ ID NO: 137 | SEQ ID NO: 138 | SEQ ID NO: 106 |
| ID374 | SEQ ID NO: 137 | SEQ ID NO: 138 | SEQ ID NO: 109 |
| ID375 | SEQ ID NO: 137 | SEQ ID NO: 138 | SEQ ID NO: 112 |
| ID376 | SEQ ID NO: 137 | SEQ ID NO: 138 | SEQ ID NO: 115 |
| ID377 | SEQ ID NO: 137 | SEQ ID NO: 138 | SEQ ID NO: 118 |
| ID378 | SEQ ID NO: 137 | SEQ ID NO: 138 | SEQ ID NO: 121 |
| ID379 | SEQ ID NO: 137 | SEQ ID NO: 138 | SEQ ID NO: 124 |
| ID380 | SEQ ID NO: 137 | SEQ ID NO: 138 | SEQ ID NO: 127 |
| ID381 | SEQ ID NO: 137 | SEQ ID NO: 138 | SEQ ID NO: 130 |
| ID382 | SEQ ID NO: 137 | SEQ ID NO: 138 | SEQ ID NO: 133 |
| ID383 (positive control) | SEQ ID NO: 140 | SEQ ID NO: 141 | |
| ID384 (negative control) | SEQ ID NO: 140 | SEQ ID NO: 141 | SEQ ID NO: 142 |
| ID385 | SEQ ID NO: 140 | SEQ ID NO: 141 | SEQ ID NO: 94 |
| ID386 | SEQ ID NO: 140 | SEQ ID NO: 141 | SEQ ID NO: 97 |
| ID387 | SEQ ID NO: 140 | SEQ ID NO: 141 | SEQ ID NO: 100 |
| ID388 | SEQ ID NO: 140 | SEQ ID NO: 141 | SEQ ID NO: 103 |
| ID389 | SEQ ID NO: 140 | SEQ ID NO: 141 | SEQ ID NO: 106 |
| ID390 | SEQ ID NO: 140 | SEQ ID NO: 141 | SEQ ID NO: 109 |
| ID391 | SEQ ID NO: 140 | SEQ ID NO: 141 | SEQ ID NO: 112 |
| ID392 | SEQ ID NO: 140 | SEQ ID NO: 141 | SEQ ID NO: 115 |
| ID393 | SEQ ID NO: 140 | SEQ ID NO: 141 | SEQ ID NO: 118 |
| ID394 | SEQ ID NO: 140 | SEQ ID NO: 141 | SEQ ID NO: 121 |
| ID395 | SEQ ID NO: 140 | SEQ ID NO: 141 | SEQ ID NO: 124 |

TABLE 3-continued

Sequences used to generate competition constructs.

| Identifier for sequence combinations | Heavy chain | Light chain | Competing light chain |
|---|---|---|---|
| ID396 | SEQ ID NO: 140 | SEQ ID NO: 141 | SEQ ID NO: 127 |
| ID397 | SEQ ID NO: 140 | SEQ ID NO: 141 | SEQ ID NO: 130 |
| ID398 | SEQ ID NO: 140 | SEQ ID NO: 141 | SEQ ID NO: 133 |
| ID399 (positive control) | SEQ ID NO: 143 | SEQ ID NO: 144 | |
| ID400 (negative control) | SEQ ID NO: 143 | SEQ ID NO: 144 | SEQ ID NO: 145 |
| ID401 | SEQ ID NO: 143 | SEQ ID NO: 144 | SEQ ID NO: 94 |
| ID402 | SEQ ID NO: 143 | SEQ ID NO: 144 | SEQ ID NO: 97 |
| ID403 | SEQ ID NO: 143 | SEQ ID NO: 144 | SEQ ID NO: 100 |
| ID404 | SEQ ID NO: 143 | SEQ ID NO: 144 | SEQ ID NO: 103 |
| ID405 | SEQ ID NO: 143 | SEQ ID NO: 144 | SEQ ID NO: 106 |
| ID406 | SEQ ID NO: 143 | SEQ ID NO: 144 | SEQ ID NO: 109 |
| ID407 | SEQ ID NO: 143 | SEQ ID NO: 144 | SEQ ID NO: 112 |
| ID408 | SEQ ID NO: 143 | SEQ ID NO: 144 | SEQ ID NO: 115 |
| ID409 | SEQ ID NO: 143 | SEQ ID NO: 144 | SEQ ID NO: 118 |
| ID410 | SEQ ID NO: 143 | SEQ ID NO: 144 | SEQ ID NO: 121 |
| ID411 | SEQ ID NO: 143 | SEQ ID NO: 144 | SEQ ID NO: 124 |
| ID412 | SEQ ID NO: 143 | SEQ ID NO: 144 | SEQ ID NO: 127 |
| ID413 | SEQ ID NO: 143 | SEQ ID NO: 144 | SEQ ID NO: 130 |
| ID414 | SEQ ID NO: 143 | SEQ ID NO: 144 | SEQ ID NO: 133 |
| ID415 (positive control) | SEQ ID NO: 146 | SEQ ID NO: 147 | |
| ID416 (negative control) | SEQ ID NO: 146 | SEQ ID NO: 147 | SEQ ID NO: 148 |
| ID417 | SEQ ID NO: 146 | SEQ ID NO: 147 | SEQ ID NO: 94 |
| ID418 | SEQ ID NO: 146 | SEQ ID NO: 147 | SEQ ID NO: 97 |
| ID419 | SEQ ID NO: 146 | SEQ ID NO: 147 | SEQ ID NO: 100 |
| ID420 | SEQ ID NO: 146 | SEQ ID NO: 147 | SEQ ID NO: 103 |
| ID421 | SEQ ID NO: 146 | SEQ ID NO: 147 | SEQ ID NO: 106 |
| ID422 | SEQ ID NO: 146 | SEQ ID NO: 147 | SEQ ID NO: 109 |
| ID423 | SEQ ID NO: 146 | SEQ ID NO: 147 | SEQ ID NO: 112 |
| ID424 | SEQ ID NO: 146 | SEQ ID NO: 147 | SEQ ID NO: 115 |
| ID425 | SEQ ID NO: 146 | SEQ ID NO: 147 | SEQ ID NO: 118 |
| ID426 | SEQ ID NO: 146 | SEQ ID NO: 147 | SEQ ID NO: 121 |
| ID427 | SEQ ID NO: 146 | SEQ ID NO: 147 | SEQ ID NO: 124 |
| ID428 | SEQ ID NO: 146 | SEQ ID NO: 147 | SEQ ID NO: 127 |
| ID429 | SEQ ID NO: 146 | SEQ ID NO: 147 | SEQ ID NO: 130 |
| ID430 | SEQ ID NO: 146 | SEQ ID NO: 147 | SEQ ID NO: 133 |
| ID431 (positive control) | SEQ ID NO: 149 | SEQ ID NO: 150 | |
| ID432 (negative control) | SEQ ID NO: 149 | SEQ ID NO: 150 | SEQ ID NO: 151 |
| ID433 | SEQ ID NO: 149 | SEQ ID NO: 150 | SEQ ID NO: 94 |
| ID434 | SEQ ID NO: 149 | SEQ ID NO: 150 | SEQ ID NO: 97 |
| ID435 | SEQ ID NO: 149 | SEQ ID NO: 150 | SEQ ID NO: 100 |
| ID436 | SEQ ID NO: 149 | SEQ ID NO: 150 | SEQ ID NO: 103 |
| ID437 | SEQ ID NO: 149 | SEQ ID NO: 150 | SEQ ID NO: 106 |
| ID438 | SEQ ID NO: 149 | SEQ ID NO: 150 | SEQ ID NO: 109 |
| ID439 | SEQ ID NO: 149 | SEQ ID NO: 150 | SEQ ID NO: 112 |
| ID440 | SEQ ID NO: 149 | SEQ ID NO: 150 | SEQ ID NO: 115 |
| ID441 | SEQ ID NO: 149 | SEQ ID NO: 150 | SEQ ID NO: 118 |
| ID442 | SEQ ID NO: 149 | SEQ ID NO: 150 | SEQ ID NO: 121 |
| ID443 | SEQ ID NO: 149 | SEQ ID NO: 150 | SEQ ID NO: 124 |
| ID444 | SEQ ID NO: 149 | SEQ ID NO: 150 | SEQ ID NO: 127 |
| ID445 | SEQ ID NO: 149 | SEQ ID NO: 150 | SEQ ID NO: 130 |
| ID446 | SEQ ID NO: 149 | SEQ ID NO: 150 | SEQ ID NO: 133 |
| ID447 (positive control) | SEQ ID NO: 152 | SEQ ID NO: 153 | |
| ID448 (negative control) | SEQ ID NO: 152 | SEQ ID NO: 153 | SEQ ID NO: 154 |
| ID449 | SEQ ID NO: 152 | SEQ ID NO: 153 | SEQ ID NO: 94 |
| ID450 | SEQ ID NO: 152 | SEQ ID NO: 153 | SEQ ID NO: 97 |
| ID451 | SEQ ID NO: 152 | SEQ ID NO: 153 | SEQ ID NO: 100 |
| ID452 | SEQ ID NO: 152 | SEQ ID NO: 153 | SEQ ID NO: 103 |
| ID453 | SEQ ID NO: 152 | SEQ ID NO: 153 | SEQ ID NO: 106 |
| ID454 | SEQ ID NO: 152 | SEQ ID NO: 153 | SEQ ID NO: 109 |
| ID455 | SEQ ID NO: 152 | SEQ ID NO: 153 | SEQ ID NO: 112 |
| ID456 | SEQ ID NO: 152 | SEQ ID NO: 153 | SEQ ID NO: 115 |
| ID457 | SEQ ID NO: 152 | SEQ ID NO: 153 | SEQ ID NO: 118 |
| ID458 | SEQ ID NO: 152 | SEQ ID NO: 153 | SEQ ID NO: 121 |
| ID459 | SEQ ID NO: 152 | SEQ ID NO: 153 | SEQ ID NO: 124 |
| ID460 | SEQ ID NO: 152 | SEQ ID NO: 153 | SEQ ID NO: 127 |
| ID461 | SEQ ID NO: 152 | SEQ ID NO: 153 | SEQ ID NO: 130 |
| ID462 | SEQ ID NO: 152 | SEQ ID NO: 153 | SEQ ID NO: 133 |
| ID463 (positive control) | SEQ ID NO: 155 | SEQ ID NO: 156 | |
| ID464 (negative control) | SEQ ID NO: 155 | SEQ ID NO: 156 | SEQ ID NO: 157 |
| ID465 | SEQ ID NO: 155 | SEQ ID NO: 156 | SEQ ID NO: 94 |
| ID466 | SEQ ID NO: 155 | SEQ ID NO: 156 | SEQ ID NO: 97 |
| ID467 | SEQ ID NO: 155 | SEQ ID NO: 156 | SEQ ID NO: 100 |
| ID468 | SEQ ID NO: 155 | SEQ ID NO: 156 | SEQ ID NO: 103 |
| ID469 | SEQ ID NO: 155 | SEQ ID NO: 156 | SEQ ID NO: 106 |
| ID470 | SEQ ID NO: 155 | SEQ ID NO: 156 | SEQ ID NO: 109 |
| ID471 | SEQ ID NO: 155 | SEQ ID NO: 156 | SEQ ID NO: 112 |
| ID472 | SEQ ID NO: 155 | SEQ ID NO: 156 | SEQ ID NO: 115 |
| ID473 | SEQ ID NO: 155 | SEQ ID NO: 156 | SEQ ID NO: 118 |
| ID474 | SEQ ID NO: 155 | SEQ ID NO: 156 | SEQ ID NO: 121 |
| ID475 | SEQ ID NO: 155 | SEQ ID NO: 156 | SEQ ID NO: 124 |
| ID476 | SEQ ID NO: 155 | SEQ ID NO: 156 | SEQ ID NO: 127 |
| ID477 | SEQ ID NO: 155 | SEQ ID NO: 156 | SEQ ID NO: 130 |
| ID478 | SEQ ID NO: 155 | SEQ ID NO: 156 | SEQ ID NO: 133 |
| ID479 (positive control) | SEQ ID NO: 158 | SEQ ID NO: 159 | |
| ID480 (negative control) | SEQ ID NO: 158 | SEQ ID NO: 159 | SEQ ID NO: 160 |
| ID481 | SEQ ID NO: 158 | SEQ ID NO: 159 | SEQ ID NO: 94 |
| ID482 | SEQ ID NO: 158 | SEQ ID NO: 159 | SEQ ID NO: 97 |
| ID483 | SEQ ID NO: 158 | SEQ ID NO: 159 | SEQ ID NO: 100 |
| ID484 | SEQ ID NO: 158 | SEQ ID NO: 159 | SEQ ID NO: 103 |
| ID485 | SEQ ID NO: 158 | SEQ ID NO: 159 | SEQ ID NO: 106 |
| ID486 | SEQ ID NO: 158 | SEQ ID NO: 159 | SEQ ID NO: 109 |
| ID487 | SEQ ID NO: 158 | SEQ ID NO: 159 | SEQ ID NO: 112 |
| ID488 | SEQ ID NO: 158 | SEQ ID NO: 159 | SEQ ID NO: 115 |
| ID489 | SEQ ID NO: 158 | SEQ ID NO: 159 | SEQ ID NO: 118 |
| ID490 | SEQ ID NO: 158 | SEQ ID NO: 159 | SEQ ID NO: 121 |
| ID491 | SEQ ID NO: 158 | SEQ ID NO: 159 | SEQ ID NO: 124 |
| ID492 | SEQ ID NO: 158 | SEQ ID NO: 159 | SEQ ID NO: 127 |
| ID493 | SEQ ID NO: 158 | SEQ ID NO: 159 | SEQ ID NO: 130 |
| ID494 | SEQ ID NO: 158 | SEQ ID NO: 159 | SEQ ID NO: 133 |
| ID495 (positive control) | SEQ ID NO: 161 | SEQ ID NO: 162 | |
| ID496 (negative control) | SEQ ID NO: 161 | SEQ ID NO: 162 | SEQ ID NO: 163 |
| ID497 | SEQ ID NO: 161 | SEQ ID NO: 162 | SEQ ID NO: 94 |
| ID498 | SEQ ID NO: 161 | SEQ ID NO: 162 | SEQ ID NO: 97 |
| ID499 | SEQ ID NO: 161 | SEQ ID NO: 162 | SEQ ID NO: 100 |
| ID500 | SEQ ID NO: 161 | SEQ ID NO: 162 | SEQ ID NO: 103 |
| ID501 | SEQ ID NO: 161 | SEQ ID NO: 162 | SEQ ID NO: 106 |
| ID502 | SEQ ID NO: 161 | SEQ ID NO: 162 | SEQ ID NO: 109 |
| ID503 | SEQ ID NO: 161 | SEQ ID NO: 162 | SEQ ID NO: 112 |
| ID504 | SEQ ID NO: 161 | SEQ ID NO: 162 | SEQ ID NO: 115 |
| ID505 | SEQ ID NO: 161 | SEQ ID NO: 162 | SEQ ID NO: 118 |
| ID506 | SEQ ID NO: 161 | SEQ ID NO: 162 | SEQ ID NO: 121 |
| ID507 | SEQ ID NO: 161 | SEQ ID NO: 162 | SEQ ID NO: 124 |
| ID508 | SEQ ID NO: 161 | SEQ ID NO: 162 | SEQ ID NO: 127 |
| ID509 | SEQ ID NO: 161 | SEQ ID NO: 162 | SEQ ID NO: 130 |
| ID510 | SEQ ID NO: 161 | SEQ ID NO: 162 | SEQ ID NO: 133 |

TABLE 6

Percent pairing for heavy chains and kappa light chains in the presence of competing lambda light chains as measured by the NanoBiT assay.

| Column 1: Identifier for sequence combinations | Column 2: Percent pairing | Column 3: heavy chain polypeptide 2 (HCP2) corresponding germline | Column 4: kappa light chain polypeptide (KLCP) corresponding germline | Column 5: competing lambda light chain polypeptide (LLCP) corresponding germline |
|---|---|---|---|---|
| ID185 | 98 | VH3-33*01 (SEQ ID NO: 193) | Vk1-39*01 (SEQ ID NO: 201) | Vl3-19*01 (SEQ ID NO: 211) |
| ID189 | 82 | VH3-33*01 (SEQ ID NO: 193) | Vk1-39*01 (SEQ ID NO: 201) | Vl3-19*01 (SEQ ID NO: 211) |
| ID190 | 100 | VH3-33*01 (SEQ ID NO: 193) | Vk1-39*01 (SEQ ID NO: 201) | Vl2-14*01 (SEQ ID NO: 210) |
| ID191 | 100 | VH3-33*01 (SEQ ID NO: 193) | Vk1-39*01 (SEQ ID NO: 201) | Vl3-9*01 (SEQ ID NO: 212) |
| ID192 | 87 | VH3-33*01 (SEQ ID NO: 193) | Vk1-39*01 (SEQ ID NO: 201) | Vl10-54*01 (SEQ ID NO: 207) |
| ID198 | 93 | VH5-51*01 (SEQ ID NO: 198) | Vk3-20*01 (SEQ ID NO: 205) | Vl3-19*01 (SEQ ID NO: 211) |
| ID205 | 100 | VH5-51*01 (SEQ ID NO: 198) | Vk3-20*01 (SEQ ID NO: 205) | Vl10-54*01 (SEQ ID NO: 207) |
| ID206 | 93 | VH5-51*01 (SEQ ID NO: 198) | Vk3-20*01 (SEQ ID NO: 205) | Vl1-44*01 (SEQ ID NO: 209) |
| ID209 | 95 | VH3-13*01 (SEQ ID NO: 188) | Vk1D-16*01 (SEQ ID NO: 202) | Vl3-19*01 (SEQ ID NO: 211) |
| ID211 | 93 | VH3-13*01 (SEQ ID NO: 188) | Vk1D-16*01 (SEQ ID NO: 202) | Vl1-40*01 (SEQ ID NO: 208) |
| ID213 | 90 | VH3-13*01 (SEQ ID NO: 188) | Vk1D-16*01 (SEQ ID NO: 202) | Vl3-19*01 (SEQ ID NO: 211) |
| ID214 | 100 | VH3-13*01 (SEQ ID NO: 188) | Vk1D-16*01 (SEQ ID NO: 202) | Vl2-14*01 (SEQ ID NO: 210) |
| ID215 | 95 | VH3-13*01 (SEQ ID NO: 188) | Vk1D-16*01 (SEQ ID NO: 202) | Vl3-9*01 (SEQ ID NO: 212) |
| ID216 | 96 | VH3-13*01 (SEQ ID NO: 188) | Vk1D-16*01 (SEQ ID NO: 202) | Vl10-54*01 (SEQ ID NO: 207) |
| ID217 | 100 | VH3-13*01 (SEQ ID NO: 188) | Vk1D-16*01 (SEQ ID NO: 202) | Vl10-54*01 (SEQ ID NO: 207) |
| ID218 | 100 | VH3-13*01 (SEQ ID NO: 188) | Vk1D-16*01 (SEQ ID NO: 202) | Vl1-44*01 (SEQ ID NO: 209) |
| ID222 | 100 | VH1-3*01 (SEQ ID NO: 185) | Vk3D-20*01 (SEQ ID NO: 206) | Vl3-19*01 (SEQ ID NO: 211) |
| ID229 | 98 | VH1-3*01 (SEQ ID NO: 185) | Vk3D-20*01 (SEQ ID NO: 206) | Vl10-54*01 (SEQ ID NO: 207) |
| ID230 | 83 | VH1-3*01 (SEQ ID NO: 185) | Vk3D-20*01 (SEQ ID NO: 206) | Vl1-44*01 (SEQ ID NO: 209) |
| ID228 | 93 | VH1-3*01 (SEQ ID NO: 185) | Vk3D-20*01 (SEQ ID NO: 206) | Vl10-54*01 (SEQ ID NO: 207) |
| ID235 | 90 | VH3-30*01 (SEQ ID NO: 192) | Vk3-20*01 (SEQ ID NO: 205) | Vl1-40*01 (SEQ ID NO: 208) |
| ID236 | 100 | VH3-30*01 (SEQ ID NO: 192) | Vk3-20*01 (SEQ ID NO: 205) | Vl3-19*01 (SEQ ID NO: 211) |
| ID242 | 100 | VH3-30*01 (SEQ ID NO: 192) | Vk3-20*01 (SEQ ID NO: 205) | Vl1-44*01 (SEQ ID NO: 209) |
| ID241 | 100 | VH3-30*01 (SEQ ID NO: 192) | Vk3-20*01 (SEQ ID NO: 205) | Vl10-54*01 (SEQ ID NO: 207) |
| ID259 | 75 | VH1-18*01 (SEQ ID NO: 183) | Vk3-20*01 (SEQ ID NO: 205) | Vl1-40*01 (SEQ ID NO: 208) |
| ID262 | 90 | VH1-18*01 (SEQ ID NO: 183) | Vk3-20*01 (SEQ ID NO: 205) | Vl2-14*01 (SEQ ID NO: 210) |
| ID288 | 95 | VH3-23*01 (SEQ ID NO: 191) | Vk1-27*01 (SEQ ID NO: 200) | Vl10-54*01 (SEQ ID NO: 207) |
| ID289 | 100 | VH3-23*01 (SEQ ID NO: 191) | Vk1-27*01 (SEQ ID NO: 200) | Vl10-54*01 (SEQ ID NO: 207) |
| ID284 | 84 | VH3-23*01 (SEQ ID NO: 191) | Vk1-27*01 (SEQ ID NO: 200) | Vl3-19*01 (SEQ ID NO: 211) |
| ID286 | 81 | VH3-23*01 (SEQ ID NO: 191) | Vk1-27*01 (SEQ ID NO: 200) | Vl2-14*01 (SEQ ID NO: 210) |
| ID290 | 96 | VH3-23*01 (SEQ ID NO: 191) | Vk1-27*01 (SEQ ID NO: 200) | Vl1-44*01 (SEQ ID NO: 209) |
| ID295 | 95 | VH3-21*01 (SEQ ID NO: 190) | Vk3-20*01 (SEQ ID NO: 205) | Vl1-40*01 (SEQ ID NO: 208) |
| ID299 | 99 | VH3-21*01 (SEQ ID NO: 190) | Vk3-20*01 (SEQ ID NO: 205) | Vl3-9*01 (SEQ ID NO: 212) |
| ID302 | 100 | VH3-21*01 (SEQ ID NO: 190) | Vk3-20*01 (SEQ ID NO: 205) | Vl1-44*01 (SEQ ID NO: 209) |
| ID301 | 100 | VH3-21*01 (SEQ ID NO: 190) | Vk3-20*01 (SEQ ID NO: 205) | Vl10-54*01 (SEQ ID NO: 207) |

TABLE 6-continued

Percent pairing for heavy chains and kappa light chains in the presence of competing lambda light chains as measured by the NanoBiT assay.

| Column 1: Identifier for sequence combinations | Column 2: Percent pairing | Column 3: heavy chain polypeptide 2 (HCP2) corresponding germline | Column 4: kappa light chain polypeptide (KLCP) corresponding germline | Column 5: competing lambda light chain polypeptide (LLCP) corresponding germline |
|---|---|---|---|---|
| ID306 | 94 | VH3-33*01 (SEQ ID NO: 193) | Vk3-11*01 (SEQ ID NO: 204) | Vl3-19*01 (SEQ ID NO: 211) |
| ID307 | 98 | VH3-33*01 (SEQ ID NO: 193) | Vk3-11*01 (SEQ ID NO: 204) | Vl1-40*01 (SEQ ID NO: 208) |
| ID308 | 100 | VH3-33*01 (SEQ ID NO: 193) | Vk3-11*01 (SEQ ID NO: 204) | Vl3-19*01 (SEQ ID NO: 211) |
| ID309 | 93 | VH3-33*01 (SEQ ID NO: 193) | Vk3-11*01 (SEQ ID NO: 204) | Vl3-19*01 (SEQ ID NO: 211) |
| ID310 | 94 | VH3-33*01 (SEQ ID NO: 193) | Vk3-11*01 (SEQ ID NO: 204) | Vl2-14*01 (SEQ ID NO: 210) |
| ID312 | 88 | VH3-33*01 (SEQ ID NO: 193) | Vk3-11*01 (SEQ ID NO: 204) | Vl10-54*01 (SEQ ID NO: 207) |
| ID313 | 100 | VH3-33*01 (SEQ ID NO: 193) | Vk3-11*01 (SEQ ID NO: 204) | Vl10-54*01 (SEQ ID NO: 207) |
| ID314 | 100 | VH3-33*01 (SEQ ID NO: 193) | Vk3-11*01 (SEQ ID NO: 204) | Vl1-44*01 (SEQ ID NO: 209) |
| ID317 | 100 | VH3-9*01 (SEQ ID NO: 196) | Vk1-12*01 (SEQ ID NO: 199) | Vl3-19*01 (SEQ ID NO: 211) |
| ID318 | 99 | VH3-9*01 (SEQ ID NO: 196) | Vk1-12*01 (SEQ ID NO: 199) | Vl3-19*01 (SEQ ID NO: 211) |
| ID320 | 100 | VH3-9*01 (SEQ ID NO: 196) | Vk1-12*01 (SEQ ID NO: 199) | Vl3-19*01 (SEQ ID NO: 211) |
| ID324 | 100 | VH3-9*01 (SEQ ID NO: 196) | Vk1-12*01 (SEQ ID NO: 199) | Vl10-54*01 (SEQ ID NO: 207) |
| ID323 | 84 | VH3-9*01 (SEQ ID NO: 196) | Vk1-12*01 (SEQ ID NO: 199) | Vl3-9*01 (SEQ ID NO: 212) |
| ID246 | 100 | VH5-51*01 (SEQ ID NO: 198) | Vk3-20*01 (SEQ ID NO: 205) | Vl3-19*01 (SEQ ID NO: 211) |
| ID253 | 80 | VH5-51*01 (SEQ ID NO: 198) | Vk3-20*01 (SEQ ID NO: 205) | Vl10-54*01 (SEQ ID NO: 207) |
| ID254 | 100 | VH5-51*01 (SEQ ID NO: 198) | Vk3-20*01 (SEQ ID NO: 205) | Vl1-44*01 (SEQ ID NO: 209) |
| ID274 | 79 | VH4-4*01 (SEQ ID NO: 197) | Vk2-28*01 (SEQ ID NO: 203) | Vl2-14*01 (SEQ ID NO: 210) |
| ID278 | 79 | VH4-4*01 (SEQ ID NO: 197) | Vk2-28*01 (SEQ ID NO: 203) | Vl1-44*01 (SEQ ID NO: 209) |
| ID336 | 76 | VH3-23*01 (SEQ ID NO: 191) | Vk3-11*01 (SEQ ID NO: 204) | Vl10-54*01 (SEQ ID NO: 207) |
| ID341 | 100 | VH3-66*01 (SEQ ID NO: 194) | Vk1-39*01 (SEQ ID NO: 201) | Vl3-19*01 (SEQ ID NO: 211) |
| ID349 | 100 | VH3-66*01 (SEQ ID NO: 194) | Vk1-39*01 (SEQ ID NO: 201) | Vl10-54*01 (SEQ ID NO: 207) |
| ID344 | 100 | VH3-66*01 (SEQ ID NO: 194) | Vk1-39*01 (SEQ ID NO: 201) | Vl3-19*01 (SEQ ID NO: 211) |
| ID342 | 100 | VH3-66*01 (SEQ ID NO: 194) | Vk1-39*01 (SEQ ID NO: 201) | Vl3-19*01 (SEQ ID NO: 211) |
| ID343 | 84 | VH3-66*01 (SEQ ID NO: 194) | Vk1-39*01 (SEQ ID NO: 201) | Vl1-40*01 (SEQ ID NO: 208) |
| ID347 | 100 | VH3-66*01 (SEQ ID NO: 194) | Vk1-39*01 (SEQ ID NO: 201) | Vl3-9*01 (SEQ ID NO: 212) |
| ID348 | 100 | VH3-66*01 (SEQ ID NO: 194) | Vk1-39*01 (SEQ ID NO: 201) | Vl10-54*01 (SEQ ID NO: 207) |
| ID350 | 100 | VH3-66*01 (SEQ ID NO: 194) | Vk1-39*01 (SEQ ID NO: 201) | Vl1-44*01 (SEQ ID NO: 209) |

TABLE 7

Percent pairing for heavy chains and lambda light chains in the presence of competing kappa light chains as measured by the NanoBiT assay.

| Column 1: Identifier for sequence combinations | Column 2: Percent pairing | Column 3: heavy chain polypeptide 1 (HCP1) corresponding germline | Column 4: lambda light chain polypeptide (LLCP) corresponding germline | Column 5: competing kappa light chain polypeptide (KLCP) corresponding germline |
|---|---|---|---|---|
| ID357 | 96 | VH1-69*01 (SEQ ID NO: 187) | Vl3-19*01 (SEQ ID NO: 211) | Vk3-20*01 (SEQ ID NO: 205) |

TABLE 7-continued

Percent pairing for heavy chains and lambda light chains in the presence of competing kappa light chains as measured by the NanoBiT assay.

| Column 1: Identifier for sequence combinations | Column 2: Percent pairing | Column 3: heavy chain polypeptide 1 (HCP1) corresponding germline | Column 4: lambda light chain polypeptide (LLCP) corresponding germline | Column 5: competing kappa light chain polypeptide (KLCP) corresponding germline |
|---|---|---|---|---|
| ID359 | 95 | VH1-69*01 (SEQ ID NO: 187) | Vl3-19*01 (SEQ ID NO: 211) | Vk3-20*01 (SEQ ID NO: 205) |
| ID363 | 100 | VH1-69*01 (SEQ ID NO: 187) | Vl3-19*01 (SEQ ID NO: 211) | Vk3-11*01 (SEQ ID NO: 204) |
| ID366 | 100 | VH1-69*01 (SEQ ID NO: 187) | Vl3-19*01 (SEQ ID NO: 211) | Vk1-39*01 (SEQ ID NO: 201) |
| ID378 | 94 | VH3-20*01 (SEQ ID NO: 189) | Vl3-19*01 (SEQ ID NO: 211) | Vk3-20*01 (SEQ ID NO: 205) |
| ID379 | 100 | VH3-20*01 (SEQ ID NO: 189) | Vl3-19*01 (SEQ ID NO: 211) | Vk3-11*01 (SEQ ID NO: 204) |
| ID372 | 100 | VH3-20*01 (SEQ ID NO: 189) | Vl3-19*01 (SEQ ID NO: 211) | Vk3D-20*01 (SEQ ID NO: 206) |
| ID374 | 100 | VH3-20*01 (SEQ ID NO: 189) | Vl3-19*01 (SEQ ID NO: 211) | Vk3-20*01 (SEQ ID NO: 205) |
| ID380 | 95 | VH3-20*01 (SEQ ID NO: 189) | Vl3-19*01 (SEQ ID NO: 211) | Vk1-12*01 (SEQ ID NO: 199) |
| ID386 | 96 | VH5-51*01 (SEQ ID NO: 198) | Vl1-40*01 (SEQ ID NO: 208) | Vk3-20*01 (SEQ ID NO: 205) |
| ID392 | 93 | VH5-51*01 (SEQ ID NO: 198) | Vl1-40*01 (SEQ ID NO: 208) | Vk2-28*01 (SEQ ID NO: 203) |
| ID393 | 91 | VH5-51*01 (SEQ ID NO: 198) | Vl1-40*01 (SEQ ID NO: 208) | Vk1-27*01 (SEQ ID NO: 200) |
| ID395 | 100 | VH5-51*01 (SEQ ID NO: 198) | Vl1-40*01 (SEQ ID NO: 208) | Vk3-11*01 (SEQ ID NO: 204) |
| ID462 | 79 | VH1-69*01 (SEQ ID NO: 187) | Vl3-9*01 (SEQ ID NO: 212) | Vk1-39*01 (SEQ ID NO: 201) |
| ID472 | 90 | VH1-2*01 (SEQ ID NO: 184) | Vl10-54*01 (SEQ ID NO: 207) | Vk2-28*01 (SEQ ID NO: 203) |
| ID475 | 80 | VH1-2*01 (SEQ ID NO: 184) | Vl10-54*01 (SEQ ID NO: 207) | Vk3-11*01 (SEQ ID NO: 204) |
| ID476 | 77 | VH1-2*01 (SEQ ID NO: 184) | Vl10-54*01 (SEQ ID NO: 207) | Vk1-12*01 (SEQ ID NO: 199) |
| ID477 | 100 | VH1-2*01 (SEQ ID NO: 184) | Vl10-54*01 (SEQ ID NO: 207) | Vk3-11*01 (SEQ ID NO: 204) |
| ID478 | 100 | VH1-2*01 (SEQ ID NO: 184) | Vl10-54*01 (SEQ ID NO: 207) | Vk1-39*01 (SEQ ID NO: 201) |
| ID481 | 100 | VH3-7*01 (SEQ ID NO: 195) | Vl10-54*01 (SEQ ID NO: 207) | Vk1-39*01 (SEQ ID NO: 201) |
| ID482 | 89 | VH3-7*01 (SEQ ID NO: 195) | Vl10-54*01 (SEQ ID NO: 207) | Vk3-20*01 (SEQ ID NO: 205) |
| ID483 | 99 | VH3-7*01 (SEQ ID NO: 195) | Vl10-54*01 (SEQ ID NO: 207) | Vk1D-16*01 (SEQ ID NO: 202) |
| ID484 | 100 | VH3-7*01 (SEQ ID NO: 195) | Vl10-54*01 (SEQ ID NO: 207) | Vk3D-20*01 (SEQ ID NO: 206) |
| ID485 | 98 | VH3-7*01 (SEQ ID NO: 195) | Vl10-54*01 (SEQ ID NO: 207) | Vk3-20*01 (SEQ ID NO: 205) |
| ID486 | 95 | VH3-7*01 (SEQ ID NO: 195) | Vl10-54*01 (SEQ ID NO: 207) | Vk3-20*01 (SEQ ID NO: 205) |
| ID488 | 97 | VH3-7*01 (SEQ ID NO: 195) | Vl10-54*01 (SEQ ID NO: 207) | Vk2-28*01 (SEQ ID NO: 203) |
| ID493 | 99 | VH3-7*01 (SEQ ID NO: 195) | Vl10-54*01 (SEQ ID NO: 207) | Vk3-11*01 (SEQ ID NO: 204) |
| ID494 | 99 | VH3-7*01 (SEQ ID NO: 195) | Vl10-54*01 (SEQ ID NO: 207) | Vk1-39*01 (SEQ ID NO: 201) |
| ID402 | 100 | VH3-9*01 (SEQ ID NO: 196) | Vl3-19*01 (SEQ ID NO: 211) | Vk3-20*01 (SEQ ID NO: 205) |
| ID404 | 80 | VH3-9*01 (SEQ ID NO: 196) | Vl3-19*01 (SEQ ID NO: 211) | Vk3D-20*01 (SEQ ID NO: 206) |
| ID405 | 93 | VH3-9*01 (SEQ ID NO: 196) | Vl3-19*01 (SEQ ID NO: 211) | Vk3-20*01 (SEQ ID NO: 205) |
| ID407 | 100 | VH3-9*01 (SEQ ID NO: 196) | Vl3-19*01 (SEQ ID NO: 211) | Vk3-20*01 (SEQ ID NO: 205) |
| ID408 | 86 | VH3-9*01 (SEQ ID NO: 196) | Vl3-19*01 (SEQ ID NO: 211) | Vk2-28*01 (SEQ ID NO: 203) |
| ID409 | 90 | VH3-9*01 (SEQ ID NO: 196) | Vl3-19*01 (SEQ ID NO: 211) | Vk1-27*01 (SEQ ID NO: 200) |
| ID411 | 100 | VH3-9*01 (SEQ ID NO: 196) | Vl3-19*01 (SEQ ID NO: 211) | Vk3-11*01 (SEQ ID NO: 204) |
| ID412 | 100 | VH3-9*01 (SEQ ID NO: 196) | Vl3-19*01 (SEQ ID NO: 211) | Vk1-12*01 (SEQ ID NO: 199) |

TABLE 7-continued

Percent pairing for heavy chains and lambda light chains in the presence of competing kappa light chains as measured by the NanoBiT assay.

| Column 1: Identifier for sequence combinations | Column 2: Percent pairing | Column 3: heavy chain polypeptide 1 (HCP1) corresponding germline | Column 4: lambda light chain polypeptide (LLCP) corresponding germline | Column 5: competing kappa light chain polypeptide (KLCP) corresponding germline |
|---|---|---|---|---|
| ID414 | 100 | VH3-9*01 (SEQ ID NO: 196) | Vl3-19*01 (SEQ ID NO: 211) | Vk1-39*01 (SEQ ID NO: 201) |
| ID418 | 100 | VH3-20*01 (SEQ ID NO: 189) | Vl3-19*01 (SEQ ID NO: 211) | Vk3-20*01 (SEQ ID NO: 205) |
| ID420 | 84 | VH3-20*01 (SEQ ID NO: 189) | Vl3-19*01 (SEQ ID NO: 211) | Vk3D-20*01 (SEQ ID NO: 206) |
| ID421 | 77 | VH3-20*01 (SEQ ID NO: 189) | Vl3-19*01 (SEQ ID NO: 211) | Vk3-20*01 (SEQ ID NO: 205) |
| ID422 | 100 | VH3-20*01 (SEQ ID NO: 189) | Vl3-19*01 (SEQ ID NO: 211) | Vk3-20*01 (SEQ ID NO: 205) |
| ID423 | 100 | VH3-20*01 (SEQ ID NO: 189) | Vl3-19*01 (SEQ ID NO: 211) | Vk3-20*01 (SEQ ID NO: 205) |
| ID424 | 81 | VH3-20*01 (SEQ ID NO: 189) | Vl3-19*01 (SEQ ID NO: 211) | Vk2-28*01 (SEQ ID NO: 203) |
| ID430 | 100 | VH3-20*01 (SEQ ID NO: 189) | Vl3-19*01 (SEQ ID NO: 211) | Vk1-39*01 (SEQ ID NO: 201) |
| ID434 | 90 | VH1-46*01 (SEQ ID NO: 186) | Vl2-14*01 (SEQ ID NO: 210) | Vk3-20*01 (SEQ ID NO: 205) |
| ID435 | 90 | VH1-46*01 (SEQ ID NO: 186) | Vl2-14*01 (SEQ ID NO: 210) | Vk1D-16*01 (SEQ ID NO: 202) |
| ID436 | 81 | VH1-46*01 (SEQ ID NO: 186) | Vl2-14*01 (SEQ ID NO: 210) | Vk3D-20*01 (SEQ ID NO: 206) |
| ID440 | 75 | VH1-46*01 (SEQ ID NO: 186) | Vl2-14*01 (SEQ ID NO: 210) | Vk2-28*01 (SEQ ID NO: 203) |
| ID441 | 79 | VH1-46*01 (SEQ ID NO: 186) | Vl2-14*01 (SEQ ID NO: 210) | Vk1-27*01 (SEQ ID NO: 200) |
| ID443 | 100 | VH1-46*01 (SEQ ID NO: 186) | Vl2-14*01 (SEQ ID NO: 210) | Vk3-11*01 (SEQ ID NO: 204) |
| ID446 | 87 | VH1-46*01 (SEQ ID NO: 186) | Vl2-14*01 (SEQ ID NO: 210) | Vk1-39*01 (SEQ ID NO: 201) |
| ID498 | 100 | VH3-33*01 (SEQ ID NO: 193) | Vl1-44*01 (SEQ ID NO: 209) | Vk3-20*01 (SEQ ID NO: 205) |
| ID499 | 100 | VH3-33*01 (SEQ ID NO: 193) | Vl1-44*01 (SEQ ID NO: 209) | Vk1D-16*01 (SEQ ID NO: 202) |
| ID500 | 100 | VH3-33*01 (SEQ ID NO: 193) | Vl1-44*01 (SEQ ID NO: 209) | Vk3D-20*01 (SEQ ID NO: 206) |
| ID501 | 100 | VH3-33*01 (SEQ ID NO: 193) | Vl1-44*01 (SEQ ID NO: 209) | Vk3-20*01 (SEQ ID NO: 205) |
| ID502 | 80 | VH3-33*01 (SEQ ID NO: 193) | Vl1-44*01 (SEQ ID NO: 209) | Vk3-20*01 (SEQ ID NO: 205) |
| ID506 | 100 | VH3-33*01 (SEQ ID NO: 193) | Vl1-44*01 (SEQ ID NO: 209) | Vk3-20*01 (SEQ ID NO: 205) |

TABLE 8a

Two-way pairs based on NanoBiT data.

| Identifier for sequence combinations | Percent pairing | Identifier for sequence combinations | Percent pairing |
|---|---|---|---|
| ID205 | 100 | ID482 | 89 |
| ID206 | 93 | ID498 | 100 |
| ID214 | 100 | ID435 | 90 |
| ID217 | 100 | ID483 | 99 |
| ID218 | 100 | ID499 | 100 |
| ID222 | 100 | ID372 | 100 |
| ID229 | 98 | ID484 | 100 |
| ID230 | 83 | ID500 | 100 |
| ID236 | 100 | ID405 | 93 |
| ID242 | 100 | ID501 | 100 |
| ID241 | 100 | ID485 | 98 |
| ID259 | 75 | ID392 | 93 |
| ID284 | 84 | ID409 | 90 |
| ID286 | 81 | ID441 | 79 |
| ID302 | 100 | ID506 | 100 |
| ID306 | 94 | ID379 | 100 |
| ID307 | 98 | ID395 | 100 |
| ID308 | 100 | ID411 | 100 |
| ID310 | 94 | ID443 | 100 |
| ID312 | 88 | ID475 | 80 |
| ID318 | 99 | ID380 | 95 |
| ID320 | 100 | ID412 | 100 |
| ID324 | 100 | ID476 | 77 |
| ID246 | 100 | ID374 | 100 |
| ID253 | 80 | ID486 | 95 |
| ID254 | 100 | ID502 | 80 |
| ID274 | 79 | ID440 | 75 |
| ID336 | 76 | ID477 | 100 |
| ID341 | 100 | ID366 | 100 |
| ID349 | 100 | ID494 | 99 |
| ID344 | 100 | ID414 | 100 |
| ID347 | 100 | ID462 | 79 |
| ID348 | 100 | ID478 | 100 |

TABLE 8b

Corresponding germline sequences of two-way pairs based on NanoBiT data

| Column 1: Identifier for sequence combinations | Column 2: heavy chain polypeptide 1 (HCP1) corresponding germline | Column 3: lambda light chain polypeptide (LLCP) corresponding germline | Column 4: Identifier for sequence combinations | Column 5: heavy chain polypeptide 2 (HCP2) corresponding germline | Column 6: kappa light chain polypeptide (KLCP) corresponding germline |
|---|---|---|---|---|---|
| ID205 | VH5-51*01 (SEQ ID NO: 198) | VK3-20*01 (SEQ ID NO: 205) | ID482 | VH3-7*01 (SEQ ID NO: 195) | Vl10-54*01 (SEQ ID NO: 207) |
| ID206 | VH5-51*01 (SEQ ID NO: 198) | VK3-20*01 (SEQ ID NO: 205) | ID498 | VH3-33*01 (SEQ ID NO: 193) | Vl1-44*01 (SEQ ID NO: 209) |
| ID214 | VH3-13*01 (SEQ ID NO: 188) | VK1D-16*01 (SEQ ID NO: 202) | ID435 | VH1-46*01 (SEQ ID NO: 186) | Vl2-14*01 (SEQ ID NO: 210) |
| ID217 | VH3-13*01 (SEQ ID NO: 188) | VK1D-16*01 (SEQ ID NO: 202) | ID483 | VH3-7*01 (SEQ ID NO: 195) | Vl10-54*01 (SEQ ID NO: 207) |
| ID218 | VH3-13*01 (SEQ ID NO: 188) | VK1D-16*01 (SEQ ID NO: 202) | ID499 | VH3-33*01 (SEQ ID NO: 193) | Vl1-44*01 (SEQ ID NO: 209) |
| ID222 | VH1-3*01 (SEQ ID NO: 185) | VK3D-20*01 (SEQ ID NO: 206) | ID372 | VH3-20*01 (SEQ ID NO: 189) | Vl3-19*01 (SEQ ID NO: 211) |
| ID229 | VH1-3*01 (SEQ ID NO: 185) | VK3D-20*01 (SEQ ID NO: 206) | ID484 | VH3-7*01 (SEQ ID NO: 195) | Vl10-54*01 (SEQ ID NO: 207) |
| ID230 | VH1-3*01 (SEQ ID NO: 185) | VK3D-20*01 (SEQ ID NO: 206) | ID500 | VH3-33*01 (SEQ ID NO: 193) | Vl1-44*01 (SEQ ID NO: 209) |
| ID236 | VH3-30*01 (SEQ ID NO: 192) | VK3-20*01 (SEQ ID NO: 205) | ID405 | VH3-9*01 (SEQ ID NO: 196) | Vl3-19*01 (SEQ ID NO: 211) |
| ID242 | VH3-30*01 (SEQ ID NO: 192) | VK3-20*01 (SEQ ID NO: 205) | ID501 | VH3-33*01 (SEQ ID NO: 193) | Vl1-44*01 (SEQ ID NO: 209) |
| ID241 | VH3-30*01 (SEQ ID NO: 192) | VK3-20*01 (SEQ ID NO: 205) | ID485 | VH3-7*01 (SEQ ID NO: 195) | Vl10-54*01 (SEQ ID NO: 207) |
| ID259 | VH1-18*01 (SEQ ID NO: 183) | VK3-20*01 (SEQ ID NO: 205) | ID392 | VH5-51*01 (SEQ ID NO: 198) | Vl1-40*01 (SEQ ID NO: 208) |
| ID284 | VH3-23*01 (SEQ ID NO: 191) | VK1-27*01 (SEQ ID NO: 200) | ID409 | VH3-9*01 (SEQ ID NO: 196) | Vl3-19*01 (SEQ ID NO: 211) |
| ID286 | VH3-23*01 (SEQ ID NO: 191) | VK1-27*01 (SEQ ID NO: 200) | ID441 | VH1-46*01 (SEQ ID NO: 186) | Vl2-14*01 (SEQ ID NO: 210) |
| ID302 | VH3-21*01 (SEQ ID NO: 190) | VK3-20*01 (SEQ ID NO: 205) | ID506 | VH3-33*01 (SEQ ID NO: 193) | Vl1-44*01 (SEQ ID NO: 209) |
| ID306 | VH3-33*01 (SEQ ID NO: 193) | Vk3-11*01 (SEQ ID NO: 204) | ID379 | VH3-20*01 (SEQ ID NO: 189) | Vl3-19*01 (SEQ ID NO: 211) |
| ID307 | VH3-33*01 (SEQ ID NO: 193) | Vk3-11*01 (SEQ ID NO: 204) | ID395 | VH5-51*01 (SEQ ID NO: 198) | Vl1-40*01 (SEQ ID NO: 208) |
| ID308 | VH3-33*01 (SEQ ID NO: 193) | Vk3-11*01 (SEQ ID NO: 204) | ID411 | VH3-9*01 (SEQ ID NO: 196) | Vl3-19*01 (SEQ ID NO: 211) |
| ID310 | VH3-33*01 (SEQ ID NO: 193) | Vk3-11*01 (SEQ ID NO: 204) | ID443 | VH1-46*01 (SEQ ID NO: 186) | Vl2-14*01 (SEQ ID NO: 210) |
| ID312 | VH3-33*01 (SEQ ID NO: 193) | Vk3-11*01 (SEQ ID NO: 204) | ID475 | VH1-2*01 (SEQ ID NO: 184) | Vl10-54*01 (SEQ ID NO: 207) |
| ID318 | VH3-9*01 (SEQ ID NO: 196) | Vk1-12*01 (SEQ ID NO: 199) | ID380 | VH3-20*01 (SEQ ID NO: 189) | Vl3-19*01 (SEQ ID NO: 211) |
| ID320 | VH3-9*01 (SEQ ID NO: 196) | Vk1-12*01 (SEQ ID NO: 199) | ID412 | VH3-9*01 (SEQ ID NO: 196) | Vl3-19*01 (SEQ ID NO: 211) |

TABLE 8b-continued

Corresponding germline sequences of two-way pairs based on NanoBiT data

| Column 1: Identifier for sequence combinations | Column 2: heavy chain polypeptide 1 (HCP1) corresponding germline | Column 3: lambda light chain polypeptide (LLCP) corresponding germline | Column 4: Identifier for sequence combinations | Column 5: heavy chain polypeptide 2 (HCP2) corresponding germline | Column 6: kappa light chain polypeptide (KLCP) corresponding germline |
|---|---|---|---|---|---|
| ID324 | VH3-9*01 (SEQ ID NO: 196) | Vk1-12*01 (SEQ ID NO: 199) | ID476 | VH1-2*01 (SEQ ID NO: 184) | Vl10-54*01 (SEQ ID NO: 207) |
| ID246 | VH5-51*01 (SEQ ID NO: 198) | VK3-20*01 (SEQ ID NO: 205) | ID374 | VH3-20*01 (SEQ ID NO: 189) | Vl3-19*01 (SEQ ID NO: 211) |
| ID253 | VH5-51*01 (SEQ ID NO: 198) | VK3-20*01 (SEQ ID NO: 205) | ID486 | VH3-7*01 (SEQ ID NO: 195) | Vl10-54*01 (SEQ ID NO: 207) |
| ID254 | VH5-51*01 (SEQ ID NO: 198) | VK3-20*01 (SEQ ID NO: 205) | ID502 | VH3-33*01 (SEQ ID NO: 193) | Vl1-44*01 (SEQ ID NO: 209) |
| ID274 | VH4-4*01 (SEQ ID NO: 197) | VK2-28*01 (SEQ ID NO: 203) | ID440 | VH1-46*01 (SEQ ID NO: 186) | Vl2-14*01 (SEQ ID NO: 210) |
| ID336 | VH3-23*01 (SEQ ID NO: 191) | Vk3-11*01 (SEQ ID NO: 204) | ID477 | VH1-2*01 (SEQ ID NO: 184) | Vl10-54*01 (SEQ ID NO: 207) |
| ID341 | VH3-66*01 (SEQ ID NO: 194) | Vk1-39*01 (SEQ ID NO: 201) | ID366 | VH1-69*01 (SEQ ID NO: 187) | Vl3-19*01 (SEQ ID NO: 211) |
| ID349 | VH3-66*01 (SEQ ID NO: 194) | Vk1-39*01 (SEQ ID NO: 201) | ID494 | VH3-7*01 (SEQ ID NO: 195) | Vl10-54*01 (SEQ ID NO: 207) |
| ID344 | VH3-66*01 (SEQ ID NO: 194) | Vk1-39*01 (SEQ ID NO: 201) | ID414 | VH3-9*01 (SEQ ID NO: 196) | Vl3-19*01 (SEQ ID NO: 211) |
| ID347 | VH3-66*01 (SEQ ID NO: 194) | Vk1-39*01 (SEQ ID NO: 201) | ID462 | VH1-69*01 (SEQ ID NO: 187) | Vl3-9*01 (SEQ ID NO: 212) |
| ID348 | VH3-66*01 (SEQ ID NO: 194) | Vk1-39*01 (SEQ ID NO: 201) | ID478 | VH1-2*01 (SEQ ID NO: 184) | Vl10-54*01 (SEQ ID NO: 207) |

Example 2

Figure 5:
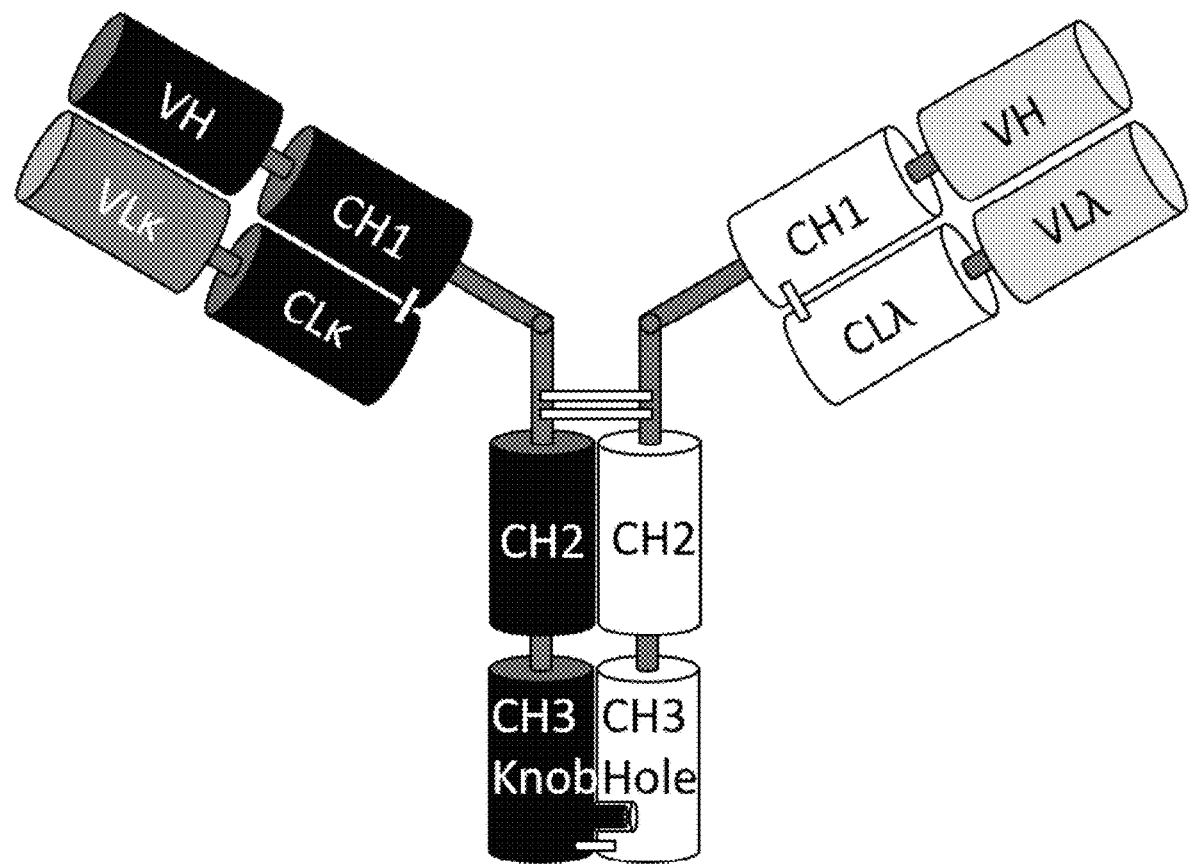
FIG. 5 depicts a schematic representation of an exemplary multispecific antibody molecule of the present invention. The multispecific antibody molecule comprises a first Fab comprising a kappa light chain polypeptide; a second Fab comprising a lambda light chain polypeptide; and an Fc domain, wherein the Fc domain contains a paired protuberance/cavity, e.g., knob and hole pair. In one embodiment, the first Fab binds to IGF1R and the second Fab binds to HER3 (e.g., multispecific molecule 1 described in Example 2). In one embodiment, the first Fab binds to mesothelin and the second Fab binds to PD-L1 (e.g., multispecific molecule 2 described in Example 3). In one embodiment, the first Fab binds to CTLA-4 and the second Fab binds to IL12β (e.g., multispecific molecule 3 described in Example 4). In one embodiment, the first Fab binds to CTLA-4 and the second Fab binds to TRAILR2 (e.g., multispecific molecule 4 described in Example 5). In one embodiment, the first Fab binds to CTLA-4 and the second Fab binds to CD221 (e.g., multispecific molecule 5 described in Example 6). In one embodiment, the first Fab binds to PD-1 and the second Fab binds to TRAILR2 (e.g., multispecific molecule 6 described in Example 7). In one embodiment, the first Fab binds to PD-1 and the second Fab binds to PDL1 (e.g., multispecific molecule 7 described in Example 8).

Multispecific molecule 1 comprises an α-IGF1R arm and an α-HERS arm. The α-IGF1R arm comprises a first chain of the amino acid sequence of SEQ ID NO: 179 and a second chain of the amino acid sequence of SEQ ID NO: 118. The α-HERS arm comprises a first chain of the amino acid sequence of SEQ ID NO: 178 and a second chain of the amino acid sequence of SEQ ID NO: 145. The configuration of multispecific molecule 1 is shown in FIG. 5.

Figure 11:
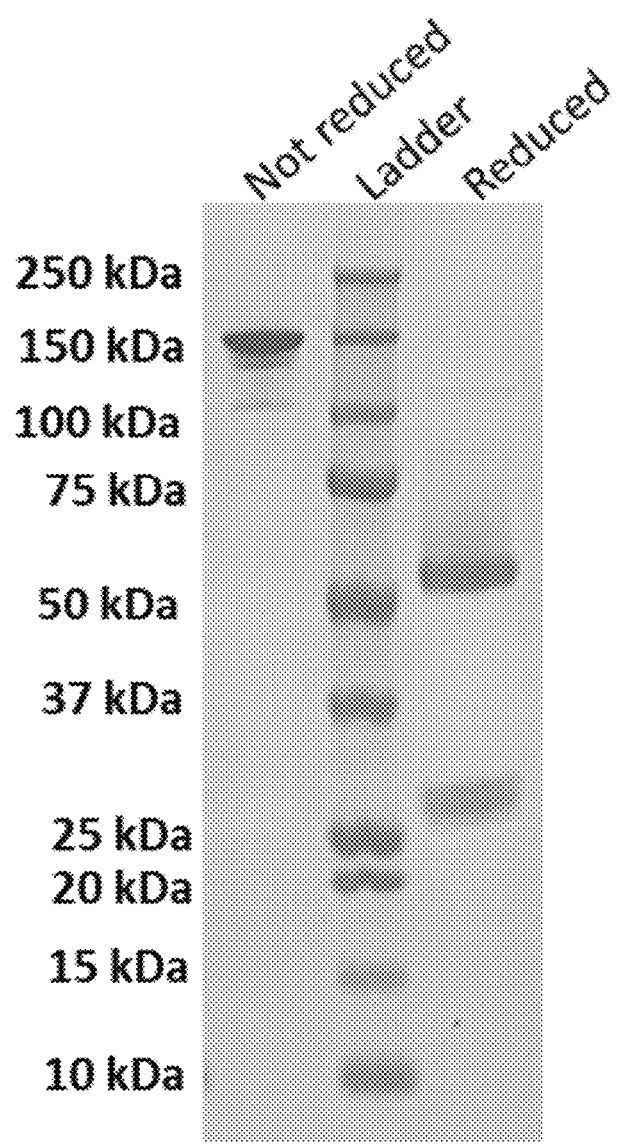
FIG. 11. Gel of multispecific molecule 1.
Figure 19:
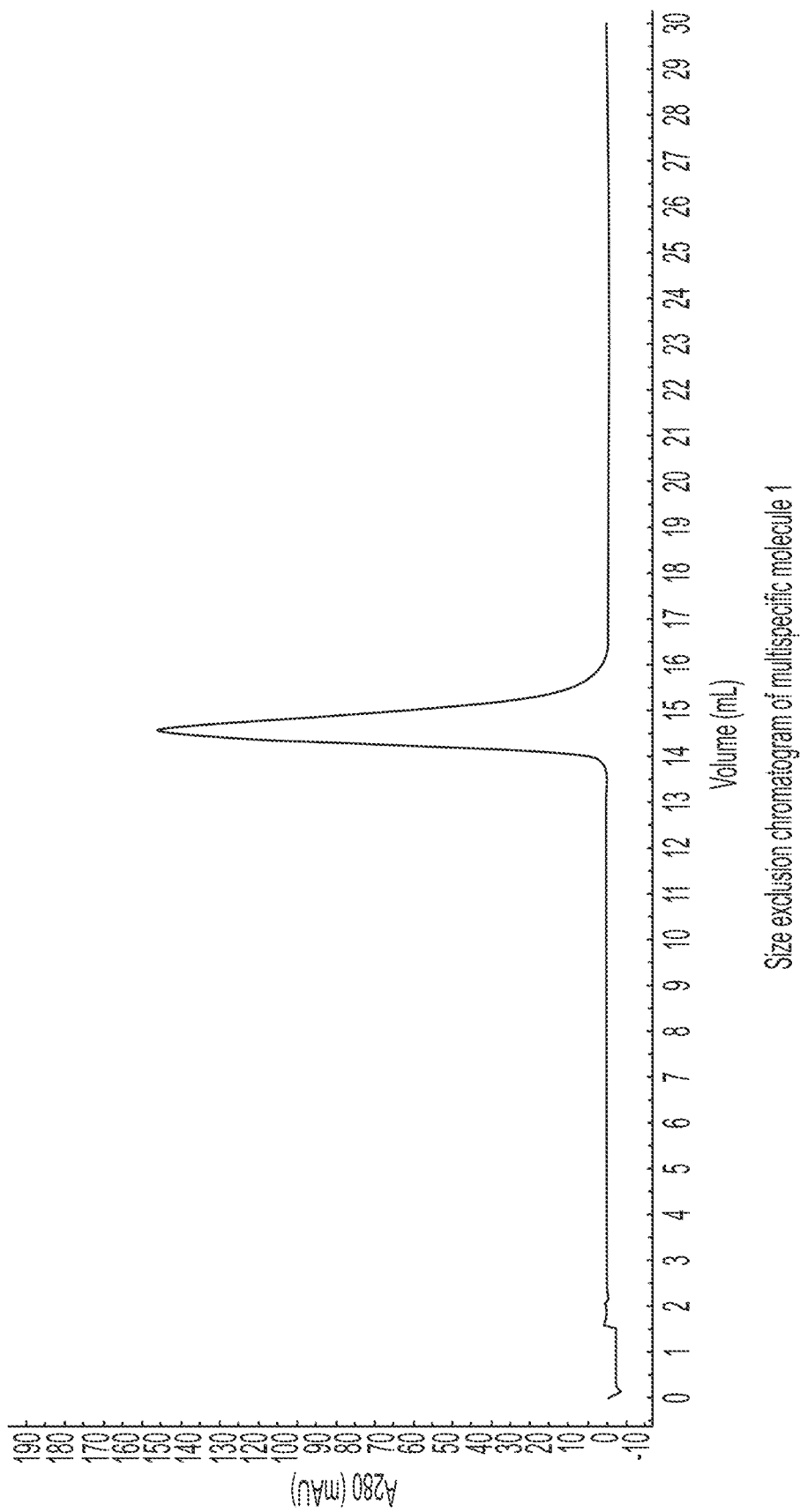
FIG. 19. Size exclusion chromatogram of multispecific molecule 1.
Figure 24:
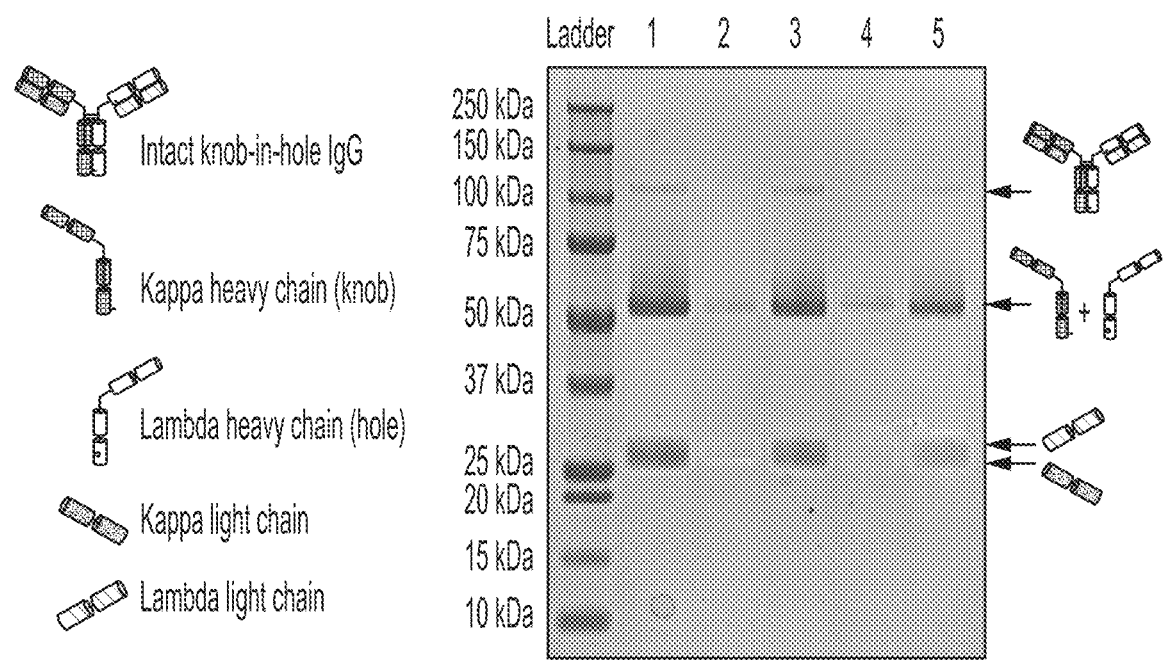
FIG. 24. Gel of reduced samples of multispecific molecule 1 following kappa/lambda select analysis. Lane 1 is the load, lane 2 is the flow-through from the KappaSelect column, lane 3 is the elution from the KappaSelect column, lane 4 is the flow-through from the LambdaFabSelect column, and lane 5 is the elution from the LambdaFabSelect column.

Multispecific molecule 1 was expressed by co-transfecting cells with expression vectors comprising polynucleotide sequences of SEQ ID NO: 86, SEQ ID NO: 54, SEQ ID NO: 87, and SEQ ID NO: 27. Multispecific molecule 1 was purified and a SDS-PAGE gel of the final product is shown in FIG. 11. FIG. 19 shows the size exclusion chromatogram of multispecific molecule 1. A KappaSelect and LambdaFabSelect analysis was performed with multispecific molecule 1, shown in FIG. 24. The gel shows a small amount of protein in the flow-through from the KappaSelect and LambdaFab columns. The quantitative results of this analysis are shown in Table 9, giving 85% fidelity for the kappa chain and 85% fidelity for the lambda chain. These results correlate with the NanoBiT data of ID284 and ID409, which have the same Fab arms, with 84% and 90% fidelity, respectively.

TABLE 9

Results of quantitative kappa/lambda select analysis.

| Construct | Percent pairing from KappaSelect column | Percent pairing from LambdaFabSelect |
|---|---|---|
| Multispecific molecule 1 | 85 | 85 |
| Multispecific molecule 2 | 88 | 86 |

Example 3

Multispecific molecule 2 comprises an α-mesothelin arm and an α-PDL1 arm. The an α-mesothelin arm comprises a first chain of the amino acid sequence of SEQ ID NO: 164 and a second chain of the amino acid sequence of SEQ ID NO: 165. The α-PDL1 arm comprises a first chain of the amino acid sequence of SEQ ID NO: 166 and a second chain of the amino acid sequence of SEQ ID NO: 167. The configuration of multispecific molecule 2 is shown in FIG. 5.

Figure 23:
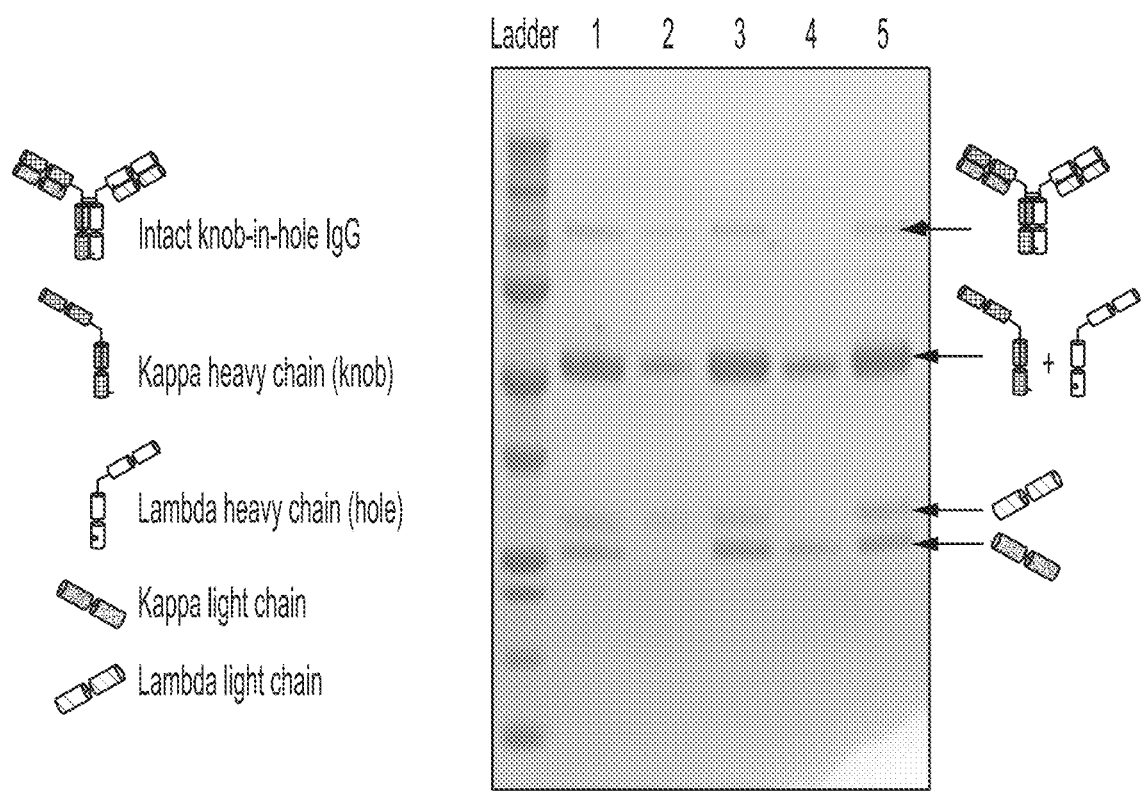
FIG. 23. Gel of reduced samples of multispecific molecule 2 following kappa/lambda select analysis. Lane 1 is the load, lane 2 is the flow-through from the KappaSelect column, lane 3 is the elution from the KappaSelect column, lane 4 is the flow-through from the LambdaFabSelect column, and lane 5 is the elution from the LambdaFabSelect column.

Multispecific molecule 2 was expressed by co-transfecting cells with expression vectors comprising polynucleotide sequences of SEQ ID NO: 82, SEQ ID NO: 83, SEQ ID NO: 84, and SEQ ID NO: 85. A KappaSelect and LambdaFabSelect analysis was performed with multispecific molecule 2, shown in FIG. 23. The gel shows a small amount of protein in the flow-through from the KappaSelect and LambdaFab columns. The quantitative results of this analysis are shown in Table 9. The fidelity for the KappaSelect column is 88% and the fidelity for the LambdaFabSelect column is 86%.

Example 4

Multispecific molecule 3 comprises an α-CTLA4 arm and an α-IL12β arm. The α-CTLA4 arm comprises a first chain of the amino acid sequence of SEQ ID NO: 168 and a second chain of the amino acid sequence of SEQ ID NO: 106. The α-IL12β arm comprises a first chain of the amino acid sequence of SEQ ID NO: 170 and a second chain of the amino acid sequence of SEQ ID NO: 163. The configuration of multispecific molecule 3 is shown in FIG. 5.

Figure 12:
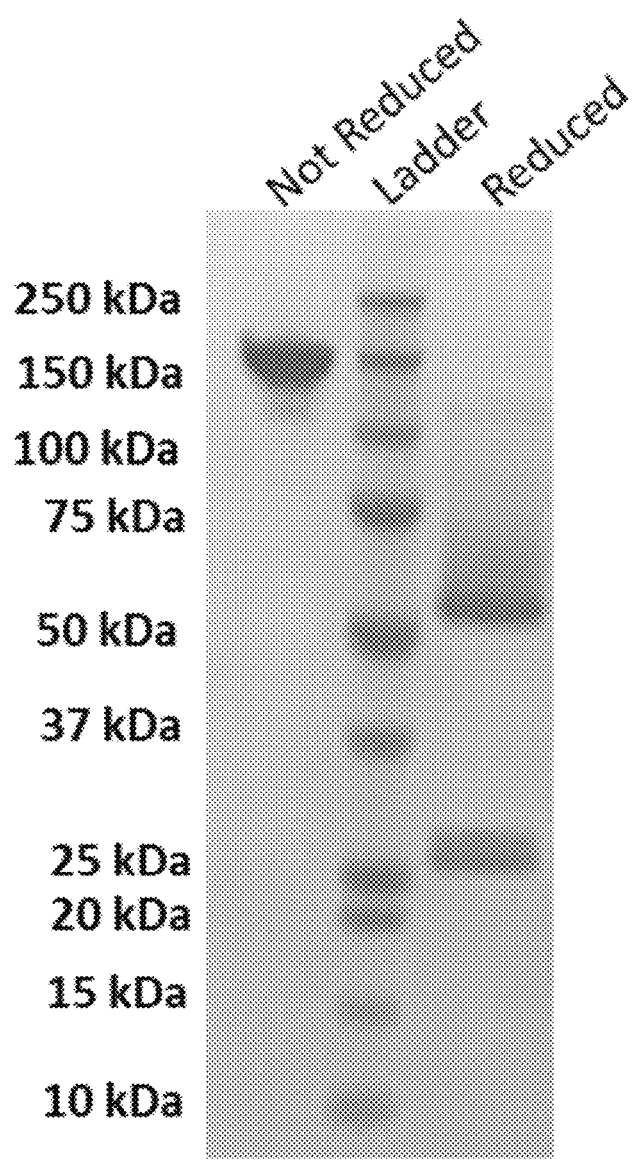
FIG. 12. Gel of multispecific molecule 3.
Figure 20:
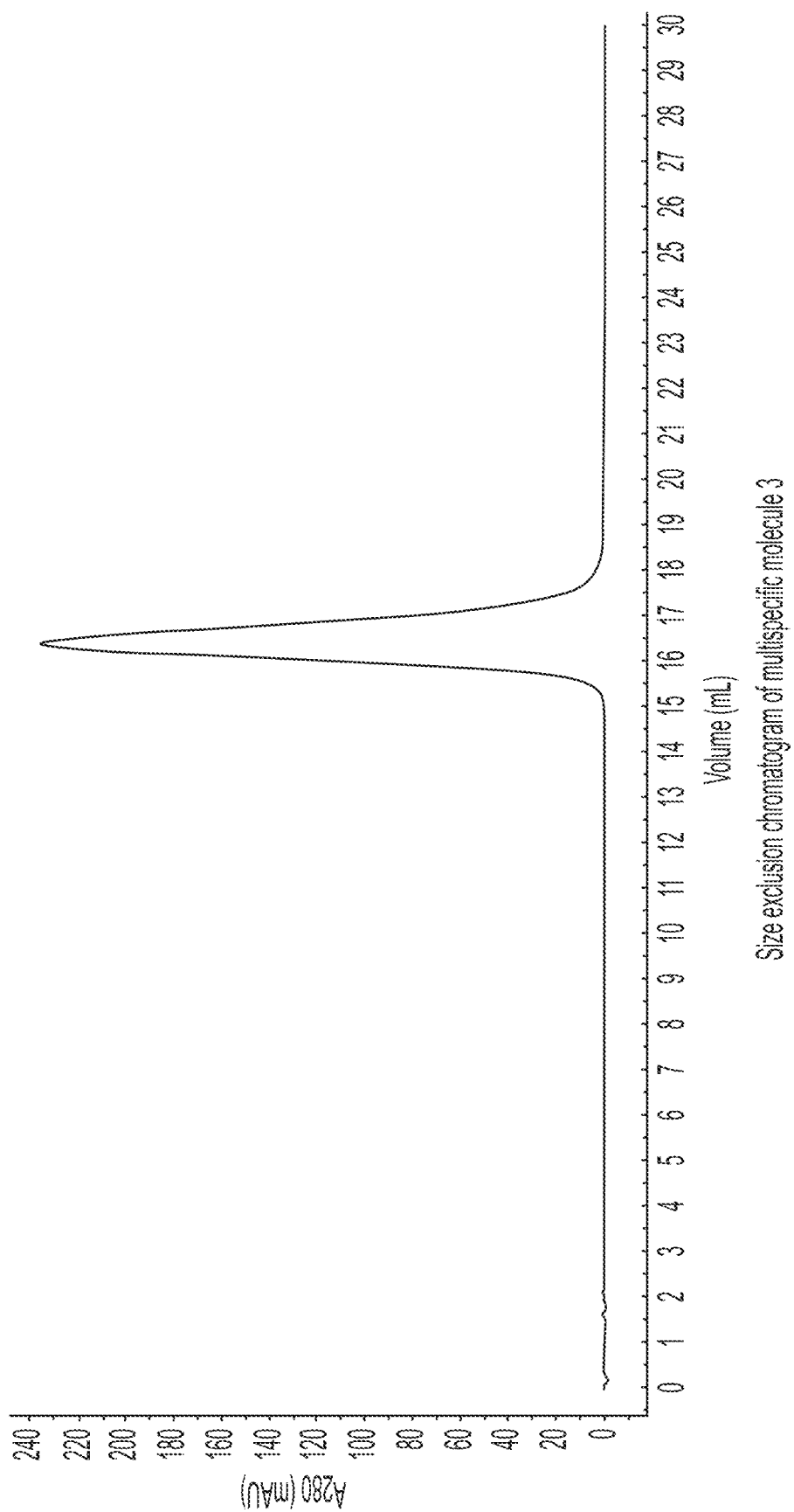
FIG. 20. Size exclusion chromatogram of multispecific molecule 3.
Figure 25:
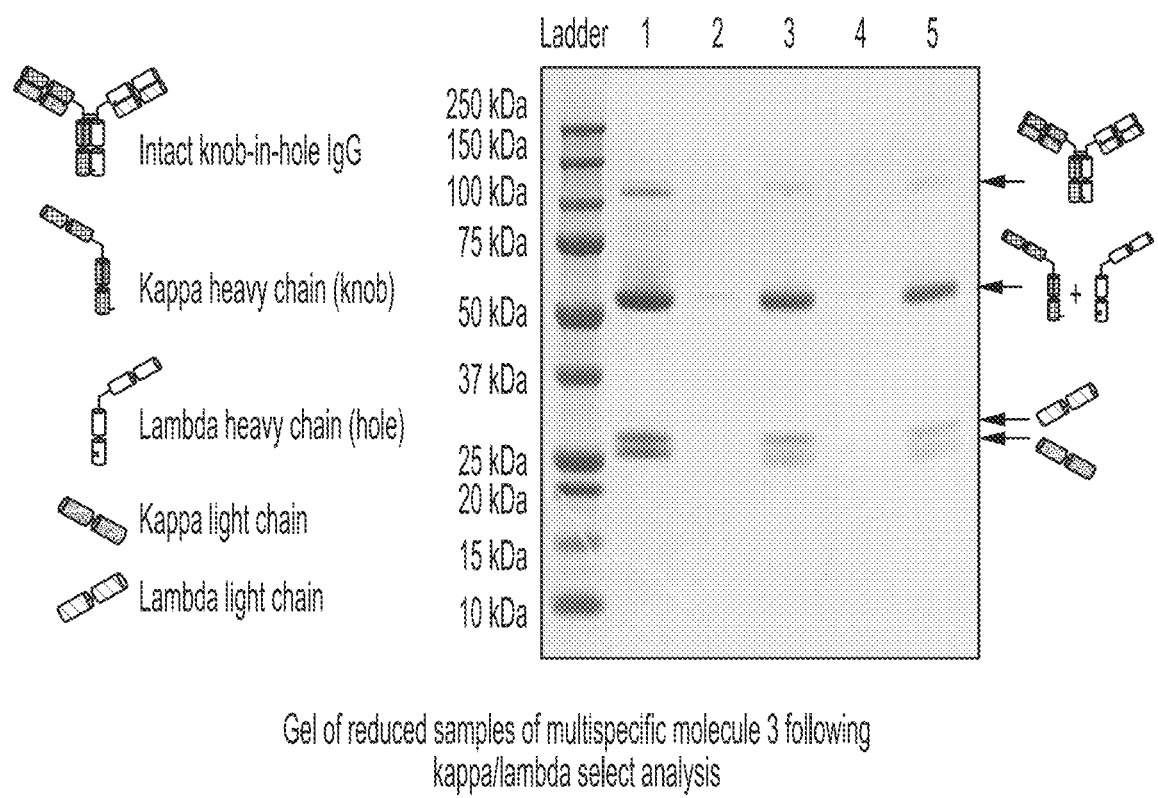
FIG. 25. Gel of reduced samples of multispecific molecule 3 following kappa/lambda select analysis. Lane 1 is the load, lane 2 is the flow-through from the KappaSelect column, lane 3 is the elution from the KappaSelect column, lane 4 is the flow-through from the LambdaFabSelect column, and lane 5 is the elution from the LambdaFabSelect column.
Figure 31:
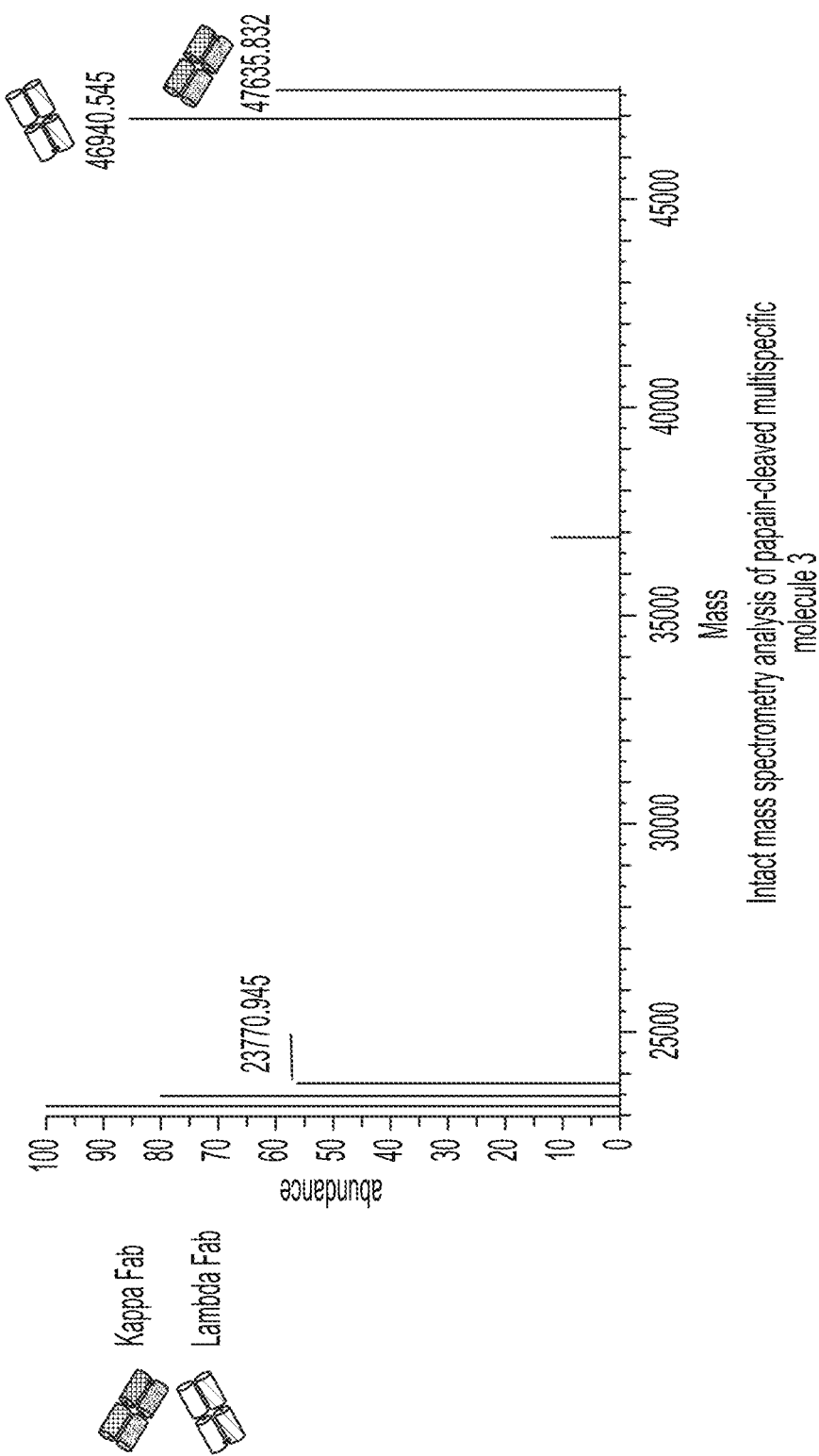
FIG. 31. Intact mass spectrometry analysis of papain-cleaved multispecific molecule 3.
Figure 32:
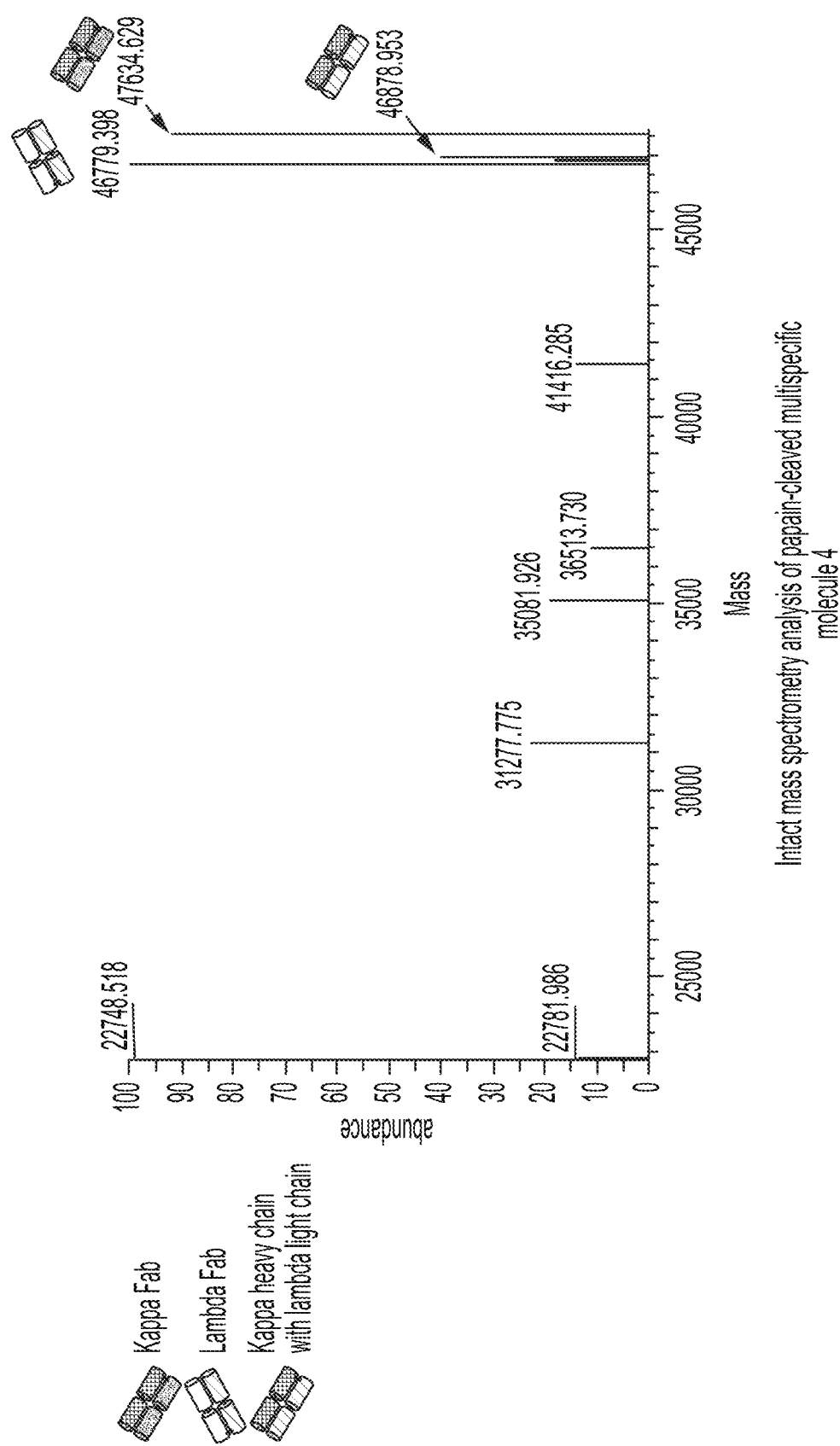
FIG. 32. Intact mass spectrometry analysis of papain-cleaved multispecific molecule 4.

Multispecific molecule 3 was expressed by co-transfecting cells with expression vectors comprising polynucleotide sequences of SEQ ID NO: 78, SEQ ID NO: 15, SEQ ID NO: 91, and SEQ ID NO: 72. Multispecific molecule 3 was purified and a SDS-PAGE gel of the final product is shown in FIG. 12. FIG. 20. shows the size exclusion chromatogram of multispecific molecule 3. A KappaSelect and LambdaFabSelect analysis was performed with multispecific molecule 3, shown in FIG. 25. The gel shows no protein in the flow-through of the KappaSelect or LambdaFabSelect columns, suggesting correct light chain pairing. The mass spectrometry data of the papain cleavage of multispecific molecule 3 is shown in FIG. 31 and summarized in Table 10. This data only shows correctly paired Fabs, further illustrating that there is no mispairing for these kappa and lambda chains. These results also correlate with the NanoBiT data of ID242 and ID501, which have the same Fab arms, and both showed 100% chain fidelity.

TABLE 10

Mass spectrometry results for multispecific molecule 3.

| Fab Pairing | Predicted Mass (Da) | Observed Mass (Da) |
|---|---|---|
| Kappa heavy chain/kappa light chain | 47652.9 | 47634.9 |
| Kappa heavy chain/lambda light chain | 47390.4 | N/A |
| Lambda heavy chain/lambda light chain | 46974.6 | 46940.4 |
| Lambda heavy chain/kappa light chain | 47237.2 | N/A |

Example 5

Multispecific molecule 4 comprises an α-CTLA4 arm and an α-TRAILR2 arm. The α-CTLA4 arm comprises a first chain of the amino acid sequence of SEQ ID NO: 168 and a second chain of the amino acid sequence of SEQ ID NO: 106. The α-TRAILR2 arm comprises a first chain of the amino acid sequence of SEQ ID NO: 177 and a second chain of the amino acid sequence of SEQ ID NO: 148. The configuration of multispecific molecule 4 is shown in FIG. 5.

Figure 13:
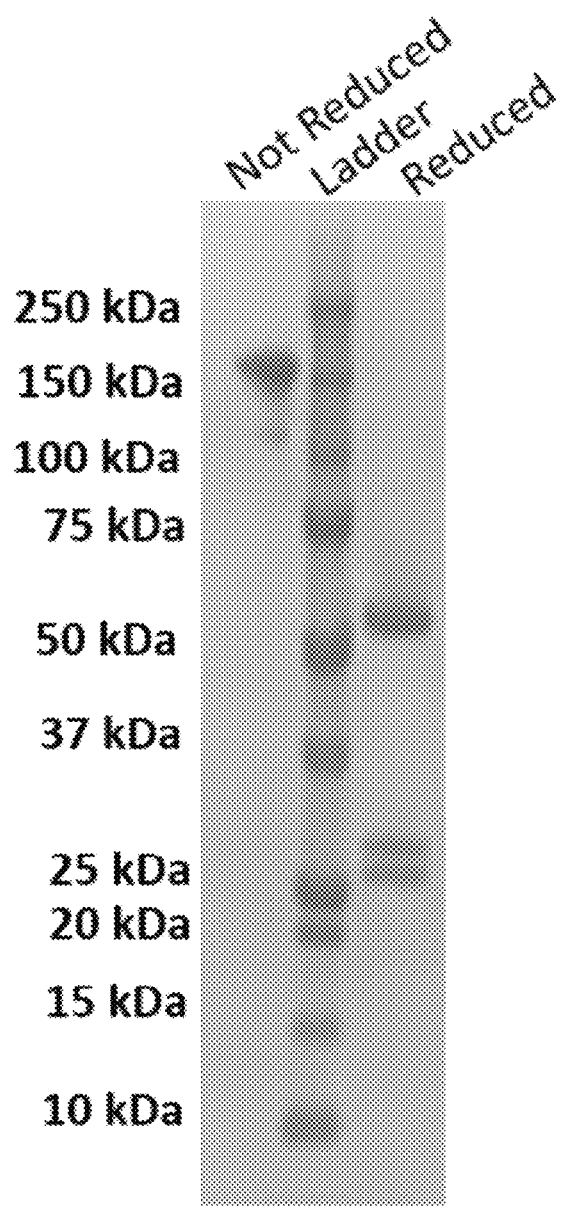
FIG. 13. Gel of multispecific molecule 4.

Multispecific molecule 4 was expressed by co-transfecting cells with expression vectors comprising polynucleotide sequences of SEQ ID NO: 78, SEQ ID NO: 15, SEQ ID NO: 81, and SEQ ID NO: 57. Multispecific molecule 4 was purified and a SDS-PAGE gel of the final product is shown in FIG. 13. The mass spectrometry data of the papain cleavage of multispecific molecule 4 is shown in FIG. 31 and summarized in Table 11. This data shows one incorrect Fab pairing where the kappa heavy chain is paired with the lambda light chain. This correlates with the NanoBiT data of ID237 and ID421, which have the same Fab arms as multispecific molecule 4, where chain fidelity is seen in one direction: the lambda heavy chain with the competing kappa light chain.

TABLE 11

Mass spectrometry results for multispecific molecule 4.

| Fab Pairing | Predicted Mass (Da) | Observed Mass (Da) |
|---|---|---|
| Kappa heavy chain/kappa light chain | 47634.9 | 47634.6 |
| Kappa heavy chain/lambda light chain | 46880.4 | 46879.0 |
| Lambda heavy chain/lambda light chain | 46779.2 | 46779.4 |
| Lambda heavy chain/kappa light chain | 47481.7 | N/A |

Example 6

Multispecific molecule 5 comprises an α-CTLA4 arm and an α-CD221 arm. The α-CTLA4 arm comprises a first chain of the amino acid sequence of SEQ ID NO: 168 and a second chain of the amino acid sequence of SEQ ID NO: 106. The α-TRAILR2 arm comprises a first chain of the amino acid sequence of SEQ ID NO: 180 and a second chain of the amino acid sequence of SEQ ID NO: 136. The configuration of multispecific molecule 5 is shown in FIG. 5.

Figure 14:
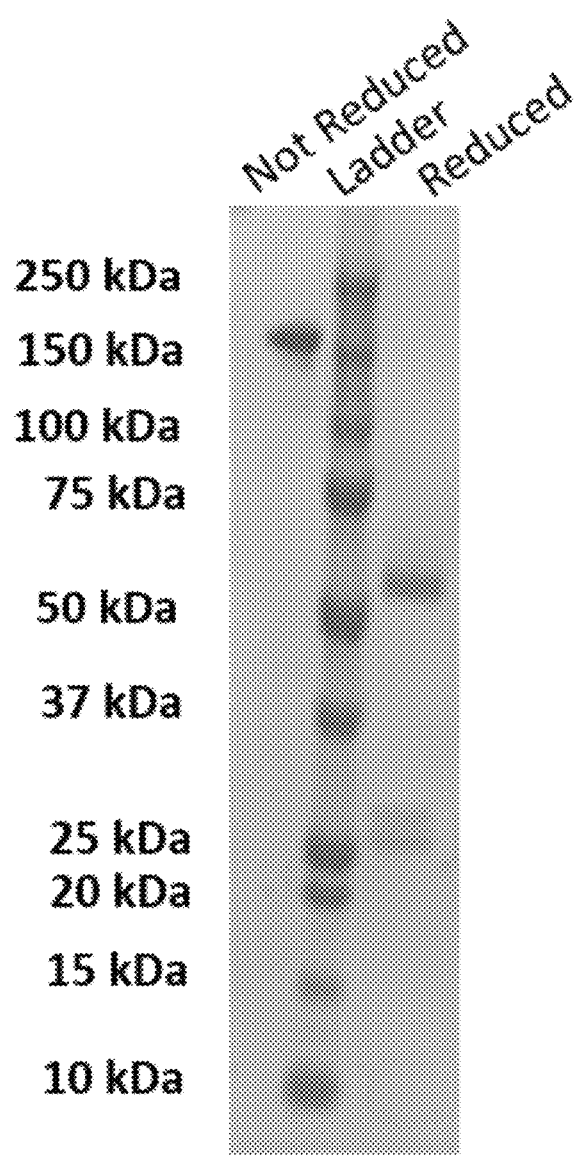
FIG. 14. Gel of multispecific molecule 5.
Figure 33:
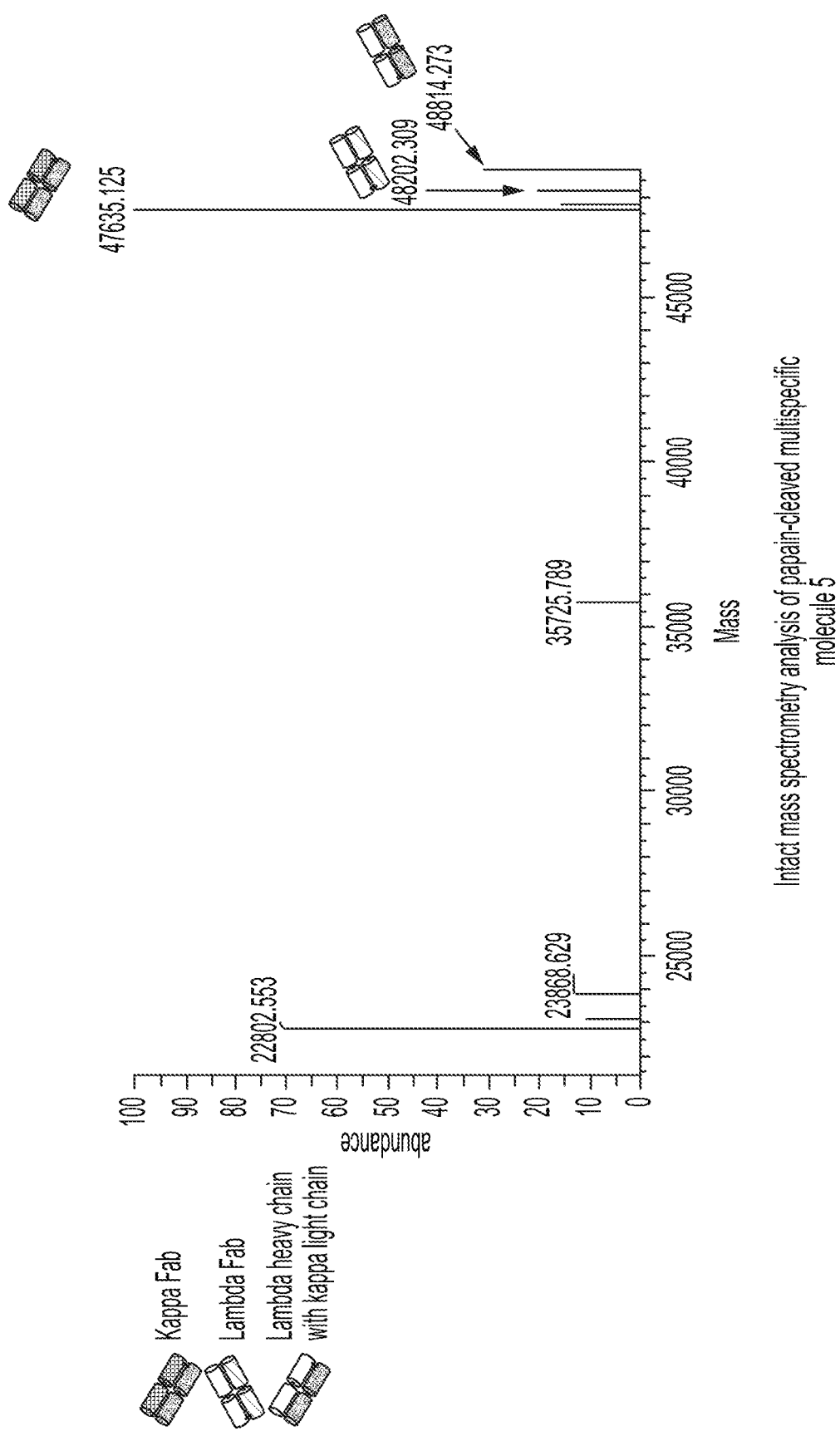
FIG. 33. Intact mass spectrometry analysis of papain-cleaved multispecific molecule 5.

Multispecific molecule 5 was expressed by co-transfecting cells with expression vectors comprising polynucleotide sequences of SEQ ID NO: 78, SEQ ID NO: 15, SEQ ID NO: 88, and SEQ ID NO: 45. Multispecific molecule 5 was purified and a SDS-PAGE gel of the final product is shown in FIG. 14. The mass spectrometry data of the papain cleavage of multispecific molecule 5 is shown in FIG. 33 and summarized in Table 12, where there is one incorrect Fab pairing with the lambda heavy chain paired with the kappa light chain.

TABLE 12

Mass spectrometry results for multispecific molecule 5.

| Fab Pairing | Predicted Mass (Da) | Observed Mass (Da) |
|---|---|---|
| Kappa heavy chain/kappa light chain | 47634.9 | 47635.1 |
| Kappa heavy chain/lambda light chain | 47652.9 | N/A |
| Lambda heavy chain/lambda light chain | 48205.1 | 48202.3 |
| Lambda heavy chain/kappa light chain | 48817.2 | 48814.3 |

Example 7

Multispecific molecule 6 comprises an α-PD1 arm and an α-TRAILR2 arm. The α-PD1 arm comprises a first chain of the amino acid sequence of SEQ ID NO: 181 and a second chain of the amino acid sequence of SEQ ID NO: 182. The α-TRAILR2 arm comprises a first chain of the amino acid sequence of SEQ ID NO: 177 and a second chain of the amino acid sequence of SEQ ID NO: 148. The configuration of multispecific molecule 6 is shown in FIG. 5.

Figure 15:
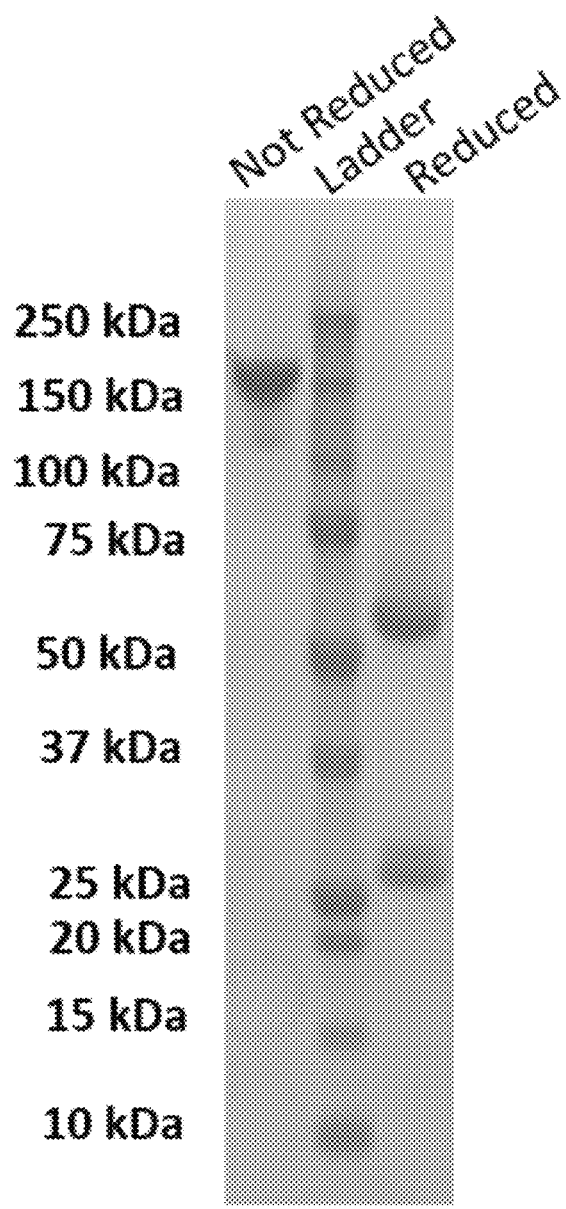
FIG. 15. Gel of multispecific molecule 6.
Figure 34:
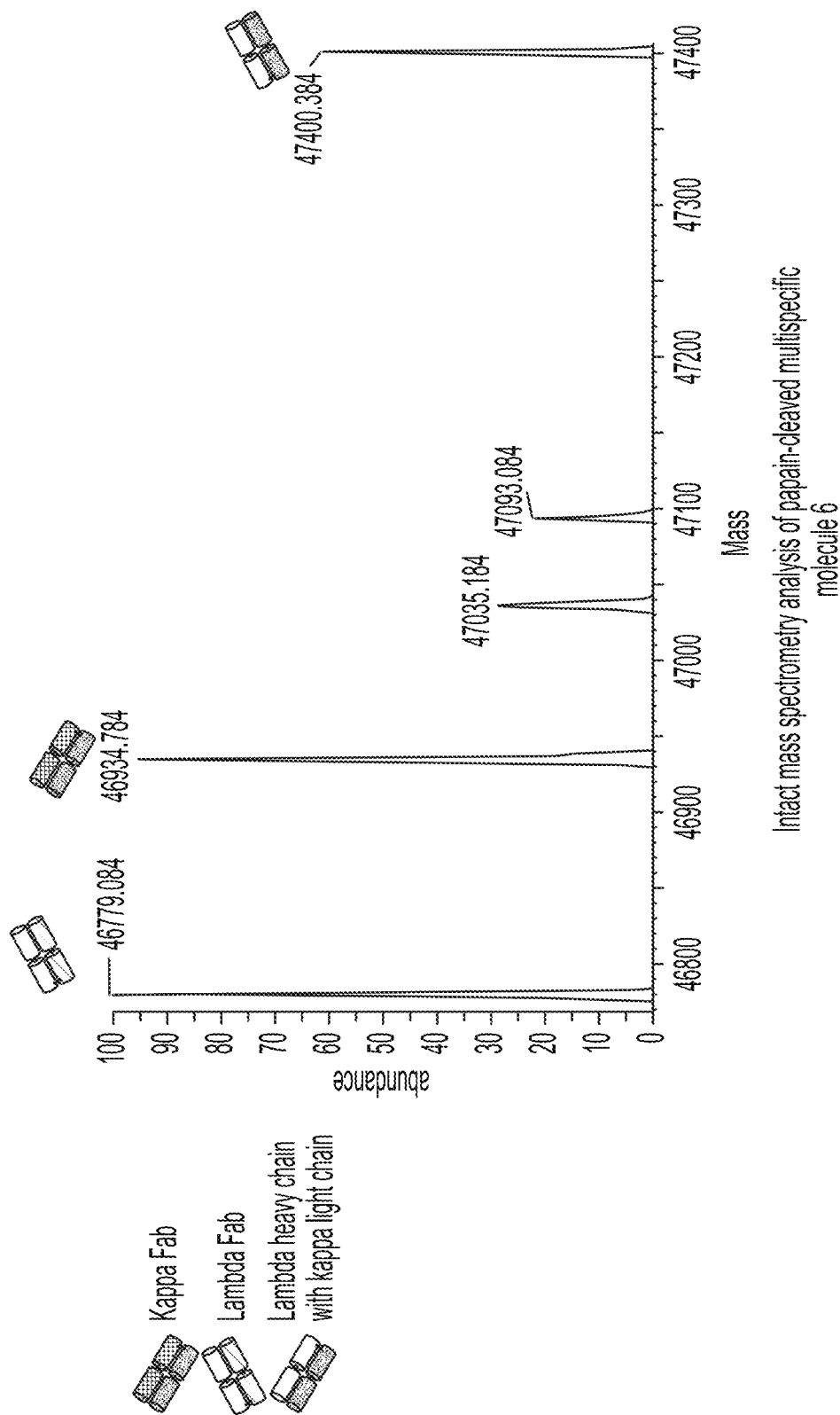
FIG. 34. Intact mass spectrometry analysis of papain-cleaved multispecific molecule 6.

Multispecific molecule 6 was expressed by co-transfecting cells with expression vectors comprising polynucleotide sequences of SEQ ID NO: 89, SEQ ID NO: 90, SEQ ID NO: 81, and SEQ ID NO: 57. Multispecific molecule 6 was purified and a SDS-PAGE gel of the final product is shown in FIG. 15. The mass spectrometry data of the papain cleavage of multispecific molecule 6 is shown in FIG. 34 and summarized in Table 13, where there is one incorrect Fab pairing with the lambda heavy chain paired with the kappa light chain.

TABLE 13

Mass spectrometry results for multispecific molecule 6.

| Fab Pairing | Predicted Mass (Da) | Observed Mass (Da) |
|---|---|---|
| Kappa heavy chain/kappa light chain | 46933.9 | 46934.8 |
| Kappa heavy chain/lambda light chain | 46329.6 | N/A |
| Lambda heavy chain/lambda light chain | 46779.2 | 46779.0 |
| Lambda heavy chain/kappa light chain | 47400.5 | 47400.4 |

Example 8

Multispecific molecule 7 comprises an α-PD1 arm and an α-PDL1 arm. The α-PD1 arm comprises a first chain of the amino acid sequence of SEQ ID NO: 181 and a second chain of the amino acid sequence of SEQ ID NO: 182. The α-PDL1 arm comprises a first chain of the amino acid sequence of SEQ ID NO: 166 and a second chain of the amino acid sequence of SEQ ID NO: 167. The configuration of multispecific molecule 7 is shown in FIG. 5.

Figure 16:
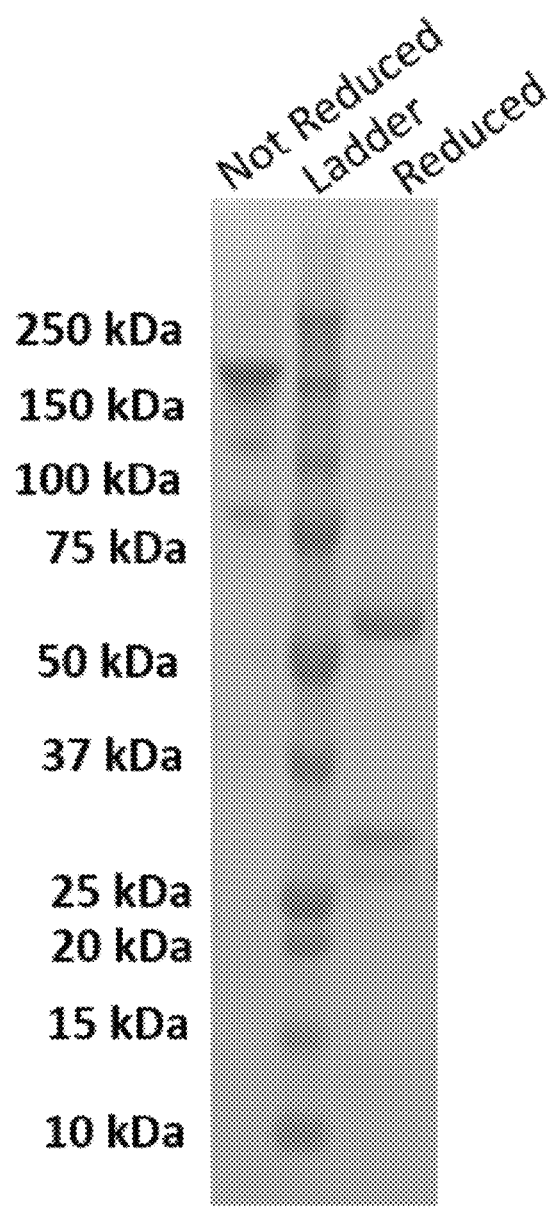
FIG. 16. Gel of multispecific molecule 7.
Figure 35:
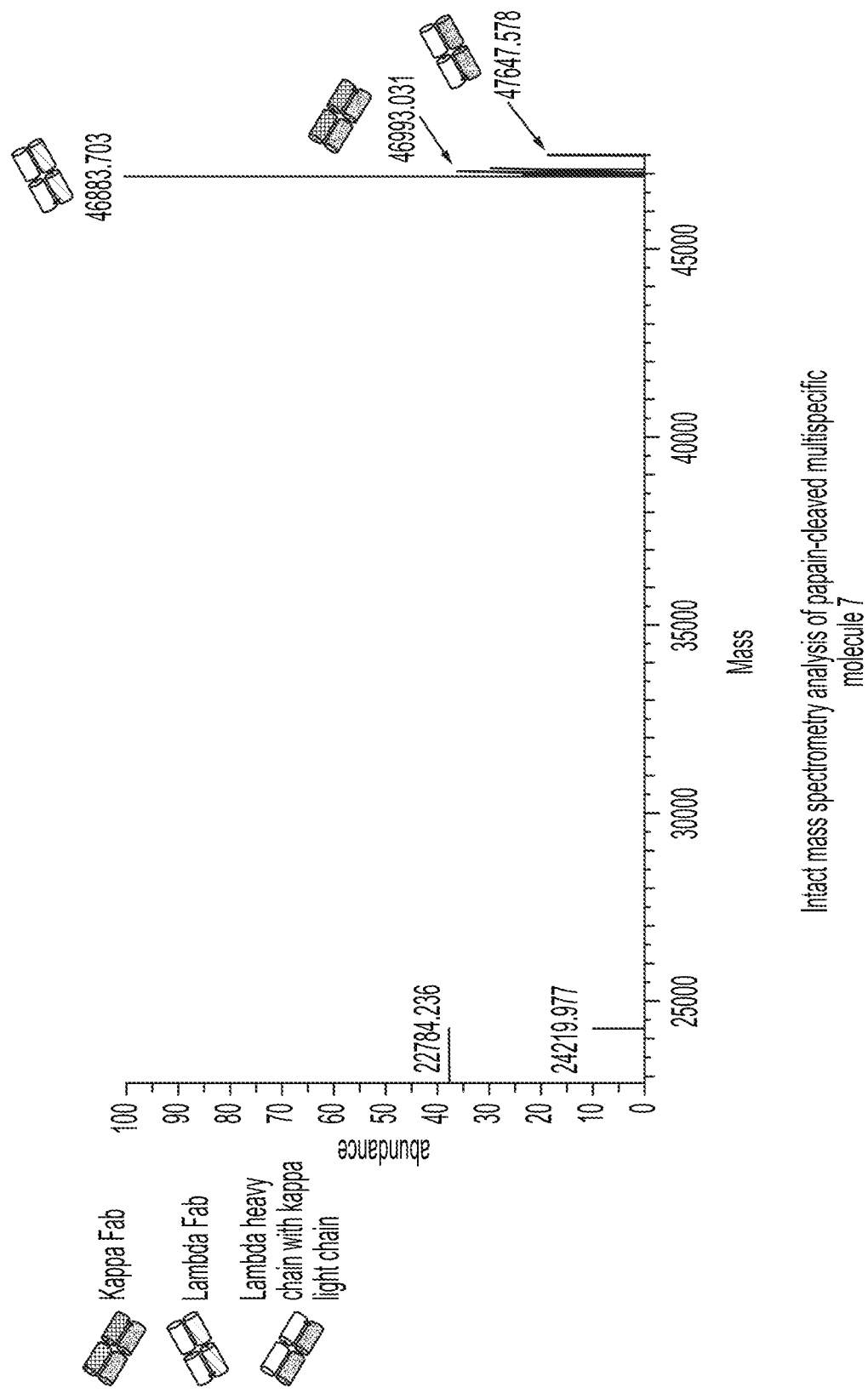
FIG. 35. Intact mass spectrometry analysis of papain-cleaved multispecific molecule 7.

Multispecific molecule 7 was expressed by co-transfecting cells with expression vectors comprising polynucleotide sequences of SEQ ID NO: 89, SEQ ID NO: 90, SEQ ID NO: 84, and SEQ ID NO: 85. Multispecific molecule 7 was purified and a SDS-PAGE gel of the final product is shown in FIG. 16. The mass spectrometry data of the papain cleavage of multispecific molecule 7 is shown in FIG. 35 and summarized in Table 14, where there is one incorrect Fab pairing with the lambda heavy chain paired with the kappa light chain.

TABLE 14

Mass spectrometry results for multispecific molecule 7.

| Fab Pairing | Predicted Mass (Da) | Observed Mass (Da) |
|---|---|---|
| Kappa heavy chain/kappa light chain | 46933.9 | 46933.0 |
| Kappa heavy chain/lambda light chain | 46382.56 | N/A |
| Lambda heavy chain/lambda light chain | 46882.7 | 46883.7 |
| Lambda heavy chain/kappa light chain | 47469.0 | 47467.6 |

Example 9

Figure 7:
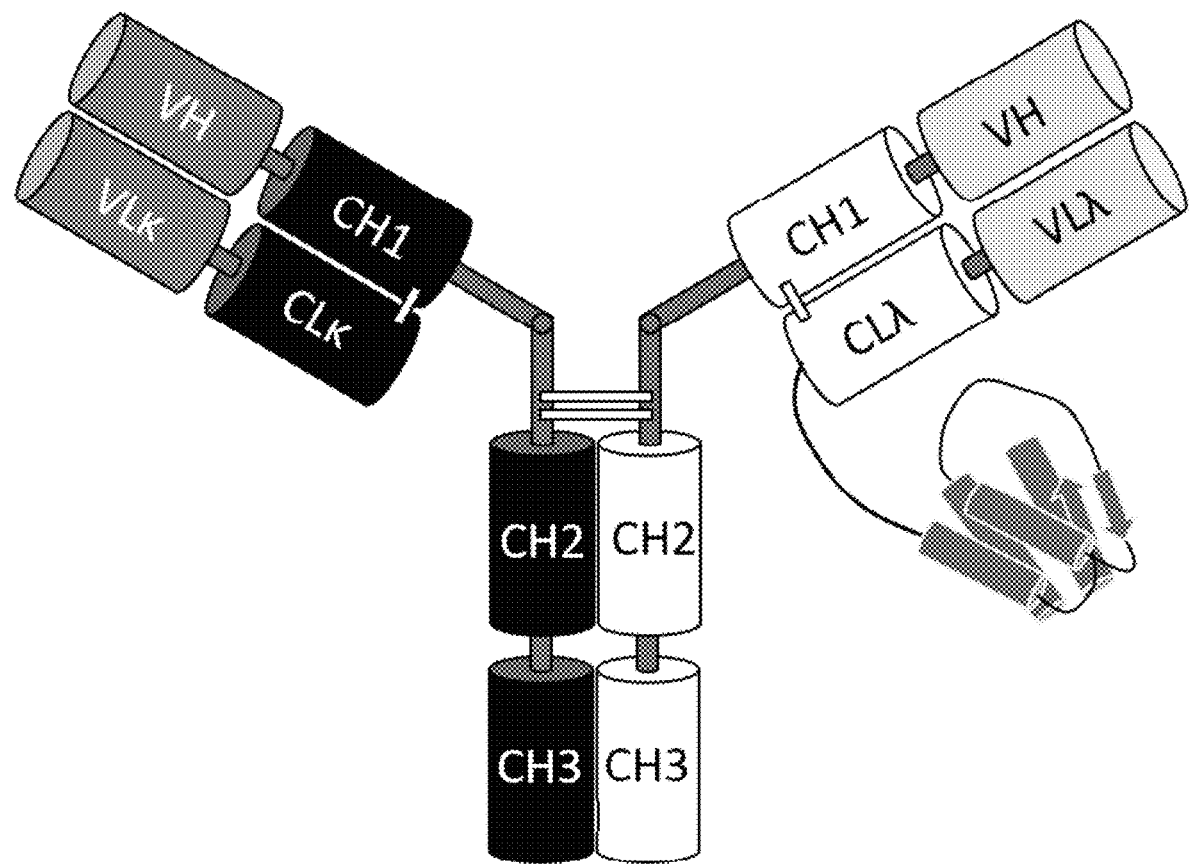
FIG. 7 depicts a schematic representation of an exemplary multispecific antibody molecule of the present invention. The multispecific antibody molecule comprises a first Fab comprising a kappa light chain polypeptide; a second Fab comprising a lambda light chain polypeptide; a polypeptide attached to the C terminus of the lambda light chain polypeptide; and an Fc domain, wherein the Fc domain does not contain a paired protuberance/cavity, e.g., knob and hole pair (e.g., the Fc domain is a naturally existing Fc domain). In one embodiment, the first Fab binds to CTLA4, the second Fab binds to IL12β, and the polypeptide that is attached to the C terminus of the lambda light chain polypeptide comprises interleukin 2, or fragment or variant thereof (e.g., multispecific molecule 8 described in Example 9).

Multispecific molecule 8 comprises an α-CTLA4 arm, an α-IL12β arm, and an IL-2 polypeptide. The IL-2 polypeptide is fused to the C-terminus of the lambda light chain of the α-IL12β arm. The α-CTLA4 arm comprises a first chain of the amino acid sequence of SEQ ID NO: 171 and a second chain of the amino acid sequence of SEQ ID NO: 106. The α-IL12β arm, together with the fused IL-2 polypeptide, comprises a first chain of the amino acid sequence of SEQ ID NO: 172 and a second chain of the amino acid sequence of SEQ ID NO: 173. The two heavy chains of multispecific molecule 8 do not comprise the knobs-into-holes mutations. The configuration of multispecific molecule 8 is shown in FIG. 7.

Figure 17:
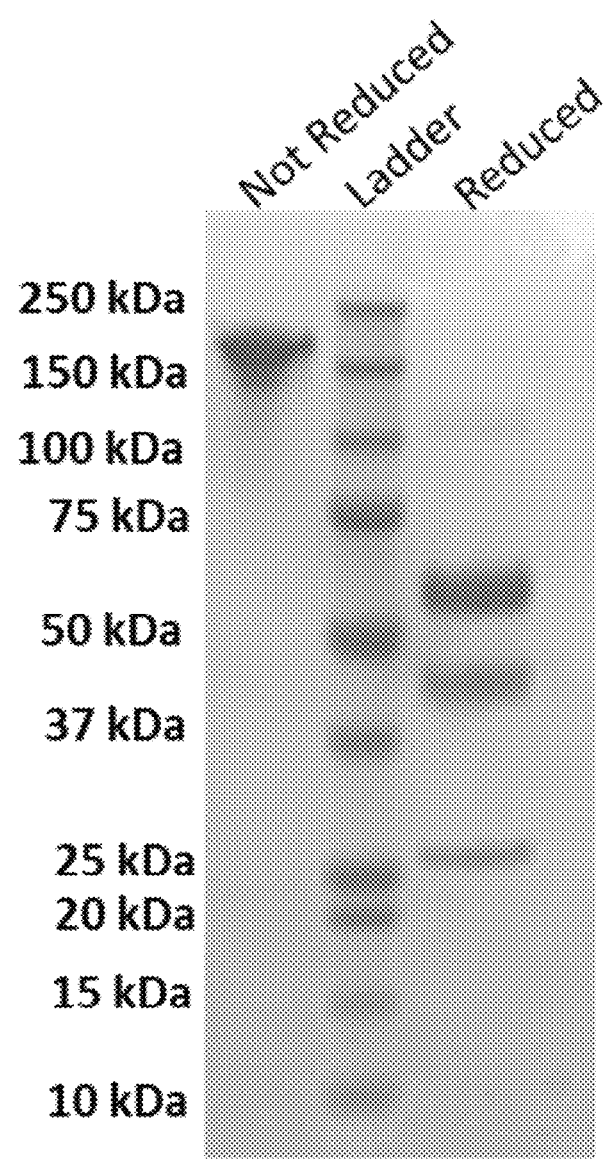
FIG. 17. Gel of multispecific molecule 8.
Figure 21:
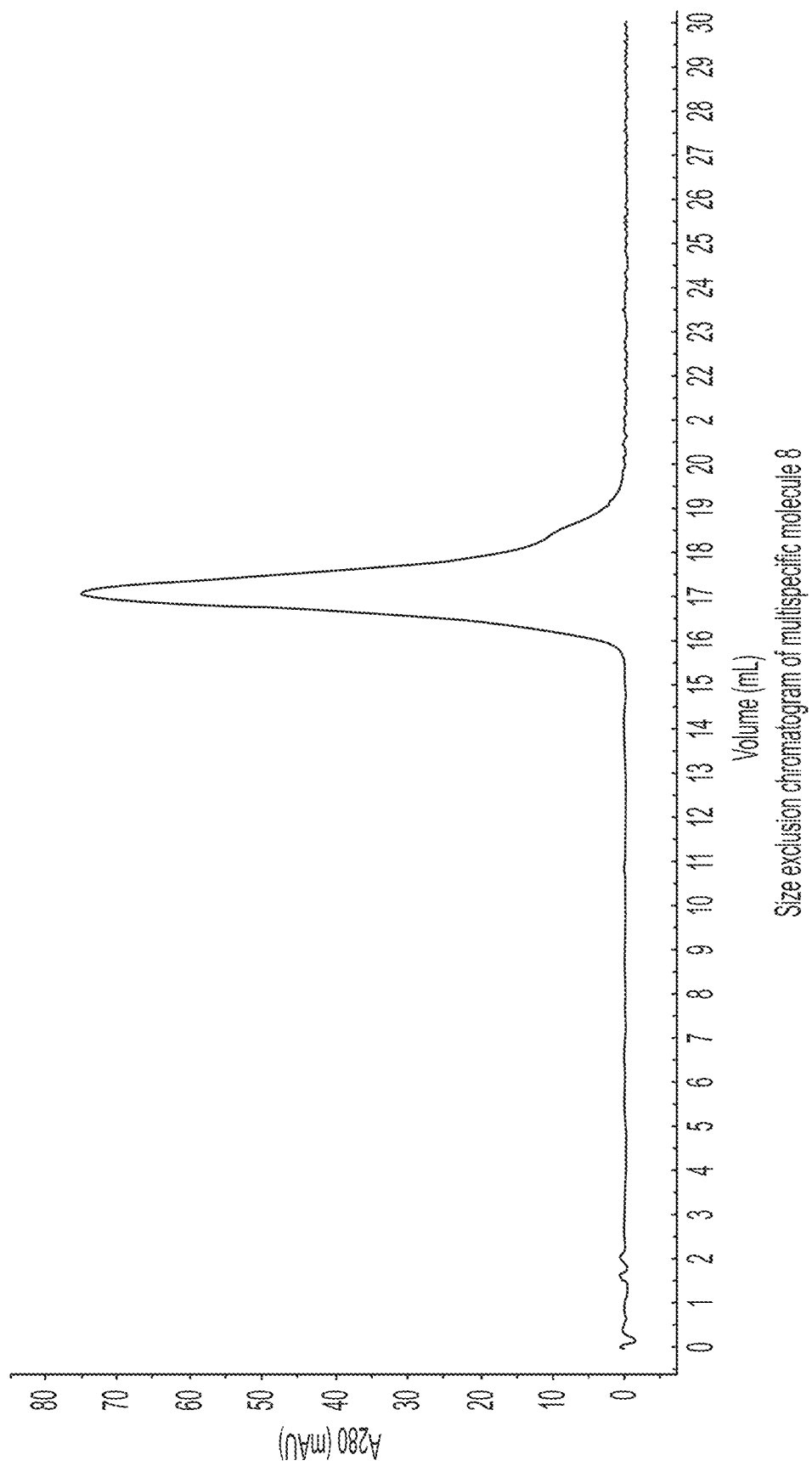
FIG. 21. Size exclusion chromatogram of multispecific molecule 8.
Figure 26:
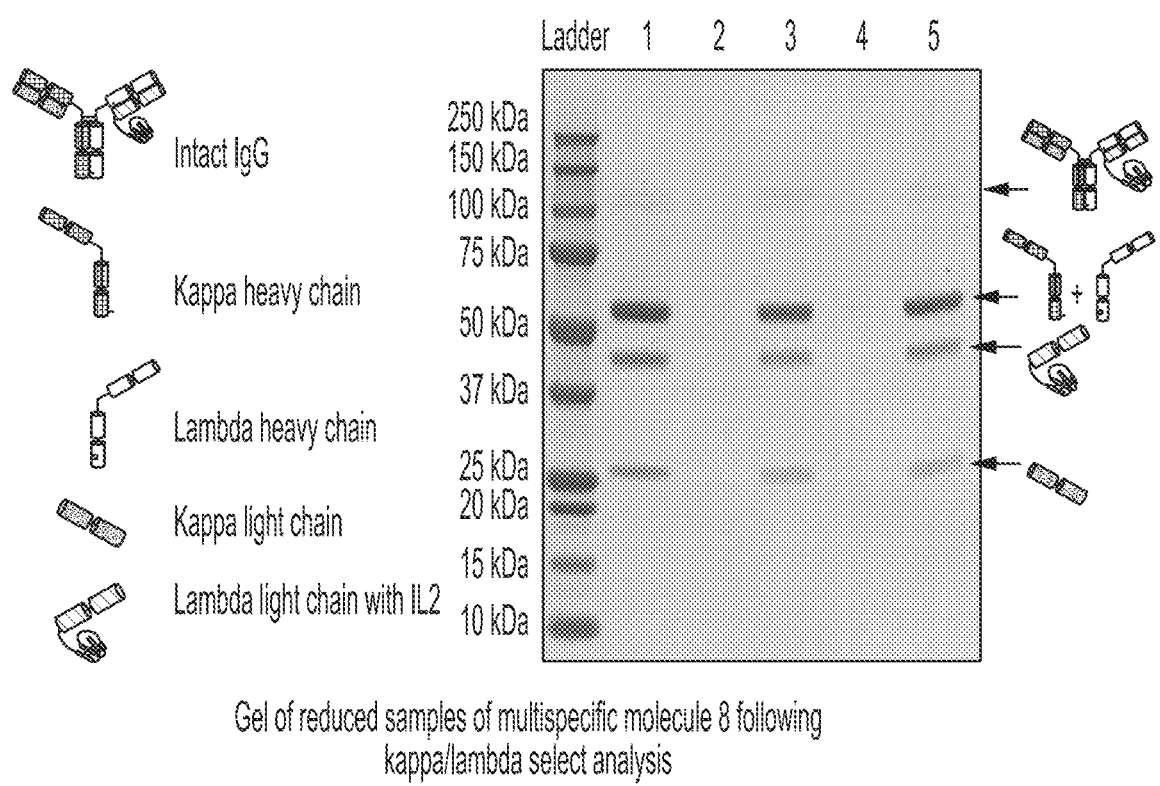
FIG. 26. Gel of reduced samples of multispecific molecule 8 following kappa/lambda select analysis. Lane 1 is the load, lane 2 is the flow-through from the KappaSelect column, lane 3 is the elution from the KappaSelect column, lane 4 is the flow-through from the LambdaFabSelect column, and lane 5 is the elution from the LambdaFabSelect column.

Multispecific molecule 8 was expressed by co-transfecting cells with expression vectors comprising polynucleotide sequences of SEQ ID NO: 73, SEQ ID NO: 15, SEQ ID NO: 74, and SEQ ID NO: 75. Multispecific molecule 8 was purified and a SDS-PAGE gel of the final product is shown in FIG. 17. FIG. 21 shows the size exclusion chromatogram of multispecific molecule 8. A KappaSelect and LambdaFabSelect analysis was performed with multispecific molecule 8, shown in FIG. 26. Both the KappaSelect and LambdaFabSelect flow-through fractions contained no protein, suggesting good chain fidelity.

Example 10

Figure 6:
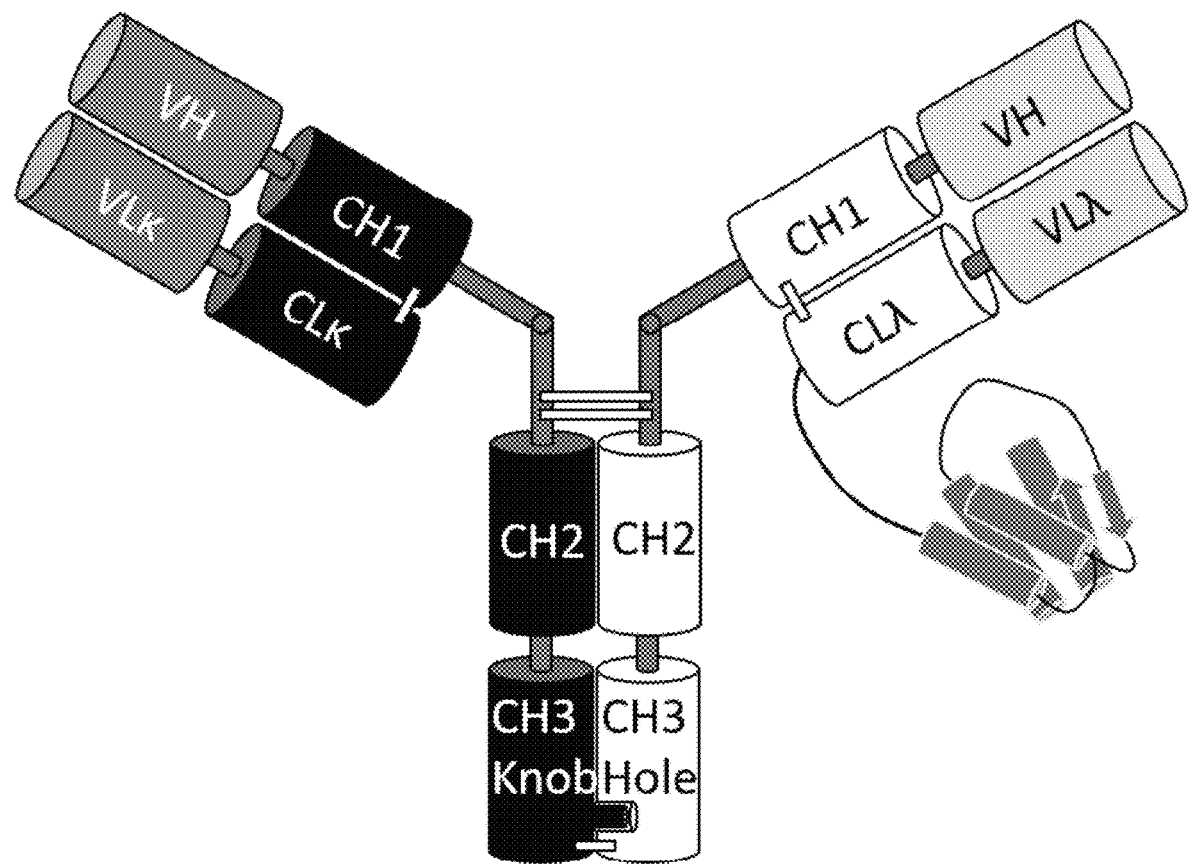
FIG. 6 depicts a schematic representation of an exemplary multispecific antibody molecule of the present invention. The multispecific antibody molecule comprises a first Fab comprising a kappa light chain polypeptide; a second Fab comprising a lambda light chain polypeptide; a polypeptide attached to the C terminus of the lambda light chain polypeptide; and an Fc domain, wherein the Fc domain contains a paired protuberance/cavity, e.g., knob and hole pair. In one embodiment, the first Fab binds to CTLA4, the second Fab binds to IL12β, and the polypeptide that is attached to the C terminus of the lambda light chain polypeptide comprises interleukin 2, or fragment or variant thereof (e.g., multispecific molecule 9 described in Example 10).

Multispecific molecule 9 comprises an α-CTLA4 arm, an α-IL12β arm, and an IL-2 polypeptide. The IL-2 polypeptide is fused to the C-terminus of the lambda light chain of the α-IL12β arm. The α-CTLA4 arm comprises a first chain of the amino acid sequence of SEQ ID NO: 168 and a second chain of the amino acid sequence of SEQ ID NO: 106. The α-IL12β arm, together with the fused IL-2 polypeptide, comprises a first chain of the amino acid sequence of SEQ ID NO: 170 and a second chain of the amino acid sequence of SEQ ID NO: 173. Different from multispecific molecule 8, the two heavy chains of multispecific molecule 9 comprise the knobs-into-holes mutations. The configuration of multispecific molecule 9 is shown in FIG. 6.

Figure 18:
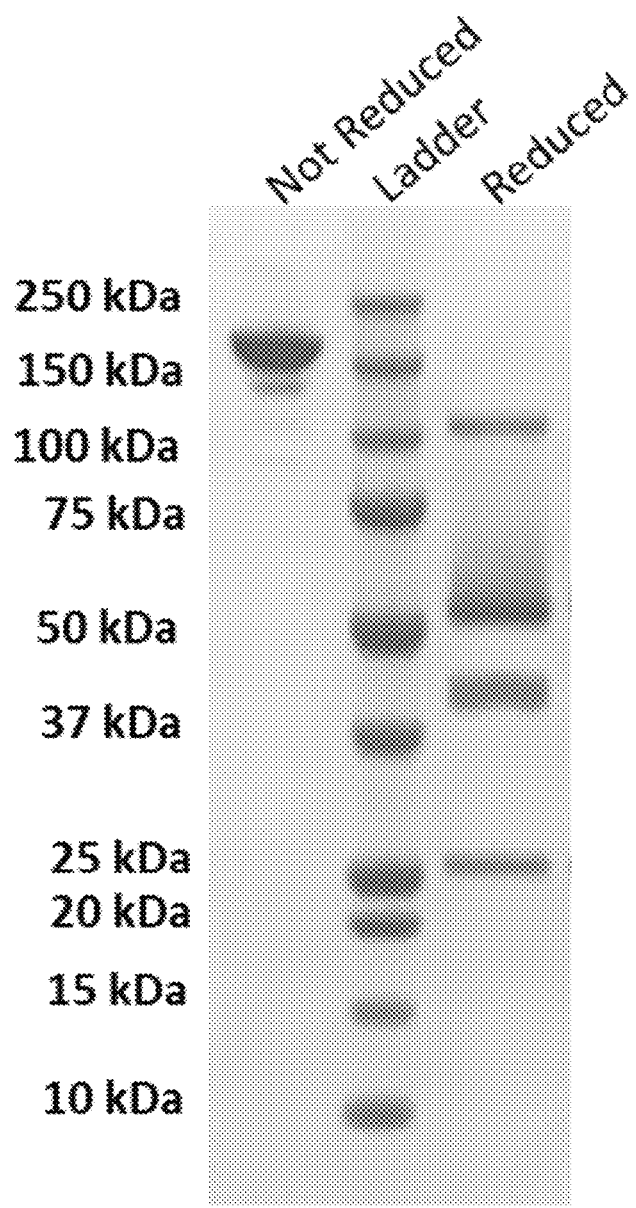
FIG. 18. Gel of multispecific molecule 9.
Figure 22:
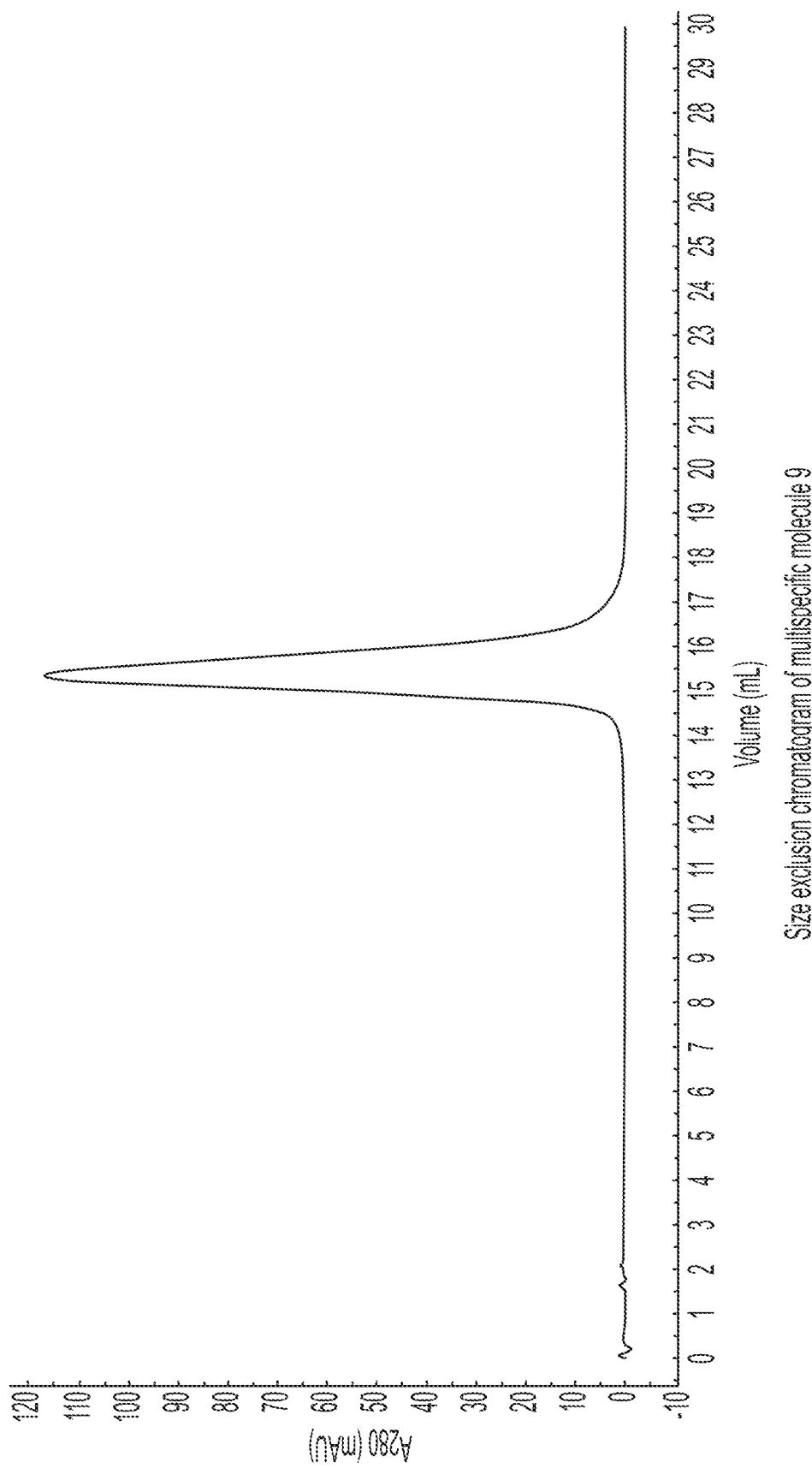
FIG. 22. Size exclusion chromatogram of multispecific molecule 9.
Figure 27:
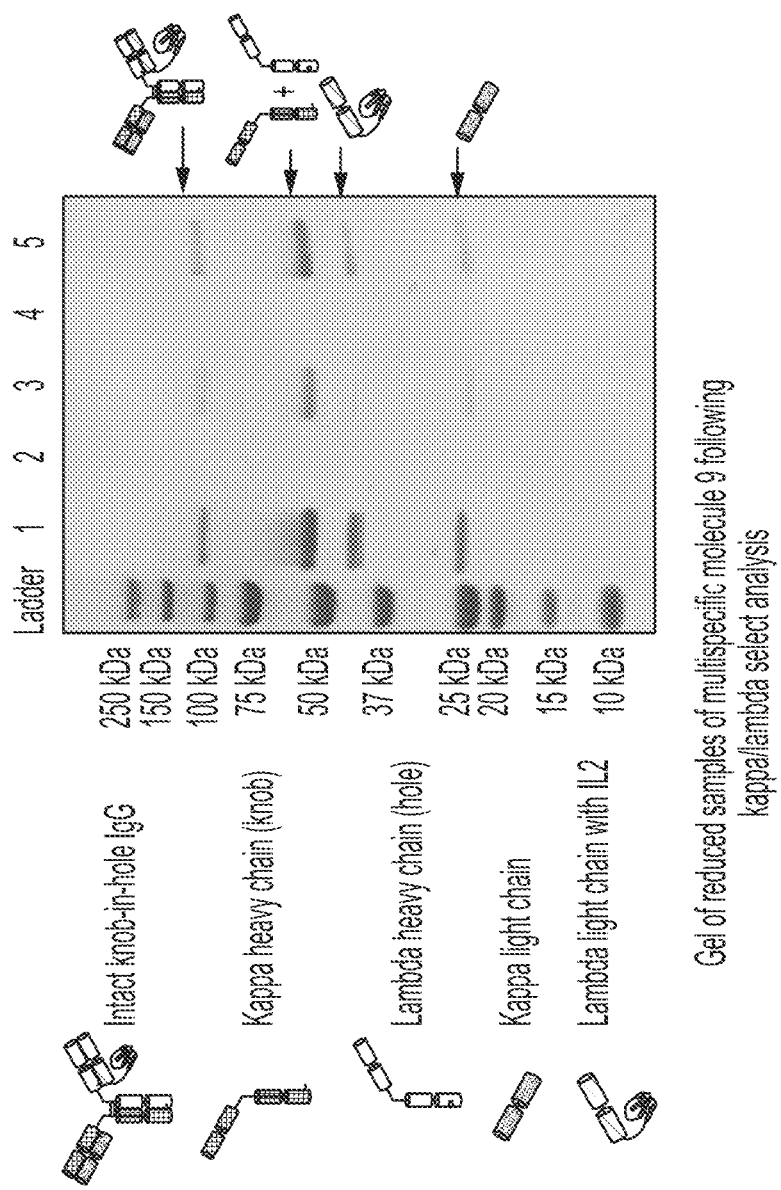
FIG. 27. Gel of reduced samples of multispecific molecule 9 following kappa/lambda select analysis. Lane 1 is the load, lane 2 is the flow-through from the KappaSelect column, lane 3 is the elution from the KappaSelect column, lane 4 is the flow-through from the LambdaFabSelect column, and lane 5 is the elution from the LambdaFabSelect column.

Multispecific molecule 9 was expressed by co-transfecting cells with expression vectors comprising polynucleotide sequences of SEQ ID NO: 78, SEQ ID NO: 15, SEQ ID NO: 91, and SEQ ID NO: 75. Multispecific molecule 9 was purified and a SDS-PAGE gel of the final product is shown in FIG. 18. FIG. 22 shows the size exclusion chromatogram of multispecific molecule 9. A KappaSelect and LambdaFabSelect analysis was performed with multispecific molecule 9, shown in FIG. 27. Both the KappaSelect and LambdaFabSelect flow-through fractions contained no protein, suggesting good chain fidelity.

Example 11

Figure 9:
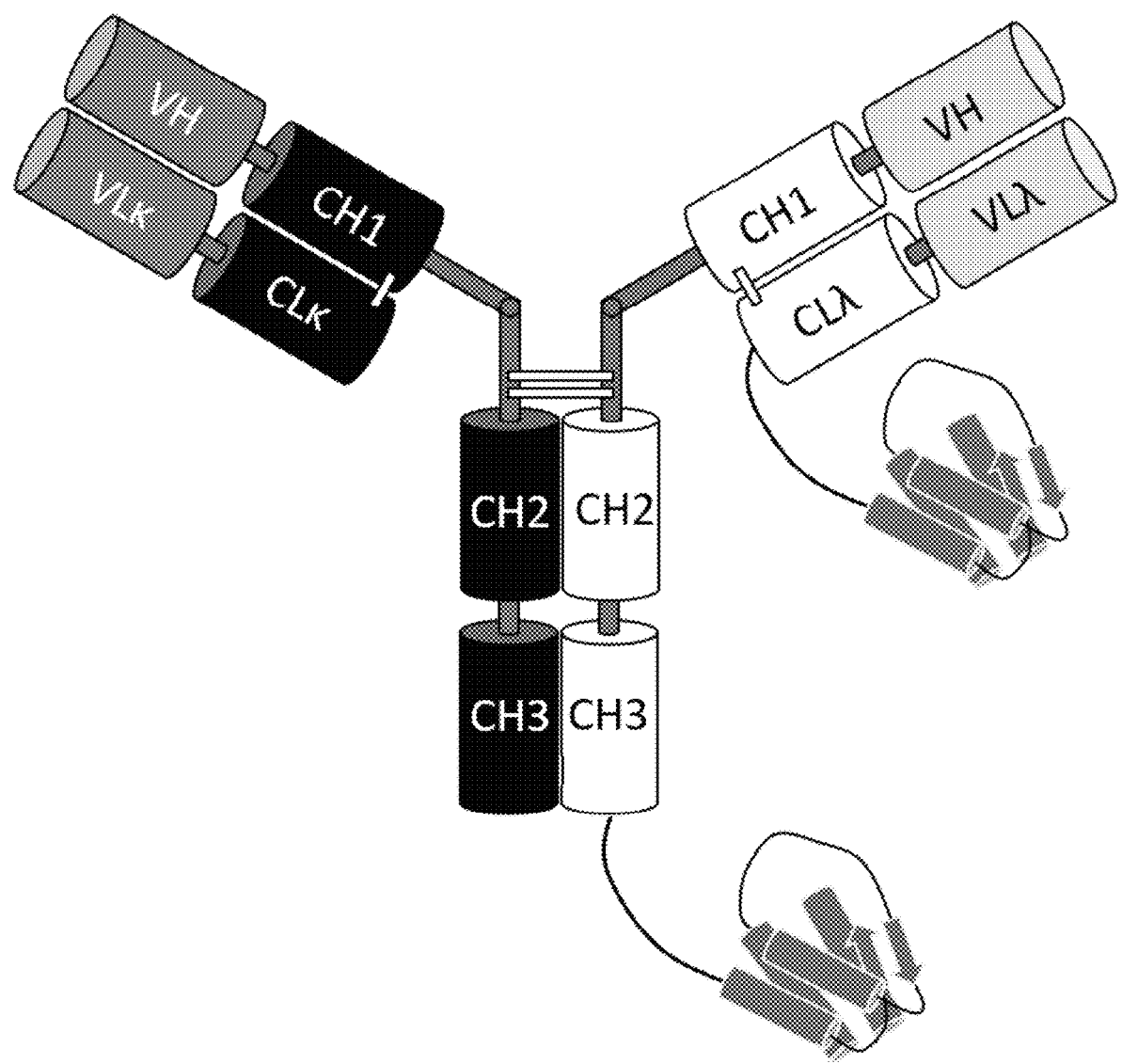
FIG. 9 depicts a schematic representation of an exemplary multispecific antibody molecule of the present invention. The multispecific antibody molecule comprises a first Fab comprising a kappa light chain polypeptide; a second Fab comprising a lambda light chain polypeptide; a first polypeptide attached to the C terminus of the lambda light chain polypeptide; a second polypeptide attached to the C terminus of the heavy chain polypeptide that associates with the lambda light chain polypeptide; and an Fc domain, wherein the Fc domain does not contain a paired protuberance/cavity, e.g., knob and hole pair (e.g., the Fc domain is a naturally existing Fc domain). In one embodiment, the first Fab binds to CTLA4, the second Fab binds to IL12β, the first polypeptide comprises interleukin 2, or fragment or variant thereof, and the second polypeptide comprises interleukin 2, or fragment or variant thereof (e.g., multispecific molecule 10 described in Example 11).

Multispecific molecule 10 comprises an α-CTLA4 arm, an α-IL12β arm, and two IL-2 polypeptides. The first IL-2 polypeptide is fused to the C-terminus of the lambda light chain of the α-IL12β arm. The second IL-2 polypeptide is fused to the C-terminus of the heavy chain of the α-IL12β arm. The α-CTLA4 arm comprises a first chain of the amino acid sequence of SEQ ID NO: 171 and a second chain of the amino acid sequence of SEQ ID NO: 106. The α-IL12β arm, together with the two fused IL-2 polypeptides, comprises a first chain of the amino acid sequence of SEQ ID NO: 175 and a second chain of the amino acid sequence of SEQ ID NO: 173. The two heavy chains of multispecific molecule 10 do not comprise the knobs-into-holes mutations. The configuration of multispecific molecule 10 is shown in FIG. 9.

Figure 29:
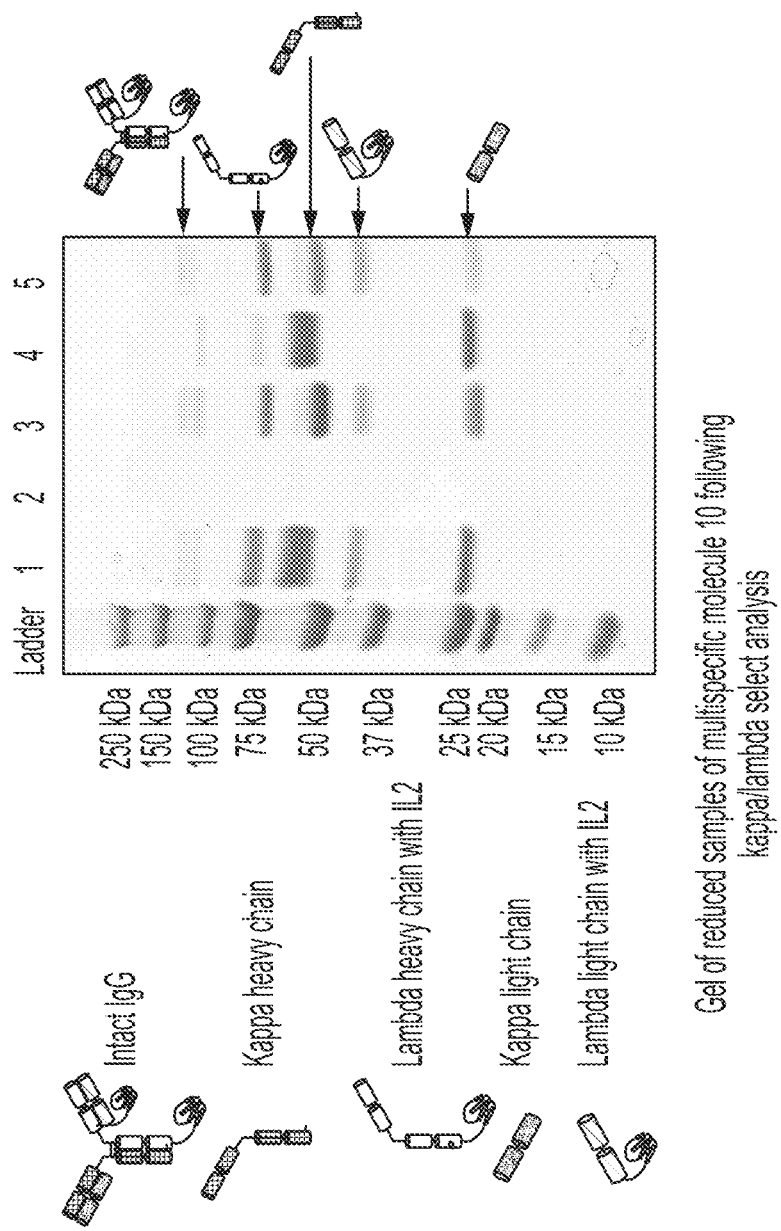
FIG. 29. Gel of reduced samples of multispecific molecule 10 following kappa/lambda select analysis. Lane 1 is the load, lane 2 is the flow-through from the KappaSelect column, lane 3 is the elution from the KappaSelect column, lane 4 is the flow-through from the LambdaFabSelect column, and lane 5 is the elution from the LambdaFabSelect column.

Multispecific molecule 10 was expressed by co-transfecting cells with expression vectors comprising polynucleotide sequences of SEQ ID NO: 73, SEQ ID NO: 15, SEQ ID NO: 77, and SEQ ID NO: 75. A KappaSelect and LambdaFabSelect analysis was performed with multispecific molecule 10, shown in FIG. 29. The flow-through from the KappaSelect column contained no protein, while the flow-through from the LambdaFabSelect column had protein primarily composed of the kappa heavy chain (knob) and kappa light chain. This suggests that the expression for the kappa pieces was greater than that of the lambda chains, rather than an issue with chain fidelity.

Example 12

Figure 8:
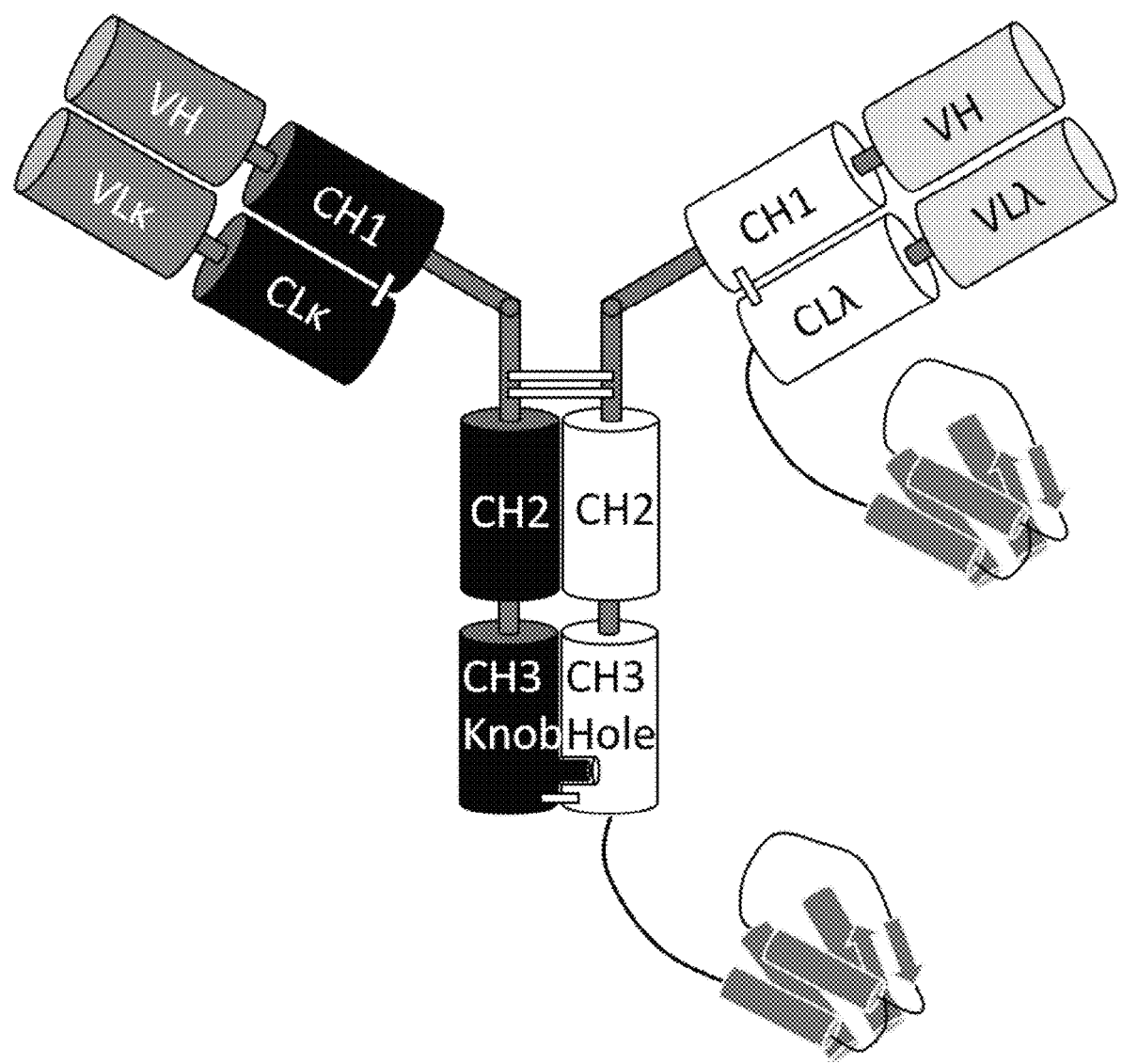
FIG. 8 depicts a schematic representation of an exemplary multispecific antibody molecule of the present invention. The multispecific antibody molecule comprises a first Fab comprising a kappa light chain polypeptide; a second Fab comprising a lambda light chain polypeptide; a first polypeptide attached to the C terminus of the lambda light chain polypeptide; a second polypeptide attached to the C terminus of the heavy chain polypeptide that associates with the lambda light chain polypeptide; and an Fc domain, wherein the Fc domain contains a paired protuberance/cavity, e.g., knob and hole pair. In one embodiment, the first Fab binds to CTLA4, the second Fab binds to IL12β, the first polypeptide comprises interleukin 2, or fragment or variant thereof, and the second polypeptide comprises interleukin 2, or fragment or variant thereof (e.g., multispecific molecule 11 described in Example 12).

Multispecific molecule 11 comprises an α-CTLA4 arm, an α-IL12β arm, and two IL-2 polypeptides. The first IL-2 polypeptide is fused to the C-terminus of the lambda light chain of the α-IL12β arm. The second IL-2 polypeptide is fused to the C-terminus of the heavy chain of the α-IL12β arm. The α-CTLA4 arm comprises a first chain of the amino acid sequence of SEQ ID NO: 168 and a second chain of the amino acid sequence of SEQ ID NO: 106. The α-IL12β arm, together with the two fused IL-2 polypeptides, comprises a first chain of the amino acid sequence of SEQ ID NO: 174 and a second chain of the amino acid sequence of SEQ ID NO: 173. Different from multispecific molecule 10, the two heavy chains of multispecific molecule 11 comprise the knobs-into-holes mutations. The configuration of multispecific molecule 11 is shown in FIG. 8.

Figure 28:
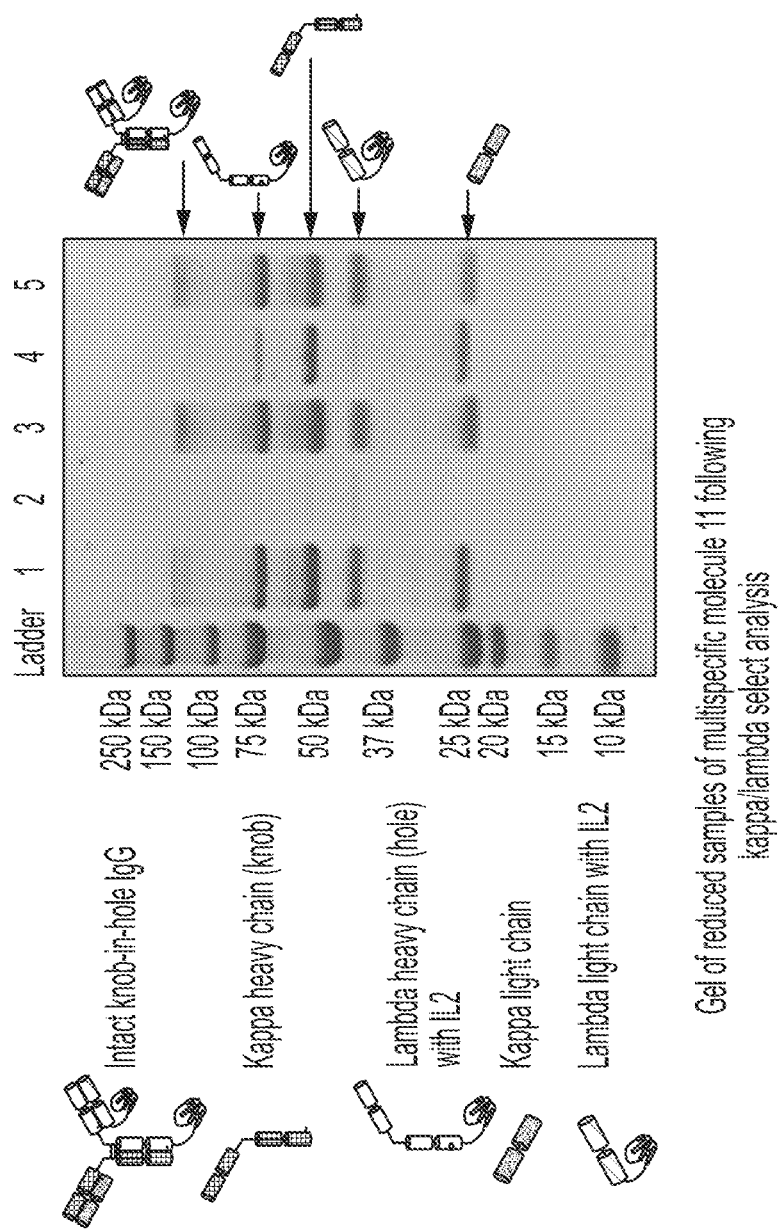
FIG. 28. Gel of reduced samples of multispecific molecule 11 following kappa/lambda select analysis. Lane 1 is the load, lane 2 is the flow-through from the KappaSelect column, lane 3 is the elution from the KappaSelect column, lane 4 is the flow-through from the LambdaFabSelect column, and lane 5 is the elution from the LambdaFabSelect column.

Multispecific molecule 11 was expressed by co-transfecting cells with expression vectors comprising polynucleotide sequences of SEQ ID NO: 78, SEQ ID NO: 15, SEQ ID NO: 76, and SEQ ID NO: 75. A KappaSelect and LambdaFabSelect analysis was performed with multispecific molecule 11, shown in FIG. 28. The flow-through from the KappaSelect column contained no protein, while the flow-through from the LambdaFabSelect column had protein primarily composed of the kappa heavy chain (knob) and kappa light chain. This suggests that the expression for the kappa pieces was greater than that of the lambda chains, rather than an issue with chain fidelity. This agrees with the what was seen with multispecific molecule 10, which is the same molecule except for the absence of the knob-in-hole mutations.

Example 13

Figure 10:
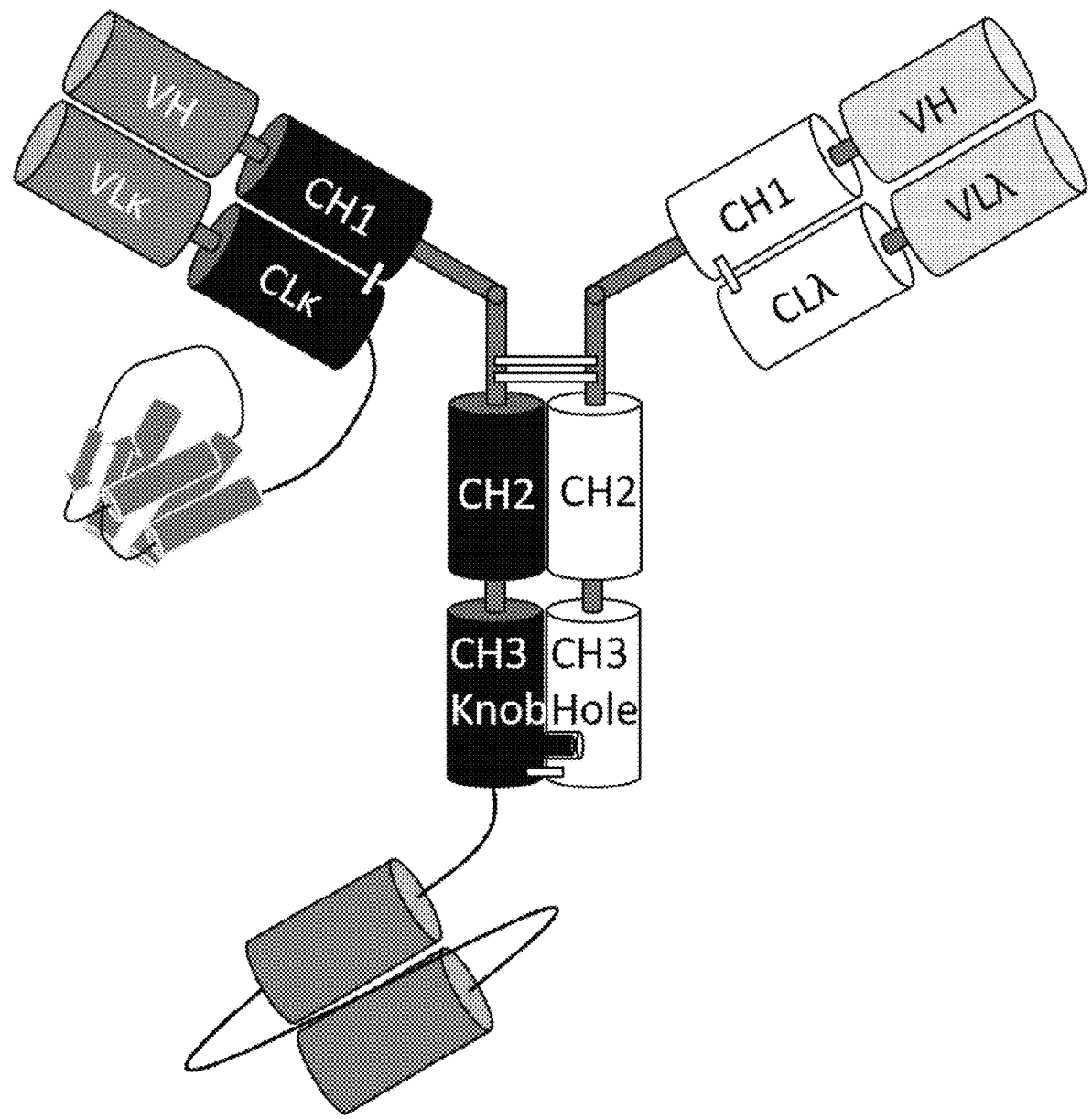
FIG. 10 depicts a schematic representation of an exemplary multispecific antibody molecule of the present invention. The multispecific antibody molecule comprises a first Fab comprising a kappa light chain polypeptide; a second Fab comprising a lambda light chain polypeptide; a first polypeptide attached to the C terminus of the kappa light chain polypeptide; a second polypeptide attached to the C terminus of the heavy chain polypeptide that associates with the kappa light chain polypeptide; and an Fc domain, wherein the Fc domain contains a paired protuberance/cavity, e.g., knob and hole pair. In one embodiment, the first Fab binds to CTLA4, the second Fab binds to TRAILR2, the first polypeptide comprises interleukin 2, or fragment or variant thereof, and the second polypeptide comprises an scFv (e.g., multispecific molecule 12 described in Example 13).

Multispecific molecule 12 comprises an α-CTLA4 arm, an α-TRAILR2 arm, a scFv targeting arm, and an IL-2 polypeptide. The IL-2 polypeptide is fused to the C-terminus of the kappa light chain of the α-CTLA4 arm. The scFv is fused to the C-terminus of the heavy chain of the α-CTLA4 arm. The α-CTLA4 arm, together with the fused IL-2 polypeptide and the scFv, comprises a first chain of the amino acid sequence of SEQ ID NO: 169 and a second chain of the amino acid sequence of SEQ ID NO: 176. The α-TRAILR2 arm comprises a first chain of the amino acid sequence of SEQ ID NO: 177 and a second chain of the amino acid sequence of SEQ ID NO: 148. The two heavy chains of multispecific molecule 12 comprise the knobs-into-holes mutations. The configuration of multispecific molecule 12 is shown in FIG. 10.

Figure 30:
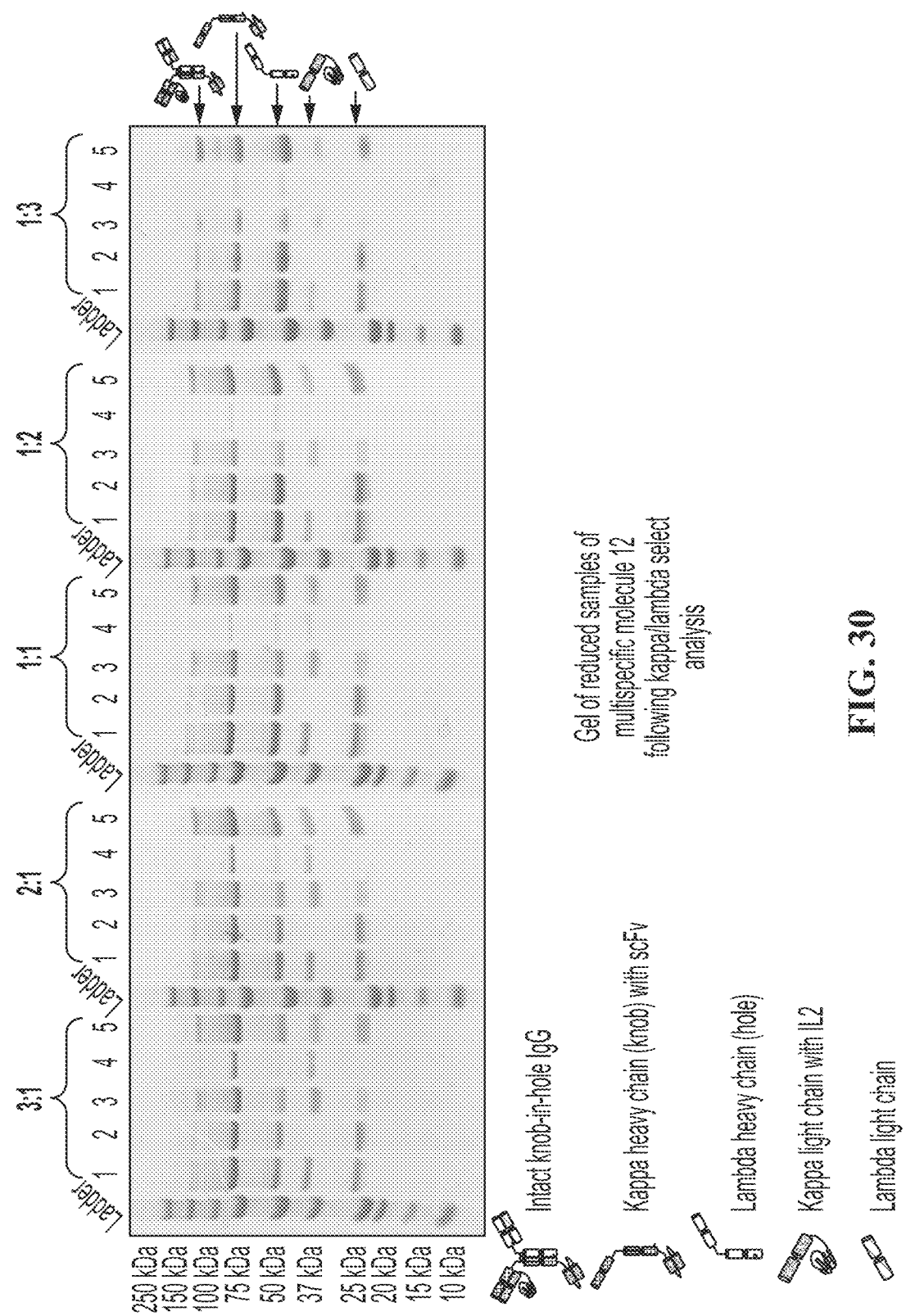
FIG. 30. Gel of reduced samples of multispecific molecule 12 following kappa/lambda select analysis. Lane 1 is the load, lane 2 is the flow-through from the KappaSelect column, lane 3 is the elution from the KappaSelect column, lane 4 is the flow-through from the LambdaFabSelect column, and lane 5 is the elution from the LambdaFabSelect column. The ratios indicate the DNA ratio used in the transfection from 3:1 to 1:3 of knob to hole.

Multispecific molecule 12 was expressed by co-transfecting cells with expression vectors comprising polynucleotide sequences of SEQ ID NO: 79, SEQ ID NO: 80, SEQ ID NO: 81, and SEQ ID NO: 57. A KappaSelect and LambdaFabSelect analysis was performed with multispecific molecule 12, shown in FIG. 30. The ratios indicate the ratios of DNA used at the time of transfection, varying from 3:1 to 1:3 of kappa to lambda. In all cases, there is protein in the flow-through of both the KappaSelect and LambdaFabSelect columns. The protein in the KappaSelect flow-through is composed of the kappa heavy chain, lambda heavy chain, and lambda light chain. The protein in the LambdaFabSelect flow-through is composed of the kappa heavy and light chains and diminishes as the ratio of the lambda chains increases. These data are in agreement with the data from multispecific molecule 4, which has the same Fab components and only shows the lambda light chain pairing with the kappa heavy chain and not vice versa.

We claim:

1. A multispecific antibody molecule comprising
i) a) a first heavy chain polypeptide (HCP1) comprising a first heavy chain constant region sequence (HCCRS), and
b) a lambda light chain polypeptide (LLCP) comprising a lambda light chain constant region sequence (LLC-CRS), and
ii) a) a second heavy chain polypeptide (HCP2) comprising a second heavy chain constant region sequence (HCCRS), and
b) a kappa light chain polypeptide (KLCP) comprising a kappa light chain constant region sequence (KLC-CRS),
wherein:
1) the multispecific antibody molecule does not comprise a mutation in the first HCCRS that increases the affinity of the HCP1 to the LLCP, or the multispecific antibody molecule does not comprise a mutation in the LLCCRS that increases the affinity of the HCP1 to the LLCP; and
2) the multispecific antibody molecule does not comprise a mutation in the second HCCRS that increases the affinity of the HCP2 to the KLCP, or the multispecific antibody molecule does not comprise a mutation in the KLCCRS that increases the affinity of the HCP2 to the KLCP;
wherein:
(i) (a) the HCP1 and the LLCP comprise the amino acid sequences of:
SEQ ID NO: 403 and SEQ ID NO: 404, respectively;
SEQ ID NO: 407 and SEQ ID NO: 408, respectively;
SEQ ID NO: 411 and SEQ ID NO: 412, respectively;
SEQ ID NO: 415 and SEQ ID NO: 416, respectively;
SEQ ID NO: 178 and SEQ ID NO: 145, respectively;
SEQ ID NO: 166 and SEQ ID NO: 167, respectively;
SEQ ID NO: 170 and SEQ ID NO: 163, respectively;
SEQ ID NO: 177 and SEQ ID NO: 148, respectively;
SEQ ID NO: 180 and SEQ ID NO: 136, respectively;
SEQ ID NO: 172 and SEQ ID NO: 173, respectively;
SEQ ID NO: 170 and SEQ ID NO: 173, respectively;
SEQ ID NO: 175 and SEQ ID NO: 173, respectively; or
SEQ ID NO: 174 and SEQ ID NO: 173, respectively; and
(b) the HCP2 and the KLCP comprise the amino acid sequences of:
SEQ ID NO: 401 and SEQ ID NO: 402, respectively;
SEQ ID NO: 405 and SEQ ID NO: 406, respectively;
SEQ ID NO: 409 and SEQ ID NO: 410, respectively;
SEQ ID NO: 413 and SEQ ID NO: 414, respectively;
SEQ ID NO: 417 and SEQ ID NO: 418, respectively;
SEQ ID NO: 179 and SEQ ID NO: 118, respectively;
SEQ ID NO: 164 and SEQ ID NO: 165, respectively;
SEQ ID NO: 168 and SEQ ID NO: 106, respectively;
SEQ ID NO: 181 and SEQ ID NO: 182, respectively;
SEQ ID NO: 171 and SEQ ID NO: 106, respectively; or
SEQ ID NO: 169 and SEQ ID NO: 176, respectively; or
(ii) the HCP1, the LLCP, the HCP2, and the KLCP comprise the amino acid sequences of:
SEQ ID NO: 403, SEQ ID NO: 404, SEQ ID NO: 401, and SEQ ID NO: 402, respectively;
SEQ ID NO: 407, SEQ ID NO: 408, SEQ ID NO: 401, and SEQ ID NO: 402, respectively;
SEQ ID NO: 411, SEQ ID NO: 412, SEQ ID NO: 401, and SEQ ID NO: 402, respectively;
SEQ ID NO: 415, SEQ ID NO: 416, SEQ ID NO: 401, and SEQ ID NO: 402, respectively;
SEQ ID NO: 403, SEQ ID NO: 404, SEQ ID NO: 405, and SEQ ID NO: 406, respectively;
SEQ ID NO: 407, SEQ ID NO: 408, SEQ ID NO: 405, and SEQ ID NO: 406, respectively;
SEQ ID NO: 411, SEQ ID NO: 412, SEQ ID NO: 405, and SEQ ID NO: 406, respectively;
SEQ ID NO: 415, SEQ ID NO: 416, SEQ ID NO: 405, and SEQ ID NO: 406, respectively;
SEQ ID NO: 403, SEQ ID NO: 404, SEQ ID NO: 409, and SEQ ID NO: 410, respectively;
SEQ ID NO: 407, SEQ ID NO: 408, SEQ ID NO: 409, and SEQ ID NO: 410, respectively;
SEQ ID NO: 411, SEQ ID NO: 412, SEQ ID NO: 409, and SEQ ID NO: 410, respectively;
SEQ ID NO: 415, SEQ ID NO: 416, SEQ ID NO: 409, and SEQ ID NO: 410, respectively;
SEQ ID NO: 403, SEQ ID NO: 404, SEQ ID NO: 413, and SEQ ID NO: 414, respectively;
SEQ ID NO: 407, SEQ ID NO: 408, SEQ ID NO: 413, and SEQ ID NO: 414, respectively;
SEQ ID NO: 411, SEQ ID NO: 412, SEQ ID NO: 413, and SEQ ID NO: 414, respectively;
SEQ ID NO: 415, SEQ ID NO: 416, SEQ ID NO: 413, and SEQ ID NO: 414, respectively;

SEQ ID NO: 403, SEQ ID NO: 404, SEQ ID NO: 417, and SEQ ID NO: 418, respectively;
SEQ ID NO: 407, SEQ ID NO: 408, SEQ ID NO: 417, and SEQ ID NO: 418, respectively;
SEQ ID NO: 411, SEQ ID NO: 412, SEQ ID NO: 417, and SEQ ID NO: 418, respectively;
SEQ ID NO: 415, SEQ ID NO: 416, SEQ ID NO: 417, and SEQ ID NO: 418, respectively;
SEQ ID NO: 178, SEQ ID NO: 145, SEQ ID NO: 179, and SEQ ID NO: 118, respectively;
SEQ ID NO: 166, SEQ ID NO: 167, SEQ ID NO: 164, and SEQ ID NO: 165, respectively;
SEQ ID NO: 170, SEQ ID NO: 163, SEQ ID NO: 168, and SEQ ID NO: 106, respectively;
SEQ ID NO: 177, SEQ ID NO: 148, SEQ ID NO: 168, and SEQ ID NO: 106, respectively;
SEQ ID NO: 180, SEQ ID NO: 136, SEQ ID NO: 168, and SEQ ID NO: 106, respectively;
SEQ ID NO: 177, SEQ ID NO: 148, SEQ ID NO: 181, and SEQ ID NO: 182, respectively;
SEQ ID NO: 166, SEQ ID NO: 167, SEQ ID NO: 181, and SEQ ID NO: 182, respectively;
SEQ ID NO: 172, SEQ ID NO: 173, SEQ ID NO: 171, and SEQ ID NO: 106, respectively;
SEQ ID NO: 170, SEQ ID NO: 173, SEQ ID NO: 168, and SEQ ID NO: 106, respectively;
SEQ ID NO: 175, SEQ ID NO: 173, SEQ ID NO: 171, and SEQ ID NO: 106, respectively;
SEQ ID NO: 174, SEQ ID NO: 173, SEQ ID NO: 168, and SEQ ID NO: 106, respectively; or
SEQ ID NO: 177, SEQ ID NO: 148, SEQ ID NO: 169, and SEQ ID NO: 176, respectively;
wherein:
(A) the HCP1 is complexed or interfaced with the HCP2;
(B) the LLCP binds to the HCP1 with a higher affinity than the affinity of the LLCP to the HCP2, or the KLCP binds to the HCP2 with a higher affinity than the affinity of the KLCP to the HCP1; and
(C) the HCP1 binds to the HCP2 with a higher affinity than the affinity of the HCP1 to a second molecule of the HCP1; the HCP2 binds to the HCP1 with a higher affinity than the affinity of the HCP2 to a second molecule of the HCP2; or a combination thereof; and
wherein the HCP1 and the HCP2 comprise different sequences.

2. The multispecific antibody molecule of claim 1, wherein:
1) the multispecific antibody molecule does not comprise a mutation in the first HCCRS, or the multispecific antibody molecule does not comprise a mutation in the LLCCRS; and
2) the multispecific antibody molecule does not comprise a mutation in the second HCCRS, or the multispecific antibody molecule does not comprise a mutation in the KLCCRS.

3. The multispecific antibody molecule of claim 1, wherein the multispecific antibody molecule does not comprise a mutation in any one of the first HCCRS, the LLCCRS, the second HCCRS, and the KLCCRS.

4. The multispecific antibody molecule of claim 1, wherein:

1) the first HCCRS comprises a naturally existing heavy chain constant region sequence, or the LLCCRS comprises a naturally existing lambda light chain constant region sequence; and
2) the second HCCRS comprises a naturally existing heavy chain constant region sequence, or the KLCCRS comprises a naturally existing kappa light chain constant region sequence.

5. The multispecific antibody molecule of claim 4, wherein:
i) the first HCCRS comprises the naturally existing heavy chain constant region sequence,
ii) the LLCCRS comprises the naturally existing lambda light chain constant region sequence,
iii) the second HCCRS comprises the naturally existing heavy chain constant region sequence, and
iv) the KLCCRS comprises the naturally existing kappa light chain constant region sequence.

6. The multispecific antibody molecule of claim 1, wherein:
the HCP1 binds to the LLCP with a higher affinity than the affinity of the HCP1 to the KLCP;
the HCP2 binds to the KLCP with a higher affinity than the affinity of the HCP2 to the LLCP; or
a combination thereof.

7. The multispecific antibody molecule of claim 1, wherein:
the HCP1 and the HCP2 are members of a paired protuberance/cavity;
HCP1-HCP2 pairing is promoted by an electrostatic interaction; or
HCP1-HCP2 pairing is promoted by strand exchange; and
wherein self-dimerization of the HCP1, self-dimerization of the HCP2, or a combination thereof is lower than heterodimerization of the HCP1 and the HCP2.

8. The multispecific antibody molecule of claim 1, wherein:
(i) the first HCCRS does not comprise a mutation; the second HCCRS does not comprise a mutation; or a combination thereof; or
(ii)(a) the HCP1 comprises a first CH2 domain sequence and a first CH3 domain sequence, wherein the first CH2 domain sequence and the first CH3 domain sequence do not comprise a mutation;
(b) the HCP2 comprises a second CH2 domain sequence and a second CH3 domain sequence, wherein the second CH2 domain sequence and the second CH3 domain sequence do not comprise a mutation; or
(c) a combination thereof.

9. A pharmaceutical composition comprising the multispecific antibody molecule of claim 1 and a pharmaceutically acceptable diluent or excipient.

10. A method of treating cancer in a subject in need thereof, the method comprising: administering to the subject any one of the multispecific antibody molecule of claim 1, wherein the multispecific antibody molecule is administered in an effective amount to treat the cancer in the subject.

* * * * *